United States Patent
Harikrishnan et al.

(10) Patent No.: US 10,336,761 B2
(45) Date of Patent: Jul. 2, 2019

(54) TGFβ RECEPTOR ANTAGONIST

(71) Applicant: BRISTOL-MYERS SQUIBB COMPANY, Princeton, NJ (US)

(72) Inventors: Lalgudi S. Harikrishnan, Skillman, NJ (US); Brian E. Fink, Yardley, PA (US); Robert M. Borzilleri, Carversville, PA (US); Gopikishan Tonukunuru, Bangalore (IN); Hasibur Rahaman, Bangalore (IN); Jayakumar Sankara Warrier, Bangalore (IN); Balaji Seshadri, Hosur (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/746,597

(22) PCT Filed: Jul. 21, 2016

(86) PCT No.: PCT/US2016/043252
§ 371 (c)(1),
(2) Date: Jan. 22, 2018

(87) PCT Pub. No.: WO2017/015425
PCT Pub. Date: Jan. 26, 2017

(65) Prior Publication Data
US 2018/0215761 A1    Aug. 2, 2018

Related U.S. Application Data

(60) Provisional application No. 62/195,854, filed on Jul. 23, 2015.

(51) Int. Cl.
*A61K 31/53* (2006.01)
*A61K 31/541* (2006.01)
*C07D 487/04* (2006.01)

(52) U.S. Cl.
CPC ............ *C07D 487/04* (2013.01); *A61K 31/53* (2013.01); *A61K 31/541* (2013.01)

(58) Field of Classification Search
CPC .................................................. C07D 487/04
See application file for complete search history.

(56) References Cited

U.S. PATENT DOCUMENTS

2005/0004143 A1    1/2005    Dugar et al.

FOREIGN PATENT DOCUMENTS

WO    WO 2004/065392 A1    8/2004

OTHER PUBLICATIONS

Patani et al. "Bioisosterism: A Rational Approach in Drug Design" Chemical Reviews, 1996, vol. 96, pp. 3147-3176.*
Hou, Xiaonan, et al., "Dual IGF-1R/InsR Inhibitor BMS-754807 Synergizes with Hormonal Agents in Treatment of Estrogen-Dependent Breast Cancer", Cancer Research, 2011, vol. 71, No. 24, pp. 7597-7607.

* cited by examiner

*Primary Examiner* — Joseph R Kosack
(74) *Attorney, Agent, or Firm* — Elliott Korsen

(57) ABSTRACT

The invention relates generally to compounds that modulate the activity of TGFβR-1 and TGFβ R-2, pharmaceutical compositions containing said compounds and methods of treating proliferative disorders and disorders of dysregulated apoptosis, such as cancer, utilizing the compounds of the invention.

6 Claims, No Drawings

TGFβ RECEPTOR ANTAGONIST

CROSS-REFERENCE TO RELATED APPLICATIONS

This application claims the benefit of U.S. Provisional Application No. 62/195,854, filed Jul. 23, 2015, the disclosure of which is incorporated herein by reference in its entirety.

FIELD OF THE INVENTION

The invention relates generally to compounds that modulate the activity of TGFβR-1 and TGFβR-2, pharmaceutical compositions containing said compounds and methods of treating proliferative disorders and disorders of dysregulated apoptosis, such as cancer, utilizing the compounds of the invention.

BACKGROUND OF THE INVENTION

TGFβ is a multifunctional cytokine that regulates a wide variety of biological processes that include cell proliferation and differentiation, migration and adhesion, extracellular matrix modification including tumor stroma and immunosuppression, angiogenesis and desmoplasia (Ling and Lee, Current Pharmaceutical Biotech. 2011, 12:2190-2202), processes supporting tumor progression and late stage disease.

The active form of TGFβ is a dimer that signals through the formation of a membrane bound heterotetramer composed of the serine threonine type 1 and type 2 receptors, TGFβR-1 (ALK5) and TGFβR-2, respectively. Upon binding of two type 1 and two type 2 receptors, the type 2 constitutively activated receptors phosphorylate the type 1 receptors in the glycine and serine rich "GS region" activating a signaling cascade through the intracellular signaling effector molecules, Smad2 or Smad3. TGFβR-1 phosphorylates the receptor Smad2 and/or Smad3 (RSmads) that form a complex with Smad4 (Shi and Massague, Cell 2003, 113:685-700). These complexes then translocate to the nucleus where they elicit a wide variety of transcriptional responses resulting in altered gene expression (Weiss and Attisano, WIREs Developmental Biology, 2013, 2:47-63). The TGFβ proteins are prototypic members of a large family of related factors in mammals with a number of these also identified in other phyla. Generally, two groups have been characterized, the TGFβ-like and BMP-like ligands. In addition, in vertebrates, seven type1 receptors and five type 2 receptors have been identified. An additional layer of complexity in ligand/receptor binding is the potential of co-receptors known as type 3 that facilitate ligand binding to the type 1 and 2 receptor complex. These type 3 receptors, also known as Betaglycan and Endoglin are comprised of large extracellular domains and short cytoplasmic tails and bind different TGFβ family members (Bernabeu et al., Biochem Biophys Acta 2009, 1792:954-73). Although type 3 receptors facilitate signaling, cleavage of the extracellular domain can generate soluble proteins that sequester ligands and can potentially inhibit signaling (Bernabeu et al., Biochem Biophys Acta 2009, 1792:954-73). While multiple redundancies in this large family present challenges to identifying a selective inhibitor, TGFβR-1 and -2 are relatively selective targets for TGFβ ligand engagement.

Alteration in TGFβ signaling are associated with a wide variety of human disorders including fibrosis, inflammatory, skeletal, muscular and cardiovascular disorders as well as cancer (Harradine, et al, 2006, Annals of Medicine 38:403-14). In human cancer, TGFβ signaling alterations can occur in the germline or arise spontaneously in various cancer types. TGFβ is also a potent inducer of angiogenesis, which provides a critical support system for solid tumors as well as a mechanism for tumor cell dissemination (Buijs et al., 2011, Curr Pharmaceutical Biotech, 12:2121-37). Therefore multiple strategies to inhibit TGFβ signaling have been exploited in various disease states.

SUMMARY OF THE INVENTION

In a first aspect of the present invention, there is provided a compound of formula (I)

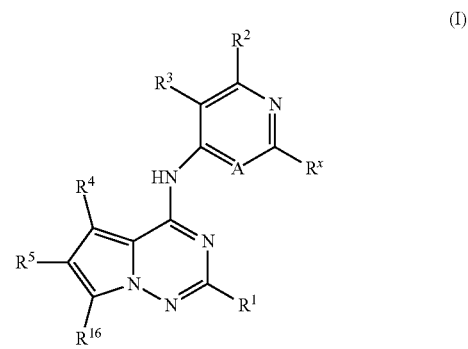

wherein:
A is $CR^y$ or N;
$R^1$ is aryl or heteroaryl, optionally substituted with 1-5 $R^6$;
$R^2$ is hydrogen or $NHCOR^7$;
$R^3$ is hydrogen, halogen, $-CONR^8R^9$ or $-OR^{10}$;
$R^4$ is hydrogen, optionally substituted ($C_1$-$C_6$)alkyl, $-CH_2NR^{11}R^{12}$ or $-CONR^{11}R^{12}$;
$R^5$ is hydrogen, $-CONHR^{13}$, $-CH_2NHR^{14}R^{15}$, $-CH_2NH(CH_2)_m$ optionally substituted heterocyclyl or $-NHR^{14}R^{15}$;
$R^x$ is hydrogen, halogen, optionally substituted ($C_1$-$C_6$) alkyl or $-NHCO(C_1$-$C_6)$alkyl;
$R^y$ is hydrogen, F, Cl or $NH_2$;
$R^6$ is hydrogen, halogen, optionally substituted ($C_1$-$C_6$) alkyl, optionally substituted ($C_1$-$C_6$)alkoxy, $-CHF_2$, $CF_3$, optionally substituted ($C_3$-$C_8$)cycloalkyl, $-NH_2$ or $NHSO_2$($C_1$-$C_6$)alkyl;
$R^7$ is optionally substituted ($C_1$-$C_6$)alkyl, optionally substituted ($C_1$-$C_6$)alkoxy, amino($C_1$-$C_6$)alkyl or hydroxy($C_1$-$C_6$)alkyl;
$R^8$ is hydrogen, optionally substituted ($C_1$-$C_6$)alkoxy or optionally substituted ($C_1$-$C_6$)alkyl;
$R^9$ is hydrogen or optionally substituted heterocyclyl;
$R^{10}$ is optionally substituted ($C_1$-$C_6$)alkyl;
$R^{11}$ is hydrogen, amino($C_1$-$C_6$)alkyl or hydroxy($C_1$-$C_6$) alkyl;
$R^{12}$ is hydrogen, amino($C_1$-$C_6$)alkyl or hydroxy($C_1$-$C_6$) alkyl; or
$R^{11}$ and $R^{12}$ are taken together with the nitrogen to which they are attached to form a heterocyclic group;
$R^{13}$ is hydrogen or optionally substituted ($C_1$-$C_6$)alkyl;
$R^{14}$ is hydrogen or optionally substituted ($C_1$-$C_6$)alkyl
$R^{15}$ is hydrogen or optionally substituted ($C_1$-$C_6$)alkyl; or
$R^{14}$ and $R^{15}$ are taken together with the nitrogen to which they are attached to form a heterocyclic group;
$R^{16}$ is hydrogen, halogen, $-CN$, $-COOR^{13}$ or $-CONR^{13}R^{14}$;

and/or a pharmaceutically acceptable salt, tautomer or stereoisomer thereof.

In another aspect, there is provided a pharmaceutical composition comprising a compound of the invention or a pharmaceutically acceptable salt thereof and one or more pharmaceutically acceptable carriers, diluents or excipients.

In another aspect, there is provided a compound of the invention or a pharmaceutically acceptable salt thereof for use in therapy. In particular, there is provided a compound for use in the treatment of a disease or condition for which a TGFβR antagonist is indicated.

In another aspect, there is provided a method of treating cancers, fibrosis, inflammatory, skeletal, muscular and cardiovascular disorders which comprise administering to a subject in need thereof a therapeutically effective amount of a TGFβR antagonist.

DETAILED DESCRIPTION OF THE INVENTION

In a first aspect of the present invention, there is provided a compound of formula (I)

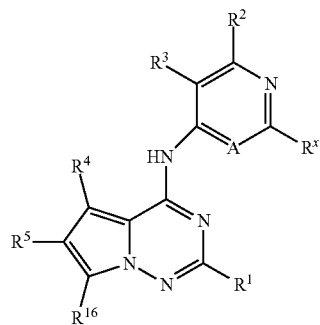

(I)

wherein:

A is CH or N;

$R^1$ is aryl or heteroaryl, optionally substituted with 1-5 $R^6$;

$R^2$ is hydrogen or $NHCOR^7$;

$R^3$ is hydrogen, halogen, $—CONR^8R^9$ or $—OR^{10}$;

$R^4$ is hydrogen, optionally substituted $(C_1-C_6)$alkyl, $—CH_2NR^{11}R^{12}$ or $—CONR^{11}R^{12}$;

$R^5$ is hydrogen, $—CONHR^{13}$, $—CH_2NHR^{14}R^{15}$, $—CH_2NH(CH_2)_m$ optionally substituted heterocyclyl or $—NHR^{14}R^{15}$;

$R^x$ is hydrogen, halogen, optionally substituted $(C_1-C_6)$alkyl or $—NHCO(C_1-C_6)$alkyl;

$R^6$ is hydrogen, halogen, optionally substituted $(C_1-C_6)$alkyl, optionally substituted $(C_1-C_6)$alkoxy, $—CHF_2$, $CF_3$, optionally substituted $(C_3-C_8)$cycloalkyl, $—NH_2$ or $NHSO_2(C_1-C_6)$alkyl;

$R^7$ is optionally substituted $(C_1-C_6)$alkyl, optionally substituted $(C_1-C_6)$alkoxy, amino$(C_1-C_6)$alkyl or hydroxy$(C_1-C_6)$alkyl;

$R^8$ is hydrogen, optionally substituted $(C_1-C_6)$alkoxy or optionally substituted $(C_1-C_6)$alkyl;

$R^9$ is hydrogen or optionally substituted heterocyclyl;

$R^{10}$ is optionally substituted $(C_1-C_6)$alkyl;

$R^{11}$ is hydrogen, amino$(C_1-C_6)$alkyl or hydroxy$(C_1-C_6)$alkyl;

$R^{12}$ is hydrogen, amino$(C_1-C_6)$alkyl or hydroxy$(C_1-C_6)$alkyl; or $R^{11}$ and $R^{12}$ are taken together with the nitrogen to which they are attached to form a heterocyclic group;

$R^{13}$ is hydrogen or optionally substituted $(C_1-C_6)$alkyl;

$R^{14}$ is hydrogen or optionally substituted $(C_1-C_6)$alkyl $R^{15}$ is hydrogen, optionally substituted $(C_1-C_6)$alkyl; or $R^{14}$ and $R^{15}$ are taken together with the nitrogen to which they are attached to form a heterocyclic group;

$R^{16}$ is hydrogen, halogen, $—CN$, $—COOR^{13}$ or $—CONR^{13}R^{14}$;

and/or a pharmaceutically acceptable salt, tautomer or stereoisomer thereof.

In a second aspect of the present invention, there is provided a compound of formula (II)

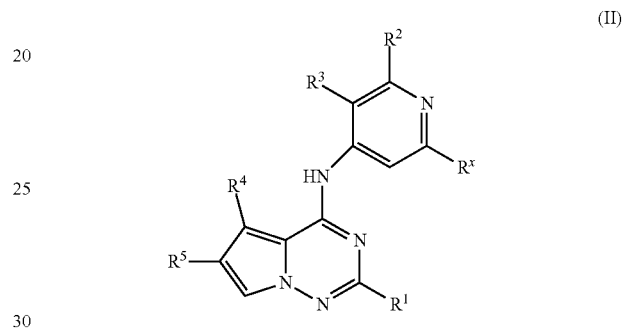

(II)

wherein:

$R^1$ is aryl or heteroaryl, optionally substituted with 1-5 $R^6$;

$R^2$ is hydrogen or $NHCOR^7$;

$R^3$ is hydrogen, halogen, $—CONR^8R^9$ or $—OR^{10}$;

$R^4$ is hydrogen, optionally substituted $(C_1-C_6)$alkyl, $—CH_2NR^{11}R^{12}$ or $—CONR^{11}R^{12}$;

$R^5$ is hydrogen, $—CONHR^{13}$, $—CH_2NHR^{14}R^{15}$, $—CH_2NH(CH_2)_m$ optionally substituted heterocyclyl or $—NHR^{14}R^{15}$;

$R^x$ is hydrogen, halogen, optionally substituted $(C_1-C_6)$alkyl or $—NHCO(C_1-C_6)$alkyl;

$R^6$ is hydrogen, halogen, optionally substituted $(C_1-C_6)$alkyl, optionally substituted $(C_1-C_6)$alkoxy, $—CHF_2$, $CF_3$, optionally substituted $(C_3-C_8)$cycloalkyl, $—NH_2$ or $NHSO_2(C_1-C_6)$alkyl;

$R^7$ is optionally substituted $(C_1-C_6)$alkyl, optionally substituted $(C_1-C_6)$alkoxy, amino$(C_1-C_6)$alkyl or hydroxy$(C_1-C_6)$alkyl;

$R^8$ is hydrogen, optionally substituted $(C_1-C_6)$alkoxy or optionally substituted $(C_1-C_6)$alkyl;

$R^9$ is hydrogen or optionally substituted heterocyclyl;

$R^{10}$ is optionally substituted $(C_1-C_6)$alkyl;

$R^{11}$ is hydrogen, amino$(C_1-C_6)$alkyl or hydroxy$(C_1-C_6)$alkyl;

$R^{12}$ is hydrogen, amino$(C_1-C_6)$alkyl or hydroxy$(C_1-C_6)$alkyl; or $R^{11}$ and $R^{12}$ are taken together with the nitrogen to which they are attached to form a heterocyclic group;

$R^{13}$ is hydrogen or optionally substituted $(C_1-C_6)$alkyl;

$R^{14}$ is hydrogen or optionally substituted $(C_1-C_6)$alkyl $R^{15}$ is hydrogen, optionally substituted $(C_1-C_6)$alkyl; or $R^{14}$ and $R^{15}$ are taken together with the nitrogen to which they are attached to form a heterocyclic group;

and/or a pharmaceutically acceptable salt, tautomer or stereoisomer thereof.

In a third aspect of the present invention, there is provided a compound of formula (III)

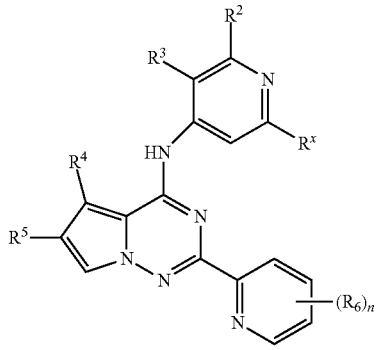

(III)

wherein:

R² is hydrogen or NHCOR⁷;

R³ is hydrogen, halogen, —CONR⁸R⁹ or —OR¹⁰;

R⁴ is hydrogen, optionally substituted $(C_1\text{-}C_6)$alkyl, —CH$_2$NR¹¹R¹² or —CONR¹¹R¹²;

R⁵ is hydrogen, —CONHR¹³, —CH$_2$NHR¹⁴R¹⁵, —CH$_2$NH(CH$_2$)$_m$ optionally substituted heterocyclyl or —NHR¹⁴R¹⁵;

R$^x$ is hydrogen, halogen, optionally substituted $(C_1\text{-}C_6)$ alkyl or —NHCO$(C_1\text{-}C_6)$alkyl;

R⁶ is hydrogen, halogen, optionally substituted $(C_1\text{-}C_6)$ alkyl, optionally substituted $(C_1\text{-}C_6)$alkoxy, —CHF$_2$, CF$_3$, optionally substituted $(C_3\text{-}C_8)$cycloalkyl, —NH$_2$ or NHSO$_2$ $(C_1\text{-}C_6)$alkyl;

R⁷ is optionally substituted $(C_1\text{-}C_6)$alkyl, optionally substituted $(C_1\text{-}C_6)$alkoxy, amino$(C_1\text{-}C_6)$alkyl or hydroxy$(C_1\text{-}C_6)$alkyl;

R⁸ is hydrogen, optionally substituted $(C_1\text{-}C_6)$alkoxy or optionally substituted $(C_1\text{-}C_6)$alkyl;

R⁹ is hydrogen or optionally substituted heterocyclyl

R¹⁰ is optionally substituted $(C_1\text{-}C_6)$alkyl;

R¹¹ is hydrogen, amino$(C_1\text{-}C_6)$alkyl or hydroxy$(C_1\text{-}C_6)$alkyl;

R¹² is hydrogen, amino$(C_1\text{-}C_6)$alkyl or hydroxy$(C_1\text{-}C_6)$alkyl; or R¹¹ and R¹² are taken together with the nitrogen to which they are attached to form a heterocyclic group;

R¹³ is hydrogen or optionally substituted $(C_1\text{-}C_6)$alkyl;

R¹⁴ is hydrogen or optionally substituted $(C_1\text{-}C_6)$alkyl

R¹⁵ is hydrogen, optionally substituted $(C_1\text{-}C_6)$alkyl; or

R¹⁴ and R¹⁵ are taken together with the nitrogen to which they are attached to form a heterocyclic group;

n is 1, 2, 3, 4, or 5;

and/or a pharmaceutically acceptable salt, tautomer or stereoisomer thereof.

In a fourth aspect of the present invention, there is provided a compound of formula (III)

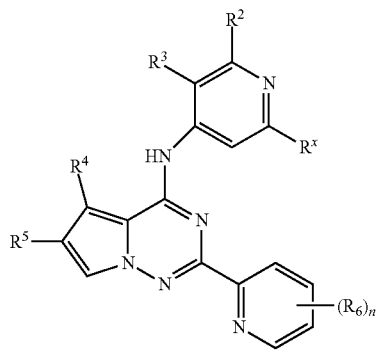

(III)

wherein:

R² is hydrogen or NHCOR⁷;

R³ is hydrogen, halogen, —CONR⁸R⁹ or —OR¹⁰;

R⁴ is hydrogen, optionally substituted $(C_1\text{-}C_6)$alkyl, —CH$_2$NR¹¹R¹² or —CONR¹¹R¹²;

R⁵ is hydrogen, —CONHR¹³, —CH$_2$NHR¹⁴R¹⁵, —CH$_2$NH(CH$_2$)$_m$ optionally substituted heterocyclyl or —NHR¹⁴R¹⁵;

R$^x$ is hydrogen, halogen, optionally substituted $(C_1\text{-}C_6)$ alkyl or —NHCO$(C_1\text{-}C_6)$alkyl;

R⁶ is hydrogen, halogen, optionally substituted $(C_1\text{-}C_6)$ alkyl, optionally substituted $(C_1\text{-}C_6)$alkoxy, —CHF$_2$, CF$_3$, optionally substituted $(C_3\text{-}C_8)$cycloalkyl, —NH$_2$ or NHSO$_2$ $(C_1\text{-}C_6)$alkyl;

R⁷ is optionally substituted $(C_1\text{-}C_6)$alkyl, optionally substituted $(C_1\text{-}C_6)$alkoxy, amino$(C_1\text{-}C_6)$alkyl or hydroxy$(C_1\text{-}C_6)$alkyl;

R⁸ is hydrogen, optionally substituted $(C_1\text{-}C_6)$alkoxy or optionally substituted $(C_1\text{-}C_6)$alkyl;

R⁹ is hydrogen or optionally substituted heterocyclyl;

R¹⁰ is optionally substituted $(C_1\text{-}C_6)$alkyl;

R¹¹ is hydrogen, amino$(C_1\text{-}C_6)$alkyl or hydroxy$(C_1\text{-}C_6)$ alkyl;

R¹² is hydrogen, amino$(C_1\text{-}C_6)$alkyl or hydroxy$(C_1\text{-}C_6)$ alkyl; or R¹¹ and R¹² are taken together with the nitrogen to which they are attached to form a heterocyclic group;

R¹³ is hydrogen or optionally substituted $(C_1\text{-}C_6)$alkyl;

R¹⁴ is hydrogen or optionally substituted $(C_1\text{-}C_6)$alkyl

R¹⁵ is hydrogen, optionally substituted $(C_1\text{-}C_6)$alkyl; or

R¹⁴ and R¹⁵ are taken together with the nitrogen to which they are attached to form a heterocyclic group;

n is 1, 2 or 3;

and/or a pharmaceutically acceptable salt, tautomer or stereoisomer thereof.

In a fifth aspect of the present invention, there is provided a compound of formula (III)

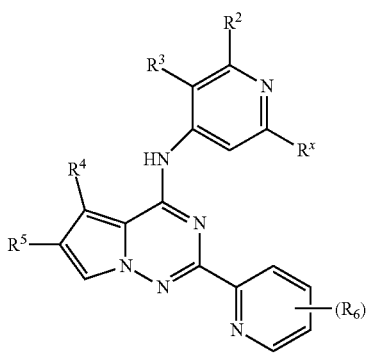

(III)

wherein:
R² is hydrogen or NHCOR⁷;
R³ is hydrogen, halogen, —CONR⁸R⁹ or —OR¹⁰;
R⁴ is hydrogen, optionally substituted (C₁-C₆)alkyl, —CH₂NR¹¹R¹² or —CONR¹¹R¹²;
R⁵ is hydrogen, —CONHR¹³, —CH₂NHR¹⁴R¹⁵, —CH₂NH(CH₂)$_m$ optionally substituted heterocyclyl or —NHR¹⁴R¹⁵;
R$^x$ is hydrogen, halogen, optionally substituted (C₁-C₆) alkyl or —NHCO(C₁-C₆)alkyl;
R⁶ is hydrogen, halogen, optionally substituted (C₁-C₆) alkyl, optionally substituted (C₁-C₆)alkoxy, —CHF₂, CF₃, optionally substituted (C₃-C₈)cycloalkyl, —NH₂ or NHSO₂ (C₁-C₆)alkyl;
R⁷ is optionally substituted (C₁-C₆)alkyl, optionally substituted (C₁-C₆)alkoxy, amino(C₁-C₆)alkyl or hydroxy(C₁-C₆)alkyl;
R⁸ is hydrogen, optionally substituted (C₁-C₆)alkoxy or optionally substituted (C₁-C₆)alkyl;
R⁹ is hydrogen or optionally substituted heterocyclyl;
R¹⁰ is optionally substituted (C₁-C₆)alkyl;
R¹¹ is hydrogen, amino(C₁-C₆)alkyl or hydroxy(C₁-C₆)alkyl;
R¹² is hydrogen, amino(C₁-C₆)alkyl or hydroxy(C₁-C₆)alkyl; or
R¹¹ and R¹² are taken together with the nitrogen to which they are attached to form a heterocyclic group;
R¹³ is hydrogen or optionally substituted (C₁-C₆)alkyl;
R¹⁴ is hydrogen or optionally substituted (C₁-C₆)alkyl
R¹⁵ is hydrogen, optionally substituted (C₁-C₆)alkyl; or
R¹⁴ and R¹⁵ are taken together with the nitrogen to which they are attached to form a heterocyclic group;
n is 1, 2 or 3;
and/or a pharmaceutically acceptable salt, tautomer or stereoisomer thereof.

In another aspect, there is provided a compound selected from the exemplified examples within the scope of the first aspect, or a pharmaceutically acceptable salt, tautomer or stereoisomer thereof.

In another aspect, there is provided a compound selected from any subset list of compounds within the scope of any of the above aspects.

In another aspect, there is provided a compound selected from the following list
N-[2-(pyridin-2-yl)pyrrolo[2,1-f][1,2,4]triazin-4-yl]pyridin-4-amine,
3-(difluoromethyl)-N-{2-[6-(trifluoromethyl)pyridin-2-yl]pyrrolo[2,1-f][1,2,4]triazin-4-yl}pyridin-4-amine,
3-chloro-N-[2-(5-fluoro-6-methylpyridin-2-yl)pyrrolo[2,1-f][1,2,4]triazin-4-yl]pyridin-4-amine,
3-chloro-N-[2-(5-fluoropyridin-2-yl)pyrrolo[2,1-f][1,2,4]triazin-4-yl]pyridin-4-amine
6-{4-[(3-fluoropyridin-4-yl)amino]pyrrolo[2,1-f][1,2,4]triazin-2-yl}pyridine-2-carboxamide,
3-chloro-N-[2-(6-methylpyrazin-2-yl)pyrrolo[2,1-f][1,2,4]triazin-4-yl]pyridin-4-amine,
2-chloro-N-{2-[6-(difluoromethyl)pyridin-2-yl]pyrrolo[2,1-f][1,2,4]triazin-4-yl}-3-fluoropyridin-4-amine,
N-(6-{4-[(pyridin-4-yl)amino]pyrrolo[2,1-f][1,2,4]triazin-2-yl}pyridin-2-yl)methanesulfonamide,
N-(6-(4-((3-fluoropyridin-4-yl)amino)pyrrolo[2,1-f][1,2,4]triazin-2-yl)pyridin-2-yl)acetamide,
3-fluoro-N-[2-(1-methyl-1H-pyrazol-5-yl)pyrrolo[2,1-f][1,2,4]triazin-4-yl]pyridin-4-amine,
N-[4-({2-[6-(difluoromethyl)-5-fluoropyridin-2-yl]pyrrolo[2,1-f][1,2,4]triazin-4-yl}amino)pyridin-2-yl]acetamide,
3-fluoro-N-[2-(4-methyl-1,3-thiazol-2-yl)pyrrolo[2,1-f][1,2,4]triazin-4-yl]pyridin-4-amine,
N-[4-({2-[6-(difluoromethyl)pyridin-2-yl]pyrrolo[2,1-f][1,2,4]triazin-4-yl}amino)pyridin-2-yl]acetamide,
3-fluoro-N-[2-(6-fluoropyridin-2-yl)pyrrolo[2,1-f][1,2,4]triazin-4-yl]pyridin-4-amine,
3-(difluoromethyl)-N-[2-(6-methoxypyridin-2-yl)pyrrolo[2,1-f][1,2,4]triazin-4-yl]pyridin-4-amine,
N-[2-(6-methoxypyridin-2-yl)-5-methylpyrrolo[2,1-f][1,2,4]triazin-4-yl]pyridin-4-amine,
N-(3-fluoropyridin-4-yl)-2-(4-(trifluoromethyl)thiazol-2-yl)pyrrolo[2,1-f][1,2,4]triazin-4-amine,
N-(4-((2-(6-(trifluoromethyl)pyridin-2-yl)pyrrolo[2,1-f][1,2,4]triazin-4-yl)amino)pyridin-2-yl)acetamide,
N-(4-{[2-(5-fluoro-6-methylpyridin-2-yl)pyrrolo[2,1-f][1,2,4]triazin-4-yl]amino}pyridin-2-yl)acetamide,
N-[3-fluoro-4-({2-[6-(trifluoromethyl)pyridin-2-yl]pyrrolo[2,1-f][1,2,4]triazin-4-yl}amino)pyridin-2-yl]acetamide,
N-[4-({2-[6-(difluoromethyl)pyridin-2-yl]pyrrolo[2,1-f][1,2,4]triazin-4-yl}amino)pyridin-2-yl]acetamide,
N-{4-[(3-fluoropyridin-4-yl)amino]-2-(6-methoxypyridin-2-yl)pyrrolo[2,1-f][1,2,4]triazin-6-yl}methanesulfonamide,
N-{2-[6-(difluoromethyl)pyridin-2-yl]-5-[(4,4-difluoropiperidin-1-yl)methyl]pyrrolo[2,1-f][1,2,4]triazin-4-yl}-3-fluoropyridin-4-amine,
N-[4-({5-[(4,4-difluoropiperidin-1-yl)methyl]-2-(pyridin-2-yl)pyrrolo[2,1-f][1,2,4]triazin-4-yl}amino)pyridin-2-yl]acetamide,
N-{5-[(4,4-difluoropiperidin-1-yl)methyl]-2-(6-methoxypyridin-2-yl)pyrrolo[2,1-f][1,2,4]triazin-4-yl}-3-fluoropyridin-4-amine,
3-fluoro-N-{5-[(4-methylpiperazin-1-yl)methyl]-2-[6-(trifluoromethyl)pyridin-2-yl]pyrrolo[2,1-f][1,2,4]triazin-4-yl}pyridin-4-amine,
N-{5-[(4,4-difluoropiperidin-1-yl)methyl]-2-(pyridin-2-yl)pyrrolo[2,1-f][1,2,4]triazin-4-yl}-3-fluoropyridin-4-amine,
1-{4-[(3-fluoropyridin-4-yl)amino]-2-(6-methoxypyridin-2-yl)pyrrolo[2,1-f][1,2,4]triazin-5-yl}ethane-1,2-diol,
6-ethyl-N-(3-fluoropyridin-4-yl)-2-(6-methoxypyridin-2-yl)pyrrolo[2,1-f][1,2,4]triazin-4-amine,
2-[4-(dimethylamino)piperidin-1-yl]-1-{4-[(3-fluoropyridin-4-yl)amino]-2-(6-methoxypyridin-2-yl)pyrrolo[2,1-f][1,2,4]triazin-5-yl}ethan-1-ol,
2-(6-methoxypyridin-2-yl)-N-(pyridin-4-ylmethyl)pyrrolo[2,1-f][1,2,4]triazin-4-amine,
1-(6-{4-[(3-fluoropyridin-4-yl)amino]pyrrolo[2,1-f][1,2,4]triazin-2-yl}pyridin-2-yl)ethan-1-ol, N-[4-({2-[6-(difluoromethyl)pyridin-2-yl]pyrrolo[2,1-f][1,2,4]triazin-4-yl}amino)pyridin-2-yl]-2-(pyrrolidin-1-yl)acetamide,
2-N-[2-(4,4-difluoropiperidin-1-yl)ethyl]-4-N-[2-(6-methoxypyridin-2-yl)pyrrolo[2,1-f][1,2,4]triazin-4-yl]pyridine-2,4-diamine,
N-[2-(1,1-dioxo-1,4-thiomorpholin-4-yl)ethyl]-4-{[2-(5-fluoro-6-methylpyridin-2-yl)pyrrolo[2,1-f][1,2,4]triazin-4-yl]amino}pyridine-3-carboxamide,
N-(3-(1,1-dioxidothiomorpholino)propyl)-4-((2-(6-methylpyridin-2-yl)pyrrolo[2,1-f][1,2,4]triazin-4-yl)amino)nicotinamide,
N-[3-(pyrrolidin-1-yl)propyl]-4-({2-[6-(trifluoromethyl)pyridin-2-yl]pyrrolo[2,1-f][1,2,4]triazin-4-yl}amino)pyridine-3-carboxamide,
N-[2-(6-methoxypyridin-2-yl)pyrrolo[2,1-f][1,2,4]triazin-4-yl]-3-{[3-(morpholin-4-yl)propoxy]methyl}pyridin-4-amine,
2-{4-[(3-fluoropyridin-4-yl)amino]-2-(6-methoxypyridin-2-yl)pyrrolo[2,1-f][1,2,4]triazin-6-yl}propan-2-ol,
N-{6-[(4,4-difluoropiperidin-1-yl)methyl]-2-(6-methoxy-pyridin-2-yl)pyrrolo[2,1-f][1,2,4]triazin-4-yl}-3-fluoro-pyridin-4-amine,
3-fluoro-N-[7-fluoro-2-(6-methoxypyridin-2-yl)pyrrolo[2,1-f][1,2,4]triazin-4-yl]pyridin-4-amine,
N-[6-ethyl-2-(6-methoxypyridin-2-yl)pyrrolo[2,1-f][1,2,4]triazin-4-yl]-3-fluoropyridin-4-amine,
3-fluoro-N-[2-(6-methoxypyridin-2-yl)-6-[4-(4-methylpiperazin-1-yl)butyl]pyrrolo[2,1-f][1,2,4]triazin-4-yl]pyridin-4-amine,
3-fluoro-N-[2-(6-methoxypyridin-2-yl)-6-[2-(4-methylpiperazin-1-yl)ethyl]pyrrolo[2,1-f][1,2,4]triazin-4-yl]pyridin-4-amine,
3-fluoro-N-[2-(6-methoxypyridin-2-yl)-5-[2-(pyrrolidin-1-yl)ethoxy]pyrrolo[2,1-f][1,2,4]triazin-4-yl]pyridin-4-amine,
2-{4-[(3-fluoropyridin-4-yl)amino]-2-(6-methoxypyridin-2-yl)pyrrolo[2,1-f][1,2,4]triazin-5-yl}ethan-1-ol,
N-(4-{[2-(6-methoxypyridin-2-yl)pyrrolo[2,1-f][1,2,4]triazin-4-yl]amino}pyridin-3-yl)acetamide,
2-{4-[(3-fluoropyridin-4-yl)amino]-2-(6-methoxypyridin-2-yl)pyrrolo[2,1-f][1,2,4]triazin-5-yl}propan-2-ol,
N-[2-(6-methylpyridin-2-yl)pyrrolo[2,1-f][1,2,4]triazin-4-yl]pyridin-4-amine,
-(6-methylpyridin-2-yl)-4-[(pyridin-4-yl)amino]-N-[3-(pyrrolidin-1-yl)propyl]pyrrolo[2,1-f][1,2,4]triazine-6-carboxamide,
3-[4-(dimethylamino)butoxy]-N-[2-(6-methylpyridin-2-yl)pyrrolo[2,1-f][1,2,4]triazin-4-yl]pyridin-4-amine,
4-[(3-fluoropyridin-4-yl)amino]-2-(6-methylpyridin-2-yl)pyrrolo[2,1-f][1,2,4]triazine-7-carboxylic acid,
2-(6-aminopyridin-2-yl)-N-(3-fluoropyridin-4-yl)pyrrolo[2,1-f][1,2,4]triazin-4-amine,
3-chloro-N-[2-(pyridin-2-yl)pyrrolo[2,1-f][1,2,4]triazin-4-yl]pyridin-4-amine,
3-fluoro-N-[2-(pyridin-2-yl)pyrrolo[2,1-f][1,2,4]triazin-4-yl]pyridin-4-amine,
3-fluoro-N-[2-(6-methylpyridin-2-yl)pyrrolo[2,1-f][1,2,4]triazin-4-yl]pyridin-4-amine,
3-fluoro-N-[2-(6-methoxypyridin-2-yl)pyrrolo[2,1-f][1,2,4]triazin-4-yl]pyridin-4-amine,
3-chloro-N-[2-(6-methylpyridin-2-yl)pyrrolo[2,1-f][1,2,4]triazin-4-yl]pyridin-4-amine,
3-chloro-N-[2-(6-methoxypyridin-2-yl)pyrrolo[2,1-f][1,2,4]triazin-4-yl]pyridin-4-amine,
3,5-difluoro-N-[2-(6-methylpyridin-2-yl)pyrrolo[2,1-f][1,2,4]triazin-4-yl]pyridin-4-amine,
3-fluoro-N-[2-(4-methylpyridin-2-yl)pyrrolo[2,1-f][1,2,4]triazin-4-yl]pyridin-4-amine,
N-[2-(4-chloropyridin-2-yl)pyrrolo[2,1-f][1,2,4]triazin-4-yl]-3-fluoropyridin-4-amine,
N-[2-(6-methylpyridin-2-yl)pyrrolo[2,1-f][1,2,4]triazin-4-yl]pyrimidin-4-amine,
3-fluoro-N-[2-(5-fluoropyridin-2-yl)pyrrolo[2,1-f][1,2,4]triazin-4-yl]pyridin-4-amine,
N-{2-[6-(difluoromethyl)-5-fluoropyridin-2-yl]pyrrolo[2,1-f][1,2,4]triazin-4-yl}-3-fluoropyridin-4-amine,
N-[2-(6-methoxypyridin-2-yl)pyrrolo[2,1-f][1,2,4]triazin-4-yl]pyrimidin-4-amine,
Methyl N-(4-{[2-(6-methoxypyridin-2-yl)pyrrolo[2,1-f][1,2,4]triazin-4-yl]amino}pyridin-2-yl)carbamate,
N-[2-(5-fluoro-6-methylpyridin-2-yl)pyrrolo[2,1-f][1,2,4]triazin-4-yl]pyridin-4-amine,
3-chloro-N-[2-(6-fluoropyridin-2-yl)pyrrolo[2,1-f][1,2,4]triazin-4-yl]pyridin-4-amine,
3-fluoro-N-[2-(6-methylpyrazin-2-yl)pyrrolo[2,1-f][1,2,4]triazin-4-yl]pyridin-4-amine,
3-ethyl-1-{4-[(3-fluoropyridin-4-yl)amino]-2-(6-methoxy-pyridin-2-yl)pyrrolo[2,1-f][1,2,4]triazin-6-yl}urea,
Methyl N-{4-[(3-fluoropyridin-4-yl)amino]-2-(6-methoxy-pyridin-2-yl)pyrrolo[2,1-f][1,2,4]triazin-6-yl}carbamate,
3-fluoro-N-[2-(5-fluoro-6-methylpyridin-2-yl)pyrrolo[2,1-f][1,2,4]triazin-4-yl]pyridin-4-amine,
3-[3-(morpholin-4-yl)propoxy]-N-{2-[6-(trifluoromethyl)pyridin-2-yl]pyrrolo[2,1-f][1,2,4]triazin-4-yl}pyridin-4-amine, 75
N-{5-[(4,4-difluoropiperidin-1-yl)methyl]-2-(6-methylpyridin-2-yl)pyrrolo[2,1-f][1,2,4]triazin-4-yl}-3-fluoropyridin-4-amine,
N-(6-{4-[(3-fluoropyridin-4-yl)amino]pyrrolo[2,1-f][1,2,4]triazin-2-yl}pyridin-2-yl)methanesulfonamide,
N-{2-[6-(difluoromethyl)pyridin-2-yl]pyrrolo[2,1-f][1,2,4]triazin-4-yl}-3-fluoropyridin-4-amine,
3-(prop-2-en-1-yloxy)-N-[2-(pyridin-2-yl)pyrrolo[2,1-f][1,2,4]triazin-4-yl]pyridin-4-amine,
3-chloro-N-{2-[6-(difluoromethyl)pyridin-2-yl]pyrrolo[2,1-f][1,2,4]triazin-4-yl}pyridin-4-amine,
3-chloro-N-[2-(1-methyl-1H-pyrazol-5-yl)pyrrolo[2,1-f][1,2,4]triazin-4-yl]pyridin-4-amine,
2-chloro-N-{2-[6-(trifluoromethyl)pyridin-2-yl]pyrrolo[2,1-f][1,2,4]triazin-4-yl}pyridin-4-amine,
4-{[2-(pyridin-2-yl)pyrrolo[2,1-f][1,2,4]triazin-4-yl]amino}pyridine-3-carboxamide,
3-fluoro-N-{2-[6-(trifluoromethyl)pyridin-2-yl]pyrrolo[2,1-f][1,2,4]triazin-4-yl}pyridin-4-amine,
N-{2-[6-(trifluoromethyl)pyridin-2-yl]pyrrolo[2,1-f][1,2,4]triazin-4-yl}pyridin-4-amine,
3-chloro-N-{2-[6-(trifluoromethyl)pyridin-2-yl]pyrrolo[2,1-f][1,2,4]triazin-4-yl}pyridin-4-amine,
3-chloro-N-[2-(4-methyl-1,3-thiazol-2-yl)pyrrolo[2,1-f][1,2,4]triazin-4-yl]pyridin-4-amine,
N-[2-(4-methyl-1,3-thiazol-2-yl)pyrrolo[2,1-f][1,2,4]triazin-4-yl]pyridin-4-amine,
3-fluoro-N-[2-(1H-pyrrol-2-yl)pyrrolo[2,1-f][1,2,4]triazin-4-yl]pyridin-4-amine,
N-(6-{4-[(3-chloropyridin-4-yl)amino]pyrrolo[2,1-f][1,2,4]triazin-2-yl}pyridin-2-yl)methanesulfonamide,
N-[5-chloro-2-(6-methoxypyridin-2-yl)pyrrolo[2,1-f][1,2,4]triazin-4-yl]pyridin-4-amine,
N-[2-(6-methoxypyridin-2-yl)pyrrolo[2,1-f][1,2,4]triazin-4-yl]-2-methylpyridin-4-amine,
2-chloro-N-[2-(6-methoxypyridin-2-yl)pyrrolo[2,1-f][1,2,4]triazin-4-yl]pyridin-4-amine, 2-fluoro-N-[2-(6-methoxypyridin-2-yl)pyrrolo[2,1-f][1,2,4]triazin-4-yl]pyridin-4-amine,
4-N-[2-(6-methoxypyridin-2-yl)pyrrolo[2,1-f][1,2,4]triazin-4-yl]pyridine-3,4-diamine,
2-fluoro-N-[2-(6-methoxypyridin-2-yl)-5-methylpyrrolo[2,1-f][1,2,4]triazin-4-yl]pyridin-4-amine,
N-(4-{[2-(6-methoxypyridin-2-yl)pyrrolo[2,1-f][1,2,4]triazin-4-yl]amino}pyridin-2-yl)acetamide,
4-{[2-(6-methoxypyridin-2-yl)pyrrolo[2,1-f][1,2,4]triazin-4-yl]amino}pyridine-3-carboxamide,
N-[2-(6-methoxypyridin-2-yl)pyrrolo[2,1-f][1,2,4]triazin-4-yl]-2-(morpholin-4-yl)pyridin-4-amine,
3-fluoro-N-{2-[2-(trifluoromethyl)pyrimidin-4-yl]pyrrolo[2,1-f][1,2,4]triazin-4-yl}pyridin-4-amine,
3-fluoro-N-[2-(2-methoxypyrimidin-4-yl)pyrrolo[2,1-f][1,2,4]triazin-4-yl]pyridin-4-amine,
N-[2-(6-ethoxypyridin-2-yl)pyrrolo[2,1-f][1,2,4]triazin-4-yl]-3-fluoropyridin-4-amine,
4-N-(3-fluoropyridin-4-yl)-2-(6-methoxypyridin-2-yl)pyrrolo[2,1-f][1,2,4]triazine-4,6-diamine,
N-{4-[(3-fluoropyridin-4-yl)amino]-2-(6-methoxypyridin-2-yl)pyrrolo[2,1-f][1,2,4]triazin-6-yl}acetamide,
N-{4-[(3-fluoropyridin-4-yl)amino]-2-(6-methoxypyridin-2-yl)pyrrolo[2,1-f][1,2,4]triazin-6-yl}morpholine-4-carboxamide,
N-{4-[(3-fluoropyridin-4-yl)amino]-2-(6-methoxypyridin-2-yl)pyrrolo[2,1-f][1,2,4]triazin-6-yl}-2-(morpholin-4-yl)acetamide,
N-{4-[(3-fluoropyridin-4-yl)amino]-2-(6-methoxypyridin-2-yl)pyrrolo[2,1-f][1,2,4]triazin-6-yl}cyclopropanesulfonamide,
tert-butyl N-[({4-[(3-fluoropyridin-4-yl)amino]-2-(6-methoxypyridin-2-yl)pyrrolo[2,1-f][1,2,4]triazin-6-yl}carbamoyl)methyl]carbamate,
2-amino-N-{4-[(3-fluoropyridin-4-yl)amino]-2-(6-methoxypyridin-2-yl)pyrrolo[2,1-f][1,2,4]triazin-6-yl}acetamide
N-{4-[(3-fluoropyridin-4-yl)amino]-2-(6-methoxypyridin-2-yl)pyrrolo[2,1-f][1,2,4]triazin-6-yl}-2-methanesulfonamidoacetamide,
N-{4-[(3-fluoropyridin-4-yl)amino]-2-[6-(trifluoromethyl)pyridin-2-yl]pyrrolo[2,1-f][1,2,4]triazin-6-yl}-N-methanesulfonylmethanesulfonamide,
3-fluoro-N-[2-(6-methoxypyridin-2-yl)-5-[2-(4-methylpiperazin-1-yl)ethyl]pyrrolo[2,1-f][1,2,4]triazin-4-yl]pyridin-4-amine,
3-fluoro-N-[2-(6-methoxypyridin-2-yl)-5-[2-(morpholin-4-yl)ethyl]pyrrolo[2,1-f][1,2,4]triazin-4-yl]pyridin-4-amine,
N-{5-[2-(4-aminopiperidin-1-yl)ethyl]-2-(6-methoxypyridin-2-yl)pyrrolo[2,1-f][1,2,4]triazin-4-yl}-3-fluoropyridin-4-amine,
N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine,
1-[({2-[6-(difluoromethyl)pyridin-2-yl]-4-[(3-fluoropyridin-4-yl)amino]pyrrolo[2,1-f][1,2,4]triazin-5-yl}methyl)amino]-2-methylpropan-2-ol,
N-{4-[(5-{[(2-hydroxy-2-methylpropyl)amino]methyl}-2-(pyridin-2-yl)pyrrolo[2,1-f][1,2,4]triazin-4-yl)amino]pyridin-2-yl}acetamide,
1-[({4-[(3-fluoropyridin-4-yl)amino]-2-(6-methoxypyridin-2-yl)pyrrolo[2,1-f][1,2,4]triazin-5-yl}methyl)amino]-2-methylpropan-2-ol,
3-fluoro-N-[2-(6-methoxypyridin-2-yl)-5-({[2-(pyrrolidin-1-yl)ethyl]amino}methyl)pyrrolo[2,1-f][1,2,4]triazin-4-yl]pyridin-4-amine,
(3R)-3-fluoro-4-[({4-[(3-fluoropyridin-4-yl)amino]-2-(6-methoxypyridin-2-yl)pyrrolo[2,1-f][1,2,4]triazin-5-yl}methyl)amino]-2-methylbutan-2-ol,
3-fluoro-N-[2-(6-methoxypyridin-2-yl)-5-[(4-methylpiperazin-1-yl)methyl]pyrrolo[2,1-f][1,2,4]triazin-4-yl]pyridin-4-amine,
N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine,
N-{5-[(4,4-difluoropiperidin-1-yl)methyl]-2-[6-(trifluoromethyl)pyridin-2-yl]pyrrolo[2,1-f][1,2,4]triazin-4-yl}-3-fluoropyridin-4-amine,
1-[({4-[(3-fluoropyridin-4-yl)amino]-2-[6-(trifluoromethyl)pyridin-2-yl]pyrrolo[2,1-f][1,2,4]triazin-5-yl}methyl)amino]-2-methylpropan-2-ol,
1-[({4-[(3-fluoropyridin-4-yl)amino]-2-(pyridin-2-yl)pyrrolo[2,1-f][1,2,4]triazin-5-yl}methyl)amino]-2-methylpropan-2-ol,
(3R,4R)-4-amino-1-({4-[(3-fluoropyridin-4-yl)amino]-2-(pyridin-2-yl)pyrrolo[2,1-f][1,2,4]triazin-5-yl}methyl)piperidin-3-ol,
3-fluoro-N-{5-[(4-methylpiperazin-1-yl)methyl]-2-(pyridin-2-yl)pyrrolo[2,1-f][1,2,4]triazin-4-yl}pyridin-4-amine,
1-{4-[(3-fluoropyridin-4-yl)amino]-2-(6-methoxypyridin-2-yl)pyrrolo[2,1-f][1,2,4]triazin-5-yl}-2-(4-methylpiperazin-1-yl)ethan-1-ol,
2-(4,4-difluoropiperidin-1-yl)-1-{4-[(3-fluoropyridin-4-yl)amino]-2-(6-methoxypyridin-2-yl)pyrrolo[2,1-f][1,2,4]triazin-5-yl}ethan-1-ol,
1-{4-[(3-fluoropyridin-4-yl)amino]-2-(6-methoxypyridin-2-yl)pyrrolo[2,1-f][1,2,4]triazin-5-yl}-2-{[2-(piperidin-1-yl)ethyl]amino}ethan-1-ol,
4-{2-[(2-{4-[(3-fluoropyridin-4-yl)amino]-2-(6-methoxypyridin-2-yl)pyrrolo[2,1-f][1,2,4]triazin-5-yl}-2-hydroxyethyl)amino]ethyl}-1,4-thiomorpholine-1,1-dione,
1-{2-[(4-{[2-(6-methoxypyridin-2-yl)pyrrolo[2,1-f][1,2,4]triazin-4-yl]amino}pyridin-2-yl)amino]ethyl}piperidin-4-ol,
1-[(4-{[2-(6-methoxypyridin-2-yl)pyrrolo[2,1-f][1,2,4]triazin-4-yl]amino}pyridin-2-yl)amino]-2-methylpropan-2-ol,
4-[(4-{[2-(6-methoxypyridin-2-yl)pyrrolo[2,1-f][1,2,4]triazin-4-yl]amino}pyridin-2-yl)amino]-2-methylbutan-2-ol,
2-N-[3-(dimethylamino)propyl]-4-N-[2-(6-methoxypyridin-2-yl)pyrrolo[2,1-f][1,2,4]triazin-4-yl]pyridine-2,4-diamine,
1-{2-[(4-{[2-(6-methoxypyridin-2-yl)-5-methylpyrrolo[2,1-f][1,2,4]triazin-4-yl]amino}pyridin-2-yl)amino]ethyl}piperidin-4-ol,
4-N-[2-(6-methoxypyridin-2-yl)-5-methylpyrrolo[2,1-f][1,2,4]triazin-4-yl]-2-N-[2-(morpholin-4-yl)ethyl]pyridine-2,4-diamine,
1-[(4-{[2-(6-methoxypyridin-2-yl)-5-methylpyrrolo[2,1-f][1,2,4]triazin-4-yl]amino}pyridin-2-yl)amino]-2-methylpropan-2-ol,
4-N-[2-(6-methoxypyridin-2-yl)pyrrolo[2,1-f][1,2,4]triazin-4-yl]-2-N-[2-(morpholin-4-yl)ethyl]pyridine-2,4-diamine,
N-[3-(1,1-dioxo-1,4-thiomorpholin-4-yl)propyl]-4-{[2-(5-fluoro-6-methylpyridin-2-yl)pyrrolo[2,1-f][1,2,4]triazin-4-yl]amino}pyridine-3-carboxamide,
4-{[2-(5-fluoro-6-methylpyridin-2-yl)pyrrolo[2,1-f][1,2,4]triazin-4-yl]amino}-N-[2-(piperidin-1-yl)ethyl]pyridine-3-carboxamide, 4-{[2-(pyridin-2-yl)pyrrolo[2,1-f][1,2,4]triazin-4-yl]amino}-N-[2-(pyrrolidin-1-yl)ethyl]pyridine-3-carboxamide, N-[2-(diethylamino)ethyl]-4-{[2-(pyridin-2-yl)pyrrolo[2,1-f][1,2,4]triazin-4-yl]amino}pyridine-3-carboxamide, N-[2-(piperidin-1-yl)ethyl]-4-{[2-(pyridin-2-yl)pyrrolo[2,1-f][1,2,4]triazin-4-yl]amino}pyridine-3-carboxamide, tert-butyl 4-{2-[(4-{[2-(pyridin-2-yl)pyrrolo[2,1-f][1,2,4]triazin-4-yl]amino}pyridin-3-yl)formamido]ethyl}piperazine-1-carboxylate, N-{2-[cis-2,6-dimethylmorpholin-4-yl]ethyl}-4-{[2-(pyridin-2-yl)pyrrolo[2,1-f][1,2,4]triazin-4-yl]amino}pyridine-3-carboxamide, N-[2-(1,1-dioxo-1,4-thiomorpholin-4-yl)ethyl]-4-{[2-(pyridin-2-yl)pyrrolo[2,1-f][1,2,4]triazin-4-yl]amino}pyridine-3-carboxamide, N-[3-(1,1-dioxo-1,4-thiomorpholin-4-yl)propyl]-4-{[2-(pyridin-2-yl)pyrrolo[2,1-f][1,2,4]triazin-4-yl]amino}pyridine-3-carboxamide, N-[3-(2-oxopyrrolidin-1-yl)propyl]-4-{[2-(pyridin-2-yl)pyrrolo[2,1-f][1,2,4]triazin-4-yl]amino}pyridine-3-carboxamide, 4-{[2-(pyridin-2-yl)pyrrolo[2,1-f][1,2,4]triazin-4-yl]amino}-N-[3-(pyrrolidin-1-yl)propyl]pyridine-3-carboxamide, N-[2-(piperazin-1-yl)ethyl]-4-{[2-(pyridin-2-yl)pyrrolo[2,1-f][1,2,4]triazin-4-yl]amino}pyridine-3-carboxamide, 4-{[2-(6-methylpyridin-2-yl)pyrrolo[2,1-f][1,2,4]triazin-4-yl]amino}-N-[2-(pyrrolidin-1-yl)ethyl]pyridine-3-carboxamide, N-[2-(1,1-dioxo-1,4-thiomorpholin-4-yl)ethyl]-4-{[2-(6-methylpyridin-2-yl)pyrrolo[2,1-f][1,2,4]triazin-4-yl]amino}pyridine-3-carboxamide, N-[(4-hydroxy-1-methylpiperidin-4-yl)methyl]-4-{[2-(6-methylpyridin-2-yl)pyrrolo[2,1-f][1,2,4]triazin-4-yl]amino}pyridine-3-carboxamide, 4-{[2-(6-methylpyridin-2-yl)pyrrolo[2,1-f][1,2,4]triazin-4-yl]amino}-N-[2-(piperidin-1-yl)ethyl]pyridine-3-carboxamide, N-(2-hydroxy-2-methylpropyl)-4-{[2-(6-methylpyridin-2-yl)pyrrolo[2,1-f][1,2,4]triazin-4-yl]amino}pyridine-3-carboxamide, N-(1-hydroxy-2-methylpropan-2-yl)-4-{[2-(6-methylpyridin-2-yl)pyrrolo[2,1-f][1,2,4]triazin-4-yl]amino}pyridine-3-carboxamide, N-[(2S)-2,3-dihydroxypropyl]-4-{[2-(6-methylpyridin-2-yl)pyrrolo[2,1-f][1,2,4]triazin-4-yl]amino}pyridine-3-carboxamide, N-(3-hydroxypropyl)-4-{[2-(6-methylpyridin-2-yl)pyrrolo[2,1-f][1,2,4]triazin-4-yl]amino}pyridine-3-carboxamide, N-[3-(4-methylpiperazin-1-yl)propyl]-4-{[2-(6-methylpyridin-2-yl)pyrrolo[2,1-f][1,2,4]triazin-4-yl]amino}pyridine-3-carboxamide, 4-{[2-(6-methylpyridin-2-yl)pyrrolo[2,1-f][1,2,4]triazin-4-yl]amino}-N-(oxolan-3-yl)pyridine-3-carboxamide, N-[2-(dimethylamino)ethyl]-N-methyl-4-{[2-(6-methylpyridin-2-yl)pyrrolo[2,1-f][1,2,4]triazin-4-yl]amino}pyridine-3-carboxamide, N-[2-(6-methylpyridin-2-yl)pyrrolo[2,1-f][1,2,4]triazin-4-yl]-3-(morpholine-4-carbonyl)pyridin-4-amine, 4-{[2-(6-methylpyridin-2-yl)pyrrolo[2,1-f][1,2,4]triazin-4-yl]amino}-N-(oxan-4-yl)pyridine-3-carboxamide, 4-{[2-(6-methylpyridin-2-yl)pyrrolo[2,1-f][1,2,4]triazin-4-yl]amino)}-N-(oxetan-3-yl)pyridine-3-carboxamide, 4-{[2-(6-methylpyridin-2-yl)pyrrolo[2,1-f][1,2,4]triazin-4-yl]amino}-N-(propan-2-yl)pyridine-3-carboxamide, 4-({2-[6-(difluoromethyl)pyridin-2-yl]pyrrolo[2,1-f][1,2,4]triazin-4-yl}amino)-N-[2-(1,1-dioxo-1,4-thiomorpholin-4-yl)ethyl]pyridine-3-carboxamide, 4-({2-[6-(difluoromethyl)pyridin-2-yl]pyrrolo[2,1-f][1,2,4]triazin-4-yl}amino)-N-[3-(1,1-dioxo-1,4-thiomorpholin-4-yl)propyl]pyridine-3-carboxamide, N-[3-(morpholin-4-yl)propyl]-4-({2-[6-(trifluoromethyl)pyridin-2-yl]pyrrolo[2,1-f][1,2,4]triazin-4-yl}amino)pyridine-3-carboxamide, N-[2-(pyrrolidin-1-yl)ethyl]-4-({2-[6-(trifluoromethyl)pyridin-2-yl]pyrrolo[2,1-f][1,2,4]triazin-4-yl}amino)pyridine-3-carboxamide, N-[2-(piperidin-1-yl)ethyl]-4-({2-[6-(trifluoromethyl)pyridin-2-yl]pyrrolo[2,1-f][1,2,4]triazin-4-yl}amino)pyridine-3-carboxamide, 4-({2-[6-(difluoromethyl)pyridin-2-yl]pyrrolo[2,1-f][1,2,4]triazin-4-yl}amino)-N-(3-ethoxypropyl)pyridine-3-carboxamide, N-[2-(tert-butoxy)ethyl]-4-({2-[6-(difluoromethyl)pyridin-2-yl]pyrrolo[2,1-f][1,2,4]triazin-4-yl}amino)pyridine-3-carboxamide, 4-({2-[6-(difluoromethyl)pyridin-2-yl]pyrrolo[2,1-f][1,2,4]triazin-4-yl}amino)-N-[2-(2-hydroxyethoxy)ethyl]pyridine-3-carboxamide, 4-({2-[6-(difluoromethyl)pyridin-2-yl]pyrrolo[2,1-f][1,2,4]triazin-4-yl}amino)-N-[(1S,2S)-2-hydroxycyclohexyl]pyridine-3-carboxamide, 4-({2-[6-(difluoromethyl)pyridin-2-yl]pyrrolo[2,1-f][1,2,4]triazin-4-yl}amino)-N-[3-(4-methylpiperazin-1-yl)propyl]pyridine-3-carboxamide, 4-({2-[6-(difluoromethyl)pyridin-2-yl]pyrrolo[2,1-f][1,2,4]triazin-4-yl}amino)-N-(oxolan-3-yl)pyridine-3-carboxamide, 4-({2-[6-(difluoromethyl)pyridin-2-yl]pyrrolo[2,1-f][1,2,4]triazin-4-yl}amino)-N-(oxan-4-yl)pyridine-3-carboxamide, N-[2-(1,1-dioxo-1,4-thiomorpholin-4-yl)ethyl]-4-({2-[6-(trifluoromethyl)pyridin-2-yl]pyrrolo[2,1-f][1,2,4]triazin-4-yl}amino)pyridine-3-carboxamide, 4-({2-[6-(difluoromethyl)pyridin-2-yl]pyrrolo[2,1-f][1,2,4]triazin-4-yl}amino)-N-[(1R,2R)-2-hydroxycyclohexyl]pyridine-3-carboxamide, 4-({2-[6-(difluoromethyl)pyridin-2-yl]pyrrolo[2,1-f][1,2,4]triazin-4-yl}amino)-N-(pyridin-2-ylmethyl)pyridine-3-carboxamide, 4-({2-[6-(difluoromethyl)pyridin-2-yl]pyrrolo[2,1-f][1,2,4]triazin-4-yl}amino)-N-[(5-ethyl-1,3,4-oxadiazol-2-yl)methyl]pyridine-3-carboxamide, 4-({2-[6-(difluoromethyl)pyridin-2-yl]pyrrolo[2,1-f][1,2,4]triazin-4-yl}amino)-N-(1,3-thiazol-2-ylmethyl)pyridine-3-carboxamide, 4-({2-[6-(difluoromethyl)pyridin-2-yl]pyrrolo[2,1-f][1,2,4]triazin-4-yl}amino)-N-propylpyridine-3-carboxamide, 1-[4-({2-[6-(difluoromethyl)pyridin-2-yl]pyrrolo[2,1-f][1,2,4]triazin-4-yl}amino)pyridine-3-carbonyl]-4-phenylpiperidin-4-ol, N-{2-[6-(difluoromethyl)pyridin-2-yl]pyrrolo[2,1-f][1,2,4]triazin-4-yl}-3-(pyrrolidine-1-carbonyl)pyridin-4-amine, 4-({2-[6-(difluoromethyl)pyridin-2-yl]pyrrolo[2,1-f][1,2,4]triazin-4-yl}amino)-N-(3-hydroxy-3-methylbutyl)pyridine-3-carboxamide, 4-({2-[6-(difluoromethyl)pyridin-2-yl]pyrrolo[2,1-f][1,2,4]triazin-4-yl}amino)-N-(2-hydroxy-2-methylpropyl)pyridine-3-carboxamide, 3-(azetidine-1-carbonyl)-N-{2-[6-(difluoromethyl)pyridin-2-yl]pyrrolo[2,1-f][1,2,4]triazin-4-yl}pyridin-4-amine, Ethyl 2-{[4-({2-[6-(difluoromethyl)pyridin-2-yl]pyrrolo[2,1-f][1,2,4]triazin-4-yl}amino)pyridin-3-yl]formamido}acetate,
4-({2-[6-(difluoromethyl)pyridin-2-yl]pyrrolo[2,1-f][1,2,4]triazin-4-yl}amino)-N-(1H-1,2,4-triazol-3-ylmethyl)pyridine-3-carboxamide,
4-({2-[6-(difluoromethyl)pyridin-2-yl]pyrrolo[2,1-f][1,2,4]triazin-4-yl}amino)-N-(2-hydroxyethyl)pyridine-3-carboxamide,
N-cyclobutyl-4-({2-[6-(difluoromethyl)pyridin-2-yl]pyrrolo[2,1-f][1,2,4]triazin-4-yl}amino)pyridine-3-carboxamide,
4-({2-[6-(difluoromethyl)pyridin-2-yl]pyrrolo[2,1-f][1,2,4]triazin-4-yl}amino)-N-(propan-2-yl)pyridine-3-carboxamide,
4-({2-[6-(difluoromethyl)pyridin-2-yl]pyrrolo[2,1-f][1,2,4]triazin-4-yl}amino)-N-(1,3-oxazol-4-ylmethyl)pyridine-3-carboxamide,
tert-butyl 2-{[4-({2-[6-(difluoromethyl)pyridin-2-yl]pyrrolo[2,1-f][1,2,4]triazin-4-yl}amino)pyridin-3-yl]formamido}acetate,
4-({2-[6-(difluoromethyl)pyridin-2-yl]pyrrolo[2,1-f][1,2,4]triazin-4-yl}amino)-N-(1H-pyrazol-5-ylmethyl)pyridine-3-carboxamide,
4-({2-[6-(difluoromethyl)pyridin-2-yl]pyrrolo[2,1-f][1,2,4]triazin-4-yl}amino)-N-[(1R,2S)-2-hydroxycyclopentyl]pyridine-3-carboxamide,
4-({2-[6-(difluoromethyl)pyridin-2-yl]pyrrolo[2,1-f][1,2,4]triazin-4-yl}amino)-N-[(1S,2S)-2-hydroxycyclopentyl]pyridine-3-carboxamide,
1-[4-({2-[6-(difluoromethyl)pyridin-2-yl]pyrrolo[2,1-f][1,2,4]triazin-4-yl}amino)pyridine-3-carbonyl]piperidin-4-ol,
N-(4,4-difluorocyclohexyl)-4-({2-[6-(difluoromethyl)pyridin-2-yl]pyrrolo[2,1-f][1,2,4]triazin-4-yl}amino)pyridine-3-carboxamide,
4-({2-[6-(difluoromethyl)pyridin-2-yl]pyrrolo[2,1-f][1,2,4]triazin-4-yl}amino)-N-(3,3,3-trifluoropropyl)pyridine-3-carboxamide,
N-{2-[6-(difluoromethyl)pyridin-2-yl]pyrrolo[2,1-f][1,2,4]triazin-4-yl}-3-(4,4-difluoropiperidine-1-carbonyl)pyridin-4-amine,
Ethyl 3-{[4-({2-[6-(difluoromethyl)pyridin-2-yl]pyrrolo[2,1-f][1,2,4]triazin-4-yl}amino)pyridin-3-yl]formamido}propanoate,
4-({2-[6-(difluoromethyl)pyridin-2-yl]pyrrolo[2,1-f][1,2,4]triazin-4-yl}amino)-N-{[3-(methoxymethyl)-1,2,4-oxadiazol-5-yl]methyl}pyridine-3-carboxamide,
(4-{[2-(6-methoxypyridin-2-yl)pyrrolo[2,1-f][1,2,4]triazin-4-yl]amino}pyridin-3-yl)methanol,
1-[({4-[(3-fluoropyridin-4-yl)amino]-2-(6-methoxypyridin-2-yl)pyrrolo[2,1-f][1,2,4]triazin-6-yl}methyl)amino]-2-methylpropan-2-ol,
(3R)-3-fluoro-4-[({4-[(3-fluoropyridin-4-yl)amino]-2-(6-methoxypyridin-2-yl)pyrrolo[2,1-f][1,2,4]triazin-6-yl}methyl)amino]-2-methylbutan-2-ol,
4-{3-[({4-[(3-fluoropyridin-4-yl)amino]-2-(6-methoxypyridin-2-yl)pyrrolo[2,1-f][1,2,4]triazin-6-yl}methyl)amino]propyl}-1,4-thiomorpholine-1,1-dione,
N-[6-ethenyl-2-(6-methoxypyridin-2-yl)pyrrolo[2,1-f][1,2,4]triazin-4-yl]-3-fluoropyridin-4-amine,
(3E)-4-{4-[(3-fluoropyridin-4-yl)amino]-2-(6-methoxypyridin-2-yl)pyrrolo[2,1-f][1,2,4]triazin-6-yl}but-3-en-1-ol,
N-(4-{[2-(6-methoxypyridin-2-yl)pyrrolo[2,1-f][1,2,4]triazin-4-yl]amino}pyridin-3-yl)-2-(morpholin-4-yl)acetamide,
N-[2-(6-fluoropyridin-2-yl)pyrrolo[2,1-f][1,2,4]triazin-4-yl]pyridin-4-amine,
N-[2-(6-methoxypyridin-2-yl)pyrrolo[2,1-f][1,2,4]triazin-4-yl]pyridin-4-amine,
N-{2-[2-(methylsulfanyl)pyrimidin-4-yl]pyrrolo[2,1-f][1,2,4]triazin-4-yl}pyridin-4-amine,
Ethyl 2-(6-methylpyridin-2-yl)-4-[(pyridin-4-yl)amino]pyrrolo[2,1-f][1,2,4]triazine-6-carboxylate,
2-(6-methylpyridin-2-yl)-N-phenyl-4-[(pyridin-4-yl)amino]pyrrolo[2,1-f][1,2,4]triazine-6-carboxamide,
N,N-dimethyl-2-(6-methylpyridin-2-yl)-4-[(pyridin-4-yl)amino]pyrrolo[2,1-f][1,2,4]triazine-6-carboxamide,
2-(6-methylpyridin-2-yl)-4-[(pyridin-4-yl)amino]pyrrolo[2,1-f][1,2,4]triazine-6-carboxamide,
N-methyl-2-(6-methylpyridin-2-yl)-4-[(pyridin-4-yl)amino]pyrrolo[2,1-f][1,2,4]triazine-6-carboxamide,
4-{[2-(6-methylpyridin-2-yl)pyrrolo[2,1-f][1,2,4]triazin-4-yl]amino}-N-[3-(pyrrolidin-1-yl)propyl]pyridine-3-carboxamide,
N-[2-(6-methylpyridin-2-yl)pyrrolo[2,1-f][1,2,4]triazin-4-yl]-3-[3-(morpholin-4-yl)propoxy]pyridin-4-amine,
4-({2-[6-(difluoromethyl)-5-fluoropyridin-2-yl]pyrrolo[2,1-f][1,2,4]triazin-4-yl}amino)pyridine-3-carboxamide,
N-[4-({2-[6-(difluoromethyl)pyridin-2-yl]pyrrolo[2,1-f][1,2,4]triazin-4-yl}amino)-5-fluoropyridin-2-yl]acetamide,
N-[5-fluoro-4-({2-[6-(trifluoromethyl)pyridin-2-yl]pyrrolo[2,1-f][1,2,4]triazin-4-yl}amino)pyridin-2-yl]acetamide,
N-(4-{[2-(5-fluoropyridin-2-yl)pyrrolo[2,1-f][1,2,4]triazin-4-yl]amino}pyridin-2-yl)acetamide,
4-({2-[6-(difluoromethyl)pyridin-2-yl]pyrrolo[2,1-f][1,2,4]triazin-4-yl}amino)pyridine-3-carboxamide,
N-[4-({2-[6-(difluoromethyl)pyridin-2-yl]pyrrolo[2,1-f][1,2,4]triazin-4-yl}amino)-3-fluoropyridin-2-yl]acetamide,
2-(1H-pyrazol-3-yl)-N-{2-[6-(trifluoromethyl)pyridin-2-yl]pyrrolo[2,1-f][1,2,4]triazin-4-yl}pyridin-4-amine,
2-[4-({4-[(3-fluoropyridin-4-yl)amino]-2-(pyridin-2-yl)pyrrolo[2,1-f][1,2,4]triazin-5-yl}methyl)piperazin-1-yl]ethan-1-ol,
(3S)-1-({4-[(3-fluoropyridin-4-yl)amino]-2-(pyridin-2-yl)pyrrolo[2,1-f][1,2,4]triazin-5-yl}methyl)pyrrolidin-3-ol,
(3R)-1-({4-[(3-fluoropyridin-4-yl)amino]-2-(pyridin-2-yl)pyrrolo[2,1-f][1,2,4]triazin-5-yl}methyl)pyrrolidin-3-ol,
3-fluoro-N-[2-(5-fluoropyridin-2-yl)-5-[(4-methylpiperazin-1-yl)methyl]pyrrolo[2,1-f][1,2,4]triazin-4-yl]pyridin-4-amine,
1-({[2-(5-fluoropyridin-2-yl)-4-[(3-fluoropyridin-4-yl)amino]pyrrolo[2,1-f][1,2,4]triazin-5-yl]methyl}amino)-2-methylpropan-2-ol,
4-[({4-[(3-fluoropyridin-4-yl)amino]-2-(pyridin-2-yl)pyrrolo[2,1-f][1,2,4]triazin-5-yl}methyl)amino]cyclohexan-1-ol,
(5R,7S)-3-[({4-[(3-fluoropyridin-4-yl)amino]-2-(pyridin-2-yl)pyrrolo[2,1-f][1,2,4]triazin-5-yl}methyl)amino]adamantan-1-ol,
3-fluoro-N-(5-{[(piperidin-4-ylmethyl)amino]methyl}-2-(pyridin-2-yl)pyrrolo[2,1-f][1,2,4]triazin-4-yl)pyridin-4-amine,
1-[({4-[(3-fluoropyridin-4-yl)amino]-2-(pyridin-2-yl)pyrrolo[2,1-f][1,2,4]triazin-5-yl}methyl)amino]propan-2-ol,
1-{2-[({4-[(3-fluoropyridin-4-yl)amino]-2-(pyridin-2-yl)pyrrolo[2,1-f][1,2,4]triazin-5-yl}methyl)amino]ethyl}cyclopentan-1-ol,
3-fluoro-N-(5-{[(1-methyl cyclobutyl)amino]methyl}-2-(pyridin-2-yl)pyrrolo[2,1-f][1,2,4]triazin-4-yl)pyridin-4-amine,
3-fluoro-N-(5-{[(4-methyloxan-4-yl)amino]methyl}-2-(pyridin-2-yl)pyrrolo[2,1-f][1,2,4]triazin-4-yl)pyridin-4-amine,
1-({4-[(3-fluoropyridin-4-yl)amino]-2-(pyridin-2-yl)pyrrolo[2,1-f][1,2,4]triazin-5-yl}methyl)piperidin-4-ol, {1-[({4-[(3-fluoropyridin-4-yl)amino]-2-(pyridin-2-yl)pyrrolo[2,1-f][1,2,4]triazin-5-yl}methyl)amino]cyclopentyl}methanol, 4-N-({4-[(3-fluoropyridin-4-yl)amino]-2-(pyridin-2-yl)pyrrolo[2,1-f][1,2,4]triazin-5-yl}methyl)-1-N,1-N-dimethylcyclohexane-1,4-diamine, 3-fluoro-N-[5-({[3-(morpholin-4-yl)propyl]amino}methyl)-2-(pyridin-2-yl)pyrrolo[2,1-f][1,2,4]triazin-4-yl]pyridin-4-amine, 3-fluoro-N-(5-{[(oxolan-2-ylmethyl)amino]methyl}-2-(pyridin-2-yl)pyrrolo[2,1-f][1,2,4]triazin-4-yl)pyridin-4-amine, 3-fluoro-N-{2-[5-(trifluoromethyl)pyridin-2-yl]pyrrolo[2,1-f][1,2,4]triazin-4-yl}pyridin-4-amine, 3-fluoro-N-[2-(2-methoxy-1,3-thiazol-4-yl)pyrrolo[2,1-f][1,2,4]triazin-4-yl]pyridin-4-amine, N-{4-[(5-{[4-(2-hydroxyethyl)piperazin-1-yl]methyl}-2-(pyridin-2-yl)pyrrolo[2,1-f][1,2,4]triazin-4-yl)amino]pyridin-2-yl}acetamide, (3S)-1-({2-[6-(difluoromethyl)pyridin-2-yl]-4-[(3-fluoropyridin-4-yl)amino]pyrrolo[2,1-f][1,2,4]triazin-5-yl}methyl)pyrrolidin-3-ol, (3S)-1-({4-[(3-fluoropyridin-4-yl)amino]-2-(6-methylpyridin-2-yl)pyrrolo[2,1-f][1,2,4]triazin-5-yl}methyl)pyrrolidin-3-ol, 2-[4-({2-[6-(difluoromethyl)pyridin-2-yl]-4-[(3-fluoropyridin-4-yl)amino]pyrrolo[2,1-f][1,2,4]triazin-5-yl}methyl)piperazin-1-yl]ethan-1-ol, N-{4-[(5-{[(2-hydroxy-2-methylpropyl)amino]methyl}-2-[6-(trifluoromethyl)pyridin-2-yl]pyrrolo[2,1-f][1,2,4]triazin-4-yl)amino]pyridin-2-yl}acetamide, N-{2-[6-(trifluoromethyl)pyridin-2-yl]pyrrolo[2,1-f][1,2,4]triazin-4-yl}pyrimidin-4-amine, 2-fluoro-N-{2-[6-(trifluoromethyl)pyridin-2-yl]pyrrolo[2,1-f][1,2,4]triazin-4-yl}pyridin-4-amine, 2-methyl-N-{2-[6-(trifluoromethyl)pyridin-2-yl]pyrrolo[2,1-f][1,2,4]triazin-4-yl}pyridin-4-amine, 1-{[(4-{[2-(ethylamino)pyridin-4-yl]amino}-2-(pyridin-2-yl)pyrrolo[2,1-f][1,2,4]triazin-5-yl)methyl]amino}-2-methylpropan-2-ol, 2-[4-({4-[(3-fluoropyridin-4-yl)amino]-2-(6-methylpyridin-2-yl)pyrrolo[2,1-f][1,2,4]triazin-5-yl}methyl)piperazin-1-yl]ethan-1-ol, 3-fluoro-N-[2-(3-fluoropyridin-2-yl)pyrrolo[2,1-f][1,2,4]triazin-4-yl]pyridin-4-amine, 3-fluoro-N-[2-(3-fluoro-6-methylpyridin-2-yl)pyrrolo[2,1-f][1,2,4]triazin-4-yl]pyridin-4-amine, 3-fluoro-N-[2-(1,3-thiazol-4-yl)pyrrolo[2,1-f][1,2,4]triazin-4-yl]pyridin-4-amine, (1R,4R)-1-N-({4-[(3-fluoropyridin-4-yl)amino]-2-(pyridin-2-yl)pyrrolo[2,1-f][1,2,4]triazin-5-yl}methyl)cyclohexane-1,4-diamine, 2-[({4-[(3-fluoropyridin-4-yl)amino]-2-(pyridin-2-yl)pyrrolo[2,1-f][1,2,4]triazin-5-yl}methyl)amino]propane-1,3-diol, 3-fluoro-N-(5-{[(piperidin-2-ylmethyl)amino]methyl}-2-(pyridin-2-yl)pyrrolo[2,1-f][1,2,4]triazin-4-yl)pyridin-4-amine, N-(5-{[(azetidin-3-ylmethyl)amino]methyl}-2-(pyridin-2-yl)pyrrolo[2,1-f][1,2,4]triazin-4-yl)-3-fluoropyridin-4-amine, 3-fluoro-N-(5-{[(piperidin-3-yl)amino]methyl}-2-(pyridin-2-yl)pyrrolo[2,1-f][1,2,4]triazin-4-yl)pyridin-4-amine, 3-fluoro-N-[2-(pyridin-2-yl)-5-{[(2,2,2-trifluoroethyl)amino]methyl}pyrrolo[2,1-f][1,2,4]triazin-4-yl]pyridin-4-amine, 3-fluoro-N-[5-({[2-(piperazin-1-yl)ethyl]amino}methyl)-2-(pyridin-2-yl)pyrrolo[2,1-f][1,2,4]triazin-4-yl]pyridin-4-amine, 3-fluoro-N-[2-(pyridin-2-yl)-5-({[2-(pyrrolidin-2-yl)ethyl]amino}methyl)pyrrolo[2,1-f][1,2,4]triazin-4-yl]pyridin-4-amine, N-(5-{[(cyclobutylmethyl)amino]methyl}-2-(pyridin-2-yl)pyrrolo[2,1-f][1,2,4]triazin-4-yl)-3-fluoropyridin-4-amine, 2-[({4-[(3-fluoropyridin-4-yl)amino]-2-(pyridin-2-yl)pyrrolo[2,1-f][1,2,4]triazin-5-yl}methyl)amino]cyclohexan-1-ol, (2S)-2-[({4-[(3-fluoropyridin-4-yl)amino]-2-(pyridin-2-yl)pyrrolo[2,1-f][1,2,4]triazin-5-yl}methyl)amino]pentan-1-ol, 4-[({4-[(3-fluoropyridin-4-yl)amino]-2-(pyridin-2-yl)pyrrolo[2,1-f][1,2,4]triazin-5-yl}methyl)amino]butan-2-ol, 3-[4-({4-[(3-fluoropyridin-4-yl)amino]-2-(pyridin-2-yl)pyrrolo[2,1-f][1,2,4]triazin-5-yl}methyl)piperazin-1-yl]phenol, 3-fluoro-N-[2-(pyridin-2-yl)-5-{[4-(pyrimidin-2-yl)piperazin-1-yl]methyl}pyrrolo[2,1-f][1,2,4]triazin-4-yl]pyridin-4-amine, 1-({4-[(3-fluoropyridin-4-yl)amino]-2-(pyridin-2-yl)pyrrolo[2,1-f][1,2,4]triazin-5-yl}methyl)-4-phenylpiperidin-4-ol, 1-[1-({4-[(3-fluoropyridin-4-yl)amino]-2-(pyridin-2-yl)pyrrolo[2,1-f][1,2,4]triazin-5-yl}methyl)piperidin-4-yl]-2,3-dihydro-1H-1,3-benzodiazol-2-one, 3-fluoro-N-(5-{[methyl(1-methylpiperidin-4-yl)amino]methyl}-2-(pyridin-2-yl)pyrrolo[2,1-f][1,2,4]triazin-4-yl)pyridin-4-amine, N-[5-({[2-(dimethylamino)ethyl]amino}methyl)-2-(pyridin-2-yl)pyrrolo[2,1-f][1,2,4]triazin-4-yl]-3-fluoropyridin-4-amine, 3-fluoro-N-[5-({[3-(1H-imidazol-1-yl)propyl]amino}methyl)-2-(pyridin-2-yl)pyrrolo[2,1-f][1,2,4]triazin-4-yl]pyridin-4-amine, N-(5-{[(adamantan-1-yl)amino]methyl}-2-(pyridin-2-yl)pyrrolo[2,1-f][1,2,4]triazin-4-yl)-3-fluoropyridin-4-amine, 3-fluoro-N-[5-({[3-(4-methylpiperazin-1-yl)propyl]amino}methyl)-2-(pyridin-2-yl)pyrrolo[2,1-f][1,2,4]triazin-4-yl]pyridin-4-amine, 3-fluoro-N-[5-({[2-(piperidin-1-yl)ethyl]amino}methyl)-2-(pyridin-2-yl)pyrrolo[2,1-f][1,2,4]triazin-4-yl]pyridin-4-amine, N-[5-({[(3S)-1-benzylpyrrolidin-3-yl]amino}methyl)-2-(pyridin-2-yl)pyrrolo[2,1-f][1,2,4]triazin-4-yl]-3-fluoropyridin-4-amine, N-(5-{[(3-aminopropyl)amino]methyl}-2-(pyridin-2-yl)pyrrolo[2,1-f][1,2,4]triazin-4-yl)-3-fluoropyridin-4-amine, (2S)-3-[({4-[(3-fluoropyridin-4-yl)amino]-2-(pyridin-2-yl)pyrrolo[2,1-f][1,2,4]triazin-5-yl}methyl)amino]propane-1,2-diol, (1R,4R)-4-[({4-[(3-fluoropyridin-4-yl)amino]-2-(pyridin-2-yl)pyrrolo[2,1-f][1,2,4]triazin-5-yl}methyl)amino]cyclohexan-1-ol, 3-fluoro-N-{2-[6-(trifluoromethoxy)pyridin-2-yl]pyrrolo[2,1-f][1,2,4]triazin-4-yl}pyridin-4-amine, 3-fluoro-N-[5-(morpholin-4-ylmethyl)-2-(pyridin-2-yl)pyrrolo[2,1-f][1,2,4]triazin-4-yl]pyridin-4-amine, N-(4-{[2-(6-fluoropyridin-2-yl)pyrrolo[2,1-f][1,2,4]triazin-4-yl]amino}pyridin-2-yl)acetamide, 4-({2-[6-(trifluoromethyl)pyridin-2-yl]pyrrolo[2,1-f][1,2,4]triazin-4-yl}amino)pyridine-2-carbonitrile, N-(4-{[5-(morpholin-4-ylmethyl)-2-(pyridin-2-yl)pyrrolo[2,1-f][1,2,4]triazin-4-yl]amino}pyridin-2-yl)acetamide,
N-(5-{[(2H-1,3-benzodioxol-5-ylmethyl)amino]methyl}-2-(pyridin-2-yl)pyrrolo[2,1-f][1,2,4]triazin-4-yl)-3-fluoropyridin-4-amine,
N-({4-[(3-fluoropyridin-4-yl)amino]-2-(pyridin-2-yl)pyrrolo[2,1-f][1,2,4]triazin-5-yl}methyl)-2-methyl-1,3-benzothiazol-6-amine,
(3-{[({4-[(3-fluoropyridin-4-yl)amino]-2-(pyridin-2-yl)pyrrolo[2,1-f][1,2,4]triazin-5-yl}methyl)amino]methyl}oxetan-3-yl)methanol,
3-fluoro-N-[5-({[4-(1,3-oxazol-5-yl)phenyl]amino}methyl)-2-(pyridin-2-yl)pyrrolo[2,1-f][1,2,4]triazin-4-yl]pyridin-4-amine,
3-fluoro-N-(5-{[(5-phenyl-1H-pyrazol-3-yl)amino]methyl}-2-(pyridin-2-yl)pyrrolo[2,1-f][1,2,4]triazin-4-yl)pyridin-4-amine,
3-fluoro-N-(5-{[(morpholin-2-ylmethyl)amino]methyl}-2-(pyridin-2-yl)pyrrolo[2,1-f][1,2,4]triazin-4-yl)pyridin-4-amine,
N-[5-({[(2R)-3,3-dimethylbutan-2-yl]amino}methyl)-2-(pyridin-2-yl)pyrrolo[2,1-f][1,2,4]triazin-4-yl]-3-fluoropyridin-4-amine,
3-fluoro-N-[2-(pyridin-2-yl)-5-({[2-(pyridin-2-yl)propan-2-yl]amino}methyl)pyrrolo[2,1-f][1,2,4]triazin-4-yl]pyridin-4-amine,
3-fluoro-N-[5-({[1-(propan-2-yl)-1H-pyrazol-4-yl]amino}methyl)-2-(pyridin-2-yl)pyrrolo[2,1-f][1,2,4]triazin-4-yl]pyridin-4-amine,
3-fluoro-N-[5-({[2-(1-methylpiperidin-4-yl)ethyl]amino}methyl)-2-(pyridin-2-yl)pyrrolo[2,1-f][1,2,4]triazin-4-yl]pyridin-4-amine,
3-fluoro-N-[2-(pyridin-2-yl)-5-({[2-(pyridin-2-yl)ethyl]amino}methyl)pyrrolo[2,1-f][1,2,4]triazin-4-yl]pyridin-4-amine,
3-fluoro-N-[5-({[(5-methylpyrazin-2-yl)methyl]amino}methyl)-2-(pyridin-2-yl)pyrrolo[2,1-f][1,2,4]triazin-4-yl]pyridin-4-amine,
N-({4-[(3-fluoropyridin-4-yl)amino]-2-(pyridin-2-yl)pyrrolo[2,1-f][1,2,4]triazin-5-yl}methyl)-1H-1,2,3-benzotriazol-5-amine,
3-fluoro-N-(5-{[(piperidin-4-yl)amino]methyl}-2-(pyridin-2-yl)pyrrolo[2,1-f][1,2,4]triazin-4-yl)pyridin-4-amine,
3-fluoro-N-(5-{[(5-methyl-1,3,4-thiadiazol-2-yl)amino]methyl}-2-(pyridin-2-yl)pyrrolo[2,1-f][1,2,4]triazin-4-yl)pyridin-4-amine,
(3S,4S)-4-amino-1-({4-[(3-fluoropyridin-4-yl)amino]-2-(pyridin-2-yl)pyrrolo[2,1-f][1,2,4]triazin-5-yl}methyl)piperidin-3-ol,
(1R)-2-[({4-[(3-fluoropyridin-4-yl)amino]-2-(pyridin-2-yl)pyrrolo[2,1-f][1,2,4]triazin-5-yl}methyl)amino]-1-phenylethan-1-ol,
N-(5-{[(azetidin-3-yl)amino]methyl}-2-(pyridin-2-yl)pyrrolo[2,1-f][1,2,4]triazin-4-yl)-3-fluoropyridin-4-amine,
Methyl N-[4-({2-[6-(trifluoromethyl)pyridin-2-yl]pyrrolo[2,1-f][1,2,4]triazin-4-yl}amino)pyridin-2-yl]carbamate,
N-[4-({2-[6-(trifluoromethyl)pyridin-2-yl]pyrrolo[2,1-f][1,2,4]triazin-4-yl}amino)pyridin-2-yl]propanamide,
3-methyl-N-[4-({2-[6-(trifluoromethyl)pyridin-2-yl]pyrrolo[2,1-f][1,2,4]triazin-4-yl}amino)pyridin-2-yl]butanamide,
4-({2-[6-(trifluoromethyl)pyridin-2-yl]pyrrolo[2,1-f][1,2,4]triazin-4-yl}amino)pyridine-2-carboxamide,
2-(4-methylpiperazin-1-yl)-N-[4-({2-[6-(trifluoromethyl)pyridin-2-yl]pyrrolo[2,1-f][1,2,4]triazin-4-yl}amino)pyridin-2-yl]acetamide,
2-chloro-5-fluoro-N-[2-(5-fluoropyridin-2-yl)pyrrolo[2,1-f][1,2,4]triazin-4-yl]pyridin-4-amine,
N-[4-({2-[6-(trifluoromethyl)pyridin-2-yl]pyrrolo[2,1-f][1,2,4]triazin-4-yl}amino)pyridin-2-yl]methanesulfonamide,
2-[4-(2-hydroxyethyl)piperazin-1-yl]-N-[4-({2-[6-(trifluoromethyl)pyridin-2-yl]pyrrolo[2,1-f][1,2,4]triazin-4-yl}amino)pyridin-2-yl]acetamide,
2-(4-acetylpiperazin-1-yl)-N-[4-({2-[6-(trifluoromethyl)pyridin-2-yl]pyrrolo[2,1-f][1,2,4]triazin-4-yl}amino)pyridin-2-yl]acetamide,
3,3-dimethyl-N-[4-({2-[6-(trifluoromethyl)pyridin-2-yl]pyrrolo[2,1-f][1,2,4]triazin-4-yl}amino)pyridin-2-yl]butanamide,
2-(piperazin-1-yl)-N-[4-({2-[6-(trifluoromethyl)pyridin-2-yl]pyrrolo[2,1-f][1,2,4]triazin-4-yl}amino)pyridin-2-yl]acetamide,
N-(5-fluoro-4-{[2-(5-fluoropyridin-2-yl)pyrrolo[2,1-f][1,2,4]triazin-4-yl]amino}pyridin-2-yl)acetamide,
N-(2-hydroxy-2-methylpropyl)-4-({2-[6-(trifluoromethyl)pyridin-2-yl]pyrrolo[2,1-f][1,2,4]triazin-4-yl}amino)pyridine-2-carboxamide,
2-[(3S)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide,
(2S)—N-[4-({2-[6-(trifluoromethyl)pyridin-2-yl]pyrrolo[2,1-f][1,2,4]triazin-4-yl}amino)pyridin-2-yl]pyrrolidine-2-carboxamide,
2-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide,
3-fluoro-N-(5-{[(1-methylpiperidin-4-yl)oxy]methyl}-2-(pyridin-2-yl)pyrrolo[2,1-f][1,2,4]triazin-4-yl)pyridin-4-amine,
2-(piperidin-1-yl)-N-[4-({2-[6-(trifluoromethyl)pyridin-2-yl]pyrrolo[2,1-f][1,2,4]triazin-4-yl}amino)pyridin-2-yl]acetamide,
2-[(2-hydroxy-2-methylpropyl)amino]-N-[4-({2-[6-(trifluoromethyl)pyridin-2-yl]pyrrolo[2,1-f][1,2,4]triazin-4-yl}amino)pyridin-2-yl]acetamide,
2-(morpholin-4-yl)-N-[4-({2-[6-(trifluoromethyl)pyridin-2-yl]pyrrolo[2,1-f][1,2,4]triazin-4-yl}amino)pyridin-2-yl]acetamide,
N-[4-({2-[5-(trifluoromethyl)pyridin-2-yl]pyrrolo[2,1-f][1,2,4]triazin-4-yl}amino)pyridin-2-yl]acetamide,
N-(5-fluoro-4-{[2-(5-fluoro-6-methylpyridin-2-yl)pyrrolo[2,1-f][1,2,4]triazin-4-yl]amino}pyridin-2-yl)acetamide,
3-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]propanamide,
N-[4-({2-[6-(trifluoromethyl)pyridin-2-yl]pyrrolo[2,1-f][1,2,4]triazin-4-yl}amino)pyridin-2-yl]cyclopropanecarboxamide,
2-methoxy-N-[4-({2-[6-(trifluoromethyl)pyridin-2-yl]pyrrolo[2,1-f][1,2,4]triazin-4-yl}amino)pyridin-2-yl]acetamide,
4,4,4-trifluoro-N-[4-({2-[6-(trifluoromethyl)pyridin-2-yl]pyrrolo[2,1-f][1,2,4]triazin-4-yl}amino)pyridin-2-yl]butanamide,
3-cyano-N-[4-({2-[6-(trifluoromethyl)pyridin-2-yl]pyrrolo[2,1-f][1,2,4]triazin-4-yl}amino)pyridin-2-yl]propanamide,
N-(5-fluoro-4-{[2-(6-fluoropyridin-2-yl)pyrrolo[2,1-f][1,2,4]triazin-4-yl]amino}pyridin-2-yl)acetamide,
3-(4-hydroxypiperidin-1-yl)-N-[4-({2-[6-(trifluoromethyl)pyridin-2-yl]pyrrolo[2,1-f][1,2,4]triazin-4-yl}amino)pyridin-2-yl]propanamide, 3-(3,3-difluoroazetidin-1-yl)-N-[4-({2-[6-(trifluoromethyl)pyridin-2-yl]pyrrolo[2,1-f][1,2,4]triazin-4-yl}amino)pyridin-2-yl]propanamide, 2,2-dimethyl-N-[4-({2-[6-(trifluoromethyl)pyridin-2-yl]pyrrolo[2,1-f][1,2,4]triazin-4-yl}amino)pyridin-2-yl]propanamide, 3-methoxy-N-[4-({2-[6-(trifluoromethyl)pyridin-2-yl]pyrrolo[2,1-f][1,2,4]triazin-4-yl}amino)pyridin-2-yl]propanamide, 3,3,3-trifluoro-N-[4-({2-[6-(trifluoromethyl)pyridin-2-yl]pyrrolo[2,1-f][1,2,4]triazin-4-yl}amino)pyridin-2-yl]propanamide, N-(4-{[2-(5-fluoro-6-methylpyridin-2-yl)pyrrolo[2,1-f][1,2,4]triazin-4-yl]amino}pyridin-2-yl)cyclopropanecarboxamide, or a pharmaceutically acceptable salt, tautomer or stereoisomer thereof.

II. Other Embodiments of the Invention

In another embodiment, the invention provides a pharmaceutical composition, comprising a pharmaceutically acceptable carrier and a therapeutically effective amount of at least one of the compounds of the invention or a stereoisomer, a tautomer, a pharmaceutically acceptable salt, or a solvate thereof.

In another embodiment, the invention provides a process for making a compound of the invention or a stereoisomer, a tautomer, a pharmaceutically acceptable salt, or a solvate thereof.

In another embodiment, the invention provides a method for the treatment and/or prophylaxis of various types of cancer, comprising administering to a patient in need of such treatment and/or prophylaxis a therapeutically effective amount of one or more compounds of the invention, alone, or, optionally, in combination with another compound of the invention and/or at least one other type of therapeutic agent.

In another embodiment, the invention provides a method for the treatment and/or prophylaxis of various types of cancer, including without limitation, small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In another embodiment, the invention provides a method for the treatment and/or prophylaxis of various types of cancer, including without limitation, small cell lung cancer, non-small cell lung cancer, triple-negative breast cancer, colorectal cancer, prostate cancer, melanoma, pancreatic cancer, multiple myeloma, T-acute lymphoblastic leukemia or AML.

In another embodiment, the invention provides a method for the treatment and/or prophylaxis of Marfan's syndrome and associated diseases, disorders and conditions associated with aberrant TGF-β expression.

In another embodiment, the invention provides a method for the treatment and/or prophylaxis of fibrosis such as hepatic or pulmonary fibrosis.

In another embodiment, the invention provides a compound of the present invention for use in therapy.

In another embodiment, the invention provides a combined preparation of a compound of the present invention and additional therapeutic agent(s) for simultaneous, separate or sequential use in therapy.

III. Therapeutic Applications

The compounds of formula (I) of the invention are TGFβR antagonists and have potential utility in the treatment of diseases and conditions for which a TGFβR antagonist is indicated.

In one embodiment there is provided a method for the treatment of a disease or condition, for which a TGFβR antagonists is indicated, in a subject in need thereof which comprises administering a therapeutically effective amount of compound of formula (I) or a pharmaceutically acceptable salt thereof.

In another embodiment there is provided a method for treatment of a chronic autoimmune and/or inflammatory condition, in a subject in need thereof which comprises administering a therapeutically effective amount of one or more compounds of formula (I) or a pharmaceutically acceptable salt thereof.

In a further embodiment there is provided a method for treatment of cancer in a subject in need thereof which comprises administering a therapeutically effective amount of one or more compounds of formula (I) or a pharmaceutically acceptable salt thereof.

In one embodiment the subject in need thereof is a mammal, particularly a human.

TGFβR antagonists are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

TGFβR antagonists may be useful in the treatment of fibrotic conditions such as idiopathic pulmonary fibrosis, renal fibrosis, post-operative stricture, keloid formation, scleroderma and cardiac fibrosis.

TGFβR antagonists may be useful in the treatment of cancer, including hematological, epithelial including lung, breast and colon carcinomas, midline carcinomas, mesenchymal, hepatic, renal and neurological tumours.

The term "diseases or conditions for which a TGFβR antagonists is indicated" is intended to include any of or all of the above disease states.

While it is possible that for use in therapy, a compound of formula (I) as well as pharmaceutically acceptable salts thereof may be administered as the compound itself, it is more commonly presented as a pharmaceutical composition.

Pharmaceutical compositions may be presented in unit dose forms containing a predetermined amount of active ingredient pep unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Compounds of the invention are useful for the treatment of certain types of cancer by themselves or in combination or co-administration with other therapeutic agents or radiation therapy. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

Further provided herein are methods of treatment wherein compounds of the invention are administered with one or more immuno-oncology agents. The immuno-oncology agents used herein, also known as cancer immunotherapies, are effective to enhance, stimulate, and/or up-regulate immune responses in a subject. In one aspect, the administration of a compound of the invention with an immuno-oncology agent has a synergic effect in inhibiting tumor growth.

In one aspect, the compound(s) of the invention are sequentially administered prior to administration of the immuno-oncology agent. In another aspect, compound(s) of the invention are administered concurrently with the immunology-oncology agent. In yet another aspect, compound(s) of the invention are sequentially administered after administration of the immuno-oncology agent.

In another aspect, compounds of the invention may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, the immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In one aspect, T cell responses can be stimulated by a combination of a compound of the invention and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of the invention for the treatment of cancer include antagonists of inhibitory receptors on NK cells or agonists of activating receptors on NK cells. For example, compounds of the invention can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of the invention can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the patient being treated and the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof, (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

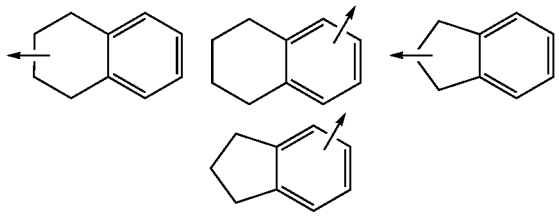

Arrowed lines drawn from the ring system indicate that the bond may be attached to any of the suitable ring atoms.

The term "benzyl," as used herein, refers to a methyl group on which one of the hydrogen atoms is replaced by a phenyl group.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of"cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O-heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy,* $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J (Editor). *Prodrugs and Targeted Delivery (Methods and Principles in Medicinal Chemistry*), Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabo-* lism. *Chemistry, Biochemistry and Enzymology*, VCHA and Wiley-VCH, Zurich, Switzerland (2003); Wermuth, C. G., ed., *The Practice of Medicinal Chemistry*, 3$^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H (hydrogen), $^2$H (deuterium) and $^3$H (tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being affected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Compounds of Formula (I) may be prepared by reference to the methods illustrated in the following Schemes. As shown therein the end product is a compound having the same structural formula as Formula (I). It will be understood that any compound of Formula (I) may be produced by the schemes by the suitable selection of reagents with appropriate substitution. Solvents, temperatures, pressures, and other reaction conditions may readily be selected by one of ordinary skill in the art. Starting materials are commercially available or readily prepared by one of ordinary skill in the art. Constituents of compounds are as defined herein or elsewhere in the specification.

The synthesis of the compounds of Formula (I) can be made using the methods summarized in Schemes A to G.

Compounds of general formula A can be prepared according to the method outlined in Scheme A. Selective displacement of the chlorine atom at the 4 position with amine nucleophiles can afford monochloro intermediate A2. Palladium mediated coupling of monochloro intermediate A2 with organometallic reagents can afford compounds of general formula A.

form phenyl ether C3. Displacement of phenoxide with amine followed by reduction of the ester can afford primary alcohol C5, which can be activated and displaced with nucleophiles to form compounds of general formula C.

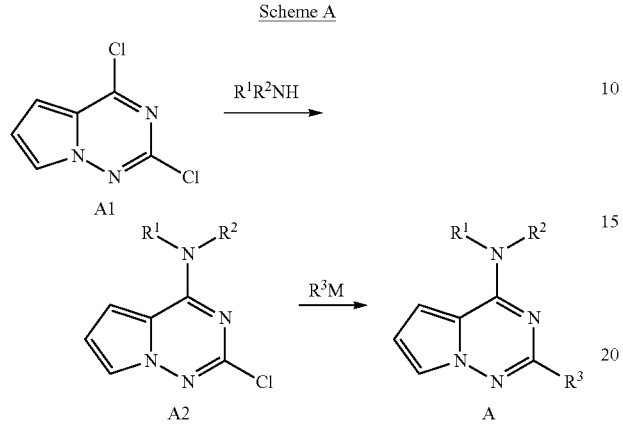

Scheme A

Alternatively, the order of reactions can be modified to change the overall synthesis in order to allow for significant variations at the 4-position, as outlined in Scheme B. Selective displacement of the chlorine at the 4-position of compound A1 with phenolate can form the phenyl ether B1. Palladium mediated coupling of mono chloro intermediate B1 with various organometallic reagents can afford intermediate B2. The phenoxy compound B2 may be reacted with various amines to yield compounds of general formula A

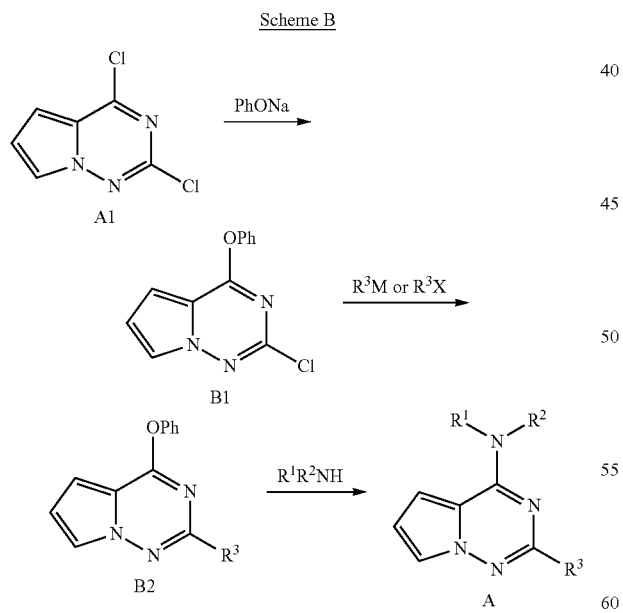

Scheme B

Another variation involves the synthesis of differentially substituted pyrrolotriazine core as outlined in Scheme C. This will allow for variations at the 5-position by using the ester as a synthetic handle. Reaction of ester C1 with phenolate followed by palladium mediated coupling can

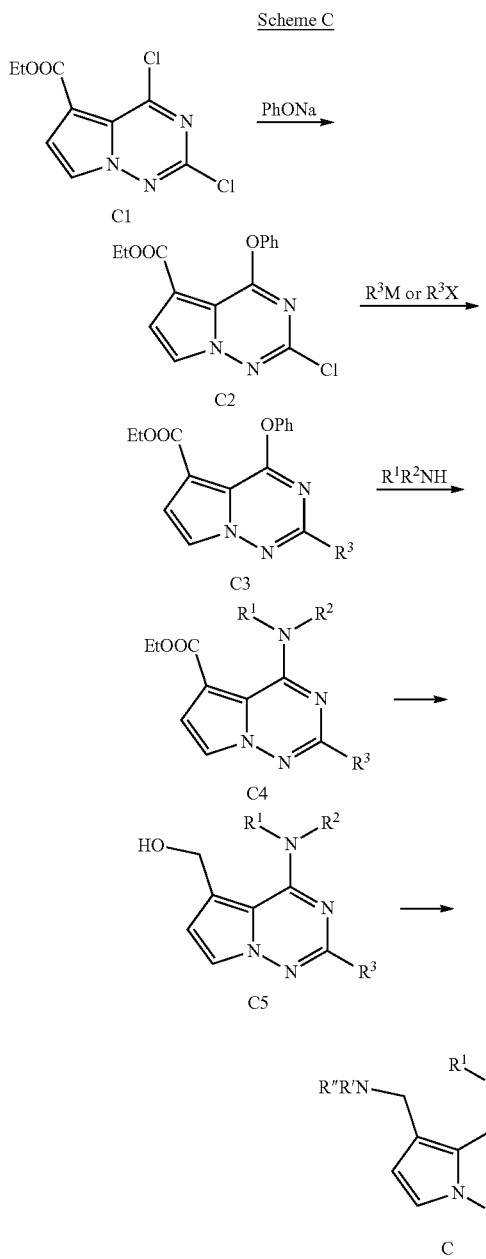

Scheme C

It should also be noted and obvious to those skilled in the art that synthetic manipulation of the incorporated R groups is possible. This is exemplified in Schemes D and E. One variation involves the introduction of a synthetic handle in one of the reagents that would allow for variations at a late stage of synthesis. This is outlined in Scheme D. Displacement of the phenoxide in B2 with substituted aminopyridine can afford ester D1. Saponification of the ester followed by coupling with amines can afford amides of general formula D.

Scheme D

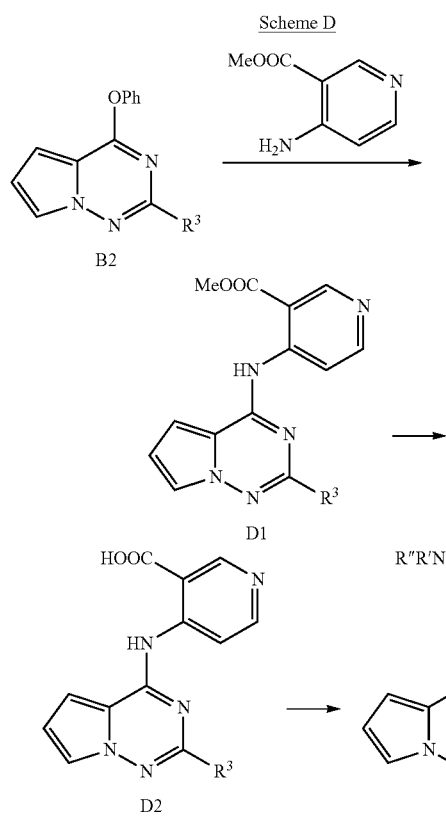

Another variation of the synthetic handle can be a halogen as outlined in Scheme E. Reaction of phenoxy intermediate B2 with amines bearing a halogen can yield halo compound E1. The halogen in intermediate E1 can be used as a synthetic handle to access amides or amines via metal mediated or thermal conditions to afford compounds of general formula E.

Scheme E

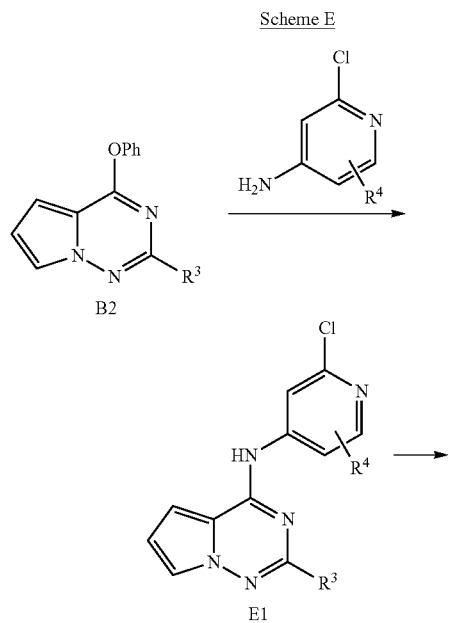

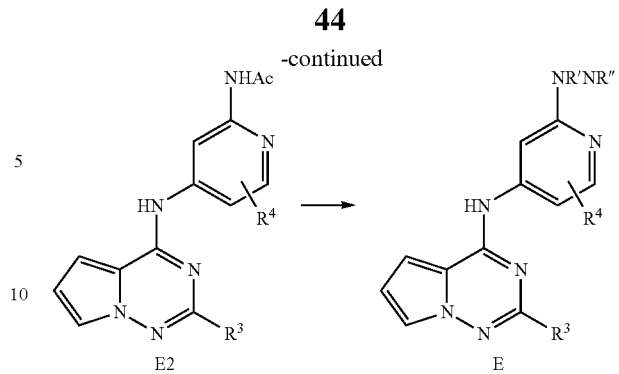

Another variation of substituted pyrrolotriazine is the 6-nitro intermediate F1. Selective displacement of chlorine with an amine nucleophile followed by palladium mediated coupling can yield nitro intermediate F3. Reduction of the nitro group in F3 followed by alkylation and/or acylation with various electrophiles can afford compounds of general formula F.

Scheme F

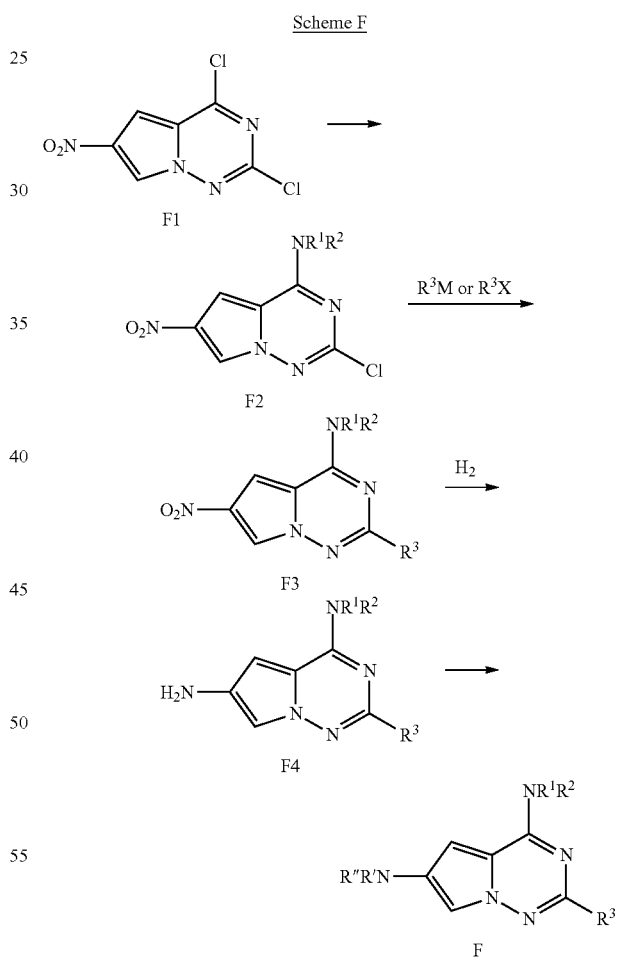

An additional variation of the synthetic handle can be a carboxylic acid at the 7-position as outlined in Scheme G. Selective displacement of chlorine in trihalo compound G1 can give ethoxy intermediate G2. Metal bromine exchange on bromocompound G2, followed by reaction with carbon-dioxide may yield carboxylic acid G3. Palladium mediated coupling of chlorocompound G3 followed by displacement of ethoxide can afford compounds of general formula G that can be derivatized by using the carboxylic acid as a synthetic handle.

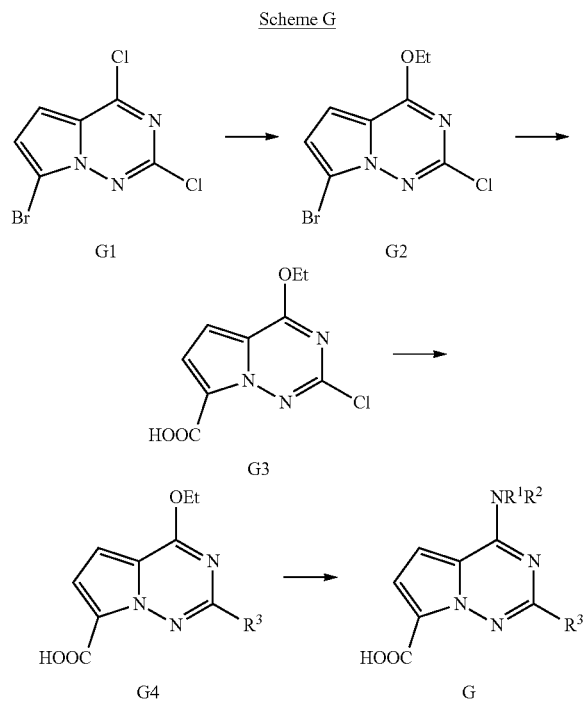

Scheme G

HPLC Conditions:

A: Waters Acquity UPLC BEH C18 (2.1×50 mm), 1.7 micron; Solvent A=100% water with 0.05% TFA; Solvent B=100% acetonitrile with 0.05% TFA; Gradient=2-98% B over 1 minute, then a 0.5-minute hold at 98% B; Flow rate: 0.8 mL/min; Detection: UV at 220 nm.

B: Waters Acquity BEH C18 (2.1×50 mm) 1.7 micron; Buffer: 5 mM Ammonium Acetate pH 3.5, Solvent A: Buffer: ACN (95:5), Solvent B: Buffer: ACN (5:95), Method: % B: 0 min—5%: 1.1 min—95%: 1.7 min—95%, Flow: 0.8 mL/min.

C: Ascentis Express C18 (2.1×50 mm), 2.7 micron; Solvent A: 5:95 acetonitrile:water with 10 mM NH$_4$OAc; Solvent B: 95:5 acetonitrile:water with 10 mM NH$_4$OAc; Temperature: 50° C.; Gradient: 0-100% B over 3 minutes; Flow rate: 1.1 mL/min; Detection: UV at 220 nm.

D: Column: Ascentis Express C18 (50×2.1) mm, 2.7 micron; Solvent A: 5:95 Acetonitrile:water with 0.1% TFA; Solvent B: 95:5 Acetonitrile:water with 0.1% TFA; Temperature: 50° C.; Gradient: 0-100% B over 3 minutes; Flow: 1.1 mL/min.

E: Kinetex XB-C18 (75×3 mm) 2.6 micron; Solvent A: 10 mM ammonium formate in water:acetonitrile (98:02); Mobile Phase B: 10 mM ammonium formate in water:acetonitrile (02:98); Temperature: 50° C.; Gradient: 0-100% B over 3 minutes; Flow rate: 1.1 mL/min; Detection: UV at 220 nm.

F: Waters Acquity UPLC BEH C18 (2.1×50 mm), 1.7 micron; Solvent A: 5:95 acetonitrile:water with 10 mM ammonium acetate; Solvent B: 95:5 acetonitrile:water with 10 mM ammonium acetate; Temperature: 50° C.; Gradient: 0-100% B over 3 minutes, then a 0.75-minute hold at 100% B; Flow: 1.11 mL/min; Detection: UV at 220 nm.

G. Waters Acquity UPLC BEH C18 (2.1×50 mm), 1.7 micron; Solvent A: 5:95 acetonitrile:water with 0.1% trifluoroacetic acid; Solvent B: 95:5 acetonitrile:water with 0.1% trifluoroacetic acid; Temperature: 50° C.; Gradient: 0-100% B over 3 minutes, then a 0.75-minute hold at 100% B; Flow: 1.11 mL/min; Detection: UV at 220 nm.

H: Column: Waters Acquity UPLC BEH C18 (2.1×50 mm), 1.7µ; Mobile phase A: 0.1% TFA in water; Mobile phase B: 0.1% TFA in Acetonitrile; Gradient=20-90% B over 1.1 minute, then a 0.6 minute hold at 90% B; Temperature: 50° C.; Flow rate: 0.7 mL/min; Detection: UV at 220 nm.

I: Column: Waters Acquity UPLC BEH C18 (2.1×50 mm) 1.7µ, Mobile phase A: 10 mM NH$_4$OAc, Acetonitrile (95:5); Mobile phase B: 10 mM NH$_4$OAc: Acetonitrile (5:95), Gradient=20-90% B over 1.1 minute, then a 0.6 minute hold at 90% B; Temperature: 50° C.; Flow rate: 0.7 mL/min; Detection: UV at 220 nm.

J: Column: Kinetex XB-C18 (75×3 mm) 2.6µ; Mobile phase A: 10 mM Ammonium formate:Acetonitrile (98:2), Mobile phase B: 10 mM Ammonium formate:Acetonitrile (2:98), Gradient=20-100% B over 4 minutes, then a 0.6 minute hold at 100% B; Temperature: 27° C.; Flow rate: 1.0 mL/min; Detection: UV at 220 nm.

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather is defined by the claims appended hereto.

| Abbreviations | |
|---|---|
| Ac$_2$O | acetic anhydride |
| ACN | acetonitrile |
| CH$_3$CN | acetonitrile |
| Cs$_2$CO$_3$ | cesium carbonate |
| DCM | dichloromethane |
| DMAP | dimethylaminopyridine |
| DMF | dimethylformamide |
| DMSO | dimethyl sulfoxide |
| Et$_3$N | triethyl amine |
| EtOAc | ethyl acetate |
| g | gram |
| h | hour(s) |
| H$_2$O | water |
| HPLC | high pressure liquid chromatography |
| K$_2$CO$_3$ | potassium carbonate |
| LCMS | Liquid Chromatography-Mass Spectroscopy |
| MeI | methyl iodide |
| MeOH | methanol |
| min | minute(s) |
| MgSO$_4$ | magnesium sulfate |
| mL | milliliter |
| mmol | millimolar |
| NaHCO$_3$ | sodium bicarbonate |
| NaOH | sodium hydroxide |
| NBS | N-bromosuccinamide |
| NH$_4$OAc | ammonium acetate |
| NH$_4$OH | ammonium hydroxide |
| PdCl$_2$(dppf) | [1,1'-bis(diphenylphosphino)ferrocene]dichloropalladium |
| Pd(Ph$_3$P)$_4$ | tetrakis(triphenylphosphine)palladium |
| RT | retention time |
| TBAF | tetrabutylammonium fluoride |
| TEA | triethylamine |
| TFA | trifluoroacetic acid |
| THF | tetrahydrofuran |
| Ac$_2$O | acetic anhydride |

Scheme 1

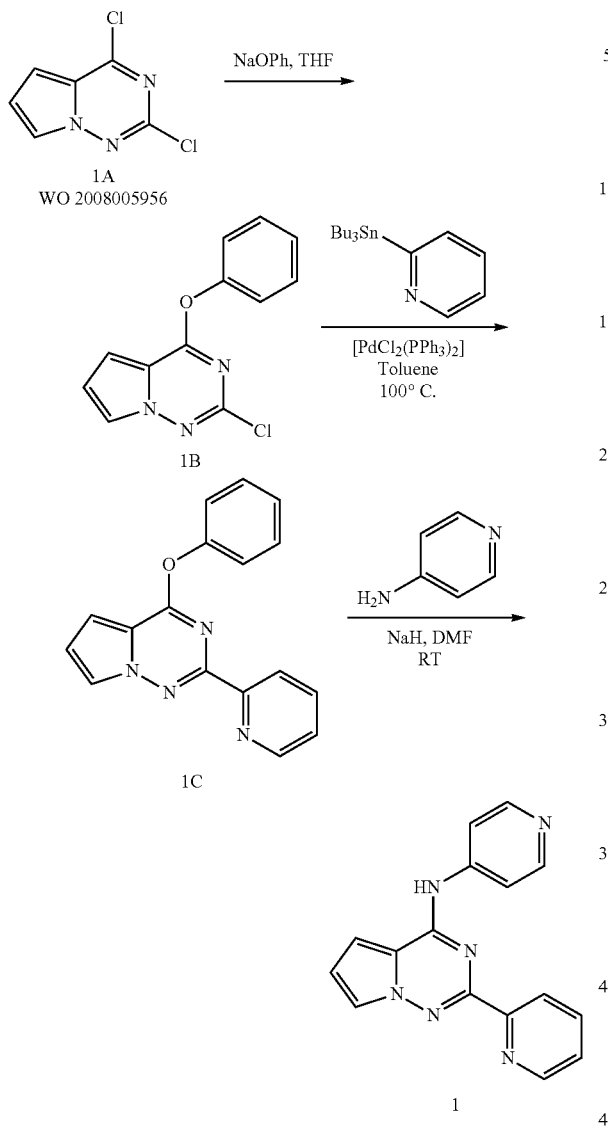

Example 1

N-[2-(pyridin-2-yl)pyrrolo[2,1-f][1,2,4]triazin-4-yl]pyridin-4-amine

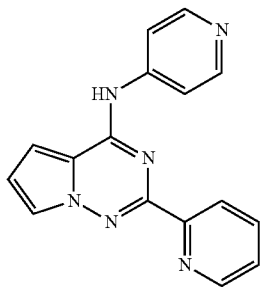 [SMILES: c1ccc(-c2nc(Nc3ccncc3)c3cccn3n2)nc1]

Intermediate 1B: 2-chloro-4-phenoxypyrrolo[2,1-f][1,2,4]triazine

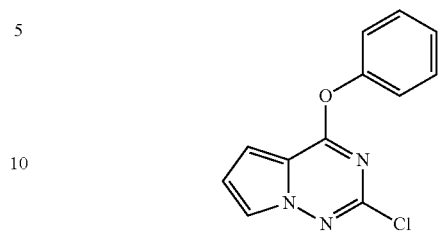

To a 100 mL flask was added 2,4-dichloropyrrolo[2,1-f][1,2,4]triazine (3 g, 15.96 mmol), tetrahydrofuran (40 mL) and stirred. To the resulting solution was portionwise added sodium phenolate (2.038 g, 17.55 mmol). After 1 h, an aliquot of the reaction mixture was diluted with methanol and analyzed by LCMS to ensure complete conversion. The reaction mixture was concentrated. To the residue was added water, stirred, filtered, washed extensively with water and dried. Obtained 2-chloro-4-phenoxypyrrolo[2,1-f][1,2,4]triazine (3.71 g, 15.10 mmol, 95% yield) as an off-white solid. LCMS m/z 245.9 (M+H); rt 1.05 min; Conditions A. $^1$H NMR: (300 MHz, DMSO-$d_6$) δ 8.13 (dd, J=2.6, 1.5 Hz, 1H), 7.56-7.48 (m, 2H), 7.42-7.34 (m, 3H), 7.15 (dd, J=4.5, 1.5 Hz, 1H), 6.99 (dd, J=4.5, 2.6 Hz, 1H).

Intermediate 1C: 4-phenoxy-2-(pyridin-2-yl)pyrrolo[2,1-f][1,2,4]triazine

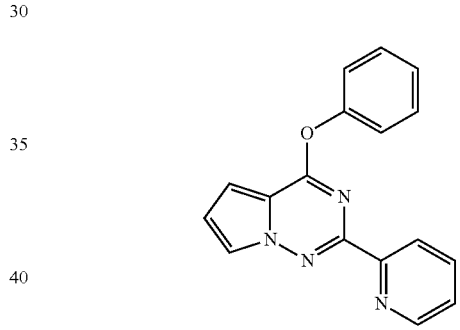

To a 40 mL scintillation vial was added 2-chloro-4-phenoxypyrrolo[2,1-f][1,2,4]triazine (0.983 g, 4 mmol), 2-(tributylstannyl)pyridine (1.767 g, 4.80 mmol), bis(triphenylphosphine)palladium(II)dichloride (0.140 g, 0.200 mmol) and toluene (10 mL). The resulting reaction mixture was degassed by bubbling nitrogen gas through the solution. The vial was capped with a pressure-safe septum cap and heated at 90° C. for 18 h. An aliquot of the reaction mixture was analyzed by LCMS to ensure completion of reaction. The reaction mixture was concentrated and the residue was purified by silica gel chromatography using 0-50% ethyl acetate in hexanes to get intermediate 1B (0.949 g, 3.29 mmol, 82% yield) as a colorless solid. LCMS m/z 290.1 (M+H); rt 0.77 min; Conditions A. $^1$H NMR (Chloroform-d) δ 8.74-8.87 (m, 1H), 7.99-8.12 (m, 2H), 7.74 (td, J=7.8, 1.7 Hz, 1H), 7.48-7.58 (m, 2H), 7.32-7.44 (m, 4H), 7.02 (dd, J=4.4, 1.5 Hz, 1H), 6.91 (dd, J=4.4, 2.7 Hz, 1H).

To a 1 dram vial was added intermediate 1B (15 mg, 0.052 mmol), pyridin-4-amine (14.69 mg, 0.156 mmol), DMF (0.4 mL) and a 60% dispersion of sodium hydride (4.16 mg, 0.104 mmol) in mineral oil. The resulting reaction mixture was stirred at 20° C. for 1 h. LCMS indicated completion of reaction. The reaction mixture was quenched carefully with wet methanol (~10 methanol:1 water), diluted with DMF and purified by reverse phase HPLC. Example 1 was obtained (13.4 mg, 89%): LCMS m/z 289 (M+H); rt 1.16 min; Conditions B. $^1$H NMR (DMSO-d6) δ 10.31 (s, 1H), 8.76 (d, J=4.4 Hz, 1H), 8.54 (d, J=5.7 Hz, 2H), 8.28 (d, J=7.7 Hz, 1H), 8.13 (d, J=6.1 Hz, 2H), 7.94-8.06 (m, 2H), 7.54 (dd, J=7.1, 5.0 Hz, 1H), 7.33 (d, J=3.4 Hz, 1H), 6.91 (dd, J=4.0, 2.7 Hz, 1H).

Scheme 2

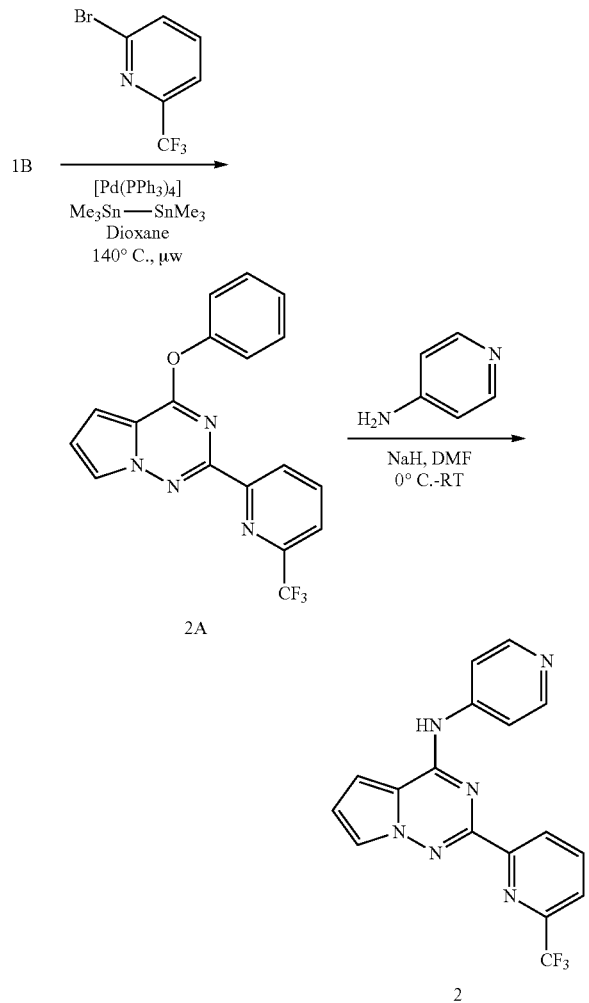

Example 2

3-(difluoromethyl)-N-{2-[6-(trifluoromethyl)pyridin-2-yl]pyrrolo[2,1-f][1,2,4]triazin-4-yl}pyridin-4-amine

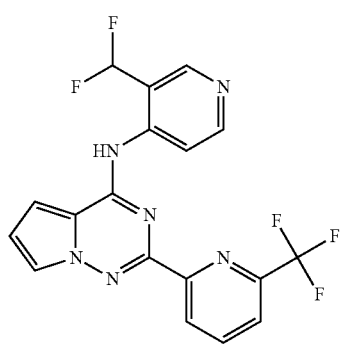 [SMILES: FC(F)c1cnccc1Nc1nc(-c2cccc(C(F)(F)F)n2)nn2cccc12]

Intermediate-2A: 4-phenoxy-2-(6-(trifluoromethyl)pyridin-2-yl)pyrrolo[2,1-f][1,2,4]triazine

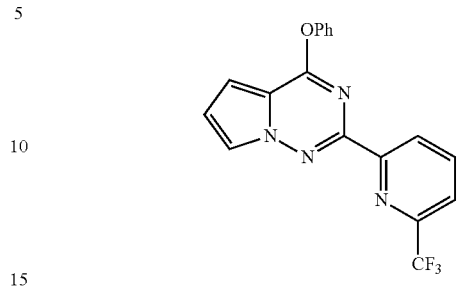

To a stirred solution of 2-chloro-4-phenoxypyrrolo[2,1-f][1,2,4]triazine 1B (1.5 g, 6.11 mmol), 2-bromo-6-(trifluoromethyl)pyridine (1.518 g, 6.72 mmol) and hexamethylditin (1.266 mL, 6.11 mmol) in dioxane (5 mL) degassed with nitrogen for 5 minutes, tetrakis(triphenylphosphine)palladium(0) (0.353 g, 0.305 mmol) was added. The reaction mixture was again degassed for 10 minutes, and heated at 140° C. for 1 h under microwave irradiation. The reaction mixture was filtered on celite bed and washed with ethyl acetate (150 mL). The filtrate was concentrated. The crude product was purified by silica gel chromatography using petroleum ether and ethyl acetate as eluent. The fractions containing the desired product were collected and concentrated to get 4-phenoxy-2-(6-(trifluoromethyl)pyridin-2-yl)pyrrolo[2,1-f][1,2,4]triazine 2A (1.2 g, 3.37 mmol, 55.2% yield) as a white solid. LCMS m/z 357.2 (M+H); rt 0.90 min; Conditions B.

Example 2 (13 mg, 22.8%) was synthesized employing the procedure described for Example 1 (Scheme 1): LCMS m/z 407.2 (M+H); rt 1.38 min; Conditions C. $^1$H NMR (400 MHz, DMSO-d6) δ 10.42 (s, 1H), 8.84 (s, 1H), 8.75 (d, J=4.8 Hz, 1H), 8.35 (d, J=8.0 Hz, 1H), 8.21-8.25 (m, 1H), 8.10 (s, 1H), 8.01 (d, J=7.6 Hz, 1H), 7.61-7.89 (m, 2H), 7.25 (d, J=3.2 Hz, Hz, 1H), 6.93-6.95 (m, 1H). $^{19}$F NMR (400 MHz, DMSO-d6) δ −66.5, −115.5

Scheme-3

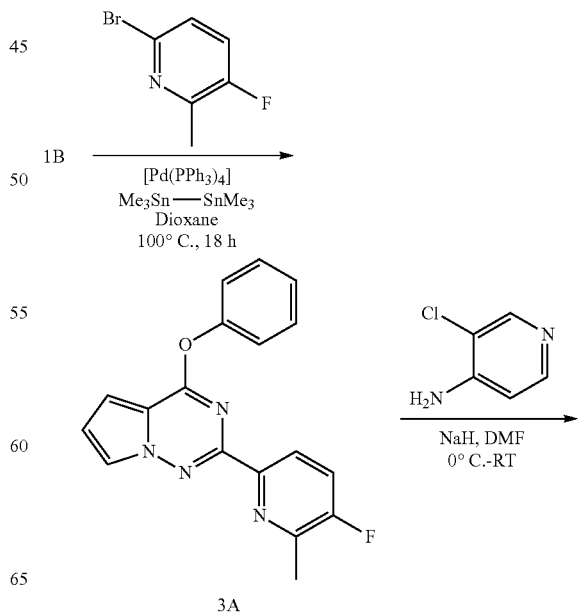

Example 3

3-chloro-N-[2-(5-fluoro-6-methylpyridin-2-yl)pyrrolo[2,1-f][1,2,4]triazin-4-yl]pyridin-4-amine

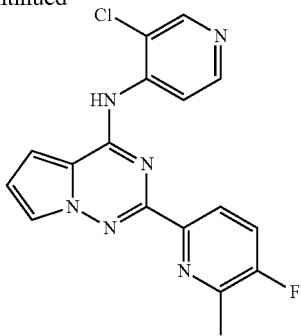

Intermediate 3A: 2-(5-fluoro-6-methylpyridin-2-yl)-4-phenoxypyrrolo[2,1-f][1,2,4]triazine

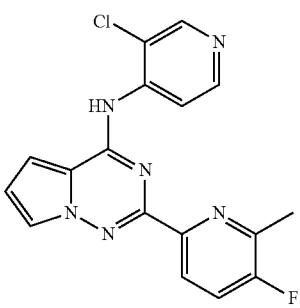 [SMILES: Cc1nc(-c2nc(Nc3ccncc3Cl)c3cccn3n2)ccc1F]

To a sealed tube, was added 2-chloro-4-phenoxypyrrolo[2,1-f][1,2,4]triazine (100 mg, 0.407 mmol) 6-bromo-3-fluoro-2-methylpyridine (85 mg, 0.448 mmol) hexamethylditin (0.084 mL, 0.407 mmol) in dioxane (3 mL). The solution was degassed with argon and tetrakis(triphenylphosphine)palladium(0) (47.0 mg, 0.041 mmol) was added. The reaction mixture was stirred at 100° C. for 18 h. An aliquot of the reaction mixture was diluted with methanol and analyzed by LCMS to ensure complete conversion. The reaction mixture was partitioned between water and ethyl acetate. The organic layer was washed with brine, dried over sodium sulfate and evaporated. Crude residue was purified by silica gel column chromatography using hexane-ethyl acetate (0-50%) to get 2-(5-fluoro-6-methylpyridin-2-yl)-4-phenoxypyrrolo[2,1-f][1,2,4]triazine (70 mg, 0.219 mmol, 53.7% yield) as brown solid. LCMS m/z 321.2 (M+H); rt 3.37 min; Conditions E.

Example 3 (23 mg, 23%) was synthesized employing the procedure described for Example 1 (Scheme 1): LCMS m/z 355.2 (M+H); rt 1.82 min; Conditions C. $^1$H NMR (400 MHz, DMSO-d6) δ 10.02 (s, 1H), 8.74 (s, 1H), 8.57 (d, J=5.2 Hz, 1H), 7.96-8.10 (m, 3H), 7.34-7.76 (m, 1H), 7.28 (s, 1H), 6.88 (s, 1H), 2.52 (overlapping with residual DMSO peak, 3H). $^{19}$F NMR (400 MHz DMSO-d6) δ −124.29.

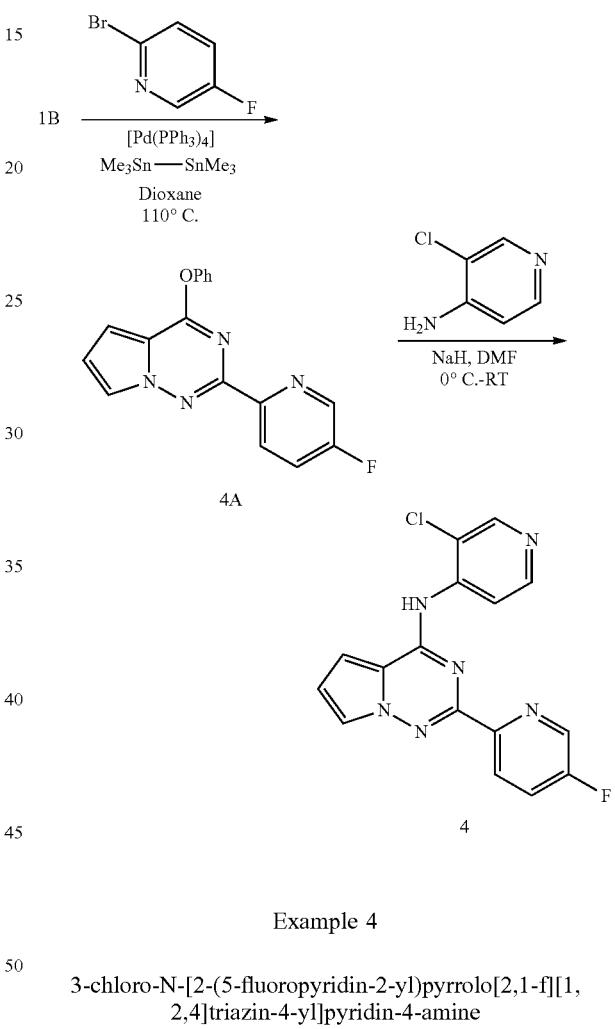

Example 4

3-chloro-N-[2-(5-fluoropyridin-2-yl)pyrrolo[2,1-f][1,2,4]triazin-4-yl]pyridin-4-amine

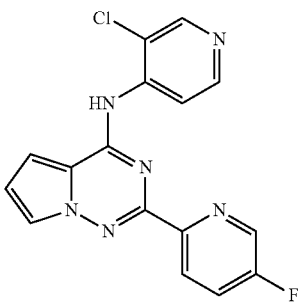 [SMILES: Fc1ccc(-c2nc(Nc3ccncc3Cl)c3cccn3n2)nc1]

Intermediate 4A: 2-(5-fluoropyridin-2-yl)-4-phenoxypyrrolo[2,1-f][1,2,4]triazine

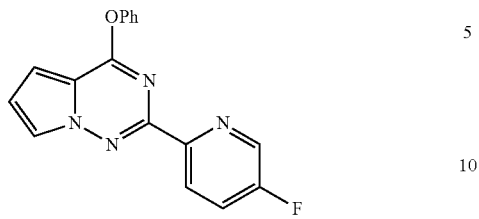

To a solution of 2-chloro-4-phenoxypyrrolo[2,1-f][1,2,4]triazine (700 mg, 2.85 mmol) and 2-bromo-5-fluoropyridine (501 mg, 2.85 mmol) in 1,4-dioxane (50 mL) was added hexamethylditin (0.650 mL, 3.13 mmol) and the reaction mixture was degassed with argon. Then Pd(Ph$_3$P)$_4$ (329 mg, 0.285 mmol) was added and the reaction mixture was degassed once again and stirred at 105° C. for 18 h. Then the reaction mixture was cooled down to room temperature. The reaction mixture was concentrated under reduced pressure to get a brown solid. The crude product was purified by silica gel chromatography (ethyl acetate:Petroleum ether, 25/75) to obtain 2-(5-fluoropyridin-2-yl)-4-phenoxypyrrolo[2,1-f][1,2,4]triazine (715 mg, 2.334 mmol, 82% yield). LCMS m/z 307.0 (M+H); rt 1.23 min; Conditions B.

Example 4 (9 mg, 16%) was synthesized employing the procedure described for Example 1 (Scheme 1): LCMS m/z 341.1 (M+H); rt 1.61 min; Conditions C. $^1$H NMR (400 MHz, DMSO-d6) δ 10.07 (s, 1H), 8.76 (s, 1H), 8.69 (d, J=3.2 Hz, 1H), 8.58 (d, J=5.2 Hz, 1H), 7.84-8.16 (m, 4H), 7.30-7.31 (m, 1H), 6.90-6.91 (m, 1H). $^{19}$F NMR (400 MHz, DMSO-d6) δ −126.0

Scheme-5

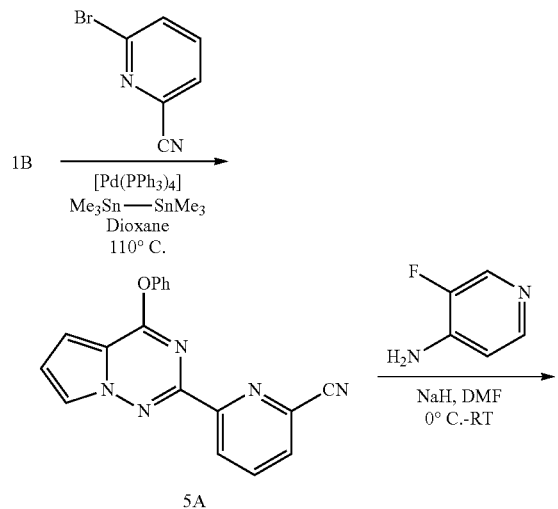

Example 5

6-{4-[(3-fluoropyridin-4-yl)amino]pyrrolo[2,1-f][1,2,4]triazin-2-yl}pyridine-2-carboxamide

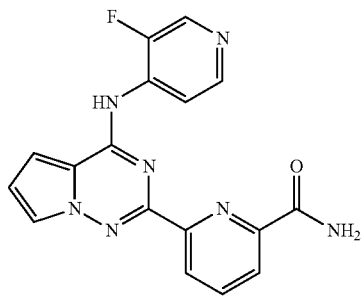 [SMILES: NC(=O)c1cccc(-c2nc(Nc3ccncc3F)c3cccn3n2)n1]

Intermediate 5A: 6-(4-phenoxypyrrolo[2,1-f][1,2,4]triazin-2-yl)picolinonitrile

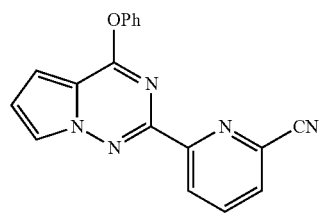 [SMILES: N#Cc1cccc(-c2nc(Oc3ccccc3)c3cccn3n2)n1]

To a solution of 2-chloro-4-phenoxypyrrolo[2,1-f][1,2,4]triazine (80 mg, 0.326 mmol), 6-bromopicolinonitrile (59.6 mg, 0.326 mmol) and hexamethylditin (0.068 mL, 0.326 mmol) in 1,4-dioxane (7 mL) was added tetrakis(triphenylphosphine)palladium(0) (37.6 mg, 0.033 mmol). The reaction mixture was degassed with argon and was stirred at 100° C. for 18 h. The solvent was removed under reduced pressure to get a light yellow liquid. The crude residue was purified by silica gel chromatography (ethyl acetate:Petroleum ether, 10/90) to obtain the desired product 6-(4-phenoxypyrrolo[2,1-f][1,2,4]triazin-2-yl)picolinonitrile (76 mg, 0.243 mmol, 74.5% yield). LCMS m/z 314.4 (M+H); rt 1.56 min; Conditions B.

Example 5 (8 mg, 18%) was synthesized employing the procedure described for Example 1 (Scheme 1): LCMS m/z 350.2 (M+H); rt 1.04 min; Conditions C. $^1$H NMR (400 MHz, DMSO-d6) δ 10.31 (s, 1H), 8.67 (s, 1H), 8.36-8.67 (m, 3H), 7.92-8.18 (m, 5H), 7.42 (d, J=3.6 Hz, 1H), 6.94 (s, 1H). $^{19}$F NMR (400 MHz, DMSO-d6) δ −136.93

Scheme-6

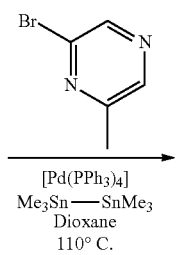

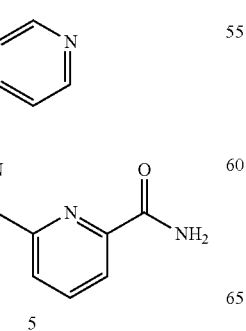

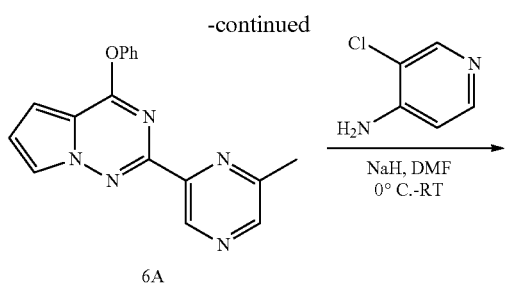

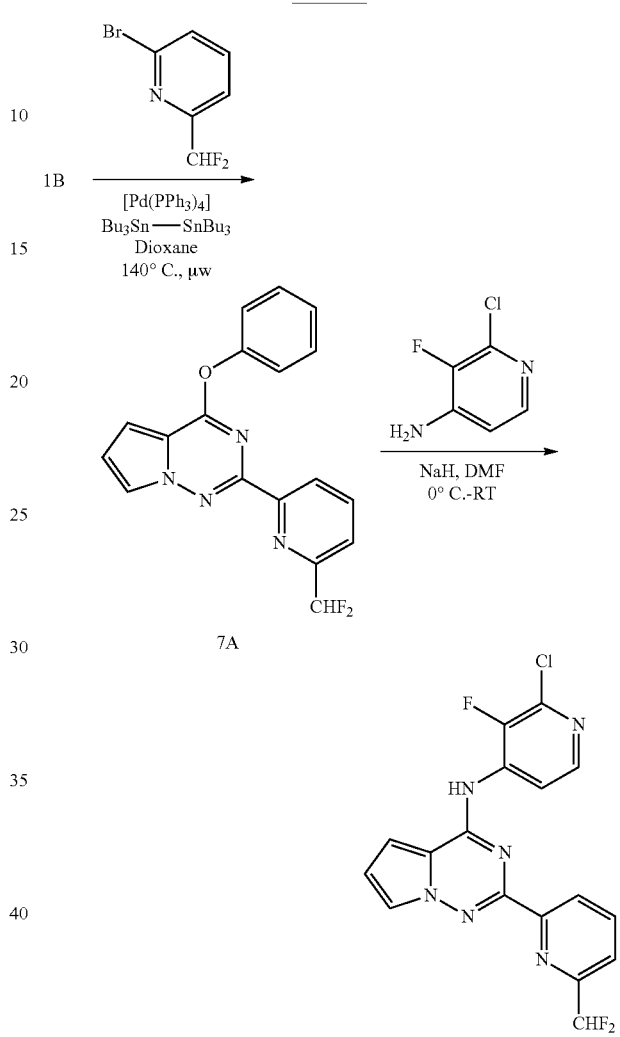

Example 6

3-chloro-N-[2-(6-methylpyrazin-2-yl)pyrrolo[2,1-f][1,2,4]triazin-4-yl]pyridin-4-amine

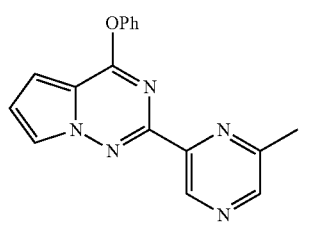 [SMILES: Cc1cncc(-c2nc(Oc3ccccc3)c3cccn3n2)n1]

Intermediate 6A: 2-(6-methylpyrazin-2-yl)-4-phenoxypyrrolo[2,1-f][1,2,4]triazine

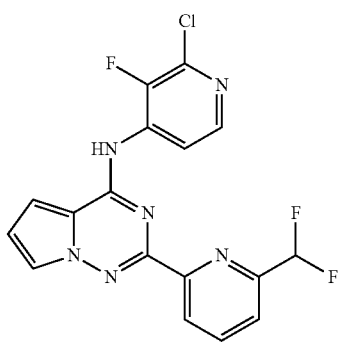 [SMILES: Fc1c(Nc2nc(-c3cccc(C(F)F)n3)nn3cccc23)ccnc1Cl]

To a solution of 2-chloro-4-phenoxypyrrolo[2,1-f][1,2,4]triazine (100 mg, 0.407 mmol), 2-bromo-6-methylpyrazine (70.4 mg, 0.407 mmol) and hexamethylditin (0.084 mL, 0.407 mmol) in 1,4-dioxane (7 mL) was added tetrakis(triphenylphosphine)palladium(0) (47.0 mg, 0.041 mmol). The reaction mixture was degassed with argon and was stirred at 100° C. for 18 h. The solvent was removed under reduced pressure to get a brown solid. The crude residue was purified by silica gel chromatography (ethyl acetate:Petroleum ether, 10/90) to obtain 2-(6-methylpyrazin-2-yl)-4-phenoxypyrrolo[2,1-f][1,2,4]triazine (85 mg, 0.280 mmol, 68.8% yield). LCMS m/z 304.4 (M+H); rt 1.45 min; Conditions B.

Example 6 (7 mg, 12%) was synthesized employing the procedure described for Example 1 (Scheme 1): LCMS m/z 338.1 (M+H); rt 1.33 min; Conditions C. $^1$H NMR (400 MHz, DMSO-d6) δ 10.13 (s, 1H), 9.04 (s, 1H), 8.77 (s, 1H), 8.60-8.64 (m, 2H), 8.08-8.12 (m, 2H), 7.33 (d, J=3.6 Hz, 1H), 2.6 (s, 3H).

Example 7

2-chloro-N-{2-[6-(difluoromethyl)pyridin-2-yl]pyrrolo[2,1-f][1,2,4]triazin-4-yl}-3-fluoropyridin-4-amine

Intermediate-7A: 2-(6-(difluoromethyl)pyridin-2-yl)-4-phenoxypyrrolo[2,1-f][1,2,4]triazine

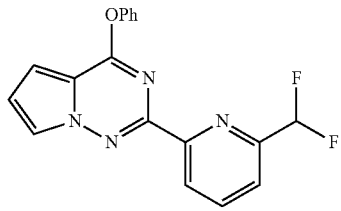 [SMILES: FC(F)c1cccc(-c2nc(Oc3ccccc3)c3cccn3n2)n1]

To a sealed tube, was added 2-bromo-6-(difluoromethyl)pyridine (200 mg, 0.962 mmol), hexamethylditin (0.199 mL, 0.962 mmol) and DMF (5 mL). The solution was degassed with argon and tetrakis(triphenylphosphine)palladium(0) (111 mg, 0.096 mmol) was added. The reaction mixture was stirred at 110° C. for 4 h. An aliquot of the reaction mixture was diluted with methanol and analyzed by LCMS to ensure complete conversion. To the reaction mixture, was added 2-chloro-4-phenoxypyrrolo[2,1-f][1,2,4]triazine (547 mg, 2.227 mmol) and tetrakis(triphenylphosphine)palladium(0) (257 mg, 0.223 mmol). The solution was degassed with argon and stirred at 110° C. for 18 h. An aliquot of the reaction mixture was diluted with methanol and analyzed by LCMS to ensure complete conversion. The reaction mixture was partitioned between water and ethyl acetate. The organic layer was washed with brine, dried over sodium sulfate and evaporated. The crude residue was purified by silica gel column chromatography using hexane-ethyl acetate to get 2-(6-(difluoromethyl)pyridin-2-yl)-4-phenoxypyrrolo[2,1-f][1,2,4]triazine (150 mg, 0.443 mmol, 19.91% yield) as a pale brown solid. LCMS m/z 339.2 (M+H); rt 3.1 min; Conditions E.

Example 7 (3 mg, 5%) was synthesized employing the procedure described for Example 1 (Scheme 1): LCMS m/z 391.1 (M+H); rt 1.89 min; Conditions B. 1HNMR (400 MHz, DMSO-d6) δ 10.47 (s, 1H), 8.45-8.48 (m, 1H), 8.31-8.33 (m, 2H), 8.18 (t, J=8.0 Hz, 1H), 8.12 (s, 1H), 7.82 (d, J=7.6 Hz, 1H), 7.42 (d, J=3.6 Hz, 1H), 7.09 (t, J=5.4 Hz, 1H), 6.94-6.96 (m, 1H). $^{19}$F NMR (400 MHz, DMSO-d6) δ −115.4, −129.0.

Scheme-8

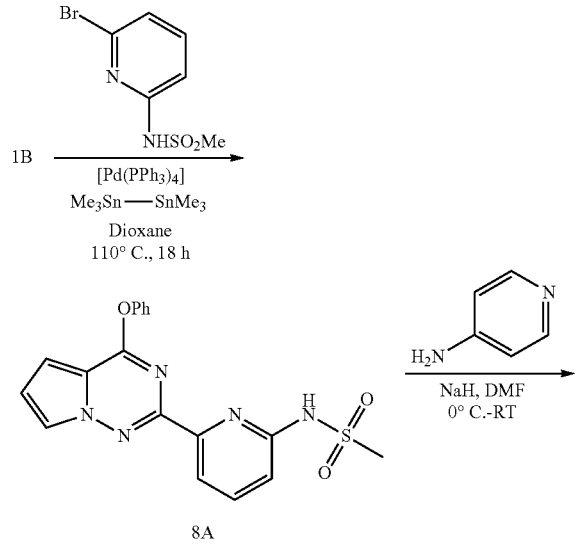

Example 8

N-(6-{4-[(pyridin-4-yl)amino]pyrrolo[2,1-f][1,2,4]triazin-2-yl}pyridin-2-yl)methanesulfonamide

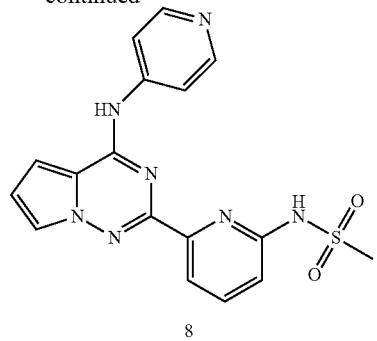

Intermediate 8A: N-(6-(4-phenoxypyrrolo[2,1-f][1,2,4]triazin-2-yl)pyridin-2-yl)methanesulfonamide

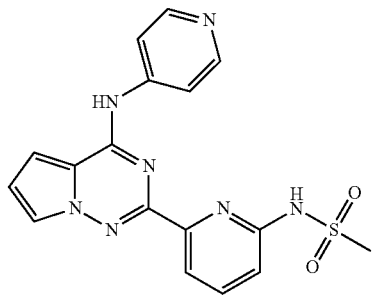 [SMILES: CS(=O)(=O)Nc1cccc(-c2nc(Nc3ccncc3)c3cccn3n2)n1]

To a sealed tube, was added 2-chloro-4-phenoxypyrrolo[2,1-f][1,2,4]triazine (100 mg, 0.407 mmol), N-(6-bromopyridin-2-yl)methanesulfonamide (112 mg, 0.448 mmol) and hexamethylditin (0.084 mL, 0.407 mmol) in dioxane (3 mL). The solution was degassed with argon and tetrakis(triphenylphosphine)palladium(0)(47.0 mg, 0.041 mmol) was added. The reaction mixture was stirred at 100° C. for 18 h. An aliquot of the reaction mixture was diluted with methanol and analyzed by LCMS to ensure complete conversion. The reaction mixture was partitioned between water and ethyl acetate. The organic layer was washed with brine, dried over sodium sulfate and evaporated. The crude residue was purified by silica gel chromatography using hexane-ethyl acetate to get N-(6-(4-phenoxypyrrolo[2,1-f][1,2,4]triazin-2-yl)pyridin-2-yl)methanesulfonamide (70 mg, 0.184 mmol, 45.1% yield) as brown solid. LCMS m/z 381.2 (M+H); rt 3.0 min; Conditions E.

Example 8 (4 mg, 13.3%) was synthesized employing the procedure described for Example 1 (Scheme 1): LCMS m/z 382.2 (M+H); rt 1.0 min; Conditions A. $^1$H NMR (400 MHz, DMSO-d6) δ=10.82 (s, 1H), 10.23 (br. s, 1H), 8.54 (d, J=6.0

Hz, 2H), 8.21 (d, J=6.0 Hz, 2H), 7.96 (dd, J=1.5, 2.5 Hz, 1H), 7.93-7.88 (m, 2H), 7.35 (dd, J=1.5, 4.5 Hz, 1H), 7.05 (quin, J=4.3 Hz, 1H), 6.91 (dd, J=2.8, 4.3 Hz, 1H), 3.51 (s, 3H)

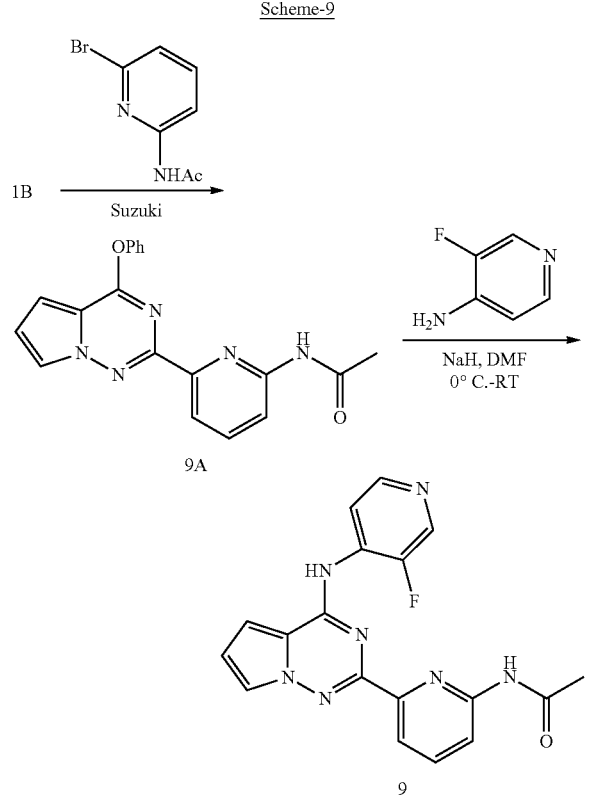

Example 9

N-(6-(4-((3-fluoropyridin-4-yl)amino)pyrrolo[2,1-f][1,2,4]triazin-2-yl)pyridin-2-yl)acetamide

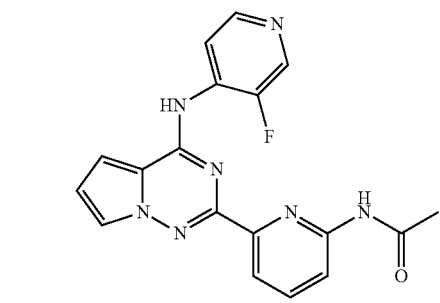 [SMILES: CC(=O)Nc1cccc(-c2nc(Nc3ccncc3F)c3cccn3n2)n1]

Intermediate-9A: N-(6-(4-phenoxypyrrolo[2,1-f][1,2,4]triazin-2-yl)pyridin-2-yl)acetamide

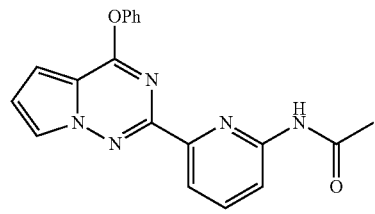 [SMILES: CC(=O)Nc1cccc(-c2nc(Oc3ccccc3)c3cccn3n2)n1]

To a sealed tube, was added 2-chloro-4-phenoxypyrrolo[2,1-f][1,2,4]triazine (100 mg, 0.407 mmol) bispinacolatodiboron (155 mg, 0.611 mmol), potassium acetate (100 mg, 1.018 mmol) and dioxane (2 mL). The solution was degassed with argon and 1,1'-bis(diphenylphosphino)ferrocene-palladium(II)-dichloride dichloromethane complex (16.62 mg, 0.020 mmol) was added. The reaction mixture was stirred at 90° C. for 18 h. To the reaction mixture, was added tripotassium phosphate (0.611 mL, 1.221 mmol)(2 M aqueous solution), N-(6-bromopyridin-2-yl)acetamide (88 mg, 0.407 mmol) and additional 1,1'-bis(diphenylphosphino)ferrocene-palladium(II)-dichloride dichloromethane complex (16.62 mg, 0.020 mmol) and stirred at 90° C. for 18 h. An aliquot of the reaction mixture was diluted with methanol and analyzed by LCMS to ensure complete conversion. The reaction mixture was partitioned between water and ethyl acetate. The organic layer was washed with brine, dried over sodium sulfate and evaporated. The crude residue was purified by silica gel chromatography using hexane-ethyl acetate to get N-(6-(4-phenoxypyrrolo[2,1-f][1,2,4]triazin-2-yl)pyridin-2-yl)acetamide (120 mg, 0.139 mmol, 34.1% yield) as pale yellow solid. LCMS m/z 346.3 (M+H); rt 2.78 min; Conditions E.

Example 9 (1.5 mg, 3.9%) was synthesized employing the procedure described for Example 1 (Scheme 1): LCMS m/z 346.2 (M+H); rt 1.23 min; Conditions C. $^1$H NMR (400 MHz, DMSO-d6) δ 10.73 (s, 1H), 8.56 (br. s, 1H), 8.38 (d, J=5.0 Hz, 1H), 8.20-8.06 (m, 2H), 7.94-7.76 (m, 3H), 7.17 (br. s, 1H), 6.80 (br. s, 1H), 2.13 (s, 3H).

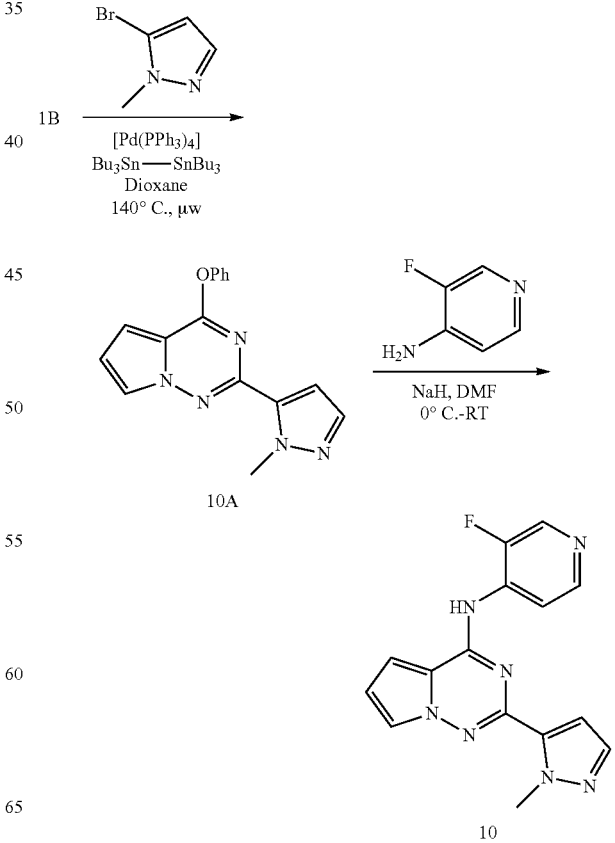

Example 10

3-fluoro-N-[2-(1-methyl-1H-pyrazol-5-yl)pyrrolo[2,1-f][1,2,4]triazin-4-yl]pyridin-4-amine

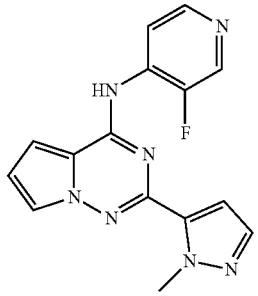 [SMILES: Cn1nccc1-c1nc(Nc2ccncc2F)c2cccn2n1]

Intermediate 10A: 2-(1-methyl-1H-pyrazol-5-yl)-4-phenoxypyrrolo[2,1-f][1,2,4]triazine

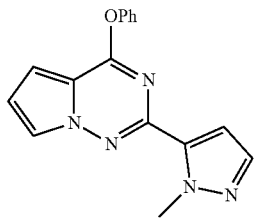 [SMILES: Cn1nccc1-c1nc(Oc2ccccc2)c2cccn2n1]

To a degassed solution of 2-chloro-4-phenoxypyrrolo[2,1-f][1,2,4]triazine (0.1 g, 0.407 mmol), 1-methyl-1H-pyrazole-5-boronic acid pinacol ester (0.102 g, 0.488 mmol) and tripotassium phosphate (0.259 g, 1.221 mmol) in 1,4-dioxane (10 mL) and water (3.33 mL) was added 1,1'-bis(diphenylphosphino)ferrocene-palladium(II)-dichloride dichloromethane complex (0.017 g, 0.020 mmol). The reaction mixture was heated to 100° C. for 12 h. The reaction mixture was cooled to room temperature and filtered through a pad of celite. The filtrate was evaporated and the residue was purified by silica gel chromatography (ethyl acetate/petroleum ether) to get 2-(1-methyl-1H-pyrazol-5-yl)-4-phenoxypyrrolo[2,1-f][1,2,4]triazine (100 mg, 0.292 mmol, 71.7% yield) as off white solid. LCMS m/z 292.1 (M+H); rt 1.12 min; Conditions B.

Example 10 (17 mg, 32%) was synthesized employing the procedure described for Example 1: LCMS m/z 310.2 (M+H); rt 1.32 min; Conditions D. $^1$H NMR (400 MHz, DMSO-d6) δ 10.31 (s, 1H), 8.67 (d, J=3.0 Hz, 1H), 8.47 (d, J=5.0 Hz, 1H), 8.05 (dd, J=6.8, 5.3 Hz, 1H), 7.95 (dd, J=2.5, 1.5 Hz, 1H), 7.48 (d, J=2.0 Hz, 1H), 7.33 (dd, J=4.0, 1.5 Hz, 1H), 6.91-6.71 (m, 2H), 4.11 (s, 3H).

Scheme-11

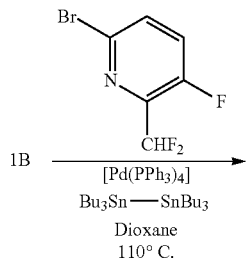

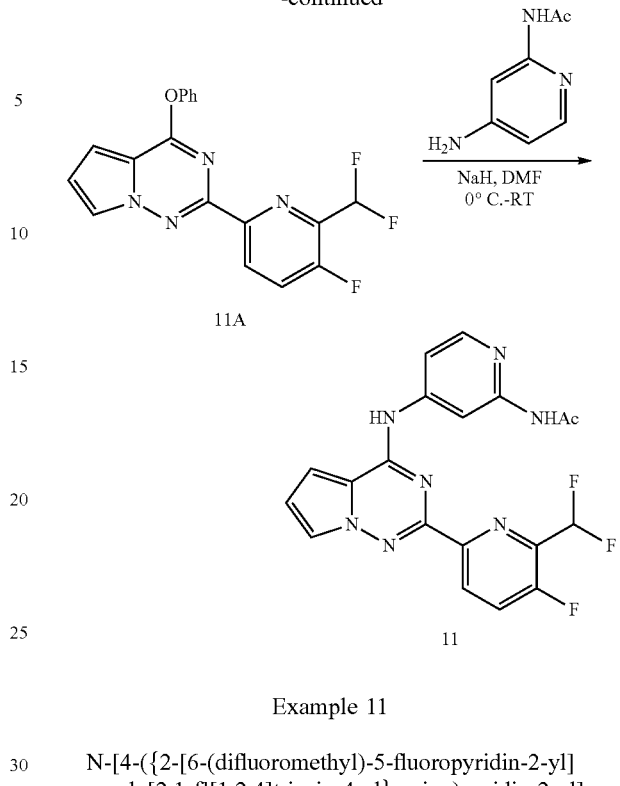

Example 11

N-[4-({2-[6-(difluoromethyl)-5-fluoropyridin-2-yl]pyrrolo[2,1-f][1,2,4]triazin-4-yl}amino)pyridin-2-yl]acetamide

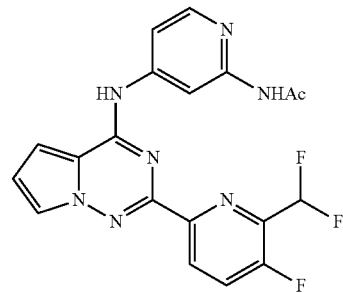 [SMILES: CC(=O)Nc1cc(Nc2nc(-c3ccc(F)c(C(F)F)n3)nn3cccc23)ccn1]

Intermediate 11A: 2-(6-(difluoromethyl)-5-fluoropyridin-2-yl)-4-phenoxypyrrolo[2,1-f][1,2,4]triazine

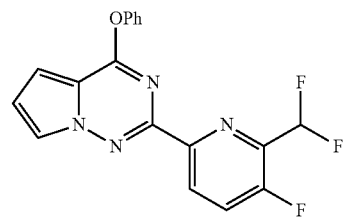 [SMILES: Fc1ccc(-c2nc(Oc3ccccc3)c3cccn3n2)nc1C(F)F]

2-chloro-4-phenoxypyrrolo[2,1-f][1,2,4]triazine (0.5 g, 2.035 mmol), 6-bromo-3-fluoro-2-(fluoromethyl)pyridine (0.508 g, 2.442 mmol) and hexamethylditin (0.445 mL, 2.035 mmol) were dissolve in 1,4-dioxane (20 mL). The reaction mixture was degassed for 5 min then added tetrakis(triphenylphosphine)palladium(0)(0.235 g, 0.204 mmol). The resulting reaction mixture was heated to 110° C. in sealed tube for 12 h. The reaction mixture was filtered through celite pad washed with ethyl acetate and evaporated under reduced pressure to get crude compound which was purified by silica gel chromatography (ethyl acetate/petroleum ether) to get 2-(6-(difluoromethyl)-5-fluoropyridin-2-yl)-4-phenoxypyrrolo[2,1-f][1,2,4]triazine (0.6 g, 1.566 mmol, 77% yield) as off white solid. LCMS m/z 357.1 (M+H); rt 1.29 min; Conditions B.

Example 11 (1.7 mg, 2.8%) was synthesized employing the procedure described for Example 1 (Scheme 1): LCMS m/z 414.2 (M+H); rt 1.49 min; Conditions C. $^1$H NMR (400 MHz, DMSO-d6) δ 10.47 (s, 1H), 10.42-10.34 (m, 1H), 8.84-8.79 (m, 1H), 8.78-8.72 (m, 1H), 8.27 (d, J=5.5 Hz, 1H), 8.12-7.97 (m, 3H), 7.27 (s, 2H), 6.92-6.85 (m, 1H), 2.15 (s, 3H).

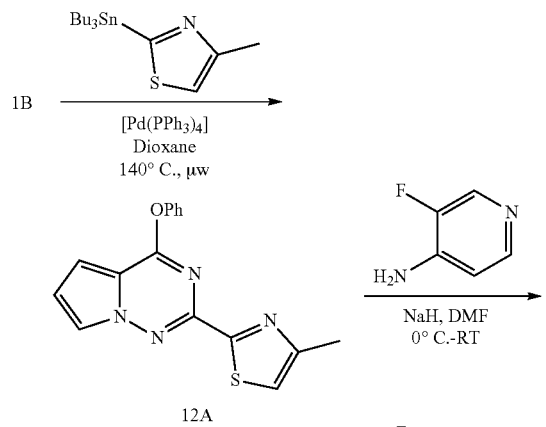

Scheme-12

Example 12

3-fluoro-N-[2-(4-methyl-1,3-thiazol-2-yl)pyrrolo[2,1-f][1,2,4]triazin-4-yl]pyridin-4-amine

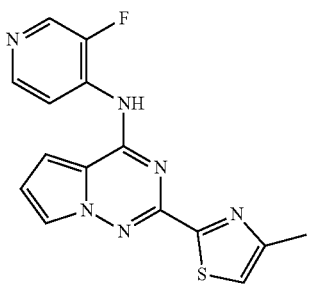 [SMILES: Cc1csc(-c2nc(Nc3ccncc3F)c3cccn3n2)n1]

Intermediate-12A: 4-methyl-2-(4-phenoxypyrrolo[2,1-f][1,2,4]triazin-2-yl)thiazole (A0482-166)

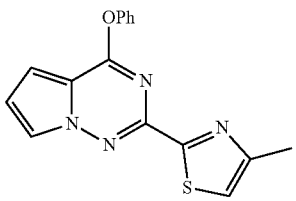 [SMILES: Cc1csc(-c2nc(Oc3ccccc3)c3cccn3n2)n1]

To a stirred solution of 2-chloro-4-phenoxypyrrolo[2,1-f][1,2,4]triazine (0.15 g, 0.611 mmol) and 4-methyl-2-(tributylstannyl)thiazole (0.237 g, 0.611 mmol) in dioxane (3 mL) degassed with nitrogen for 5 minutes was added tetrakis(triphenylphosphine)palladium(0)(0.035 g, 0.031 mmol) and again degassed for 10 minutes. The reaction mixture was heated at 140° C. for 1 h under microwave irradiation. The reaction mixture was filtered on a celite bed and washed with ethyl acetate (50 mL). The filtrate was concentrated. The crude product was purified by silica gel chromatography (petroleum ether and ethyl acetate) to get 4-methyl-2-(4-phenoxypyrrolo[2,1-f][1,2,4]triazin-2-yl)thiazole (0.075 g, 0.243 mmol, 39.8% yield) as a yellow solid. LCMS m/z 309.2 (M+H); rt 1.12 min; Conditions B.

Example 12 (5 mg, 18%) was synthesized employing the procedure described for Example 1 (Scheme 1): LCMS m/z 327.1 (M+H); rt 1.03 min; Conditions C. $^1$H NMR (400 MHz, DMSO-d6) δ 10.29-10.41 (m, 1H) 8.64-8.71 (m, 1H) 8.44-8.54 (m, 1H) 8.14-8.26 (m, 1H) 7.97-8.04 (m, 1H) 7.43-7.49 (m, 1H) 7.34-7.40 (m, 1H) 6.85-6.96 (m, 1H) 2.42-2.47 (m, 3H).

Scheme-13

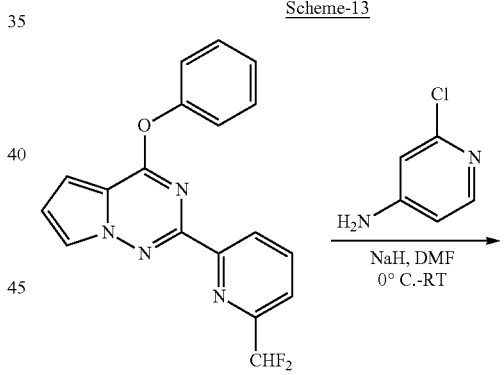

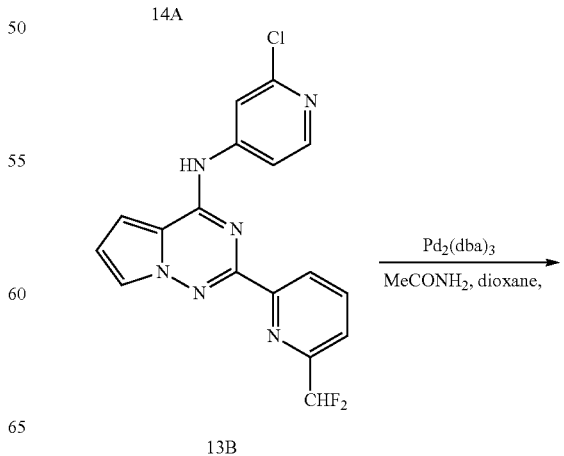

-continued

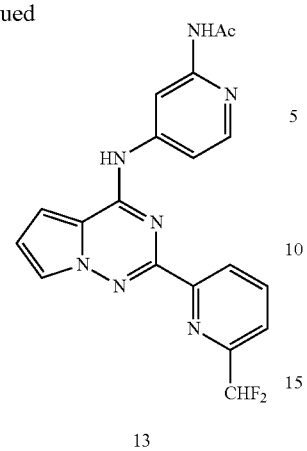

13

Example 13

N-[4-({2-[6-(difluoromethyl)pyridin-2-yl]pyrrolo[2,1-f][1,2,4]triazin-4-yl}amino)pyridin-2-yl]acetamide

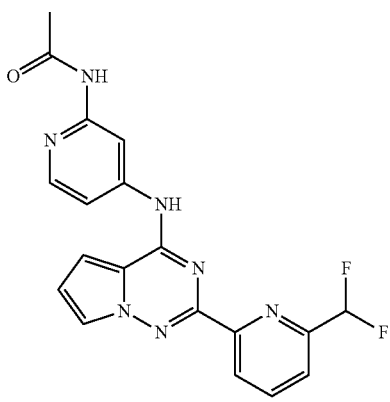 [SMILES: CC(=O)Nc1cc(Nc2nc(-c3cccc(C(F)F)n3)nn3cccc23)ccn1]

Intermediate: 13B: N-(2-chloropyridin-4-yl)-2-(6-(difluoromethyl)pyridin-2-yl)pyrrolo[2,1-f][1,2,4]triazin-4-amine

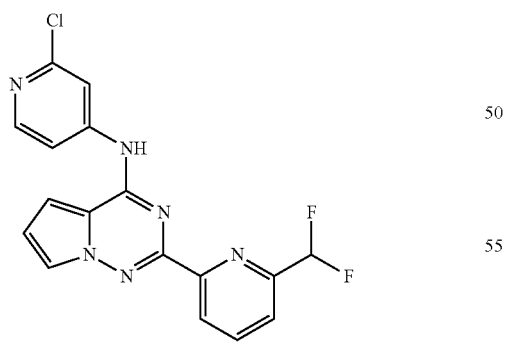

To a stirred solution of 2-(6-(difluoromethyl)pyridin-2-yl)-4-phenoxypyrrolo[2,1-f][1,2,4]triazine (0.09 g, 0.266 mmol) and 2-chloropyridin-4-amine (0.068 g, 0.532 mmol) in DMF (2 mL), sodium hydride (0.013 g, 0.319 mmol) was added and allowed to stir for 1 h at room temperature. The reaction mixture was cooled to 0° C. and added water (5 mL). The mixture was extracted with ethyl acetate. The organic layer was dried over anhydrous sodium sulfate and evaporated to get N-(2-chloropyridin-4-yl)-2-(6-(difluoromethyl)pyridin-2-yl)pyrrolo[2,1-f][1,2,4]triazin-4-amine (0.07 g, 0.188 mmol, 70.6% yield) as an white solid. LCMS m/z 373.3 (M+H); rt 0.99 min; Conditions B.

Example 13 (8 mg, 12%) was synthesized employing the procedure described for Example 1 (Scheme 1): LCMS m/z 397.2 (M+H); rt 1.49 min; Conditions B. $^1$H NMR (400 MHz, DMSO-d6) δ 10.70-10.86 (m, 1H) 10.46-10.59 (m, 1H) 8.60-8.71 (m, 1H) 8.27-8.33 (m, 1H) 8.15-8.24 (m, 1H) 8.04-8.14 (m, 1H) 7.80-7.88 (m, 1H) 7.37-7.44 (m, 1H) 6.96-7.27 (m, 1H) 6.87-6.95 (m, 1H) 2.17 (s, 3H).

Scheme-14

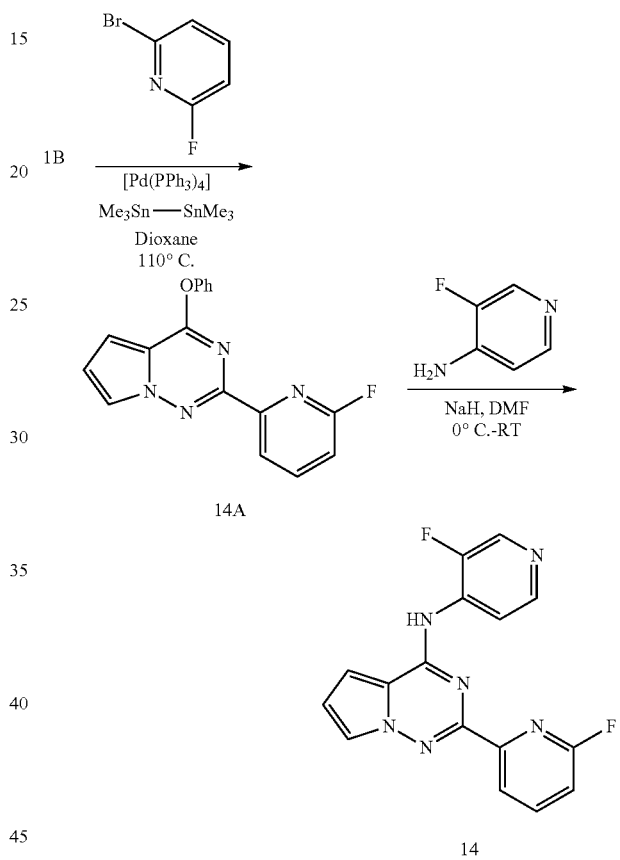

Example 14

3-fluoro-N-[2-(6-fluoropyridin-2-yl)pyrrolo[2,1-f][1,2,4]triazin-4-yl]pyridin-4-amine

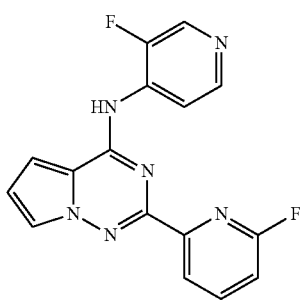 [SMILES: Fc1cccc(-c2nc(Nc3ccncc3F)c3cccn3n2)n1]

Intermediate 14A: 2-(6-fluoropyridin-2-yl)-4-phenoxypyrrolo[2,1-f][1,2,4]triazine

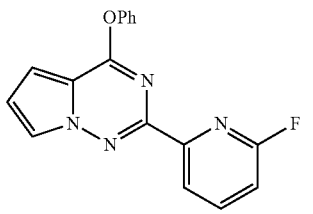 [SMILES: Fc1cccc(-c2nc(Oc3ccccc3)c3cccn3n2)n1]

To a stirred solution 2-chloro-4-phenoxypyrrolo[2,1-f][1,2,4]triazine (0.15 g, 0.611 mmol) in dioxane (5 mL) was added 2-fluoro-6-(tributylstannyl)pyridine (0.283 g, 0.733 mmol). The reaction mixture was degassed with nitrogen for 10 min. To the reaction mixture was added tetrakis(triphenylphosphine)palladium(0) (0.071 g, 0.061 mmol) and degassed for an additional 10 min. The reaction was heated at 100° C. for 18 h. The reaction was monitored by LC-MS. The reaction mixture was cooled to room temperature and evaporated under reduced pressure. To the crude product was added water (30 mL) and extracted with DCM (3×30 mL). The organic layer was dried over anhydrous sodium sulfate and evaporated under reduced pressure. The resulting crude product was purified by silica gel chromatography (ethyl acetate/petroleum ether) to get 2-(6-fluoropyridin-2-yl)-4-phenoxypyrrolo[2,1-f][1,2,4]triazine (0.09 g, 0.285 mmol, 46.7% yield) as an off-white solid. LCMS m/z 307 (M+H); rt 1.12 min; Conditions B.

Example 14 (10 mg, 31%) was synthesized employing the procedure described for Example 1 (Scheme 1): LCMS m/z 325.2 (M+H); rt 1.04 min; Conditions A. $^1$H NMR: (400 MHz, DMSO-d6) δ 10.32-10.26 (m, 1H), 8.67 (s, 1H), 8.48 (d, J=5.0 Hz, 1H), 8.29-8.20 (m, 1H), 8.18-8.06 (m, 2H), 8.05-7.99 (m, 1H), 7.40-7.34 (m, 1H), 7.32-7.23 (m, 1H), 6.94-6.90 (m, 1H).

Scheme 15

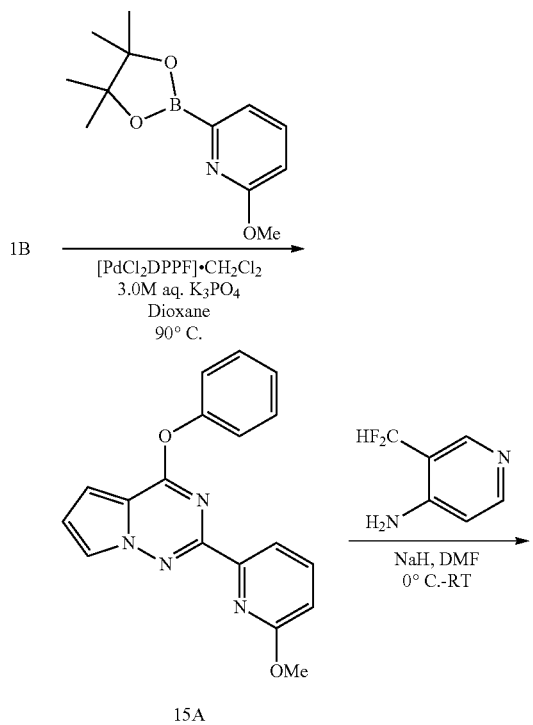

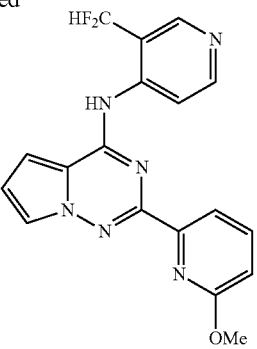

15

Example 15

3-(difluoromethyl)-N-[2-(6-methoxypyridin-2-yl)pyrrolo[2,1-f][1,2,4]triazin-4-yl]pyridin-4-amine

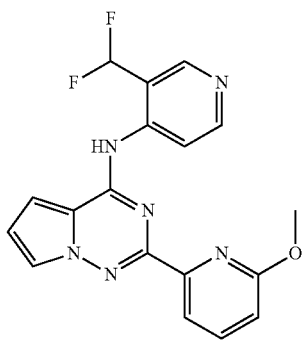 [SMILES: COc1cccc(-c2nc(Nc3ccncc3C(F)F)c3cccn3n2)n1]

Intermediate-15A: 2-(6-methoxypyridin-2-yl)-4-phenoxypyrrolo[2,1-f][1,2,4]triazine

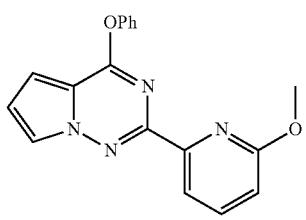 [SMILES: COc1cccc(-c2nc(Oc3ccccc3)c3cccn3n2)n1]

A stirred solution of 2-chloro-4-phenoxypyrrolo[2,1-f][1,2,4]triazine (1 g, 4.07 mmol), 2-methoxy-6-(4,4,5,5-tetramethyl-1,3,2-dioxaborolan-2-yl)pyridine (1.244 g, 5.29 mmol) and tripotassium phosphate (2.59 g, 12.21 mmol) in 1,4-dioxane (25 mL) and water (5 mL) mixture was degassed for with nitrogen for 3 min. To the resulting mixture was added 1,1'-bis(diphenylphosphino)ferrocenepalladium(II)-dichloride dichloromethane complex (0.166 g, 0.204 mmol) and degassed for an additional 1 min. The reaction mixture was heated to 100° C. for 12 h. The reaction mixture was cooled to room temperature and filtered over a pad oc celite. The filtrate was evaporated to get the crude product which was purified by silica gel chromatography (ethyl acetate/petroleum ether) to get 2-(6-methoxypyridin-2-yl)-4-phenoxypyrrolo[2,1-f][1,2,4]triazine (1.3 g, 3.92 mmol, 96% yield) as off white solid. LCMS m/z 319.1 (M+H); rt 1.12 min; Conditions B.

To a solution of 4-phenoxypyrrolo triazine 15A (50 mg, 0.157 mmol) and 3-(difluoromethyl)pyridin-4-amine (42.5 mg, 0.236 mmol) in DMF (0.5 mL) was added sodium hydride (0.187 mmol) and stirred at room temperature for 2 h. The reaction mixture was quenched with methanol and purified by reverse phase preparative HPLC to afford Example 15 (12 mg, 19.7%): LCMS m/z 369.12 (M+H); rt 1.73 min; Conditions C. $^1$H NMR (400 MHz, DMSO-d6) δ 8.23 (s, 1H), 8.59 (d, J=5.2 Hz, 1H), 7.81-7.96 (m, 4H), 7.12-7.49 (m, 1H), 7.02 (d, J=8.0 Hz, 1H), 6.77 (s, 1H), 4.06 (s, 3H); $^{19}$F NMR (400 MHz, DMSO-d6) δ −120.7.

Scheme-16

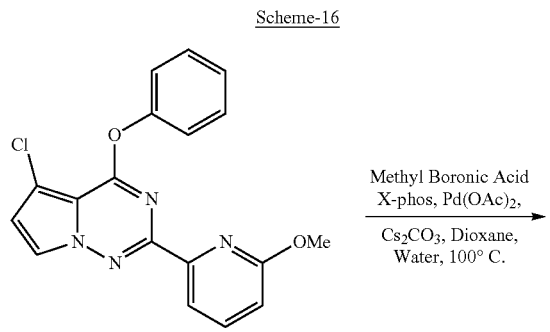

Example 16

N-[2-(6-methoxypyridin-2-yl)-5-methylpyrrolo[2,1-f][1,2,4]triazin-4-yl]pyridin-4-amine

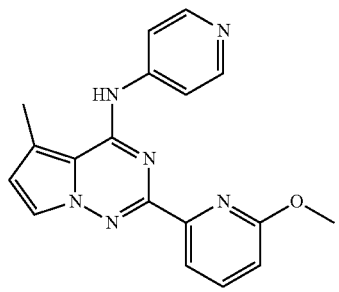 [SMILES: COc1cccc(-c2nc(Nc3ccncc3)c3c(C)ccn3n2)n1]

Intermediate 16A: 2-(6-methoxypyridin-2-yl)-5-methyl-4-phenoxypyrrolo[2,1-f][1,2,4]triazine

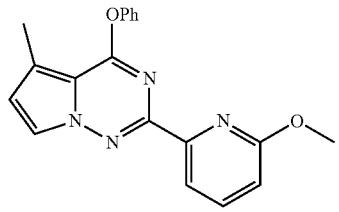 [SMILES: COc1cccc(-c2nc(Oc3ccccc3)c3c(C)ccn3n2)n1]

To a stirred solution of 5-chloro-2-(6-methoxypyridin-2-yl)-4-phenoxypyrrolo[2,1-f][1,2,4]triazine (150 mg, 0.425 mmol) in 1,4-dioxane (10 mL) and H2O (2 mL) was added methyl boronicacid (127 mg, 2.126 mmol), tripotassium phosphate (271 mg, 1.276 mmol) and 2-(dicyclohexylphosphino)-2',4',6'-triisopropylbiphenyl (60.8 mg, 0.128 mmol). The reaction mixture was degassed with nitrogen for 1 min, and then added palladium acetate (9.55 mg, 0.043 mmol). The reaction mixture was heated to 100° C. for 12 h. The reaction was monitored by LCMS. The reaction mixture was cooled to room temperature and filtered through a pad of celite. The filtrate was evaporated under reduced pressure and purified by silica gel chromatography (ethyl acetate/petroleum ether) to get 2-(6-methoxypyridin-2-yl)-5-methyl-4-phenoxypyrrolo[2,1-f][1,2,4]triazine (120 mg, 0.311 mmol, 73.0% yield) as pale yellow solid. LCMS m/z 333.8 (M+H); rt 1.21 min; Conditions B.

Example 16 (2 mg, 2.8%) was synthesized employing the procedure described for Example 1 (Scheme 1): LCMS m/z 333.2 (M+H); rt 1.76 min; Conditions C. $^1$H NMR (400 MHz, DMSO-d6) δ 8.86-8.82 (m, 1H), 8.52-8.48 (m, 2H), 8.18-8.13 (m, 2H), 7.86 (s, 3H), 6.99-6.93 (m, 1H), 6.74-6.71 (m, 1H), 4.06 (s, 3H), 2.70 (s, 3H).

Scheme 17

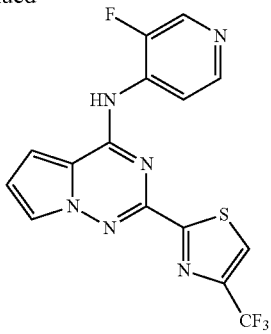

17

Example 17

N-(3-fluoropyridin-4-yl)-2-(4-(trifluoromethyl)thiazol-2-yl)pyrrolo[2,1-f][1,2,4]triazin-4-amine

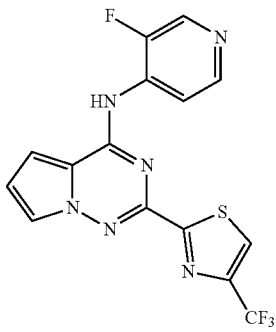 [SMILES: Fc1cnccc1Nc1nc(-c2nc(C(F)(F)F)cs2)nn2cccc12]

Intermediate 17A: 2-(4-phenoxypyrrolo[2,1-f][1,2,4]triazin-2-yl)-4-(trifluoromethyl)thiazole

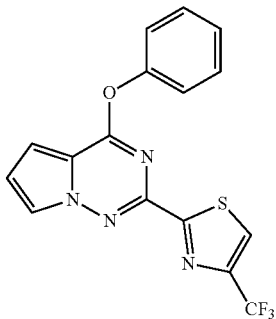 [SMILES: FC(F)(F)c1csc(-c2nc(Oc3ccccc3)c3cccn3n2)n1]

To a tall scintillation vial with a stir bar was added intermediate 1B (0.2 g, 0.814 mmol), bispinocolatodiboron (0.310 g, 1.221 mmol), potassium acetate (0.200 g, 2.035 mmol), 1,1'-bis(diphenylphosphino)ferrocene-palladium(II)-dichloride dichloromethane complex (0.033 g, 0.041 mmol) and 1,4-dioxane (4 mL). The resulting reaction mixture was degassed with nitrogen. The vial was capped with a pressure-safe septum cap and heated at 90° C. for 2.5 h. The reaction mixture was cooled to room temperature. To the reaction mixture was added aqueous 3.0 M tripotassium phosphate (0.814 mL, 2.442 mmol) and degassed by bubbling nitrogen. After 5 min, added 2-bromo-4-(trifluoromethyl)thiazole (0.189 g, 0.814 mmol) and additional 1,1'-bis(diphenylphosphino)ferrocene-palladium(II)-dichloride dichloromethane complex (0.033 g, 0.041 mmol). The resulting reaction mixture was degassed with nitrogen. The vial was capped and heated at 90° C. for 1 h. LCMS showed desired product as the minor product and the dechlorinated starting material as the major product. The reaction mixture was cooled to room temperature. The aqueous phase was removed. The organic phase was concentrated and the residue was purified by silica gel chromatography using 0-40% ethylacetate in hexanes to obtain intermediate 17A (41 mg, 14% yield). LCMS m/z 363.0 (M+H); rt 1.13 min; Conditions A. $^1$H NMR (Chloroform-d) δ 8.02 (dd, J=2.7, 1.5 Hz, 1H), 7.80 (d, J=0.7 Hz, 1H), 7.47-7.58 (m, 2H), 7.32-7.41 (m, 3H), 7.07 (dd, J=4.5, 1.5 Hz, 1H), 6.94 (dd, J=4.4, 2.7 Hz, 1H).

To a vial containing intermediate 17A (40 mg, 0.11 mmol) and 3-fluoropyridin-4-amine (25 mg, 0.22 mmol) was added anhydrous DMF (1 mL). To the resulting pale brown solution was carefully added a 60% dispersion of sodium hydride (8.83 mg, 0.221 mmol) in mineral oil. The resulting reaction mixture was stirred under nitrogen atmosphere for 1 h. LCMS indicated complete conversion. The reaction mixture was carefully quenched with wet dimethylformamide (1 water: 9 DMF) and purified by reverse phase preparative HPLC to obtain Example 17 (16.8 mg, 38% yield): LCMS m/z 381.0 (M+H); rt 1.70 min; Conditions B. $^1$H NMR (DMSO-d6) δ 8.59-8.78 (m, 2H), 8.50 (d, J=5.3 Hz, 1H), 8.02-8.22 (m, 2H), 7.43 (d, J=3.5 Hz, 1H), 6.96 (dd, J=4.1, 2.7 Hz, 1H).

Scheme 18

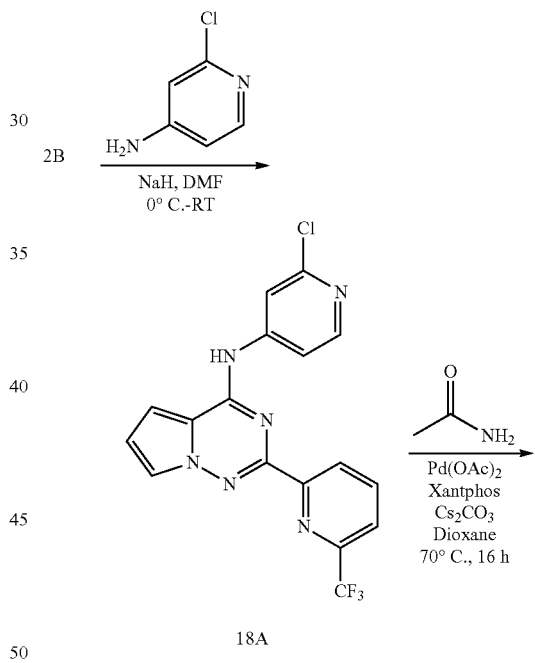

18A

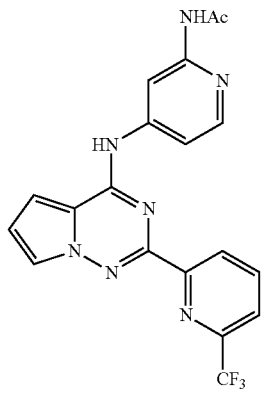 [SMILES: CC(=O)Nc1cc(Nc2nc(-c3cccc(C(F)(F)F)n3)nn3cccc23)ccn1]

18

Example 18

N-(4-((2-(6-(trifluoromethyl)pyridin-2-yl)pyrrolo[2,1-f][1,2,4]triazin-4-yl)amino)pyridin-2-yl)acetamide

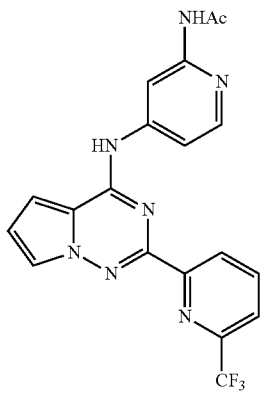

Intermediate 18A: N-(2-chloropyridin-4-yl)-2-(6-(trifluoromethyl)pyridin-2-yl)pyrrolo[2,1-f][1,2,4]triazin-4-amine (A482-239)

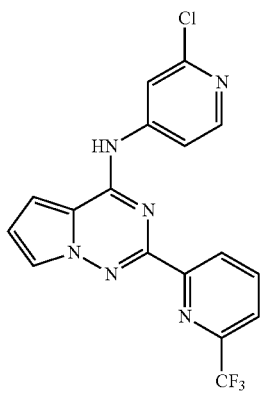 [SMILES: FC(F)(F)c1cccc(-c2nc(Nc3ccnc(Cl)c3)c3cccn3n2)n1]

To a stirred solution of 4-phenoxy-2-(6-(trifluoromethyl)pyridin-2-yl)pyrrolo[2,1-f][1,2,4]triazine (0.49 g, 1.375 mmol) and 2-chloropyridin-4-amine (0.194 g, 1.513 mmol) in DMF (5 mL), sodium hydride (0.083 g, 2.063 mmol) was added at 0° C. and allowed to stir at room temperature for 1 h under nitrogen atmosphere. The reaction mixture was cooled to 0° C. and water (10 mL) was added. The resulting precipitate was filtered and dried to get N-(2-chloropyridin-4-yl)-2-(6-(trifluoromethyl)pyridin-2-yl)pyrrolo[2,1-f][1,2,4]triazin-4-amine (0.4 g, 1.024 mmol, 74.4% yield) as an off white solid. LCMS m/z 391.0 (M+H); rt 3.0 min; Conditions E.

To a stirred solution of N-(2-chloropyridin-4-yl)-2-(6-(trifluoromethyl)pyridin-2-yl)pyrrolo[2,1-f][1,2,4]triazin-4-amine (0.5 g, 1.280 mmol), acetamide (0.113 g, 1.919 mmol), cesium carbonate (0.834 g, 2.56 mmol) and 4,5-bis(diphenylphosphino)-9,9-dimethylxanthene (0.148 g, 0.256 mmol) in 1,4-dioxane (10 mL) in a seal tube degassed with nitrogen for 5 minutes palladium(II)acetate (0.086 g, 0.128 mmol) was added and degassed with nitrogen for an additional 10 min. The reaction mixture was heated at 70° C. for 16 h. The reaction mixture was filtered on celite bed and concentrated. The crude product was purified by reverse phase HPLC to afford Example 18 (325 mg, 0.779 mmol, 30.4% yield) as an off white solid. LCMS m/z 414.2 (M+H); rt 2.4 min; Conditions E. $^1$H NMR (400 MHz, DMSO-d6) δ 2.15 (s, 3H) 6.90-6.94 (m, 1H) 7.39-7.44 (m, 1H) 8.00-8.05 (m, 1H) 8.07-8.12 (m, 2H) 8.22-8.31 (m, 2H) 8.73-8.84 (m, 2H) 10.37 (s, 1H) 10.45 (s, 1H).

Scheme-19

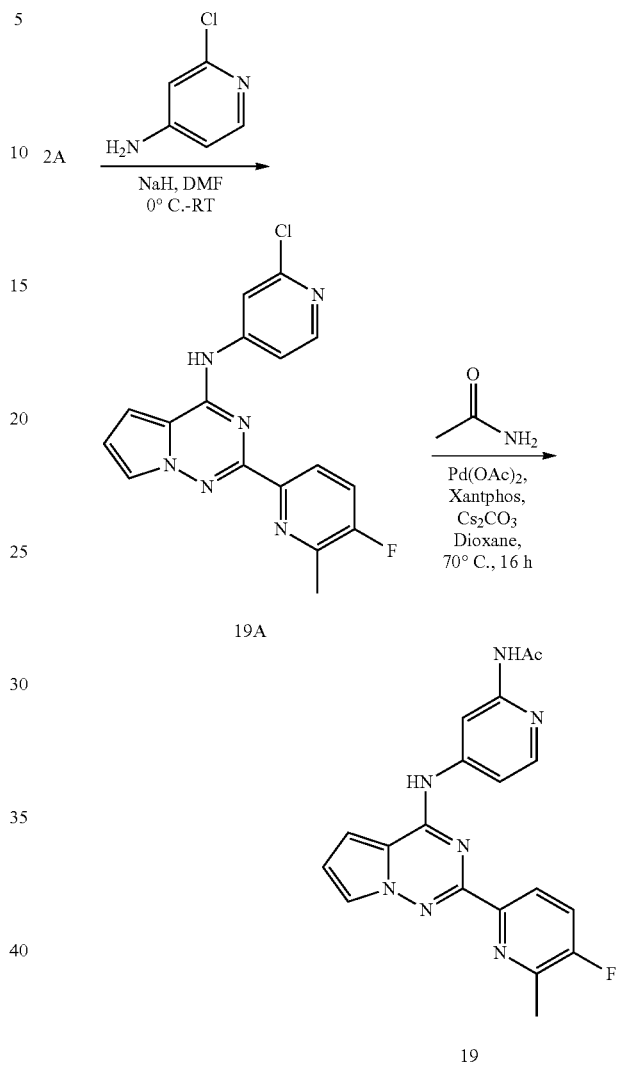

Example 19

N-(4-{[2-(5-fluoro-6-methylpyridin-2-yl)pyrrolo[2,1-f][1,2,4]triazin-4-yl]amino}pyridin-2-yl)acetamide

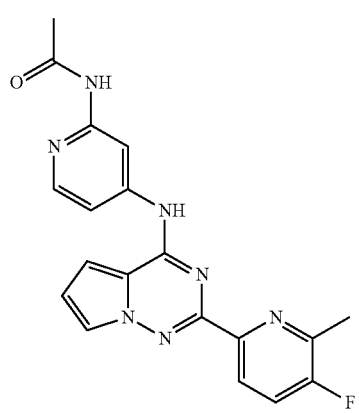 [SMILES: CC(=O)Nc1cc(Nc2nc(-c3ccc(F)c(C)n3)nn3cccc23)ccn1]

Intermediate 19A: N-(2-chloropyridin-4-yl)-2-(5-fluoro-6-methylpyridin-2-yl)pyrrolo[2,1-f][1,2,4]triazin-4-amine

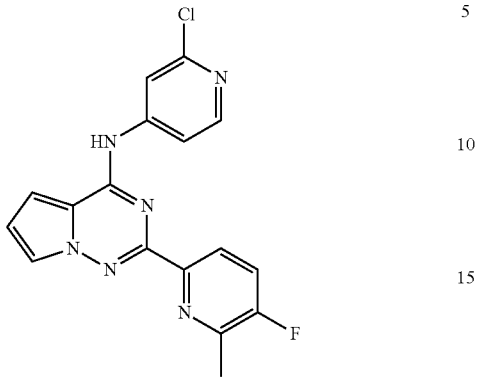

To a solution of 2-(5-fluoro-6-methylpyridin-2-yl)-4-phenoxypyrrolo[2,1-f][1,2,4]triazine (170 mg, 0.531 mmol) and 2-chloropyridin-4-amine (136 mg, 1.061 mmol) in DMF (2 mL) was added sodium hydride (31.8 mg, 0.796 mmol) at 0° C. The reaction mixture was warmed to room temperature and stirred at the same temperature for 2 h. The reaction mixture was poured in to water (10 mL). The resulting precipitate was filtered and dried. The isolated crude product was used in the next reaction without further purification. LCMS m/z 355.3 (M+H); rt 0.81 min; Conditions B.

To a solution of intermediate 19A (50 mg, 0.141 mmol), acetamide (16.65 mg, 0.282 mmol), cesium carbonate (92 mg, 0.282 mmol) and 4,5-bis(diphenylphosphino)-9,9-dimethylxanthene (16.31 mg, 0.028 mmol) in 1,4-dioxane (5 mL) was added Pd(OAc)$_2$ (9.49 mg, 0.014 mmol). The reaction mixture was degassed for 5 minutes and heated at 110° C. for 16 h. The reaction mixture was filtered through a pad of celite. The filtrate was evaporated to get the crude product that was purified by reverse phase HPLC to afford Example 19 (2 mg, 4%): LCMS m/z 378.2 (M+H); rt 1.34 min; Conditions C. $^1$H NMR (400 MHz, DMSO-d6) δ 10.46 (s, 1H), 10.31 (s, 1H), 8.76 (s, 1H), 8.39-8.42 (m, 1H), 8.27 (d, J=5.6 Hz, 1H), 8.01-8.04 (m, 2H), 7.73-7.78 (m, 1H), 7.34-7.39 (m, 1H), 6.84-6.89 (m, 1H), 2.58 (s, 3H), 2.14 (s, 3H). $^{19}$F NMR (400 MHz, DMSO-d6) δ −123.89.

Scheme 20

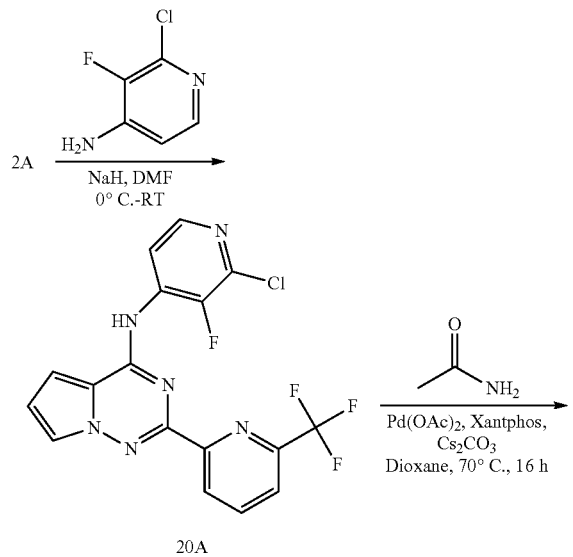

-continued

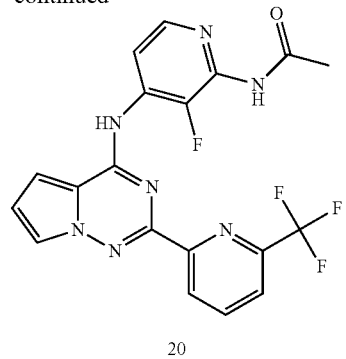

Example 20

N-[3-fluoro-4-({2-[6-(trifluoromethyl)pyridin-2-yl]pyrrolo[2,1-f][1,2,4]triazin-4-yl}amino)pyridin-2-yl]acetamide

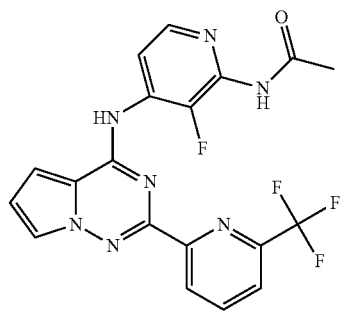 [SMILES: CC(=O)Nc1nccc(Nc2nc(-c3cccc(C(F)(F)F)n3)nn3cccc23)c1F]

Intermediate 20A: N-(2-chloro-3-fluoropyridin-4-yl)-2-(6-(trifluoromethyl)pyridin-2-yl)pyrrolo[2,1-f][1,2,4]triazin-4-amine

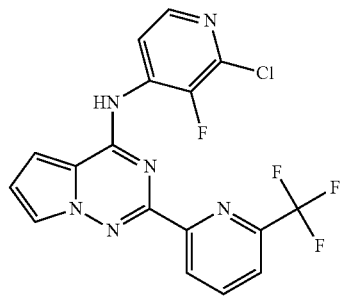 [SMILES: Fc1c(Nc2nc(-c3cccc(C(F)(F)F)n3)nn3cccc23)ccnc1Cl]

To a 50 mL flask, was added 2-chloro-3-fluoropyridin-4-amine (16.45 mg, 0.112 mmol) in DMF (1 mL) and cooled to 0° C. To the resulting solution was added sodium hydride (3.37 mg, 0.084 mmol) and stirred for 5 min. A solution of 4-phenoxy-2-(6-(trifluoromethyl)pyridin-2-yl)pyrrolo[2,1-f][1,2,4]triazine (20 mg, 0.056 mmol) in DMF was added drop wise and stirred at room temperature for 2 h. An aliquot of the reaction mixture was diluted with methanol and analyzed by LCMS to ensure complete conversion. The reaction mixture was poured into ice and extracted with ethyl acetate. The organic layer was washed with brine, dried over sodium sulfate and concentrated to get N-(2-chloro-3-fluoropyridin-4-yl)-2-(6-(trifluoromethyl)pyridin-2-yl)pyrrolo[2,1-f][1,2,4]triazin-4-amine (Crude 40 mg) as a pale brown solid. LCMS m/z 409.0 (M+H); rt 0.98 min; Conditions A Example 20 (42 mg, 33%) was synthesized employing the procedure described for Example 19 (Scheme 19): LCMS m/z 432.0 (M+H); rt 2.04 min; Conditions E. $^1$H NMR (400 MHz, DMSO-d6) δ 10.40 (br. s., 1H), 10.31 (s, 1H), 8.59 (d, J=8.0 Hz, 1H), 8.28-8.20 (m, 2H), 8.19-8.14 (m, 1H), 8.10 (br. s, 1H), 8.01 (d, J=7.5 Hz, 1H), 7.41 (d, J=4.0 Hz, 1H), 6.92 (dd, J=4.3, 2.8 Hz, 1H), 2.12 (s, 3H).

m/z 395.8 (M+H); rt 2.76 min; Conditions E. $^1$H NMR (400 MHz, DMSO-d6) δ 10.53-10.27 (m, 2H), 8.85-8.77 (m, 1H), 8.69-8.63 (m, 1H), 8.33-8.25 (m, 1H), 8.22-8.15 (m, 1H), 8.08-7.99 (m, 2H), 7.88-7.76 (m, 1H), 7.48-7.36 (m, 1H), 7.26-6.95 (m, 2H), 6.90-6.79 (m, 1H), 2.15 (s, 3H).

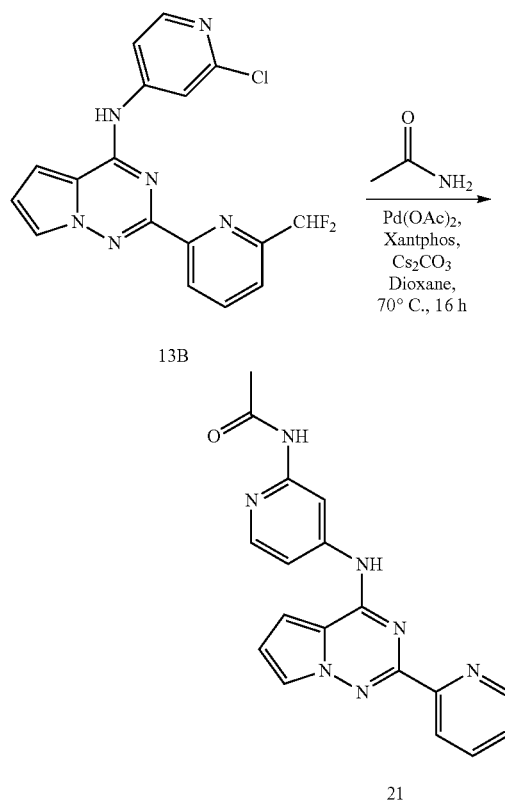

Scheme-21

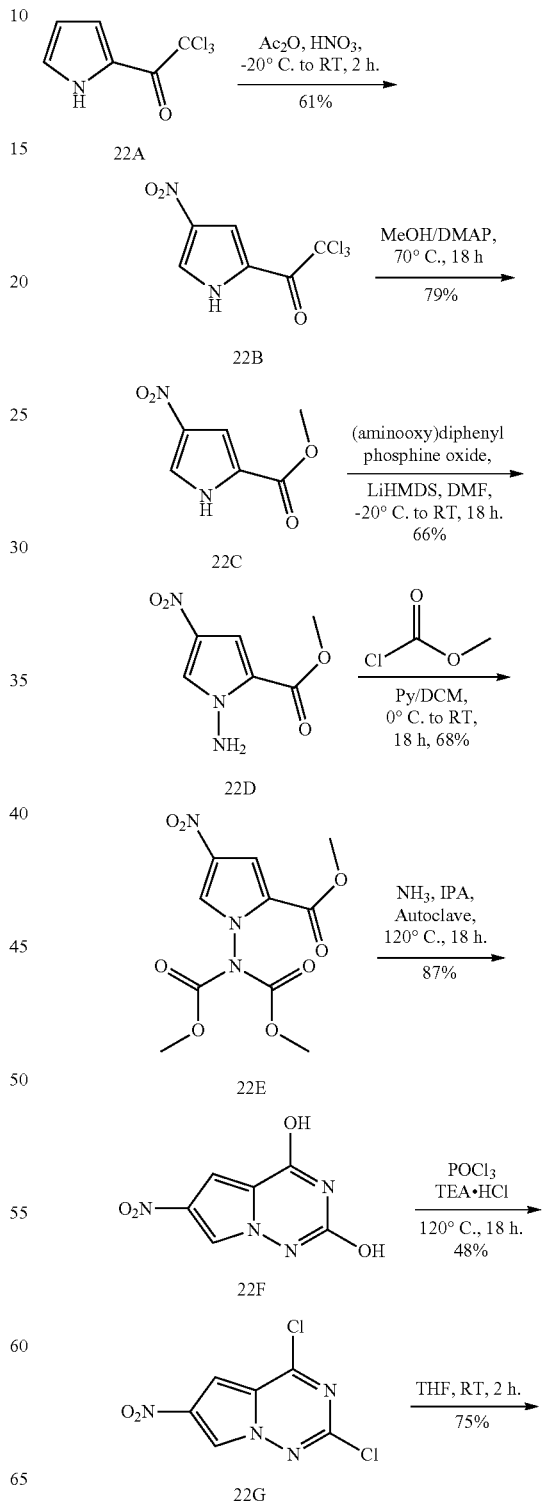

Scheme 22

Example 21

N-[4-({2-[6-(difluoromethyl)pyridin-2-yl]pyrrolo[2,1-f][1,2,4]triazin-4-yl}amino)pyridin-2-yl]acetamide

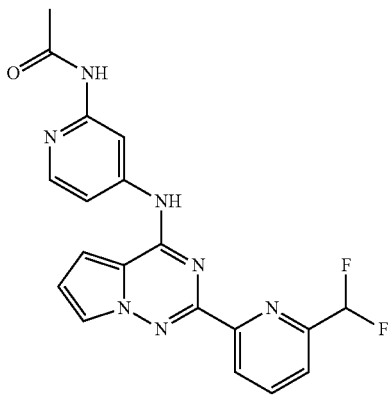 [SMILES: CC(=O)Nc1cc(Nc2nc(-c3cccc(C(F)F)n3)nn3cccc23)ccn1]

Example 21 was obtained (8.5 mg, 5.6%) employing the procedure described for Example 19 (Scheme 19): LCMS

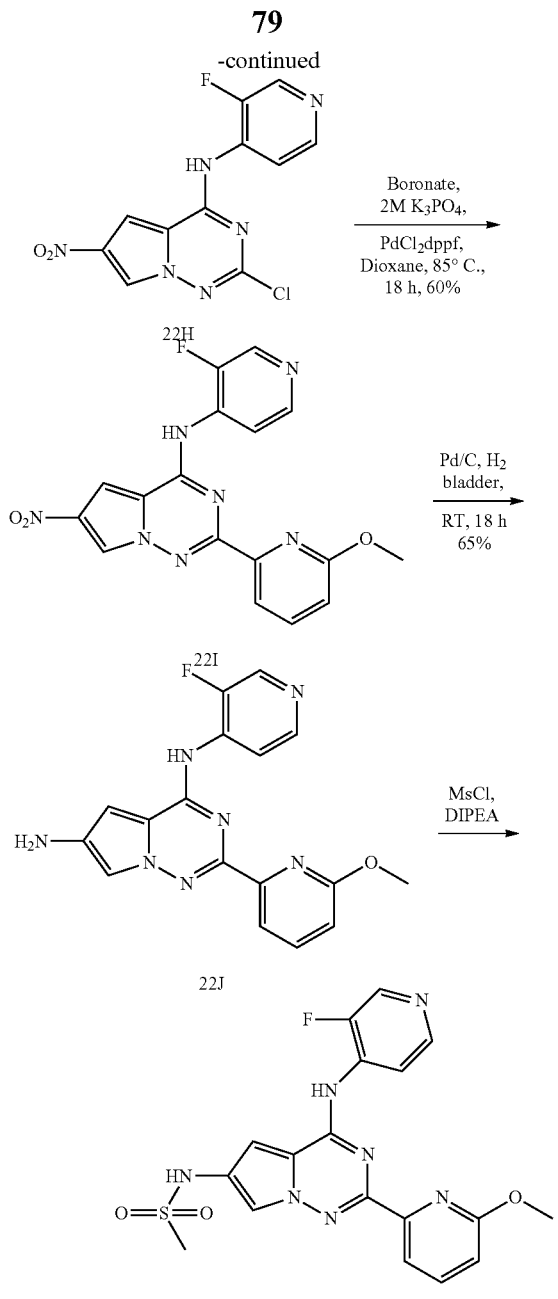

Example 22

N-{4-[(3-fluoropyridin-4-yl)amino]-2-(6-methoxy-pyridin-2-yl)pyrrolo[2,1-f][1,2,4]triazin-6-yl}methanesulfonamide

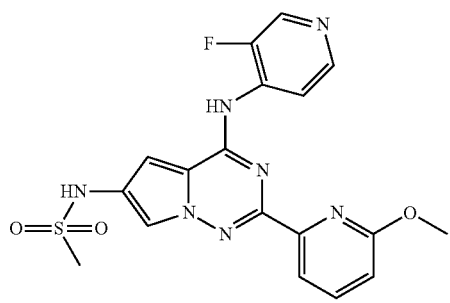 [SMILES: COc1cccc(-c2nc(Nc3ccncc3F)c3cc(NS(C)(=O)=O)cn3n2)n1]

Intermediate 22B: 2,2,2-trichloro-1-(4-nitro-1H-pyrrol-2-yl)ethanone

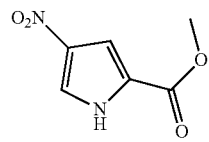

In a 500 mL flask, was taken 2,2,2-trichloro-1-(1H-pyrrol-2-yl)ethanone (10 g, 47.1 mmol) in acetin anhydride (50 mL, 530 mmol) and cooled to −20° C. Nitric acid (5 mL, 78 mmol) was added drop wise to the cooled solution. The reaction mixture was slowly brought to room temperature and stirred for 2 h. An aliquot of the reaction mixture was diluted with methanol and analyzed by LCMS to ensure complete conversion. The reaction mixture was poured into ice and extracted with ethyl acetate. The organic layer was washed with brine, dried over sodium sulfate and concentrated. The crude residue was purified by silica gel column chromatography using 20-30% ethyl acetate in hexane to get 2,2,2-trichloro-1-(4-nitro-1H-pyrrol-2-yl)ethanone (22 g, 85 mmol, 61.1% yield) as yellow solid.
LCMS m/z 256.8 (M+H); rt 3.88 min; Conditions E Intermediate 22C: methyl 4-nitro-1H-pyrrole-2-carboxylate

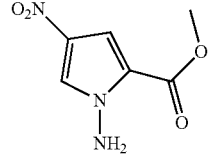

To a 250 mL flask was added 2,2,2-trichloro-1-(4-nitro-1H-pyrrol-2-yl)ethanone (8 g, 31.1 mmol), DMAP (0.759 g, 6.21 mmol), MeOH (80 mL) and heated at 70° C. for 18 h. An aliquot of the reaction mixture was diluted with methanol and analyzed by LCMS to ensure complete conversion. The reaction mixture was evaporated and the residue was triturated with petroleum ether. The solid was filtered and dried under vacuum to get methyl 4-nitro-1H-pyrrole-2-carboxylate (11 g, 64.7 mmol, 79% yield) as a brown solid.
LCMS m/z 169.0 (M+H); rt 1.35 min; Conditions E Intermediate 22D: methyl 1-amino-4-nitro-1H-pyrrole-2-carboxylate

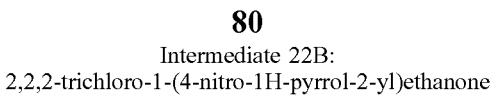

To a 250 mL flask was added methyl 4-nitro-1H-pyrrole-2-carboxylate (5.5 g, 32.3 mmol) in DMF (100 mL) and cooled to −20° C. To the resulting mixture was added LiHMDS (38.8 mL, 38.8 mmol) and stirred for 15 min. To the resulting mixture was portionwise added (aminooxy)

diphenylphosphine oxide (11.31 g, 48.5 mmol). The reaction mixture was warmed up to room temperature and stirred for 18 h. An aliquot of the reaction mixture was diluted with methanol and analyzed by LCMS to ensure complete conversion. The reaction mixture was quenched with cold water and extracted with ethyl acetate. The organic layer was washed with brine, dried over sodium sulfate and concentrated. The crude residue was purified by silica gel column chromatography using 0-15% ethyl acetate in petroleum ether to get methyl 1-amino-4-nitro-1H-pyrrole-2-carboxylate (8 g, 43.2 mmol, 66.7% yield) as a pale brown solid. LCMS m/z 184.0 (M+H); rt 1.60 min; Conditions E.

Intermediate 22E: methyl 1-[bis(methoxycarbonyl)amino]-4-nitro-1H-pyrrole-2-carboxylate

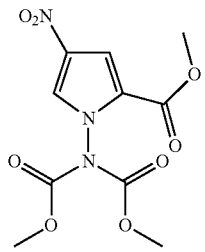 [SMILES: COC(=O)c1cc([N+](=O)[O-])cn1N(C(=O)OC)C(=O)OC]

To a 250 mL flask, was added methyl 1-amino-4-nitro-1H-pyrrole-2-carboxylate (9 g, 48.6 mmol) pyridine (11.80 mL, 146 mmol) and DCM (100 mL) and the resulting solution was cooled to 0° C. To the resulting solution was dropwise added methyl chloroformate (7.53 mL, 97 mmol) and stirred at room temperature for 18 h. An aliquot of the reaction mixture was diluted with methanol and analyzed by LCMS to ensure complete conversion. The reaction mixture was diluted with DCM. The organic layer was washed with 10% citric acid solution, water, brine, dried over sodium sulfate and concentrated to get methyl 1-[bis(methoxycarbonyl)amino]-4-nitro-1H-pyrrole-2-carboxylate (10 g, 33.2 mmol, 68.3% yield) as pale yellow solid. LCMS m/z 319.0 (M+H); rt 2.38 min; Conditions E Intermediate 22F: 6-nitropyrrolo[2,1-f][1,2,4]triazine-2,4(1H,3H)-dione

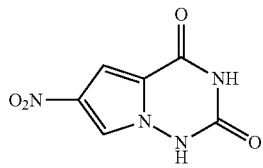 [SMILES: O=c1[nH]c(=O)c2cc([N+](=O)[O-])cn2[nH]1]

To a 250 mL RB flask was added methyl 1-((methoxycarbonyl)amino)-4-nitro-1H-pyrrole-2-carboxylate (10 g, 41.1 mmol), ammonia (aq.) (100 mL, 4621 mmol) and isopropyl alcohol (100 mL). The resulting mixture was cooled to −78° C. Ammonia gas was bubbled through the resulting solution for 10 min. The reaction mixture was heated at 120° C. in an autoclave for 18 h. An aliquot of the reaction mixture was diluted with methanol and analyzed by LCMS to ensure complete conversion. The reaction mixture was concentrated. The residue was triturated with ethyl acetate. The solid obtained was filtered, washed with ethyl acetate and dried under vacuum to get 6-nitropyrrolo[2,1-f][1,2,4]triazine-2,4(1H,3H)-dione (7 g, 35.7 mmol, 87% yield) as a brown solid. LCMS m/z 195.0 (M+H); rt 0.86 min; Conditions E.

Intermediate 22G: 2,4-dichloro-6-nitropyrrolo[2,1-f][1,2,4]triazine

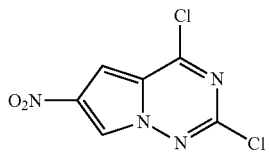 [SMILES: O=[N+]([O-])c1cc2c(Cl)nc(Cl)nn2c1]

To a 250 mL flask was added 6-nitropyrrolo[2,1-f][1,2,4]triazine-2,4(1H,3H)-dione (7 g, 35.7 mmol) triethylamine hydrochloride (14.74 g, 107 mmol), POCl₃ (70 mL, 751 mmol) and heated at 120° C. for 18 h. An aliquot of the reaction mixture was diluted with methanol and analyzed by LCMS to ensure complete conversion. The reaction mixture was concentrated to remove the POCl₃. The residue was taken in ethyl acetate and the pH was adjusted to 8 by the addition of 10% sodium bicarbonate solution under constant stirring. The organic layer was separated and washed with water, brine, dried over anhydrous sodium sulfate and concentrated. The crude residue was purified by silica gel column chromatography using 0-5% ethylacetate in hexane to get 2,4-dichloro-6-nitropyrrolo[2,1-f][1,2,4]triazine (4 g, 17.17 mmol, 48.1% yield) as yellow solid. LCMS m/z 213.0 (M+H); rt 2.3 min; Conditions E Intermediate 22H: 2-chloro-N-(3-fluoropyridin-4-yl)-6-nitropyrrolo[2,1-f][1,2,4]triazin-4-amine

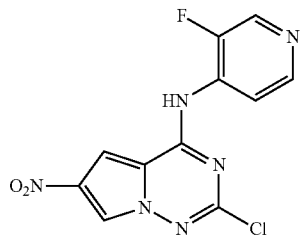 [SMILES: O=[N+]([O-])c1cc2c(Nc3ccncc3F)nc(Cl)nn2c1]

To a 100 mL flask was added 2,4-dichloro-6-nitropyrrolo[2,1-f][1,2,4]triazine (1 g, 4.29 mmol) 3-fluoropyridin-4-amine (0.481 g, 4.29 mmol), THF (20 mL) and stirred at room temperature for 1 h. An aliquot of the reaction mixture was diluted with methanol and analyzed by LCMS to ensure complete conversion. The reaction mixture was evaporated and the residue was basified using 10% sodium bicarbonate solution. The aqueous layer was extracted with ethyl acetate, washed with water, brine, dried over sodium sulfate and concentrated to get 2-chloro-N-(3-fluoropyridin-4-yl)-6-nitropyrrolo[2,1-f][1,2,4]triazin-4-amine (1 g, 3.24 mmol, 75% yield) as a yellow solid.

LCMS m/z 309.0 (M+H); rt 2.2 min; Conditions E.

Intermediate 22I: N-(3-fluoropyridin-4-yl)-2-(6-methoxypyridin-2-yl)-6-nitropyrrolo[2,1-f][1,2,4]triazin-4-amine

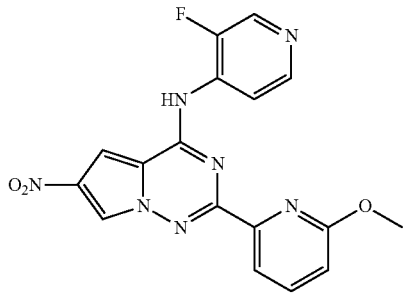 [SMILES: COc1cccc(-c2nc(Nc3ccncc3F)c3cc([N+](=O)[O-])cn3n2)n1]

To a sealed tube, was added 2-chloro-N-(3-fluoropyridin-4-yl)-6-nitropyrrolo[2,1-f][1,2,4]triazin-4-amine (200 mg, 0.648 mmol), 2-methoxy-6-(4,4,5,5-tetramethyl-1,3,2-dioxaborolan-2-yl)pyridine (183 mg, 0.778 mmol), tripotassium phosphate (2 M aqueous) (0.972 mL, 1.944 mmol) and dioxane (4 mL). The solution was degassed with argon and 1,1'-bis(diphenylphosphino)ferrocene-palladium(II)-dichloride dichloromethane complex (33.2 mg, 0.045 mmol) was added. The reaction mixture was heated at 80° C. for 18 h. An aliquot of the reaction mixture was diluted with methanol and analyzed by LCMS to ensure complete conversion. The reaction mixture was extracted with ethyl acetate, washed with water, brine, dried over sodium sulfate and concentrated. The crude residue was titurated with ethyl acetate and filtered to get N-(3-fluoropyridin-4-yl)-2-(6-methoxypyridin-2-yl)-6-nitropyrrolo[2,1-f][1,2,4]triazin-4-amine (150 mg, 0.393 mmol, 60.7% yield) as a brown solid. LCMS m/z 382.1 (M+H); rt 0.79 min; Conditions A Intermediate 22J: N4-(3-fluoropyridin-4-yl)-2-(6-methoxypyridin-2-yl)pyrrolo[2,1-f][1,2,4]triazine-4,6-diamine

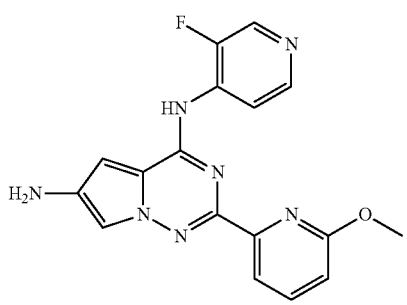

To a solution of N-(3-fluoropyridin-4-yl)-2-(6-methoxypyridin-2-yl)-6-nitropyrrolo[2,1-f][1,2,4]triazin-4-amine (150 mg, 0.393 mmol) in THF (4 mL) was added palladium on carbon (10%) (25 mg, 0.235 mmol) and the reaction mixture was hydrogenated under bladder pressure 15 psi at room temperature for 18 h. The reaction mixture was filtered through a pad of celite. The filtrate was evaporated to get N4-(3-fluoropyridin-4-yl)-2-(6-methoxypyridin-2-yl)pyrrolo[2,1-f][1,2,4]triazine-4,6-diamine (90 mg, 0.256 mmol, 65.1% yield). LCMS m/z 352.2 (M+H); rt 1.18 min; Conditions C To a solution of N4-(3-fluoropyridin-4-yl)-2-(6-methoxypyridin-2-yl)pyrrolo[2,1-f][1,2,4]triazine-4,6-diamine (10 mg, 0.028 mmol) in DCM (0.2 mL) at 0° C. was added pyridine (4.60 µl, 0.057 mmol) followed by methaneslfonyl chloride (2.66 µL, 0.034 mmol). The reaction mixture was stirred at room temperature for 2 h. The reaction mass was diluted with DCM, washed with water, brine, dried over sodium sulfate and evaporated to get the crude product that was purified by reverse phase HPLC to get Example 22 (3 mg, 24%): LCMS m/z 430.2 (M+H); rt 0.9 min; Conditions D. ¹H NMR (400 MHz, DMSO-d6) δ 10.22 (s, 1H), 9.99 (s, 1H), 8.67-8.60 (m, 2H), 8.41 (d, J=5.5 Hz, 1H), 7.89-7.76 (m, 2H), 7.74 (d, J=2.0 Hz, 1H), 7.31 (d, J=1.5 Hz, 1H), 6.93 (dd, J=1.0, 8.0 Hz, 1H), 4.00 (s, 3H), 3.04 (s, 3H).

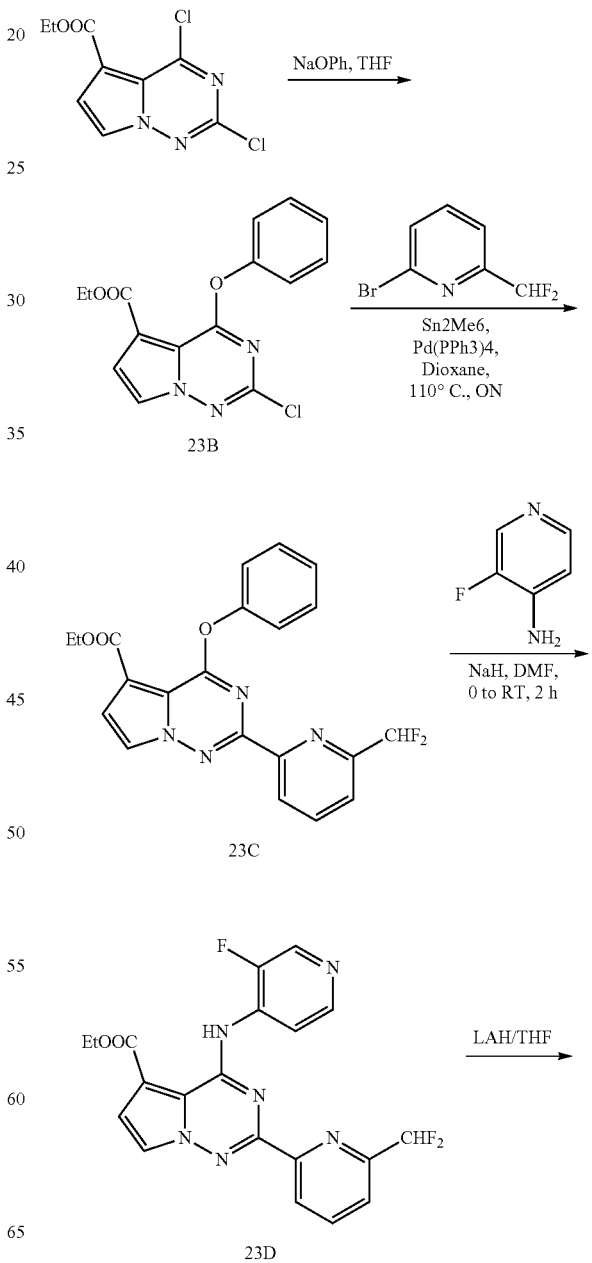

Scheme 23

85

-continued

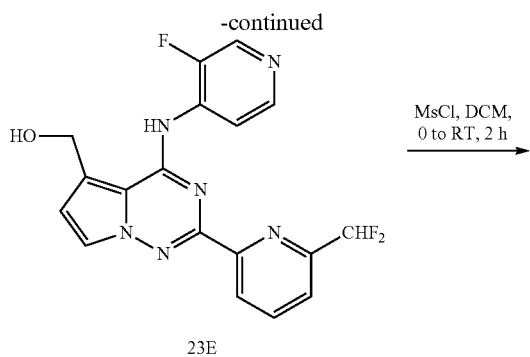

23E

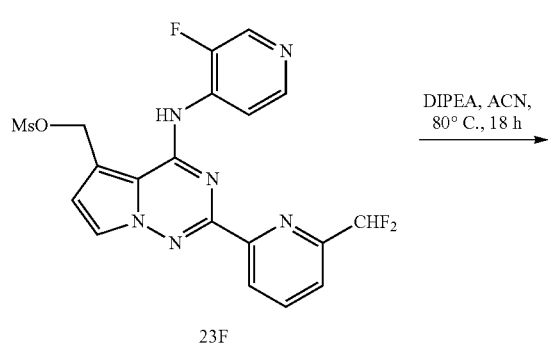

23F

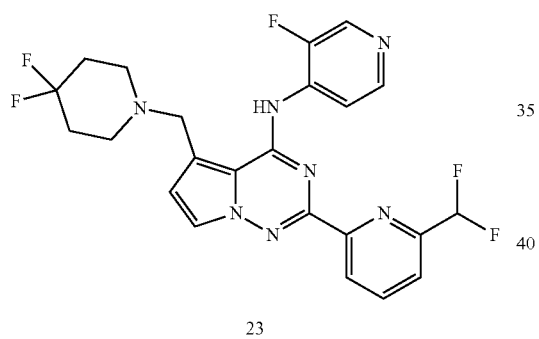

23

Example 23

N-{2-[6-(difluoromethyl)pyridin-2-yl]-5-[(4,4-difluoropiperidin-1-yl)methyl]pyrrolo[2,1-f][1,2,4]triazin-4-yl}-3-fluoropyridin-4-amine

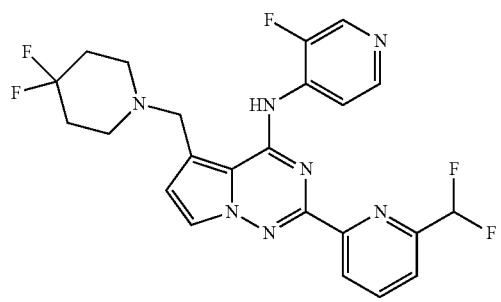 [SMILES: Fc1cnccc1Nc1nc(-c2cccc(C(F)F)n2)nn2ccc(CN3CCC(F)(F)CC3)c12]

86

Intermediate 23B: See intermediate 27B.

Intermediate 23C: ethyl 2-(6-(difluoromethyl)pyridin-2-yl)-4-phenoxypyrrolo[2,1-f][1,2,4]triazine-5-carboxylate

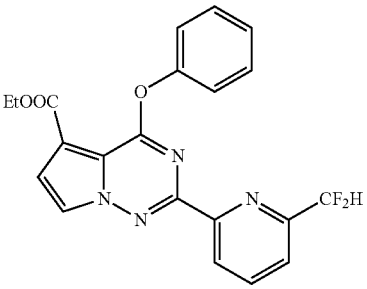 [SMILES: CCOC(=O)c1ccn2nc(-c3cccc(C(F)F)n3)nc(Oc3ccccc3)c12]

In a sealed tube, was taken ethyl 2-chloro-4-phenoxypyrrolo[2,1-f][1,2,4]triazine-5-carboxylate (0.5 g, 1.574 mmol), 2-bromo-6-(difluoromethyl)pyridine (0.192 mL, 1.574 mmol), hexamethylditin (0.326 mL, 1.574 mmol) and dioxane (15 mL). The solution was degassed with argon and tetrakis(triphenylphosphine)palladium(0)(0.182 g, 0.157 mmol) was added. The reaction mixture was stirred at 110° C. for 16 h. An aliquot of the reaction mixture was diluted with methanol and analyzed by LCMS to ensure complete conversion. The reaction mixture was partitioned between water and ethyl acetate. The organic layer was washed with brine, dried over sodium sulfate and evaporated. Crude residue was purified by silica gel column chromatography (hexane-ethyl acetate) to get ethyl 2-(6-(difluoromethyl)pyridin-2-yl)-4-phenoxypyrrolo[2,1-f][1,2,4]triazine-5-carboxylate (1.6 g, 3.90 mmol, 66.7% yield) as an off white solid. LCMS m/z 411.2 (M+H); rt 1.18 min; Conditions B.

Intermediate 23D: ethyl 2-(6-(difluoromethyl)pyridin-2-yl)-4-((3-fluoropyridin-4-yl)amino)pyrrolo[2,1-f][1,2,4]triazine-5-carboxylate

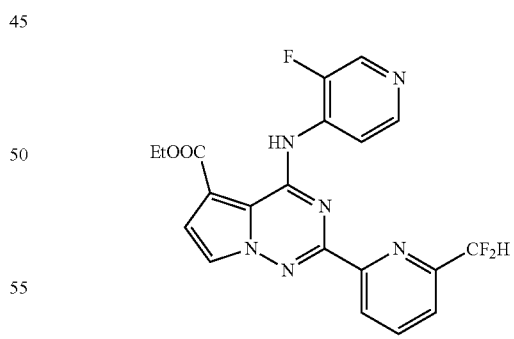

In a 50 mL flask, was taken 3-fluoropyridin-4-amine (437 mg, 3.90 mmol) in DMF (8 mL) and cooled to 0° C. Sodium hydride (94 mg, 2.339 mmol) was added to the cooled solution and stirred for 5 min. A solution of ethyl 2-(6-(difluoromethyl)pyridin-2-yl)-4-phenoxypyrrolo[2,1-f][1,2,4]triazine-5-carboxylate (800 mg, 1.949 mmol) in DMF was added drop wise and stirred at room temperature for 2 h. An aliquot of the reaction mixture was diluted with methanol and analyzed by LCMS to ensure complete conversion. The reaction mixture was poured into ice and the solid obtained was filtered, washed with water and dried to get ethyl 2-(6-(difluoromethyl)pyridin-2-yl)-4-((3-fluoropyridin-4-yl)amino)pyrrolo[2,1-f][1,2,4]triazine-5-carboxylate (720 mg, 1.681 mmol, 86% yield) as a pale yellow solid. LCMS m/z 429.1 (M+H); rt 1.19 min; Conditions B Intermediate 23E: (2-(6-(difluoromethyl)pyridin-2-yl)-4-((3-fluoropyridin-4-yl)amino)pyrrolo[2,1-f][1,2,4]triazin-5-yl)methanol

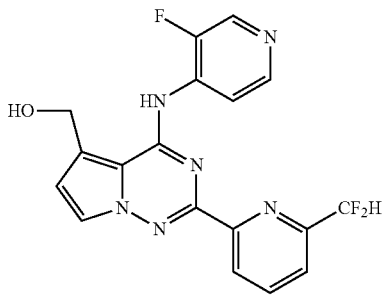 [SMILES: OCc1ccn2nc(-c3cccc(C(F)F)n3)nc(Nc3ccncc3F)c12]

In a 50 mL flask, was taken ethyl 2-(6-(difluoromethyl)pyridin-2-yl)-4-((3-fluoropyridin-4-yl)amino)pyrrolo[2,1-f][1,2,4]triazine-5-carboxylate (100 mg, 0.233 mmol) in THF (4 mL) and cooled to −78° C. LAH (0.117 mL, 0.280 mmol) was added drop wise to the cooled solution and the reaction mixture was gradually warmed up to 0° C. An aliquot of the reaction mixture was diluted with methanol and analyzed by LCMS to ensure complete conversion. The reaction mixture was cooled to −40° C. and quenched with 5 drops of ethyl acetate followed by a saturated solution of sodium sulfate. The aqueous layer was extracted with ethyl acetate. The combined organic layer was washed with water, brine, dried over sodium sulfate and evaporated to get (2-(6-(difluoromethyl)pyridin-2-yl)-4-((3-fluoropyridin-4-yl)amino)pyrrolo[2,1-f][1,2,4]triazin-5-yl)methanol (50 mg, 0.129 mmol, 55.4% yield) as a pale yellow solid. LCMS m/z 387.2 (M+H); rt 2.15 min; Conditions E.

Intermediate 23F: (2-(6-(difluoromethyl)pyridin-2-yl)-4-((3-fluoropyridin-4-yl)amino)pyrrolo[2,1-f][1,2,4]triazin-5-yl)methyl methanesulfonate

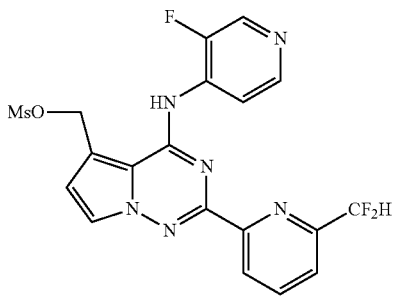 [SMILES: CS(=O)(=O)OCc1ccn2nc(-c3cccc(C(F)F)n3)nc(Nc3ccncc3F)c12]

In a 50 mL flask, was taken (2-(6-(difluoromethyl)pyridin-2-yl)-4-((3-fluoropyridin-4-yl)amino)pyrrolo[2,1-f][1,2,4]triazin-5-yl)methanol (150 mg, 0.388 mmol) and TEA (0.162 mL, 1.165 mmol) in DCM (5 mL) and cooled to 0° C. Methanesulfonyl chloride (0.061 mL, 0.777 mmol) was added drop wise to the cooled solution and the reaction was gradually warmed up to room temperature. An aliquot of the reaction mixture was diluted with methanol and analyzed by LCMS to ensure complete conversion. The reaction mixture was diluted with DCM. The organic layer was washed with water, brine, dried over sodium sulfate and evaporated to get crude (2-(6-(difluoromethyl)pyridin-2-yl)-4-((3-fluoropyridin-4-yl)amino)pyrrolo[2,1-f][1,2,4]triazin-5-yl)methyl methanesulfonate (160 mg) as a yellow solid. LCMS m/z 470.2 (M+H); rt 0.65 min; Conditions A.

Example 23 (16 mg, 15%) was synthesized employing the procedure described for Example 40 (Scheme 40): LCMS m/z 490.2 (M+H); rt 3.26 min; Conditions E. $^1$H NMR (400 MHz, DMSO-d6) δ 11.82 (s, 1H), 8.94 (dd, J=5.5, 7.5 Hz, 1H), 8.65 (d, J=3.0 Hz, 1H), 8.47 (d, J=5.5 Hz, 1H), 8.41 (d, J=7.0 Hz, 1H), 8.21 (t, J=7.8 Hz, 1H), 8.03 (d, J=2.5 Hz, 1H), 7.85 (d, J=7.5 Hz, 1H), 7.28-6.94 (m, 1H), 6.90 (d, J=2.5 Hz, 1H), 3.98 (s, 2H), 2.73 (br. s, 4H), 2.14-1.98 (m, 4H).

Scheme-24

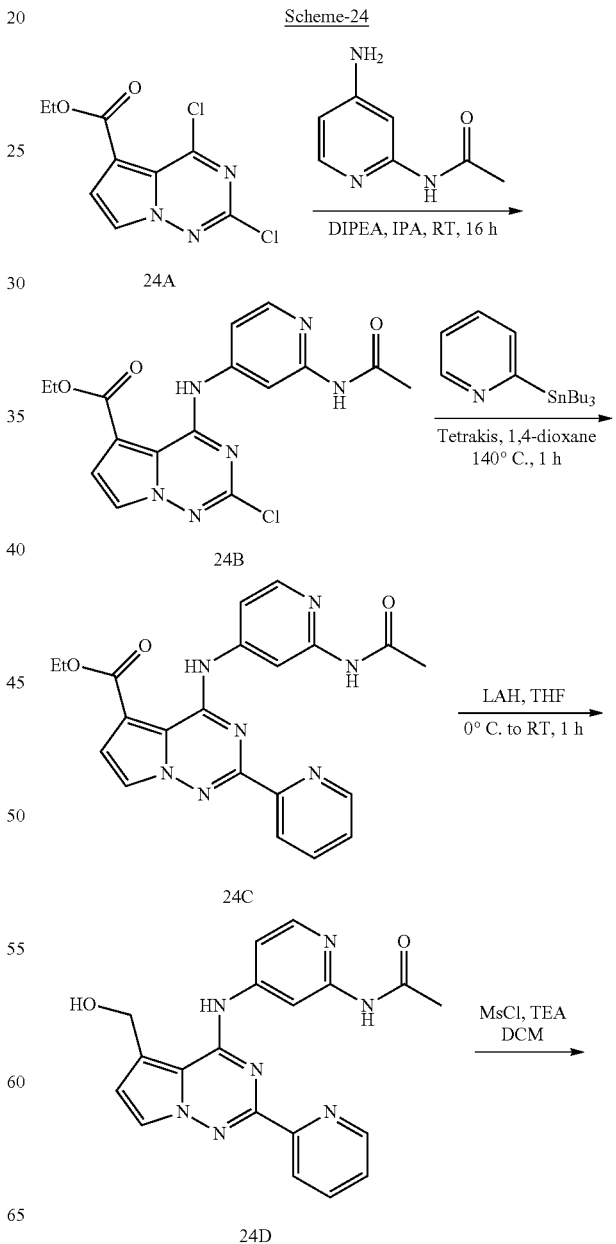

-continued

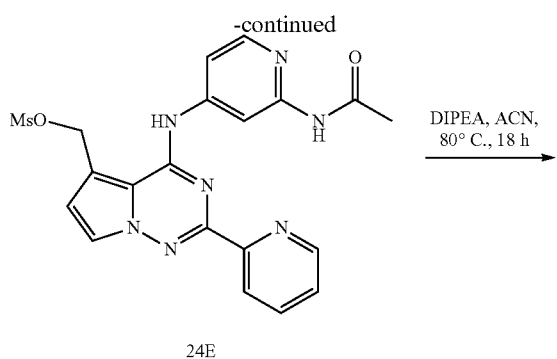

24E

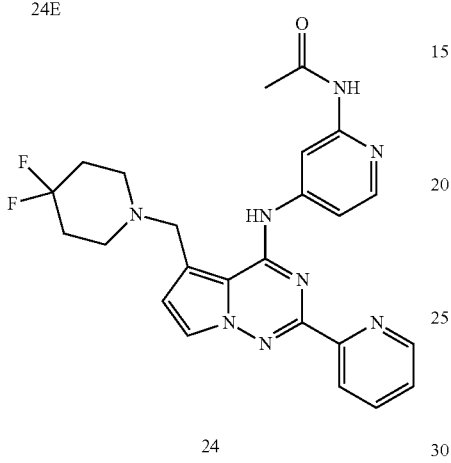

24

Example 24

N-[4-({5-[(4,4-difluoropiperidin-1-yl)methyl]-2-(pyridin-2-yl)pyrrolo[2,1-f][1,2,4]triazin-4-yl}amino)pyridin-2-yl]acetamide Intermediate 24A: Same as Intermediate 23A Intermediate-24B: ethyl 4-((2-acetamidopyridin-4-yl)amino)-2-chloropyrrolo[2,1-f][1,2,4]triazine-5-carboxylate

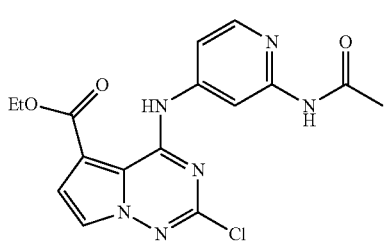 [SMILES: CCOC(=O)c1ccn2nc(Cl)nc(Nc3ccnc(NC(C)=O)c3)c12]

To a stirred solution of ethyl 2,4-dichloropyrrolo[2,1-f][1,2,4]triazine-5-carboxylate (2 g, 7.69 mmol) N-(4-aminopyridin-2-yl)acetamide (1.744 g, 11.54 mmol) in 2-propanol (20 mL) DIPEA (4.03 mL, 23.07 mmol) was added. The reaction mixture was stirred at 50° C. for 3 h. The reaction mixture was cooled to room temperature and filtered. The residue was taken in 5% methanol in DCM washed with aqueous sodium bicarbonate. The organic phase was concentrated to get ethyl 4-((2-acetamidopyridin-4-yl)amino)-2-chloropyrrolo[2,1-f][1,2,4]triazine-5-carboxylate (1.4 g, 3.74 mmol, 48.6% yield) as a white solid. LCMS m/z 375.1 (M+H); rt 1.25 min; Conditions B Intermediate 24C: ethyl 4-((2-acetamidopyridin-4-yl)amino)-2-(pyridin-2-yl)pyrrolo[2,1-f][1,2,4]triazine-5-carboxylate

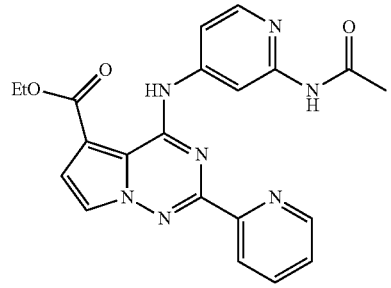 [SMILES: CCOC(=O)c1ccn2nc(-c3ccccn3)nc(Nc3ccnc(NC(C)=O)c3)c12]

To a stirred solution of ethyl 4-((2-acetamidopyridin-4-yl)amino)-2-chloropyrrolo[2,1-f][1,2,4]triazine-5-carboxylate (0.7 g, 1.868 mmol) and 2-(tributylstannyl)pyridine (0.730 mL, 2.241 mmol) in dioxane (8 mL) degassed with nitrogen, tetrakis(triphenylphosphine)palladium(0)(0.216 g, 0.187 mmol) was added and degassed for 10 minutes. The reaction mixture was heated at 140° C. for 1 h under microwave irradiation. The reaction mixture was filtered on a bed of celite. The filtrate was concentrated and purified by silica gel chromatography (DCM/methanol) to get ethyl 4-((2-acetamidopyridin-4-yl)amino)-2-(pyridin-2-yl)pyrrolo[2,1-f][1,2,4]triazine-5-carboxylate (1.0 g, 2.396 mmol, 64.1% yield) as a white solid. LCMS m/z 418.1 (M+H); rt 1.11 min; Conditions B.

Intermediate 24D: N-(4-((5-(hydroxymethyl)-2-(pyridin-2-yl)pyrrolo[2,1-f][1,2,4]triazin-4-yl)amino)pyridin-2-yl)acetamide

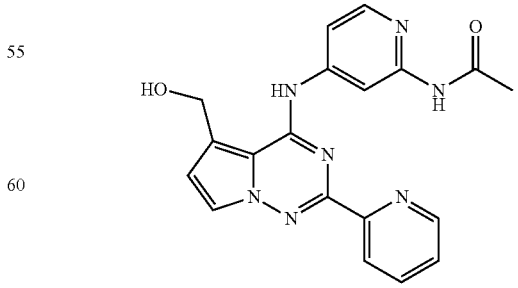

To a stirred solution of ethyl 4-((2-acetamidopyridin-4-yl)amino)-2-(pyridin-2-yl)pyrrolo[2,1-f][1,2,4]triazine-5- carboxylate (0.2 g, 0.479 mmol) in THF (20 mL) at −78° C. was dropwise added LAH (0.220 mL, 0.527 mmol) (2.4 M). The reaction mixture was warmed up to room temperature and stirred for 2 h. The reaction mixture was cooled to 0° C., quenched with water (2 mL) and 10% sodium hydroxide. The mixture was filtered on a bed of celite, dried over sodium sulphate and concentrated. The crude product was purified by silica gel chromatography (DCM/methanol) to get N-(4-((5-(hydroxymethyl)-2-(pyridin-2-yl)pyrrolo[2,1-f][1,2,4]triazin-4-yl)amino)pyridin-2-yl)acetamide (0.1 g, 0.186 mmol, 38.9% yield) as a white solid. LCMS m/z 376.2 (M+H); rt 1.25 min; Conditions E Intermediate 24E: (4-((2-acetamidopyridin-4-yl) amino)-2-(pyridin-2-yl)pyrrolo[2,1-f][1,2,4]triazin-5-yl)methyl methanesulfonate

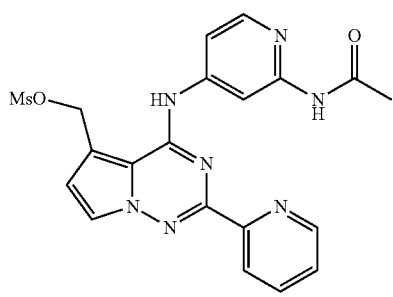 [SMILES: CC(=O)Nc1cc(Nc2nc(-c3ccccn3)nn3ccc(COS(C)(=O)=O)c23)ccn1]

To a solution of N-(4-((5-(hydroxymethyl)-2-(pyridin-2-yl)pyrrolo[2,1-f][1,2,4]triazin-4-yl)amino)pyridin-2-yl)acetamide (0.1 g, 0.266 mmol) in DCM (5 mL) at 0° C., triethylamine (0.111 mL, 0.799 mmol) was added and stirred for 5 minutes. To the resulting reaction mixture was added methanesulfonyl chloride (0.025 mL, 0.320 mmol) and warmed up to room temperature and stirred for 1 h. The reaction mixture was diluted with DCM (100 mL), washed with aqueous sodium bicarbonate, dried over sodium sulphate and concentrated to get crude (4-((2-acetamidopyridin-4-yl)amino)-2-(pyridin-2-yl)pyrrolo[2,1-f][1,2,4]triazin-5-yl)methyl methanesulfonate as a yellow oil.

Example 24 (10 mg, 8%) was synthesized employing the procedure described for Example 40 (Scheme 40): LCMS m/z 479.0 (M+H); rt 2.53 min; Conditions E. $^1$H NMR (400 MHz, DMSO-d6) δ 11.90-11.96 (m, 1H) 10.47-10.53 (m, 1H) 8.70-8.77 (m, 1H) 8.38-8.49 (m, 1H) 8.26-8.35 (m, 1H) 7.87-8.08 (m, 3H) 7.48-7.57 (m, 1H) 6.79-6.86 (m, 1H) 3.96-4.01 (m, 2H) 2.11-2.19 (m, 4H).

Scheme-25

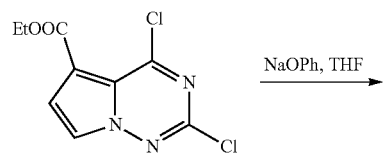

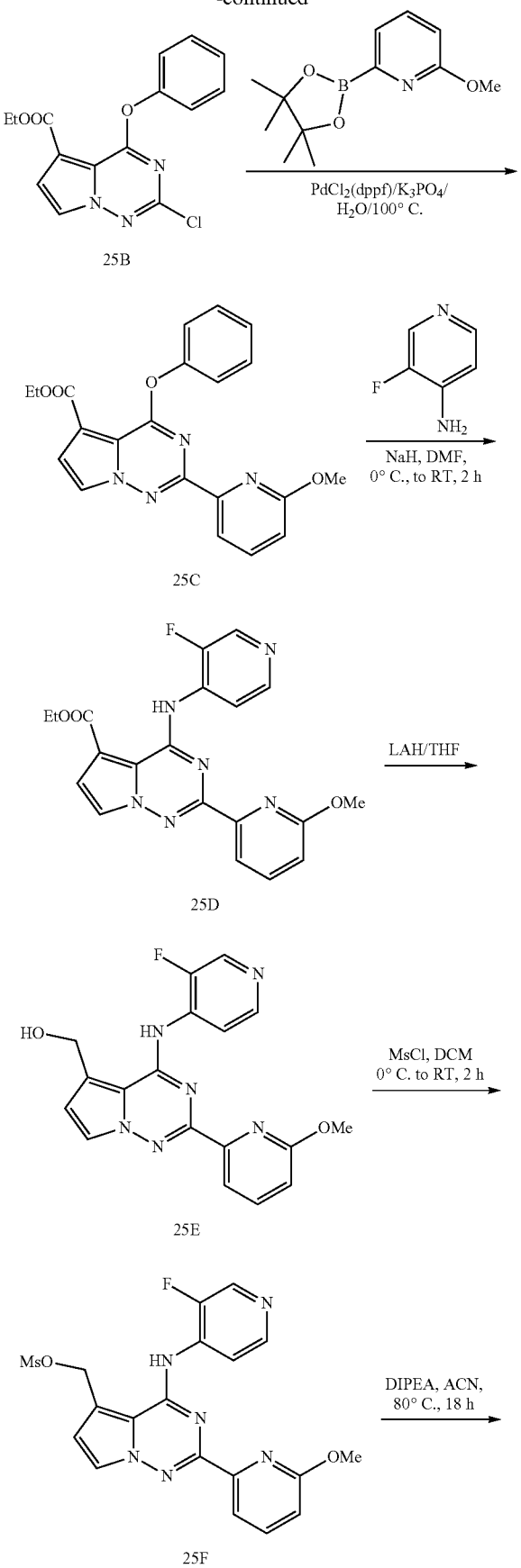

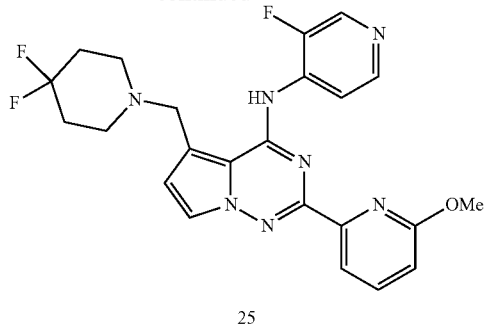

25

Example 25

N-{5-[(4,4-difluoropiperidin-1-yl)methyl]-2-(6-methoxypyridin-2-yl)pyrrolo[2,1-f][1,2,4]triazin-4-yl}-3-fluoropyridin-4-amine

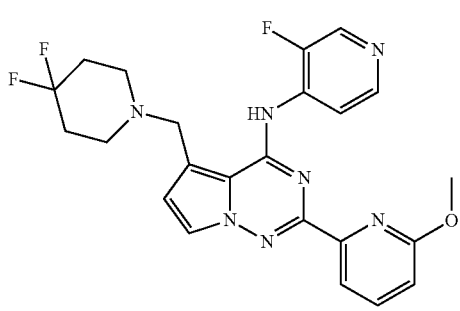 [SMILES: COc1cccc(-c2nc(Nc3ccncc3F)c3c(CN4CCC(F)(F)CC4)ccn3n2)n1]

Intermediate-25C: (ethyl 2-(6-methoxypyridin-2-yl)-4-phenoxypyrrolo[2,1-f][1,2,4]triazine-5-carboxylate)

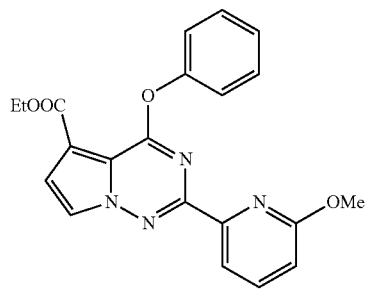 [SMILES: CCOC(=O)c1ccn2nc(-c3cccc(OC)n3)nc(Oc3ccccc3)c12]

To a scintillation vial was added ethyl 2-chloro-4-phenoxypyrrolo[2,1-f][1,2,4]triazine-5-carboxylate (0.35 g, 1.102 mmol), 2-methoxy-6-(4,4,5,5-tetramethyl-1,3,2-dioxaborolan-2-yl)pyridine (0.311 g, 1.322 mmol), tripotassium phosphate (0.701 g, 3.30 mmol), 1,1'-bis(diphenylphosphino)ferrocene-palladium(II)-dichloride dichloromethane complex (0.045 g, 0.055 mmol), dioxane (2 mL) and water (0.2 mL).

The resulting reaction mixture was degassed with nitrogen. The vial was capped with a pressure-safe septum cap and heated at 100° C. for 18 h. An aliquot of the reaction mixture was analyzed by LCMS to ensure completion of reaction. The reaction mixture was concentrated. The residue was dissolved in ethylacetate and filtered through celite and concentrated. The crude product was purified by silica gel chromatography using 0-20% ethyl acetate in hexanes to get intermediate 21B (0.3 g, 0.768 mmol, 69% yield) as a off white solid. LCMS m/z 337.0 (M+H); rt 3.40 min; Conditions E.

Intermediate-25D: (ethyl 4-((3-fluoropyridin-4-yl)amino)-2-(6-methoxypyridin-2-yl)pyrrolo[2,1-f][1,2,4]triazine-5-carboxylate)

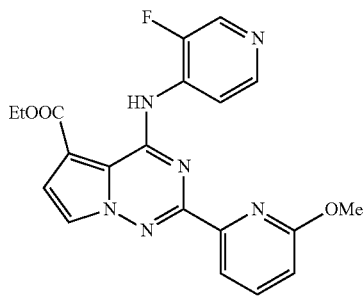 [SMILES: CCOC(=O)c1ccn2nc(-c3cccc(OC)n3)nc(Nc3ccncc3F)c12]

To a solution of 3-fluoropyridin-4-amine (0.103 g, 0.922 mmol) in DMF (5 mL) at 0° C. was added sodium hydride (0.092 g, 2.305 mmol) and stirred for 15 min. To the resulting reaction mixture was added ethyl 2-(6-methoxypyridin-2-yl)-4-phenoxypyrrolo[2,1-f][1,2,4]triazine-5-carboxylate (0.3 g, 0.768 mmol). The reaction mixture was warmed up to room temperature and stirred for 3 h. An aliquot of the reaction mixture was analyzed by LCMS to ensure completion of reaction. Reaction mixture was quenched with water and extracted with ethylacetate. The organic layer was separated, washed with water, brine, dried over sodium sulfate and concentrated. The crude product was purified by silica gel chromatography using 0-5% methanol in chloroform to get intermediate 25D (0.1 g, 0.245 mmol, 31.9%) as an off white solid. LCMS m/z 337.0 (M+H); rt 3.40 min; Conditions E.

Intermediate-25E: (ethyl 4-((3-fluoropyridin-4-yl)amino)-2-(6-methoxypyridin-2-yl)pyrrolo[2,1-f][1,2,4]triazine-5-carboxylate)

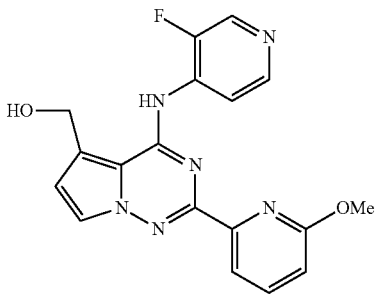 [SMILES: COc1cccc(-c2nc(Nc3ccncc3F)c3c(CO)ccn3n2)n1]

To a solution of ethyl 4-((3-fluoropyridin-4-yl)amino)-2-(6-methoxypyridin-2-yl)pyrrolo[2,1-f][1,2,4]triazine-5-carboxylate (0.3 g, 0.735 mmol) in THF (10 mL) at −78° C. was added LAH (0.918 mL, 1.836 mmol) and stirred at room temperature for 1 h. the reaction mixture was quenched with water and sodium sulfate, and extracted with ethylacetate. The organic layer was separated, washed with water, brine, dried over sodium sulfate and concentrated to get intermediate 25E (0.15 g, 0.409 mmol, 55.7%): LCMS m/z 367.2 (M+H); rt 2.26 min; Conditions E.

Intermediate-25F: (ethyl 4-((3-fluoropyridin-4-yl)amino)-2-(6-methoxypyridin-2-yl)pyrrolo[2,1-f][1,2,4]triazine-5-carboxylate)

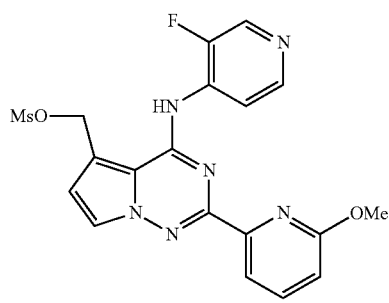 [SMILES: COc1cccc(-c2nc(Nc3ccncc3F)c3c(COS(C)(=O)=O)ccn3n2)n1]

To a solution of (4-((3-fluoropyridin-4-yl)amino)-2-(6-methoxypyridin-2-yl)pyrrolo[2,1-f][1,2,4]triazin-5-yl)methanol (0.1 g, 0.273 mmol) in DCM (2 mL) was added methanesulfonyl chloride (0.032 mL, 0.409 mmol) and triethylamine (0.076 mL, 0.546 mmol). The reaction mixture was stirred at room temperature for 2 h. An aliquot of the reaction mixture was analyzed by LCMS to ensure completion of reaction. The reaction mixture was diluted with DCM. The organic layer was washed with water, brine, dried over $Na_2SO_4$ and evaporated to get crude 7F (0.12 g). The reaction mixture was concentrated to get 7F (0.12 g, 0.270 mmol, 99%). LCMS m/z 450.3 (M+H5); rt 0.69 min; Conditions A.

Example 25 (4 mg, 12%) was synthesized employing the procedure described for Example 40 (Scheme 40): LCMS m/z 470.3 (M+H); rt 2.30 min; Conditions C. $^1$H NMR (400 MHz, DMSO-d6) δ 9.28 (dd, J=5.5, 7.0 Hz, 1H), 8.64 (s, 1H), 8.40 (s, 1H), 7.96 (s, 1H), 7.88 (d, J=3.5 Hz, 2H), 6.98 (d, J=4.0 Hz, 1H), 6.87 (s, 1H), 4.06 (s, 3H), 3.97 (s, 2H), 2.80-2.65 (m, 3H), 2.33 (t, J=2.0 Hz, 1H), 2.13-2.00 (m, 4H).

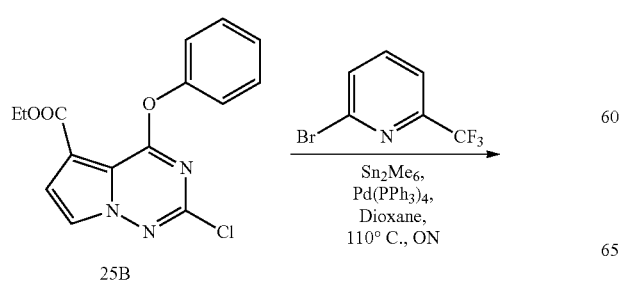

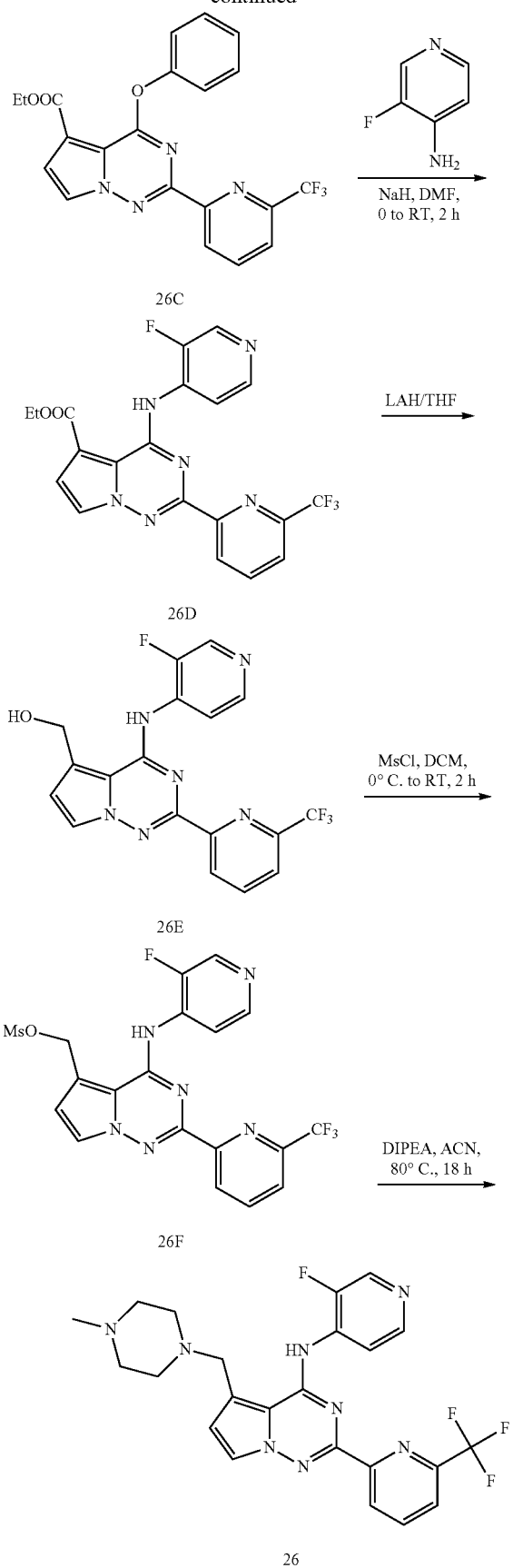

Example 26

3-fluoro-N-{5-[(4-methylpiperazin-1-yl)methyl]-2-[6-(trifluoromethyl)pyridin-2-yl]pyrrolo[2,1-f][1,2,4]triazin-4-yl}pyridin-4-amine

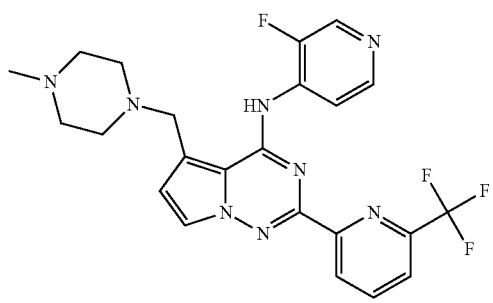 [SMILES: CN1CCN(Cc2ccn3nc(-c4cccc(C(F)(F)F)n4)nc(Nc4ccncc4F)c23)CC1]

Intermediate 26C: (ethyl 2-(6-methoxypyridin-2-yl)-4-phenoxypyrrolo[2,1-f][1,2,4]triazine-5-carboxylate)

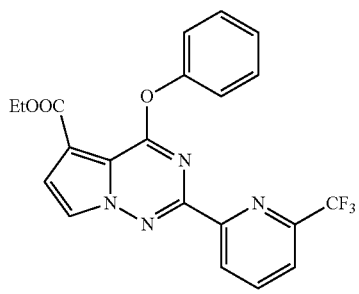 [SMILES: CCOC(=O)c1ccn2nc(-c3cccc(C(F)(F)F)n3)nc(Oc3ccccc3)c12]

To a 40 mL scintillation vial was added 2-bromo-6-(trifluoromethyl)pyridine (2 g, 8.85 mmol), hexamethylditin (2.75 mL, 13.27 mmol), tetrakis(triphenylphosphine)palladium(0) (0.511 g, 0.442 mmol) and dioxane (15 mL). The resulting reaction mixture was degassed with nitrogen. The vial was capped with a pressure-safe septum cap and heated at 100° C. for 4 h. The resulting mixture containing the stannyl intermediate was added to a solution of ethyl 2-chloro-4-phenoxypyrrolo[2,1-f][1,2,4]triazine-5-carboxylate (0.6 g, 1.888 mmol) and tetrakis(triphenylphosphine)palladium(0) (0.511 g, 0.442 mmol). The resulting reaction mixture was degassed with nitrogen. The vial was capped with a pressure-safe septum cap and heated at 100° C. for 18 h. An aliquot of the reaction mixture was analyzed by LCMS to ensure completion of reaction. The reaction mixture was concentrated. To the residue was added ethyl acetate and filtered through celite. The filtrate was concentrated and purified by silica gel chromatography using 0-20% ethyl acetate in hexanes to get intermediate 7C (0.3 g, 0.700 mmol, 37.1%) as an off-white solid. LCMS m/z 429.0 (M+H); rt 3.46 min; Conditions E Intermediate 26D: (ethyl 4-((3-fluoropyridin-4-yl)amino)-2-(6-methoxypyridin-2-yl)pyrrolo[2,1-f][1,2,4]triazine-5-carboxylate)

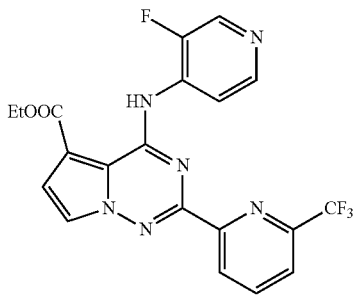 [SMILES: CCOC(=O)c1ccn2nc(-c3cccc(C(F)(F)F)n3)nc(Nc3ccncc3F)c12]

To a solution of 3-fluoropyridin-4-amine (0.236 g, 2.101 mmol) in DMF (5 mL) at 0° C. was added sodium hydride (0.056 g, 1.401 mmol) and stirred for 15 min. To the resulting reaction mixture was added ethyl 4-phenoxy-2-(6-(trifluoromethyl)pyridin-2-yl)pyrrolo[2,1-f][1,2,4]triazine-5-carboxylate (0.3 g, 0.700 mmol) and stirred at room temperature for 3 h. An aliquot of the reaction mixture was analyzed by LCMS to ensure completion of reaction. To the reaction mixture was added water, stirred and filtered to get the intermediate 7D (0.28 g, 0.627 mmol, 90%) as an off white solid. LCMS m/z 447.2 (M+H); rt 3.86 min; Conditions E.

Intermediate 26E: Intermediate 7E (ethyl 4-((3-fluoropyridin-4-yl)amino)-2-(6-methoxypyridin-2-yl)pyrrolo[2,1-f][1,2,4]triazine-5-carboxylate)

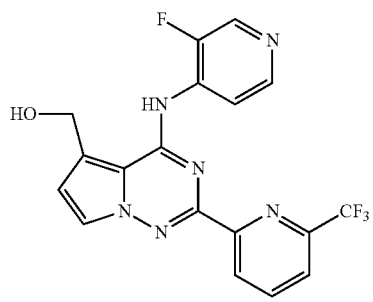 [SMILES: OCc1ccn2nc(-c3cccc(C(F)(F)F)n3)nc(Nc3ccncc3F)c12]

To a solution of ethyl 4-((3-fluoropyridin-4-yl)amino)-2-(6-(trifluoromethyl)pyridin-2-yl)pyrrolo[2,1-f][1,2,4]triazine-5-carboxylate (0.3 g, 0.672 mmol) in THF (10 mL) at −78° C. was added LAH (0.739 mL, 0.739 mmol). The reaction mixture was stirred at room temperature for 1 h. the reaction mixture was quenched with water and sodium sulfate, and extracted with ethylacetate. The organic layer was separated and washed with water, brine, dried over sodium sulfate and concentrated to get 7E (0.15 g, 0.409 mmol, 55.7%) LCMS m/z 405.2 (M+H); rt 2.52 min; Conditions E.

Intermediate 26F: (ethyl 4-((3-fluoropyridin-4-yl)amino)-2-(6-methoxypyridin-2-yl)pyrrolo[2,1-f][1,2,4]triazine-5-carboxylate)

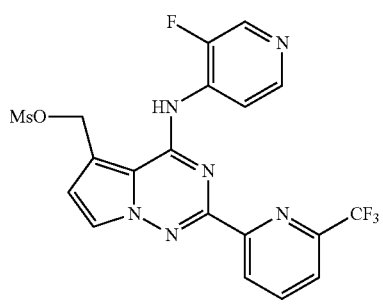 [SMILES: CS(=O)(=O)OCc1ccn2nc(-c3cccc(C(F)(F)F)n3)nc(Nc3ccncc3F)c12]

To a solution of (4-((3-fluoropyridin-4-yl)amino)-2-(6-(trifluoromethyl)pyridin-2-yl)pyrrolo[2,1-f][1,2,4]triazin-5-yl)methanol (0.1 g, 0.247 mmol) in DCM (2 mL) was added methanesulfonyl chloride (0.029 mL, 0.371 mmol) and triethylamine (0.069 mL, 0.495 mmol). The reaction mixture was stirred at room temperature for 2 h. An aliquot of the reaction mixture was analyzed by LCMS to ensure completion of reaction. The reaction mixture was diluted with DCM. The organic layer was washed with water, brine, dried over Na$_2$SO$_4$ and evaporated to get crude 7F (0.12 g). LCMS m/z 488.1 (M+5H); rt 0.68 min; Conditions A.

Example 26 (12 mg, 38%) was synthesized employing the procedure described for Example 40 (Scheme 40): LCMS m/z 487.2 (M+H); rt 3.56 min; Conditions E. $^1$H NMR (400 MHz, DMSO-d6) δ 8.9 (br s, 1H), 8.65-8.66 (d, J=3.0 Hz, 1H), 8.50-8.52 (d, J=5.5 Hz, 1H), 8.40-8.42 (d, J=5.5 Hz, 1H), 8.27-8.32 (m, 1H), 8.03-8.05 (m, 2H), 3.90 (s, 2H), 2.69 (s, 3H), 2.30-2.40 (m, 5H), 2.07-2.25 (m, 3H).

Scheme-27

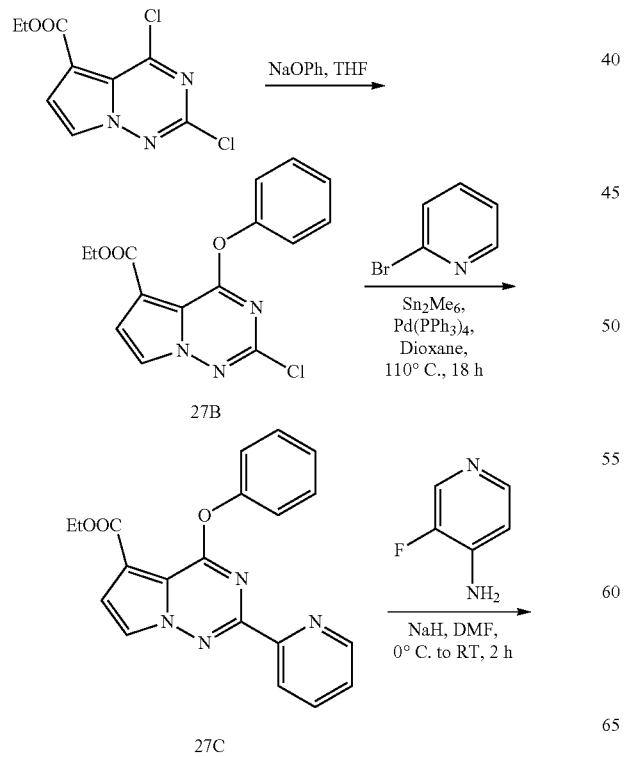

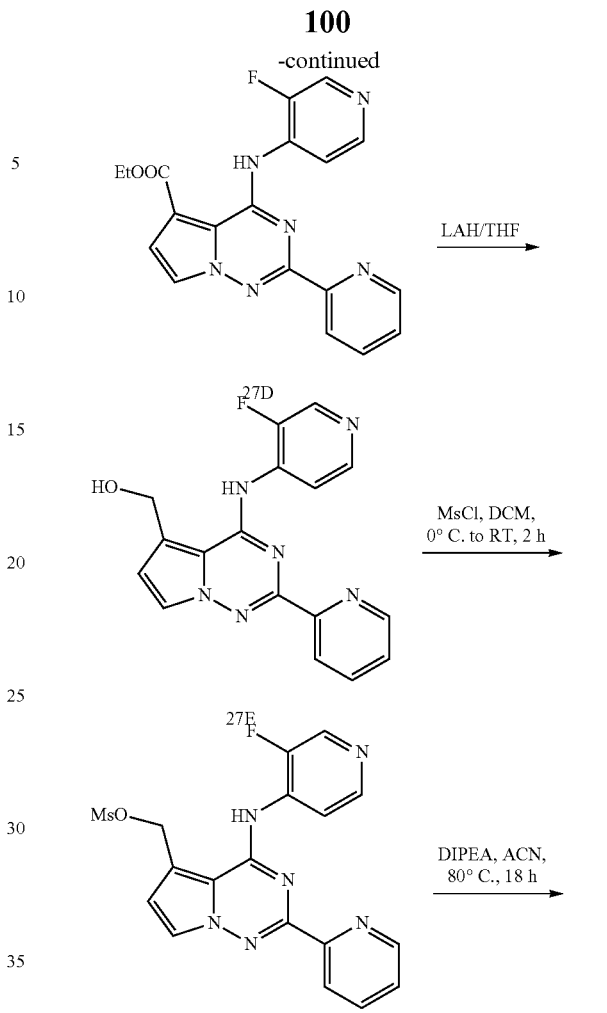

Example 27
N-{5-[(4,4-difluoropiperidin-1-yl)methyl]-2-(pyridin-2-yl)pyrrolo[2,1-f][1,2,4]triazin-4-yl}-3-fluoropyridin-4-amine

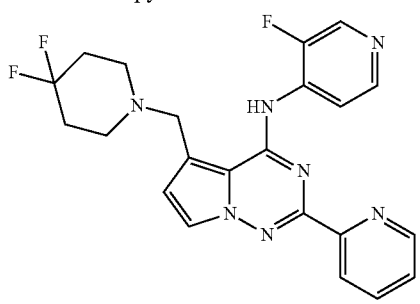

Intermediate-27B: ethyl 2-chloro-4-phenoxypyrrolo[2,1-f][1,2,4]triazine-5-carboxylate

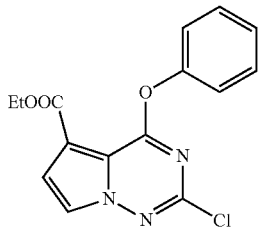 [SMILES: CCOC(=O)c1ccn2nc(Cl)nc(Oc3ccccc3)c12]

To a flask was added sodium phenolate (0.491 g, 4.23 mmol), ethyl 2,4-dichloropyrrolo[2,1-f][1,2,4]triazine-5-carboxylate (1.0 g, 3.85 mmol) and tetrahydrofuran (20 mL). The reaction mixture was stirred at room temperature for 3 h. The reaction mixture was concentrated under reduced pressure. To the crude product was added water (300 mL), stirred for 20 min and filtered to get ethyl 2-chloro-4-phenoxypyrrolo[2,1-f][1,2,4]triazine-5-carboxylate (0.5 g, 1.558 mmol, 40.5% yield) as a brown solid. LCMS m/z 318.0 (M+H); rt 3.129 min; Conditions E. $^1$H NMR: (400 MHz, DMSO-d6) δ 8.16 (d, J=3.0 Hz, 1H), 7.59-7.49 (m, 2H), 7.40-7.30 (m, 4H), 4.28 (q, J=7.0 Hz, 2H), 1.29-1.19 (m, 3H).

Intermediate-27C: ethyl 4-phenoxy-2-(pyridin-2-yl)pyrrolo[2,1-f][1,2,4]triazine-5-carboxylate

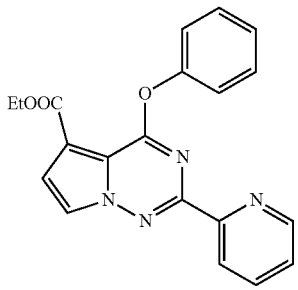 [SMILES: CCOC(=O)c1ccn2nc(-c3ccccn3)nc(Oc3ccccc3)c12]

To a stirred solution ethyl 2-chloro-4-phenoxypyrrolo[2,1-f][1,2,4]triazine-5-carboxylate (0.4 g, 1.259 mmol) in dioxane (10 mL) was added 2-(tributylstannyl)pyridine (0.556 g, 1.511 mmol). The reaction mixture was degassed with nitrogen for 10 min followed by the addition of tetrakis(triphenylphosphine)palladium(0) (0.145 g, 0.126 mmol). The reaction mixture was degassed for an additional 10 min and then heated at 110° C. for 18 h. The reaction was monitored by LC-MS. The reaction mixture was quenched with ice cold water (50 mL) and was extracted with ethyl acetate (3×100 mL). The combined organic layer was dried over anhydrous sodium sulfate, filtered and evaporated under reduced pressure to get crude (0.54 g). The crude compound was purified by silica gel chromatography (ethyl acetate/petroleum ether) to get ethyl 4-phenoxy-2-(pyridin-2-yl)pyrrolo[2,1-f][1,2,4]triazine-5-carboxylate (0.32 g, 0.861 mmol, 68.4% yield) as a pale yellow solid. LCMS m/z 361.0 (M+H); rt 2.84 min; Conditions C

Intermediate-27D: ethyl 4-((3-fluoropyridin-4-yl)amino)-2-(pyridin-2-yl)pyrrolo[2,1-f][1,2,4]triazine-5-carboxylate

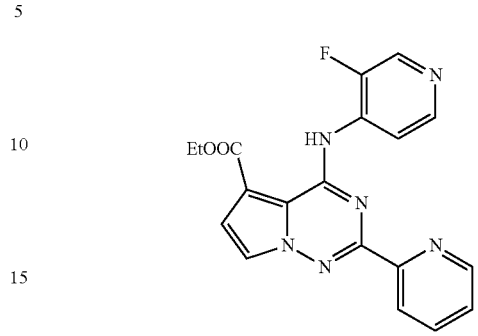

To a solution of 3-fluoropyridin-4-amine (0.047 g, 0.416 mmol) in DMF (5 mL) at 0° C. was added sodium hydride (0.015 g, 0.624 mmol) and stirred for 10 min. To the resulting reaction mixture was added ethyl 4-phenoxy-2-(pyridin-2-yl)pyrrolo[2,1-f][1,2,4]triazine-5-carboxylate (0.15 g, 0.416 mmol). The reaction mixture was stirred at room temperature for 1 h. The reaction was monitored by LC-MS. The reaction mixture was quenched with ice cold water (100 mL) and stirred for 10 min. The precipitate formed was filtered and dried to get ethyl 4-((3-fluoropyridin-4-yl)amino)-2-(pyridin-2-yl)pyrrolo[2,1-f][1,2,4]triazine-5-carboxylate (0.075 g, 0.176 mmol, 42.4% yield) as a brown solid. LCMS m/z 379.0 (M+H); rt 3.18 min; Conditions C.

Intermediate-27E: (4-((3-fluoropyridin-4-yl)amino)-2-(pyridin-2-yl)pyrrolo[2,1-f][1,2,4]triazin-5-yl)methanol

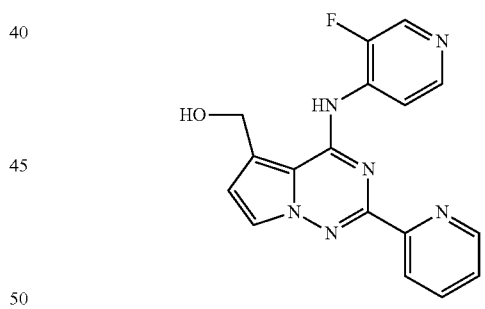

To a solution of ethyl 4-((3-fluoropyridin-4-yl)amino)-2-(pyridin-2-yl)pyrrolo[2,1-f][1,2,4]triazine-5-carboxylate (0.3 g, 0.793 mmol) in tetrahydrofuran (5 mL) at 0° C. was added LiAlH4 (1.189 mL, 2.379 mmol). The reaction mixture was gradually warmed up to room temperature and stirring was continued for 3 hours. The reaction was monitored by LC-MS. The reaction mixture was quenched with ice cold water (50 mL) and 1.5 N aqueous sodium hydroxide (20 mL). The reaction mixture was evaporated under reduced pressure and extracted with ethyl acetate (3×100 mL). The combined organic layer was dried over anhydrous sodium sulfate and evaporated under reduced pressure to get (4-((3-fluoropyridin-4-yl)amino)-2-(pyridin-2-yl)pyrrolo[2,1-f][1,2,4]triazin-5-yl)methanol (0.24 g, 0.592 mmol, 74.7% yield) as a yellow solid. LCMS m/z 337.0 (M+H); rt 1.68 min; Conditions C Intermediate-27F: (4-((3-fluoropyridin-4-yl)amino)-2-(pyridin-2-yl)pyrrolo[2,1-f][1,2,4]triazin-5-yl)methyl methanesulfonate

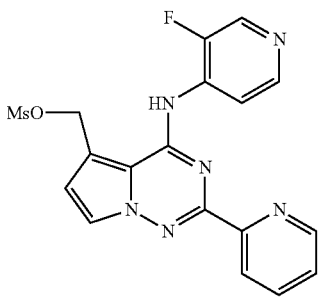 [SMILES: CS(=O)(=O)OCc1ccn2nc(-c3ccccn3)nc(Nc3ccncc3F)c12]

To a solution of (4-((3-fluoropyridin-4-yl)amino)-2-(pyridin-2-yl)pyrrolo[2,1-f][1,2,4]triazin-5-yl)methanol (0.24 g, 0.714 mmol) in DCM (6 mL) was added triethylamine (0.298 mL, 2.141 mmol) and methanesulfonyl chloride (0.067 mL, 0.856 mmol). The reaction mixture was stirred at room temperature for 2 h. The reaction was monitored by LC-MS. Reaction mixture was quenched with ice cold water (20 mL) and was extracted with ethyl acetate (3×50 mL). The combined organic layer was dried over anhydrous sodium sulfate, filtered and evaporated under reduced pressure to get crude product (250 mg) as a brown gum, LCMS m/z 420.0 (M+Li); rt 2.46 min; Conditions E.

Example 27 (20 mg, 18%) was synthesized employing the procedure described for Example 19 (Scheme 19): LCMS m/z 440.2 (M+H); rt 2.85 min; Conditions E. $^1$H NMR: (400 MHz, Methanol-d4) δ 2.06-2.16 (m, 4H) 2.70-2.92 (m, 4H) 4.00 (s, 2H) 6.79-6.89 (m, 1H) 7.52-7.62 (m, 1H) 7.82-7.90 (m, 1H) 7.99-8.10 (m, 1H) 8.34-8.47 (m, 2H) 8.52-8.57 (m, 1H) 8.69-8.76 (m, 1H) 8.89-8.99 (m, 1H).

Scheme 28

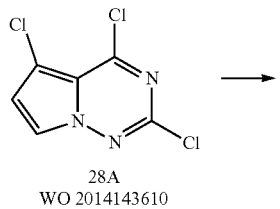

28A
WO 2014143610

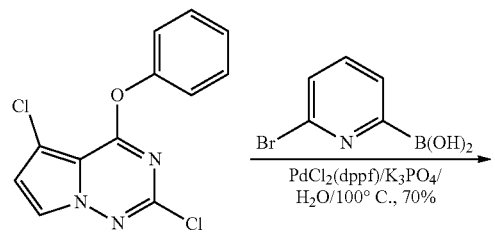

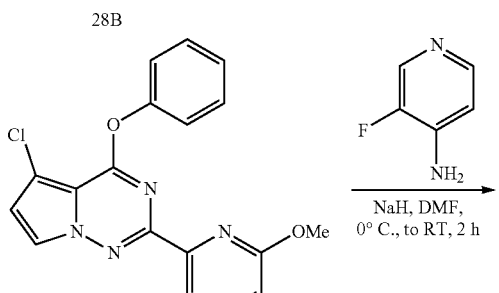

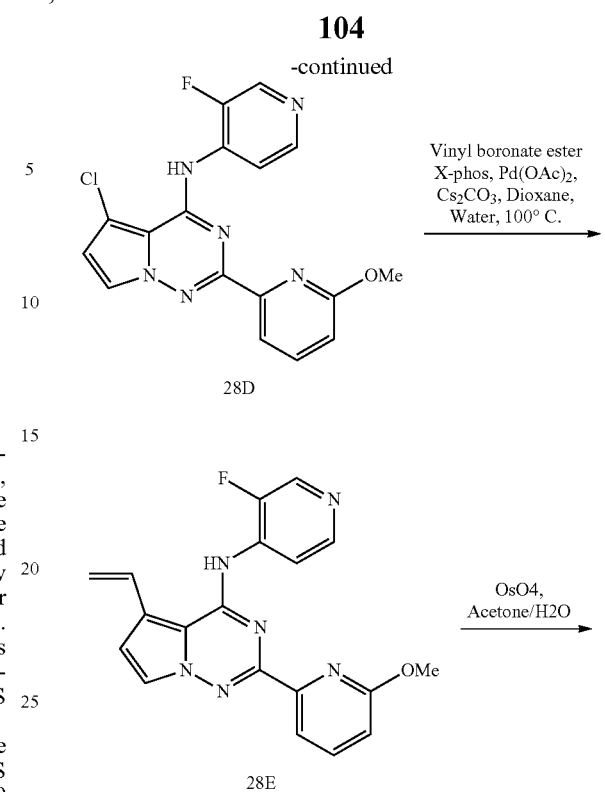

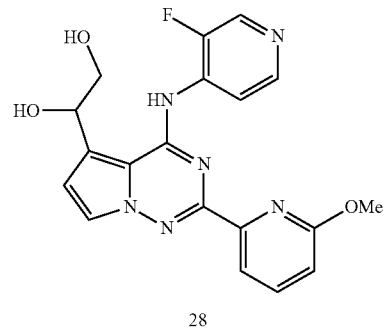

Example 28

1-{4-[(3-fluoropyridin-4-yl)amino]-2-(6-methoxypyridin-2-yl)pyrrolo[2,1-f][1,2,4]triazin-5-yl}ethane-1,2-diol

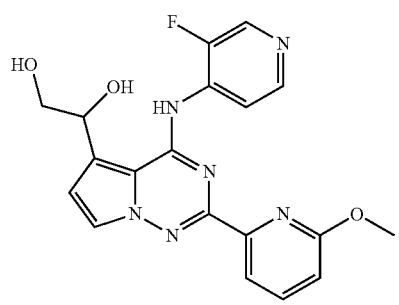 [SMILES: COc1cccc(-c2nc(Nc3ccncc3F)c3c(C(O)CO)ccn3n2)n1]

Intermediate 28B: 2,5-dichloro-4-phenoxypyrrolo[2,1-f][1,2,4]triazine

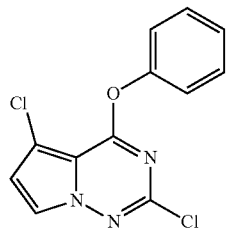 [SMILES: Clc1nc(Oc2ccccc2)c2c(Cl)ccn2n1]

Sodium phenolate (2.87 g, 24.72 mmol) was portionwise added to a stirred solution of 2,4,5-trichloropyrrolo[2,1-f][1,2,4]triazine (5.00 g, 22.48 mmol) in tetrahydrofuran (15 mL) at 0° C. The reaction mixture was stirred at room temperature for 3 h and then concentrated. To the residue was added water (20 mL) and stirred for 20 min. The suspension was filtered, washed with water (20 mL) and dried to get 2,5-dichloro-4-phenoxypyrrolo[2,1-f][1,2,4]triazine (6 g, 20.13 mmol, 90% yield) as an off white solid. LCMS m/z 280.0 (M+H); rt 1.17 min; Conditions B.

Intermediate 28C: 5-chloro-2-(6-methoxypyridin-2-yl)-4-phenoxypyrrolo[2,1-f][1,2,4]triazine

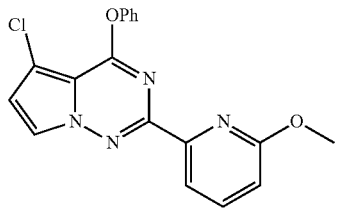

To a flask was added 2,5-dichloro-4-phenoxypyrrolo[2,1-f][1,2,4]triazine (0.5 g, 1.785 mmol), 2-methoxy-6-(4,4,5,5-tetramethyl-1,3,2-dioxaborolan-2-yl)pyridine (0.546 g, 2.321 mmol) and tripotassium phosphate (1.137 g, 5.36 mmol) and 1,4-dioxane (7 mL) and water (3 mL). The reaction mixture was degassed with nitrogen and then added 1,1'-bis(diphenylphosphino)ferrocene-palladium(II)-dichloride dichloromethane complex (0.073 g, 0.089 mmol). The reaction mixture was degassed again and then heated to 100° C. for 12 h. The reaction was monitored by LCMS. The reaction mixture was concentrated. To the residue was added water (20 mL) and stirred for 20 min. The resulting suspension was filtered, washed with water (20 mL) and dried to get 5-chloro-2-(6-methoxypyridin-2-yl)-4-phenoxypyrrolo[2,1-f][1,2,4]triazine (0.53 g, 1.337 mmol, 74.9% yield) as an off white solid. LCMS m/z 353.1 (M+H); rt 1.12 min; Conditions B.

Intermediate 28D: 5-chloro-N-(3-fluoropyridin-4-yl)-2-(6-methoxypyridin-2-yl)pyrrolo[2,1-f][1,2,4]triazin-4-amine

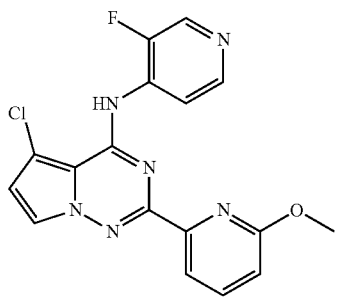 [SMILES: COc1cccc(-c2nc(Nc3ccncc3F)c3c(Cl)ccn3n2)n1]

Sodium hydride (3.40 mg, 0.085 mmol) was added to a solution of 5-chloro-2-(6-methoxypyridin-2-yl)-4-phenoxypyrrolo[2,1-f][1,2,4]triazine (20 mg, 0.057 mmol) and 3-fluoropyridin-4-amine (9.53 mg, 0.085 mmol) in DMF (2 mL). The reaction mixture was stirred at room temperature for 12 h. The reaction was monitored by LCMS. The reaction mixture was quenched with methanol and purified by preparative HPLC to get (11 mg): LCMS purity=97%. Two analytical LC/MS injections were used to determine the final purity. LCMS m/z 371.0 (M+H); rt 1.53 min; Conditions D

Intermediate 28E: N-(3-fluoropyridin-4-yl)-2-(6-methoxypyridin-2-yl)-5-vinylpyrrolo[2,1-f][1,2,4]triazin-4-amine

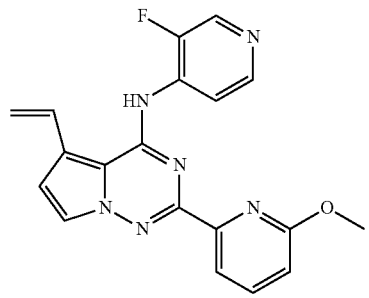 [SMILES: C=Cc1ccn2nc(-c3cccc(OC)n3)nc(Nc3ccncc3F)c12]

Sodium hydride (125 mg, 5.23 mmol) was added to a solution of 2-(6-methoxypyridin-2-yl)-4-phenoxy-5-vinylpyrrolo[2,1-f][1,2,4]triazine (300 mg, 0.871 mmol) and 3-fluoropyridin-4-amine (146 mg, 1.307 mmol) in DMF (8 mL). The reaction mixture was stirred at room temperature for 3 h. The reaction mixture was poured into ice-cold water and extracted with diethyl ether (100 mL×2). The combined organic layer was washed with brine, dried over anhydrous sodium sulfate and evaporated. The crude product was purified by silica gel chromatography (ethyl acetate/petroleum ether) to get N-(3-fluoropyridin-4-yl)-2-(6-methoxypyridin-2-yl)-5-vinylpyrrolo[2,1-f][1,2,4]triazin-4-amine (180 mg, 0.477 mmol, 54.7% yield) as a pale yellow solid. LCMS m/z 363.1 (M+H); rt 1.21 min; Conditions B Osmium tetroxide in t-butanol (3.31 µl, 8.28 µmol) was added to a stirred solution of N-(3-fluoropyridin-4-yl)-2-(6-methoxypyridin-2-yl)-5-vinylpyrrolo[2,1-f][1,2,4]triazin-4-amine (30 mg, 0.083 mmol) in acetone (3.0 mL) and water (1.0 mL). The reaction mixture was stirred at room temperature for 36 h. The reaction mixture was concentrated to get crude product that was purified by reverse phase HPLC to afford Example 28 (5 mg, 15%): LCMS m/z 397.2 (M+H); rt 1.34 min; Conditions D. $^1$H NMR (400 MHz, DMSO-d6) δ 12.01-11.84 (m, 1H), 9.49-9.35 (m, 1H), 8.67-8.50 (m, 1H), 8.42-8.32 (m, 1H), 8.07-7.98 (m, 1H), 7.90-7.79 (m, 1H), 7.29-7.22 (m, 1H), 7.04-6.91 (m, 1H), 6.87-6.76 (m, 1H), 5.07-4.96 (m, 1H), 4.88-4.82 (m, 1H), 4.08 (s, 3H), 3.64-3.53 (m, 2H).

Scheme 29

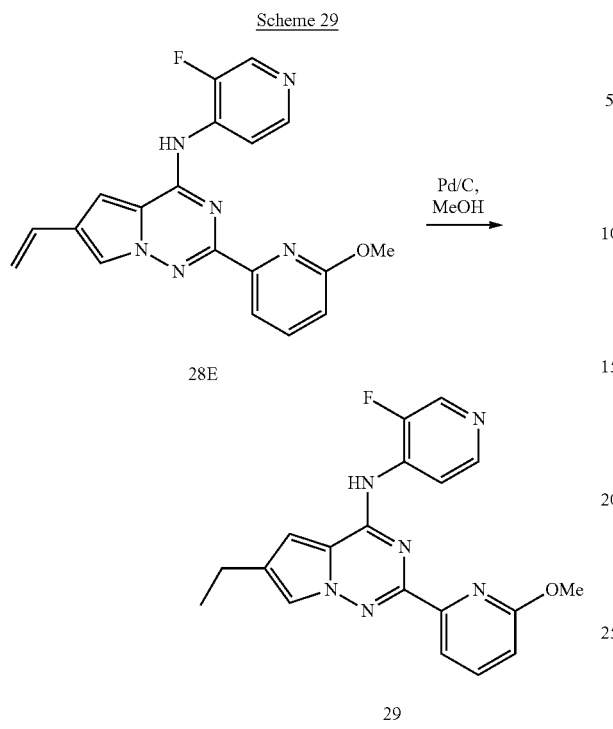

28E

Example 29

6-ethyl-N-(3-fluoropyridin-4-yl)-2-(6-methoxypyridin-2-yl)pyrrolo[2,1-f][1,2,4]triazin-4-amine

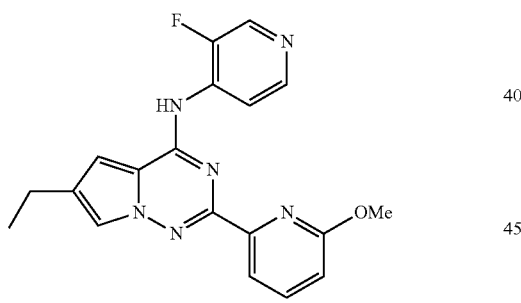

To solution of N-(3-fluoropyridin-4-yl)-2-(6-methoxypyridin-2-yl)-6-vinylpyrrolo[2,1-f][1,2,4]triazin-4-amine (25 mg, 0.069 mmol) in Methanol was added Pd—C (5 mg, 0.047 mmol) and stirred under hydrogen balloon pressure for two hours. The Catalyst was filtered through celite pad and the filtrate was concentrated to get crude product that was purified by reverse phase HPLC to afford Example 29 (5 mg 20%) Example # was obtained (5 mg, 19.89%): Column: Ascentis Express C18 (50×2.1) mm, 2.7 m; Mobile Phase A: 5:95 Acetonitrile:water with 10 mM NH4OAc; Mobile Phase B: 95:5 Acetonitrile:water with 10 mM NH4OAc; Temperature: 50° C.; Gradient: 0-100% B over 3 minutes; Flow: 1.1 ml/min RT—2.012, Purity—100%, LCMS m/z 365.2 (M+H); rt 1.49 min; Conditions D; 1H NMR (400 MHz, DMSO-d6) δ ppm 10.00 (s, 1H)) 8.73 (dd, J=7.03, 5.52 Hz, 1H)) 8.63 (d, J=3.01 Hz, 1H) 8.41 (d, J=5.52 Hz, 1H) 7.80-7.90 (m, 3H) 7.29 (d, J=1.51 Hz, 1H) 6.93 (dd, J=7.53, 1.51 Hz, 1H) 4.02 (s, 3H) 2.67-2.77 (m, 2H) 1.33 (t, J=7.6 Hz, 1H)

Scheme 30

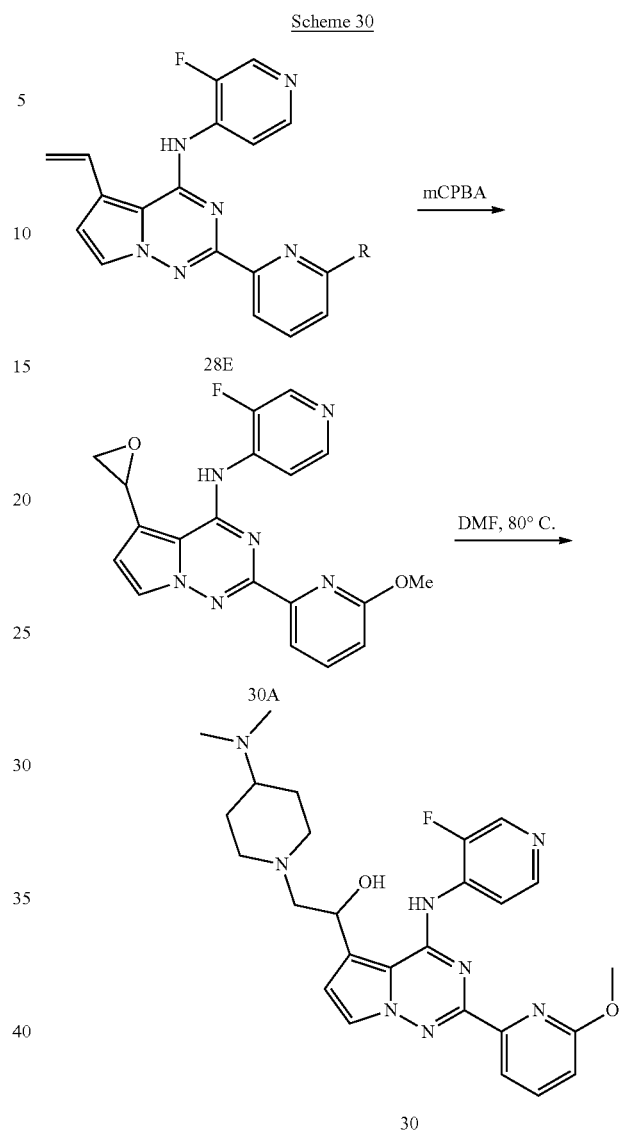

Example 30

2-[4-(dimethylamino)piperidin-1-yl]-1-{4-[(3-fluoropyridin-4-yl)amino]-2-(6-methoxypyridin-2-yl)pyrrolo[2,1-f][1,2,4]triazin-5-yl}ethan-1-ol

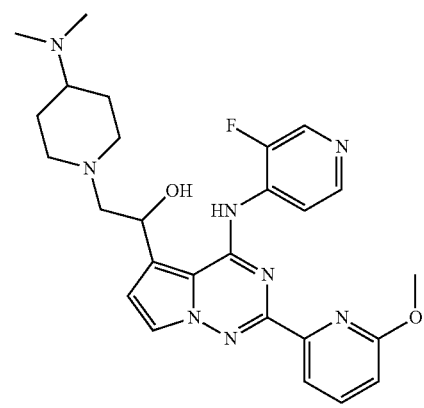

Intermediate 30A: N-(3-fluoropyridin-4-yl)-2-(6-methoxypyridin-2-yl)-5-(oxiran-2-yl)pyrrolo[2,1-f][1,2,4]triazin-4-amine

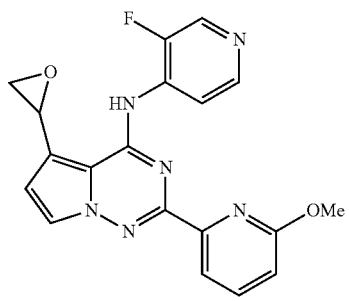 [SMILES: COc1cccc(-c2nc(Nc3ccncc3F)c3c(C4CO4)ccn3n2)n1]

To a solution of N-(3-fluoropyridin-4-yl)-2-(6-methoxypyridin-2-yl)-5-vinylpyrrolo[2,1-f][1,2,4]triazin-4-amine (250 mg, 0.690 mmol) in DCM (15 mL) at −10° C., sodium bicarbonate (116 mg, 1.380 mmol) and mCPBA (357 mg, 1.035 mmol) were added sequentially. The resulting solution was stirred at −10° C. for 1 h, then warmed to room temperature and stirred at this temperature for an additional 5 h. The reaction was quenched with a mixture of saturated aqueous sodium bicarbonate (30 mL) and sat aqueous sodium thiosulfate (20 mL) and extracted with DCM (3×30 mL). The combined organic layer was dried over sodium sulfate and concentrated. The crude product was purified by silica gel chromatography (methanol/chloroform) to get N-(3-fluoropyridin-4-yl)-2-(6-methoxypyridin-2-yl)-5-(oxiran-2-yl)pyrrolo[2,1-f][1,2,4]triazin-4-amine (50 mg, 0.132 mmol, 19.15% yield). LCMS m/z 379.3 (M+H); rt 1.14 min; Conditions B.

To a solution of N-(3-fluoropyridin-4-yl)-2-(6-methoxypyridin-2-yl)-5-(oxiran-2-yl)pyrrolo[2,1-f][1,2,4]triazin-4-amine (40 mg, 0.106 mmol) in DMF (1 mL) was added N,N-dimethylpiperidin-4-amine (27.1 mg, 0.211 mmol) and the reaction mixture was heated at 80° C. for 24 h. The solvent was removed under reduced pressure to get crude product that was purified by reverse phase HPLC to afford Example 30 (6 mg, 11.2%): LCMS m/z 507.4 (M+H); rt 1.21 min; Conditions C. $^1$H NMR (400 MHz, DMSO-d6) δ 12.72 (s, 1H), 9.28-9.32 (m, 1H), 8.61 (d, J=2.8 Hz, 1H), 8.37 (d, J=5.6 Hz, 1H), 7.94 (d, J=2.8 Hz, 1H), 7.86-7.90 (m, 2H), 6.96-6.98 (m, 1H), 6.82 (d, J=2.4 Hz, 1H), 4.81 (bs, 1H), 4.06 (s, 3H), 3.64-3.87 (m, 3H), 3.33 (merged with residual dmso-d6 peak, 3H), 3.00-3.18 (m, 1H), 2.14-2.22 (m, 1H), 2.07 (s, 6H), 1.52-1.83 (m, 3H), 1.19-1.24 (m, 1H). $^{19}$F NMR (400 MHz, DMSO-d6) δ −140.99.

Scheme 31

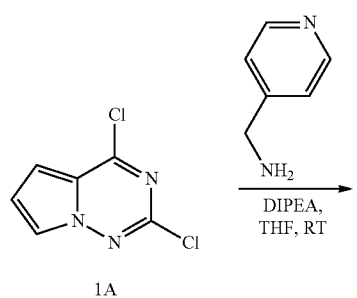

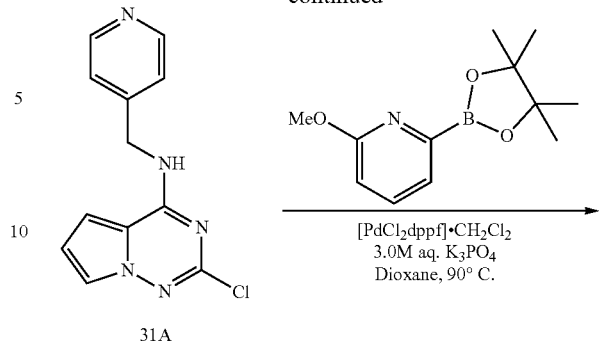

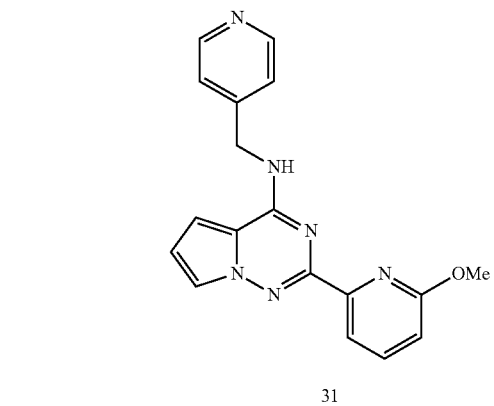

Example 31

2-(6-methoxypyridin-2-yl)-N-(pyridin-4-ylmethyl)pyrrolo[2,1-f][1,2,4]triazin-4-amine

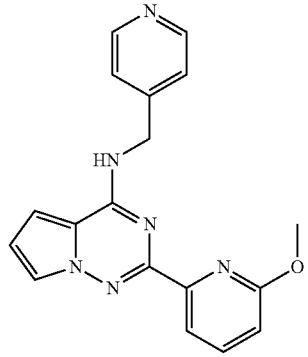 [SMILES: COc1cccc(-c2nc(NCc3ccncc3)c3cccn3n2)n1]

Intermediate-31A: 2-chloro-N-(pyridin-4-ylmethyl)pyrrolo[2,1-f][1,2,4]triazin-4-amine

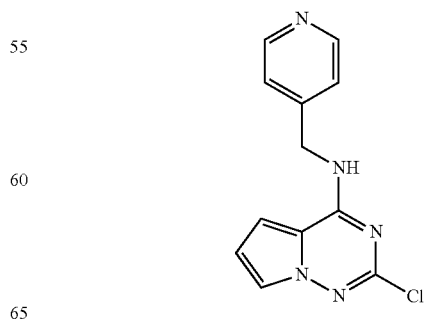

To stirred solution of pyridin-4-ylmethanamine (0.086 g, 0.798 mmol) in dioxane (5 mL) was dropwise added DIPEA (0.279 mL, 1.596 mmol) and stirred for 15 min at room temperature. To the resulting reaction mixture was added 2,4-dichloropyrrolo[2,1-f][1,2,4]triazine (0.15 g, 0.798 mmol) stirred at room temperature for 1 h. The reaction was monitored by LC-MS. The reaction mixture was concentrated under reduced pressure. To the residue was added water (50 mL) and extracted with ethyl acetate (3×80 mL). The combined organic phase was dried over anhydrous sodium sulfate filtered and evaporated. The resulting crude product was purified by silica gel flash chromatography (ethyl acetate/petroleum ether) to get 2-chloro-N-(pyridin-4-ylmethyl)pyrrolo[2,1-f][1,2,4]triazin-4-amine (0.14 g, 0.518 mmol, 64.9% yield) as a brown solid. LCMS m/z 260.0 (M+H); rt 1.8 min; Conditions E. $^1$H NMR: (300 MHz, DMSO-d6) δ 9.37-9.28 (m, 1H), 8.58-8.48 (m, 2H), 7.70 (dd, J=2.6, 1.5 Hz, 1H), 7.38-7.30 (m, 2H), 7.03 (dd, J=4.5, 1.5 Hz, 1H), 6.67 (dd, J=4.2, 2.6 Hz, 1H), 4.75 (d, J=6.0 Hz, 2H).

To a stirred solution 2-chloro-N-(pyridin-4-ylmethyl)pyrrolo[2,1-f][1,2,4]triazin-4-amine (0.04 g, 0.154 mmol) in dioxane (3 mL) and water (1 mL) was added 2-methoxy-6-(4,4,5,5-tetramethyl-1,3,2-dioxaborolan-2-yl)pyridine (0.043 g, 0.185 mmol) and tripotassium phosphate (0.098 g, 0.462 mmol). The reaction mixture was degassed with nitrogen followed by the addition of 1,1'-bis(diphenylphosphino)ferrocene-palladium(II)-dichloride (5.64 mg, 7.70 μmol). The reaction was heated to 100° C. for 18 h. The solvent was removed under reduced pressure to get crude product that was purified by reverse phase HPLC to afford Example 31 (10 mg, 18%): LCMS m/z 333.2 (M+H); rt 1.32 min; Conditions C. $^1$H NMR: (400 MHz, DMSO-d6) δ 9.02-8.93 (m, 1H), 8.57-8.45 (m, 2H), 7.77 (s, 3H), 7.47-7.38 (m, 2H), 7.02-6.97 (m, 1H), 6.93-6.84 (m, 1H), 6.76-6.67 (m, 1H), 4.90-4.81 (m, 2H), 3.92 (s, 3H).

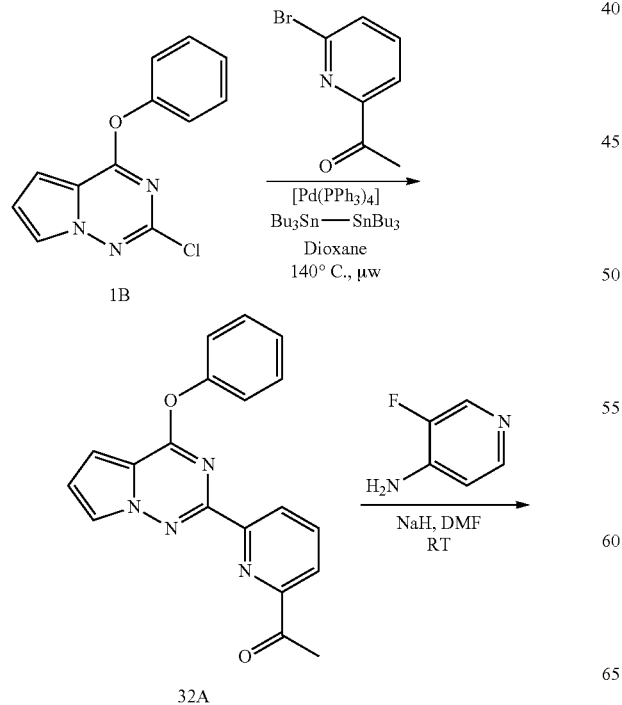

Scheme 32

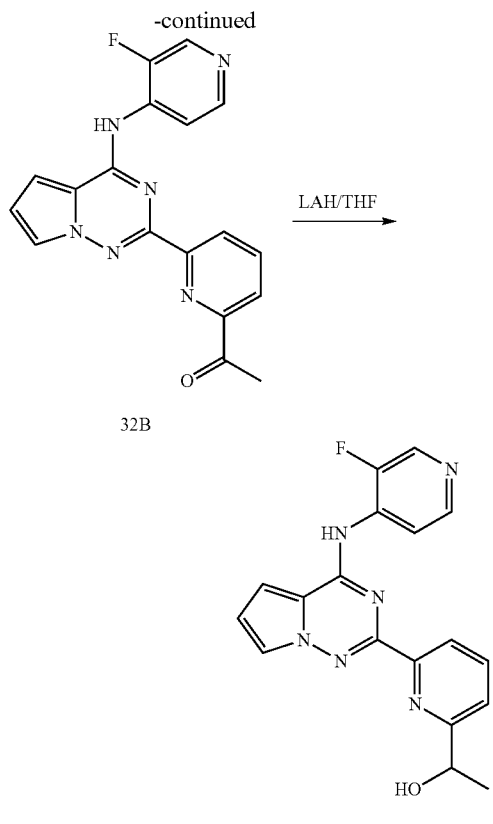

32B

Example 32

1-(6-{4-[(3-fluoropyridin-4-yl)amino]pyrrolo[2,1-f][1,2,4]triazin-2-yl}pyridin-2-yl)ethan-1-ol

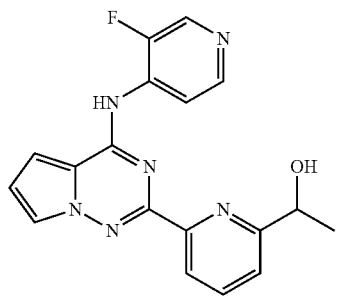 [SMILES: CC(O)c1cccc(-c2nc(Nc3ccncc3F)c3cccn3n2)n1]

Intermediate 32A: 1-(6-(4-phenoxypyrrolo[2,1-f][1,2,4]triazin-2-yl)pyridin-2-yl)ethanone

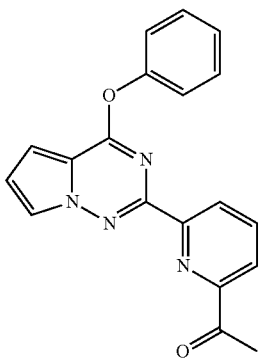 [SMILES: CC(=O)c1cccc(-c2nc(Oc3ccccc3)c3cccn3n2)n1]

To a stirred solution of 1-(6-bromopyridin-2-yl)ethanone (0.05 g, 0.250 mmol) in toluene (5 mL) was added hexamethylditin (0.106 g, 0.325 mmol). The reaction mixture was degassed with nitrogen and then tetrakis(triphenylphosphine)palladium(0) (0.029 g, 0.025 mmol) was added. The reaction mixture was heated at 80° C. for 18 h. The reaction mixture was cooled to room temperature and added 2-chloro-4-phenoxypyrrolo[2,1-f][1,2,4]triazine (0.061 g, 0.250 mmol) and tetrakis(triphenylphosphine)palladium(0) (0.029 g, 0.025 mmol). The reaction mixture was heated at 110° C. for 5 h. The reaction was monitored by LC-MS. The reaction mixture was evaporated under reduced pressure. To the resulting crude product was added water (30 mL) and extracted with DCM (3×30 mL). The combined organic layer was dried over anhydrous sodium sulfate and evaporated. The crude product was purified by silica gel chromatography (ethyl acetate/petroleum ether) to get 1-(6-(4-phenoxypyrrolo[2,1-f][1,2,4]triazin-2-yl)pyridin-2-yl)ethanone (0.05 g, 0.136 mmol, 54.5% yield) as yellow solid. LCMS m/z 331.0 (M+H); rt 3.22 min; Conditions C. $^1$H NMR: (300 MHz, DMSO-d6) δ 8.25 (dd, J=2.6, 1.5 Hz, 1H), 8.21-8.16 (m, 1H), 8.10 (t, J=7.7 Hz, 1H), 8.04-7.98 (m, 1H), 7.51 (d, J=2.3 Hz, 4H), 7.38 (d, J=6.8 Hz, 1H), 7.14 (dd, J=4.5, 1.5 Hz, 1H), 7.08-7.04 (m, 1H), 2.65 (s, 3H).

Intermediate 32B: 1-(6-(4-((3-fluoropyridin-4-yl)amino)pyrrolo[2,1-f][1,2,4]triazin-2-yl)pyridin-2-yl)ethanone

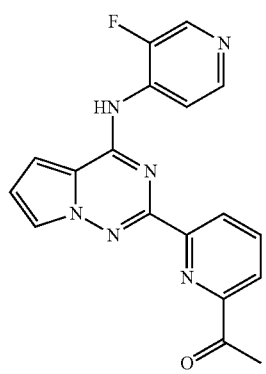 [SMILES: CC(=O)c1cccc(-c2nc(Nc3ccncc3F)c3cccn3n2)n1]

To a solution of 3-fluoropyridin-4-amine (0.017 g, 0.151 mmol) in DMF (4 mL) at 0° C. was added sodium hydride (10.90 mg, 0.454 mmol) and stirred for 10 min. To the resulting reaction mixture was added 1-(6-(4-phenoxypyrrolo[2,1-f][1,2,4]triazin-2-yl)pyridin-2-yl)ethanone (0.05 g, 0.151 mmol) and stirred at room temperature for 1 hour. The reaction was monitored by LC-MS. The reaction mixture was quenched with ice cold water (10 mL) and extracted with ethyl acetate (3×50 mL). The combined organic layer was dried over anhydrous sodium sulfate, filtered and evaporated under reduced pressure. The resulting crude product was used in the next step without purification. LCMS m/z 349.0 (M+H); rt 2.3 min; Conditions C.

To a solution of 1-(6-(4-((3-fluoropyridin-4-yl)amino)pyrrolo[2,1-f][1,2,4]triazin-2-yl)pyridin-2-yl)ethanone (0.04 g, 0.115 mmol) in tetrahydrofuran (3 mL) at 0° C. was dropwise added LiAlH4 (0.069 mL, 0.138 mmol). The reaction mixture was warmed up to room temperature and stirred for 1.5 h. The reaction mixture was concentrated and filtered through a pad of celite. The filtrate was concentrated. The resulting crude product was purified by reverse phase HPLC to afford Example 32 (1 mg, 2.3%): LCMS m/z 351.2 (M+H); rt 0.83 min; Conditions C. $^1$H NMR: (400 MHz, DMSO-d6) δ 10.23-10.16 (m, 1H), 8.65-8.60 (m, 1H), 8.53-8.37 (m, 2H), 8.09-7.88 (m, 3H), 7.66-7.57 (m, 1H), 7.44-7.29 (m, 1H), 6.91-6.82 (m, 1H), 5.49-5.43 (m, 1H), 4.89-4.76 (m, 1H), 3.10-2.96 (m, 2H), 1.75-1.67 (m, 2H), 1.49-1.39 (m, 3H).

Scheme 33

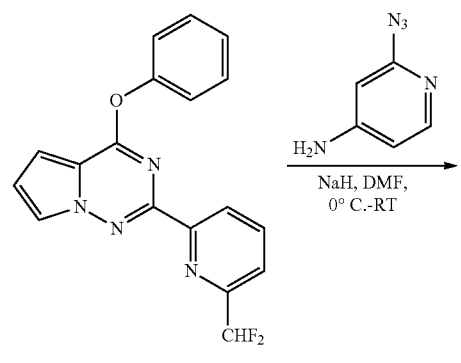

7A

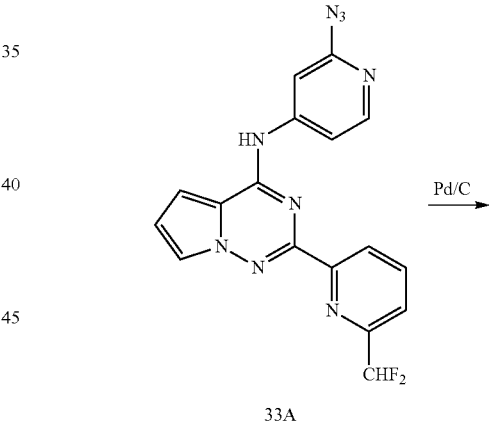

33A

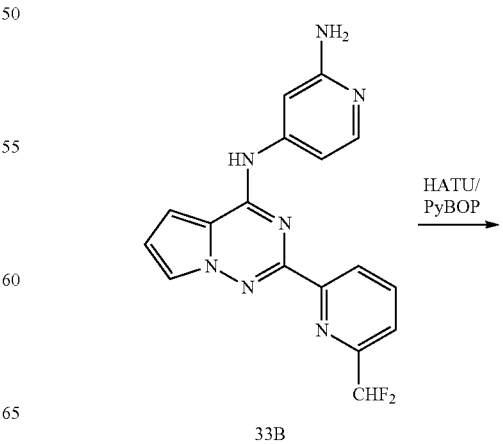

33B

Example 33

N-[4-({2-[6-(difluoromethyl)pyridin-2-yl]pyrrolo[2,1-f][1,2,4]triazin-4-yl}amino)pyridin-2-yl]-2-(pyrrolidin-1-yl)acetamide

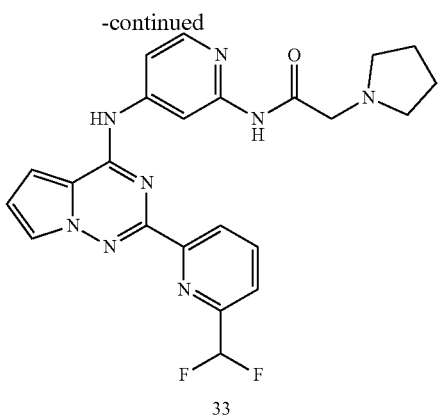

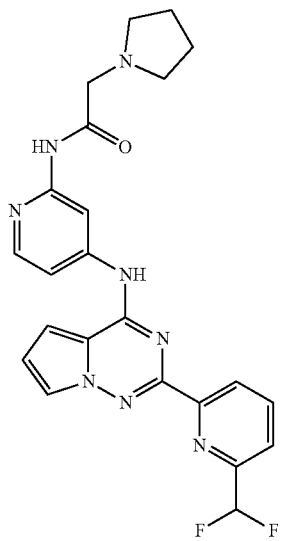 [SMILES: O=C(CN1CCCC1)Nc1cc(Nc2nc(-c3cccc(C(F)F)n3)nn3cccc23)ccn1]

Intermediate 33A: N-(2-azidopyridin-4-yl)-2-(6-(difluoromethyl)pyridin-2-yl)pyrrolo[2,1-f][1,2,4]triazin-4-amine

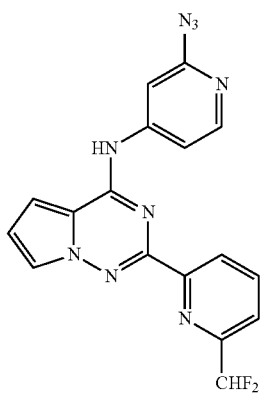 [SMILES: [N-]=[N+]=Nc1cc(Nc2nc(-c3cccc(C(F)F)n3)nn3cccc23)ccn1]

2-(6-(difluoromethyl)pyridin-2-yl)-4-phenoxypyrrolo[2,1-f][1,2,4]triazine (100 mg, 0.296 mmol) was added to a stirred solution of 2-azidopyridin-4-amine (147 mg, 0.591 mmol) and DMF (5 mL) at 0° C. The reaction mixture was stirred at room temperature for 3 h. The reaction mixture was poured into ice-cold water and extracted with diethyl ether (100 mL×2). The combined organic phase was washed with brine dried over anhydrous sodium sulfate and evaporated to get N-(2-azidopyridin-4-yl)-2-(6-(difluoromethyl)pyridin-2-yl)pyrrolo[2,1-f][1,2,4]triazin-4-amine (80 mg, 0.211 mmol, 71.3% yield) as a pale yellow solid. LCMS m/z 378.1 (M+H); rt 0.93 min; Conditions B Intermediate 33B: N4-(2-(6-(difluoromethyl)pyridin-2-yl)pyrrolo[2,1-f][1,2,4]triazin-4-yl)pyridine-2,4-diamine

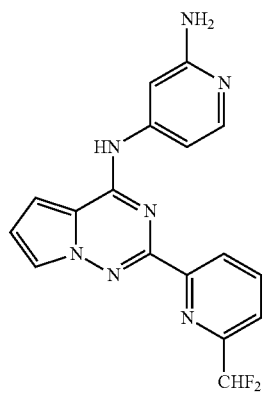 [SMILES: Nc1cc(Nc2nc(-c3cccc(C(F)F)n3)nn3cccc23)ccn1]

Palladium on carbon (30 mg, 0.028 mmol) was added to a suspension of N-(2-azidopyridin-4-yl)-2-(6-(difluoromethyl)pyridin-2-yl)pyrrolo[2,1-f][1,2,4]triazin-4-amine (60 mg, 0.158 mmol) in DCM (10 mL) and MeOH (1 mL). The resulting reaction mixture was stirred under hydrogen atmosphere for 12 h. The reaction mixture was filtered through a pad of celite and evaporated to get N4-(2-(6-(difluoromethyl)pyridin-2-yl)pyrrolo[2,1-f][1,2,4]triazin-4-yl)pyridine-2,4-diamine (60 mg, 0.143 mmol, 90% yield) as a pale yellow solid, LCMS m/z 354.2 (M+H); rt 2.1 min; Conditions E 2-(pyrrolidin-1-yl)acetic acid (30 mg, 0.232 mmol) was added to a stirred solution of N4-(2-(6-(difluoromethyl)pyridin-2-yl)pyrrolo[2,1-f][1,2,4]triazin-4-yl)pyridine-2,4-diamine (82 mg, 0.232 mmol), HATU (88 mg, 0.232 mmol) and DIPEA (0.122 mL, 0.697 mmol) in dry DMF (5 mL). The reaction mixture was stirred at room temperature for 36 h. The solvent was removed under reduced pressure to get the crude product that was purified by reverse phase HPLC to afford Example 33 (3 mg, 2.7%): LCMS m/z 465.3 (M+H); rt 1.02 min; Conditions D. $^1$H NMR (400 MHz, DMSO-d6) δ 10.53-10.31 (m, 1H), 9.88 (s, 1H), 8.89 (d, J=2.0 Hz, 1H), 8.69 (s, 1H), 8.28 (d, J=5.5 Hz, 1H), 8.17 (s, 1H), 8.08-7.95 (m, 2H), 7.84 (d, J=7.5 Hz, 1H), 7.43-7.34 (m, 1H), 7.30-7.16 (m, 1H), 7.11 (s, 2H), 6.92 (dd, J=4.3, 2.8 Hz, 3H), 3.36 (s, 4H), 2.70-2.63 (m, 4H)

Scheme 34

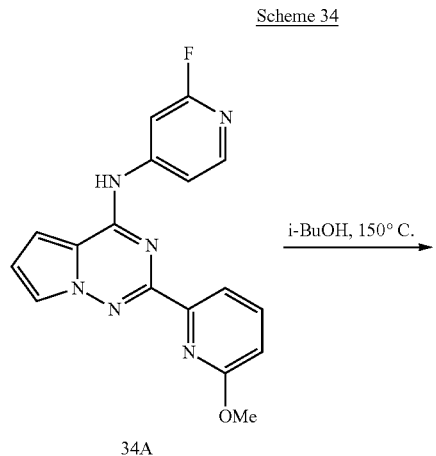

34A

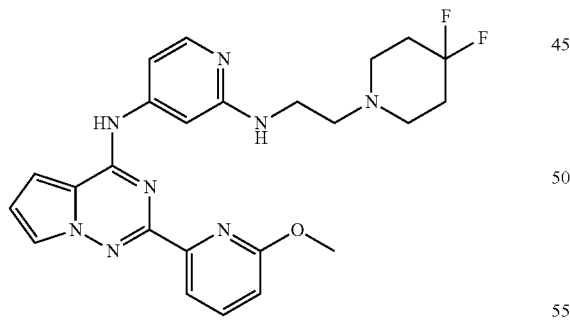

34

Example 34

2-N-[2-(4,4-difluoropiperidin-1-yl)ethyl]-4-N-[2-(6-methoxypyridin-2-yl)pyrrolo[2,1-f][1,2,4]triazin-4-yl]pyridine-2,4-diamine To a vial was added N-(2-fluoropyridin-4-yl)-2-(6-methoxypyridin-2-yl)pyrrolo[2,1-f][1,2,4]triazin-4-amine (50 mg, 0.149 mmol), 2-(4,4-difluoropiperidin-1-yl)ethanamine (195 mg, 1.189 mmol), 2-(4,4-difluoropiperidin-1-yl)ethanamine (195 mg, 1.189 mmol) and isobutanol (10 mL). The reaction mixture was heated at 150° C. for 2 days. The reaction mixture was cooled to room temperature and concentrated to get crude product that was purified via preparative LC/MS to afford Example 34 (16 mg, 22% yield): LCMS m/z 481.3 (M+H); rt 1.87 min; Conditions C.

Scheme 35

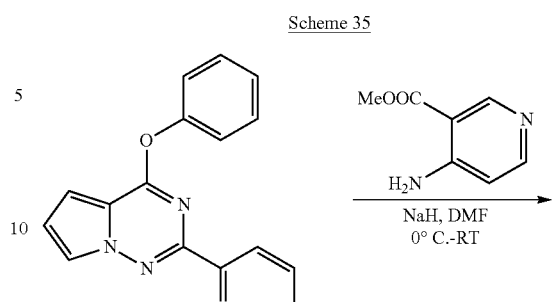

3A

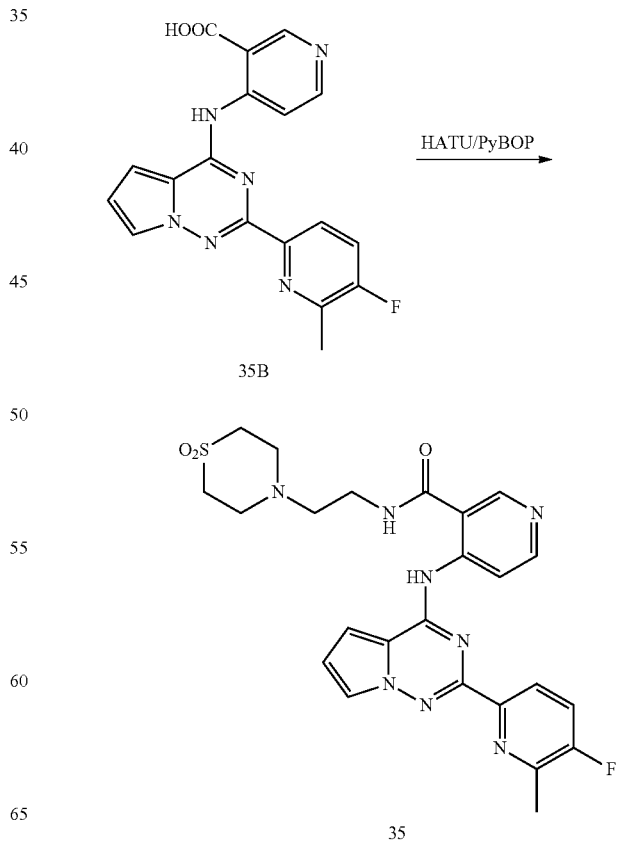

35

Example 35

N-[2-(1,1-dioxo-1,4-thiomorpholin-4-yl)ethyl]-4-{[2-(5-fluoro-6-methylpyridin-2-yl)pyrrolo[2,1-f][1,2,4]triazin-4-yl]amino}pyridine-3-carboxamide

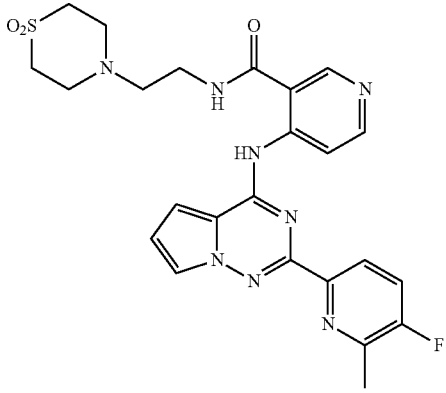 [SMILES: Cc1nc(-c2nc(Nc3ccncc3C(=O)NCCN3CCS(=O)(=O)CC3)c3cccn3n2)ccc1F]

Intermediate 35A: methyl 4-((2-(5-fluoro-6-methyl-pyridin-2-yl)pyrrolo[2,1-f][1,2,4]triazin-4-yl)amino)nicotinate

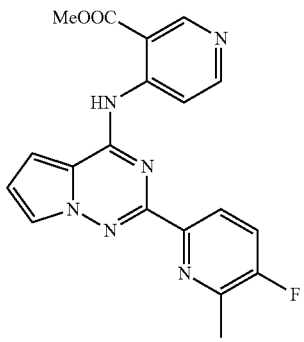 [SMILES: COC(=O)c1cnccc1Nc1nc(-c2ccc(F)c(C)n2)nn2cccc12]

To a solution of 2-(5-fluoro-6-methylpyridin-2-yl)-4-phenoxypyrrolo[2,1-f][1,2,4]triazine (280 mg, 0.874 mmol) and methyl 4-aminonicotinate (186 mg, 1.224 mmol) in DMF (5 mL) at 0° C. was added sodium hydride (76 mg, 1.748 mmol). The reaction mixture was warmed up to room temperature and stirred for 2 h. The reaction was quenched with cold water and concentrated. The crude product was used in the saponification step without further purification. LCMS m/z 379.3 (M+H); rt 1.07 min; Conditions B.

Intermediate 35B: 4 4-((2-(5-fluoro-6-methylpyridin-2-yl)pyrrolo[2,1-f][1,2,4]triazin-4-yl)amino)nicotinic acid

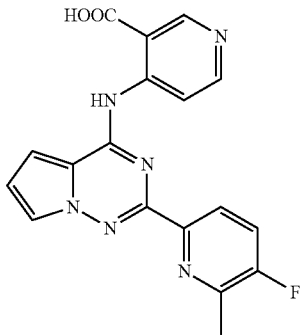 [SMILES: Cc1nc(-c2nc(Nc3ccncc3C(=O)O)c3cccn3n2)ccc1F]

To a stirred solution of methyl 4-((2-(5-fluoro-6-methyl-pyridin-2-yl)pyrrolo[2,1-f][1,2,4]triazin-4-yl)amino)nicotinate (0.35 g, 0.925 mmol) in tetrahydrofuran (3 mL) and methanol (1.5 mL), was added aqueous 2.0 N lithium hydroxide (1.388 mL, 2.78 mmol). The reaction mixture was stirred at room temperature for 16 h. The crude product was purified by solid phase extraction using Dowex acid resin to get 4-((2-(5-fluoro-6-methylpyridin-2-yl)pyrrolo[2,1-f][1,2,4]triazin-4-yl)amino)nicotinic acid (250 mg, 0.686 mmol, 74.2% yield) as an light yellow solid. LCMS m/z 365.4 (M+H); rt 0.66 min; Conditions B.

To a stirred solution of 4-((2-(5-fluoro-6-methylpyridin-2-yl)pyrrolo[2,1-f][1,2,4]triazin-4-yl)amino)nicotinic acid (80 mg, 0.220 mmol) in DMF (1.5 mL) was added PyBOP (229 mg, 0.439 mmol) and stirred for 30 min. After the reaction mixture turned clear, 4-(2-aminoethyl)thiomorpholine 1,1-dioxide (78 mg, 0.439 mmol) was added and stirred at room temperature for 24 h. The solvent were removed under reduced pressure to get crude compound which was dissolved in DCM (10 mL) and washed with water (10 mL). The aqueous layer was back extracted with DCM. The combined organic layer was washed with brine dried over sodium sulfate and concentrated under reduced pressure. The residue was purified by preparative HPLC to afford Example 35 (5 mg, 4%): LCMS m/z 525.3 (M+H); rt 1.45 min; Conditions C. $^1$H NMR (400 MHz, DMSO-d6) δ 12.8 (s, 1H), 9.32-9.37 (m, 2H), 9.08 (s, 1H), 8.83 (d, J=6.0 Hz, 1H), 8.14-8.24 (m, 2H), 7.79-7.84 (m, 1H), 6.94-7.02 (m, 2H), 3.59-3.61 (m, 2H), 3.34-3.38 (m, 8H), 3.10-3.17 (m, 2H), 2.55 (s, 3H). $^{19}$F NMR (400 MHz, DMSO-d6) δ −123.2.

Scheme 36

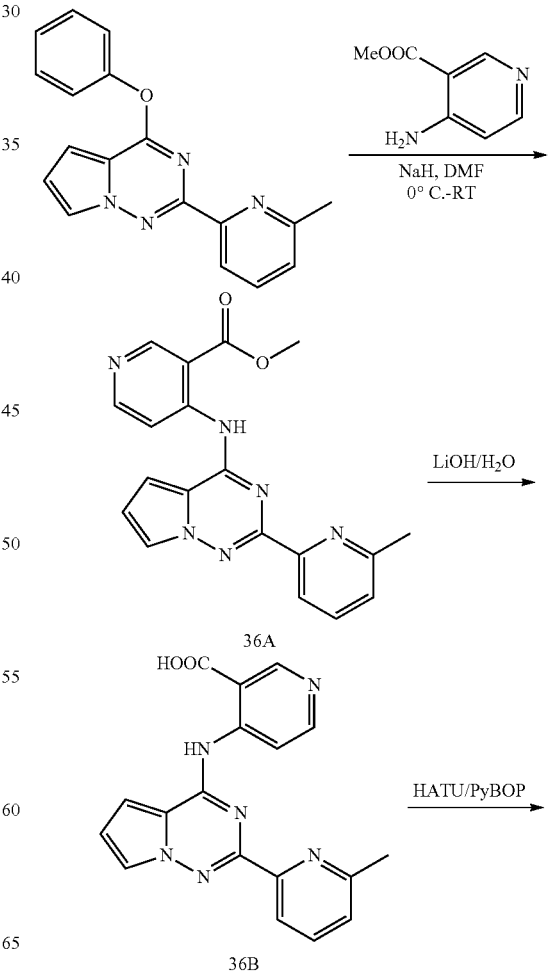

-continued

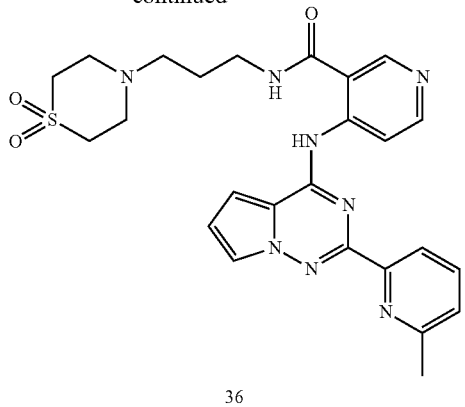

36

Example 36

N-(3-(1,1-dioxidothiomorpholino)propyl)-4-((2-(6-methylpyridin-2-yl)pyrrolo[2,1-f][1,2,4]triazin-4-yl)amino)nicotinamide

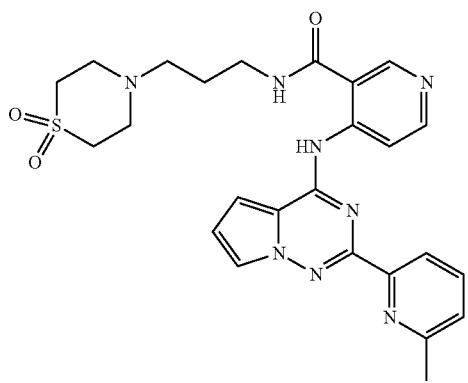 [SMILES: Cc1cccc(-c2nc(Nc3ccncc3C(=O)NCCCN3CCS(=O)(=O)CC3)c3cccn3n2)n1]

Intermediate 36A: methyl 4-((2-(6-methylpyridin-2-yl)pyrrolo[2,1-f][1,2,4]triazin-4-yl)amino)nicotinate

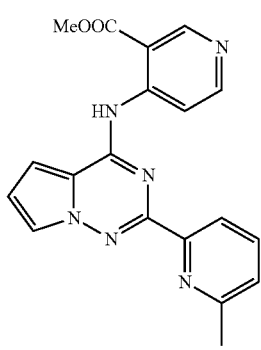 [SMILES: COC(=O)c1cnccc1Nc1nc(-c2cccc(C)n2)nn2cccc12]

Sodium hydride (0.060 g, 2.481 mmol) was added to a solution of 2-(6-methylpyridin-2-yl)-4-phenoxypyrrolo[2,1-f][1,2,4]triazine (0.3 g, 0.992 mmol) and methyl 4-aminonicotinate (0.302 g, 1.985 mmol) in DMF (5 mL). The reaction mixture was stirred at room temperature for 2 h. The reaction was monitored by LCMS. The reaction mixture was quenched with methanol and evaporated under reduced pressure to get crude methyl 4-((2-(6-methylpyridin-2-yl)pyrrolo[2,1-f][1,2,4]triazin-4-yl)amino)nicotinate (0.35 g, 0.971 mmol, 98% yield) which was used to next step without purification. LCMS m/z 347.0 (M-15); rt 0.63 min; Conditions B.

Intermediate 36B: 4-((2-(6-methylpyridin-2-yl)pyrrolo[2,1-f][1,2,4]triazin-4-yl)amino)nicotinic acid

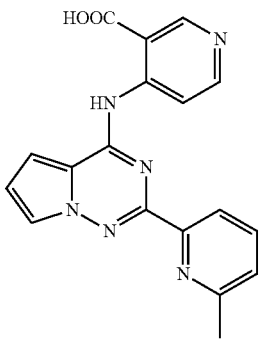 [SMILES: Cc1cccc(-c2nc(Nc3ccncc3C(=O)O)c3cccn3n2)n1]

LiOH (0.070 g, 2.91 mmol) was added to a stirred solution of methyl 4-((2-(6-methylpyridin-2-yl)pyrrolo[2,1-f][1,2,4]triazin-4-yl)amino)nicotinate (0.35 g, 0.971 mmol) in tetrahydrofuran (5 mL), methanol (1 mL) and water (5 mL). The reaction mixture was stirred at room temperature for 12 h. The solvent was removed under reduced pressure to get the crude product which was purified using Dowex WX50 ion exchange resin to get 4-((2-(6-methylpyridin-2-yl)pyrrolo[2,1-f][1,2,4]triazin-4-yl)amino)nicotinic acid (0.3 g, 0.823 mmol, 85% yield) as an off white solid. LCMS m/z 347.0 (M+H); rt 1.18 min; Conditions E.

4-(3-aminopropyl)thiomorpholine 1,1-dioxide (333 mg, 0.866 mmol) was added to a stirred solution of 4-((2-(6-methylpyridin-2-yl)pyrrolo[2,1-f][1,2,4]triazin-4-yl)amino)nicotinic acid (100 mg, 0.289 mmol), PyBOP (376 mg, 0.722 mmol) and DIPEA (0.151 mL, 0.866 mmol) in dry DMF (5 mL) at 0° C. The reaction mixture was stirred at room temperature for 36 h. The solvent was removed under reduced pressure to get the crude product which was purified by reverse phase preparative HPLC to afford Example 36 (24 mg, 15.8%): LCMS m/z 521.2 (M+H); rt 1.8 min; Conditions E. $^1$H NMR (400 MHz, DMSO-d6) δ 12.68-12.63 (m, 1H), 9.14-9.06 (m, 2H), 9.01-8.98 (m, 1H), 8.73-8.67 (m, 1H), 8.16-8.06 (m, 2H), 7.92-7.86 (m, 1H), 7.44-7.38 (m, 1H), 6.99-6.87 (m, 2H), 3.44-3.36 (m, 2H), 3.13-3.04 (m, 4H), 2.94-2.85 (m, 4H), 2.61 (s, 3H), 2.55-2.52 (m, 3H), 1.78-1.68 (m, 2H).

Scheme-37

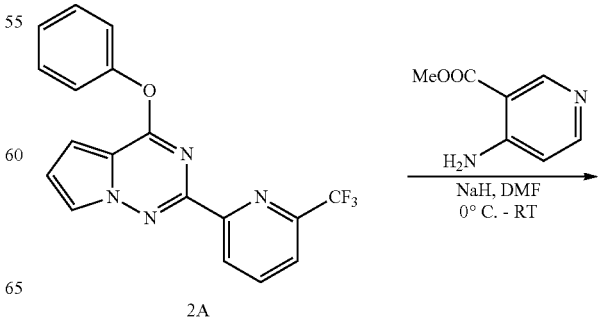

2A

123
-continued

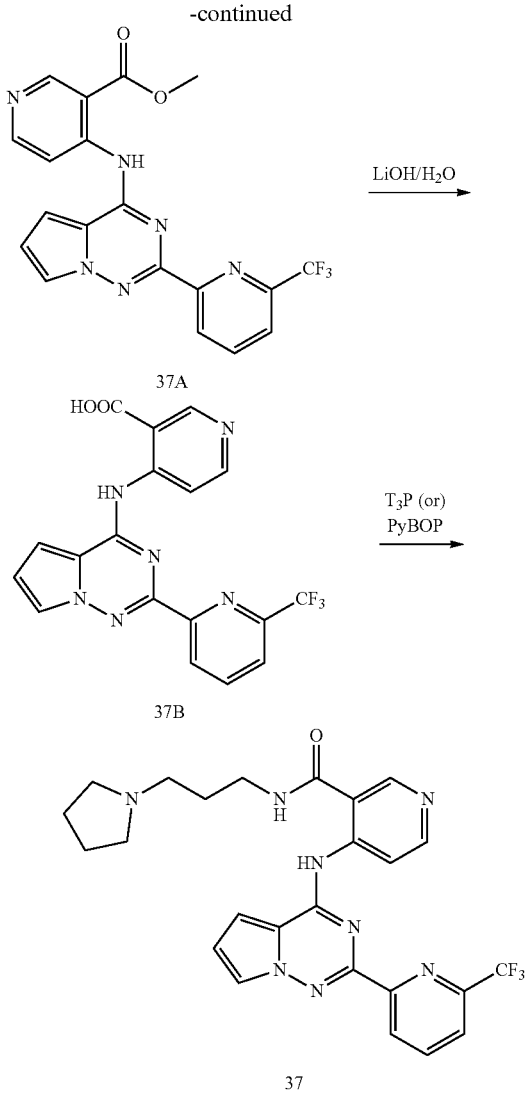

37A

T₃P (or) PyBOP

LiOH/H₂O

37B

37

Example 37

N-[3-(pyrrolidin-1-yl)propyl]-4-({2-[6-(trifluoromethyl)pyridin-2-yl]pyrrolo[2,1-f]1,2,4]triazin-4-yl}amino)pyridine-3-carboxamide

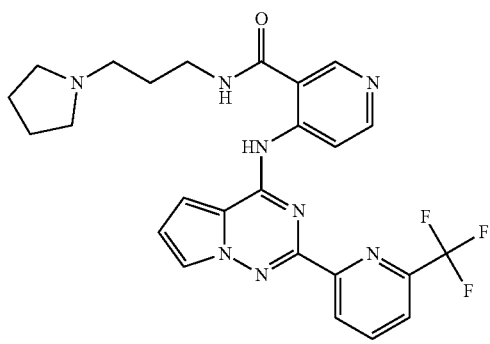 [SMILES: O=C(NCCCN1CCCC1)c1cnccc1Nc1nc(-c2cccc(C(F)(F)F)n2)nn2cccc12]

124

Intermediate 37A: methyl 4-((2-(6-(trifluoromethyl)pyridin-2-yl)pyrrolo[2,1-f][1,2,4]triazin-4-yl)amino)nicotinate

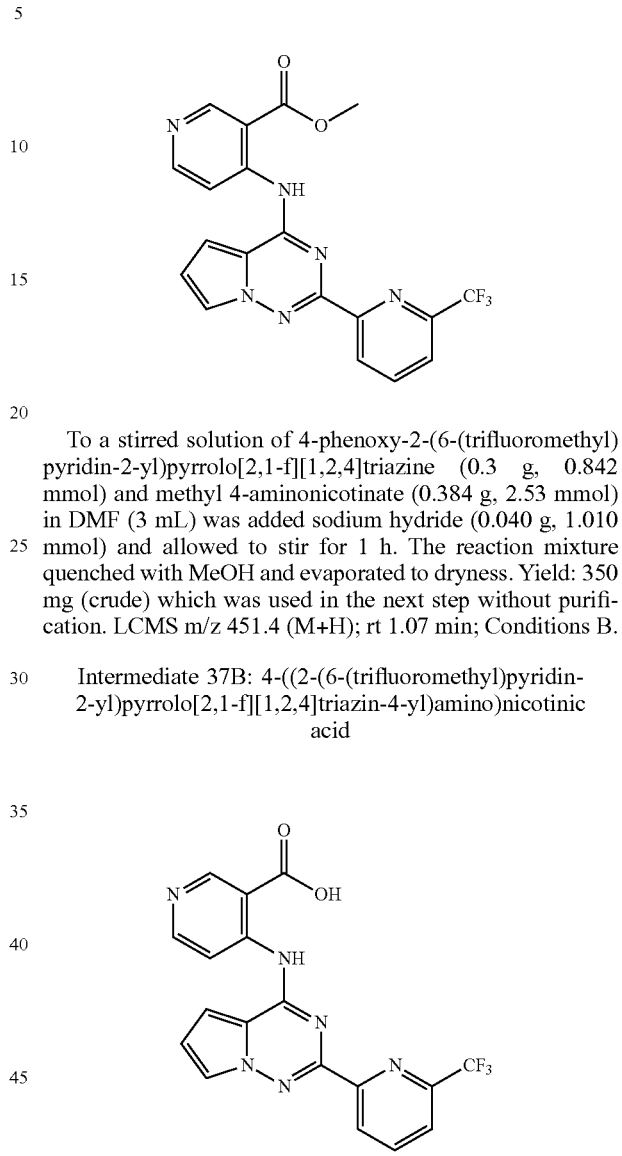

To a stirred solution of 4-phenoxy-2-(6-(trifluoromethyl)pyridin-2-yl)pyrrolo[2,1-f][1,2,4]triazine (0.3 g, 0.842 mmol) and methyl 4-aminonicotinate (0.384 g, 2.53 mmol) in DMF (3 mL) was added sodium hydride (0.040 g, 1.010 mmol) and allowed to stir for 1 h. The reaction mixture quenched with MeOH and evaporated to dryness. Yield: 350 mg (crude) which was used in the next step without purification. LCMS m/z 451.4 (M+H); rt 1.07 min; Conditions B.

Intermediate 37B: 4-((2-(6-(trifluoromethyl)pyridin-2-yl)pyrrolo[2,1-f][1,2,4]triazin-4-yl)amino)nicotinic acid To a stirred solution of methyl 4-((2-(6-(trifluoromethyl)pyridin-2-yl)pyrrolo[2,1-f][1,2,4]triazin-4-yl)amino)nicotinate (0.35 g, 0.845 mmol) in tetrahydrofuran (4 mL) and methanol (2 mL), 2.0 N aqueous LiOH (1.267 mL, 2.53 mmol) was added. The reaction mixture was stirred at room temperature for 16 h. The reaction mixture was concentrated under reduced pressure. The crude product was purified using Dowex ion exchange resin to get 4-((2-(6-(trifluoromethyl)pyridin-2-yl)pyrrolo[2,1-f][1,2,4]triazin-4-yl)amino)nicotinic acid (0.25 g, 0.625 mmol, 73.9% yield) as an white solid. LCMS m/z 401.3 (M+H); rt 0.75 min; Conditions A.

To a stirred solution of 4-((2-(6-(trifluoromethyl)pyridin-2-yl)pyrrolo[2,1-f][1,2,4]triazin-4-yl)amino)nicotinic acid (0.04 g, 0.100 mmol) in DMF (1 mL) was added 2,4,6-tripropyl-1,3,5,2,4,6-trioxatriphosphorinane-2,4,6-trioxide (0.120 mL, 0.200 mmol) and heated at 50° C. for 1 h. To the resulting reaction mixture was added 3-(pyrrolidin-1-yl)propan-1-amine (0.077 g, 0.600 mmol) and stirred for 5 minutes at 50° C. The reaction mixture was allowed to warm up to room temperature. To the reaction mixture was added methanol (1 mL) and purified by reverse phase HPLC to afford Example 37 (7 mg, 13%): LCMS m/z 511.3 (M+H); rt 1.52 min; Conditions C. $^1$H NMR (400 MHz, DMSO-d6) δ 12.65-12.77 (m, 1H) 9.60-9.79 (m, 1H) 9.24-9.40 (m, 1H) 9.14-9.22 (m, 1H) 9.01-9.10 (m, 1H) 8.67-8.75 (m, 1H) 8.57-8.64 (m, 1H) 8.29-8.38 (m, 1H) 8.15-8.22 (m, 1H) 8.05-8.11 (m, 1H) 6.99-7.08 (m, 1H) 6.90-6.97 (m, 1H) 3.49-3.62 (m, 3H) 3.18-3.29 (m, 3H) 2.92-3.07 (m, 2H) 1.92-2.08 (m, 4H) 1.79-1.89 (m, 2H).

Scheme 38

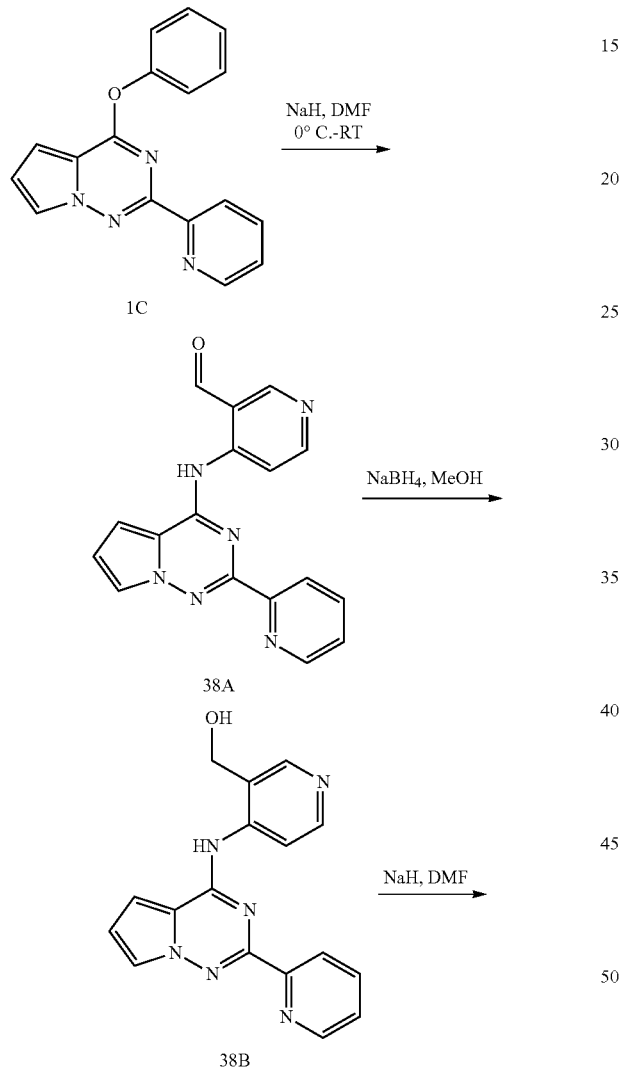

Example 38

N-[2-(6-methoxypyridin-2-yl)pyrrolo[2,1-f][1,2,4]triazin-4-yl]-3-{[3-(morpholin-4-yl)propoxy]methyl}pyridin-4-amine

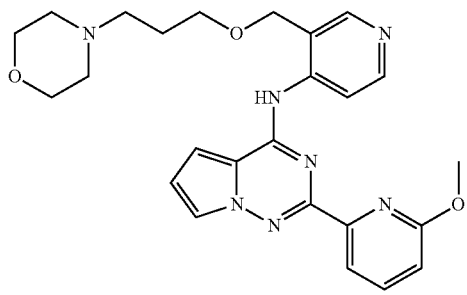 [SMILES: COc1cccc(-c2nc(Nc3ccncc3COCCCN3CCOCC3)c3cccn3n2)n1]

Intermediate 38A: 4-((2-(pyridin-2-yl)pyrrolo[2,1-f][1,2,4]triazin-4-yl)amino)nicotinaldehyde

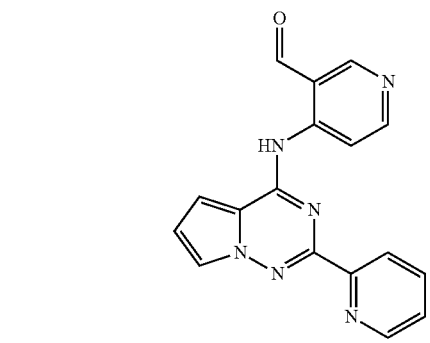 [SMILES: O=Cc1cnccc1Nc1nc(-c2ccccn2)nn2cccc12]

To a solution of 2-(6-methoxypyridin-2-yl)-4-phenoxy-pyrrolo[2,1-f][1,2,4]triazine (300 mg, 0.942 mmol) and 4-aminonicotinaldehyde (173 mg, 1.414 mmol) in DMF (5 mL) at 0° C. was added sodium hydride (82 mg, 1.885 mmol) and the reaction mixture was warmed to room temperature and stirred for 2 h. The reaction mixture was poured in to 30 mL water. The resulting precipitate was filtered and dried. The isolated solid was used in the next step without further purification. LCMS m/z 347.3 (M+H); rt 0.94 min; Conditions B.

Example 38B: (4-{[2-(6-methoxypyridin-2-yl)pyrrolo[2,1-f][1,2,4]triazin-4-yl]amino}pyridin-3-yl)methanol

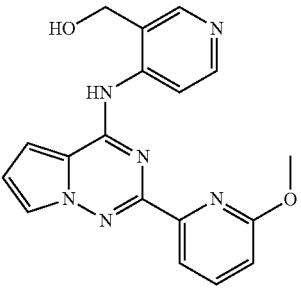 [SMILES: COc1cccc(-c2nc(Nc3ccncc3CO)c3cccn3n2)n1]

To a solution of 4-((2-(6-methoxypyridin-2-yl)pyrrolo[2,1-f][1,2,4]triazin-4-yl)amino)nicotinaldehyde (350 mg, 1.011 mmol) in methanol (10 mL) was portionwise added sodium borohydride (382 mg, 10.11 mmol) at room temperature and stirred for 2 h. The solvent was removed under reduced pressure and the residue was dissolved in DCM. The organic phase was washed with water, brine and dried over sodium sulfate. The organic layer was evaporated under reduced pressure and the crude product was purified by reverse phase HPLC to get Example 38B (285 mg, 81%): LCMS m/z 349.2 (M+H); rt 1.14 min; Conditions C. $^1$HNMR (400 MHz, DMSO-d6) δ 10.10 ((s, 1H), 8.50-8.62 (m, 3H), 8.00 (s, 1H), 7.84-7.89 (m, 2H), 6.91-6.99 (m, 3H), 6.07 (bs, 1H), 4.82 (d, J=4.4 Hz, 2H), 4.01 (s, 3H).

To a solution of (4-((2-(6-methoxypyridin-2-yl)pyrrolo[2,1-f][1,2,4]triazin-4-yl)amino)pyridin-3-yl)methanol (50 mg, 0.144 mmol) and 3-morpholinopropyl methanesulfonate (32.0 mg, 0.144 mmol) in DMF (2 mL) at 0° C., was added was added sodium hydride (12.53 mg, 0.287 mmol). The reaction mixture was warmed up to room temperature and stirred for 16 h. The reaction mixture was quenched with methanol and concentrated. The crude product was purified by reverse phase HPLC to afford Example 38 (6 mg, 8.6%): LCMS m/z 476.3 (M+H); rt 1.23 min; Conditions C. $^1$H NMR (400 MHz, DMSO-d6) δ 8.71 (d, J=7.2 Hz, 1H), 8.04-8.07 (m, 2H), 7.79-7.85 (m, 2H), 7.70-7.71 (m, 1H), 6.89-6.91 (m, 1H), 6.67-6.71 (m, 2H), 4.67 (s, 2H), 4.18 (t, J=6.8 Hz, 2H), 4.00 (s, 3H), 3.35-3.59 (m, 4H), 2.23-2.33 (m, 4H), 2.24-2.30 (m, 2H) 1.94-1.98 (m, 2H)

Scheme 39

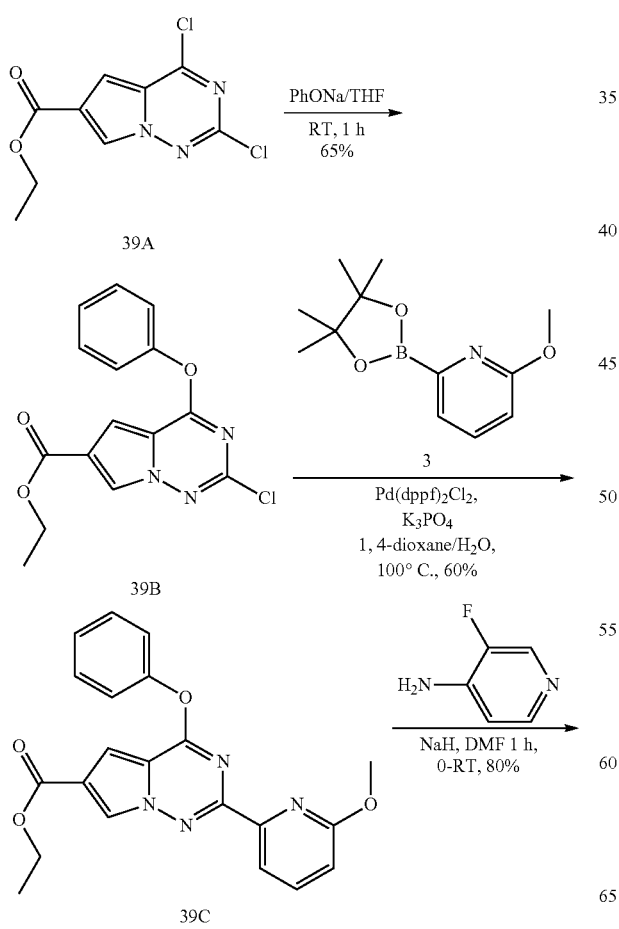

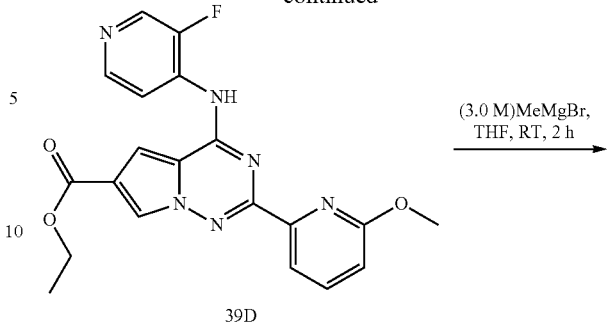

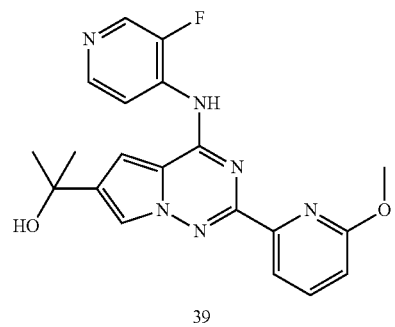

39

Example 39

2-{4-[(3-fluoropyridin-4-yl)amino]-2-(6-methoxypyridin-2-yl)pyrrolo[2,1-f][1,2,4]triazin-6-yl}propan-2-ol

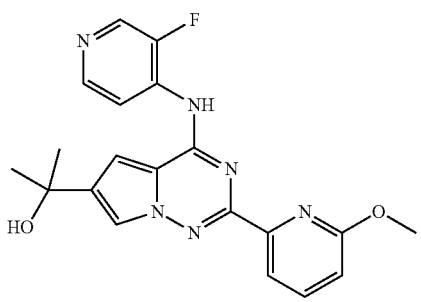 [SMILES: COc1cccc(-c2nc(Nc3ccncc3F)c3cc(C(C)(C)O)cn3n2)n1]

Intermediate 39B was synthesized employing the procedure described for intermediate 1B (Scheme 1).

Intermediate 39C: ethyl 2-(6-methoxypyridin-2-yl)-4-phenoxypyrrolo[2,1-f][1,2,4]triazine-6-carboxylate

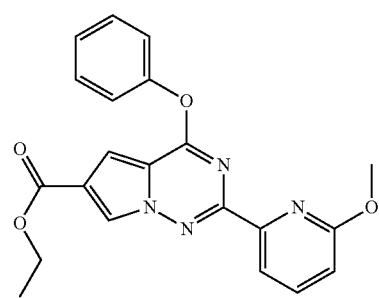 [SMILES: CCOC(=O)c1cc2c(Oc3ccccc3)nc(-c3cccc(OC)n3)nn2c1]

To a stirred solution of ethyl 2-chloro-4-phenoxypyrrolo[2,1-f][1,2,4]triazine-6-carboxylate (1.5 g, 4.72 mmol) and 2-methoxy-6-(4,4,5,5-tetramethyl-1,3,2-dioxaborolan-2-yl)pyridine (1.665 g, 7.08 mmol) in dioxane (24 mL) and water (8 mL), was added tripotassium phosphate (3.01 g, 14.16 mmol) and the reaction mixture was degassed with nitrogen. To the reaction mixture was added 1,1'-bis(diphenylphosphino)ferrocene-palladium(II)-dichloride (0.173 g, 0.236 mmol) and heated to 100° C. for 12 h. The volatile components were removed; the resulting residue was dissolved in DCM and filtered through a pad of celite. The organic layer was concentrated under reduced pressure. The crude product was purified by silica gel chromatography (ethyl acetate:petroleum ether) to get ethyl 2-(6-methoxypyridin-2-yl)-4-phenoxypyrrolo[2,1-f][1,2,4]triazine-6-carboxylate (1.512 g, 3.87 mmol, 82% yield). LCMS m/z 391.2 (M+H); rt 1.29 min; Conditions B.

Intermediate 39D: ethyl 4-((3-fluoropyridin-4-yl)amino)-2-(6-methoxypyridin-2-yl)pyrrolo[2,1-f][1,2,4]triazine-6-carboxylate To a stirred suspension of sodium hydride (0.096 g, 2.395 mmol) in DMF (5 mL) at 0° C., was added 3-fluoropyridin-4-amine (0.244 g, 2.177 mmol) in DMF (0.2 mL) and stirred for 5 minutes. To the reaction mixture at 0° C. was added a solution of ethyl 2-(6-methoxypyridin-2-yl)-4-phenoxypyrrolo[2,1-f][1,2,4]triazine-6-carboxylate (0.85 g, 2.177 mmol) in DMF (0.5 mL) and stirred at room temperature for 1 h. The reaction mixture was cooled to 0° C., added water (10 mL) and extracted with ethyl acetate (500 mL). The organic layer was dried over anhydrous sodium sulphate and evaporated. The crude product was purified by silica gel chromatography (petroleum ether and ethyl acetate) to get ethyl 4-((3-fluoropyridin-4-yl)amino)-2-(6-methoxypyridin-2-yl)pyrrolo[2,1-f][1,2,4]triazine-6-carboxylate (500 mg, 1.224 mmol, 56.2% yield) as a white solid. LCMS m/z 409.3 (M+H); rt 2.85 min; Conditions C To a stirred solution of ethyl 4-((3-fluoropyridin-4-yl)amino)-2-(6-methoxypyridin-2-yl)pyrrolo[2,1-f][1,2,4]triazine-6-carboxylate (0.05 g, 0.122 mmol) in tetrahydrofuran (1 mL) cooled to 0° C. methylmagnesium bromide (0.408 mL, 1.224 mmol) (3 M solution in THF) was added dropwise. The reaction mixture was allowed to warm up to room temperature and stirred for 2 h. The reaction mixture was quenched with methanol and purified by reverse phase HPLC to afford Example 39 (20 mg, 41%): LCMS m/z 395.2 (M+H); rt 1.43 min; Conditions C. $^1$H NMR (400 MHz, DMSO-d6) δ 10.02-10.10 (m, 1H) 8.69-8.76 (m, 1H) 8.62 (d, J=3.01 Hz, 1H) 8.40 (d, J=5.40 Hz, 1H) 7.77-7.91 (m, 3H) 7.39 (d, J=1.76 Hz, 1H) 6.88-6.96 (m, 1H) 5.09 (s, 1H) 4.01 (s, 3H).

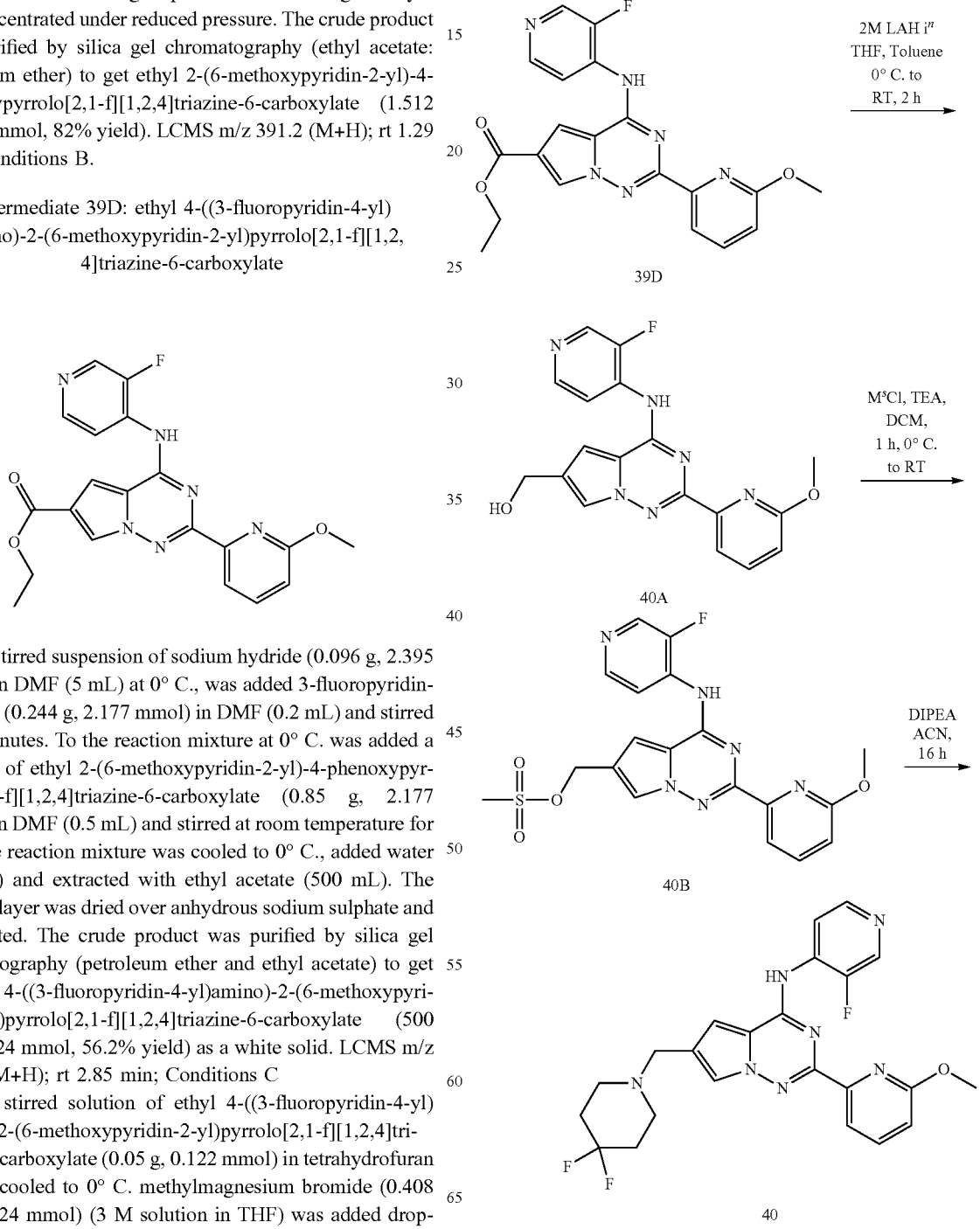

Example 40

N-{6-[(4,4-difluoropiperidin-1-yl)methyl]-2-(6-methoxypyridin-2-yl)pyrrolo[2,1-f][1,2,4]triazin-4-yl}-3-fluoropyridin-4-amine

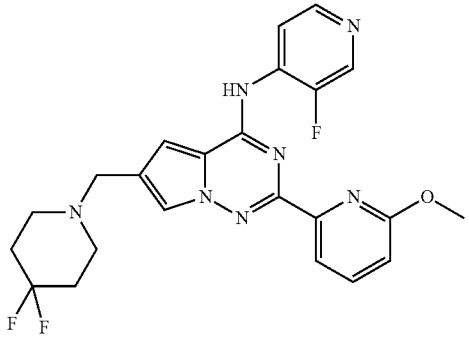 [SMILES: COc1cccc(-c2nc(Nc3ccncc3F)c3cc(CN4CCC(F)(F)CC4)cn3n2)n1]

Intermediate 40A: (4-((3-fluoropyridin-4-yl)amino)-2-(6-methoxypyridin-2-yl)pyrrolo[2,1-f][1,2,4]triazin-6-yl)methanol

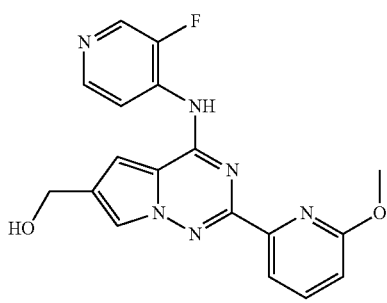 [SMILES: COc1cccc(-c2nc(Nc3ccncc3F)c3cc(CO)cn3n2)n1]

To a solution of ethyl 4-((3-fluoropyridin-4-yl)amino)-2-(6-methoxypyridin-2-yl)pyrrolo[2,1-f][1,2,4]triazine-6-carboxylate (1.0 g, 2.449 mmol) in THF (10 mL) at −78° C., was added LAH (3.67 mL, 3.67 mmol). The reaction mixture was warmed up to room temperature and stirred for 1 h. The reaction mixture was cooled to 0° C., quenched with water (2 mL) and sodium sulphate (10 g). The resulting mixture was filtered through celite. The celite bed was washed with THF (200 mL) and the combined filtare was concentrated under reduced pressure to get (4-((3-fluoropyridin-4-yl)amino)-2-(6-methoxypyridin-2-yl)pyrrolo[2,1-f][1,2,4]triazin-6-yl)methanol (360 mg, 0.983 mmol, 40.1% yield). LCMS m/z 376.1 (M+H); rt 0.64 min; Conditions A.

Intermediate 40B: (4-((3-fluoropyridin-4-yl)amino)-2-(6-methoxypyridin-2-yl)pyrrolo[2,1-f][1,2,4]triazin-6-yl)methyl methanesulfonate

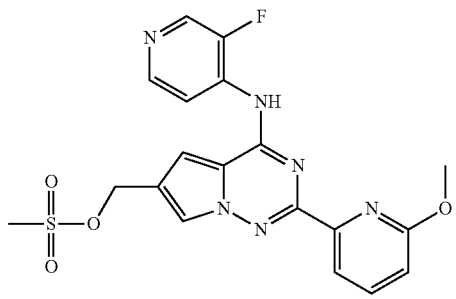

To a solution of (4-((3-fluoropyridin-4-yl)amino)-2-(6-methoxypyridin-2-yl)pyrrolo[2,1-f][1,2,4]triazin-6-yl)methanol (250 mg, 0.682 mmol) in DCM (25 mL) at 0° C. was added TEA (0.238 mL, 1.706 mmol) and methanesulfonyl chloride (0.080 mL, 1.024 mmol). The resulting solution stirred at room temperature for 1 h. The reaction mixture was concentrated and the residue was titurated with ether (2×10 mL) to get intermediate 40B (200 mg, 0.288 mmol) as a light green solid. LCMS m/z 450.3 (M+Li); rt 0.64 min; Conditions A.

To a solution of 4,4-difluoropiperidine (35.5 mg, 0.225 mmol), DIPEA (0.039 mL, 0.225 mmol) in acetonitrile (5 mL) at 60° C., a solution of mesyl intermediate 40B (50 mg, 0.113 mmol) in acetonitrile (5 mL) was added dropwise. The reaction mixture was heated at 80° C. for 16 h. The reaction mixture was concentrated and the residue was purified by reverse phase HPLC to afford Example 40 (9 mg, 17.4%): LCMS m/z 470.3 (M+H); rt 1.96 min; Conditions C; $^1$H NMR (400 MHz, DMSO-d6) δ 10.05 (br. s, 1H) 8.69 (t, J=6.02 Hz, 1H) 8.63 (s, 1H) 8.40 (d, J=5.52 Hz, 1H) 7.93 (s, 1H) 7.78-7.87 (m, 2H) 7.35 (br. s, 1H) 6.93 (dd, J=7.53, 1.00 Hz, 1H) 4.01 (s, 3H) 3.69 (s, 2H) 2.56 (br. s, 4H) 1.92-2.06 (m, 4H).

Scheme 41

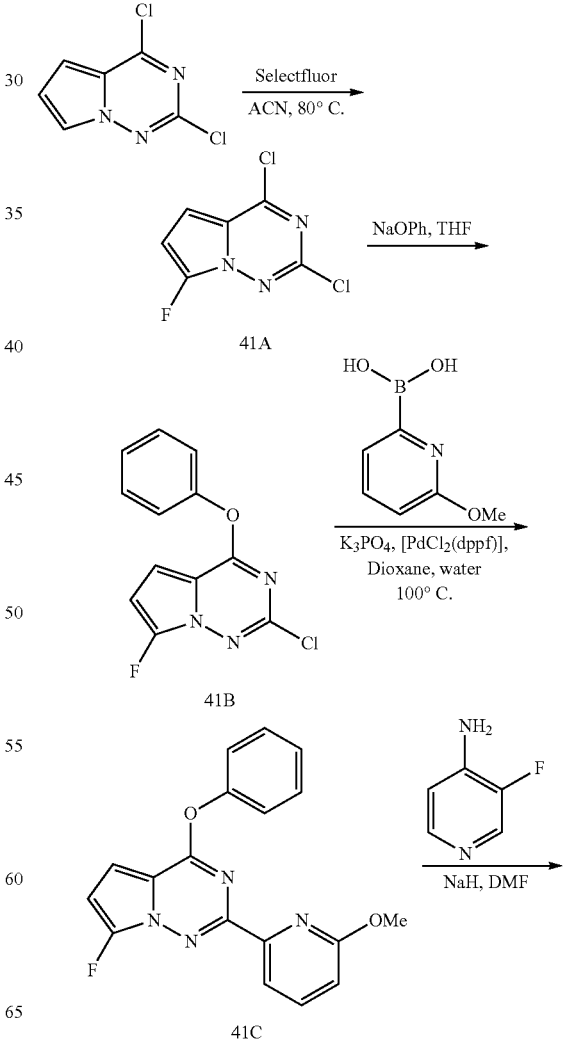

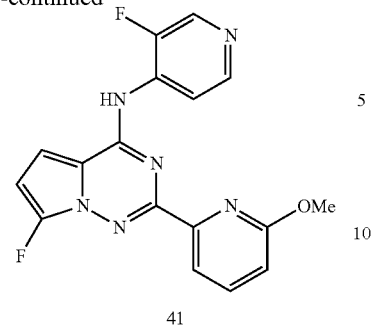

41

Example 41

3-fluoro-N-[7-fluoro-2-(6-methoxypyridin-2-yl)pyrrolo[2,1-f][1,2,4]triazin-4-yl]pyridin-4-amine Intermediate-41A: (2,4-dichloro-7-fluoropyrrolo[2,1-f][1,2,4]triazine)

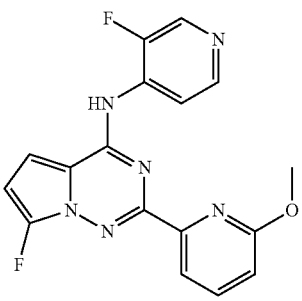 [SMILES: COc1cccc(-c2nc(Nc3ccncc3F)c3ccc(F)n3n2)n1]

To a solution of 2,4-dichloropyrrolo[2,1-f][1,2,4]triazine (0.4 g, 2.127 mmol) in acetonitrile (10 mL) added Selectfluor (3.75 g, 10.66 mmol) and stirred at 80° C. for 16 h. The reaction mixture was concentrated and purified by silica gel chromatography (ethylacetate/petroleum ether) to get the 2,4-dichloro-7-fluoropyrrolo[2,1-f][1,2,4]triazine (0.2 g, 46%), LCMS m/z 204.0 (M+H); rt 0.53 min; Conditions E.

Intermediate-41B: (2-chloro-7-fluoro-4-phenoxypyrrolo[2,1-f][1,2,4]triazine)

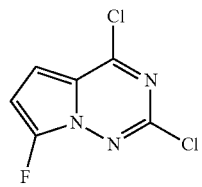 [SMILES: Fc1ccc2c(Cl)nc(Cl)nn12]

To a 100 mL flask was added 2,4-dichloro-7-fluoropyrrolo[2,1-f][1,2,4]triazine (0.1 g, 0.484 mmol), tetrahydrofuran (10 mL) and stirred. To the resulting solution was portionwise added sodium phenolate (0.06 g, 0.532 mmol). After 1 h, an aliquot of the reaction mixture was diluted with methanol and analyzed by LCMS to ensure complete conversion. The reaction mixture was concentrated. To the residue was added water, stirred, filtered and dried to get 2-chloro-7-fluoro-4-phenoxypyrrolo[2,1-f][1,2,4]triazine (0.09 g, 0.38 mmol, 75%) as an off-white solid. LCMS m/z 264.0 (M+H); rt 3.25 min; Conditions E.

Intermediate-41C: (7-fluoro-2-(6-methoxypyridin-2-yl)-4-phenoxypyrrolo[2,1-f][1,2,4]triazine)

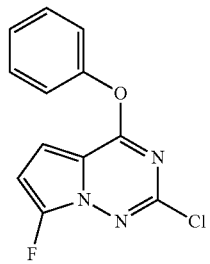 [SMILES: Fc1ccc2c(Oc3ccccc3)nc(Cl)nn12]

To a scintillation vial was added 2-chloro-7-fluoro-4-phenoxypyrrolo[2,1-f][1,2,4]triazine (6-methoxypyridin-2-yl)boronic acid (0.045 g, 0.296 mmol), tripotassium phosphate (0.157 g, 0.740 mmol), 1,1'-bis(diphenylphosphino)ferrocene-palladium(II)-dichloride dichloromethane complex (10.07 mg, 0.012 mmol), dioxane (2 mL) and water (0.2 mL). The resulting reaction mixture was degassed with nitrogen and heated at 100° C. for 18 h. An aliquot of the reaction mixture was analyzed by LCMS to ensure completion of reaction. The reaction mixture was concentrated and the residue was purified by silica gel chromatography using 0-20% ethyl acetate in hexanes to get intermediate 21B (0.04 g, 0.119 mmol, 48% yield) as a off white solid. LCMS m/z 337.0 (M+); rt 3.64 min; Conditions E.

Example 41 (2 mg, 4.5%) was synthesized employing the procedure described for Example 15 (Scheme 15): LCMS m/z 355.2 (M+H); rt 1.78 min; Conditions C. $^{1}$H NMR (400 MHz, DMSO-d6) δ 8.70-8.62 (m, 2H), 8.43 (s, 1H), 7.89-7.79 (m, 2H), 7.43-7.35 (m, 1H), 7.00-6.93 (m, 1H), 6.64 (t, J=3.8 Hz, 1H), 4.01 (s, 3H)

Scheme 42

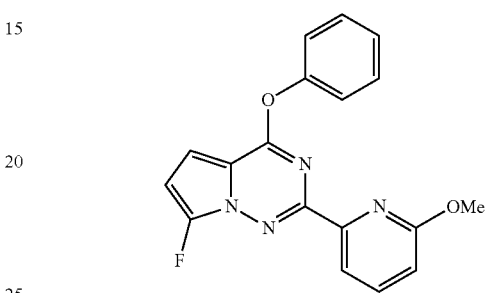

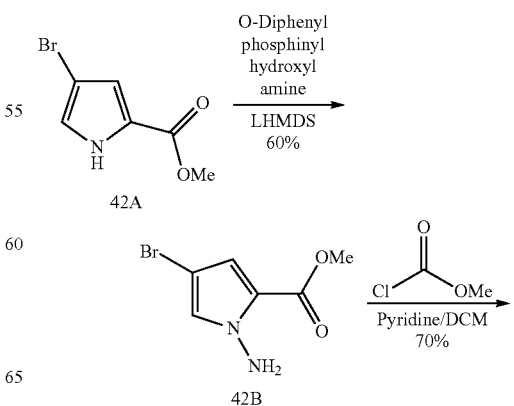

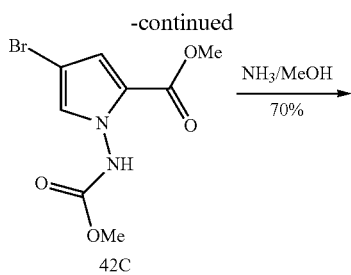

42C

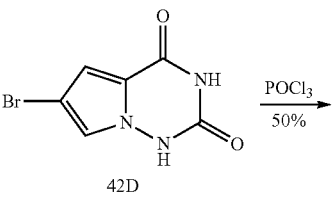

42D

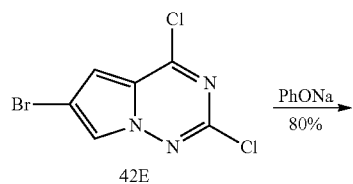

42E

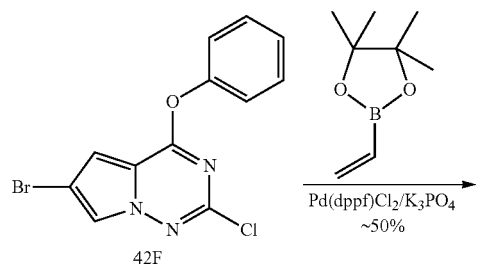

42F

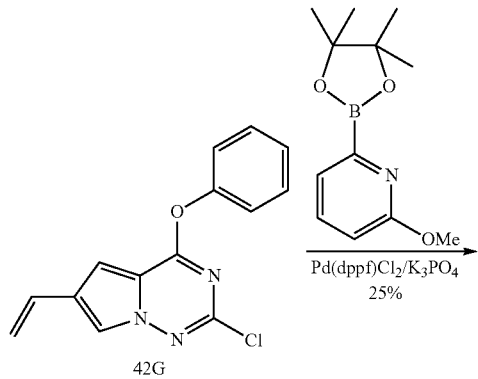

42G

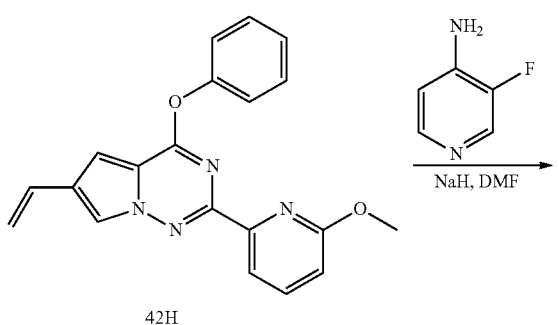

42H

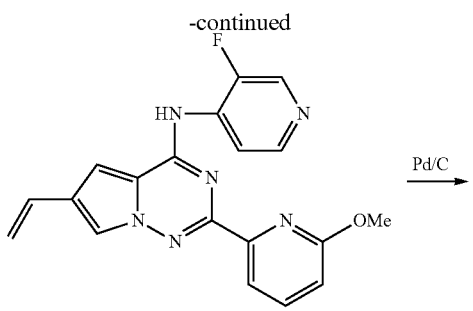

42I

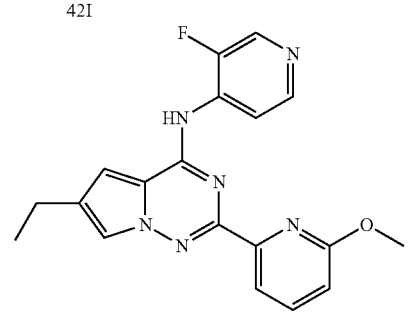

42

Example 42

N-[6-ethyl-2-(6-methoxypyridin-2-yl)pyrrolo[2,1-f][1,2,4]triazin-4-yl]-3-fluoropyridin-4-amine

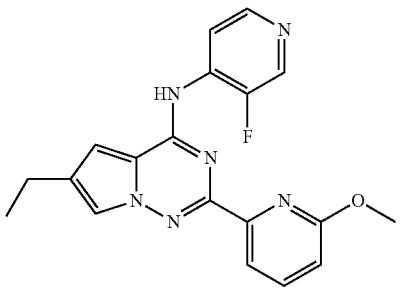 [SMILES: CCc1cc2c(Nc3ccncc3F)nc(-c3cccc(OC)n3)nn2c1]

Intermediate 42B: methyl 1-amino-4-bromo-1H-pyrrole-2-carboxylate

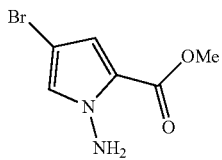 [SMILES: COC(=O)c1cc(Br)cn1N]

To a solution of methyl 4-bromo-1H-pyrrole-2-carboxylate (0.5 g, 2.451 mmol) in DMF (30 mL) at −10° C. was added LHMDS (2.70 mL, 2.70 mmol) and stirred for 15 min. To the resulting mixture was added diphenyl aminooxyphosphonate (0.975 g, 3.68 mmol) and stirred at room temperature for 15 h. The reaction mixture was diluted with ethyl acetate (50 mL), washed with water (15 mL×2), brine (20 mL×2), dried over anhydrous sodium sulphate and evaporated under reduced pressure to get intermediate 22A (250 mg, 0.936 mmol, 38.2% yield): LCMS m/z 219.0 (M+H); rt 2.27 min; Conditions E.

Intermediate 42C: methyl 4-bromo-1-((methoxycarbonyl)amino)-1H-pyrrole-2-carboxylate

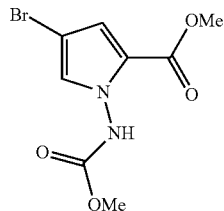 [SMILES: COC(=O)Nn1cc(Br)cc1C(=O)OC]

To a solution of methyl 1-amino-4-bromo-1H-pyrrole-2-carboxylate (12 g, 27.4 mmol) in DCM (120 mL) was added pyridine (5.54 mL, 68.5 mmol) and cooled to 0° C. To the resulting solution was dropwise added ethyl chloroformate (2.368 mL, 24.65 mmol) and stirred at room temperature for 3 h. An aliquot of the reaction mixture was analyzed by LCMS to ensure completion of reaction. The reaction mixture was diluted with DCM and washed with 10% citric acid solution, water, brine, dried over sodium sulfate and concentrated. The crude product was purified by silica gel chromatography using 3-10% ethyl acetate in hexanes to get intermediate 22B (5 g, 9.62 mmol, 56% yield): LCMS m/z 308.0 (M+H2O); rt 2.48 min; Conditions E.

Intermediate 42D: 6-bromopyrrolo[2,1-f][1,2,4]triazine-2,4(1H,3H)-dione

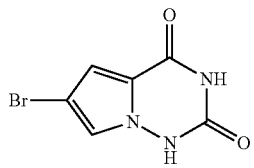 [SMILES: O=c1[nH]c(=O)c2cc(Br)cn2[nH]1]

To a solution of methyl 4-bromo-1-((ethoxycarbonyl)amino)-1H-pyrrole-2-carboxylate (3.5 g, 12.02 mmol) in MeOH (10 mL) was added aqueous ammonia (25 mL, 1155 mmol) and heated at 120° C. for 15 h in an autoclave. An aliquot of the reaction mixture was analyzed by LCMS to ensure completion of reaction. The reaction mixture was concentrated under reduced pressure. The resulting residue was washed with ethyl acetate (500 mL), filtered and dried to get 6-bromopyrrolo[2,1-f][1,2,4]triazine-2,4(1H,3H)-dione (1 g, 4.35 mmol, 36.2% yield) as a brown solid: LCMS m/z 260.0 (M+); rt 0.60 min; Conditions A.

Intermediate 42E: 6-bromo-2,4-dichloropyrrolo[2,1-f][1,2,4]triazine

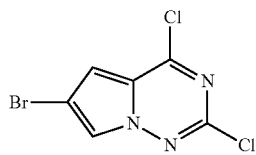 [SMILES: Clc1nc(Cl)c2cc(Br)cn2n1]

To a mixture of 6-bromopyrrolo[2,1-f][1,2,4]triazine-2,4(1H,3H)-dione (900 mg, 3.91 mmol) and triethylamine hydrochloride (1616 mg, 11.74 mmol) was added POCl3 (5 mL, 53.6 mmol) and heated at 105° C. for 24 h. An aliquot of the reaction mixture was analyzed by LCMS to ensure completion of reaction. Excess POCl3 was evaporated under reduced pressure and the crude product was quenched with ice cold saturated sodium bicarbonate solution. The mixture was extracted with ethyl acetate (250 mL×2), dried over sodium sulphate and concentrated. The crude product was purified by silica gel chromatography using 3-10% ethyl acetate in hexanes to get intermediate 22E (600 mg, 2.248 mmol, 57.5% yield). LCMS m/z 260.0 (M+); rt 0.60 min; Conditions E.

Intermediate 42F: 6-bromo-2-chloro-4-phenoxypyrrolo[2,1-f][1,2,4]triazine

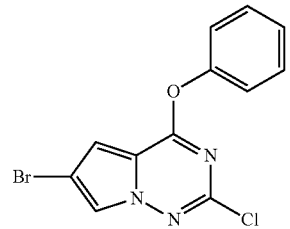 [SMILES: Clc1nc(Oc2ccccc2)c2cc(Br)cn2n1]

To a solution of 6-bromo-2,4-dichloropyrrolo[2,1-f][1,2,4]triazine (60 mg, 0.225 mmol) in THF (4 mL) was added sodium phenolate (26.1 mg, 0.225 mmol) and stirred at room temperature for 1 h. An aliquot of the reaction mixture was analyzed by LCMS to ensure completion of reaction. The reaction mixture was concentrated and the residue was dissolved in DCM (200 mL). The resulting solution was washed with water (20 mL), dried over anhydrous sodium sulphate and evaporated under reduced pressure to get 6-bromo-2-chloro-4-phenoxypyrrolo[2,1-f][1,2,4]triazine (50 mg, 0.154 mmol, 68.5% yield) as an off white solid: LCMS m/z 326.0 (M+H); rt 3.4 min; Conditions E.

Intermediate 42G: 2-chloro-4-phenoxy-6-vinylpyrrolo[2,1-f][1,2,4]triazine

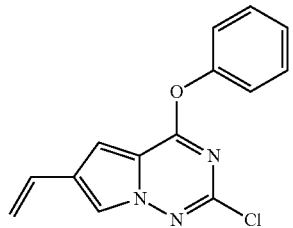 [SMILES: C=Cc1cc2c(Oc3ccccc3)nc(Cl)nn2c1]

To a 40 mL scintillation vial was added 6-bromo-2-chloro-4-phenoxypyrrolo[2,1-f][1,2,4]triazine (700 mg, 2.157 mmol), 2 M tripotassium phosphate (2.157 mL, 4.31 mmol), 1,4-dioxane (25 mL) and PdCl2(dppf)-CH2Cl2 adduct (88 mg, 0.108 mmol) and vinylboronic acid pinacol ester (332 mg, 2.157 mmol). The reaction mixture was degassed with nitrogen and heated at 90° C. for 15 h. An aliquot of the reaction mixture was analyzed by LCMS to ensure completion of reaction. The crude product was evaporated under reduced pressure and purified by silica gel chromatography using 10-15% ethyl acetate in hexanes to get intermediate 22G (250 mg, 0.506 mmol, 23.46% yield) as yellow solid. LCMS m/z 272.1 (M+); rt 1.10 min; Conditions A.

Intermediate 42H: 2-(6-methoxypyridin-2-yl)-4-phenoxy-6-vinylpyrrolo[2,1-f][1,2,4]triazine

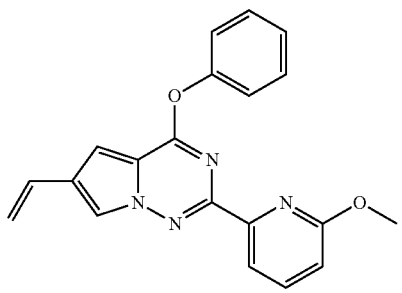 [SMILES: C=Cc1cc2c(Oc3ccccc3)nc(-c3cccc(OC)n3)nn2c1]

To a 40 mL scintillation vial was added 2-chloro-4-phenoxy-6-vinylpyrrolo[2,1-f][1,2,4]triazine (200 mg, 0.736 mmol), tripotassium phosphate (0.736 mL, 1.472 mmol) and 1,4-dioxane (10 mL). The reaction mixture was degassed and then added 1,1'-bis(diphenylphosphino)ferrocene-palladium(II)-dichloride dichloromethane complex (30.1 mg, 0.037 mmol) and heated at 90° C. for 15 h. An aliquot of the reaction mixture was analyzed by LCMS to ensure completion of reaction. The reaction mixture was concentrated and purified by silica gel chromatography using 20-40% ethyl acetate in hexanes to get intermediate 22H (45 mg, 0.131 mmol, 17.75% yield). LCMS m/z 345.1 (M+); rt 1.15 min; Conditions A.

Intermediate 42I: N-(3-fluoropyridin-4-yl)-2-(6-methoxypyridin-2-yl)-6-vinylpyrrolo[2,1-f][1,2,4]triazin-4-amine

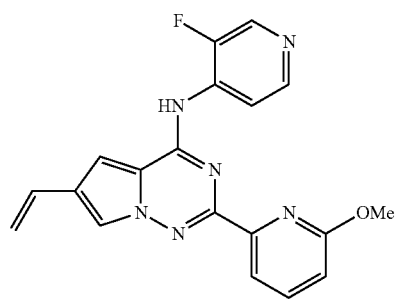 [SMILES: C=Cc1cc2c(Nc3ccncc3F)nc(-c3cccc(OC)n3)nn2c1]

To a solution of 3-fluoropyridin-4-amine (12.21 mg, 0.109 mmol) in DMF (1 mL) at 0° C. was added sodium hydride (4.36 mg, 0.109 mmol) and stirred for 5 min. To the resulting reaction mixture was added a solution of 2-(6-methoxypyridin-2-yl)-4-phenoxy-6-vinylpyrrolo[2,1-f][1,2,4]triazine (25 mg, 0.073 mmol) in DMF (1 mL) and stirred at room temperature for 2 h. An aliquot of the reaction mixture was analyzed by LCMS to ensure completion of reaction. The reaction mixture quenched with methanol and evaporated under reduced pressure. The crude product used in the next step without further purification: LCMS m/z 363.1 (M+); rt 0.82 min; Conditions A.

To a degassed solution of N-(3-fluoropyridin-4-yl)-2-(6-methoxypyridin-2-yl)-6-vinylpyrrolo[2,1-f][1,2,4]triazin-4-amine (25 mg, 0.069 mmol) in methanol was added palladium on carbon (5 mg, 0.047 mmol) and stirred under hydrogen atmosphere (1 atm) for two hours. The reaction mixture was filtered through a pad of celite. The filtrate was evaporated to afford crude Example 42 (5 mg, 19.89%): LCMS m/z 365.2 (M+H); rt 2.01 min; Conditions C. $^1$H NMR (400 MHz, DMSO-d6) δ 10.00 (s, 1H), 8.73 (dd, J=7.03, 5.52 Hz, 1H), 8.63 (d, J=3.01 Hz, 1H), 8.41 (d, J=5.52 Hz, 1H), 7.80-7.90 (m, 3H), 7.29 (d, J=1.51 Hz, 1H), 6.93 (dd, J=7.53, 1.51 Hz, 1H), 4.02 (s, 3H), 2.67-2.77 (m, 2H), 1.33 (t, J=7.6 Hz, 1H)

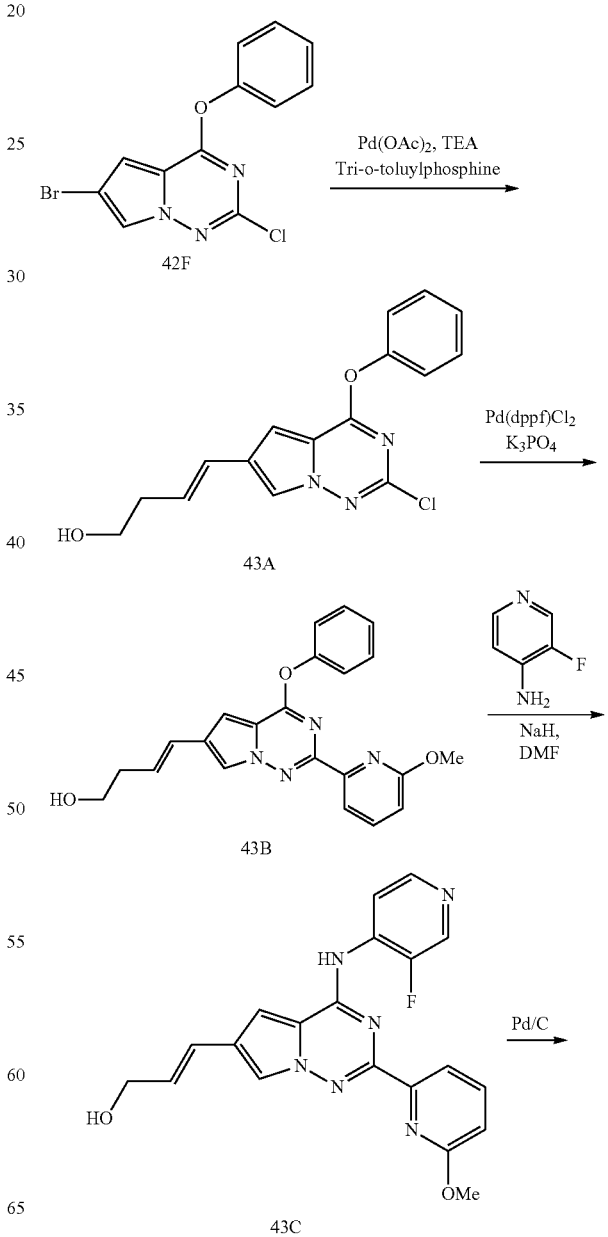

Scheme 43

141
-continued

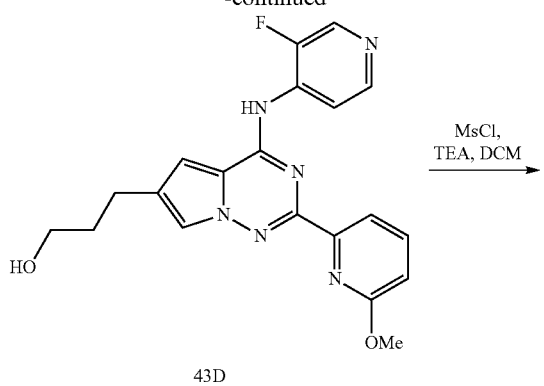

43D

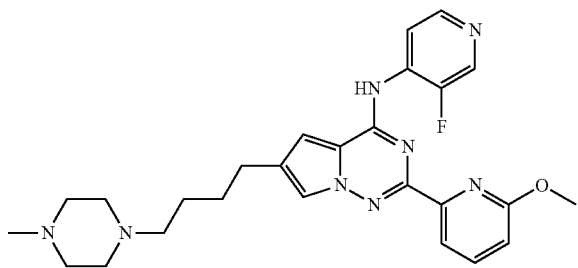

43E

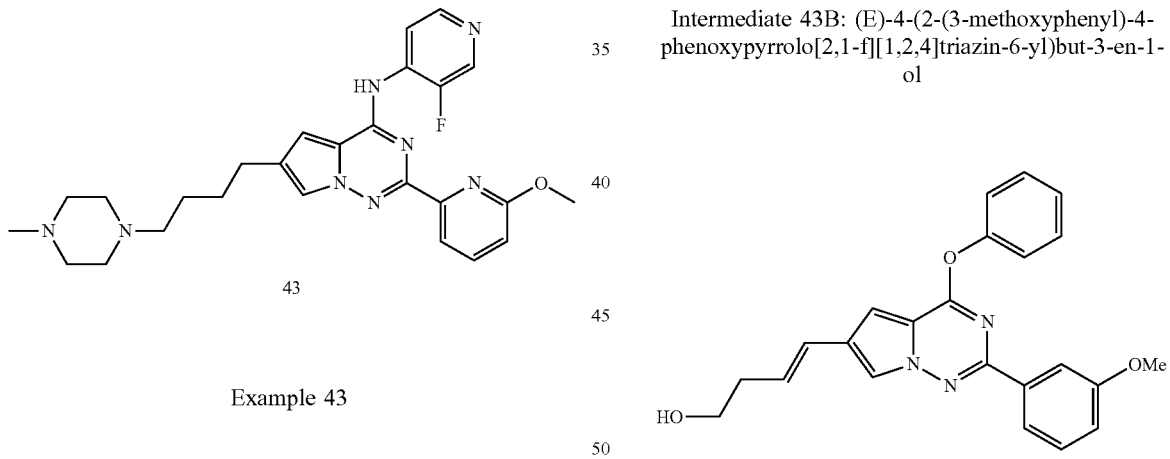

43

Example 43

3-fluoro-N-[2-(6-methoxypyridin-2-yl)-6-[4-(4-methylpiperazin-1-yl)butyl]pyrrolo[2,1-f][1,2,4]triazin-4-yl]pyridin-4-amine

142

Intermediate 43A: (E)-4-(2-chloro-4-phenoxypyrrolo[2,1-f][1,2,4]triazin-6-yl)but-3-en-1-ol

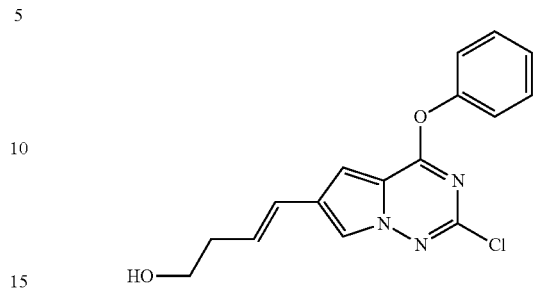

To a 40 mL scintillation vial was added 6-bromo-2-chloro-4-phenoxypyrrolo[2,1-f][1,2,4]triazine (500 mg, 1.541 mmol), tri-o-toluylphosphine (56.3 mg, 0.185 mmol) and palladium(II)acetate (34.6 mg, 0.154 mmol) and DMF (15 mL). The resulting mixture was degassed with argon and added TEA (1.074 mL, 7.70 mmol) and but-3-en-1-ol (0.669 mL, 7.70 mmol) and heated at 100° C. for 3 h. An aliquot of the reaction mixture was analyzed by LCMS to ensure completion of reaction. The reaction mixture was diluted with ethyl acetate (50 mL) and washed with brine (15 mL×2). The resulting organic layer was concentrated and purified by silica gel chromatography using 20-45% ethyl acetate in hexanes to get intermediate 23A (30 mg, 0.095 mmol, 30.8% yield) LCMS m/z 316.0 (M+); rt 0.94 min; Conditions A.

Intermediate 43B: (E)-4-(2-(3-methoxyphenyl)-4-phenoxypyrrolo[2,1-f][1,2,4]triazin-6-yl)but-3-en-1-ol To a 40 mL scintillation vial was added 4-(2-chloro-4-phenoxypyrrolo[2,1-f][1,2,4]triazin-6-yl)but-3-en-1-ol (235 mg, 0.744 mmol), 1,4-dioxane (15 mL), 2-methoxy-6-(4,4,5,5-tetramethyl-1,3,2-dioxaborolan-2-yl)pyridine (350 mg, 1.488 mmol) and tripotassium phosphate (0.744 mL, 2.233 mmol). The resulting reaction mixture was degassed with nitrogen and added 1,1'-bis(diphenylphosphino)ferrocene-palladium(II)-dichloride dichloromethane complex (30.4 mg, 0.037 mmol) and heated at 100° C. for 15 h. An aliquot of the reaction mixture was analyzed by LCMS to ensure completion of reaction. The reaction mixture was concentrated and purified by silica gel chromatography using 20-45% ethyl acetate in hexanes to get intermediate 23B (265 mg, 0.525 mmol, 58.2% yield) LCMS m/z 389.2 (M+H); rt 0.99 min; Conditions A.

Intermediate 43C: 3-(4-((3-fluoropyridin-4-yl)amino)-2-(6-methoxypyridin-2-yl)pyrrolo[2,1-f][1,2,4]triazin-6-yl)propan-1-ol

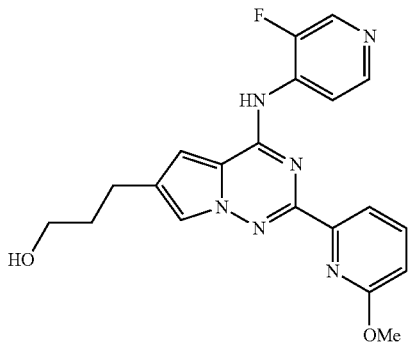 [SMILES: COc1cccc(-c2nc(Nc3ccncc3F)c3cc(CCCO)cn3n2)n1]

To a degassed solution of 4-(4-((3-fluoropyridin-4-yl)amino)-2-(6-methoxypyridin-2-yl)pyrrolo[2,1-f][1,2,4]triazin-6-yl)but-3-en-1-ol (400 mg, 0.531 mmol) in methanol (5 mL) was added palladium on carbon (56.6 mg, 0.531 mmol) and stirred at room temperature under hydrogen atmosphere (1 atm) for 2 h. An aliquot of the reaction mixture was analyzed by LCMS to ensure completion of reaction. The reaction mixture was filtered through celite and the filtrate was evaporated under reduced pressure. The residue was purified by preparative LC/MS to get (40 mg, 10% yield): LCMS m/z 409.3 (M+); rt 1.6 min; Conditions A.

Intermediate 43D: 3-(4-((3-fluoropyridin-4-yl)amino)-2-(6-methoxypyridin-2-yl)pyrrolo[2,1-f][1,2,4]triazin-6-yl)propyl methanesulfonate

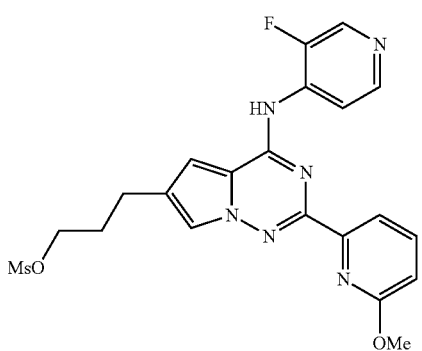 [SMILES: COc1cccc(-c2nc(Nc3ccncc3F)c3cc(CCCOS(C)(=O)=O)cn3n2)n1]

To a solution of 4-(4-((3-fluoropyridin-4-yl)amino)-2-(6-methoxypyridin-2-yl)pyrrolo[2,1-f][1,2,4]triazin-6-yl)butan-1-ol (40 mg, 0.098 mmol) in DCM (5 mL) at 0° C., was added TEA (0.027 mL, 0.196 mmol) and methanesulfonyl chloride (0.015 mL, 0.196 mmol). The resulting solution stirred at room temperature for 2 h. An aliquot of the reaction mixture was analyzed by LCMS to ensure completion of reaction. The reaction mixture was concentrated under reduced pressure to get crude 43D (40 mg) that was used in the next step without further purification. LCMS m/z 487.2 (M+H); rt 0.84 min; Conditions A.

Example 43E: (3E)-4-{4-[(3-fluoropyridin-4-yl)amino]-2-(6-methoxypyridin-2-yl)pyrrolo[2,1-f][1,2,4]triazin-6-yl}but-3-en-1-ol

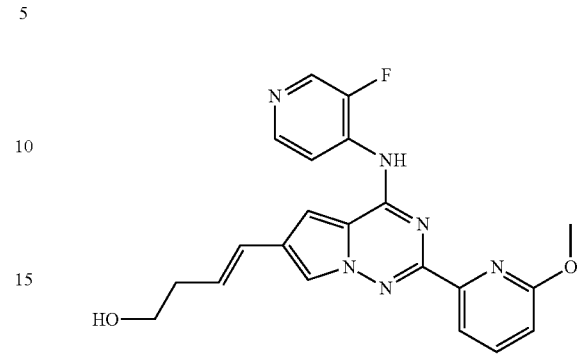

Example 43E (3 mg, 11.5%) was synthesized employing the procedure described for Example 15 (Scheme 15): LCMS m/z 407.2 (M+H); rt 1.59 min; Conditions C. $^1$H NMR (400 MHz, DMSO-d6) δ 10.08 (br. s, 1H) 8.70 (br. s, 1H) 8.61 (br. s, 1H) 8.39 (d, J=5.02 Hz, 1H) 8.02 (s, 1H) 7.77-7.89 (m, 2H) 7.43 (br. s, 1H) 6.93 (dd, J=8.0 Hz, 1H) 6.50 (d, J=14 Hz, 1H) 6.19-6.30 (m, 1H) 4.61 (t, J=5.27 Hz, 1H) 4.01 (s, 3H) 3.50-3.59 (m, 2H) 2.31-2.42 (m, 2H)

Example 43 (3 mg, 15%) was synthesized employing the procedure described for Example 40 (Scheme 40): LCMS m/z 491.4 (M+H); rt 1.47 min; Conditions C. $^1$H NMR (400 MHz, DMSO-d6) δ 10.15 (br. s, 1H) 8.66-8.80 (m, 2H) 8.45 (d, J=5.02 Hz, 1H) 7.91 (s, 1H) 7.78-7.87 (m, 2H) 7.27 (s, 2H) 7.15 (s, 1H) 7.02 (s, 1H) 6.94 (d, J=8.03 Hz, 1H) 4.01 (s, 3H) 3.02-3.73 (m, 10H) 2.81 (s, 3H) 2.70-2.76 (m, 2H) 1.70 (d, J=3.01 Hz, 4H).

Scheme 44

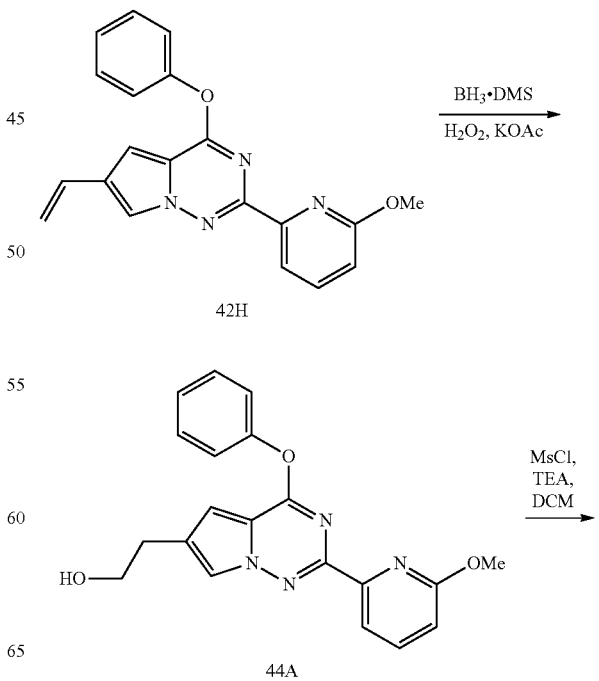

145

-continued

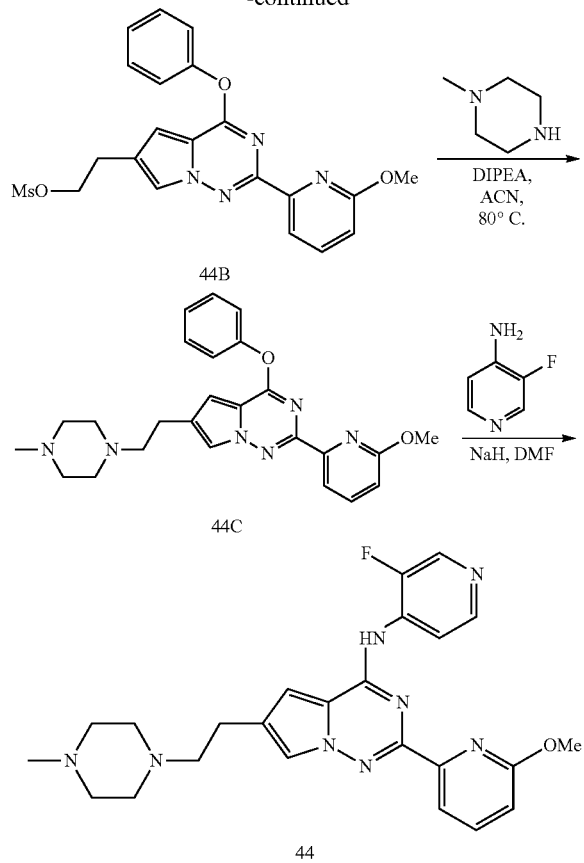

44

Example 44

3-fluoro-N-[2-(6-methoxypyridin-2-yl)-6-[2-(4-methylpiperazin-1-yl)ethyl]pyrrolo[2,1-f][1,2,4]triazin-4-yl]pyridin-4-amine Intermediate-44A: (2-(2-(6-methoxypyridin-2-yl)-4-phenoxypyrrolo[2,1-f][1,2,4]triazin-6-yl)ethanol)

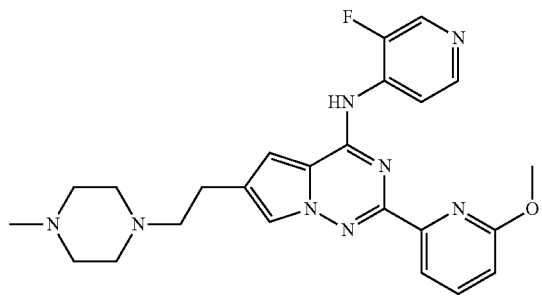

146

To a solution of 2-(6-methoxypyridin-2-yl)-4-phenoxy-6-vinylpyrrolo[2,1-f][1,2,4]triazine (0.22 g, 0.639 mmol) in THF (10 mL) at 0° C. was added BH$_3$.DMS (0.243 mL, 2.56 mmol) and stirred at room temperature for 3 h. To the reaction mixture was added hydrogen peroxide (0.020 mL, 0.639 mmol) (30% hydrogen peroxide) and potassium acetate (0.02 mL, 0.639 mmol) (3 M) and stirred for 1 h. An aliquot of the reaction mixture was analyzed by LCMS to ensure completion of reaction. The reaction mixture was extracted with ethylacetate, washed with water and brine. The resulting organic phase was dried over sodium sulfate, concentrated and purified by silica gel chromatography using 0-20% ethyl acetate in hexanes to get intermediate 24A (0.085 g, 0.235 mmol, 36.7%) as an off white solid. LCMS m/z 363.1 (M+); rt 0.95 min; Conditions A.

Intermediate-44B: (2-(2-(6-methoxypyridin-2-yl)-4-phenoxypyrrolo[2,1-f][1,2,4]triazin-6-yl)ethyl methanesulfonate)

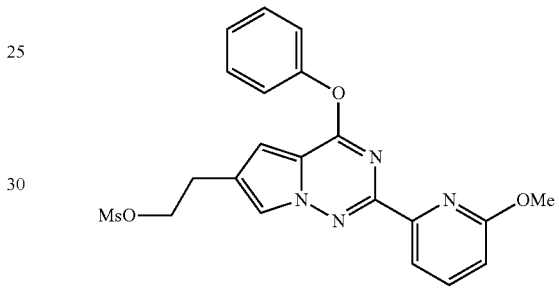

To a solution of 2-(2-(6-methoxypyridin-2-yl)-4-phenoxypyrrolo[2,1-f][1,2,4]triazin-6-yl)ethanol (0.085 g, 0.235 mmol) in DCM (2 mL) was added methanesulfonyl chloride (0.027 mL, 0.352 mmol) and TEA (0.065 mL, 0.469 mmol). The reaction mixture was stirred at room temperature for 2 h. An aliquot of the reaction mixture was analyzed by LCMS to ensure completion of reaction. The reaction mixture was concentrated to get crude 24B (0.12 g, 0.270 mmol, 99%). LCMS m/z 441.2 (M+H); rt 1.02 min; Conditions A.

Intermediate-44C: (2-(6-methoxypyridin-2-yl)-6-(2-(4-methylpiperazin-1-yl)ethyl)-4-phenoxypyrrolo[2,1-f][1,2,4]triazine)

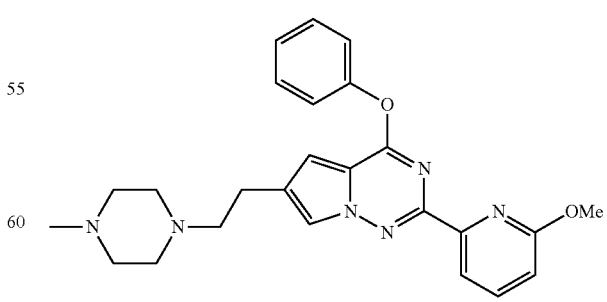

To a 40 mL scintillation vial was added 1-methylpiperazine (0.019 mL, 0.170 mmol), acetonitrile (2 mL) and diisopropylethylamine (0.059 mL, 0.341 mmol). The reaction mixture was heated to 60° C. for 10 min, and added 2-(2-(6-methoxypyridin-2-yl)-4-phenoxypyrrolo[2,1-f][1,2,4]triazin-6-yl)ethyl methanesulfonate (0.05 g, 0.114 mmol). The vial was capped and heated at 80° C. for 18 h. An aliquot of the reaction mixture was analyzed by LCMS to ensure completion of reaction. The reaction mixture was concentrated and purified by silicagel chromatography using 0-5% chloroform in methanol to get intermediate 24C (0.03 g, 0.067 mmol, 59.5%) as an off white solid): LCMS m/z 445.2 (M+H); rt 3.28 min; Conditions E.

Example 44 (3 mg, 9.5%) was synthesized employing the procedure described for Example 15 (Scheme 15): LCMS m/z 463.3 (M+H); rt 1.96 min; Conditions C. $^1$H NMR (400 MHz, DMSO-d6) δ 8.67 (br. s, 1H), 8.62 (d, J=2.5 Hz, 1H), 8.40 (d, J=5.5 Hz, 1H), 7.92 (s, 1H), 7.87-7.76 (m, 2H), 7.25 (s, 1H), 6.93 (dd, J=1.0, 7.5 Hz, 1H), 4.00 (s, 3H), 2.93-2.65 (m, 8H), 2.64-2.52 (m, 2H), 2.55 (s, 3H), 1.91 (s, 2H).

Scheme 45

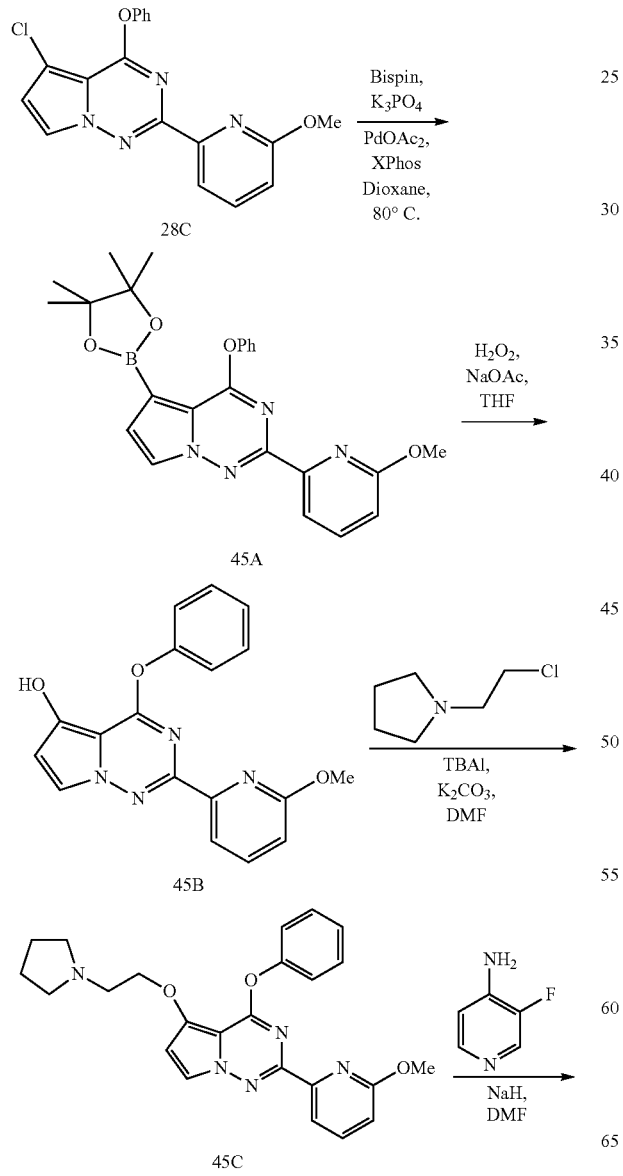

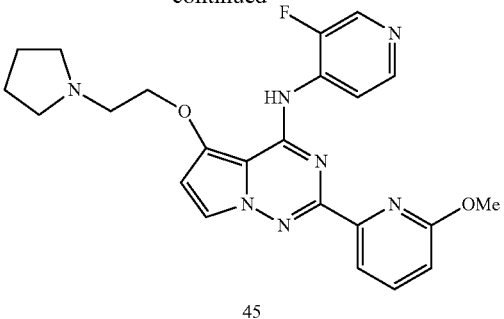

45

Example 45

3-fluoro-N-[2-(6-methoxypyridin-2-yl)-5-[2-(pyrrolidin-1-yl)ethoxy]pyrrolo[2,1-f][1,2,4]triazin-4-yl]pyridin-4-amine

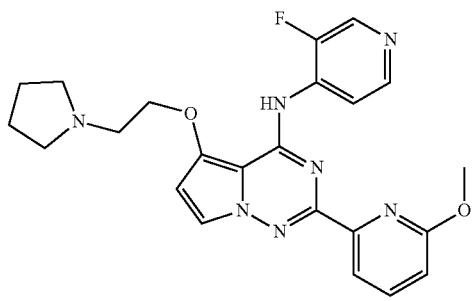 [SMILES: COc1cccc(-c2nc(Nc3ccncc3F)c3c(OCCN4CCCC4)ccn3n2)n1]

Intermediate 45A: (2-(6-methoxypyridin-2-yl)-4-phenoxy-5-(4,4,5,5-tetramethyl-1,3,2-dioxaborolan-2-yl)pyrrolo[2,1-f][1,2,4]triazine)

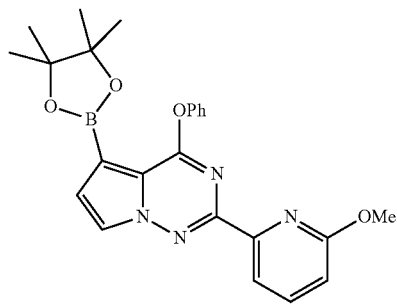 [SMILES: COc1cccc(-c2nc(Oc3ccccc3)c3c(B4OC(C)(C)C(C)(C)O4)ccn3n2)n1]

To a 40 mL scintillation vial was added 5-chloro-2-(6-methoxypyridin-2-yl)-4-phenoxypyrrolo[2,1-f][1,2,4]triazine (0.2 g, 0.567 mmol), dioxane (2 mL), tripotassium phosphate (0.361 g, 1.701 mmol), 2-(dicyclohexylphosphino)-2',4',6'-triisopropylbiphenyl (0.027 g, 0.057 mmol), palladium(II)acetate (6.36 mg, 0.028 mmol) and bis(pinacolato)diboron (0.432 g, 1.702 mmol). The resulting reaction mixture was degassed with nitrogen and heated at 100° C. for 18 h. An aliquot of the reaction mixture was analyzed by LCMS to ensure completion of reaction. The reaction mixture was concentrated. To the residue was added ethylacetate and filtered through celite. The filtrate was concentrated and purified by silica gel chromatography using 0-20% ethyl acetate in hexanes to get intermediate 26A (0.1 g, 0.18 mmol, 32%) as an off white solid. LCMS m/z 445.2 (M+); rt 3.98 min; Conditions E.

Intermediate 45B: (2-(6-methoxypyridin-2-yl)-4-phenoxy-5-(4,4,5,5-tetramethyl-1,3,2-dioxaborolan-2-yl)pyrrolo[2,1-f][1,2,4]triazine)

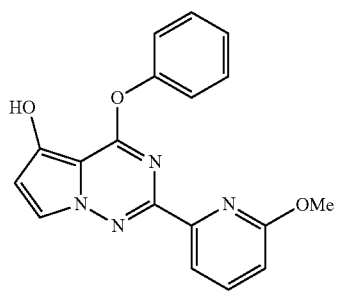 [SMILES: COc1cccc(-c2nc(Oc3ccccc3)c3c(O)ccn3n2)n1]

To a solution of 2-(6-methoxypyridin-2-yl)-4-phenoxy-5-(4,4,5,5-tetramethyl-1,3,2-dioxaborolan-2-yl)pyrrolo[2,1-f][1,2,4]triazine (0.15 g, 0.338 mmol) in THF (10 mL) at 0° C. was added hydrogen peroxide (3 mL, 48.9 mmol) and stirred at room temperature for 2 h. To the reaction mixture at 0° C. was added sodium acetate (0.018 mL, 0.338 mmol) and stirred for 1 h. An aliquot of the reaction mixture was analyzed by LCMS to ensure completion of reaction. The reaction mixture was quenched with water and extracted with ethylacetate. The organic phase was washed with water, brine, dried over sodium sulfate, concentrated and purified by silica gel chromatography using 0-25% ethyl acetate in hexanes to get intermediate 26B (0.057 g, 0.170 mmol, 50.5%) as an off white solid. LCMS m/z 335.2 (M+); rt 2.39 min; Conditions E.

Intermediate 45C: (2-(6-methoxypyridin-2-yl)-4-phenoxy-5-(2-(pyrrolidin-1-yl)ethoxy)pyrrolo[2,1-f][1,2,4]triazine

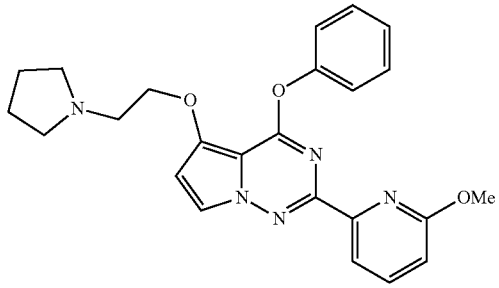 [SMILES: COc1cccc(-c2nc(Oc3ccccc3)c3c(OCCN4CCCC4)ccn3n2)n1]

To a solution of 2-(6-methoxypyridin-2-yl)-4-phenoxy-pyrrolo[2,1-f][1,2,4]triazin-5-ol (0.03 g, 0.090 mmol) in DMF (2 mL) was added $K_2CO_3$ (0.025 g, 0.179 mmol) and stirred at room temperature for 10 min. To the resulting mixture was added 1-(2-chloroethyl)pyrrolidine (0.018 g, 0.135 mmol) and tetrabutylammonium iodide (0.017 g, 0.045 mmol) and heated to 80° C. for 18 h. An aliquot of the reaction mixture was analyzed by LCMS to ensure comple- tion of reaction. The reaction mixture was quenched with water and extracted with ethylacetate. The organic phase was washed with water, brine, dried over sodium sulfate, concentrated and purified by silica gel chromatography using 0-5% methanol in chloroform to get intermediate 26C (0.025 g, 0.058 mmol, 64.6%) as an off white solid. LCMS m/z 432.2 (M+); rt 2.67 min; Conditions E.

Example 45 (3 mg, 11.4%) was synthesized employing the procedure described for Example 15 (Scheme 15): LCMS m/z 450.3 (M+H); rt 1.55 min; Conditions D. $^1$H NMR (400 MHz, DMSO-d6) δ 8.71 (d, J=7.0 Hz, 1H), 8.09-8.03 (m, 2H), 7.86-7.77 (m, 2H), 7.72-7.67 (m, 1H), 6.89 (dd, J=1.3, 7.8 Hz, 1H), 6.73-6.65 (m, 2H), 4.16 (s, 2H), 4.00 (s, 3H), 3.58 (t, J=4.5 Hz, 4H), 3.45 (br. s, 2H), 1.96 (t, J=6.8 Hz, 2H), 1.86 (s, 2H).

Scheme 46

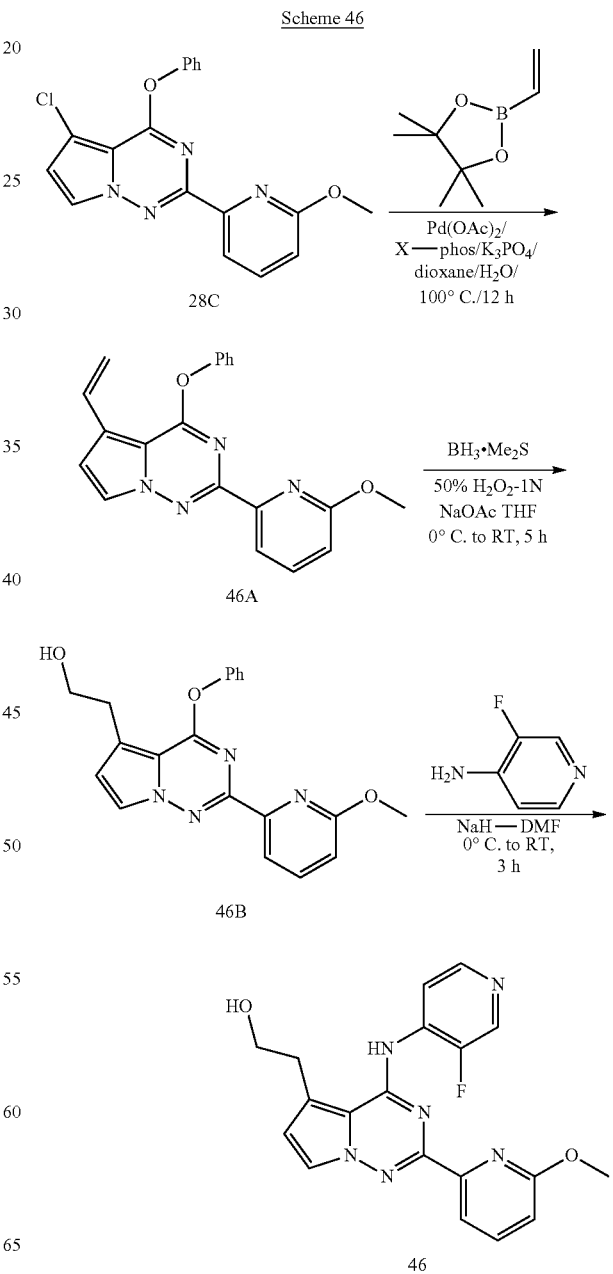

Example 46

2-{4-[(3-fluoropyridin-4-yl)amino]-2-(6-methoxy-pyridin-2-yl)pyrrolo[2,1-f][1,2,4]triazin-5-yl}ethan-1-ol

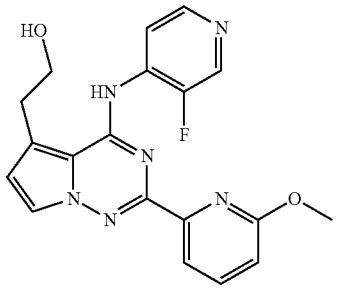 [SMILES: COc1cccc(-c2nc(Nc3ccncc3F)c3c(CCO)ccn3n2)n1]

Intermediate 46A: 2-(6-methoxypyridin-2-yl)-4-phenoxy-5-vinylpyrrolo[2,1-f][1,2,4]triazine

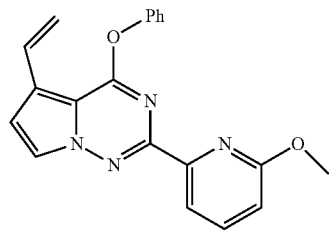 [SMILES: C=Cc1ccn2nc(-c3cccc(OC)n3)nc(Oc3ccccc3)c12]

To a stirred solution of 5-chloro-2-(6-methoxypyridin-2-yl)-4-phenoxypyrrolo[2,1-f][1,2,4]triazine (130 mg, 0.369 mmol) in 1,4-dioxane (10 mL) and water (3.33 mL) was added vinylboronic acid pinacol ester (284 mg, 1.843 mmol), tripotassium phosphate (235 mg, 1.106 mmol) and 2-(dicyclohexylphosphino)-2',4',6'-triisopropylbiphenyl (52.7 mg, 0.111 mmol). The reaction mixture was degassed with nitrogen and then added palladium(II)acetate (8.27 mg, 0.037 mmol). The reaction mixture was heated to 100° C. for 12 h. The reaction was monitored by LCMS. The reaction mixture was cooled to room temperature and filtered through a pad of celite. The filtrate was concentrated under reduced pressure. The crude product was purified by silica gel chromatography (ethyl acetate/petroleum ether) to get 2-(6-methoxypyridin-2-yl)-4-phenoxy-5-vinylpyrrolo[2,1-f][1,2,4]triazine (100 mg, 0.276 mmol, 74.9% yield) as pale yellow solid. LCMS m/z 345.0 (M+H); rt 1.23 min; Conditions B.

Intermediate 46B: 2-(2-(6-methoxypyridin-2-yl)-4-phenoxypyrrolo[2,1-f][1,2,4]triazin-5-yl)ethanol

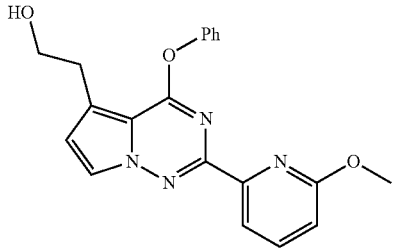 [SMILES: COc1cccc(-c2nc(Oc3ccccc3)c3c(CCO)ccn3n2)n1]

Borane-methyl sulfide complex (0.364 mL, 3.83 mmol) was added to a stirred solution of 2-(6-methoxypyridin-2-yl)-4-phenoxy-5-vinylpyrrolo[2,1-f][1,2,4]triazine (330 mg, 0.958 mmol) in tetrahydrofuran (5 mL) at 0° C. The reaction mixture was stirred at room temperature for 3 h and then cooled to 0° C. To the reaction mixture was gradually added hydrogen peroxide (1.5 mL, 0.958 mmol) and sodium acetate (1.55 mL, 1.550 mmol) and stirred at room temperature for 2 h. The reaction was monitored by TLC. The reaction mixture was diluted with ethyl acetate. The organic phase was washed with brine, dried over anhydrous sodium sulfate and concentrated under. The crude product was purified by silica gel chromatography (ethyl acetate/petroleum ether) to get intermediate 46B (75 mg, 0.207 mmol, 21.60% yield) as pale yellow solid. LCMS m/z 363.1 (M+H); rt 1.07 min; Conditions B.

Example 46 (3 mg, 13%) was synthesized employing the procedure described for Example 15 (Scheme 15): LCMS m/z 381.2 (M+H); rt 1.56 min; Conditions B. $^1$H NMR (400 MHz, DMSO-d6) δ 10.84-10.65 (m, 1H), 9.06-8.89 (m, 1H), 8.65-8.52 (m, 1H), 8.43-8.27 (m, 1H), 8.02-7.94 (m, 1H), 7.92-7.75 (m, 2H), 7.00-6.89 (m, 1H), 6.85-6.75 (m, 1H), 6.16-6.02 (m, 1H), 4.04 (s, 3H), 3.87-3.75 (m, 2H), 3.18-3.03 (m, 2H).

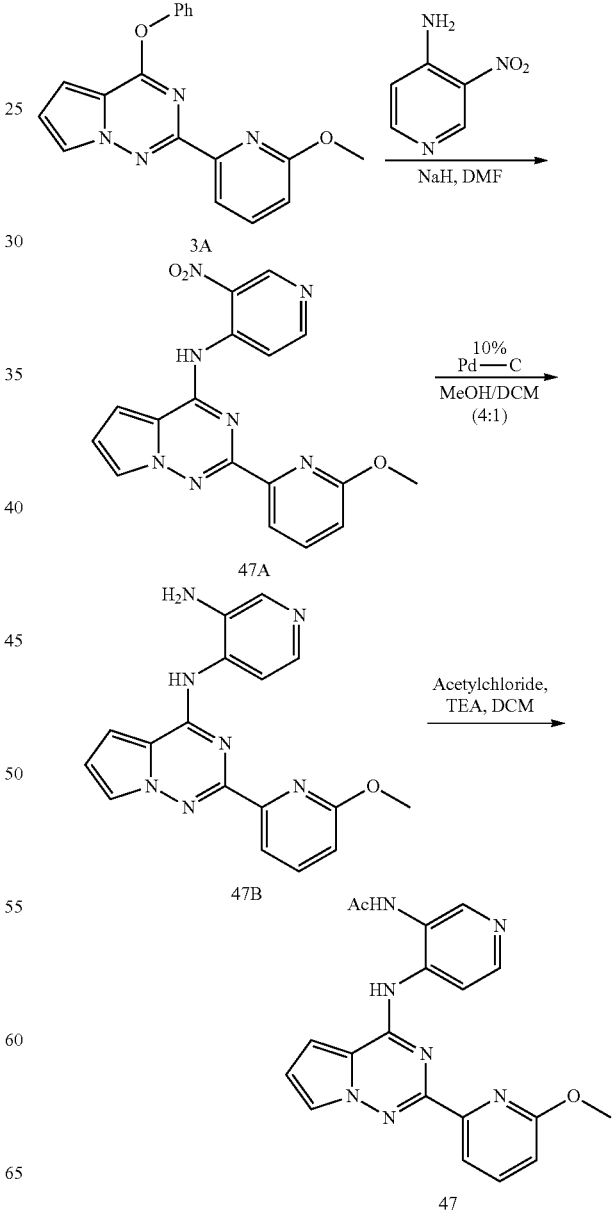

Scheme 47

Example 47

N-(4-{[2-(6-methoxypyridin-2-yl)pyrrolo[2,1-f][1,2,4]triazin-4-yl]amino}pyridin-3-yl)acetamide

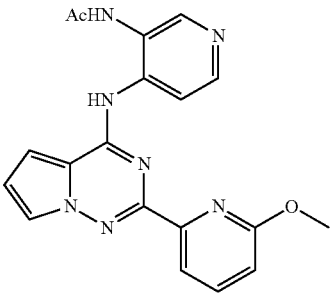 [SMILES: COc1cccc(-c2nc(Nc3ccncc3NC(C)=O)c3cccn3n2)n1]

Intermediate 47A: 2-(6-methoxypyridin-2-yl)-N-(3-nitropyridin-4-yl)pyrrolo[2,1-f][1,2,4]triazin-4-amine

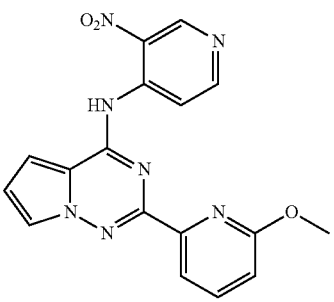 [SMILES: COc1cccc(-c2nc(Nc3ccncc3[N+](=O)[O-])c3cccn3n2)n1]

Sodium hydride (0.075 g, 3.14 mmol) was added to a solution of 2-(6-methoxypyridin-2-yl)-4-phenoxypyrrolo[2,1-f][1,2,4]triazine (0.2 g, 0.628 mmol) and 3-nitropyridin-4-amine (0.131 g, 0.942 mmol) in DMF (10 mL). The reaction mixture was stirred at room temperature for 2 h. The reaction was monitored by LCMS. The reaction mixture was poured into ice-cold water and extracted with ethyl acetate (100 mL×2). The organic phase was washed with brine, dried over anhydrous sodium sulfate and concentrated to get crude 2-(6-methoxypyridin-2-yl)-N-(3-nitropyridin-4-yl)pyrrolo[2,1-f][1,2,4]triazin-4-amine (0.35 g, 0.482 mmol, 77% yield) as pale yellow solid which was used in the next step without further purification. LCMS m/z 364.1 (M+H); rt 0.96 min; Conditions B.

Intermediate 47B: N4-(2-(6-methoxypyridin-2-yl)pyrrolo[2,1-f][1,2,4]triazin-4-yl)pyridine-3,4-diamine

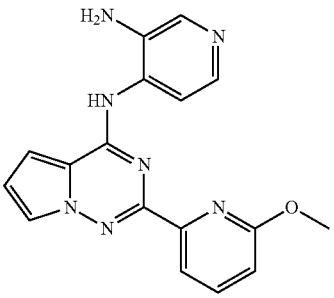

To a stirred solution of 2-(6-methoxypyridin-2-yl)-N-(3-nitropyridin-4-yl)pyrrolo[2,1-f][1,2,4]triazin-4-amine (0.2 g, 0.550 mmol) in methanol (10 mL) DCM (3.33 mL) was added palladium on carbon (50 mg, 0.047 mmol). The reaction mixture was hydrogenated (50 PSI) for 24 h. The reaction mixture was filtered through a pad of celite. The filtrate was concentrated to get N4-(2-(6-methoxypyridin-2-yl)pyrrolo[2,1-f][1,2,4]triazin-4-yl)pyridine-3,4-diamine (0.2 g, 0.330 mmol, 59.9% yield) as a light ash colored semi solid. The crude material was purified via preparative LC/MS to get intermediate 47B (4 mg, 12.67% yield): LCMS m/z 334.0 (M+H); rt 1.53 min; Conditions C.

Acetyl chloride (7.04 µl, 0.099 mmol) was slowly added to a stirred solution of N4-(2-(6-methoxypyridin-2-yl)pyrrolo[2,1-f][1,2,4]triazin-4-yl)pyridine-3,4-diamine (30 mg, 0.090 mmol) and TEA (0.031 mL, 0.225 mmol) in dry DCM (5 mL) at 0° C. The reaction mixture was stirred at room temperature for 2 h. The solvent was removed under reduced pressure to get crude product that was purified by reverse phase HPLC to afford Example 47 (4 mg, 11%): LCMS m/z 376.2 (M+H); rt 1.16 min; Conditions C. $^1$H NMR (400 MHz, DMSO-d6) δ 10.19-10.00 (m, 1H), 9.94-9.86 (m, 1H), 8.72-8.60 (m, 1H), 8.45-8.28 (m, 2H), 8.05-7.96 (m, 1H), 7.90-7.80 (m, 2H), 7.20-7.14 (m, 1H), 6.99-6.86 (m, 2H), 4.00 (s, 3H), 2.11 (s, 3H)

Scheme 48

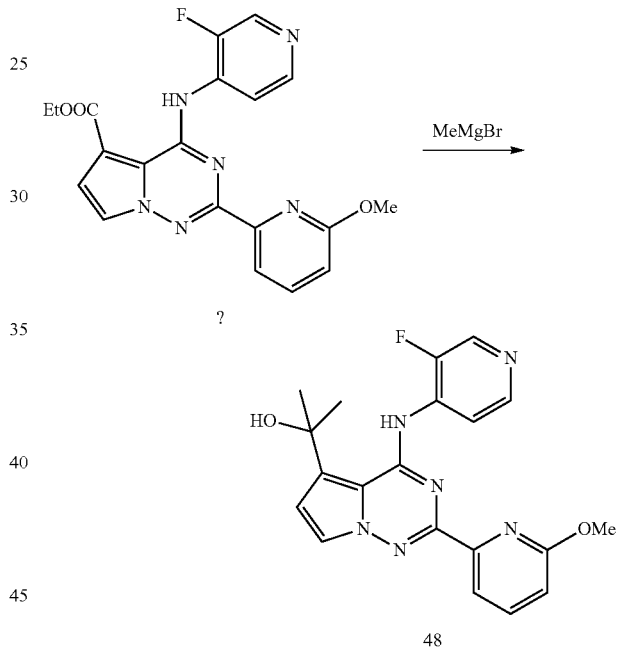

Example 48

2-{4-[(3-fluoropyridin-4-yl)amino]-2-(6-methoxypyridin-2-yl)pyrrolo[2,1-f][1,2,4]triazin-5-yl}propan-2-ol

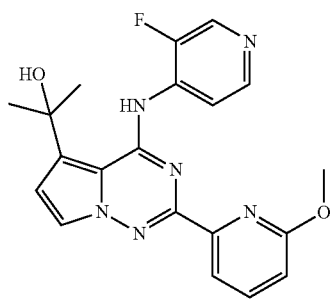 [SMILES: COc1cccc(-c2nc(Nc3ccncc3F)c3c(C(C)(C)O)ccn3n2)n1]

To a solution of ethyl 4-((3-fluoropyridin-4-yl)amino)-2-(6-methoxypyridin-2-yl)pyrrolo[2,1-f][1,2,4]triazine-5-carboxylate (0.05 g, 0.122 mmol) in THF (5 mL) at 0° C. was dropwise added methylmagnesium bromide (0.875 mL, 1.224 mmol). The reaction mixture was stirred at room temperature for 2 h. The reaction mixture was quenched with saturated NH₄Cl solution and extracted with ethylacetate. The organic layer was washed with water and brine. The organic phase was dried over anhydrous sodium sulfate and concentrated under reduced pressure to get the crude product that was purified by reverse phase HPLC to get Example 48 (2 mg, 4%): LCMS m/z 395.2 (M+H); rt 1.36 min; Conditions C. ¹H NMR (400 MHz, DMSO-d6) δ 12.50 (s, 1H), 9.61-9.42 (m, 1H), 8.57 (d, J=3.0 Hz, 1H), 8.37 (d, J=5.5 Hz, 1H), 8.03-7.81 (m, 3H), 7.08 (s, 1H), 7.02-6.93 (m, 1H), 6.84 (d, J=3.0 Hz, 1H), 4.09 (s, 3H), 1.65 (s, 6H).

palladium(II) dichloride (2.86 mg, 4.07 μmol) in toluene (0.5 mL). The resulting reaction mixture was degassed with nitrogen. The vial was capped and heated at 95° C. for 20 h. The reaction mixture was cooled to room temperature concentrated. The residue was dissolved in DMF (1 mL) and filtered via a syringe filter. The filtrate was purified via preparative LC/MS with the following conditions: Column: Waters XBridge C18, 19×200 mm, 5-μm particles; Mobile Phase A: 5:95 acetonitrile: water with 10-mM ammonium acetate; Mobile Phase B: 95:5 acetonitrile:water with 10-mM ammonium acetate; Gradient: 5-100% B over 25 minutes, then a 5-minute hold at 100% B; Flow: 20 mL/min. Fractions containing the desired product were combined and dried via centrifugal evaporation. Example 49 was obtained (12.8 mg, 52%): LCMS m/z 303 (M+H); rt 1.22 min; Conditions B. ¹H NMR (DMSO-d6) δ 8.46-8.64 (m, J=6.4 Hz, 2H), 8.07-8.22 (m, 3H), 7.93-8.06 (m, 2H), 7.89 (t, J=7.7 Hz, 1H), 7.40 (d, J=7.4 Hz, 1H), 7.32 (d, J=3.7 Hz, 1H), 6.91 (dd, J=4.4, 2.7 Hz, 1H), 2.61 (s, 3H).

Scheme 49

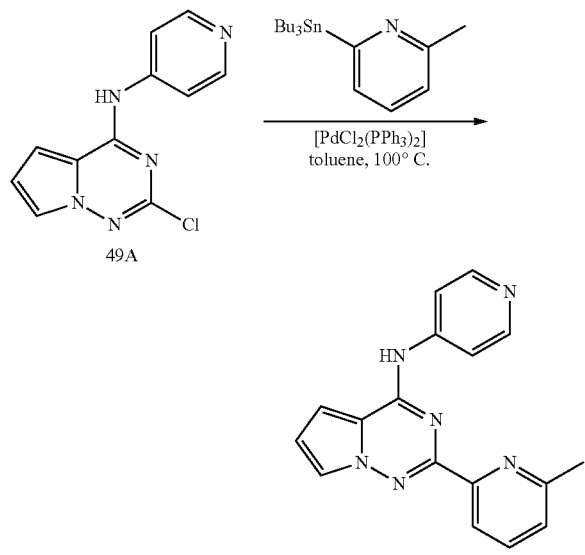

Example 49

N-[2-(6-methylpyridin-2-yl)pyrrolo[2,1-f][1,2,4]triazin-4-yl]pyridin-4-amine

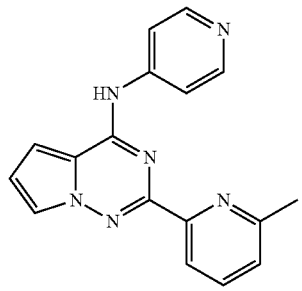 [SMILES: Cc1cccc(-c2nc(Nc3ccncc3)c3cccn3n2)n1]

To a 1 dram vial was added 2-chloro-N-(pyridin-4-yl)pyrrolo[2,1-f][1,2,4]triazin-4-amine 49A (20 mg, 0.081 mmol), 6-methyl-2-(tributylstannyl)pyridine (0.027 mL, 0.081 mmol) and a suspension of bis(triphenylphosphine)

Scheme 50

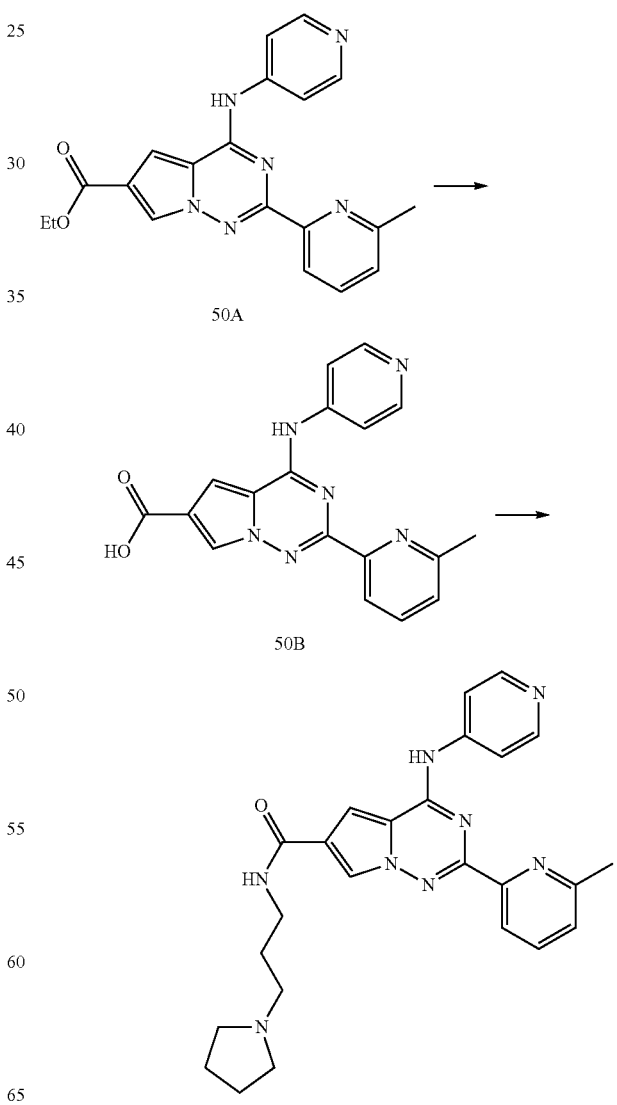

Example 50

2-(6-methylpyridin-2-yl)-4-[(pyridin-4-yl)amino]-N-[3-(pyrrolidin-1-yl)propyl]pyrrolo[2,1-f][1,2,4]triazine-6-carboxamide

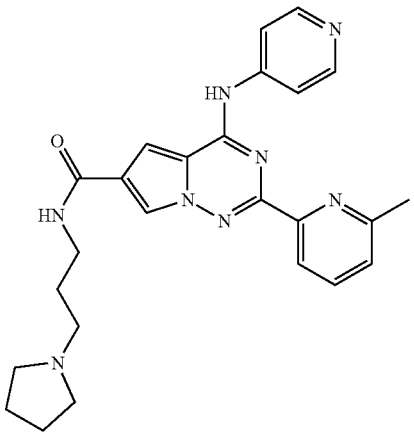 [SMILES: Cc1cccc(-c2nc(Nc3ccncc3)c3cc(C(=O)NCCCN4CCCC4)cn3n2)n1]

Intermediate 50A was prepared similar to intermediate 39D (Scheme 39).

Intermediate 50B was prepared similar to intermediate 37B (Scheme 37).

To a 1 dram vial was added 2-(6-methylpyridin-2-yl)-4-(pyridin-4-ylamino)pyrrolo[2,1-f][1,2,4]triazine-6-carboxylic acid.TFA (15 mg, 0.033 mmol), DMF (1 mL), DIPEA (0.017 mL, 0.098 mmol), 3-(pyrrolidin-1-yl)propan-1-amine (12.53 mg, 0.098 mmol) and HATU (18.58 mg, 0.049 mmol). The resulting solution was stirred at room temperature for 2 h. An aliquot of the reaction mixture was diluted with methanol and analyzed by LCMS to ensure complete conversion. The reaction mixture was purified by reverse phase HPLC to afford Example 50 (9.1 mg, 59%): LCMS m/z 457 (M+H); rt 0.94 min; Conditions B. $^1$H NMR (DMSO-d6) δ 8.55 (d, J=5.7 Hz, 2H), 8.43-8.50 (m, 1H), 8.41 (s, 1H), 8.03-8.21 (m, 3H), 7.90 (t, J=7.7 Hz, 1H), 7.71 (s, 1H), 7.42 (d, J=7.4 Hz, 1H), 3.28-3.40 (m, J=5.7 Hz, 1H), 2.40-2.71 (m, 11H), 1.65-1.83 (m, 6H).

Example 51

3-[4-(dimethylamino)butoxy]-N-[2-(6-methylpyridin-2-yl)pyrrolo[2,1-f][1,2,4]triazin-4-yl]pyridin-4-amine

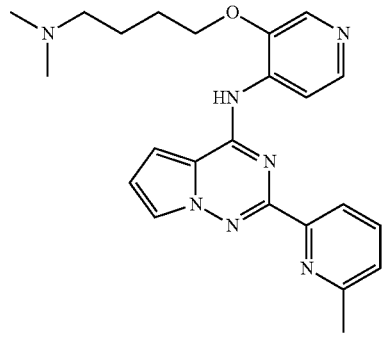 [SMILES: Cc1cccc(-c2nc(Nc3ccncc3OCCCCN(C)C)c3cccn3n2)n1]

Intermediate 51A:
3-(4-(dimethylamino)butoxy)pyridin-4-amine

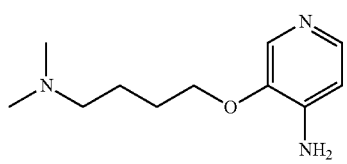

To a 40 mL scintillation vial was added KOtBu (0.256 g, 2.277 mmol), THF (3 mL), 4-(dimethylamino)butan-1-ol (0.289 g, 2.467 mmol) and then (portionwise) solid 3-fluoro-4-nitropyridine 1-oxide (0.30 g, 1.9 mmol). The reaction mixture was stirred at room temperature for 1 h. LCMS indicated the presence of the desired intermediate. The reaction mixture was concentrated. To the dark residue was added acetic acid (~6 mL) and stirred until all the solids dissolved. Then portionwise added iron powder (0.530 g, 9.49 mmol) and the resulting reaction mixture was heated to 80° C. for 2 h. The reaction mixture was cooled to room temperature and concentrated. To the residue was added water and stirred. To the resulting suspension was slowly added 50% aq NaOH and stirred. To the resulting thick slurry was added chloroform, and filtered through a pad of Celite. The biphasic filtrate was transferred to a separatory funnel. The pH of the aqueous layer was adjusted to >12 by pH paper. The phases were separated. The aq layer was extracted with chloroform (×2). The combined organic Scheme 51

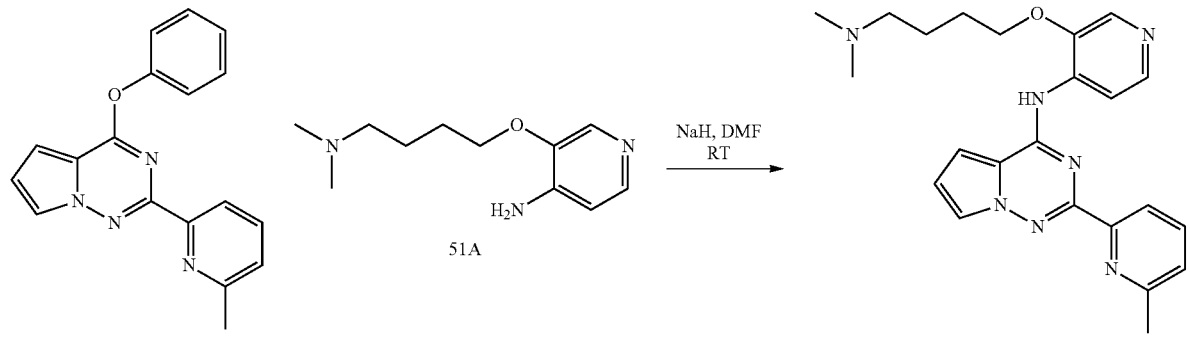

51A

51 phase was dried over sodium sulfate and concentrated to get 3-(4-(dimethylamino)butoxy)pyridin-4-amine (0.141 g, 0.674 mmol, 35.5% yield). LCMS m/z 210.0 (M+H); rt 0.39 min; Conditions A. The crude pdt was used as such in the next step.

Example 51 (4.1 mg, 19%) was prepared employing the procedure used to synthesize Example 1 (Scheme 1): LCMS m/z 418 (M+H); rt 1.13 min; Conditions F. $^1$H NMR (DMSO-d6) δ 8.44 (s, 1H), 8.27 (d, J=5.0 Hz, 1H), 8.20 (d, J=5.0 Hz, 1H), 7.97 (s, 2H), 7.83 (t, J=7.6 Hz, 1H), 7.36 (d, J=7.7 Hz, 1H), 7.17 (d, J=3.7 Hz, 1H), 6.86 (br. s, 1H), 4.20 (t, J=6.4 Hz, 2H), 3.47 (br. s, 1H), 2.57 (s, 3H), 2.15 (t, J=7.1 Hz, 2H), 2.01 (s, 6H), 1.67-1.81 (m, 2H), 1.39-1.57 (m, 2H).

Scheme 52

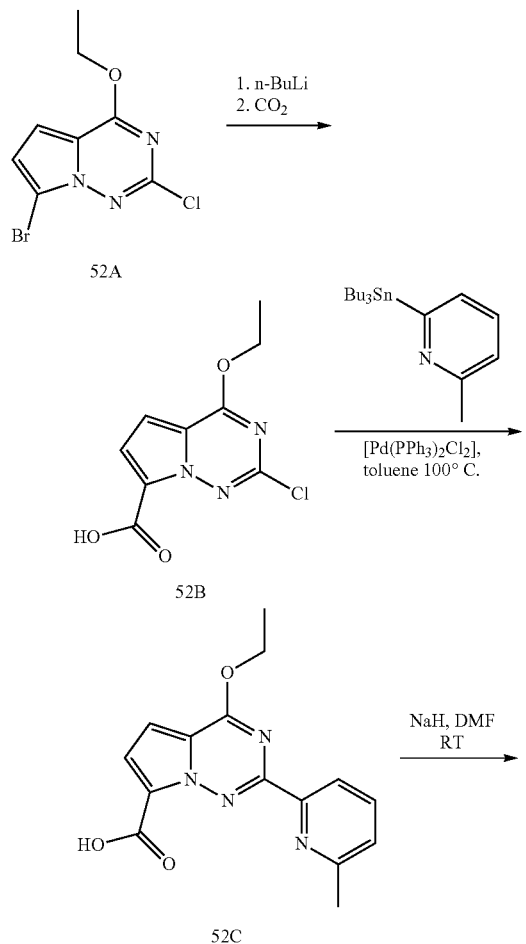

Example 52

4-[(3-fluoropyridin-4-yl)amino]-2-(6-methylpyridin-2-yl)pyrrolo[2,1-f][1,2,4]triazine-7-carboxylic acid

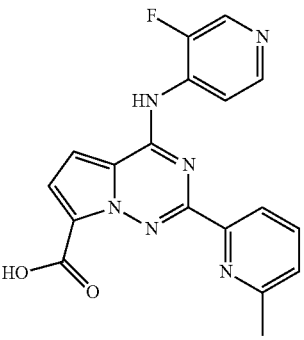 [SMILES: Cc1cccc(-c2nc(Nc3ccncc3F)c3ccc(C(=O)O)n3n2)n1]

Intermediate 52A: 7-bromo-2-chloro-4-ethoxypyrrolo[2,1-f][1,2,4]triazine

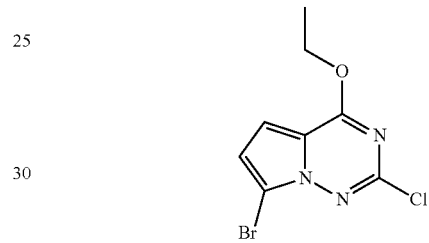

To a flask containing 7-bromo-2,4-dichloropyrrolo[2,1-f][1,2,4]triazine (13.5 g, 50.6 mmol) (WO 2008021924) was added tetrahydrofuran (100 mL) and stirred. The resulting yellow solution was cooled in an ice-water bath. To the resulting solution was gradually added a 21 wt % solution of sodium ethoxide (18.88 mL, 50.6 mmol) in denatured ethanol. The cooling bath was removed and the reaction mixture was stirred at room temperature for 30 min. LCMS indicated completion of reaction. Water (1 mL) was added and the reaction mixture was concentrated on a rotary evaporator. To the residue was added water (200 mL) and extracted with DCM (2×100 mL). The combined organic layer was washed with brine (100 mL), dried over sodium sulfate and concentrated on a rotary evaporator. The residue was purified by silica gel chromatography using hexane/ethylacetate to get 7-bromo-2-chloro-4-ethoxypyrrolo[2,1-f][1,2,4]triazine (12.79 g, 46.3 mmol, 91% yield) as an off white solid. LCMS m/z 278.0; rt 1.19 min; Conditions A. $^1$H NMR (Chloroform-d) δ 6.92 (d, J=4.6 Hz, 1H), 6.78 (d, J=4.8 Hz, 1H), 4.65 (q, J=7.0 Hz, 2H), 1.50 (t, J=7.2 Hz, 3H).

Intermediate 52B: 2-chloro-4-ethoxypyrrolo[2,1-f][1,2,4]triazine-7-carboxylic acid

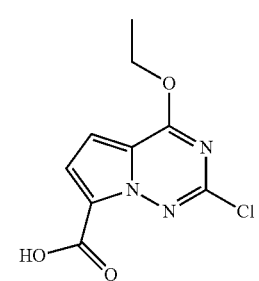 [SMILES: CCOc1nc(Cl)nn2c(C(=O)O)ccc12]

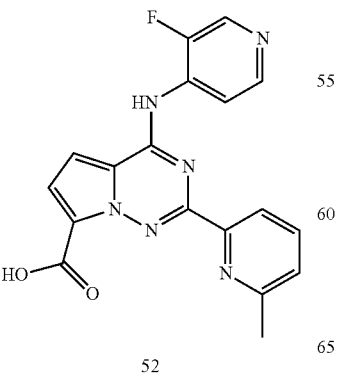

To a 1 L flask containing 7-bromo-2-chloro-4-ethoxypyrrolo[2,1-f][1,2,4]triazine (10 g, 36.2 mmol) was added anhydrous tetrahydrofuran (200 mL) and the resulting pale yellow solution was cooled in a dry-ice/acetone bath for 10 min. A 2.5 M solution of n-butyllithium (15.91 mL, 39.8 mmol) in hexanes was added. After 10 min, bubbled carbondioxide gas through the reaction mixture. After 10 min, the cooling bath was removed and the reaction mixture was allowed to warm up to room temperature while continuously bubbling carbon dioxide. The reaction mixture was quenched with water and concentrated on a rotary evaporator. The residue was suspended in water (~300 mL) and gradually added 1 N HCl until the pH was <5. The yellow ppt that was formed was collected by filtration and dried under vacuum to get crude intermediate 52B (11.2 g, 46.4 mmol, 128% yield) as a cream colored solid. LCMS: RT=0.81 min; MS(ES): m/z=224, 242; Conditions A.

Intermediate 52C: 4-ethoxy-2-(6-methylpyridin-2-yl)pyrrolo[2,1-f][1,2,4]triazine-7-carboxylic acid

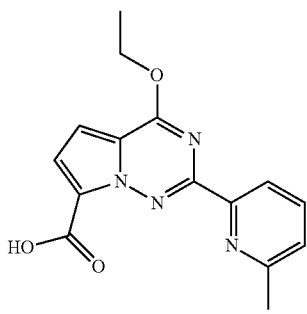 [SMILES: CCOc1nc(-c2cccc(C)n2)nn2c(C(=O)O)ccc12]

To a 2 dram vial was added crude 2-chloro-4-ethoxypyrrolo[2,1-f][1,2,4]triazine-7-carboxylic acid (150 mg, 0.621 mmol), 2-methyl-6-(tributylstannyl)pyridine (356 mg, 0.931 mmol), bis(triphenylphosphine)palladium(II) dichloride (21.79 mg, 0.031 mmol) and toluene (2 mL). The vial was capped and heated at 85° C. for 18 h. LCMS indicated completion of reaction. The reaction mixture was cooled to room temperature and concentrated. The residue was purified by silica gel chromatography to obtain 4-ethoxy-2-(6-methylpyridin-2-yl)pyrrolo[2,1-f][1,2,4]triazine-7-carboxylic acid (51 mg, 0.171 mmol, 27.5% yield). LCMS: RT=0.69 min; MS(ES): m/z=299; Conditions A. $^1$H NMR (Chloroform-d) δ 8.16 (d, J=7.7 Hz, 1H), 7.79 (t, J=7.7 Hz, 1H), 7.60 (d, J=4.8 Hz, 1H), 7.35 (d, J=7.7 Hz, 1H), 6.95 (d, J=4.8 Hz, 1H), 4.86 (q, J=7.0 Hz, 2H), 2.72 (s, 3H), 1.61 (t, J=7.2 Hz, 3H).

To a vial containing 4-ethoxy-2-(6-methylpyridin-2-yl)pyrrolo[2,1-f][1,2,4]triazine-7-carboxylic acid (51 mg, 0.171 mmol) was added DMF (2 mL), 3-fluoropyridin-4-amine (77 mg, 0.684 mmol) and stirred. To the resulting solution was portionwise added a 60% dispersion of sodium hydride (20.51 mg, 0.513 mmol) in mineral oil. The resulting reaction mixture was stirred at room temperature for 1 h. LCMS indicated completion of reaction. The reaction mixture was quenched with a few drops of water, filtered through a syringe filter and purified by reverse phase HPLC to afford Example 52 (26.6 mg, 42%): LCMS m/z 365 (M+H); rt 0.73 min; Conditions F. $^1$H NMR (DMSO-d6) δ 8.68 (d, J=2.0 Hz, 1H), 8.49 (d, J=5.4 Hz, 1H), 8.35 (br. s, 1H), 7.99 (d, J=7.7 Hz, 1H), 7.87 (t, J=7.7 Hz, 1H), 7.35-7.55 (m, 3H), 3.55 (br. s, 1H), 2.58 (s, 3H).

Scheme 53

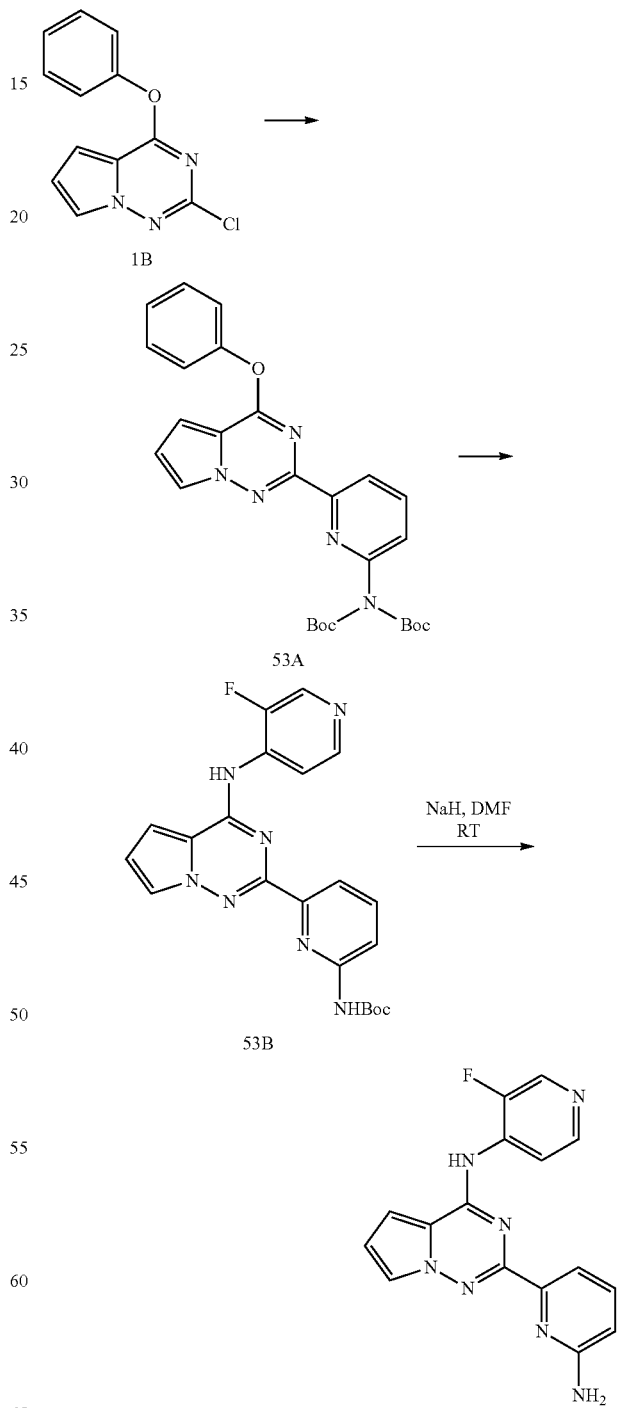

Example 53

2-(6-aminopyridin-2-yl)-N-(3-fluoropyridin-4-yl)pyrrolo[2,1-f][1,2,4]triazin-4-amine

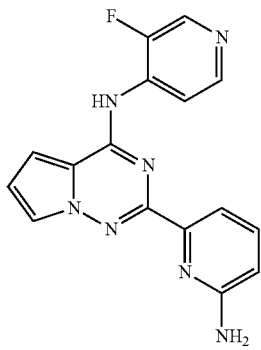 [SMILES: Nc1cccc(-c2nc(Nc3ccncc3F)c3cccn3n2)n1]

Intermediate 53A

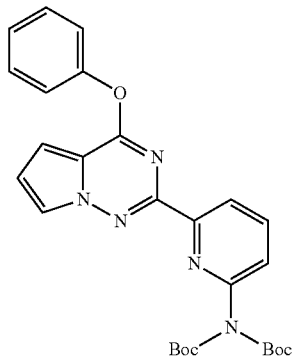 [SMILES: CC(C)(C)OC(=O)N(C(=O)OC(C)(C)C)c1cccc(-c2nc(Oc3ccccc3)c3cccn3n2)n1]

To a scintillation vial was added 2-chloro-4-phenoxypyrrolo[2,1-f][1,2,4]triazine (0.4 g, 1.628 mmol), bispinacolatodiboron (0.620 g, 2.442 mmol), potassium acetate (0.399 g, 4.07 mmol), 1,1'-bis(diphenylphosphino)ferrocene-palladium(II)-dichloride dichloromethane complex (0.066 g, 0.081 mmol) and 1,4-dioxane (4 mL). The resulting reaction mixture was degassed by bubbling nitrogen. The vial was capped with a pressure-safe septum cap and heated at 90° C. for 3.5 h. The reaction mixture was cooled to room temperature. To the reaction mixture was added aqueous 3.0 M tripotassium phosphate (1.628 mL, 4.88 mmol) and degassed with nitrogen. After 5 min, added 2-bromo-6-(bisBocamino)pyridine (0.608 g, 1.628 mmol) and additional 1,1'-bis(diphenylphosphino)ferrocene-palladium(II)-dichloride dichloromethane complex (0.066 g, 0.081 mmol). The resulting reaction mixture was degassed with nitrogen. The vial was capped with a pressure-safe septum cap and heated at 90° C. for 3 h. LCMS indicated the presence of desired product. The aqueous phase was removed. The organic phase was concentrated and purified by silica gel chromatography (hexane/ethylacetate) to get bisBoc intermediate 53A (0.714 g, 1.418 mmol, 87% yield). LCMS: RT=1.22 min; MS(ES): m/z=504 (Injection conditions: Column: Waters Acquity UPLC BEH C18, 2.1×50 mm, 1.7-μm particles; Mobile Phase A: 100% water with 0.05% TFA; Mobile Phase B: 100% MeCN with 0.05% TFA; Gradient: 2-98% B over 1 minute, then a 0.5-minute hold at 98% B; Flow: 0.8 mL/min; Detection: UV at 220 nm).

Intermediate 53B

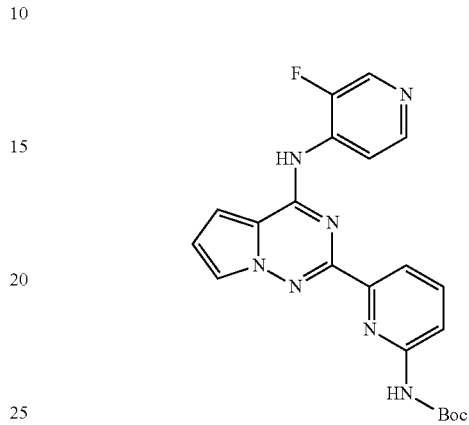

To a scintillation vial was added 2-(6'-dibocaminopyridyl-2-yl)-4-phenoxy-pyrrolotriazine (200 mg, 0.397 mmol), 3-fluoropyridin-4-amine (89 mg, 0.794 mmol), DMF (2 mL) and then a 60% dispersion of sodium hydride (47.7 mg, 1.192 mmol) in mineral oil. The resulting reaction mixture was stirred under nitrogen atmosphere at room temperature for 1 h. LCMS indicated completion of reaction. The reaction mixture was carefully quenched with dropwise addition of water and concentrated. The residue was purified by silica gel chromatography using hexane/ethylacetate system to obtain tert-butyl (6-(4-((3-fluoropyridin-4-yl)amino)pyrrolo[2,1-f][1,2,4]triazin-2-yl)pyridin-2-yl)carbamate (105 mg, 0.202 mmol, 50.8% yield). LCMS: RT=0.72 min; MS(ES): m/z=522, 422 (Injection conditions: Column: Waters Acquity UPLC BEH C18, 2.1×50 mm, 1.7-μm particles; Mobile Phase A: 100% water with 0.05% TFA; Mobile Phase B: 100% MeCN with 0.05% TFA; Gradient: 2-98% B over 1 minute, then a 0.5-minute hold at 98% B; Flow: 0.8 mL/min; Detection: UV at 220 nm). $^1$H NMR (DMSO-d$_6$) δ 10.21 (br. s, 1H), 10.00 (s, 1H), 8.66 (br. s, 1H), 8.48 (d, J=5.0 Hz, 1H), 8.28 (t, J=6.0 Hz, 1H), 7.85-8.03 (m, 3H), 7.71-7.82 (m, 1H), 7.37 (br. s, 1H), 6.91 (br. s, 1H), 1.47 (s, 9H).

To a vial containing tert-butyl (6-(4-((3-fluoropyridin-4-yl)amino)pyrrolo[2,1-f][1,2,4]triazin-2-yl)pyridin-2-yl)carbamate (94 mg, 0.181 mmol) was added DCM (2 mL) and TFA (0.500 mL). The resulting solution was stirred at room temperature for 6 h. LCMS indicated completion of reaction. The solvents were evaporated. The residue was dissolved in DMF, neutralized with DIPEA and purified by reverse phase HPLC to afford Example 53 (18 mg, 31%): LCMS m/z 322 (M+H); rt 1.10 min; Conditions F. $^1$H NMR (DMSO-d6) δ 10.18 (br. s, 1H), 8.66 (br. s, 1H), 8.48 (d, J=4.4 Hz, 1H), 8.27 (br. s, 1H), 7.95 (br. s, 1H), 7.55 (t, J=7.6 Hz, 1H), 7.23-7.43 (m, 2H), 6.88 (br. s, 1H), 6.60 (d, J=8.1 Hz, 1H).

Example 54

3-chloro-N-[2-(pyridin-2-yl)pyrrolo[2,1-f][1,2,4]triazin-4-yl]pyridin-4-amine

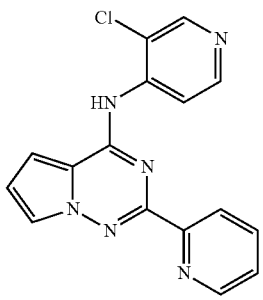 [SMILES: Clc1cnccc1Nc1nc(-c2ccccn2)nn2cccc12]

Example 54 (16 mg, 95%) was synthesized employing the procedure described for Example 1 (Scheme 1): LCMS m/z 323 (M+H); rt 1.50 min; Conditions F. ¹H NMR (DMSO-d6) δ 8.75 (br. s, 1H), 8.70 (d, J=4.0 Hz, 1H), 8.58 (br. s, 1H), 7.87-8.25 (m, 4H), 7.49 (br. s, 1H), 7.31 (br. s, 1H), 6.91 (br. s, 1H).

Example 55

2-fluoro-N-[2-(pyridin-2-yl)pyrrolo[2,1-f][1,2,4]triazin-4-yl]pyridin-4-amine

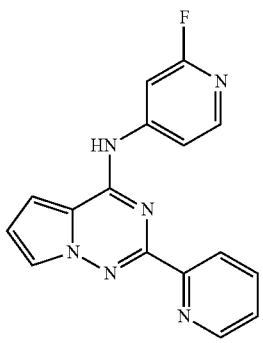 [SMILES: Fc1cc(Nc2nc(-c3ccccn3)nn3cccc23)ccn1]

Example 55 (15.0 mg, 94%) was synthesized employing the procedure described for Example 1 (Scheme 1): LCMS m/z 307 (M+H); rt 1.32 min; Conditions F. ¹H NMR (DMSO-d6) δ 8.78 (d, J=4.4 Hz, 1H), 8.14-8.31 (m, 3H), 7.83-8.08 (m, 4H), 7.50-7.60 (m, 1H), 7.33 (d, J=4.0 Hz, 1H), 6.89-6.98 (m, 1H).

Example 56

3-fluoro-N-[2-(pyridin-2-yl)pyrrolo[2,1-f][1,2,4]triazin-4-yl]pyridin-4-amine

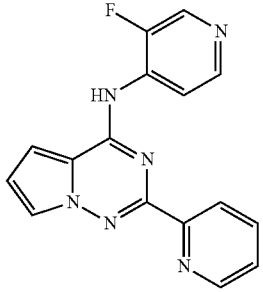

Example 56 (33 mg, 39.3%) was synthesized employing the procedure described for Example 1 (Scheme 1): LCMS m/z 307 (M+H); rt 1.64 min; Conditions E. ¹H NMR: (400 MHz, DMSO-d6) δ 8.73-8.70 (m, 1H), 8.65 (d, J=3.0 Hz, 1H), 8.46 (d, J=5.5 Hz, 1H), 8.30-8.23 (m, 1H), 8.14 (s, 1H), 8.01-7.92 (m, 2H), 7.51-7.47 (m, 1H), 7.35-7.31 (m, 1H), 6.91-6.86 (m, 1H).

Example 57

3-fluoro-N-[2-(6-methylpyridin-2-yl)pyrrolo[2,1-f][1,2,4]triazin-4-yl]pyridin-4-amine

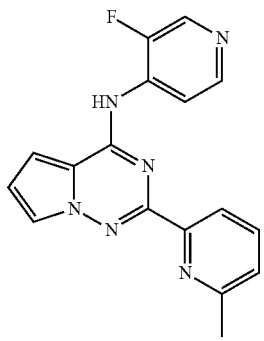 [SMILES: Cc1cccc(-c2nc(Nc3ccncc3F)c3cccn3n2)n1]

Example 57 (18.8 mg, 50%) was synthesized employing the procedure described for Example 1 (Scheme 1): LCMS m/z 321 (M+H); rt 1.32 min; Conditions F. ¹H NMR (DMSO-d6) δ 8.76 (d, J=3.0 Hz, 1H), 8.53 (d, J=5.4 Hz, 1H), 8.34-8.46 (m, 1H), 7.93-8.13 (m, 3H), 7.52 (d, J=7.4 Hz, 1H), 7.39 (br. s, 1H), 6.89-6.99 (m, 1H), 2.64 (s, 3H).

Example 58

3-fluoro-N-[2-(6-methoxypyridin-2-yl)pyrrolo[2,1-f][1,2,4]triazin-4-yl]pyridin-4-amine

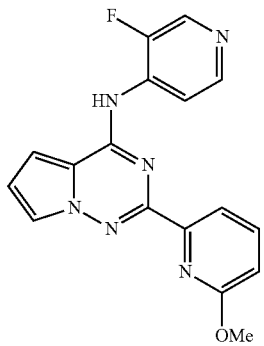 [SMILES: COc1cccc(-c2nc(Nc3ccncc3F)c3cccn3n2)n1]

Example 58 (17 mg, 80%) was synthesized employing the procedure described for Example 1 (Scheme 1): LCMS m/z 337 (M+H); rt 1.57 min; Conditions F. ¹H NMR (DMSO-d6) δ 10.18 (s, 1H), 8.60-8.71 (m, 2H), 8.43 (d, J=5.4 Hz, 1H), 8.02 (s, 1H), 7.79-7.90 (m, 2H), 7.42 (d, J=3.7 Hz, 1H), 6.86-6.98 (m, 2H), 4.02 (s, 3H).

Example 59

3-chloro-N-[2-(6-methylpyridin-2-yl)pyrrolo[2,1-f][1,2,4]triazin-4-yl]pyridin-4-amine

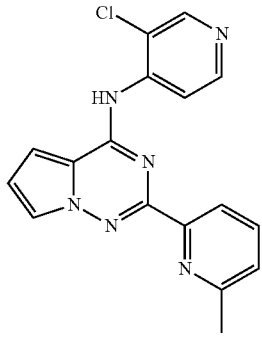 [SMILES: Cc1cccc(-c2nc(Nc3ccncc3Cl)c3cccn3n2)n1]

Example 59 (13.3 mg, 60%) was synthesized employing the procedure described for Example 1 (Scheme 1): LCMS m/z 337 (M+H); rt 1.65 min; Conditions F. $^1$H NMR (DMSO-d6) (All except methyl peak were broadened) δ 8.74 (br. s, 1H), 8.57 (br. s, 1H), 7.74-8.27 (m, 4H), 7.20-7.49 (m, 2H), 6.90 (br. s, 1H), 3.44 (br. s, 1H), 2.56 (s, 3H).

Example 60

3-chloro-N-[2-(6-methoxypyridin-2-yl)pyrrolo[2,1-f][1,2,4]triazin-4-yl]pyridin-4-amine

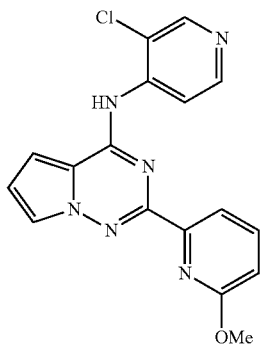 [SMILES: COc1cccc(-c2nc(Nc3ccncc3Cl)c3cccn3n2)n1]

Example 60 (15.7 mg, 71%) was synthesized employing the procedure described for Example 1 (Scheme 1): LCMS m/z 353 (M+H); rt 1.85 min; Conditions F. $^1$H NMR (DMSO-d6) Some peaks were broadened. δ 8.76 (s, 1H), 8.56 (d, J=5.4 Hz, 1H), 8.36 (br. s, 1H), 8.00 (br. s, 1H), 7.80-7.89 (m, 1H), 7.77 (d, J=7.4 Hz, 1H), 7.13-7.42 (m, 1H), 6.94 (d, J=8.1 Hz, 1H), 6.89 (br. s, 1H), 3.98 (s, 3H)

Example 61

3,5-difluoro-N-[2-(6-methylpyridin-2-yl)pyrrolo[2,1-f][1,2,4]triazin-4-yl]pyridin-4-amine

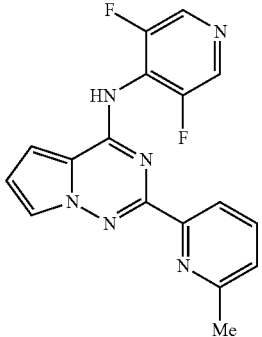 [SMILES: Cc1cccc(-c2nc(Nc3c(F)cncc3F)c3cccn3n2)n1]

Example 61 (10.4 mg, 60%) was synthesized employing the procedure described for Example 1 (Scheme 1): LCMS m/z 339 (M+H); rt 1.57 min; Conditions F. $^1$H NMR (DMSO-d6) Broad peaks were observed. δ 8.70 (br. s, 2H), 8.06 (br. s, 1H), 7.75 (br. s, 2H), 7.16-7.41 (m, 2H), 6.91 (br. s, 1H), 3.39 (s, 1H), 2.54 (br. s, 3H)

Example 62

3-fluoro-N-[2-(4-methylpyridin-2-yl)pyrrolo[2,1-f][1,2,4]triazin-4-yl]pyridin-4-amine

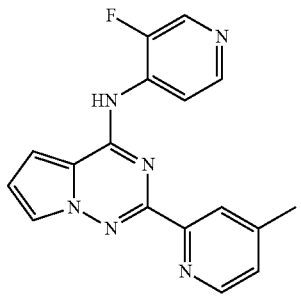 [SMILES: Cc1ccnc(-c2nc(Nc3ccncc3F)c3cccn3n2)c1]

Example 62 (11.9 mg, 75%) was synthesized employing the procedure described for Example 1 (Scheme 1): LCMS m/z 321 (M+H); rt 1.39 min; Conditions F. $^1$H NMR (DMSO-d6) δ 8.66 (d, J=2.4 Hz, 1H), 8.56 (d, J=4.7 Hz, 1H), 8.47 (d, J=5.4 Hz, 1H), 8.30 (br. s, 1H), 7.98 (br. s, 2H), 7.34 (d, J=4.0 Hz, 2H), 6.90 (br. s, 1H), 3.52 (br. s, 1H), 2.40 (s, 3H).

Example 63

N-[2-(4-chloropyridin-2-yl)pyrrolo[2,1-f][1,2,4]triazin-4-yl]-3-fluoropyridin-4-amine

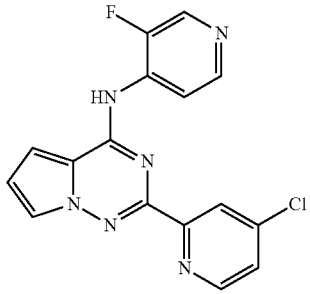 [SMILES: Fc1cnccc1Nc1nc(-c2cc(Cl)ccn2)nn2cccc12]

Example 63 (11.9 mg, 55%) was synthesized employing the procedure described for Example 1 (Scheme 1): LCMS m/z 341 (M+H); rt 1.54 min; Conditions F. $^1$H NMR (DMSO-d6) δ 10.46 (br. s, 1H), 8.55-8.72 (m, 2H), 8.43 (d, J=5.4 Hz, 1H), 8.03-8.18 (m, 2H), 7.97 (br. s, 1H), 7.61 (d, J=3.7 Hz, 1H), 7.27 (d, J=3.7 Hz, 1H), 6.91 (br. s, 1H).

Example 64

N-[2-(6-methylpyridin-2-yl)pyrrolo[2,1-f][1,2,4]triazin-4-yl]pyrimidin-4-amine

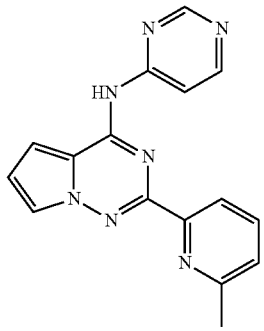 [SMILES: Cc1cccc(-c2nc(Nc3ccncn3)c3cccn3n2)n1]

Example 64 (10.5 mg, 50%) was synthesized employing the procedure described for Example 1 (Scheme 1): LCMS m/z 304 (M+H); rt 1.48 min; Conditions F. $^1$H NMR (DMSO-d6) δ 8.84-9.07 (m, 2H), 8.77 (d, J=4.4 Hz, 1H), 8.00-8.15 (m, 2H), 7.89 (t, J=7.4 Hz, 1H), 7.33-7.64 (m, 2H), 6.91 (br. s, 1H), 2.61 (br. s, 3H).

Example 65

3-fluoro-N-[2-(5-fluoropyridin-2-yl)pyrrolo[2,1-f][1,2,4]triazin-4-yl]pyridin-4-amine

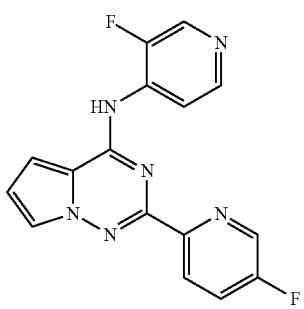 [SMILES: Fc1ccc(-c2nc(Nc3ccncc3F)c3cccn3n2)nc1]

Example 65 (9 mg, 17%) was synthesized employing the procedure described for Example 4 (Scheme 4): LCMS m/z 325.2 (M+H); rt 1.398 min; Conditions C. $^1$H NMR, 400 MHz, DMSO-d6) δ 10.27 (s, 1H), 8.71 (d, J=2.8 Hz, 1H), 8.67 (d, J=3.2 Hz, 1H), 8.47 (d, J=5.2 Hz, 1H), 8.20-8.25 (m, 2H), 7.99-8.00 (m, 1H), 7.85-7.90 (m, 1H), 7.35-7.36 (m, 1H), 6.89-6.91 (m, 1H). $^{19}$F NMR (400 MHz, DMSO-d6) δ −126.96, −136.6.

Example 66

N-{2-[6-(difluoromethyl)-5-fluoropyridin-2-yl]pyrrolo[2,1-f][1,2,4]triazin-4-yl}-3-fluoropyridin-4-amine

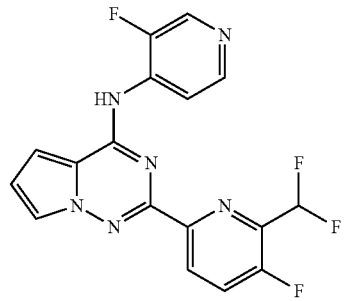 [SMILES: Fc1cnccc1Nc1nc(-c2ccc(F)c(C(F)F)n2)nn2cccc12]

Example 66 (1.6 mg, 2.86%) was synthesized employing the procedure described for Example 11 (Scheme 11): LCMS m/z 375.2 (M+H); rt 1.574 min; Conditions C. $^1$H NMR (400 MHz, DMSO-d6) δ 10.46-10.08 (m, 1H), 8.72-8.55 (m, 1H), 8.51-8.25 (m, 2H), 8.14-8.00 (m, 1H), 7.47-7.03 (m, 2H), 6.95-6.85 (m, 1H).

Example 67

N-[2-(6-methoxypyridin-2-yl)pyrrolo[2,1-f][1,2,4]triazin-4-yl]pyrimidin-4-amine

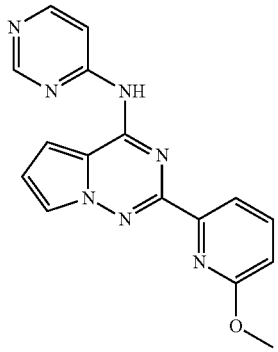 [SMILES: COc1cccc(-c2nc(Nc3ccncn3)c3cccn3n2)n1]

Example 67 was synthesized employing the procedure described for Example 3 (Scheme 3): LCMS m/z 320.2 (M+H); rt 1.60; Conditions C. $^1$H NMR (400 MHz, DMSO-d6) δ 11.24 (s, 1H), 9.27-9.18 (m, 1H), 8.96 (d, J=1.0 Hz, 1H), 8.72 (d, J=6.0 Hz, 1H), 8.03 (dd, J=2.5, 1.5 Hz, 1H), 7.96-7.82 (m, 2H), 7.58 (dd, J=4.5, 1.5 Hz, 1H), 6.98 (dd, J=7.8, 1.3 Hz, 1H), 6.91 (dd, J=4.5, 2.5 Hz, 1H), 4.07 (s, 3H)

Example 68

Methyl N-(4-{[2-(6-methoxypyridin-2-yl)pyrrolo[2,1-f][1,2,4]triazin-4-yl]amino}pyridin-2-yl)carbamate

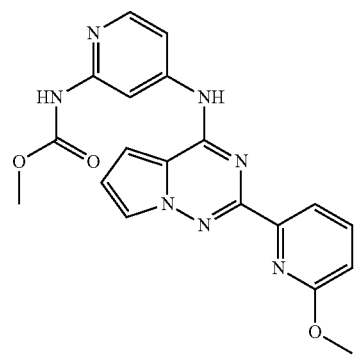 [SMILES: COC(=O)Nc1cc(Nc2nc(-c3cccc(OC)n3)nn3cccc23)ccn1]

Example 68 was synthesized employing the procedure described for Example 3 (Scheme 3). LCMS m/z 392.2 (M+H); rt 1.59; Conditions C. ¹H NMR (400 MHz, DMSO-d6) δ 10.30 (s, 1H), 10.14 (s, 1H), 8.46 (d, J=1.5 Hz, 1H), 8.32 (dd, J=5.8, 1.8 Hz, 1H), 8.19 (d, J=6.0 Hz, 1H), 8.07 (d, J=7.5 Hz, 1H), 7.98 (dd, J=2.5, 1.5 Hz, 1H), 7.91-7.84 (m, 1H), 7.37 (dd, J=4.5, 1.5 Hz, 1H), 6.99-6.93 (m, 1H), 6.88 (dd, J=4.3, 2.8 Hz, 1H), 4.03 (s, 3H), 3.72 (s, 3H).

Example 69

N-[2-(5-fluoro-6-methylpyridin-2-yl)pyrrolo[2,1-f][1,2,4]triazin-4-yl]pyridin-4-amine

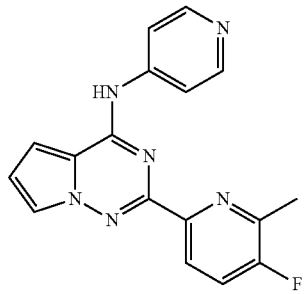 [SMILES: Cc1nc(-c2nc(Nc3ccncc3)c3cccn3n2)ccc1F]

Example 69 (2 mg, 5%) was synthesized employing the procedure described for Example 3 (Scheme 3): LCMS m/z 321.2 (M+H); rt 1.487 min; Conditions C. ¹H NMR (400 MHz, DMSO-d6) δ 10.29 (s, 1H), 8.54 (d, J=6.4 Hz, 2H), 8.19 (dd, J=4.0, 8.8 Hz, 1H), 8.11-8.13 (m, 2H), 8.01-8.02 (m, 1H), 7.79-7.84 (m, 1H), 7.31-7.32 (m, 1H), 6.88-6.90 (m, 1H), 2.58 (d, J=2.8 Hz, 3H). ¹⁹F NMR (400 MHz, DMSO-d6) δ −123.75.

Example 70

3-chloro-N-[2-(6-fluoropyridin-2-yl)pyrrolo[2,1-f][1,2,4]triazin-4-yl]pyridin-4-amine

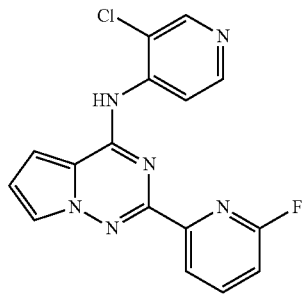 [SMILES: Fc1cccc(-c2nc(Nc3ccncc3Cl)c3cccn3n2)n1]

Example 70 (13 mg, 23%) was synthesized employing the procedure described for Example 3 (Scheme 3): LCMS m/z 341.1 (M+H); rt 1.572 min; Conditions C. ¹H NMR (400 MHz, DMSO-d6) δ 10.10 (s, 1H), 8.77 (s, 1H), 8.60 (d, J=5.2 Hz, 1H), 8.02-8.16 (m, 4H), 7.28-7.33 (m, 2H), 6.91-6.93 (m, 1H). ¹⁹F NMR (400 MHz, DMSO-d6) δ −67.0.

Example 71

3-fluoro-N-[2-(6-methylpyrazin-2-yl)pyrrolo[2,1-f][1,2,4]triazin-4-yl]pyridin-4-amine

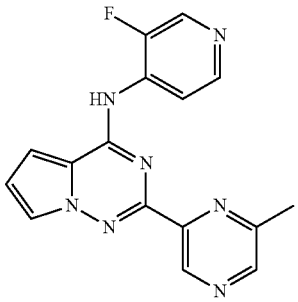 [SMILES: Cc1cncc(-c2nc(Nc3ccncc3F)c3cccn3n2)n1]

Example 71 (13 mg, 30%) was synthesized employing the procedure described for Example 5 (Scheme 5): LCMS m/z 322.2 (M+H); rt 1.111 min; Conditions C. ¹H NMR (400 MHz, DMSO-d6) δ 10.34 (s, 1H), 9.11 (s, 1H), 8.65-8.69 (m, 2H), 8.49 (d, J=5.2 Hz, 1H), 8.25-8.28 (m, 1H), 8.07-8.08 (m, 1H), 7.38 (d, J=3.2 Hz, 1H), 6.91-6.93 (m, 1H), 2.61 (s, 3H). ¹⁹F NMR (400 MHz, DMSO-d6) δ −136.64.

Example 72

3-ethyl-1-{4-[(3-fluoropyridin-4-yl)amino]-2-(6-methoxypyridin-2-yl)pyrrolo[2,1-f][1,2,4]triazin-6-yl}urea

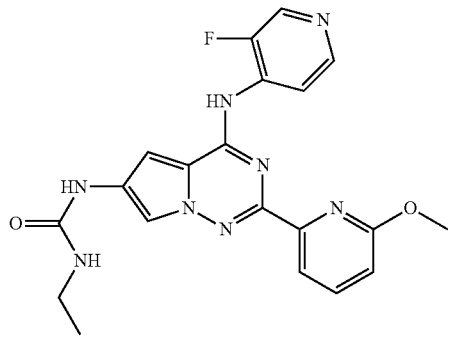 [SMILES: CCNC(=O)Nc1cc2c(Nc3ccncc3F)nc(-c3cccc(OC)n3)nn2c1]

Example 72 (5 mg, 20%) was synthesized employing the procedure described for Example 22 (Scheme 22): LCMS m/z 423.2 (M+H); rt 1.307 min; Conditions C. ¹H NMR (400 MHz, DMSO-d6) δ=9.98 (s, 1H), 8.76 (s, 1H), 8.70 (dd, J=5.5, 7.0 Hz, 1H), 8.61 (d, J=3.0 Hz, 1H), 8.39 (d, J=5.0 Hz, 1H), 8.00 (d, J=2.0 Hz, 1H), 7.87-7.76 (m, 2H), 7.25 (d, J=2.0 Hz, 1H), 6.91 (dd, J=1.5, 7.5 Hz, 1H), 6.20-6.13 (m, 1H), 4.01 (s, 3H), 3.20-3.10 (m, 2H), 1.08 (t, J=7.0 Hz, 3H).

Example 73

Methyl N-{4-[(3-fluoropyridin-4-yl)amino]-2-(6-methoxypyridin-2-yl)pyrrolo[2,1-f][1,2,4]triazin-6-yl}carbamate

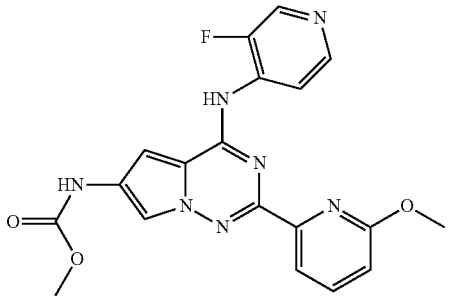 [SMILES: COC(=O)Nc1cc2c(Nc3ccncc3F)nc(-c3cccc(OC)n3)nn2c1]

Example 73 (5 mg, 14%) was synthesized employing the procedure described for Example 22 (Scheme 22): LCMS m/z 410.2 (M+H); rt 2.155 min; Conditions C. ¹H NMR (400 MHz, DMSO-d6) δ 10.17 (s, 1H), 10.09 (br. s, 1H), 8.69-8.59 (m, 2H), 8.39 (d, J=5.5 Hz, 1H), 7.93 (br. s, 1H), 7.87-7.76 (m, 2H), 7.33 (br. s, 1H), 6.96-6.87 (m, 1H), 4.01 (s, 3H), 3.76-3.67 (m, 3H).

Example 74

3-fluoro-N-[2-(5-fluoro-6-methylpyridin-2-yl)pyrrolo[2,1-f][1,2,4]triazin-4-yl]pyridin-4-amine

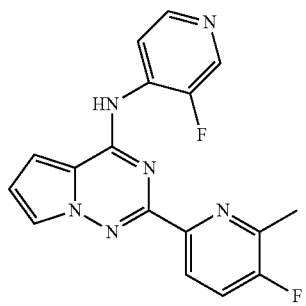 [SMILES: Cc1nc(-c2nc(Nc3ccncc3F)c3cccn3n2)ccc1F]

Example 74 (7 mg, 22%) was synthesized employing the procedure described for Example 7 (Scheme 7): LCMS m/z 339.2 (M+H); rt 1.555 min; Conditions C. ¹H NMR (400 MHz, DMSO-d6) δ 10.26 (s, 1H), 8.67 (d, J=3.0 Hz, 1H), 8.48 (d, J=5.5 Hz, 1H), 8.30 (dd, J=5.3, 6.8 Hz, 1H), 8.08-8.01 (m, 2H), 7.82-7.73 (m, 1H), 7.37 (dd, J=1.5, 4.5 Hz, 1H), 6.90 (dd, J=2.5, 4.5 Hz, 1H).

Example 75

3-[3-(morpholin-4-yl)propoxy]-N-{2-[6-(trifluoromethyl)pyridin-2-yl]pyrrolo[2,1-f][1,2,4]triazin-4-yl}pyridin-4-amine

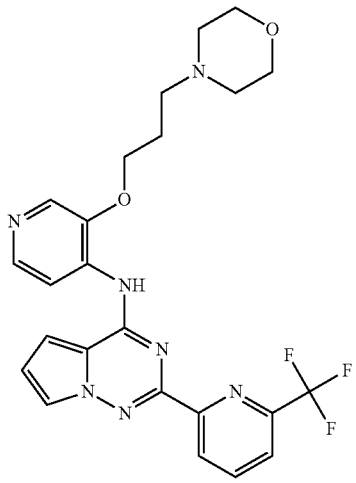 [SMILES: FC(F)(F)c1cccc(-c2nc(Nc3ccncc3OCCCN3CCOCC3)c3cccn3n2)n1]

Example 75 (2 mg, 5.7%) was synthesized employing the procedure described for Example 7 (Scheme 7): LCMS m/z 500.3 (M+H); rt 1.80 min; Conditions C. ¹H NMR (400 MHz, DMSO-d6) δ 9.57 (s, 1H) 8.39-8.49 (m, 2H) 8.17-8.29 (m, 3H) 8.07 (dd, J=2.51, 1.51 Hz, 1H) 8.01 (d, J=7.53 Hz, 1H) 7.22-7.25 (m, 1H) 6.90 (dd, J=4.27, 2.76 Hz, 1H) 4.22 (t, J=6.27 Hz, 2H)) 4.22 (t, J=6.27 Hz, 2H) 3.46 (t, J=4.77 Hz, 4H) 2.27 (t, J=7.28 Hz, 2H) 2.19 (br. s, 4H) 1.81-1.89 (m, 2H).

Example 76

N-{5-[(4,4-difluoropiperidin-1-yl)methyl]-2-(6-methylpyridin-2-yl)pyrrolo[2,1-f][1,2,4]triazin-4-yl}-3-fluoropyridin-4-amine

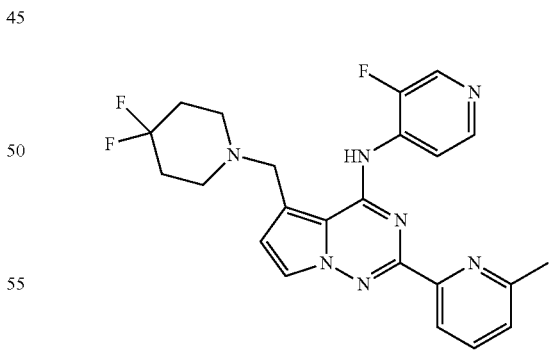

Example 76 (30 mg, 28%) was synthesized employing the procedure described for Example 23 (Scheme 23): LCMS m/z 454.2 (M+H); rt 3.124 min; Conditions C. ¹H NMR (400 MHz, DMSO-d6) δ=11.74 (s, 1H), 8.92 (dd, J=5.5, 7.0 Hz, 1H), 8.64 (d, J=3.0 Hz, 1H), 8.46 (d, J=5.5 Hz, 1H), 8.05 (d, J=7.5 Hz, 1H), 7.99 (d, J=2.5 Hz, 1H), 7.87 (t, J=7.8 Hz, 1H), 7.39 (d, J=8.0 Hz, 1H), 6.86 (d, J=2.5 Hz, 1H), 3.96 (s, 2H), 2.83-2.68 (m, 4H), 2.60 (s, 3H), 2.14-1.98 (m, 4H).

Example 77

N-(6-{4-[(3-fluoropyridin-4-yl)amino]pyrrolo[2,1-f][1,2,4]triazin-2-yl}pyridin-2-yl)methanesulfonamide

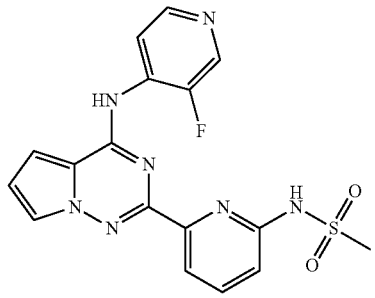 [SMILES: CS(=O)(=O)Nc1cccc(-c2nc(Nc3ccncc3F)c3cccn3n2)n1]

Example 77 (4 mg, 12%) was synthesized employing the procedure described for Example 8 (Scheme 8): LCMS m/z 400.2 (M+H); rt 1.274 min; Conditions C. $^1$H NMR (400 MHz, DMSO-d6) δ 10.75 (br. s, 1H), 10.17 (br. s, 1H), 8.65 (d, J=2.5 Hz, 1H), 8.50-8.44 (m, 1H), 8.42 (d, J=7.0 Hz, 1H), 7.98 (d, J=2.5 Hz, 1H), 7.92-7.79 (m, 2H), 7.39 (d, J=3.0 Hz, 1H), 7.03 (d, J=8.5 Hz, 1H), 6.92 (dd, J=2.5, 4.5 Hz, 1H), 3.43 (s, 3H).

Example 78

N-{2-[6-(difluoromethyl)pyridin-2-yl]pyrrolo[2,1-f][1,2,4]triazin-4-yl}-3-fluoropyridin-4-amine

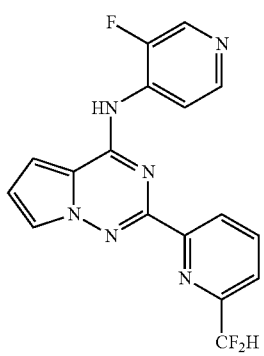 [SMILES: Fc1cnccc1Nc1nc(-c2cccc(C(F)F)n2)nn2cccc12]

Example 78 (32.6 mg, 69%) was synthesized employing the procedure described for Example 8 (Scheme 8): LCMS m/z 357 (M+H); rt 1.55 min; Conditions F. $^1$H NMR (DMSO-d6) δ 10.33 (s, 1H), 8.68 (d, J=2.5 Hz, 1H), 8.49 (d, J=5.3 Hz, 1H), 8.27-8.40 (m, 2H), 8.18 (t, J=7.8 Hz, 1H), 8.09 (s, 1H), 7.82 (d, J=7.7 Hz, 1H), 7.40 (d, J=4.3 Hz, 1H), 6.89-7.24 (m, 2H).

Example 79

3-(prop-2-en-1-yloxy)-N-[2-(pyridin-2-yl)pyrrolo[2,1-f][1,2,4]triazin-4-yl]pyridin-4-amine

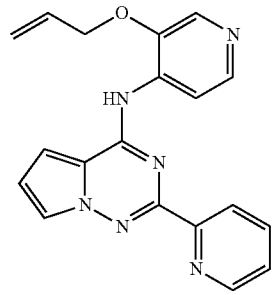 [SMILES: C=CCOc1cnccc1Nc1nc(-c2ccccn2)nn2cccc12]

Example 223 (7.2 mg, 19%) was synthesized employing the procedure described for Example 51 (Scheme 51): LCMS m/z 345 (M+H); rt 1.53 min; Conditions F. $^1$H NMR (DMSO-d6) δ 8.70 (d, J=4.0 Hz, 1H), 8.43 (s, 1H), 8.28 (s, 2H), 8.16 (d, J=8.1 Hz, 1H), 7.90-8.01 (m, 2H), 7.46-7.55 (m, 1H), 7.25 (br. s, 1H), 6.88 (br. s, 1H), 5.98-6.12 (m, 1H), 5.40 (d, J=17.5 Hz, 1H), 5.25 (d, J=10.4 Hz, 1H), 4.81 (d, J=4.7 Hz, 2H).

Example 80

3-chloro-N-{2-[6-(difluoromethyl)pyridin-2-yl]pyrrolo[2,1-f][1,2,4]triazin-4-yl}pyridin-4-amine

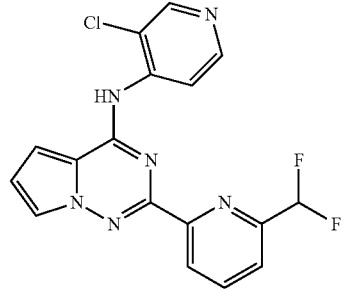 [SMILES: FC(F)c1cccc(-c2nc(Nc3ccncc3Cl)c3cccn3n2)n1]

Example 80 (2 mg, 5%) was synthesized employing the procedure described for Example 8 (Scheme 8): LCMS m/z 373.3 (M+H); rt 1.760 min; Conditions C. $^1$H NMR (400 MHz, DMSO-d6) δ 10.08 (br. s, 1H), 8.76 (s, 1H), 8.59 (d, J=5.5 Hz, 1H), 8.24 (d, J=7.5 Hz, 1H), 8.19-8.04 (m, 2H), 7.80 (d, J=7.5 Hz, 1H), 7.33 (br. s, 1H), 7.23-6.88 (m, 3H).

Example 81

3-chloro-N-[2-(1-methyl-1H-pyrazol-5-yl)pyrrolo[2,1-f][1,2,4]triazin-4-yl]pyridin-4-amine

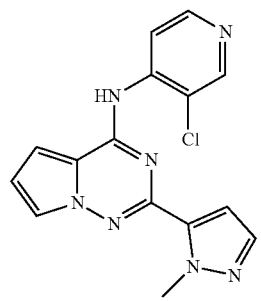 [SMILES: Cn1nccc1-c1nc(Nc2ccncc2Cl)c2cccn2n1]

Example 81 (17 mg, 30.4%) was synthesized employing the procedure described for Example 10 (Scheme 10): LCMS m/z 326.11 (M+H); rt 1.529 min; Conditions C. ¹H NMR (400 MHz, DMSO-d6) δ 10.28-10.03 (m, 1H), 8.75 (s, 1H), 8.57 (s, 1H), 7.94 (s, 2H), 7.45 (d, J=2.0 Hz, 1H), 7.33-7.22 (m, 1H), 6.91-6.82 (m, 1H), 6.73 (d, J=1.5 Hz, 1H), 4.06 (s, 3H).

Example 82

2-chloro-N-{2-[6-(trifluoromethyl)pyridin-2-yl]pyrrolo[2,1-f][1,2,4]triazin-4-yl}pyridin-4-amine

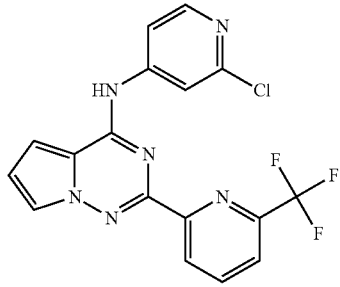 [SMILES: FC(F)(F)c1cccc(-c2nc(Nc3ccnc(Cl)c3)c3cccn3n2)n1]

Example 82 (7 mg, 46%) was synthesized employing the procedure described for Example 10 (Scheme 10): LCMS m/z 391.2 (M+H); rt 1.966 min; Conditions C. ¹H NMR (400 MHz, DMSO-d6) δ 10.51 (s, 1H), 8.68 (d, J=1.5 Hz, 1H), 8.54 (d, J=8.0 Hz, 1H), 8.39-8.25 (m, 2H), 8.12-8.02 (m, 2H), 7.96 (dd, J=5.5, 2.0 Hz, 1H), 7.35 (dd, J=4.3, 1.3 Hz, 1H), 6.97 (dd, J=4.5, 2.5 Hz, 1H).

Example 83

4-{[2-(pyridin-2-yl)pyrrolo[2,1-f][1,2,4]triazin-4-yl]amino}pyridine-3-carboxamide

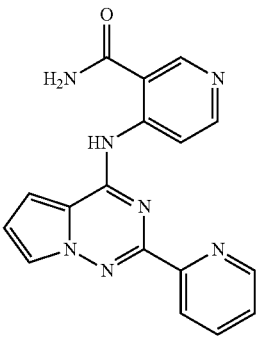 [SMILES: NC(=O)c1cnccc1Nc1nc(-c2ccccn2)nn2cccc12]

Example 83 (6 mg, 5%) was synthesized employing the procedure described for Example 10 (Scheme 10): LCMS m/z 332.2 (M+H); rt 3.679 min; Conditions E. ¹H NMR (400 MHz, DMSO-d6) δ 13.35-12.93 (m, 1H), 9.24-9.13 (m, 1H), 9.07 (s, 1H), 8.69 (br. s, 2H), 8.39-8.27 (m, 1H), 8.17-7.92 (m, 3H), 7.61-7.45 (m, 1H), 7.04-6.67 (m, 2H).

Example 84

3-fluoro-N-{2-[6-(trifluoromethyl)pyridin-2-yl]pyrrolo[2,1-f][1,2,4]triazin-4-yl}pyridin-4-amine

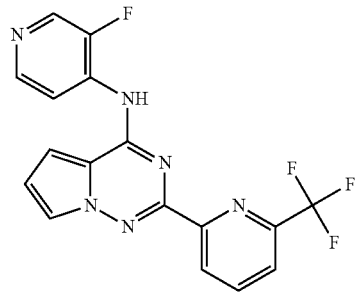 [SMILES: Fc1cnccc1Nc1nc(-c2cccc(C(F)(F)F)n2)nn2cccc12]

Example 84 (21 mg, 44%) was synthesized employing the procedure described for Example 11 (Scheme 11): LCMS m/z 375.2 (M+H); rt 1.718 min; Conditions C. ¹H NMR (400 MHz, DMSO-d6) δ 10.33 (s, 1H) 8.67 (d, J=2.95 Hz, 1H) 8.36-8.48 (m, 3H) 8.26 (s, 1H) 8.11 (dd, J=2.60, 1.47 Hz, 1H) 8.01 (dd, J=7.78, 0.88 Hz, 1H) 7.42 (dd, J=4.42, 1.41 Hz, 1H) 6.93 (dd, J=4.42, 2.67 Hz, 1H).

Example 85

N-{2-[6-(trifluoromethyl)pyridin-2-yl]pyrrolo[2,1-f][1,2,4]triazin-4-yl}pyridin-4-amine

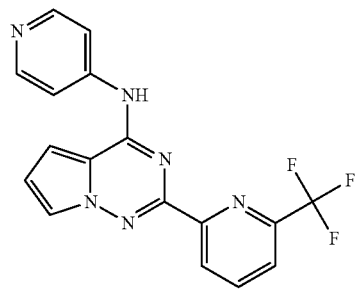 [SMILES: FC(F)(F)c1cccc(-c2nc(Nc3ccncc3)c3cccn3n2)n1]

Example 85 (18 mg, 40%) was synthesized employing the procedure described for Example 11 (Scheme 11): LCMS m/z 357.2 (M+H); rt 1.274 min; Conditions C. ¹H NMR (400 MHz, DMSO-d6) δ 6.90-6.98 (m, 1H) 7.33-7.39 (m, 1H) 8.01-8.12 (m, 2H) 8.15-8.21 (m, 2H) 8.27-8.36 (m, 1H) 8.49-8.59 (m, 3H) 10.31-10.39 (m, 1H).

Example 86

3-chloro-N-{2-[6-(trifluoromethyl)pyridin-2-yl]pyrrolo[2,1-f][1,2,4]triazin-4-yl}pyridin-4-amine

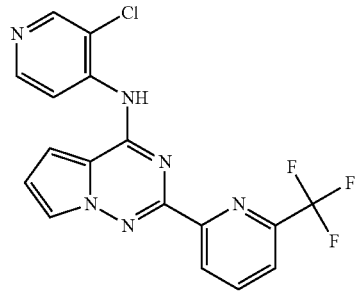 [SMILES: FC(F)(F)c1cccc(-c2nc(Nc3ccncc3Cl)c3cccn3n2)n1]

Example 86 (60 mg, 54%) was synthesized employing the procedure described for Example 11 (Scheme 11): LCMS m/z 391.0 (M+H); rt 2.875 min; Conditions E. $^1$H NMR (400 MHz, DMSO-d6) δ 10.07-10.14 (m, 1H) 8.76 (s, 1H) 8.53-8.60 (m, 1H) 8.33-8.38 (m, 1H) 8.20-8.28 (m, 1H) 8.14-8.19 (m, 1H) 8.10-8.14 (m, 1H) 7.96-8.04 (m, 1H) 7.32-7.37 (m, 1H) 6.89-6.97 (m, 1H).

Example 87

3-chloro-N-[2-(4-methyl-1,3-thiazol-2-yl)pyrrolo[2,1-f][1,2,4]triazin-4-yl]pyridin-4-amine

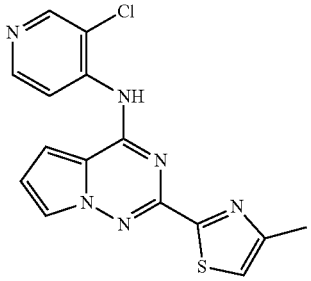

Example 87 (1 mg, 2.5%) was synthesized employing the procedure described for Example 12 (Scheme 12): LCMS m/z 343.1 (M+H); rt 1.637 min; Conditions C. $^1$H NMR (400 MHz, DMSO-d6) δ 10.11-10.22 (m, 1H) 8.73-8.81 (m, 1H) 8.55-8.62 (m, 1H) 7.94-8.14 (m, 2H) 7.37-7.52 (m, 1H) 7.26-7.35 (m, 1H) 6.86-6.95 (m, 1H) 2.40-2.46 (m, 3H).

Example 88

N-[2-(4-methyl-1,3-thiazol-2-yl)pyrrolo[2,1-f][1,2,4]triazin-4-yl]pyridin-4-amine

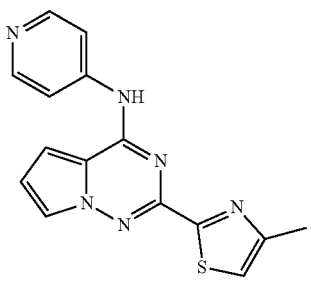 [SMILES: Cc1csc(-c2nc(Nc3ccncc3)c3cccn3n2)n1]

Example 88 (6 mg, 17%) was synthesized employing the procedure described for Example 12 (Scheme 12): LCMS m/z 309.2 (M+H); rt 1.354 min; Conditions C. $^1$H NMR (400 MHz, DMSO-d6) δ 11.06-11.16 (m, 1H) 8.71-8.82 (m, 1H) 8.43-8.51 (m, 1H) 8.07-8.17 (m, 1H) 7.55-7.63 (m, 1H) 7.36-7.47 (m, 1H) 6.99-7.04 (m, 1H).

Example 89

3-fluoro-N-[2-(1H-pyrrol-2-yl)pyrrolo[2,1-f][1,2,4]triazin-4-yl]pyridin-4-amine

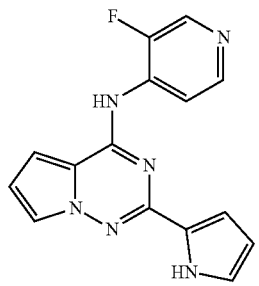 [SMILES: Fc1cnccc1Nc1nc(-c2ccc[nH]2)nn2cccc12]

Example 89 was synthesized employing the procedure described for Example 13 (Scheme 13): LCMS m/z 295.2 (M+H); rt 1.41 min; Conditions C. $^1$H NMR (300 MHz, DMSO-d6) δ 11.38 (br. s, 1H), 9.98 (s, 1H), 8.64 (d, J=3.0 Hz, 1H), 8.47 (d, J=5.3 Hz, 1H), 8.28 (dd, J=6.8, 5.7 Hz, 1H), 7.84-7.70 (m, 1H), 7.29 (dd, J=4.3, 1.3 Hz, 1H), 6.90 (d, J=1.9 Hz, 1H), 6.80-6.68 (m, 2H), 6.22-6.07 (m, 1H).

Example 90

N-(6-{4-[(3-chloropyridin-4-yl)amino]pyrrolo[2,1-f][1,2,4]triazin-2-yl}pyridin-2-yl)methanesulfonamide

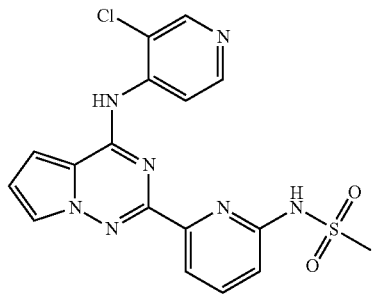 [SMILES: CS(=O)(=O)Nc1cccc(-c2nc(Nc3ccncc3Cl)c3cccn3n2)n1]

Example 90 (3 mg, 9.3%) was synthesized employing the procedure described for Example 08 (Scheme 08): LCMS m/z 416.2 (M+H); rt 1.367 min; Conditions C. $^1$H NMR (400 MHz, DMSO-d6) δ 8.73 (s, 1H), 8.56 (d, J=5.0 Hz, 1H), 8.22 (br. s, 1H), 7.96 (br. s, 1H), 7.89-7.83 (m, 1H), 7.79 (br. s, 1H), 7.31 (br. s, 1H), 7.35-7.25 (m, 1H), 7.01 (d, J=8.0 Hz, 1H), 6.91 (br. s, 1H), 3.44-3.35 (m, 3H).

Example 91

N-[5-chloro-2-(6-methoxypyridin-2-yl)pyrrolo[2,1-f][1,2,4]triazin-4-yl]pyridin-4-amine

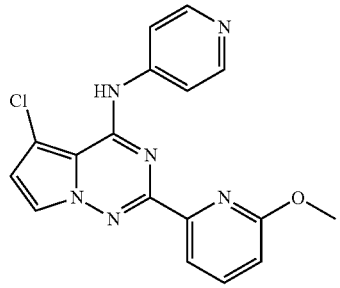

Example 91 (9 mg, 44%) was synthesized employing the procedure described for Example 15 (Scheme 15): LCMS m/z 353.2 (M+H); rt 1.77 min; Conditions C. $^1$H NMR (400 MHz, DMSO-d6) δ 10.16-9.84 (m, 1H), 8.74 (d, J=7.5 Hz, 2H), 8.58-8.45 (m, 2H), 8.21 (d, J=3.0 Hz, 1H), 7.96-7.82 (m, 2H), 7.12 (d, J=3.0 Hz, 1H), 7.05-6.95 (m, 1H), 4.04 (s, 3H).

Example 92

N-[2-(6-methoxypyridin-2-yl)pyrrolo[2,1-f][1,2,4]triazin-4-yl]-2-methylpyridin-4-amine

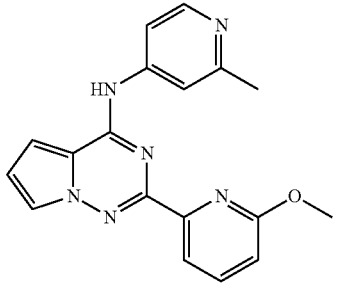 [SMILES: COc1cccc(-c2nc(Nc3ccnc(C)c3)c3cccn3n2)n1]

Example 92 (3 mg, 5%) was synthesized employing the procedure described for Example 16 (Scheme 16): LCMS m/z 333.2 (M+H); rt 1.516 min; Conditions C. $^1$H NMR (400 MHz, DMSO-d6) δ 10.18-10.09 (m, 1H), 8.40-8.22 (m, 2H), 7.90 (s, 2H), 7.33-7.30 (m, 1H), 6.99-6.95 (m, 1H), 6.91-6.87 (m, 1H), 4.06 (s, 3H), 2.48 (s, 3H).

Example 93

2-chloro-N-[2-(6-methoxypyridin-2-yl)pyrrolo[2,1-f][1,2,4]triazin-4-yl]pyridin-4-amine

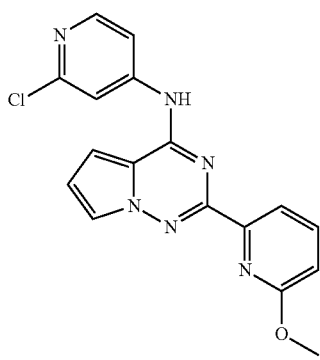 [SMILES: COc1cccc(-c2nc(Nc3ccnc(Cl)c3)c3cccn3n2)n1]

Example 93 (7 mg, 46.2%) was synthesized employing the procedure described for Example 16 (Scheme 16): LCMS m/z 353.2 (M+H); rt 1.881 min; Conditions C. $^1$H NMR (400 MHz, DMSO-d6) δ 10.42 (s, 1H), 8.59 (d, J=2.0 Hz, 1H), 8.33 (d, J=5.5 Hz, 1H), 8.11 (dd, J=5.8, 1.8 Hz, 1H), 8.02 (dd, J=2.8, 1.3 Hz, 1H), 7.96-7.83 (m, 2H), 7.32 (dd, J=4.5, 1.5 Hz, 1H), 7.04-6.88 (m, 2H), 4.09 (s, 3H).

Example 94

2-fluoro-N-[2-(6-methoxypyridin-2-yl)pyrrolo[2,1-f][1,2,4]triazin-4-yl]pyridin-4-amine

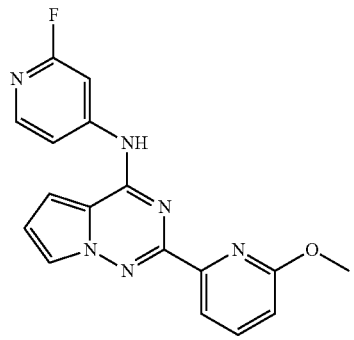 [SMILES: COc1cccc(-c2nc(Nc3ccnc(F)c3)c3cccn3n2)n1]

Example 94 (5 mg, 71%) was synthesized employing the procedure described for Example 16 (Scheme 16): LCMS m/z 337.2 (M+H); rt 1.772 min; Conditions C. $^1$H NMR (400 MHz, DMSO-d6) δ 10.55 (s, 1H), 8.63 (d, J=1.5 Hz, 1H), 8.16 (d, J=5.5 Hz, 1H), 8.02 (dd, J=2.5, 1.5 Hz, 1H), 7.94-7.80 (m, 3H), 7.32 (dd, J=4.5, 1.5 Hz, 1H), 7.01-6.88 (m, 2H), 4.11-4.03 (m, 3H).

Example 95

4-N-[2-(6-methoxypyridin-2-yl)pyrrolo[2,1-f][1,2,4]triazin-4-yl]pyridine-3,4-diamine

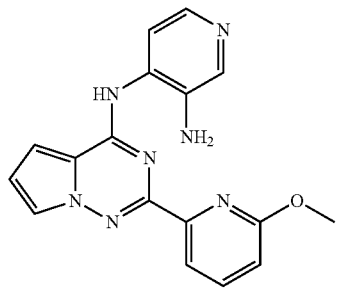 [SMILES: COc1cccc(-c2nc(Nc3ccncc3N)c3cccn3n2)n1]

Example 95 (4 mg, 12.6%) was synthesized employing the procedure described for Example 16 (Scheme 16): LCMS m/z 334.2 (M+H); rt 1.524 min; Conditions C. $^1$H NMR (400 MHz, DMSO-d6) δ 9.69-9.45 (m, 1H), 8.37-8.19 (m, 1H), 8.05-7.96 (m, 1H), 7.91-7.85 (m, 1H), 7.80-7.59 (m, 2H), 7.19-6.97 (m, 2H), 6.92-6.72 (m, 3H), 6.54-6.34 (m, 2H), 3.92 (s, 3H).

Example 96

2-fluoro-N-[2-(6-methoxypyridin-2-yl)-5-methylpyrrolo[2,1-f][1,2,4]triazin-4-yl]pyridin-4-amine

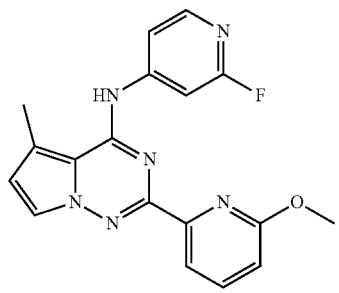 [SMILES: COc1cccc(-c2nc(Nc3ccnc(F)c3)c3c(C)ccn3n2)n1]

Example 96 (8 mg, 53%) was synthesized employing the procedure described for Example 16 (Scheme 16): LCMS m/z 351.2 (M+H); rt 2.074 min; Conditions C. $^1$H NMR (400 MHz, DMSO-d6) δ 9.09 (s, 1H), 8.33 (d, J=2.0 Hz, 1H), 8.14 (d, J=6.0 Hz, 1H), 7.93 (d, J=2.5 Hz, 1H), 7.89-7.79 (m, 3H), 6.99-6.90 (m, 1H), 6.75 (d, J=2.0 Hz, 1H), 4.05 (s, 3H), 2.69 (s, 3H).

Example 97

N-(4-{[2-(6-methoxypyridin-2-yl)pyrrolo[2,1-f][1,2,4]triazin-4-yl]amino}pyridin-2-yl)acetamide

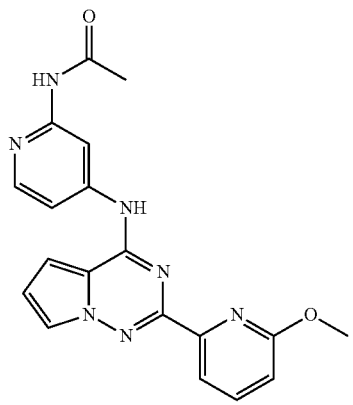 [SMILES: COc1cccc(-c2nc(Nc3ccnc(NC(C)=O)c3)c3cccn3n2)n1]

Example 97 (6 mg, 5%) was synthesized employing the procedure described for Example 16 (Scheme 16): LCMS m/z 376.2 (M+H); rt 1.188 min; Conditions C. $^1$H NMR (400 MHz, DMSO-d6) δ 2.1 (s, 3H) 4.0 (s, 3H) 6.87-7.01 (m, 2H) 7.35-7.42 (m, 1H) 7.84-7.90 (m, 1H) 7.97-8.05 (m, 2H) 8.22-8.30 (m, 1H) 8.40-8.46 (m, 1H) 8.51-8.59 (m, 1H) 10.53-10.62 (m, 1H) 10.84-10.95 (m, 1H).

Example 98

4-{[2-(6-methoxypyridin-2-yl)pyrrolo[2,1-f][1,2,4]triazin-4-yl]amino}pyridine-3-carboxamide

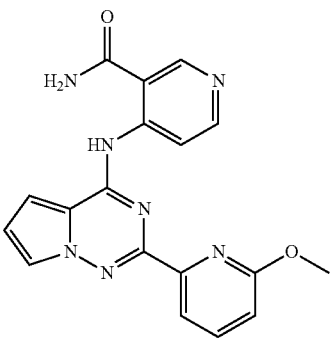 [SMILES: COc1cccc(-c2nc(Nc3ccncc3C(N)=O)c3cccn3n2)n1]

Example 98 (1 mg, 1.7%) was synthesized employing the procedure described for Example 16 (Scheme 16): LCMS m/z 362.2 (M+H); rt 1.204 min; Conditions C. $^1$H NMR (400 MHz, DMSO-d6) δ 13.63-12.92 (m, 2H), 9.65-9.39 (m, 1H), 9.22-8.97 (m, 1H), 8.76-8.47 (m, 2H), 8.26-8.09 (m, 1H), 8.09-7.72 (m, 3H), 7.09-6.92 (m, 2H), 6.89-6.64 (m, 1H), 4.08 (s, 3H).

Example 99

N-[2-(6-methoxypyridin-2-yl)pyrrolo[2,1-f][1,2,4]triazin-4-yl]-2-(morpholin-4-yl)pyridin-4-amine

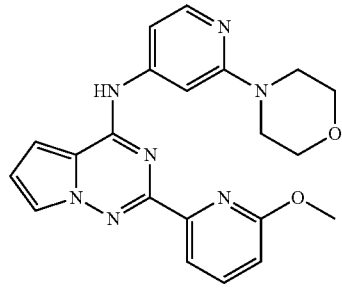 [SMILES: COc1cccc(-c2nc(Nc3ccnc(N4CCOCC4)c3)c3cccn3n2)n1]

Example 99 (4 mg, 3.1%) was synthesized employing the procedure described for Example 16 (Scheme 16): LCMS m/z 404.3 (M+H); rt 1.700 min; Conditions C. $^1$H NMR (400 MHz, DMSO-d6) δ 10.16-10.03 (m, 1H), 8.09 (d, J=5.5 Hz, 1H), 7.96 (dd, J=2.5, 1.5 Hz, 1H), 7.91-7.82 (m, 2H), 7.71 (dd, J=5.5, 1.5 Hz, 1H), 7.59 (d, J=1.5 Hz, 1H), 7.30 (dd, J=4.5, 1.5 Hz, 1H), 7.02-6.92 (m, 1H), 6.87 (dd, J=4.5, 2.5 Hz, 1H), 4.01 (s, 3H), 3.79-3.69 (m, 4H), 3.52-3.42 (m, 4H).

Example 100

3-fluoro-N-{2-[2-(trifluoromethyl)pyrimidin-4-yl]pyrrolo[2,1-f][1,2,4]triazin-4-yl}pyridin-4-amine

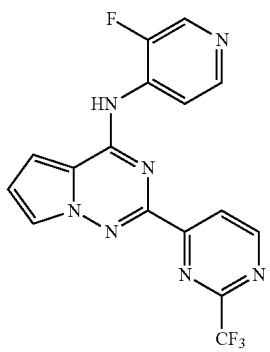 [SMILES: Fc1cnccc1Nc1nc(-c2ccnc(C(F)(F)F)n2)nn2cccc12]

Intermediate 100A: 4-phenoxy-2-(2-(trifluoromethyl)pyrimidin-4-yl)pyrrolo[2,1-f][1,2,4]triazine

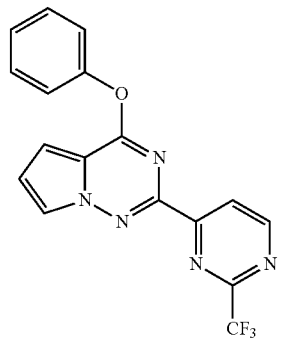 [SMILES: FC(F)(F)c1nccc(-c2nc(Oc3ccccc3)c3cccn3n2)n1]

Intermediate 100A (240 mg, 0.672 mmol, 83% yield) was synthesized employing the procedure described for intermediate 17A (Scheme 17). LCMS m/z 358 (M+H); rt 1.08 min; Conditions A. $^1$H NMR (Chloroform-d) δ 8.96 (d, J=5.2 Hz, 1H), 8.10 (d, J=5.2 Hz, 1H), 8.07 (dd, J=2.8, 1.4 Hz, 1H), 7.49-7.55 (m, 2H), 7.33-7.41 (m, 3H), 7.10 (dd, J=4.4, 1.4 Hz, 1H), 6.99 (dd, J=4.4, 2.8 Hz, 1H).

Example 100 (9.9 mg, 31%) was synthesized employing the procedure described for Example 17 (Scheme 17): LCMS m/z 376 (M+H); rt 1.56 min; Conditions F. $^1$H NMR (DMSO-d6) δ 9.22 (d, J=4.9 Hz, 1H), 8.68 (br. s, 1H), 8.47 (d, J=5.0 Hz, 1H), 8.40 (d, J=5.0 Hz, 1H), 8.32 (t, J=5.8 Hz, 1H), 8.16 (br. s, 1H), 7.44 (br. s, 1H), 7.00 (br. s, 1H).

Example 101

3-fluoro-N-[2-(2-methoxypyrimidin-4-yl)pyrrolo[2,1-f][1,2,4]triazin-4-yl]pyridin-4-amine

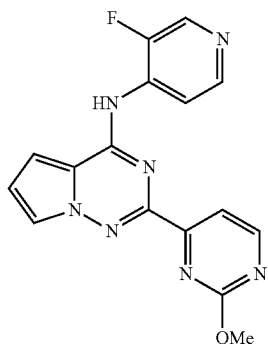 [SMILES: COc1nccc(-c2nc(Nc3ccncc3F)c3cccn3n2)n1]

Intermediate 101A: 2-(2-methoxypyrimidin-4-yl)-4-phenoxypyrrolo[2,1-f][1,2,4]triazine

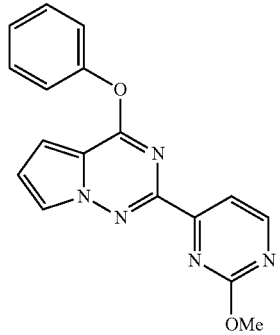 [SMILES: COc1nccc(-c2nc(Oc3ccccc3)c3cccn3n2)n1]

Intermediate 101A (51 mg, 0.160 mmol, 19.65% yield) was synthesized employing the procedure described for intermediate 17A (Scheme 17). LCMS m/z 320 (M+H); rt 1.0.91 min; Conditions A. $^1$H NMR (Chloroform-d) δ 8.60 (d, J=5.5 Hz, 1H), 8.02 (dd, J=2.6, 1.5 Hz, 1H), 7.41-7.54 (m, 4H), 7.28-7.32 (m, 1H), 6.98 (dd, J=4.4, 1.7 Hz, 1H), 6.93 (dd, J=4.4, 2.8 Hz, 1H), 6.76 (d, J=5.5 Hz, 1H), 3.98 (s, 3H).

Example 101 (13.6 mg, 41%) was synthesized employing the procedure described for Example 17 (Scheme 17): LCMS m/z 338 (M+H); rt 1.14 min; Conditions F. $^1$H NMR (DMSO-d6) δ 10.21 (br. s, 1H), 8.83 (br. s, 1H), 8.67 (d, J=5.6 Hz, 1H), 8.62 (d, J=2.4 Hz, 1H), 8.39 (d, J=5.4 Hz, 1H), 8.04 (br. s, 1H), 7.45 (br. s, 1H), 7.05 (d, J=5.6 Hz, 1H), 6.95 (br. s, 1H), 4.07 (s, 3H).

Example 102

N-[2-(6-ethoxypyridin-2-yl)pyrrolo[2,1-f][1,2,4]triazin-4-yl]-3-fluoropyridin-4-amine

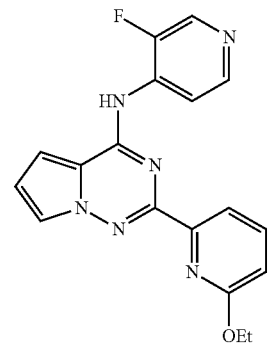 [SMILES: CCOc1cccc(-c2nc(Nc3ccncc3F)c3cccn3n2)n1]

Intermediate 102A: 2-(6-ethoxypyridin-2-yl)-4-phenoxypyrrolo[2,1-f][1,2,4]triazine

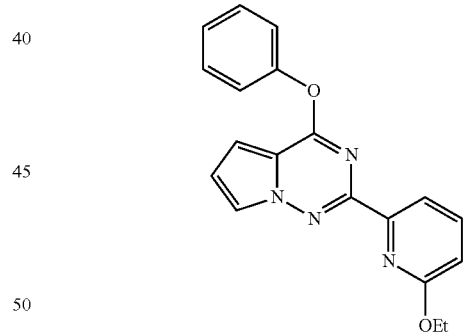

Intermediate 102A (230 mg, 0.692 mmol, 85% yield) was synthesized employing the procedure described for intermediate 17A (Scheme 17). LCMS m/z 333 (M+H); rt 1.15 min; Conditions A. $^1$H NMR (Chloroform-d) δ 7.94 (dd, J=2.6, 1.5 Hz, 1H), 7.64-7.69 (m, 1H), 7.57-7.63 (m, 1H), 7.46-7.53 (m, 2H), 7.39-7.44 (m, 2H), 7.30-7.38 (m, 1H), 7.00 (dd, J=4.3, 1.5 Hz, 1H), 6.89 (dd, J=4.4, 2.8 Hz, 1H), 6.79 (dd, J=8.0, 0.8 Hz, 1H), 4.50 (q, J=7.2 Hz, 2H), 1.44 (t, J=7.2 Hz, 3H).

Example 102 (22.3 mg, 71%) was synthesized employing the procedure described for Example 17 (Scheme 17): LCMS m/z 351 (M+H); rt 1.77 min; Conditions F. $^1$H NMR (DMSO-d6) δ 10.20 (br. s, 1H), 8.54-8.70 (m, 2H), 8.41 (d, J=5.2 Hz, 1H), 8.00 (br. s, 1H), 7.72-7.89 (m, 2H), 7.39 (d, J=3.8 Hz, 1H), 6.90 (d, J=6.7 Hz, 2H), 4.48 (q, J=6.8 Hz, 2H), 1.39 (t, J=6.9 Hz, 3H).

Example 103

4-N-(3-fluoropyridin-4-yl)-2-(6-methoxypyridin-2-yl)pyrrolo[2,1-f][1,2,4]triazine-4,6-diamine

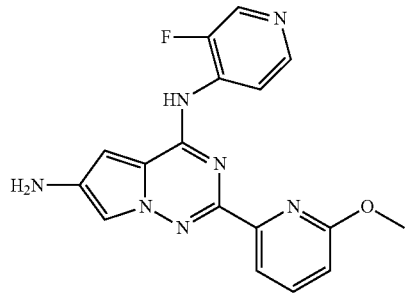 [SMILES: COc1cccc(-c2nc(Nc3ccncc3F)c3cc(N)cn3n2)n1]

Example 103 (8 mg, 65.5%) was synthesized employing the procedure described for Example 22 (Scheme 22): LCMS m/z 352.2 (M+H); rt 1.180 min; Conditions C. $^1$H NMR (400 MHz, DMSO-d6) δ 9.67 (s, 1H), 8.74 (dd, J=5.5, 7.0 Hz, 1H), 8.57 (d, J=3.0 Hz, 1H), 8.35 (d, J=5.5 Hz, 1H), 7.86-7.73 (m, 2H), 7.37 (d, J=1.5 Hz, 1H), 6.91-6.84 (m, 1H), 6.71 (d, J=1.5 Hz, 1H), 4.98 (br. s, 2H), 4.01 (s, 3H).

Example 104

N-{4-[(3-fluoropyridin-4-yl)amino]-2-(6-methoxypyridin-2-yl)pyrrolo[2,1-f][1,2,4]triazin-6-yl}acetamide

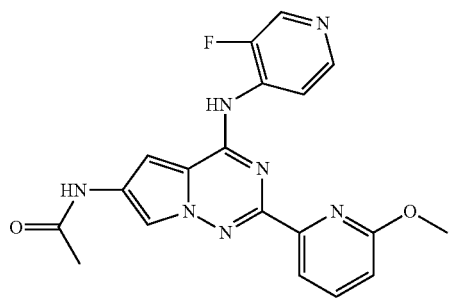 [SMILES: COc1cccc(-c2nc(Nc3ccncc3F)c3cc(NC(C)=O)cn3n2)n1]

Example 104 (2 mg, 5.9%) was synthesized employing the procedure described for Example 22 (Scheme 22): LCMS m/z 394.2 (M+H); rt 1.935 min; Conditions C. $^1$H NMR (400 MHz, DMSO-d6) δ 10.45 (s, 1H), 10.17 (s, 1H), 8.68-8.58 (m, 2H), 8.40 (d, J=5.5 Hz, 1H), 8.11 (d, J=1.5 Hz, 1H), 7.88-7.77 (m, 2H), 7.38 (s, 1H), 6.92 (dd, J=1.3, 7.8 Hz, 1H), 4.00 (s, 3H), 2.13-2.06 (m, 3H).

Example 105

N-{4-[(3-fluoropyridin-4-yl)amino]-2-(6-methoxypyridin-2-yl)pyrrolo[2,1-f][1,2,4]triazin-6-yl}morpholine-4-carboxamide

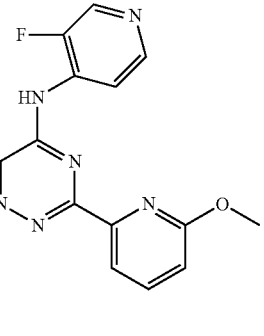

Example 105 (14 mg, 35%) was synthesized employing the procedure described for Example 22 (Scheme 22): LCMS m/z 465.3 (M+H); rt 1.137 min; Conditions C. $^1$H NMR (400 MHz, DMSO-d6) δ 10.33 (d, J=13.1 Hz, 1H), 9.17 (s, 1H), 8.89 (br. s, 1H), 8.77 (d, J=4.0 Hz, 1H), 8.48 (d, J=5.5 Hz, 1H), 8.11-8.03 (m, 1H), 7.90-7.78 (m, 2H), 7.42 (br. s, 1H), 6.95-6.88 (m, 1H), 4.05-3.98 (m, 3H), 3.68-3.59 (m, 4H), 3.52-3.43 (m, 4H).

Example 106

N-{4-[(3-fluoropyridin-4-yl)amino]-2-(6-methoxypyridin-2-yl)pyrrolo[2,1-f][1,2,4]triazin-6-yl}-2-(morpholin-4-yl)acetamide Example 106 (17 mg, 41.6%) was synthesized employing the procedure described for Example 22 (Scheme 22): LCMS m/z 479.2 (M+H); rt 0.986 min; Conditions C. $^1$H NMR (400 MHz, DMSO-d6) δ 10.28 (s, 1H), 8.67-8.57 (m, 2H), 8.41-8.33 (m, 1H), 8.15 (d, J=2.0 Hz, 1H), 7.87-7.76 (m, 2H), 7.48 (d, J=1.5 Hz, 1H), 6.96-6.87 (m, 1H), 4.00 (s, 3H), 3.71-3.62 (m, 4H), 3.23-3.17 (m, 2H), 2.53 (d, J=4.5 Hz, 4H), 1.90-1.83 (m, 3H).

Example 107

N-{4-[(3-fluoropyridin-4-yl)amino]-2-(6-methoxy-pyridin-2-yl)pyrrolo[2,1-f][1,2,4]triazin-6-yl}cyclopropanesulfonamide

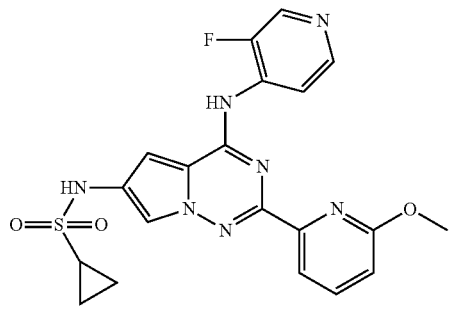 [SMILES: COc1cccc(-c2nc(Nc3ccncc3F)c3cc(NS(=O)(=O)C4CC4)cn3n2)n1]

Example 107 (11 mg, 33%) was synthesized employing the procedure described for Example 22 (Scheme 22): LCMS m/z 456.2 (M+H); rt 1.219 min; Conditions C.; 1HNMR (400 MHz, DMSO-d6) δ 10.22 (s, 1H), 10.00 (s, 1H), 8.69-8.60 (m, 2H), 8.40 (d, J=5.5 Hz, 1H), 7.88-7.77 (m, 2H), 7.73 (d, J=1.5 Hz, 1H), 7.34 (d, J=2.0 Hz, 1H), 6.93 (dd, J=1.0, 8.0 Hz, 1H), 4.00 (s, 3H), 2.71 (s, 1H), 1.05-0.93 (m, 4H).

Example 108 tert-butyl N-[({4-[(3-fluoropyridin-4-yl)amino]-2-(6-methoxypyridin-2-yl)pyrrolo[2,1-f][1,2,4]triazin-6-yl}carbamoyl)methyl]carbamate

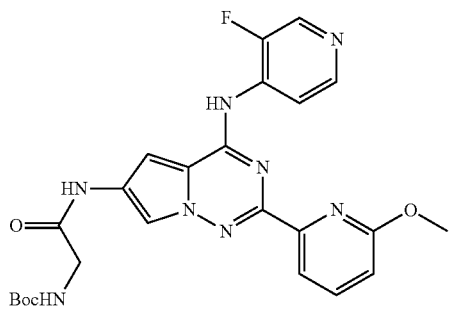 [SMILES: COc1cccc(-c2nc(Nc3ccncc3F)c3cc(NC(=O)CNC(=O)OC(C)(C)C)cn3n2)n1]

Example 108 (4 mg, 18.4%) was synthesized employing the procedure described for Example 22 (Scheme 22): LCMS m/z 509.2 (M+H); rt 1.340 min; Conditions C.; $^1$H NMR (400 MHz, DMSO-d6) δ 10.45 (s, 1H), 10.19 (br. s, 1H), 8.70-8.56 (m, 2H), 8.39 (d, J=5.5 Hz, 1H), 8.12 (s, 1H), 7.87-7.76 (m, 2H), 7.41 (br. s, 1H), 7.12 (t, J=6.0 Hz, 1H), 6.96-6.86 (m, 1H), 4.01 (s, 3H), 3.78 (d, J=6.0 Hz, 2H), 1.41 (s, 9H).

Example 109

2-amino-N-{4-[(3-fluoropyridin-4-yl)amino]-2-(6-methoxypyridin-2-yl)pyrrolo[2,1-f][1,2,4]triazin-6-yl}acetamide

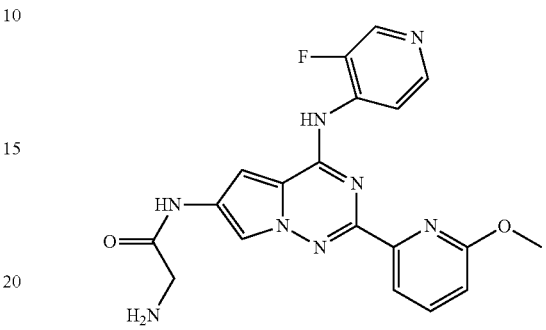

Example 109 (40 mg, 100%) was synthesized employing the procedure described for Example 22 (Scheme 22): LCMS m/z 409.3 (M+H); rt 0.879 min; Conditions C. $^1$H NMR (400 MHz, DMSO-d6) δ 8.62 (d, J=3.0 Hz, 2H), 8.40 (d, J=5.5 Hz, 1H), 8.18 (d, J=1.5 Hz, 1H), 7.88-7.77 (m, 2H), 7.50 (br. s, 1H), 6.92 (dd, J=1.3, 7.8 Hz, 1H), 4.01 (s, 3H), 2.54 (s, 4H), 1.91 (s, 1H).

Example 110

N-{4-[(3-fluoropyridin-4-yl)amino]-2-(6-methoxy-pyridin-2-yl)pyrrolo[2,1-f][1,2,4]triazin-6-yl}-2-methanesulfonamidoacetamide

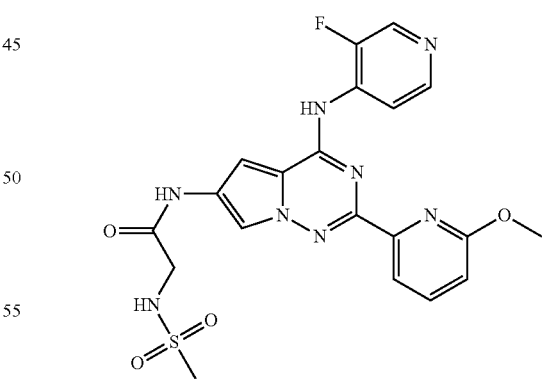

Example 110 (6 mg, 25%) was synthesized employing the procedure described for Example 22 (Scheme 22): LCMS m/z 487.2 (M+H); rt 1.329 min; Conditions C. $^1$H NMR (400 MHz, DMSO-d6) δ 10.54 (s, 1H), 8.65-8.53 (m, 2H), 8.37 (d, J=5.0 Hz, 1H), 8.11 (s, 1H), 7.87-7.75 (m, 2H), 7.38 (br. s, 1H), 6.96-6.86 (m, 1H), 4.00 (s, 3H), 3.90 (s, 2H), 3.01 (s, 3H).

Example 111

N-{4-[(3-fluoropyridin-4-yl)amino]-2-[6-(trifluoromethyl)pyridin-2-yl]pyrrolo[2,1-f][1,2,4]triazin-6-yl}-N-methanesulfonylmethanesulfonamide

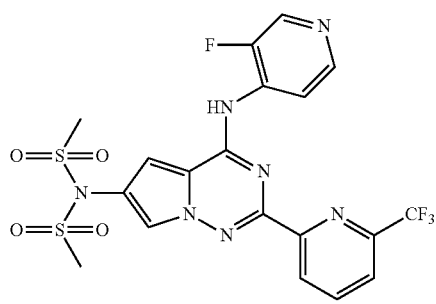 [SMILES: CS(=O)(=O)N(c1cc2c(Nc3ccncc3F)nc(-c3cccc(C(F)(F)F)n3)nn2c1)S(C)(=O)=O]

Example 111 (2 mg, 3.5%) was synthesized employing the procedure described for Example 22 (Scheme 22): LCMS m/z 546.2 (M+H); rt 1.677 min; Conditions C.; ¹H NMR (400 MHz, DMSO-d6) δ 10.47 (s, 1H), 8.69 (d, J=2.5 Hz, 1H), 8.55 (d, J=1.5 Hz, 1H), 8.49-8.40 (m, 3H), 8.29 (t, J=7.8 Hz, 1H), 8.05 (d, J=8.0 Hz, 1H), 7.60 (d, J=2.0 Hz, 1H), 3.64-3.53 (m, 6H).

Scheme 54

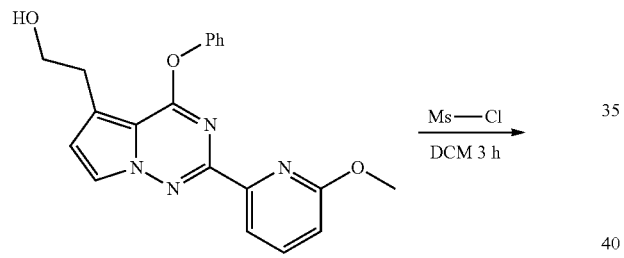

Example 46

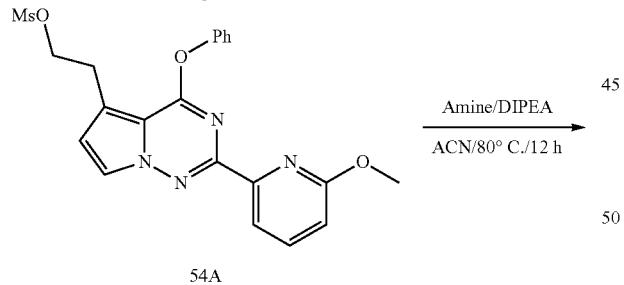

54A

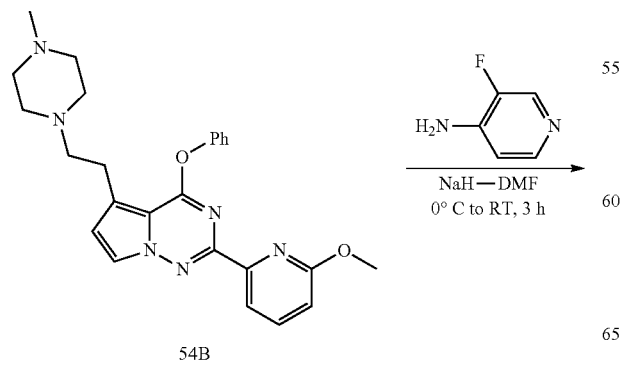

54B

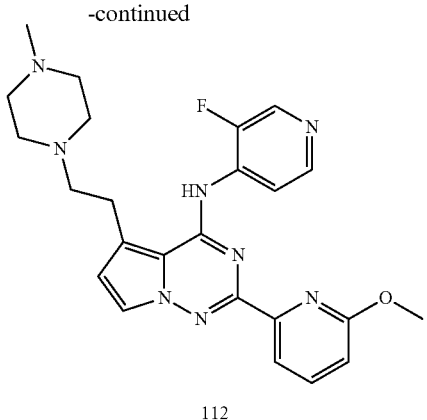

112

Example 112

3-fluoro-N-[2-(6-methoxypyridin-2-yl)-5-[2-(4-methylpiperazin-1-yl)ethyl]pyrrolo[2,1-f][1,2,4]triazin-4-yl]pyridin-4-amine

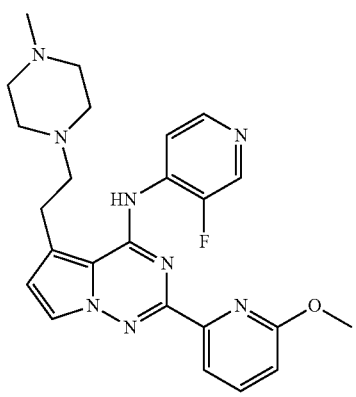 [SMILES: COc1cccc(-c2nc(Nc3ccncc3F)c3c(CCN4CCN(C)CC4)ccn3n2)n1]

Intermediate 54A: 2-(2-(6-methoxypyridin-2-yl)-4-phenoxypyrrolo[2,1-f][1,2,4]triazin-5-yl)ethyl methanesulfonate

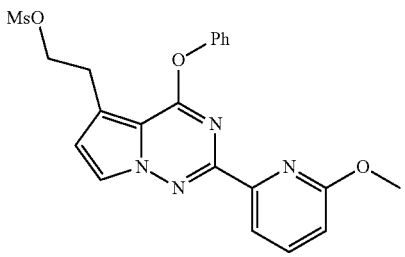 [SMILES: COc1cccc(-c2nc(Oc3ccccc3)c3c(CCOS(C)(=O)=O)ccn3n2)n1]

Methanesulfonyl chloride (0.024 mL, 0.310 mmol) was added to a stirred solution of 2-(2-(6-methoxypyridin-2-yl)-4-phenoxypyrrolo[2,1-f][1,2,4]triazin-5-yl)ethanol (75 mg, 0.207 mmol) and TEA (0.072 mL, 0.517 mmol) in DCM (10 mL) at 0° C. The resulting reaction mixture was stirred at room temperature for 3 h. The reaction was monitored by TLC. The reaction mixture was evaporated under reduced pressure. The residue was purified by silica gel chromatography using 0-30% ethyl acetate in hexanes to get 2-(2-(6-methoxypyridin-2-yl)-4-phenoxypyrrolo[2,1-f][1,2,4]triazin-5-yl)ethyl methanesulfonate (60 mg, 0.133 mmol, 64.5% yield) as a gum. LCMS m/z 441.1 (M+H); rt 1.15 min; Conditions B

Intermediate 54B: 2-(6-methoxypyridin-2-yl)-5-(2-(4-methylpiperazin-1-yl)ethyl)-4-phenoxypyrrolo[2,1-f][1,2,4]triazine

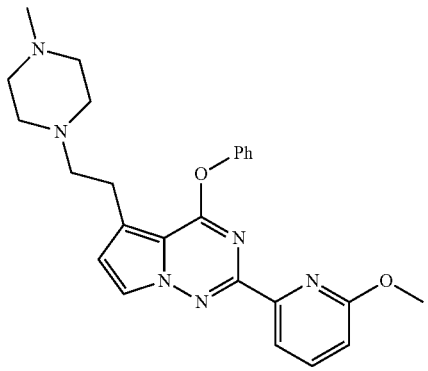 [SMILES: COc1cccc(-c2nc(Oc3ccccc3)c3c(CCN4CCN(C)CC4)ccn3n2)n1]

1-methylpiperazine (18.76 mg, 0.187 mmol) and DIPEA (0.044 mL, 0.250 mmol) were dissolved in acetonitrile (10 mL), and the mixture was heated to 50° C. for 3 min. To the reaction mixture was added 2-(2-(6-methoxypyridin-2-yl)-4-phenoxypyrrolo[2,1-f][1,2,4]triazin-5-yl)ethyl methanesulfonate (55 mg, 0.125 mmol) as solution in acetonitrile. The reaction mixture was heated at 80° C. for 12 h. An aliquot of the reaction mixture was analyzed by LCMS to ensure completion of reaction. The reaction mixture was cooled to room temperature and evaporated under reduced pressure to get 2-(6-methoxypyridin-2-yl)-5-(2-(4-methylpiperazin-1-yl)ethyl)-4-phenoxypyrrolo[2,1-f][1,2,4]triazine (80 mg, 0.125 mmol, 98% yield) as light brown gum which was used without further purification in the next step. LCMS m/z 445.1 (M+H); rt 1.00 min; Conditions B.

Example 112 (11 mg, 17%) was synthesized employing the procedure described for Example 23 (Scheme 23): LCMS m/z 463.3 (M+H); rt 1.411 min; Conditions C $^1$H NMR (400 MHz, DMSO-d6) δ=8.59 (d, J=3.0 Hz, 1H), 8.38 (d, J=5.0 Hz, 1H), 7.88-7.78 (m, 3H), 6.95 (dd, J=8.0, 1.0 Hz, 1H), 6.73 (d, J=2.5 Hz, 1H), 3.96 (s, 3H), 3.19-3.12 (m, 2H), 2.69 (t, J=6.8 Hz, 2H), 2.41 (br. s, 3H), 2.16 (br. s, 3H), 1.99 (s, 3H), 1.90 (s, 1H).

Example 113

3-fluoro-N-[2-(6-methoxypyridin-2-yl)-5-[2-(morpholin-4-yl)ethyl]pyrrolo[2,1-f][1,2,4]triazin-4-yl]pyridin-4-amine

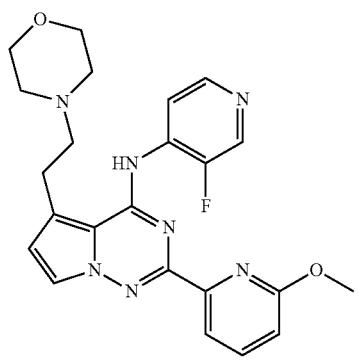 [SMILES: COc1cccc(-c2nc(Nc3ccncc3F)c3c(CCN4CCOCC4)ccn3n2)n1]

Example 113 (4 mg, 6.4%) was synthesized employing the procedure described for Example 23 (Scheme 23): LCMS m/z 450.3 (M+H); rt 1.769 min; Conditions C $^1$H NMR (400 MHz, DMSO-d6) δ 8.53-8.49 (m, 1H), 8.35-8.27 (m, 1H), 7.90-7.78 (m, 2H), 7.77-7.72 (m, 1H), 6.97-6.88 (m, 1H), 6.70-6.61 (m, 1H), 3.98-3.90 (m, 3H), 3.51-3.47 (m, 5H), 3.22-3.15 (m, 5H), 2.72-2.65 (m, 3H), 2.45-2.39 (m, 4H).

Example 114

N-{5-[2-(4-aminopiperidin-1-yl)ethyl]-2-(6-methoxypyridin-2-yl)pyrrolo[2,1-f][1,2,4]triazin-4-yl}-3-fluoropyridin-4-amine

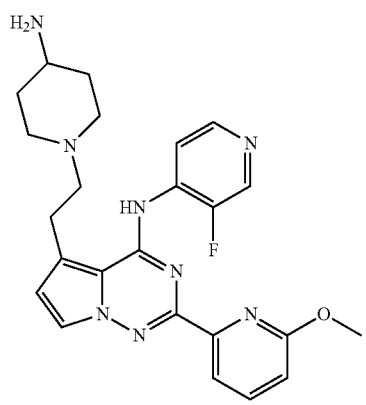 [SMILES: COc1cccc(-c2nc(Nc3ccncc3F)c3c(CCN4CCC(N)CC4)ccn3n2)n1]

Example 114 (11 mg, 37%) was synthesized employing the procedure described for Example 23 (Scheme 23): LCMS m/z 463.3 (M+H); rt 1.335 min; Conditions C $^1$H NMR (400 MHz, DMSO-d6) δ 8.73-8.57 (m, 1H), 8.47-8.40 (m, 1H), 8.28-8.20 (m, 1H), 7.80 (s, 2H), 7.70-7.62 (m, 1H), 6.97-6.82 (m, 1H), 6.63-6.54 (m, 1H), 3.97 (s, 3H), 3.20-3.11 (m, 3H), 2.86-2.77 (m, 2H), 2.69-2.59 (m, 3H), 2.09-1.96 (m, 2H), 1.70-1.58 (m, 2H), 1.29-1.07 (m, 2H).

Example 115

N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine

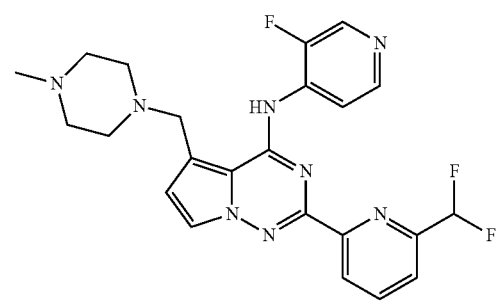 [SMILES: CN1CCN(Cc2ccn3nc(-c4cccc(C(F)F)n4)nc(Nc4ccncc4F)c23)CC1]

Example 115 (7 mg, 11%) was synthesized employing the procedure described for Example 23 (Scheme 23): LCMS m/z 469.3 (M+H); rt 0.943 min; Conditions C. $^1$H NMR (400 MHz, DMSO-d6) δ 11.47-11.32 (m, 1H), 10.00-9.84

(m, 1H), 9.24 (s, 1H), 8.72 (d, J=2.0 Hz, 1H), 8.59-8.38 (m, 2H), 8.23 (t, J=7.8 Hz, 1H), 8.06 (d, J=2.5 Hz, 1H), 7.87 (d, J=7.5 Hz, 1H), 7.27 (d, J=4.5 Hz, 1H), 7.18-6.88 (m, 3H), 3.97 (d, J=8.5 Hz, 3H), 3.46 (d, J=12.0 Hz, 2H), 3.24-3.05 (m, 4H), 2.83 (s, 3H), 2.336-2.331 (m, 2H).

Example 116

1-[({2-[6-(difluoromethyl)pyridin-2-yl]-4-[(3-fluoropyridin-4-yl)amino]pyrrolo[2,1-f][1,2,4]triazin-5-yl}methyl)amino]-2-methylpropan-2-ol

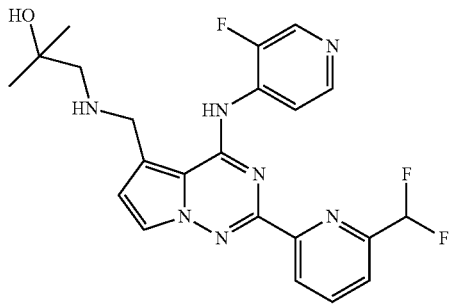 [SMILES: CC(C)(O)CNCc1ccn2nc(-c3cccc(C(F)F)n3)nc(Nc3ccncc3F)c12]

Example 116 (7 mg, 7.3%) was synthesized employing the procedure described for Example 23 (Scheme 23): LCMS m/z 458.0 (M+H); rt 2.543 min; Conditions E. $^1$H NMR (400 MHz, DMSO-d6) δ 9.07-9.00 (m, 1H), 8.86 (br. s, 1H), 8.55 (d, J=3.5 Hz, 1H), 8.45-8.36 (m, 2H), 8.21 (t, J=8.0 Hz, 1H), 7.93 (d, J=2.5 Hz, 1H), 7.84 (d, J=7.5 Hz, 1H), 7.28-6.95 (m, 1H), 6.83 (d, J=3.0 Hz, 1H), 4.45 (s, 1H), 4.13 (s, 2H), 1.05 (s, 6H).

Example 117

N-{4-[(5-{[(2-hydroxy-2-methylpropyl)amino]methyl}-2-(pyridin-2-yl)pyrrolo[2,1-f][1,2,4]triazin-4-yl)amino]pyridin-2-yl}acetamide

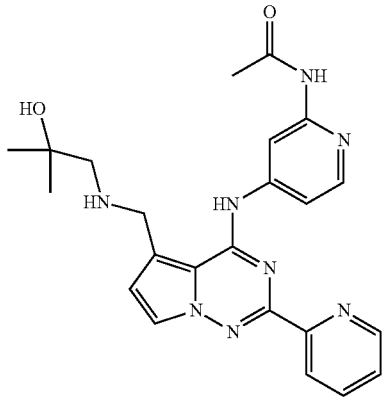 [SMILES: CC(=O)Nc1cc(Nc2nc(-c3ccccn3)nn3ccc(CNCC(C)(C)O)c23)ccn1]

Example 117 (10 mg, 8%) was synthesized employing the procedure described for Example 24 (Scheme 24): LCMS m/z 447.2 (M+H); rt 2.533 min; Conditions E $^1$H NMR (300 MHz, DMSO-d6) δ 8.81-8.91 (m, 1H) 8.63-8.70 (m, 1H) 8.23-8.30 (m, 1H) 8.14-8.21 (m, 1H) 7.96-8.03 (m, 1H) 7.86-7.93 (m, 1H) 7.80-7.84 (m, 1H) 7.33-7.39 (m, 1H) 6.84-6.93 (m, 1H) 2.12-2.15 (m, 3H) 2.10-2.15 (m, 3H).

Example 118

1-[({4-[(3-fluoropyridin-4-yl)amino]-2-(6-methoxypyridin-2-yl)pyrrolo[2,1-f][1,2,4]triazin-5-yl}methyl)amino]-2-methylpropan-2-ol

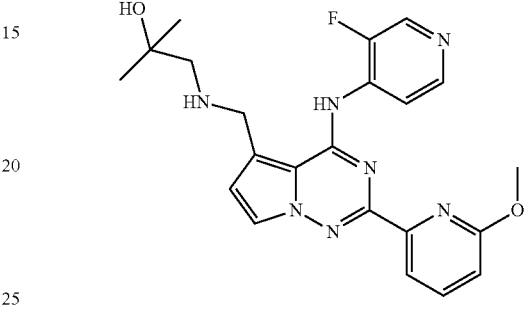

Example 118 (4 mg, 13%) was synthesized employing the procedure described for Example 25 (Scheme 25): LCMS m/z 438.3 (M+H); rt 1.747 min; Conditions C; $^1$H NMR (400 MHz, DMSO-d6) δ=9.44-9.36 (m, 1H), 8.54 (d, J=3.0 Hz, 1H), 8.33 (s, 1H), 7.91-7.81 (m, 3H), 7.00-6.92 (m, 1H), 6.81 (d, J=2.5 Hz, 1H), 4.40 (s, 1H), 4.12 (s, 2H), 4.07 (s, 3H), 2.47-2.43 (m, 1H), 1.09-1.00 (m, 6H).

Example 119

3-fluoro-N-[2-(6-methoxypyridin-2-yl)-5-({[2-(pyrrolidin-1-yl)ethyl]amino}methyl)pyrrolo[2,1-f][1,2,4]triazin-4-yl]pyridin-4-amine

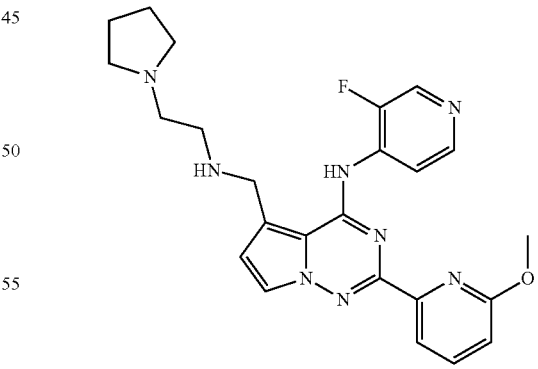

Example 119 (4 mg, 12%) was synthesized employing the procedure described for Example 25 (Scheme 25): LCMS m/z 463.3 (M+H); rt 1.52 min; Conditions C $^1$H NMR (400 MHz, DMSO-d6) δ 9.39 (d, J=5.5 Hz, 1H), 8.53 (s, 1H), 8.33 (s, 1H), 7.94-7.84 (m, 3H), 6.99-6.93 (m, 1H), 6.81 (s, 1H), 4.09 (s, 2H), 4.06 (s, 3H), 2.74 (br. s, 2H), 2.68-2.56 (m, 3H), 2.35 (d, J=17.6 Hz, 4H), 1.53 (br. s, 4H).

Example 120

(3R)-3-fluoro-4-[({4-[(3-fluoropyridin-4-yl)amino]-2-(6-methoxypyridin-2-yl)pyrrolo[2,1-f][1,2,4]triazin-5-yl}methyl)amino]-2-methylbutan-2-ol

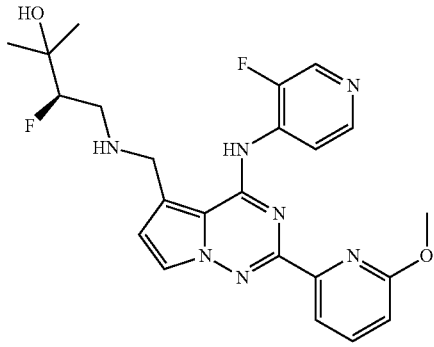 [SMILES: COc1cccc(-c2nc(Nc3ccncc3F)c3c(CNC[C@@H](F)C(C)(C)O)ccn3n2)n1]

Example 120 (2 mg, 6%) was synthesized employing the procedure described for Example 25 (Scheme 25): LCMS m/z 470.3 (M+H); rt 1.814 min; Conditions C. $^1$H NMR (400 MHz, DMSO-d6) δ 9.42-9.33 (m, 1H), 8.56 (d, J=3.0 Hz, 1H), 8.34 (d, J=5.5 Hz, 1H), 7.94-7.85 (m, 3H), 6.97 (dd, J=2.8, 6.3 Hz, 1H), 6.84 (d, J=2.5 Hz, 1H), 4.69 (s, 1H), 4.48-4.28 (m, 1H), 4.12 (s, 2H), 4.07 (s, 3H), 3.05-2.95 (m, 1H), 2.96-2.86 (m, 1H), 2.83-2.73 (m, 1H), 2.67 (t, J=1.8 Hz, 1H), 2.33 (t, J=2.0 Hz, 1H), 1.24 (s, 1H), 1.05 (d, J=13.1 Hz, 6H).

Example 121

3-fluoro-N-[2-(6-methoxypyridin-2-yl)-5-[(4-methylpiperazin-1-yl)methyl]pyrrolo[2,1-f][1,2,4]triazin-4-yl]pyridin-4-amine

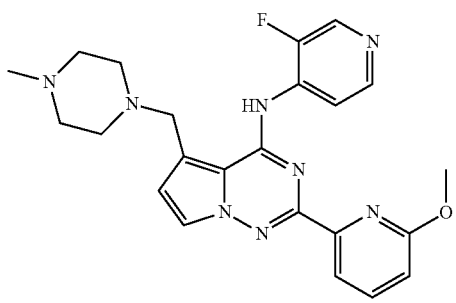

Example 121 (17 mg, 21%) was synthesized employing the procedure described for Example 25 (Scheme 25): LCMS m/z 449.1 (M+H); rt 2.571 min; Conditions E $^1$H NMR (400 MHz, CD3OD) δ 8.49-8.52 (m, 1H), 7.68 (d, J=4.0 Hz, 1H), 7.53 (d, J=4.0 Hz, 1H), 7.13-7.15 (m, 1H), 6.99-7.02 (m, 2H), 6.10 (d, J=4 Hz, 1H), 6.00 (d, J=2.4 Hz, 1H), 4.69 (s, 1H), 3.30 (s, 3H), 3.13 (s, 2H), 1.99 (br s, 7H), 1.67 (s, 1H), 1.16 (s, 1H).

Example 122

N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine

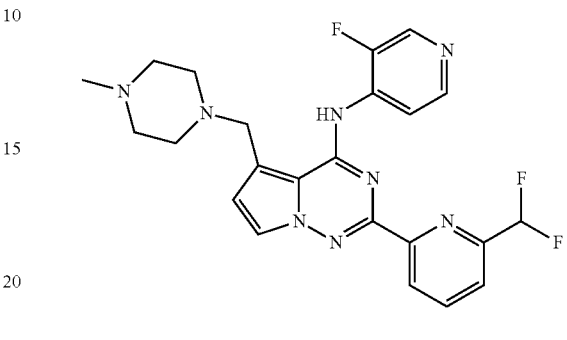

Example 122 (7 mg, 11%) was synthesized employing the procedure described for Example 26 (Scheme 26): LCMS m/z 469.3 (M+H); rt 0.943 min; Conditions C $^1$H NMR: (400 MHz, DMSO-d6) δ 11.47-11.32 (m, 1H), 10.00-9.84 (m, 1H), 9.24 (s, 1H), 8.72 (d, J=2.0 Hz, 1H), 8.59-8.38 (m, 2H), 8.23 (t, J=7.8 Hz, 1H), 8.06 (d, J=2.5 Hz, 1H), 7.87 (d, J=7.5 Hz, 1H), 7.27 (d, J=4.5 Hz, 1H), 7.18-6.88 (m, 3H), 3.97 (d, J=8.5 Hz, 3H), 3.46 (d, J=12.0 Hz, 2H), 3.24-3.05 (m, 4H), 2.83 (s, 3H), 2.336-2.331 (m, 2H).

Example 123

N-{5-[(4,4-difluoropiperidin-1-yl)methyl]-2-[6-(trifluoromethyl)pyridin-2-yl]pyrrolo[2,1-f][1,2,4]triazin-4-yl}-3-fluoropyridin-4-amine

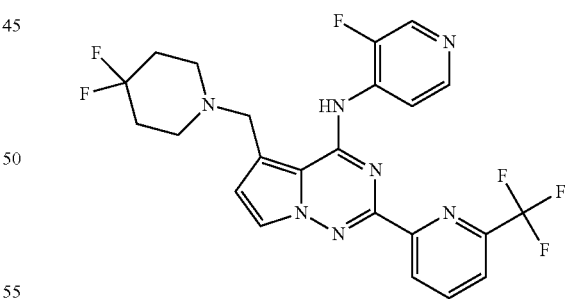

Example 123 (10 mg, 8.2%) was synthesized employing the procedure described for Example 26 (Scheme 26): LCMS m/z 508.0 (M+H); rt 2.587 min; Conditions E $^1$H NMR (400 MHz, Methanol-d4) δ 9.28 (dd, J=7.5, 5.5 Hz, 1H), 8.60 (d, J=8.0 Hz, 1H), 8.53 (d, J=3.5 Hz, 1H), 8.39 (d, J=5.5 Hz, 1H), 8.23 (t, J=8.0 Hz, 1H), 7.95 (d, J=7.0 Hz, 1H), 7.88 (d, J=3.0 Hz, 1H), 6.87 (d, J=2.5 Hz, 1H), 4.00 (s, 2H), 2.81 (br. s, 1H), 2.18-2.04 (m, 4H), 1.31 (s, 1H), 0.97 (s, 1H).

Example 124

1-[({4-[(3-fluoropyridin-4-yl)amino]-2-[6-(trifluoromethyl)pyridin-2-yl]pyrrolo[2,1-f][1,2,4]triazin-5-yl}methyl)amino]-2-methylpropan-2-ol

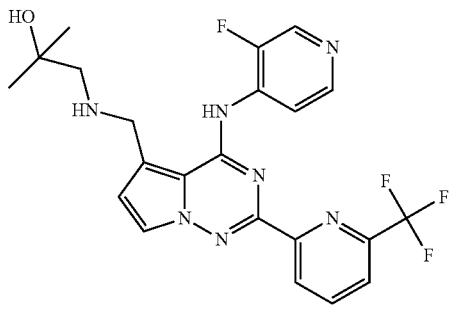 [SMILES: CC(C)(O)CNCc1ccn2nc(-c3cccc(C(F)(F)F)n3)nc(Nc3ccncc3F)c12]

Example 124 (18 mg, 18%) was synthesized employing the procedure described for Example 26 (Scheme 26): LCMS m/z 476.0 (M+H); rt 2.873 min; Conditions E $^1$H NMR (400 MHz, DMSO-d6) δ 9.07 (t, J=6.3 Hz, 1H), 8.96-8.76 (m, 1H), 8.57-8.47 (m, 2H), 8.36-8.23 (m, 2H), 8.04 (d, J=8.0 Hz, 1H), 7.94 (d, J=2.5 Hz, 1H), 6.83 (d, J=2.5 Hz, 1H), 4.44 (s, 1H), 4.13 (s, 2H), 1.05 (s, 6H).

Example 125

1-[({4-[(3-fluoropyridin-4-yl)amino]-2-(pyridin-2-yl)pyrrolo[2,1-f][1,2,4]triazin-5-yl}methyl)amino]-2-methylpropan-2-ol

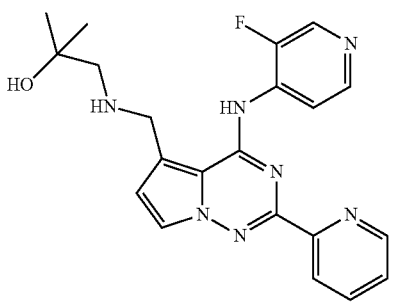 [SMILES: CC(C)(O)CNCc1ccn2nc(-c3ccccn3)nc(Nc3ccncc3F)c12]

Example 125 (243 mg, 24%) was synthesized employing the procedure described for Example 27 (Scheme 27): LCMS m/z 408.2 (M+H); rt 1.991 min; Conditions E $^1$H NMR: (400 MHz, DMSO-d6) δ 9.03-8.93 (m, 1H), 8.79-8.73 (m, 1H), 8.63-8.53 (m, 1H), 8.44-8.34 (m, 1H), 8.29-8.19 (m, 1H), 8.06-7.95 (m, 1H), 7.87 (s, 1H), 7.55-7.48 (m, 1H), 6.85-6.78 (m, 1H), 4.52-4.34 (m, 1H), 4.12 (s, 2H), 1.87 (s, 2H), 1.05 (s, 6H).

Example 126

(3R,4R)-4-amino-1-({4-[(3-fluoropyridin-4-yl)amino]-2-(pyridin-2-yl)pyrrolo[2,1-f][1,2,4]triazin-5-yl}methyl)piperidin-3-ol

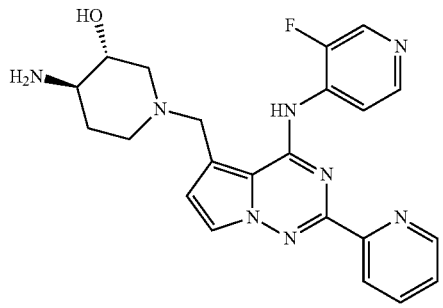 [SMILES: N[C@@H]1CCN(Cc2ccn3nc(-c4ccccn4)nc(Nc4ccncc4F)c23)C[C@H]1O]

Example 126 (8.5 mg, 5.6%) was synthesized employing the procedure described for Example 27 (Scheme 27): LCMS m/z 435.2 (M+H); rt 1.683 min; Conditions E. $^1$H NMR: (400 MHz, DMSO-d6) δ 12.34-12.16 (m, 1H), 8.91-8.81 (m, 1H), 8.75-8.71 (m, 1H), 8.63 (s, 1H), 8.53-8.40 (m, 1H), 8.34-8.19 (m, 1H), 8.02-7.90 (m, 2H), 7.65-7.48 (m, 1H), 6.88-6.80 (m, 1H), 4.96-4.82 (m, 1H), 4.00-3.89 (m, 1H), 3.84-3.76 (m, 1H), 3.17-3.08 (m, 2H), 3.01-2.92 (m, 2H), 2.73-2.64 (m, 1H), 2.35-2.28 (m, 1H), 2.21-1.98 (m, 1H), 1.88 (s, 1H), 1.80-1.68 (m, 1H), 1.46-1.29 (m, 1H).

Example 127

3-fluoro-N-{5-[(4-methylpiperazin-1-yl)methyl]-2-(pyridin-2-yl)pyrrolo[2,1-f][1,2,4]triazin-4-yl}pyridin-4-amine

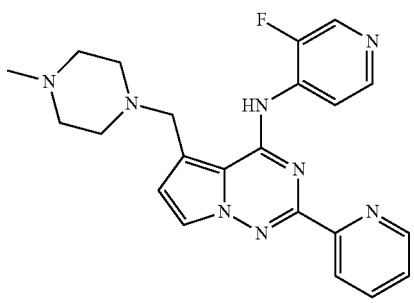 [SMILES: CN1CCN(Cc2ccn3nc(-c4ccccn4)nc(Nc4ccncc4F)c23)CC1]

Example 127 (18.2 mg, 14%) was synthesized employing the procedure described for Example 27 (Scheme 27): LCMS m/z 419.2 (M+H); rt 1.963 min; Conditions E. $^1$H NMR: (400 MHz, Methanol-d4) δ 9.04-8.97 (m, 1H), 8.77-8.72 (m, 1H), 8.53 (d, J=3.5 Hz, 1H), 8.46-8.36 (m, 2H), 8.11-8.00 (m, 1H), 7.87 (d, J=2.5 Hz, 1H), 7.65-7.53 (m, 1H), 6.86 (d, J=2.5 Hz, 1H), 3.99 (s, 2H), 3.06-2.89 (m, 7H), 2.60 (s, 3H), 2.00 (s, 2H).

Example 128

1-{4-[(3-fluoropyridin-4-yl)amino]-2-(6-methoxy-pyridin-2-yl)pyrrolo[2,1-f][1,2,4]triazin-5-yl}-2-(4-methylpiperazin-1-yl)ethan-1-ol

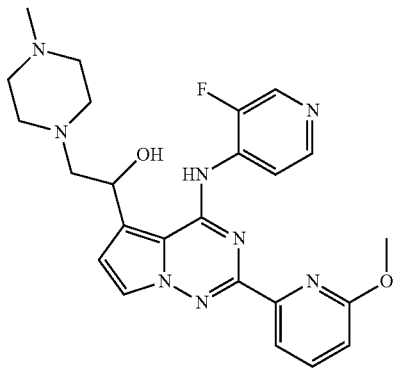 [SMILES: COc1cccc(-c2nc(Nc3ccncc3F)c3c(C(O)CN4CCN(C)CC4)ccn3n2)n1]

Example 128 (7 mg, 11%) was synthesized employing the procedure described for Example 30 (Scheme 30): LCMS m/z 479.3 (M+H); rt 1.323 min; Conditions C. $^1$H NMR (400 MHz, DMSO-d6) δ 12.41 (s, 1H), 9.33-9.34 (m, 1H), 8.61 (d, J=3.2 Hz, 1H), 8.37 (d, J=5.6 Hz, 1H), 7.94 (d, J=2.8 Hz, 1H), 7.85-7.90 (m, 2H), 6.94-6.99 (m, 1H), 6.82 (d, J=2.8 Hz, 1H), 4.83 (s, 1H), 4.06 (s, 3H), 3.86-3.90 (m, 1H), 3.69-3.89 (m, 1H), 3.58-3.59 (m, 1H), 3.32 (merged with residual dmso, 5H), 2.52-2.56 (m, 2H), 2.32-2.33 (m, 1H), 2.07 (s, 3H). $^{19}$F NMR (400 MHz, DMSO-d6) δ −140.34.

Example 129

2-(4,4-difluoropiperidin-1-yl)-1-{4-[(3-fluoropyridin-4-yl)amino]-2-(6-methoxypyridin-2-yl)pyrrolo[2,1-f][1,2,4]triazin-5-yl}ethan-1-ol

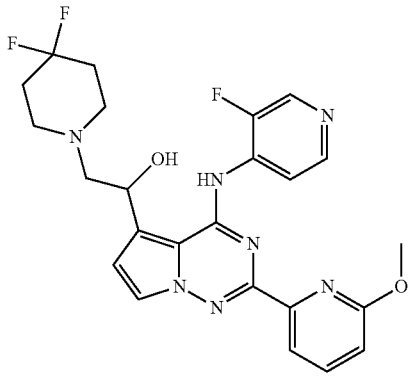 [SMILES: COc1cccc(-c2nc(Nc3ccncc3F)c3c(C(O)CN4CCC(F)(F)CC4)ccn3n2)n1]

Example 129 (20 mg, 19%) was synthesized employing the procedure described for Example 30 (Scheme 30): LCMS m/z 500.3 (M+H); rt 1.884 min; Conditions C. $^1$H NMR (400 MHz, DMSO-d6) δ 12.13 (s, 1H), 9.38-9.41 (m, 1H), 8.60 (d, J=3.2 Hz, 1H), 8.37 (d, J=5.2 Hz, 1H), 7.86-7.96 (m, 3H), 6.86-6.99 (m, 2H), 4.99 (s, 1H), 4.07 (s, 3H), 3.90-3.92 (m, 2H), 3.66-3.70 (m, 1H), 2.84-2.91 (m, 4H), 2.00-2.07 (m, 4H). $^{19}$F NMR (400 MHz, DMSO-d6) δ −95.6, −142.76.

Example 130

1-{4-[(3-fluoropyridin-4-yl)amino]-2-(6-methoxy-pyridin-2-yl)pyrrolo[2,1-f][1,2,4]triazin-5-yl}-2-{[2-(piperidin-1-yl)ethyl]amino}ethan-1-ol

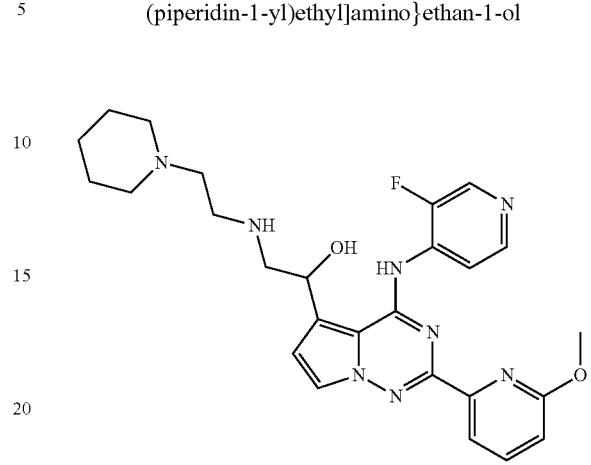

Example 130 (28 mg, 40%) was synthesized employing the procedure described for Example 30 (Scheme 30): LCMS m/z 507.4 (M+H); rt 1.544 min; Conditions C. $^1$H NMR (400 MHz, DMSO-d6) δ 9.46-9.49 (m, 1H), 8.54 (d, J=3.6 Hz, 1H), 8.33 (d, J=5.6 Hz, 1H), 7.88-7.91 (m, 3H), 6.86-6.98 (m, 2H), 5.21 (bs, 1H), 4.09-4.10 (m, 1H), 4.07 (s, 3H), 3.48-3.55 (m, 2H), 2.61-2.67 (m, 2H), 2.15-2.36 (m, 6H), 1.29-1.36 (m, 6H). $^{19}$F NMR (400 MHz, DMSO-d6) δ −139.9.

Example 131

4-{2-[(2-{4-[(3-fluoropyridin-4-yl)amino]-2-(6-methoxypyridin-2-yl)pyrrolo[2,1-f][1,2,4]triazin-5-yl}-2-hydroxyethyl)amino]ethyl}-1,4-thiomorpholine-1,1-dione

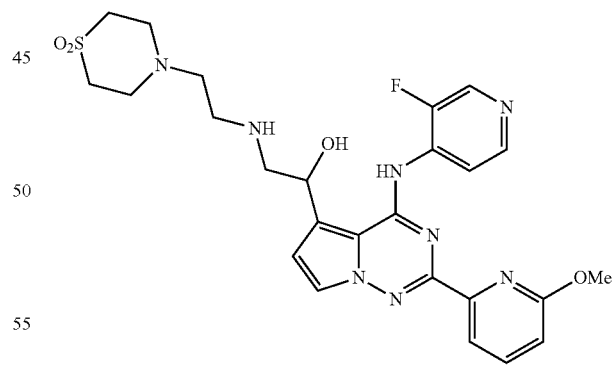

Example 131 (5 mg, 7%) was synthesized employing the procedure described for Example 30 (Scheme 30): LCMS m/z 557.3 (M+H); rt 1.524 min; Conditions C. $^1$H NMR (400 MHz, DMSO-d6) δ 9.47-9.50 (m, 1H), 8.55 (d, J=3.2 Hz, 1H), 8.34 (d, J=5.6 Hz, 1H), 7.85-7.92 (m, 3H), 6.95-6.99 (m, 1H), 6.87 (d, J=3.6 Hz, 1H), 5.26 (t, J=5.6 Hz, 1H), 4.08-4.12 (m, 2H), 4.07 (s, 3H), 3.49-3.55 (m, 2H), 2.93-3.16 (m, 2H), 2.50-2.91 (m, 11H). $^{19}$F NMR (400 MHz, DMSO-d6) δ −140.1.

Example 132

1-{2-[(4-{[2-(6-methoxypyridin-2-yl)pyrrolo[2,1-f][1,2,4]triazin-4-yl]amino}pyridin-2-yl)amino]ethyl}piperidin-4-ol

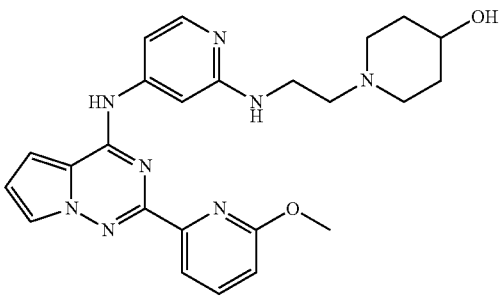 [SMILES: COc1cccc(-c2nc(Nc3ccnc(NCCN4CCC(O)CC4)c3)c3cccn3n2)n1]

Example 132 (6 mg, 8.6%) was synthesized employing the procedure described for Example 34 (Scheme 34): LCMS m/z 461.3 (M+H); rt 1.218 min; Conditions C. ¹H NMR (400 MHz, DMSO-d6) δ 9.97-9.85 (m, 1H), 7.96-7.84 (m, 4H), 7.52-7.48 (m, 1H), 7.30-7.25 (m, 1H), 7.16-7.13 (m, 1H), 6.98-6.93 (m, 1H), 6.87-6.81 (m, 1H), 6.25-6.20 (m, 1H), 4.57-4.50 (m, 1H), 4.02 (s, 3H), 3.47-3.41 (m, 1H), 2.78-2.64 (m, 2H), 2.11-2.02 (m, 1H), 1.91 (s, 3H), 1.75-1.65 (m, 2H), 1.43-1.30 (m, 2H).

Example 133

1-[(4-{[2-(6-methoxypyridin-2-yl)pyrrolo[2,1-f][1,2,4]triazin-4-yl]amino}pyridin-2-yl)amino]-2-methylpropan-2-ol

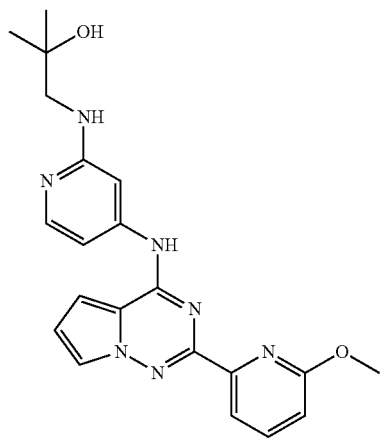 [SMILES: COc1cccc(-c2nc(Nc3ccnc(NCC(C)(C)O)c3)c3cccn3n2)n1]

Example 133 (2 mg, 8%) was synthesized employing the procedure described for Example 34 (Scheme 34): LCMS m/z 406.3 (M+H); rt 1.534 min; Conditions C ¹H NMR (400 MHz, DMSO-d6) δ 9.94 (s, 1H), 7.97-7.82 (m, 4H), 7.57-7.49 (m, 1H), 7.30 (dd, J=4.5, 1.5 Hz, 1H), 7.19 (d, J=1.5 Hz, 1H), 7.00-6.92 (m, 1H), 6.85 (dd, J=4.3, 2.8 Hz, 1H), 6.28 (t, J=5.5 Hz, 1H), 4.06-3.98 (m, 3H), 3.24 (d, J=6.0 Hz, 2H), 2.57-2.53 (m, 4H), 1.90 (s, 1H), 1.17-1.10 (m, 6H).

Example 134

4-[(4-{[2-(6-methoxypyridin-2-yl)pyrrolo[2,1-f][1,2,4]triazin-4-yl]amino}pyridin-2-yl)amino]-2-methylbutan-2-ol

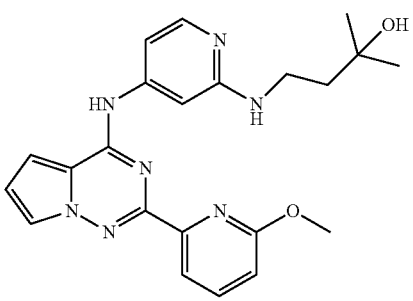 [SMILES: COc1cccc(-c2nc(Nc3ccnc(NCCC(C)(C)O)c3)c3cccn3n2)n1]

Example 134 (10 mg, 15%) was synthesized employing the procedure described for Example 34 (Scheme 34): LCMS m/z 420.3 (M+H); rt 1.438 min; Conditions C. ¹H NMR (400 MHz, DMSO-d6) δ 9.97-9.77 (m, 1H), 7.95-7.85 (m, 4H), 7.54-7.50 (m, 1H), 7.30 (dd, J=4.0, 1.5 Hz, 1H), 7.07 (d, J=1.5 Hz, 1H), 7.14-6.97 (m, 1H), 6.95 (dd, J=7.5, 1.5 Hz, 1H), 6.85 (dd, J=4.5, 2.5 Hz, 1H), 6.33 (s, 1H), 4.07 (s, 1H), 4.02 (s, 3H), 3.33-3.26 (m, 2H), 3.17 (s, 4H), 1.71-1.65 (m, 2H), 1.14 (s, 6H).

Example 135

2-N-[3-(dimethylamino)propyl]-4-N-[2-(6-methoxypyridin-2-yl)pyrrolo[2,1-f][1,2,4]triazin-4-yl]pyridine-2,4-diamine

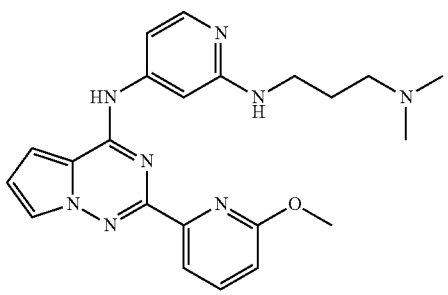 [SMILES: COc1cccc(-c2nc(Nc3ccnc(NCCCN(C)C)c3)c3cccn3n2)n1]

Example 135 (9 mg, 14%) was synthesized employing the procedure described for Example 34 (Scheme 34): LCMS m/z 419.3 (M+H); rt 1.327 min; Conditions D. ¹H NMR (400 MHz, DMSO-d6) δ 9.95-9.86 (m, 1H), 7.97-7.82 (m, 3H), 7.58-7.50 (m, 1H), 7.32-7.28 (m, 1H), 7.13-7.06 (m, 1H), 6.98-6.93 (m, 1H), 6.86-6.80 (m, 1H), 6.55-6.45 (m, 2H), 4.02 (s, 3H), 3.28-3.18 (m, 3H), 2.47-2.40 (m, 1H), 2.35-2.18 (m, 5H), 1.79-1.67 (m, 2H), 1.27-1.22 (m, 1H).

Example 136

1-{2-[(4-{[2-(6-methoxypyridin-2-yl)-5-methylpyrrolo[2,1-f][1,2,4]triazin-4-yl]amino}pyridin-2-yl)amino]ethyl}piperidin-4-ol

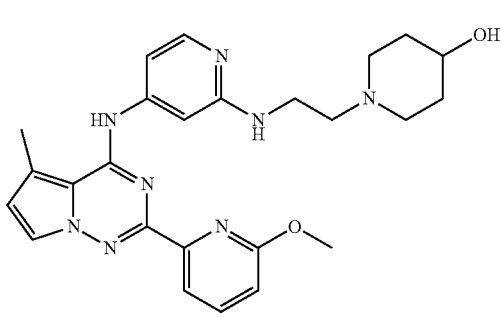 [SMILES: COc1cccc(-c2nc(Nc3ccnc(NCCN4CCC(O)CC4)c3)c3c(C)ccn3n2)n1]

Example 136 (7 mg, 10.2%) was synthesized employing the procedure described for Example 34 (Scheme 34): LCMS m/z 475.4 (M+H); rt 1.128 min; Conditions C. $^1$H NMR (400 MHz, DMSO-d6) δ 8.52-8.45 (m, 1H), 7.93-7.81 (m, 4H), 7.35-7.28 (m, 1H), 7.03-6.98 (m, 1H), 6.96-6.89 (m, 1H), 6.72-6.65 (m, 1H), 6.55-6.50 (m, 1H), 6.25-6.13 (m, 2H), 4.58-4.47 (m, 2H), 4.00 (s, 3H), 3.50-3.39 (m, 3H), 2.79-2.71 (m, 2H), 2.69-2.61 (m, 3H), 2.10-1.98 (m, 2H), 1.76-1.66 (m, 2H), 1.44-1.32 (m, 2H).

Example 137

4-N-[2-(6-methoxypyridin-2-yl)-5-methylpyrrolo[2,1-f][1,2,4]triazin-4-yl]-2-N-[2-(morpholin-4-yl)ethyl]pyridine-2,4-diamine

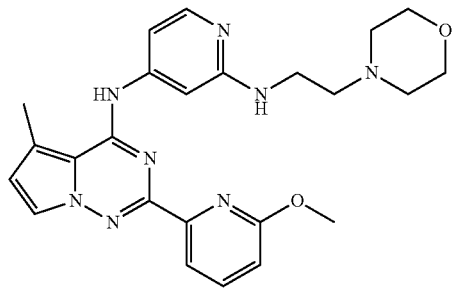 [SMILES: COc1cccc(-c2nc(Nc3ccnc(NCCN4CCOCC4)c3)c3c(C)ccn3n2)n1]

Example 137 (2 mg, 3%) was synthesized employing the procedure described for Example 34 (Scheme 34): LCMS m/z 461.3 (M+H); rt 1.143 min; Conditions C. $^1$H NMR (400 MHz, DMSO-d6) δ 8.53-8.49 (m, 1H), 7.93-7.90 (m, 1H), 7.86 (s, 3H), 7.34-7.31 (m, 1H), 7.03-7.00 (m, 1H), 6.96-6.92 (m, 1H), 6.70-6.67 (m, 1H), 6.55-6.51 (m, 1H), 6.31-6.24 (m, 1H), 4.00 (s, 3H), 3.62-3.55 (m, 4H), 3.41-3.36 (m, 3H), 2.66 (s, 4H), 2.46-2.37 (m, 4H).

Example 138

1-[(4-{[2-(6-methoxypyridin-2-yl)-5-methylpyrrolo[2,1-f][1,2,4]triazin-4-yl]amino}pyridin-2-yl)amino]-2-methylpropan-2-ol

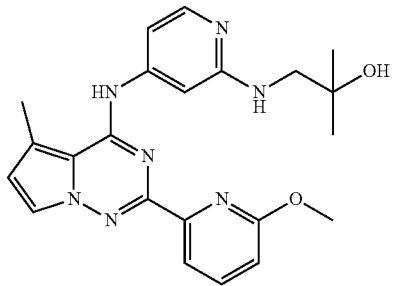 [SMILES: COc1cccc(-c2nc(Nc3ccnc(NCC(C)(C)O)c3)c3c(C)ccn3n2)n1]

Example 138 (5 mg, 8%) was synthesized employing the procedure described for Example 34 (Scheme 34): LCMS m/z 420.3 (M+H); rt 1.36 min; Conditions C. $^1$H NMR (400 MHz, DMSO-d6) δ 8.58-8.49 (m, 1H), 7.86 (s, 3H), 7.36-7.29 (m, 1H), 7.08-7.03 (m, 1H), 6.97-6.91 (m, 1H), 6.71-6.63 (m, 1H), 6.56-6.49 (m, 1H), 6.31-6.27 (m, 1H), 4.99-4.80 (m, 1H), 4.00 (s, 3H), 3.26-3.19 (m, 2H), 2.66 (s, 3H), 1.13 (s, 6H).

Example 139

4-N-[2-(6-methoxypyridin-2-yl)pyrrolo[2,1-f][1,2,4]triazin-4-yl]-2-N-[2-(morpholin-4-yl)ethyl]pyridine-2,4-diamine

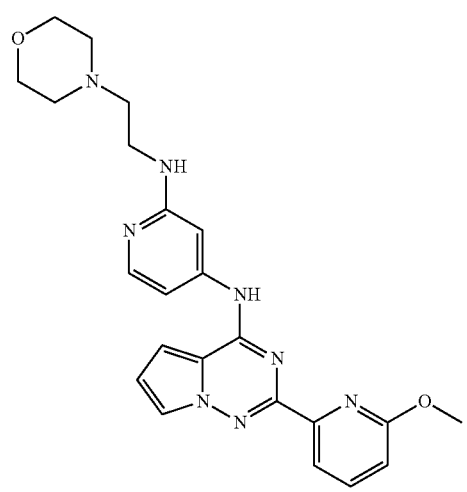 [SMILES: COc1cccc(-c2nc(Nc3ccnc(NCCN4CCOCC4)c3)c3cccn3n2)n1]

Example 139 (6 mg, 22%) was synthesized employing the procedure described for Example 34 (Scheme 34): LCMS m/z 447.3 (M+H); rt 2.108 min; Conditions C. $^1$H NMR (400 MHz, DMSO-d6) δ 9.92 (s, 1H), 7.97-7.83 (m, 4H), 7.51 (dd, J=6.0, 2.0 Hz, 1H), 7.30 (dd, J=4.5, 1.5 Hz, 1H), 7.15 (d, J=1.5 Hz, 1H), 7.01-6.92 (m, 1H), 6.88-6.82 (m, 1H), 6.28 (t, J=5.5 Hz, 1H), 4.02 (s, 3H), 3.63-3.51 (m, 4H), 2.41 (br. s, 4H).

Example 140

N-[3-(1,1-dioxo-1,4-thiomorpholin-4-yl)propyl]-4-{[2-(5-fluoro-6-methylpyridin-2-yl)pyrrolo[2,1-f][1,2,4]triazin-4-yl]amino}pyridine-3-carboxamide

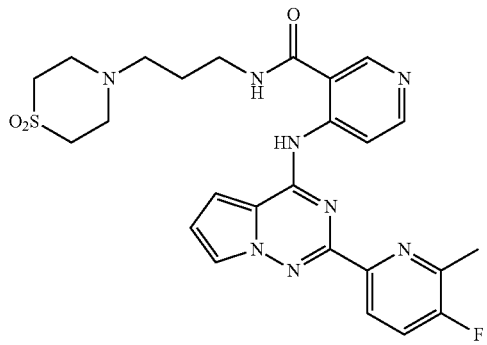 [SMILES: Cc1nc(-c2nc(Nc3ccncc3C(=O)NCCCN3CCS(=O)(=O)CC3)c3cccn3n2)ccc1F]

Example 140 (16 mg, 14%) was synthesized employing the procedure described for Example 35 (Scheme 35): LCMS m/z 339.3 (M+H); rt 1.471 min; Conditions C. $^1$H NMR (400 MHz, DMSO-d6) δ 12.75 (s, 1H), 9.20-9.25 (m, 2H), 9.05 (s, 1H), 8.77 (d, J=6.0 Hz, 1H), 8.21-8.25 (m, 1H), 8.12 (s, 1H), 7.80-7.84 (m, 1H), 6.92-7.00 (m, 2H), 3.24-3.42 (m, 12H), 2.59 (s, 3H), 1.82-1.90 (m, 2H). $^{19}$F NMR (400 MHz, DMSO-d6) δ −123.3.

Example 141

4-{[2-(5-fluoro-6-methylpyridin-2-yl)pyrrolo[2,1-f][1,2,4]triazin-4-yl]amino}-N-[2-(piperidin-1-yl)ethyl]pyridine-3-carboxamide

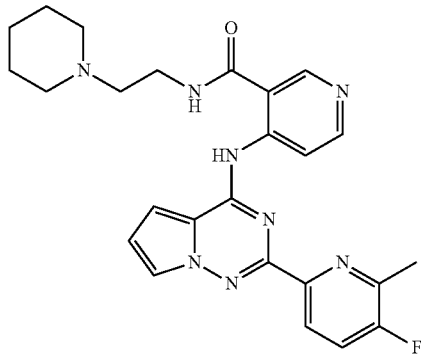 [SMILES: Cc1nc(-c2nc(Nc3ccncc3C(=O)NCCN3CCCCC3)c3cccn3n2)ccc1F]

Example 141 (3 mg, 30) was synthesized employing the procedure described for Example 35 (Scheme 35): LCMS m/z 475.3 (M+H); rt 1.632 min; Conditions C. $^1$H NMR (400 MHz, DMSO-d6) δ 8.97 (s, 1H), 8.56 (bs, 1H), 8.54 (bs, 1H), 8.18-8.21 (m, 1H), 7.91 (s, 1H), 7.76-7.80 (m, 1H), 6.84 (bs, 2H), 3.43-3.45 (merged with residual dmso-d6 moisture peak, 4H), 2.56 (s, 3H), 2.32-2.38 (m, 4H), 1.45-1.50 (m, 4H), 1.23-1.37 (m, 2H). $^{19}$F NMR (400 MHz, DMSO-d6) δ −124.5.

Example 142

4-{[2-(pyridin-2-yl)pyrrolo[2,1-f][1,2,4]triazin-4-yl]amino)}-N-[2-(pyrrolidin-1-yl)ethyl]pyridine-3-carboxamide

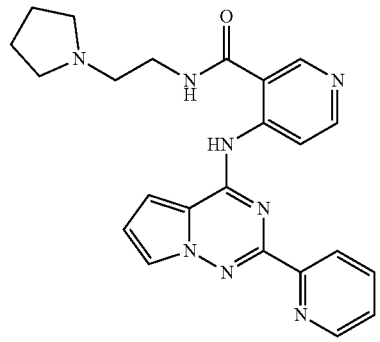 [SMILES: O=C(NCCN1CCCC1)c1cnccc1Nc1nc(-c2ccccn2)nn2cccc12]

Example 142 (30.1 mg, 56%) was synthesized employing the procedure described for Example 36 (Scheme 36): LCMS m/z 429 (M+H); rt 1.07 min; Conditions F. $^1$H NMR (DMSO-d6) δ 9.04 (d, J=5.4 Hz, 1H), 8.98 (s, 1H), 8.76 (d, J=4.0 Hz, 1H), 8.68 (d, J=5.7 Hz, 1H), 8.31 (d, J=7.7 Hz, 1H), 7.97-8.09 (m, 2H), 7.52-7.60 (m, 1H), 6.96 (d, J=2.7 Hz, 1H), 6.91 (d, J=3.7 Hz, 1H), 3.49 (br. s, 1H), 2.71 (t, J=6.4 Hz, 2H), 2.60 (br. s, 4H), 1.71 (br. s, 4H); Some proton resonance signals were obscured due to solvent and presaturation peaks.

Example 143

N-[2-(diethyl amino)ethyl]-4-{[2-(pyridin-2-yl)pyrrolo[2,1-f][1,2,4]triazin-4-yl]amino}pyridine-3-carboxamide

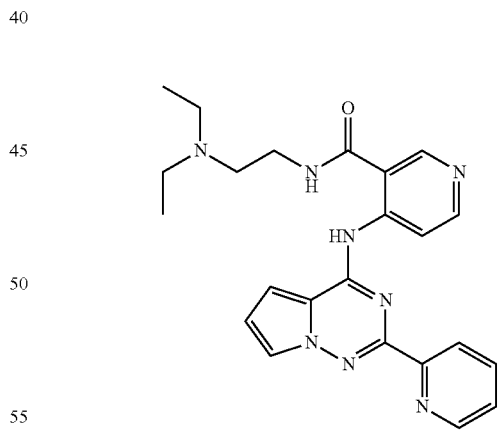

Example 143 (14.8 mg, 28%) was synthesized employing the procedure described for Example 36 (Scheme 36): LCMS m/z 431 (M+H); rt 1.12 min; Conditions F. $^1$H NMR (DMSO-d6) δ 9.04 (d, J=5.7 Hz, 1H), 8.96 (s, 1H), 8.76 (d, J=4.0 Hz, 1H), 8.68 (d, J=5.7 Hz, 1H), 8.31 (d, J=8.1 Hz, 1H), 7.95-8.10 (m, 2H), 7.51-7.61 (m, 1H), 6.94-7.02 (m, 1H), 6.91 (d, J=4.0 Hz, 1H), 3.34-3.71 (m, 1H), 2.58-2.91 (m, 5H), 1.02 (t, J=7.1 Hz, 6H); Some proton resonance signals were obscured due to solvent and presaturation peaks.

Example 144

N-[2-(piperidin-1-yl)ethyl]-4-{[2-(pyridin-2-yl)pyrrolo[2,1-f][1,2,4]triazin-4-yl]amino}pyridine-3-carboxamide

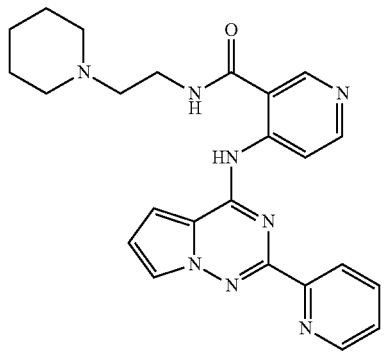 [SMILES: O=C(NCCN1CCCCC1)c1cnccc1Nc1nc(-c2ccccn2)nn2cccc12]

Example 144 (4.5 mg, 13%) was synthesized employing the procedure described for Example 36 (Scheme 36): LCMS m/z 443 (M+H); rt 1.20 min; Conditions F. $^1$H NMR (DMSO-d6) δ 9.04 (d, J=5.4 Hz, 1H), 8.97 (s, 1H), 8.76 (d, J=3.7 Hz, 1H), 8.68 (d, J=5.7 Hz, 1H), 8.32 (d, J=8.1 Hz, 1H), 7.97-8.08 (m, 2H), 7.50-7.62 (m, 1H), 6.89-6.99 (m, 2H), 3.36-3.68 (m, 1H), 2.51-2.67 (m, 8H) overlapping with DMSO peak, 1.27-1.61 (m, 6H).

Example 145 tert-butyl 4-{2-[(4-{[2-(pyridin-2-yl)pyrrolo[2,1-f][1,2,4]triazin-4-yl]amino}pyridin-3-yl)formamido]ethyl}piperazine-1-carboxylate

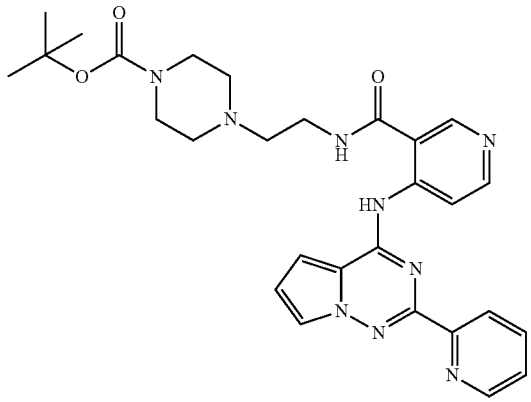 [SMILES: CC(C)(C)OC(=O)N1CCN(CCNC(=O)c2cnccc2Nc2nc(-c3ccccn3)nn3cccc23)CC1]

Example 145 (7.1 mg, 17%) was synthesized employing the procedure described for Example 36 (Scheme 36): LCMS m/z 544 (M+H); rt 1.79 min; Conditions F. $^1$H NMR (DMSO-d6) δ 9.06 (d, J=18.8 Hz, 2H), 8.95 (s, 1H), 8.76 (d, J=4.0 Hz, 1H), 8.68 (d, J=5.7 Hz, 1H), 8.31 (d, J=8.1 Hz, 1H), 7.92-8.14 (m, 2H), 7.49-7.64 (m, 1H), 6.84-7.05 (m, 2H), 3.19-3.59 (m, 6H), 2.35-2.51 (m, 6H) overlapping with DMSO peak, 1.37 (s, 9H).

Example 146

N-{2-[cis-2,6-dimethylmorpholin-4-yl]ethyl}-4-{[2-(pyridin-2-yl)pyrrolo[2,1-f][1,2,4]triazin-4-yl]amino}pyridine-3-carboxamide

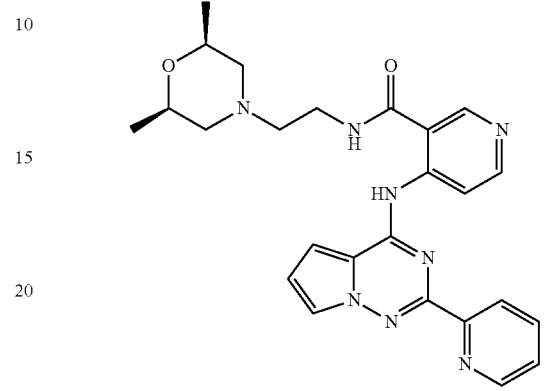

Example 146 (11.2 mg, 31%) was synthesized employing the procedure described for Example 36 (Scheme 36): LCMS m/z 473 (M+H); rt 1.52 min; Conditions F. $^1$H NMR (DMSO-d6) δ 8.73-8.89 (m, 2H), 8.69 (s, 1H), 8.37-8.57 (m, 2H), 8.06 (d, J=7.7 Hz, 1H), 7.69-7.85 (m, 2H), 7.23-7.38 (m, 1H), 6.56-6.77 (m, 2H), 3.15-3.48 (m, 4H), 2.44-2.70 (m, 2H), 2.16-2.26 (m, 2H) overlapping with DMSO peak, 1.32-1.54 (m, 2H), 0.78 (d, J=6.4 Hz, 6H).

Example 147

N-[2-(1,1-dioxo-1,4-thiomorpholin-4-yl)ethyl]-4-{[2-(pyridin-2-yl)pyrrolo[2,1-f][1,2,4]triazin-4-yl]amino}pyridine-3-carboxamide

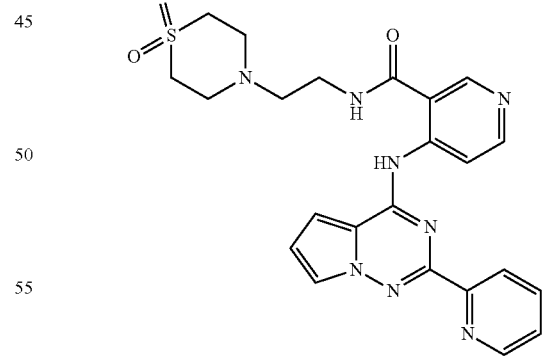

Example 147 (2.3 mg, 6%) was synthesized employing the procedure described for Example 36 (Scheme 36): LCMS m/z 493 (M+H); rt 1.26 min; Conditions F. $^1$H NMR (DMSO-d6) δ 12.62 (br. s, 1H), 9.10 (br. s, 2H), 8.99 (s, 1H), 8.78 (d, J=4.0 Hz, 1H), 8.71 (d, J=5.5 Hz, 1H), 8.32 (d, J=7.6 Hz, 1H), 7.98-8.09 (m, 2H), 7.53-7.61 (m, 1H), 6.88-7.04 (m, 2H), 3.31-3.40 (m, 2H) overlapping with water peak, 2.95-3.16 (m, 8H), 2.69-2.79 (m, 2H).

Example 148

N-[3-(1,1-dioxo-1,4-thiomorpholin-4-yl)propyl]-4-{[2-(pyridin-2-yl)pyrrolo[2,1-f][1,2,4]triazin-4-yl]amino}pyridine-3-carboxamide

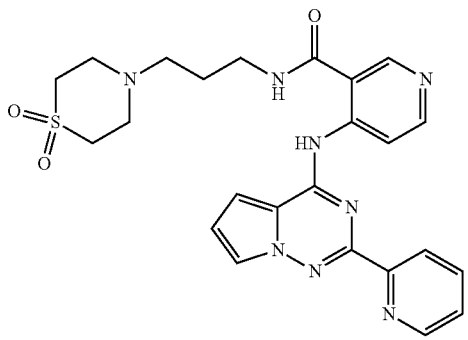 [SMILES: O=C(NCCCN1CCS(=O)(=O)CC1)c1cnccc1Nc1nc(-c2ccccn2)nn2cccc12]

Example 148 (6.3 mg, 16%) was synthesized employing the procedure described for Example 36 (Scheme 36): LCMS m/z 507 (M+H); rt 1.30 min; Conditions F. $^1$H NMR (DMSO-d6) δ 12.66 (s, 1H), 9.04-9.21 (m, 2H), 9.00 (s, 1H), 8.77 (br. s, 1H), 8.70 (d, J=5.5 Hz, 1H), 8.32 (d, J=7.9 Hz, 1H), 7.98-8.11 (m, 2H), 7.48-7.65 (m, 1H), 6.85-7.04 (m, 2H), 3.35-3.41 (m, 4H) overlapping with water of DMSO, 2.90-3.15 (m, 6H), 2.58 (t, J=6.9 Hz, 2H), 1.74 (quin, J=7.1 Hz, 2H).

Example 149

N-[3-(2-oxopyrrolidin-1-yl)propyl]-4-{[2-(pyridin-2-yl)pyrrolo[2,1-f][1,2,4]triazin-4-yl]amino}pyridine-3-carboxamide

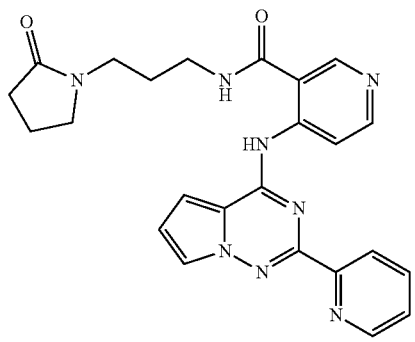 [SMILES: O=C(NCCCN1CCCC1=O)c1cnccc1Nc1nc(-c2ccccn2)nn2cccc12]

Example 149 (3.8 mg, 7%) was synthesized employing the procedure described for Example 36 (Scheme 36): LCMS m/z 457 (M+H); rt 1.34 min; Conditions F. $^1$H NMR (DMSO-d6) δ 12.60 (s, 1H), 9.04-9.18 (m, 2H), 8.99 (s, 1H), 8.77 (d, J=4.0 Hz, 1H), 8.69 (d, J=5.7 Hz, 1H), 8.32 (d, J=7.7 Hz, 1H), 7.98-8.09 (m, 2H), 7.52-7.62 (m, 1H), 6.88-7.02 (m, 2H), 3.41-3.50 (m, 2H), 3.23-3.40 (m, 4H), 2.23 (t, J=8.1 Hz, 2H), 1.88-2.00 (m, 2H), 1.78 (quin, J=6.9 Hz, 2H).

Example 150

4-{[2-(pyridin-2-yl)pyrrolo[2,1-f][1,2,4]triazin-4-yl]amino)}-N-[3-(pyrrolidin-1-yl)propyl]pyridine-3-carboxamide

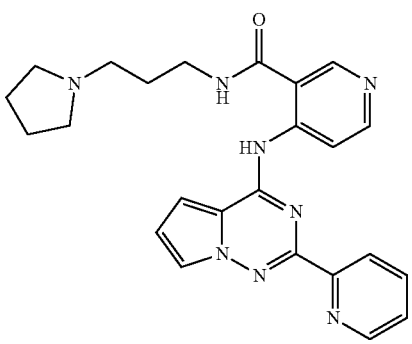 [SMILES: O=C(NCCCN1CCCC1)c1cnccc1Nc1nc(-c2ccccn2)nn2cccc12]

Example 150 (5.8 mg, 17%) was synthesized employing the procedure described for Example 36 (Scheme 36): LCMS m/z 443 (M+H); rt 1.11 min; Conditions F. $^1$H NMR (DMSO-d6) δ 9.05 (d, J=5.4 Hz, 1H), 8.96 (s, 1H), 8.77 (d, J=4.0 Hz, 1H), 8.68 (d, J=5.7 Hz, 1H), 8.32 (d, J=8.1 Hz, 1H), 7.98-8.10 (m, 2H), 7.52-7.61 (m, 1H), 6.88-7.00 (m, 2H), 3.35-3.54 (m, 2H), 2.55-2.61 (m, 6H) overlapping with DMSO peak, 1.65-1.85 (m, 6H)

Example 151

N-[2-(piperazin-1-yl)ethyl]-4-{[2-(pyridin-2-yl)pyrrolo[2,1-f][1,2,4]triazin-4-yl]amino}pyridine-3-carboxamide

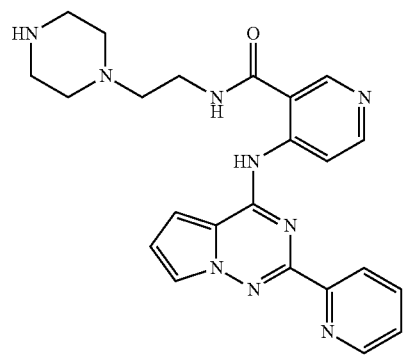 [SMILES: O=C(NCCN1CCNCC1)c1cnccc1Nc1nc(-c2ccccn2)nn2cccc12]

Example 151 (5.1 mg, 83%) was synthesized employing the procedure described for Example 36 (Scheme 36): LCMS m/z 444 (M+H); rt 1.04 min; Conditions F. $^1$H NMR (DMSO-d6) δ 9.37-9.47 (m, 1H), 9.22 (d, J=5.7 Hz, 1H), 9.04 (s, 1H), 8.78 (d, J=6.1 Hz, 2H), 8.38 (d, J=7.7 Hz, 1H), 8.03-8.19 (m, 2H), 7.56-7.69 (m, 1H), 6.93-7.07 (m, 2H), 3.54-3.73 (m, 2H), 3.13-3.34 (m, 7H); Some proton resonance signals were obscured due to solvent and presaturation peaks.

Example 152

4-{[2-(6-methylpyridin-2-yl)pyrrolo[2,1-f][1,2,4]triazin-4-yl]amino}-N-[2-(pyrrolidin-1-yl)ethyl]pyridine-3-carboxamide

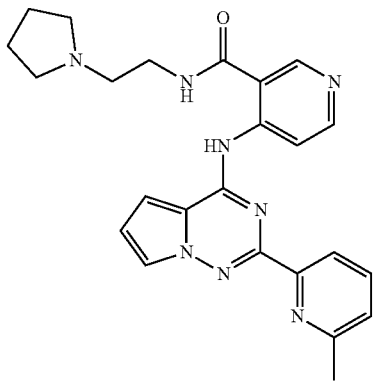 [SMILES: Cc1cccc(-c2nc(Nc3ccncc3C(=O)NCCN3CCCC3)c3cccn3n2)n1]

Example 152 (18.1 mg, 54%) was synthesized employing the procedure described for Example 36 (Scheme 36): LCMS m/z 443 (M+H); rt 0.72 min; Conditions F. $^1$H NMR (DMSO-d6) δ 8.94-9.13 (m, 2H), 8.69 (d, J=5.4 Hz, 1H), 8.13 (d, J=7.7 Hz, 1H), 8.07 (br. s, 1H), 7.90 (t, J=7.7 Hz, 1H), 7.41 (d, J=7.7 Hz, 1H), 6.84-7.00 (m, 2H), 2.52-2.76 (m, 11H), 1.70 (br. s, 4H).

Example 153

N-[2-(1,1-dioxo-1,4-thiomorpholin-4-yl)ethyl]-4-{[2-(6-methylpyridin-2-yl)pyrrolo[2,1-f][1,2,4]triazin-4-yl]amino}pyridine-3-carboxamide

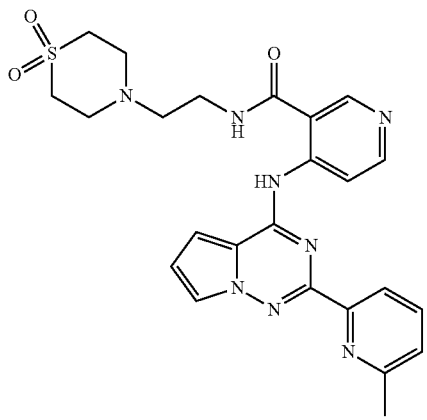 [SMILES: Cc1cccc(-c2nc(Nc3ccncc3C(=O)NCCN3CCS(=O)(=O)CC3)c3cccn3n2)n1]

Example 153 (20 mg, 14%) was synthesized employing the procedure described for Example 36 (Scheme 36): LCMS m/z 507.2 (M+H); rt 1.821 min; Conditions B. $^1$H NMR (400 MHz, DMSO-d6) δ 12.63-12.59 (m, 1H), 9.13-9.04 (m, 2H), 9.01-8.98 (m, 1H), 8.73-8.68 (m, 1H), 8.16-8.06 (m, 2H), 7.92-7.86 (m, 1H), 7.43-7.39 (m, 1H), 6.97-6.89 (m, 2H), 3.51-3.44 (m, 2H), 3.12-2.96 (m, 8H), 2.77-2.65 (m, 3H), 2.61 (s, 3H).

Example 154

N-[(4-hydroxy-1-methylpiperidin-4-yl)methyl]-4-{[2-(6-methylpyridin-2-yl)pyrrolo[2,1-f][1,2,4]triazin-4-yl]amino}pyridine-3-carboxamide

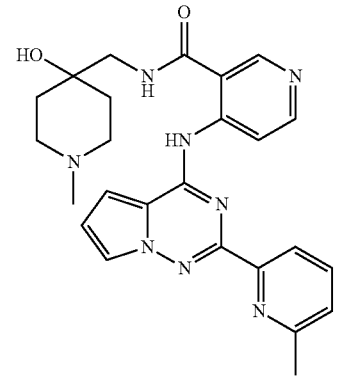 [SMILES: Cc1cccc(-c2nc(Nc3ccncc3C(=O)NCC3(O)CCN(C)CC3)c3cccn3n2)n1]

Example 154 (10.2 mg, 28%) was synthesized employing the procedure described for Example 36 (Scheme 36): LCMS m/z 473 (M+H); rt 1.11 min; Conditions F. $^1$H NMR (DMSO-d6) Shift: 8.95-9.09 (m, 2H), 8.66 (br. s, 1H), 7.98-8.22 (m, 2H), 7.89 (t, J=7.7 Hz, 1H), 7.41 (d, J=7.6 Hz, 1H), 6.83-6.99 (m, 2H), 3.37 (d, J=5.8 Hz, 1H), 2.60 (s, 3H), 2.33-2.46 (m, 2H), 2.25 (s, 3H), 1.46-1.75 (m, 4H); Some proton resonance signals were obscured due to solvent and presaturation peaks.

Example 155

4-{[2-(6-methylpyridin-2-yl)pyrrolo[2,1-f][1,2,4]triazin-4-yl]amino}-N-[2-(piperidin-1-yl)ethyl]pyridine-3-carboxamide

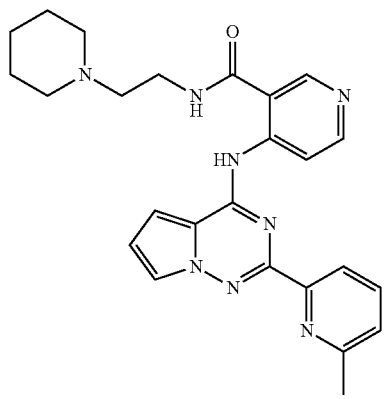 [SMILES: Cc1cccc(-c2nc(Nc3ccncc3C(=O)NCCN3CCCCC3)c3cccn3n2)n1]

Example 155 (19.9 mg, 59%) was synthesized employing the procedure described for Example 36 (Scheme 36): LCMS m/z 457 (M+H); rt 1.27 min; Conditions F. $^1$H NMR (DMSO-d6) δ 9.06 (br. s, 1H), 8.97 (s, 1H), 8.68 (br. s, 1H), 8.02-8.19 (m, 2H), 7.89 (t, J=7.7 Hz, 1H), 7.41 (d, J=7.7 Hz, 1H), 6.86-7.05 (m, 2H), 2.61 (s, 3H), 2.35-2.51 (m, 8H), 1.48 (d, J=5.0 Hz, 4H), 1.28-1.42 (m, 2H).

Example 156

N-(2-hydroxy-2-methylpropyl)-4-{[2-(6-methylpyridin-2-yl)pyrrolo[2,1-f][1,2,4]triazin-4-yl]amino}pyridine-3-carboxamide

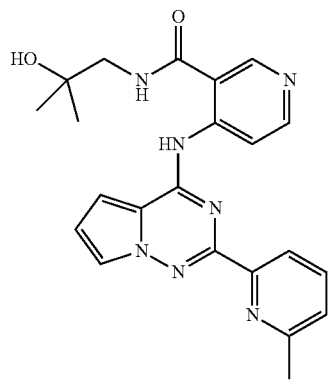 [SMILES: Cc1cccc(-c2nc(Nc3ccncc3C(=O)NCC(C)(C)O)c3cccn3n2)n1]

Example 156 (7 mg, 23%) was synthesized employing the procedure described for Example 36 (Scheme 36): LCMS m/z 418 (M+H); rt 1.45 min; Conditions F. $^1$H NMR (DMSO-d6) δ 12.43 (s, 1H), 8.92-9.18 (m, 3H), 8.70 (d, J=5.6 Hz, 1H), 8.14 (d, J=7.7 Hz, 1H), 8.06 (br. s, 1H), 7.90 (t, J=7.7 Hz, 1H), 7.42 (d, J=7.7 Hz, 1H), 6.82-7.01 (m, 2H), 2.61 (s, 3H), 2.55 (s, 2H), 1.16 (s, 6H).

Example 157

N-(1-hydroxy-2-methylpropan-2-yl)-4-{[2-(6-methylpyridin-2-yl)pyrrolo[2,1-f][1,2,4]triazin-4-yl]amino}pyridine-3-carboxamide

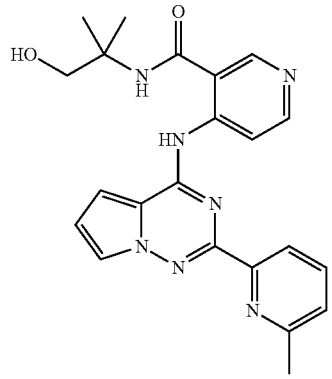 [SMILES: Cc1cccc(-c2nc(Nc3ccncc3C(=O)NC(C)(C)CO)c3cccn3n2)n1]

Example 157 (8.2 mg, 26%) was synthesized employing the procedure described for Example 36 (Scheme 36): LCMS m/z 418 (M+H); rt 1.52 min; Conditions F. $^1$H NMR (DMSO-d6) δ 12.05 (s, 1H), 8.86-8.99 (m, 2H), 8.67 (d, J=5.6 Hz, 1H), 8.21 (s, 1H), 8.13 (d, J=7.7 Hz, 1H), 8.06 (s, 1H), 7.89 (t, J=7.7 Hz, 1H), 7.40 (d, J=7.6 Hz, 1H), 6.87-7.03 (m, 2H), 2.60 (s, 3H), 1.33 (s, 6H), 0.93 (t, J=7.3 Hz, 1H); Some proton resonance signals were obscured due to solvent and presaturation peaks.

Example 158

N-[(2S)-2,3-dihydroxypropyl]-4-{[2-(6-methylpyridin-2-yl)pyrrolo[2,1-f][1,2,4]triazin-4-yl]amino}pyridine-3-carboxamide

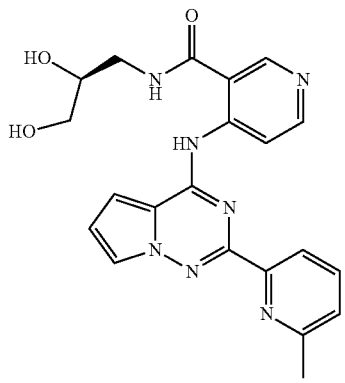 [SMILES: Cc1cccc(-c2nc(Nc3ccncc3C(=O)NC[C@H](O)CO)c3cccn3n2)n1]

Example 158 (9.2 mg, 31%) was synthesized employing the procedure described for Example 36 (Scheme 36): LCMS m/z 420 (M+H); rt 1.18 min; Conditions F. $^1$H NMR (DMSO-d6) δ 12.61 (s, 1H), 9.10 (t, J=5.8 Hz, 2H), 9.02 (s, 1H), 8.69 (d, J=5.7 Hz, 1H), 8.13 (d, J=7.7 Hz, 1H), 8.06 (br. s, 1H), 7.90 (t, J=7.7 Hz, 1H), 7.41 (d, J=7.7 Hz, 1H), 6.86-7.00 (m, 2H), 3.45-3.80 (m, 2H), 3.41 (d, J=5.3 Hz, 1H), 3.28 (dt, J=13.3, 6.6 Hz, 1H), 2.61 (s, 3H); Some proton resonance signals were obscured due to solvent and presaturation peaks.

Example 159

N-(3-hydroxypropyl)-4-{[2-(6-methylpyridin-2-yl)pyrrolo[2,1-f][1,2,4]triazin-4-yl]amino}pyridine-3-carboxamide

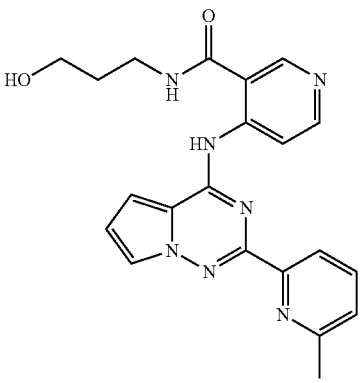 [SMILES: Cc1cccc(-c2nc(Nc3ccncc3C(=O)NCCCO)c3cccn3n2)n1]

Example 159 (4.1 mg, 9%) was synthesized employing the procedure described for Example 36 (Scheme 36): LCMS m/z 404 (M+H); rt 1.30 min; Conditions F. $^1$H NMR (DMSO-d6) δ 9.15-9.40 (m, J=4.6 Hz, 2H), 9.07 (s, 1H), 8.78 (d, J=6.0 Hz, 1H), 8.07-8.22 (m, 2H), 7.95 (t, J=7.7 Hz, 1H), 7.47 (d, J=7.7 Hz, 1H), 6.87-7.03 (m, 2H), 2.64 (s, 3H), 1.75 (quin, J=6.6 Hz, 2H); Some proton resonance signals were obscured due to solvent and presaturation peaks.

Example 160

N-[3-(4-methylpiperazin-1-yl)propyl]-4-{[2-(6-methylpyridin-2-yl)pyrrolo[2,1-f][1,2,4]triazin-4-yl]amino}pyridine-3-carboxamide

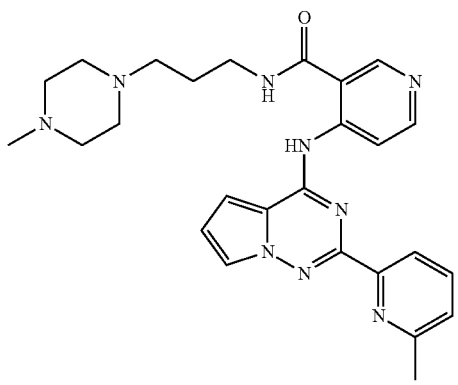 [SMILES: Cc1cccc(-c2nc(Nc3ccncc3C(=O)NCCCN3CCN(C)CC3)c3cccn3n2)n1]

Example 160 (6.9 mg, 23%) was synthesized employing the procedure described for Example 36 (Scheme 36): LCMS m/z 486 (M+H); rt 1.29 min; Conditions F. $^1$H NMR (DMSO-d6) δ 9.05 (d, J=4.2 Hz, 1H), 8.96 (s, 1H), 8.67 (d, J=5.6 Hz, 1H), 8.13 (d, J=7.7 Hz, 1H), 8.04 (br. s, 1H), 7.89 (t, J=7.7 Hz, 1H), 7.41 (d, J=7.7 Hz, 1H), 6.82-7.00 (m, 2H), 2.60 (s, 3H), 2.19-2.48 (m, 6H), 2.14 (s, 3H), 1.72 (quin, J=6.9 Hz, 2H). Some proton resonance signals were obscured due to solvent and presaturation peaks.

Example 161

4-{[2-(6-methylpyridin-2-yl)pyrrolo[2,1-f][1,2,4]triazin-4-yl]amino}-N-(oxolan-3-yl)pyridine-3-carboxamide

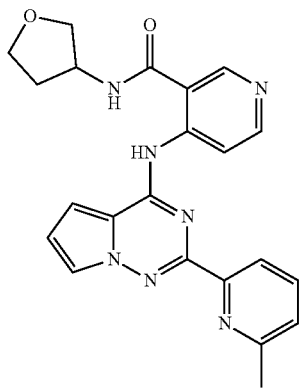 [SMILES: Cc1cccc(-c2nc(Nc3ccncc3C(=O)NC3CCOC3)c3cccn3n2)n1]

Example 161 (19.9 mg, 78%) was synthesized employing the procedure described for Example 36 (Scheme 36): LCMS m/z 416 (M+H); rt 1.48 min; Conditions F. $^1$H NMR (DMSO-d6) δ 9.04-9.38 (m, 3H), 8.77 (d, J=6.1 Hz, 1H), 8.08-8.24 (m, 2H), 7.95 (t, J=7.7 Hz, 1H), 7.47 (d, J=7.7 Hz, 1H), 6.99 (dd, J=19.9, 2.9 Hz, 2H), 4.54 (br. s, 1H), 3.64-3.97 (m, 5H), 2.64 (s, 3H), 2.11-2.30 (m, 1H), 1.91-2.02 (m, J=5.2 Hz, 1H). Some proton resonance signals were obscured due to solvent and presaturation peaks.

Example 162

N-[2-(dimethylamino)ethyl]-N-methyl-4-{[2-(6-methylpyridin-2-yl)pyrrolo[2,1-f][1,2,4]triazin-4-yl]amino}pyridine-3-carboxamide

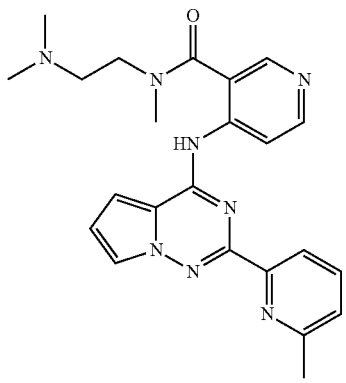 [SMILES: Cc1cccc(-c2nc(Nc3ccncc3C(=O)N(C)CCN(C)C)c3cccn3n2)n1]

Example 162 (9.2 mg, 34%) was synthesized employing the procedure described for Example 36 (Scheme 36): LCMS m/z 431 (M+H); rt 1.16 min; Conditions F. $^1$H NMR (DMSO-d6) δ 8.64 (d, J=5.6 Hz, 1H), 8.56 (s, 1H), 7.71-8.14 (m, 4H), 7.36 (d, J=7.3 Hz, 1H), 6.95-7.16 (m, 1H), 6.88 (br. s, 1H), 2.77-2.94 (m, 3H), 2.55 (s, 6H), 1.95-2.32 (m, 5H), 1.80 (br. s, 2H); Some proton resonance signals were obscured due to solvent and presaturation peaks.

Example 163

N-[2-(6-methylpyridin-2-yl)pyrrolo[2,1-f][1,2,4]triazin-4-yl]-3-(morpholine-4-carbonyl)pyridin-4-amine

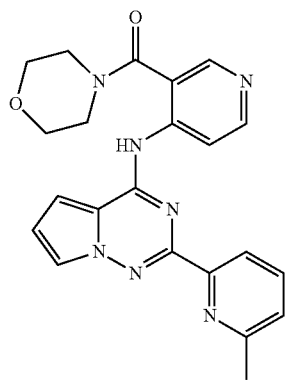 [SMILES: Cc1cccc(-c2nc(Nc3ccncc3C(=O)N3CCOCC3)c3cccn3n2)n1]

Example 163 (5.1 mg, 13%) was synthesized employing the procedure described for Example 36 (Scheme 36): LCMS m/z 416 (M+H); rt 1.23 min; Conditions F. $^1$H NMR (DMSO-d6) δ 8.68 (dd, J=9.9, 5.7 Hz, 1H), 8.63 (d, J=6.1 Hz, 1H), 7.97-8.27 (m, 3H), 7.86-7.96 (m, 1H), 7.44 (d, J=7.4 Hz, 1H), 7.07-7.13 (m, 1H), 6.92 (br. s, 1H), 2.83 (d, J=12.9 Hz, 2H), 2.60 (d, J=4.5 Hz, 2H), 2.55 (s, 3H). Some proton resonance signals were obscured due to solvent and presaturation peaks.

Example 164

4-{[2-(6-methylpyridin-2-yl)pyrrolo[2,1-f][1,2,4]triazin-4-yl]amino}-N-(oxan-4-yl)pyridine-3-carboxamide

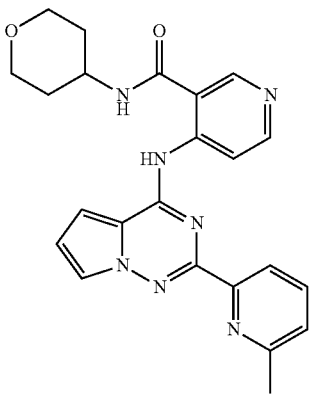 [SMILES: Cc1cccc(-c2nc(Nc3ccncc3C(=O)NC3CCOCC3)c3cccn3n2)n1]

Example 164 (8.8 mg, 21%) was synthesized employing the procedure described for Example 36 (Scheme 36): LCMS m/z 430 (M+H); rt 1.53 min; Conditions F. $^1$H NMR (DMSO-d6) δ 8.94-9.17 (m, 1H), 8.71 (d, J=5.6 Hz, 1H), 8.14 (d, J=7.7 Hz, 1H), 8.07 (br. s, 1H), 7.91 (t, J=7.7 Hz, 1H), 7.42 (d, J=7.7 Hz, 1H), 6.89-6.99 (m, 2H), 4.11 (br. s, 1H), 3.89 (d, J=9.9 Hz, 2H), 2.61 (s, 3H), 1.81 (d, J=10.7 Hz, 2H), 1.53-1.71 (m, 2H); Some proton resonance signals were obscured due to solvent and presaturation peaks.

Example 165

4-{[2-(6-methylpyridin-2-yl)pyrrolo[2,1-f][1,2,4]triazin-4-yl]amino}-N-(oxetan-3-yl)pyridine-3-carboxamide

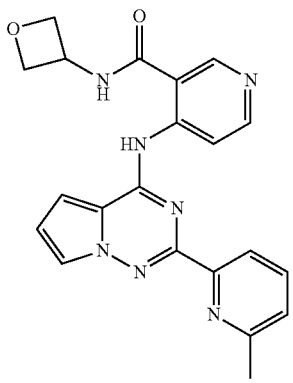 [SMILES: Cc1cccc(-c2nc(Nc3ccncc3C(=O)NC3COC3)c3cccn3n2)n1]

Example 165 (1.2 mg, 3%) was synthesized employing the procedure described for Example 36 (Scheme 36): LCMS m/z 402 (M+H); rt 1.39 min; Conditions F. $^1$H NMR (DMSO-d6) δ 9.04 (s, 1H), 8.42-8.96 (m, 2H), 8.10 (d, J=7.7 Hz, 1H), 7.76-8.00 (m, 2H), 7.37 (d, J=7.6 Hz, 1H), 6.83 (br. s, 2H), 5.02-5.23 (m, J=6.9, 6.9 Hz, 1H), 4.83 (t, J=6.9 Hz, 2H), 4.62 (t, J=6.2 Hz, 2H), 2.59 (s, 3H).

Example 166

4-{[2-(6-methylpyridin-2-yl)pyrrolo[2,1-f][1,2,4]triazin-4-yl]amino}-N-(propan-2-yl)pyridine-3-carboxamide

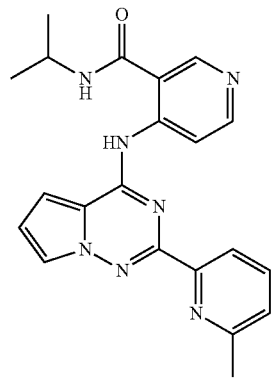 [SMILES: Cc1cccc(-c2nc(Nc3ccncc3C(=O)NC(C)C)c3cccn3n2)n1]

Example 166 (9 mg, 25%) was synthesized employing the procedure described for Example 36 (Scheme 36): LCMS m/z 388 (M+H); rt 1.70 min; Conditions F. $^1$H NMR (DMSO-d6) δ 9.16 (br. s, 1H), 8.93-9.07 (m, 2H), 8.73 (d, J=5.8 Hz, 1H), 8.15 (d, J=7.7 Hz, 1H), 8.09 (br. s, 1H), 7.93 (t, J=7.7 Hz, 1H), 7.45 (d, J=7.7 Hz, 1H), 6.89-7.02 (m, 2H), 4.12-4.29 (m, J=13.3, 6.6, 6.6, 6.6 Hz, 1H), 2.62 (s, 3H), 1.22 (d, J=6.6 Hz, 6H).

Example 167

4-({2-[6-(difluoromethyl)pyridin-2-yl]pyrrolo[2,1-f][1,2,4]triazin-4-yl}amino)-N-[2-(1,1-dioxo-1,4-thiomorpholin-4-yl)ethyl]pyridine-3-carboxamide

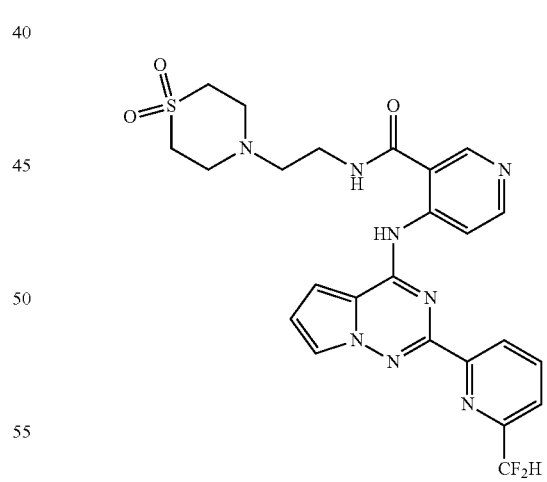

Example 167 (2.8 mg, 8%) was synthesized employing the procedure described for Example 37 (Scheme 37): LCMS m/z 419 (M+H); rt 1.02 min; Conditions G. $^1$H NMR (DMSO-d6) δ 8.90-9.22 (m, 1H), 8.68 (br. s, 1H), 8.48 (d, J=7.8 Hz, 1H), 8.22 (t, J=7.9 Hz, 1H), 8.07 (br. s, 1H), 7.85 (d, J=7.6 Hz, 1H), 6.82-7.29 (m, 3H), 3.07 (br. s, 4H), 2.98 (br. s, 4H), 2.71 (t, J=6.4 Hz, 2H); Some proton resonance signals were obscured due to solvent and presaturation peaks.

Example 168

4-({2-[6-(difluoromethyl)pyridin-2-yl]pyrrolo[2,1-f][1,2,4]triazin-4-yl}amino)-N-[3-(1,1-dioxo-1,4-thiomorpholin-4-yl)propyl]pyridine-3-carboxamide

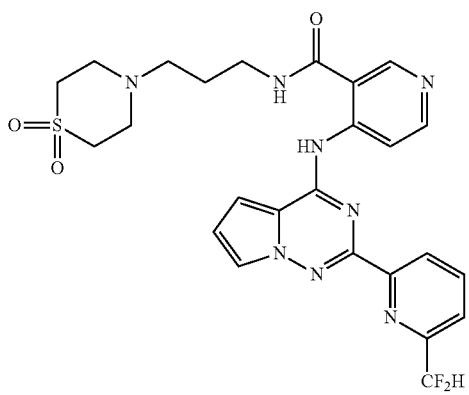 [SMILES: O=C(NCCCN1CCS(=O)(=O)CC1)c1cnccc1Nc1nc(-c2cccc(C(F)F)n2)nn2cccc12]

Example 168 (9.1 mg, 24%) was synthesized employing the procedure described for Example 37 (Scheme 37): LCMS m/z 557 (M+H); rt 0.94 min; Conditions G. $^1$H NMR (DMSO-d6) δ 9.11 (t, J=5.3 Hz, 1H), 9.05 (d, J=5.7 Hz, 1H), 8.97 (s, 1H), 8.68 (d, J=5.7 Hz, 1H), 8.48 (d, J=7.8 Hz, 1H), 8.22 (t, J=7.8 Hz, 1H), 8.07 (s, 1H), 7.86 (d, J=7.7 Hz, 1H), 6.88-7.25 (m, 3H), 3.25-3.48 (m, 2H), 3.07 (d, J=4.5 Hz, 4H), 2.90 (br. s, 4H), 1.72 (quin, J=7.0 Hz, 2H); Certain methylene proton signals were obscured by solvent and water peaks.

Example 169

N-[3-(morpholin-4-yl)propyl]-4-({2-[6-(trifluoromethyl)pyridin-2-yl]pyrrolo[2,1-f][1,2,4]triazin-4-yl}amino)pyridine-3-carboxamide

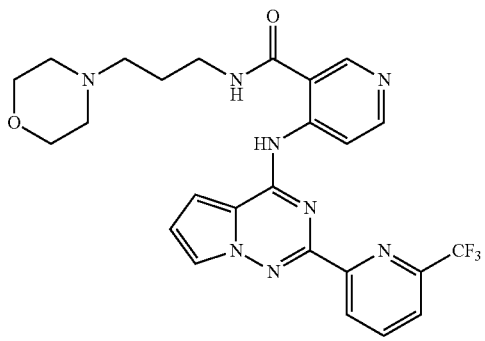 [SMILES: O=C(NCCCN1CCOCC1)c1cnccc1Nc1nc(-c2cccc(C(F)(F)F)n2)nn2cccc12]

Example 169 (2 mg, 3.8%) was synthesized employing the procedure described for Example 37 (Scheme 37): LCMS m/z 527.3 (M+H); rt 1.80 min; Conditions C. $^1$H NMR (400 MHz, DMSO-d6) δ 12.69-12.78 (m, 1H) 9.07-9.22 (m, 2H) 8.94-9.03 (m, 1H) 8.52-8.74 (m, 2H) 8.28-8.39 (m, 1H) 8.12-8.18 (m, 1H) 8.02-8.09 (m, 1H) 6.97-7.09 (m, 1H) 6.88-6.96 (m, 1H) 3.52-3.62 (m, 4H) 3.35-3.44 (m, 2H) 3.32 (s, 10H) 2.50 (t, J=2.01 Hz, 30H) 2.27-2.42 (m, 5H) 1.71-1.79 (m, 2H).

Example 170

N-[2-(pyrrolidin-1-yl)ethyl]-4-({2-[6-(trifluoromethyl)pyridin-2-yl]pyrrolo[2,1-f][1,2,4]triazin-4-yl}amino)pyridine-3-carboxamide

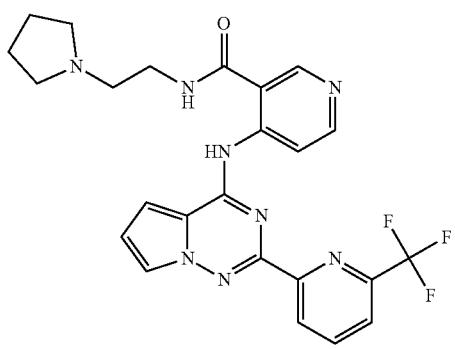 [SMILES: O=C(NCCN1CCCC1)c1cnccc1Nc1nc(-c2cccc(C(F)(F)F)n2)nn2cccc12]

Example 170 (7 mg, 9.4%) was synthesized employing the procedure described for Example 37 (Scheme 37): LCMS m/z 497.3 (M+H); rt 1.684 min; Conditions C. 1H NMR (400 MHz, DMSO-d6) δ 8.94-9.03 (m, 2H) 8.51-8.63 (m, 2H) 8.25-8.34 (m, 1H) 8.00-8.07 (m, 2H) 6.87-6.95 (m, 2H) 3.42-3.52 (m, 3H) 2.57-2.69 (m, 3H) 2.30-2.35 (m, 1H) 1.64-1.71 (m, 5H).

Example 171

N-[2-(piperidin-1-yl)ethyl]-4-({2-[6-(trifluoromethyl)pyridin-2-yl]pyrrolo[2,1-f][1,2,4]triazin-4-yl}amino)pyridine-3-carboxamide

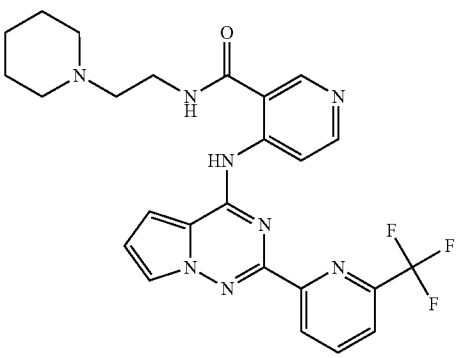 [SMILES: O=C(NCCN1CCCCC1)c1cnccc1Nc1nc(-c2cccc(C(F)(F)F)n2)nn2cccc12]

Example 171 (23 mg, 20%) was synthesized employing the procedure described for Example 37 (Scheme 37): LCMS m/z 511.2 (M+H); rt 3.162 min; Conditions E. HNMR (300 MHz, DMSO-d6) δ 9.37-9.47 (m, 1H) 9.22-9.26 (m, 1H) 8.76-8.82 (m, 1H) 8.59-8.64 (m, 1H) 8.28-8.38 (m, 1H) 8.20-8.25 (m, 1H) 8.04-8.13 (m, 1H) 6.99-7.11 (m, 2H) 3.70-3.80 (m, 2H) 3.57-3.64 (m, 2H) 3.53 (s, 19H) 3.27-3.36 (m, 2H) 2.87-3.03 (m, 2H) 2.47-2.57 (m, 25H) 1.64-1.91 (m, 5H).

Example 172

4-({2-[6-(difluoromethyl)pyridin-2-yl]pyrrolo[2,1-f][1,2,4]triazin-4-yl}amino)-N-(3-ethoxypropyl)pyridine-3-carboxamide

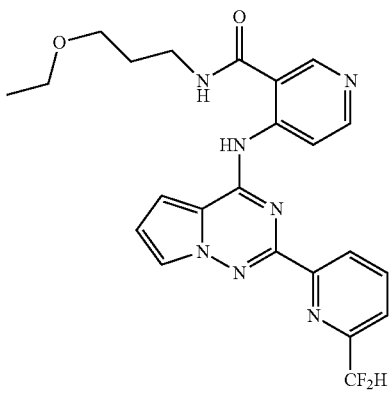 [SMILES: CCOCCCNC(=O)c1cnccc1Nc1nc(-c2cccc(C(F)F)n2)nn2cccc12]

Example 172 (3.3 mg, 12%) was synthesized employing the procedure described for Example 37 (Scheme 37): LCMS m/z 468 (M+H); rt 1.80 min; Conditions F. $^1$H NMR (DMSO-d6) δ 12.70 (s, 1H), 9.06-9.20 (m, 2H), 9.00 (s, 1H), 8.70 (d, J=5.7 Hz, 1H), 8.49 (d, J=7.8 Hz, 1H), 8.24 (t, J=7.8 Hz, 1H), 8.11 (s, 1H), 7.87 (d, J=7.7 Hz, 1H), 6.90-7.27 (m, 3H), 1.81 (quin, J=6.5 Hz, 2H), 1.12 (t, J=7.0 Hz, 3H); Certain aliphatic proton signals were obscured by solvent and water presaturation peaks.

Example 173

N-[2-(tert-butoxy)ethyl]-4-({2-[6-(difluoromethyl)pyridin-2-yl]pyrrolo[2,1-f][1,2,4]triazin-4-yl}amino)pyridine-3-carboxamide

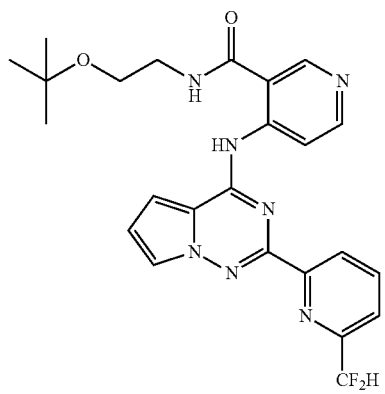 [SMILES: CC(C)(C)OCCNC(=O)c1cnccc1Nc1nc(-c2cccc(C(F)F)n2)nn2cccc12]

Example 173 (4.3 mg, 16%) was synthesized employing the procedure described for Example 37 (Scheme 37): LCMS m/z 482 (M+H); rt 1.95 min; Conditions F. $^1$H NMR (DMSO-d6) δ 9.13-9.32 (m, 2H), 9.02 (s, 1H), 8.74 (d, J=5.6 Hz, 1H), 8.49 (d, J=7.8 Hz, 1H), 8.24 (t, J=7.8 Hz, 1H), 8.13 (br. s, 1H), 7.87 (d, J=7.7 Hz, 1H), 6.90-7.32 (m, 3H), 1.14 (s, 9H); Certain methylene proton signals were obscured by water presaturation peak.

Example 174

4-({2-[6-(difluoromethyl)pyridin-2-yl]pyrrolo[2,1-f][1,2,4]triazin-4-yl}amino)-N-[2-(2-hydroxyethoxy)ethyl]pyridine-3-carboxamide

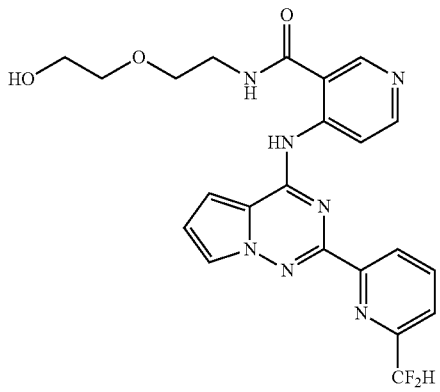 [SMILES: O=C(NCCOCCO)c1cnccc1Nc1nc(-c2cccc(C(F)F)n2)nn2cccc12]

Example 174 (11.3 mg, 44%) was synthesized employing the procedure described for Example 37 (Scheme 37): LCMS m/z 470 (M+H); rt 1.40 min; Conditions F. $^1$H NMR (DMSO-d6) δ 12.67 (s, 1H), 9.15-9.28 (m, 1H), 9.11 (d, J=5.7 Hz, 1H), 9.01 (s, 1H), 8.70 (d, J=5.6 Hz, 1H), 8.48 (d, J=7.9 Hz, 1H), 8.23 (t, J=7.8 Hz, 1H), 8.10 (s, 1H), 6.87-7.26 (m, 3H), 3.43-3.68 (m, 3H); Certain aliphatic proton signals were obscured by solvent and water presaturation peaks.

Example 175

4-({2-[6-(difluoromethyl)pyridin-2-yl]pyrrolo[2,1-f][1,2,4]triazin-4-yl}amino)-N-[(1S,2S)-2-hydroxycyclohexyl]pyridine-3-carboxamide

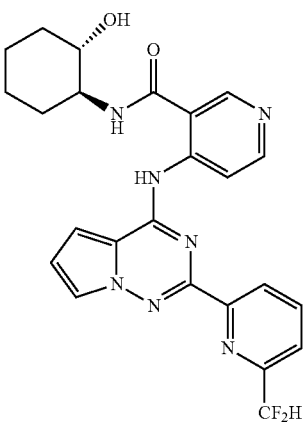 [SMILES: O=C(N[C@H]1CCCC[C@@H]1O)c1cnccc1Nc1nc(-c2cccc(C(F)F)n2)nn2cccc12]

Example 175 (6 mg, 23%) was synthesized employing the procedure described for Example 37 (Scheme 37): LCMS m/z 480 (M+H); rt 1.67 min; Conditions F. $^1$H NMR (DMSO-d6) δ 12.78 (s, 1H), 9.13 (d, J=5.7 Hz, 1H), 9.08 (s, 1H), 8.84 (d, J=8.2 Hz, 1H), 8.70 (d, J=5.6 Hz, 1H), 8.50 (d, J=7.9 Hz, 1H), 8.24 (t, J=7.8 Hz, 1H), 8.10 (s, 1H), 7.87 (d, J=7.7 Hz, 1H), 6.88-7.27 (m, 3H), 3.70-3.87 (m, J=9.3, 9.3, 9.3 Hz, 1H), 1.80-2.03 (m, 2H), 1.57-1.77 (m, 2H), 1.12-1.45 (m, 4H).

Example 176

4-({2-[6-(difluoromethyl)pyridin-2-yl]pyrrolo[2,1-f][1,2,4]triazin-4-yl}amino)-N-[3-(4-methylpiperazin-1-yl)propyl]pyridine-3-carboxamide

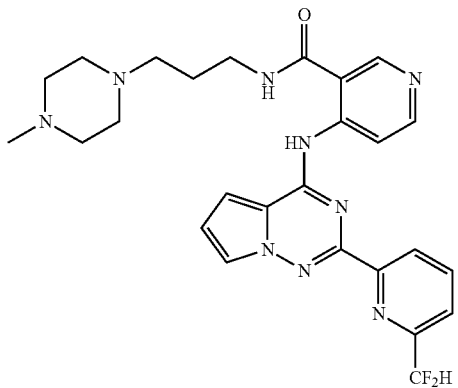 [SMILES: CN1CCN(CCCNC(=O)c2cnccc2Nc2nc(-c3cccc(C(F)F)n3)nn3cccc23)CC1]

Example 176 (15.4 mg, 54%) was synthesized employing the procedure described for Example 37 (Scheme 37): LCMS m/z 522 (M+H); rt 1.29 min; Conditions F. $^1$H NMR (DMSO-d6) Shift: 9.06 (d, J=5.6 Hz, 1H), 8.98 (s, 1H), 8.68 (d, J=5.6 Hz, 1H), 8.48 (d, J=7.9 Hz, 1H), 8.23 (t, J=7.8 Hz, 1H), 8.08 (br. s, 1H), 7.86 (d, J=7.7 Hz, 1H), 6.95-7.29 (m, 2H), 6.92 (d, J=3.9 Hz, 1H), 3.32-3.41 (m, 1H), 2.36 (t, J=6.9 Hz, 6H), 2.14 (s, 3H), 1.72 (quin, J=6.8 Hz, 2H); Certain aliphatic proton signals were obscured by solvent and water presaturation peaks.

Example 177

4-({2-[6-(difluoromethyl)pyridin-2-yl]pyrrolo[2,1-f][1,2,4]triazin-4-yl}amino)-N-(oxolan-3-yl)pyridine-3-carboxamide

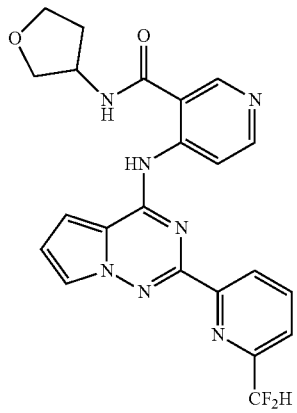 [SMILES: O=C(NC1CCOC1)c1cnccc1Nc1nc(-c2cccc(C(F)F)n2)nn2cccc12]

Example 177 (5.7 mg, 22%) was synthesized employing the procedure described for Example 37 (Scheme 37): LCMS m/z 452 (M+H); rt 1.58 min; Conditions F. $^1$H NMR (DMSO-d6) δ 9.16 (d, J=5.9 Hz, 1H), 8.94-9.06 (m, 2H), 8.69 (d, J=5.4 Hz, 1H), 8.48 (d, J=7.7 Hz, 1H), 8.22 (t, J=7.8 Hz, 1H), 8.09 (br. s, 1H), 7.86 (d, J=7.7 Hz, 1H), 6.86-7.27 (m, 3H), 4.53 (br. s, 1H), 3.80-3.96 (m, 2H), 3.59-3.79 (m, 1H), 2.10-2.26 (m, 1H), 1.96 (d, J=5.7 Hz, 1H); Certain aliphatic proton signals were obscured by water suppression peak.

Example 178

4-({2-[6-(difluoromethyl)pyridin-2-yl]pyrrolo[2,1-f][1,2,4]triazin-4-yl}amino)-N-(oxan-4-yl)pyridine-3-carboxamide

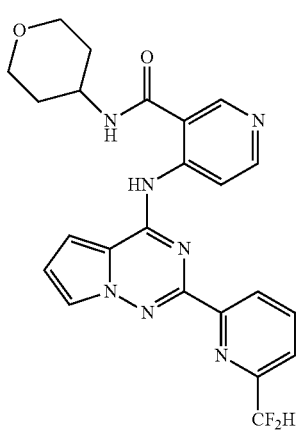 [SMILES: O=C(NC1CCOCC1)c1cnccc1Nc1nc(-c2cccc(C(F)F)n2)nn2cccc12]

Example 178 (3.6 mg, 14%) was synthesized employing the procedure described for Example 37 (Scheme 37): LCMS m/z 466 (M+H); rt 1.67 min; Conditions F. $^1$H NMR (DMSO-d6) δ 8.90-9.18 (m, 2H), 8.70 (d, J=5.2 Hz, 1H), 8.48 (d, J=7.7 Hz, 1H), 8.23 (t, J=7.7 Hz, 1H), 8.09 (br. s, 1H), 7.86 (d, J=7.6 Hz, 1H), 6.86-7.29 (m, 3H), 4.11 (br. s, 1H), 3.89 (d, J=9.3 Hz, 2H), 1.53-1.89 (m, 4H); Certain aliphatic proton signals were obscured by solvent and water presaturation peaks.

Example 179

N-[2-(1,1-dioxo-1,4-thiomorpholin-4-yl)ethyl]-4-({2-[6-(trifluoromethyl)pyridin-2-yl]pyrrolo[2,1-f][1,2,4]triazin-4-yl}amino)pyridine-3-carboxamide

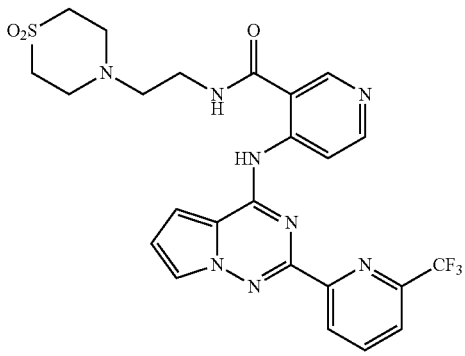 [SMILES: O=C(NCCN1CCS(=O)(=O)CC1)c1cnccc1Nc1nc(-c2cccc(C(F)(F)F)n2)nn2cccc12]

Example 179 (5 mg, 3.4%) was synthesized employing the procedure described for Example 37 (Scheme 37): LCMS m/z 561.2 (M+H); rt 2.405 min; Conditions E. $^1$H NMR (400 MHz, DMSO-d6) δ 12.63-12.74 (m, 1H) 8.95-

9.20 (m, 3H) 8.57-8.70 (m, 2H) 8.27-8.38 (m, 1H) 8.02-8.22 (m, 2H) 6.87-7.06 (m, 2H) 3.43-3.54 (m, 2H) 2.93-3.14 (m, 8H) 2.64-2.79 (m, 2H).

Example 180

4-({2-[6-(difluoromethyl)pyridin-2-yl]pyrrolo[2,1-f][1,2,4]triazin-4-yl}amino)-N-[(1R,2R)-2-hydroxycyclohexyl]pyridine-3-carboxamide

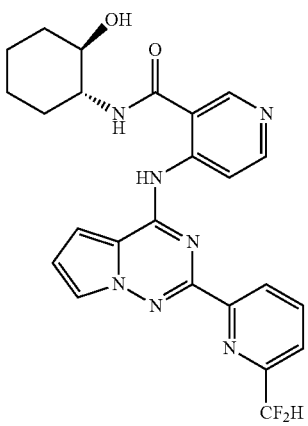 [SMILES: O=C(N[C@@H]1CCCC[C@H]1O)c1cnccc1Nc1nc(-c2cccc(C(F)F)n2)nn2cccc12]

Example 180 (2 mg, 7%) was synthesized employing the procedure described for Example 37 (Scheme 37): LCMS m/z 480 (M+H); rt 1.68 min; Conditions F. $^1$H NMR (DMSO-d6) δ 12.84 (s, 1H), 9.18 (d, J=5.8 Hz, 1H), 9.10 (s, 1H), 8.87 (d, J=8.2 Hz, 1H), 8.72 (d, J=5.8 Hz, 1H), 8.50 (d, J=7.9 Hz, 1H), 8.24 (t, J=7.8 Hz, 1H), 8.12 (s, 1H), 7.87 (d, J=7.7 Hz, 1H), 6.89-7.30 (m, 3H), 3.74-3.85 (m, J=8.7 Hz, 1H), 1.81-2.01 (m, 2H), 1.57-1.74 (m, 2H), 1.16-1.39 (m, 4H); One aliphatic proton peak was obscured by solvent peak.

Example 181

4-({2-[6-(difluoromethyl)pyridin-2-yl]pyrrolo[2,1-f][1,2,4]triazin-4-yl}amino)-N-(pyridin-2-ylmethyl)pyridine-3-carboxamide

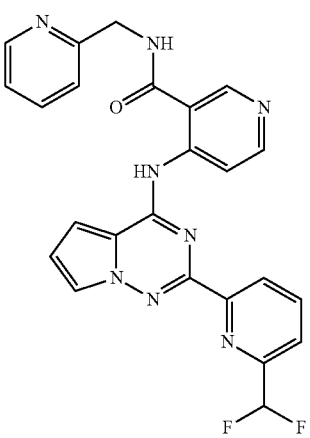 [SMILES: O=C(NCc1ccccn1)c1cnccc1Nc1nc(-c2cccc(C(F)F)n2)nn2cccc12]

Example 181 (3.5 mg, 28%) was synthesized employing the procedure described for Example 37 (Scheme 37): LCMS m/z 473.4 (M+H); rt 1.62 min; Conditions F. $^1$H NMR (500 MHz, DMSO-d6) δ 9.94 (t, J=5.4 Hz, 1H), 9.33 (d, J=6.1 Hz, 1H), 9.20 (s, 1H), 8.82 (d, J=6.3 Hz, 1H), 8.60 (d, J=4.7 Hz, 1H), 8.49 (d, J=7.9 Hz, 1H), 8.23 (t, J=7.9 Hz, 1H), 8.15 (s, 1H), 7.95-7.84 (m, 2H), 7.58 (d, J=7.9 Hz, 1H), 7.45-7.39 (m, 1H), 7.25 (d, J=7.2 Hz, 1H), 7.14 (d, J=11.0 Hz, 1H), 7.03-6.97 (m, 1H), 6.92 (d, J=3.6 Hz, 1H), 4.73 (d, J=5.6 Hz, 2H).

Example 182

4-({2-[6-(difluoromethyl)pyridin-2-yl]pyrrolo[2,1-f][1,2,4]triazin-4-yl}amino)-N-[(5-ethyl-1,3,4-oxadiazol-2-yl)methyl]pyridine-3-carboxamide

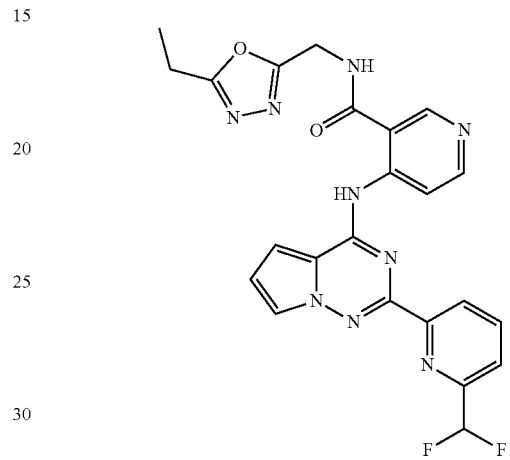

Example 182 (1.8 mg, 14%) was synthesized employing the procedure described for Example 37 (Scheme 37): LCMS m/z 492.3 (M+H); rt 1.55 min; Conditions F. $^1$H NMR (500 MHz, DMSO-d6) δ 9.84 (br. s, 1H), 9.06 (d, J=5.6 Hz, 1H), 9.03 (s, 1H), 8.72 (d, J=5.6 Hz, 1H), 8.47 (d, J=7.9 Hz, 1H), 8.22 (t, J=7.8 Hz, 1H), 8.10 (br. s, 1H), 7.86 (d, J=7.7 Hz, 1H), 7.11 (s, 1H), 7.03-6.94 (m, 2H), 6.91 (d, J=3.7 Hz, 1H), 4.76 (d, J=5.2 Hz, 2H), 2.83 (q, J=7.5 Hz, 2H), 1.23 (t, J=7.5 Hz, 4H).

Example 183

4-({2-[6-(difluoromethyl)pyridin-2-yl]pyrrolo[2,1-f][1,2,4]triazin-4-yl}amino)-N-(1,3-thiazol-2-ylmethyl)pyridine-3-carboxamide

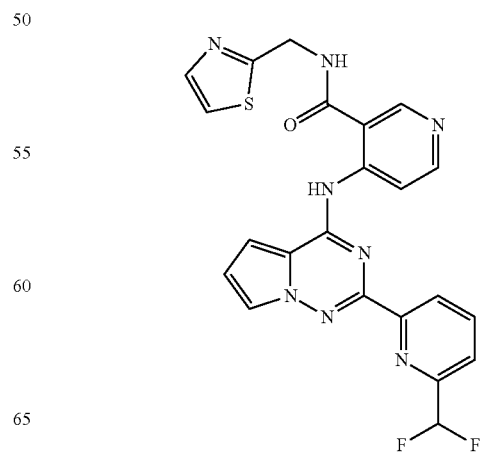

Example 183 (3.2 mg, 26%) was synthesized employing the procedure described for Example 37 (Scheme 37): LCMS m/z 479.0 (M+H); rt 1.34 min; Conditions G. ¹H NMR (500 MHz, DMSO-d6) δ 9.24 (br. s, 1H), 9.09 (s, 1H), 8.78 (d, J=5.8 Hz, 1H), 8.48 (d, J=7.7 Hz, 1H), 8.22 (t, J=7.8 Hz, 1H), 8.13 (br. s, 1H), 7.87 (d, J=7.7 Hz, 1H), 7.77 (d, J=2.9 Hz, 1H), 7.67 (d, J=2.9 Hz, 1H), 7.27 (s, 1H), 7.17 (s, 1H), 7.12 (s, 1H), 7.06 (s, 1H), 7.01 (br. s, 1H), 6.94 (br. s, 1H).

Example 184

4-({2-[6-(difluoromethyl)pyridin-2-yl]pyrrolo[2,1-f][1,2,4]triazin-4-yl}amino)-N-propylpyridine-3-carboxamide

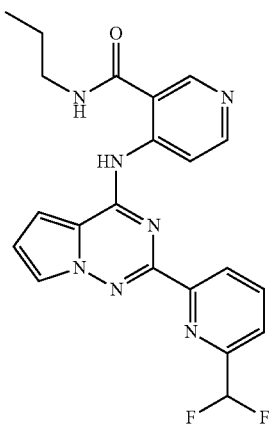 [SMILES: CCCNC(=O)c1cnccc1Nc1nc(-c2cccc(C(F)F)n2)nn2cccc12]

Example 184 (7.5 mg, 45%) was synthesized employing the procedure described for Example 37 (Scheme 37): LCMS m/z 424.2 (M+H); rt 1.83 min; Conditions F. ¹H NMR (500 MHz, DMSO-d6) δ 9.19-9.06 (m, 2H), 9.00 (br. s, 1H), 8.70 (d, J=5.1 Hz, 1H), 8.49 (d, J=7.7 Hz, 1H), 8.23 (t, J=7.4 Hz, 1H), 8.09 (br. s, 1H), 7.86 (d, J=7.5 Hz, 1H), 6.98 (br. s, 1H), 6.94 (br. s, 1H), 3.31 (d, J=6.3 Hz, 2H), 1.68-1.48 (m, 2H), 0.93 (t, J=7.1 Hz, 3H).

Example 185

1-[4-({2-[6-(difluoromethyl)pyridin-2-yl]pyrrolo[2,1-f][1,2,4]triazin-4-yl}amino)pyridine-3-carbonyl]-4-phenylpiperidin-4-ol

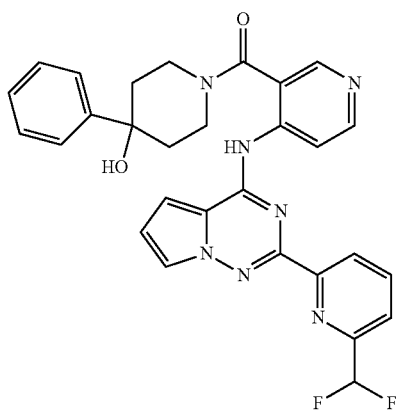 [SMILES: O=C(c1cnccc1Nc1nc(-c2cccc(C(F)F)n2)nn2cccc12)N1CCC(O)(c2ccccc2)CC1]

Example 185 (1.5 mg, 11%) was synthesized employing the procedure described for Example 37 (Scheme 37): LCMS m/z 542.1 (M+H); rt 1.4 min; Conditions G.

Example 186

N-{2-[6-(difluoromethyl)pyridin-2-yl]pyrrolo[2,1-f][1,2,4]triazin-4-yl}-3-(pyrrolidine-1-carbonyl)pyridin-4-amine

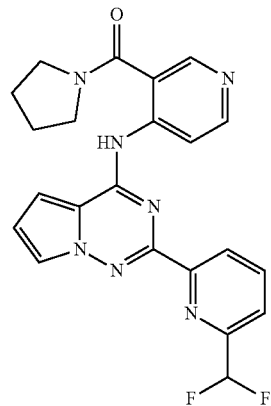 [SMILES: O=C(c1cnccc1Nc1nc(-c2cccc(C(F)F)n2)nn2cccc12)N1CCCC1]

Example 186 (7.5 mg, 44%) was synthesized employing the procedure described for Example 37 (Scheme 37): LCMS m/z 436.2 (M+H); rt 1.58 min; Conditions F. ¹H NMR (500 MHz, DMSO-d6) δ 8.60-8.87 (m, 2H), 8.32-8.52 (m, 2H), 8.19 (t, J=7.7 Hz, 1H), 8.07 (br. s., 1H), 7.84 (d, J=7.7 Hz, 1H), 6.86-7.32 (m, 3H), 3.20-3.59 (m, 4H), 1.62-1.81 (m, 2H), 1.45-1.59 (m, J=6.1 Hz, 2H).

Example 187

4-({2-[6-(difluoromethyl)pyridin-2-yl]pyrrolo[2,1-f][1,2,4]triazin-4-yl}amino)-N-(3-hydroxy-3-methylbutyl)pyridine-3-carboxamide

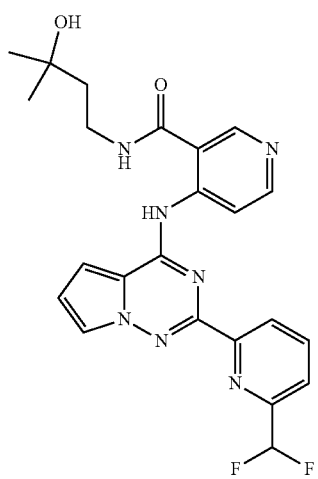 [SMILES: CC(C)(O)CCNC(=O)c1cnccc1Nc1nc(-c2cccc(C(F)F)n2)nn2cccc12]

Example 187 (4.6 mg, 25%) was synthesized employing the procedure described for Example 37 (Scheme 37): LCMS m/z 468.3 (M+H); rt 1.28 min; Conditions G. ¹H NMR (500 MHz, DMSO-d6) δ 12.76 (s, 1H), 9.03-9.17 (m, 3H), 8.97 (s, 1H), 8.69 (d, J=5.6 Hz, 1H), 8.48 (d, J=7.8 Hz, 1H), 8.23 (t, J=7.8 Hz, 1H), 8.10 (br. s., 1H), 7.86 (d, J=7.7 Hz, 1H), 6.90-7.28 (m, 3H), 1.64-1.76 (m, 2H), 1.17 (s, 6H); methylene proton signal was obscured by solvent presaturation and water signals.

Example 188

4-({2-[6-(difluoromethyl)pyridin-2-yl]pyrrolo[2,1-f][1,2,4]triazin-4-yl}amino)-N-(2-hydroxy-2-methylpropyl)pyridine-3-carboxamide

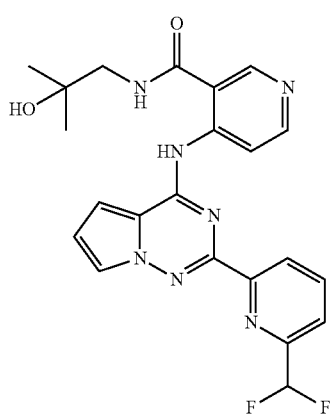 [SMILES: CC(C)(O)CNC(=O)c1cnccc1Nc1nc(-c2cccc(C(F)F)n2)nn2cccc12]

Example 188 (5.3 mg, 30%) was synthesized employing the procedure described for Example 37 (Scheme 37): LCMS m/z 454.3 (M+H); rt 1.27 min; Conditions G. ¹H NMR (500 MHz, DMSO-d6) δ 9.11-9.02 (m, 2H), 8.99 (br. s, 1H), 8.70 (d, J=5.5 Hz, 1H), 8.49 (d, J=7.7 Hz, 1H), 8.23 (t, J=7.7 Hz, 1H), 8.09 (br. s, 1H), 7.86 (d, J=7.6 Hz, 1H), 7.02-6.94 (m, 1H), 6.90 (br. s, 1H), 4.68 (br. s, 1H), 3.48 (br. s, 1H), 3.45-3.38 (m, 2H), 3.34 (d, J=5.8 Hz, 1H), 1.16 (s, 6H).

Example 189

3-(azetidine-1-carbonyl)-N-{2-[6-(difluoromethyl)pyridin-2-yl]pyrrolo[2,1-f][1,2,4]triazin-4-yl}pyridin-4-amine

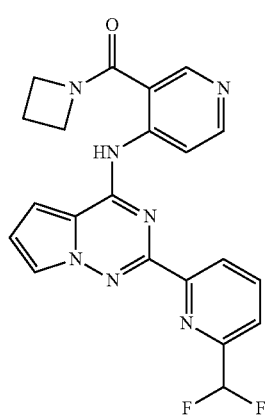 [SMILES: O=C(c1cnccc1Nc1nc(-c2cccc(C(F)F)n2)nn2cccc12)N1CCC1]

Example 189 (2.6 mg, 16%) was synthesized employing the procedure described for Example 37 (Scheme 37):

LCMS m/z 422.2 (M+H); rt 1.21 min; Conditions G. ¹H NMR (500 MHz, DMSO-d6) δ 8.78 (br. s, 1H), 8.72-8.64 (m, 2H), 8.45 (d, J=7.8 Hz, 1H), 8.22 (t, J=7.7 Hz, 1H), 8.08 (br. s, 1H), 7.86 (d, J=7.7 Hz, 1H), 6.98 (s, 2H), 4.42 (br. s, 2H), 4.06 (br. s, 2H), 2.15-2.04 (m, 2H).

Example 190

Ethyl 2-{[4-({2-[6-(difluoromethyl)pyridin-2-yl]pyrrolo[2,1-f][1,2,4]triazin-4-yl}amino)pyridin-3-yl]formamido}acetate

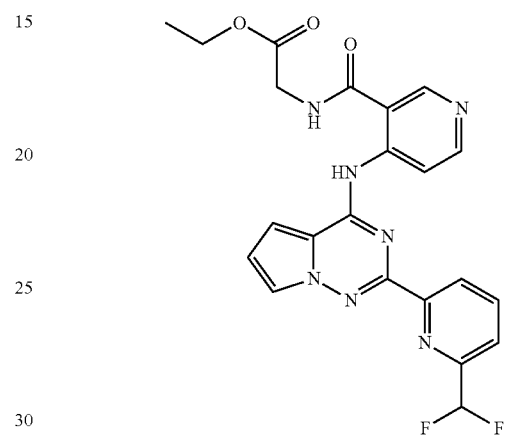

Example 190 (2.3 mg, 12%) was synthesized employing the procedure described for Example 37 (Scheme 37): LCMS m/z 468 (M+H); rt 1.73 min; Conditions F. ¹H NMR (500 MHz, DMSO-d6) δ 9.65 (br. s, 1H), 9.17 (d, J=5.7 Hz, 1H), 9.05 (s, 1H), 8.74 (d, J=5.7 Hz, 1H), 8.49 (d, J=7.9 Hz, 1H), 8.24 (t, J=7.8 Hz, 1H), 8.11 (br. s, 1H), 7.87 (d, J=7.7 Hz, 1H), 7.12 (s, 1H), 7.03-6.94 (m, 1H), 6.91 (d, J=3.7 Hz, 1H), 4.22-4.04 (m, 4H), 1.23 (t, J=7.1 Hz, 3H).

Example 191

4-({2-[6-(difluoromethyl)pyridin-2-yl]pyrrolo[2,1-f][1,2,4]triazin-4-yl}amino)-N-(1H-1,2,4-triazol-3-ylmethyl)pyridine-3-carboxamide

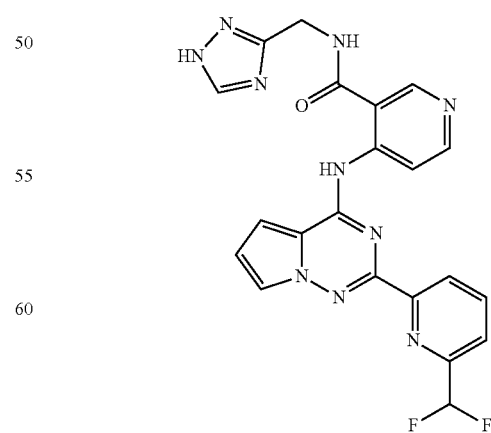

Example 191 (2.7 mg, 15%) was synthesized employing the procedure described for Example 37 (Scheme 37):

LCMS m/z 463.2 (M+H); rt 1.05 min; Conditions G. ¹H NMR (500 MHz, DMSO-d6) δ 9.88 (br. s, 1H), 9.33 (d, J=5.4 Hz, 1H), 9.14 (br. s, 1H), 8.80 (d, J=5.7 Hz, 1H), 8.50 (d, J=7.7 Hz, 1H), 8.30 (br. s, 1H), 8.24 (t, J=7.8 Hz, 1H), 8.15 (br. s, 1H), 7.88 (d, J=7.6 Hz, 1H), 7.25 (br. s, 1H), 7.14 (d, J=6.8 Hz, 1H), 7.08-6.98 (m, 2H), 6.95 (d, J=3.4 Hz, 1H), 4.68 (d, J=5.3 Hz, 2H).

Example 192

4-({2-[6-(difluoromethyl)pyridin-2-yl]pyrrolo[2,1-f][1,2,4]triazin-4-yl}amino)-N-(2-hydroxyethyl)pyridine-3-carboxamide

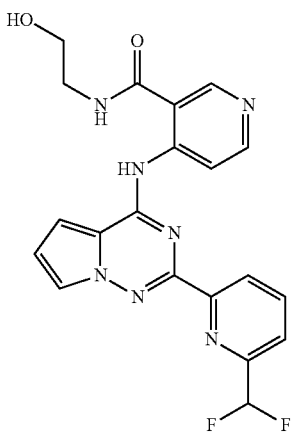 [SMILES: O=C(NCCO)c1cnccc1Nc1nc(-c2cccc(C(F)F)n2)nn2cccc12]

Example 192 (7.7 mg, 46%) was synthesized employing the procedure described for Example 37 (Scheme 37): LCMS m/z 426.2 (M+H); rt 1.36 min; Conditions F. ¹H NMR (500 MHz, DMSO-d6) δ 9.28 (s, 1H), 9.32 (s, 1H), 9.09 (s, 1H), 8.78 (d, J=6.1 Hz, 1H), 8.49 (d, J=7.8 Hz, 1H), 8.23 (t, J=7.8 Hz, 1H), 8.14 (br. s, 1H), 7.88 (d, J=7.7 Hz, 1H), 7.24 (d, J=14.1 Hz, 1H), 7.19-6.99 (m, 3H), 6.96 (d, J=4.0 Hz, 1H), 3.65-3.49 (m, 2H), 3.44 (d, J=5.6 Hz, 1H), 1.84 (br. s, 1H).

Example 193

N-cyclobutyl-4-({2-[6-(difluoromethyl)pyridin-2-yl]pyrrolo[2,1-f][1,2,4]triazin-4-yl}amino)pyridine-3-carboxamide

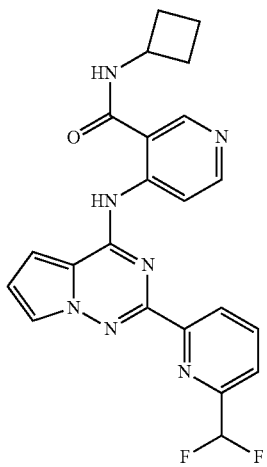 [SMILES: O=C(NC1CCC1)c1cnccc1Nc1nc(-c2cccc(C(F)F)n2)nn2cccc12]

Example 193 (3.5 mg, 20%) was synthesized employing the procedure described for Example 37 (Scheme 37): LCMS m/z 436 (M+H); rt 1.89 min; Conditions F. ¹H NMR (500 MHz, DMSO-d6) δ 9.36 (d, J=6.2 Hz, 1H), 9.23 (d, J=5.0 Hz, 1H), 9.09 (s, 1H), 8.76 (d, J=5.9 Hz, 1H), 8.48 (d, J=8.0 Hz, 1H), 8.23 (t, J=7.8 Hz, 1H), 8.13 (br. s, 1H), 7.87 (d, J=7.7 Hz, 1H), 7.12 (s, 1H), 7.01 (br. s, 1H), 6.94 (d, J=3.7 Hz, 1H), 4.57-4.42 (m, 1H), 2.26 (br. s, 2H), 2.12 (t, J=10.0 Hz, 2H), 1.79-1.67 (m, 2H).

Example 194

4-({2-[6-(difluoromethyl)pyridin-2-yl]pyrrolo[2,1-f][1,2,4]triazin-4-yl}amino)-N-(propan-2-yl)pyridine-3-carboxamide

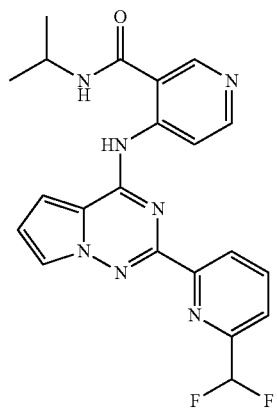 [SMILES: CC(C)NC(=O)c1cnccc1Nc1nc(-c2cccc(C(F)F)n2)nn2cccc12]

Example 194 (1.8 mg, 11%) was synthesized employing the procedure described for Example 37 (Scheme 37): LCMS m/z 424.4 (M+H); rt 1.82 min; Conditions F. ¹H NMR (500 MHz, DMSO-d6) δ 9.17 (d, J=5.6 Hz, 1H), 9.05 (br. s, 1H), 8.97 (d, J=7.0 Hz, 1H), 8.74 (d, J=5.2 Hz, 1H), 8.50 (d, J=7.9 Hz, 1H), 8.24 (t, J=7.8 Hz, 1H), 8.13 (br. s, 1H), 7.87 (d, J=7.7 Hz, 1H), 7.13 (s, 1H), 7.05-6.98 (m, 1H), 6.95 (d, J=3.6 Hz, 1H), 4.28-4.14 (m, 1H), 1.22 (d, J=6.5 Hz, 6H).

Example 195

4-({2-[6-(difluoromethyl)pyridin-2-yl]pyrrolo[2,1-f][1,2,4]triazin-4-yl}amino)-N-(1,3-oxazol-4-ylmethyl)pyridine-3-carboxamide

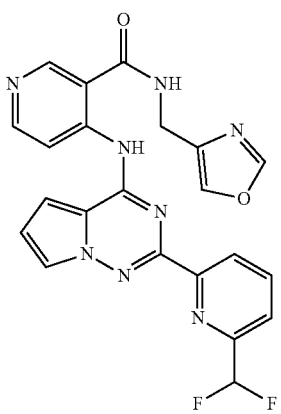 [SMILES: O=C(NCc1cocn1)c1cnccc1Nc1nc(-c2cccc(C(F)F)n2)nn2cccc12]

Example 195 (3.6 mg, 20%) was synthesized employing the procedure described for Example 37 (Scheme 37):

LCMS m/z 463.2 (M+H); rt 1.53 min; Conditions F. ¹H NMR (500 MHz, DMSO-d6) δ 12.58 (s, 1H), 9.62 (br. s, 1H), 9.10 (d, J=5.6 Hz, 1H), 9.04 (s, 1H), 8.69 (d, J=5.6 Hz, 1H), 8.48 (d, J=7.8 Hz, 1H), 8.35 (s, 1H), 8.22 (t, J=7.8 Hz, 1H), 8.10 (d, J=8.9 Hz, 2H), 7.86 (d, J=7.7 Hz, 1H), 7.11 (s, 1H), 7.04-6.87 (m, 2H), 4.47 (d, J=5.1 Hz, 2H).

Example 196 tert-butyl 2-{[4-({2-[6-(difluoromethyl)pyridin-2-yl]pyrrolo[2,1-f][1,2,4]triazin-4-yl}amino)pyridin-3-yl]formamido}acetate

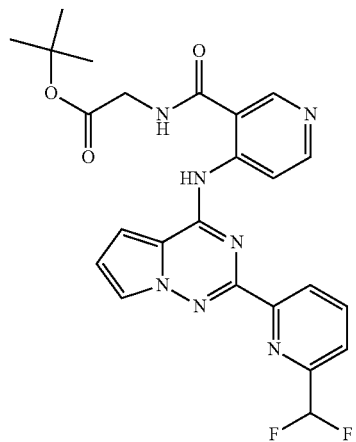 [SMILES: CC(C)(C)OC(=O)CNC(=O)c1cnccc1Nc1nc(-c2cccc(C(F)F)n2)nn2cccc12]

Example 196 (2.6 mg, 13%) was synthesized employing the procedure described for Example 37 (Scheme 37): LCMS m/z 496.1 (M+H); rt 1.59 min; Conditions G. 1HNMR (500 MHz, DMSO), 9.00 (s, 1H), 8.71 (d, J=5.1 Hz, 1H), 8.48 (d, J=7.7 Hz, 1H), 8.22 (t, J=7.8 Hz, 1H), 8.07 (br. s, 1H), 7.86 (d, J=7.7 Hz, 1H), 7.10 (s, 1H), 7.01-6.91 (m, 1H), 6.88 (d, J=3.5 Hz, 1H), 3.99 (d, J=5.3 Hz, 2H), 1.91 (s, 1H), 1.43 (s, 9H).

Example 197

4-({2-[6-(difluoromethyl)pyridin-2-yl]pyrrolo[2,1-f][1,2,4]triazin-4-yl}amino)-N-(1H-pyrazol-5-ylmethyl)pyridine-3-carboxamide

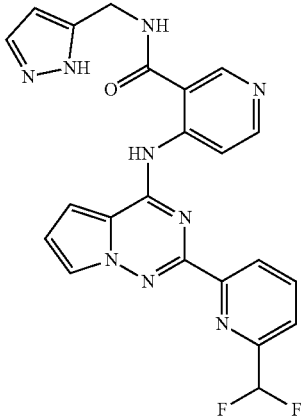 [SMILES: O=C(NCc1ccn[nH]1)c1cnccc1Nc1nc(-c2cccc(C(F)F)n2)nn2cccc12]

Example 197 (2.1 mg, 12%) was synthesized employing the procedure described for Example 37 (Scheme 37):

LCMS m/z 462 (M+H); rt 1.51 min; Conditions F. ¹H NMR (500 MHz, DMSO-d6) δ 9.66 (br. s, 1H), 9.17 (d, J=5.4 Hz, 1H), 9.04 (s, 1H), 8.71 (d, J=5.6 Hz, 1H), 8.48 (d, J=7.7 Hz, 1H), 8.22 (t, J=7.8 Hz, 1H), 8.09 (br. s, 1H), 7.86 (d, J=7.7 Hz, 1H), 7.60 (s, 1H), 6.99 (br. s, 1H), 6.95 (br. s, 1H), 6.26 (s, 1H), 4.56 (d, J=5.4 Hz, 2H).

Example 198

4-({2-[6-(difluoromethyl)pyridin-2-yl]pyrrolo[2,1-f][1,2,4]triazin-4-yl}amino)-N-[(1R,2S)-2-hydroxycyclopentyl]pyridine-3-carboxamide

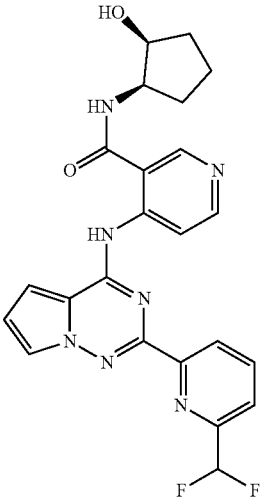 [SMILES: O=C(N[C@@H]1CCC[C@@H]1O)c1cnccc1Nc1nc(-c2cccc(C(F)F)n2)nn2cccc12]

Example 198 (4.6 mg, 25%) was synthesized employing the procedure described for Example 37 (Scheme 37): LCMS m/z 466.4 (M+H); rt 1.66 min; Conditions F.

Example 199

4-({2-[6-(difluoromethyl)pyridin-2-yl]pyrrolo[2,1-f][1,2,4]triazin-4-yl}amino)-N-[(1S,2S)-2-hydroxycyclopentyl]pyridine-3-carboxamide

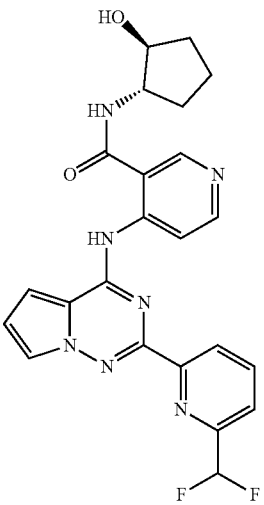 [SMILES: O=C(N[C@H]1CCC[C@@H]1O)c1cnccc1Nc1nc(-c2cccc(C(F)F)n2)nn2cccc12]

Example 199 (1.7 mg, 9%) was synthesized employing the procedure described for Example 37 (Scheme 37):

LCMS m/z 466.1 (M+H); rt 1.28 min; Conditions G. ¹H NMR (500 MHz, DMSO-d6) δ 9.01 (s, 2H), 8.66 (br. s, 1H), 8.48 (d, J=7.8 Hz, 1H), 8.22 (t, J=7.7 Hz, 1H), 8.07 (br. s, 1H), 7.85 (d, J=7.6 Hz, 1H), 7.11 (s, 1H), 6.98 (d, J=19.2 Hz, 1H), 6.91 (br. s, 1H), 4.17-4.08 (m, 1H), 4.05 (br. s, 1H), 2.04 (dd, J=13.0, 5.4 Hz, 1H), 1.94-1.81 (m, 1H), 1.76-1.61 (m, 2H), 1.59-1.43 (m, 2H).

Example 200

1-[4-({2-[6-(difluoromethyl)pyridin-2-yl]pyrrolo[2,1-f][1,2,4]triazin-4-yl}amino)pyridine-3-carbonyl]piperidin-4-ol

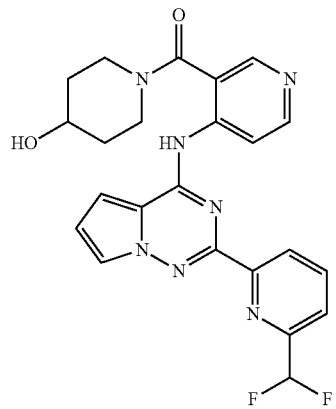 [SMILES: O=C(c1cnccc1Nc1nc(-c2cccc(C(F)F)n2)nn2cccc12)N1CCC(O)CC1]

Example 200 (1.9 mg, 10%) was synthesized employing the procedure described for Example 37 (Scheme 37): LCMS m/z 466.1 (M+H); rt 1.03 min; Conditions G. ¹H NMR (500 MHz, DMSO-d6) δ 8.72 (d, J=5.6 Hz, 1H), 8.67 (s, 1H), 8.38 (d, J=7.9 Hz, 2H), 8.18 (t, J=7.7 Hz, 1H), 8.10 (br. s., 1H), 7.84 (d, J=7.7 Hz, 1H), 6.91-7.30 (m, 3H), 2.94-3.23 (m, 2H), 1.46-1.78 (m, 2H), 1.14-1.43 (m, 2H); Certain aliphatic proton signals were obscured by solvent and water signals.

Example 201

N-(4,4-difluorocyclohexyl)-4-({2-[6-(difluoromethyl)pyridin-2-yl]pyrrolo[2,1-f][1,2,4]triazin-4-yl}amino)pyridine-3-carboxamide

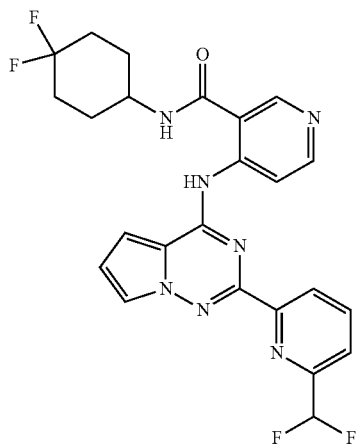 [SMILES: O=C(NC1CCC(F)(F)CC1)c1cnccc1Nc1nc(-c2cccc(C(F)F)n2)nn2cccc12]

Example 201 (1.6 mg, 8%) was synthesized employing the procedure described for Example 37 (Scheme 37): LCMS m/z 500.3 (M+H); rt 1.96 min; Conditions F. ¹H NMR (500 MHz, DMSO-d6) δ 9.25 (br. s, 1H), 9.14-9.00 (m, 2H), 8.79 (d, J=5.4 Hz, 1H), 8.48 (d, J=7.8 Hz, 1H), 8.23 (t, J=7.8 Hz, 1H), 8.15 (br. s, 1H), 7.88 (d, J=7.7 Hz, 1H), 7.14 (s, 1H), 7.03 (br. s, 1H), 6.95 (d, J=3.7 Hz, 1H), 4.12 (br. s, 1H), 2.09 (br. s, 2H), 2.02 (d, J=17.9 Hz, 2H), 1.95 (d, J=10.9 Hz, 3H), 1.84 (br. s, 1H), 1.68 (d, J=11.5 Hz, 2H).

Example 202

4-({2-[6-(difluoromethyl)pyridin-2-yl]pyrrolo[2,1-f][1,2,4]triazin-4-yl}amino)-N-(3,3,3-trifluoropropyl)pyridine-3-carboxamide

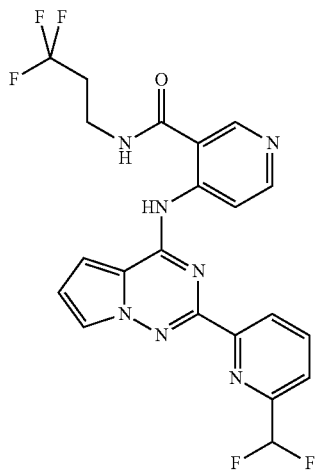 [SMILES: O=C(NCCC(F)(F)F)c1cnccc1Nc1nc(-c2cccc(C(F)F)n2)nn2cccc12]

Example 202 (1.5 mg, 8%) was synthesized employing the procedure described for Example 37 (Scheme 37): LCMS m/z 478.2 (M+H); rt 1.88 min; Conditions F. ¹H NMR (500 MHz, DMSO-d6) δ 9.44 (br. s, 1H), 9.22 (br. s, 1H), 9.02 (br. s, 1H), 8.77 (br. s, 1H), 8.48 (d, J=7.7 Hz, 1H), 8.23 (t, J=7.8 Hz, 1H), 8.14 (br. s, 1H), 7.87 (d, J=7.7 Hz, 1H), 7.14 (s, 1H), 7.01 (br. s, 1H), 6.97 (br. s, 1H), 2.70-2.57 (m, 2H), 1.86 (br. s, 1H).

Example 203

N-{2-[6-(difluoromethyl)pyridin-2-yl]pyrrolo[2,1-f][1,2,4]triazin-4-yl}-3-(4,4-difluoropiperidine-1-carbonyl)pyridin-4-amine

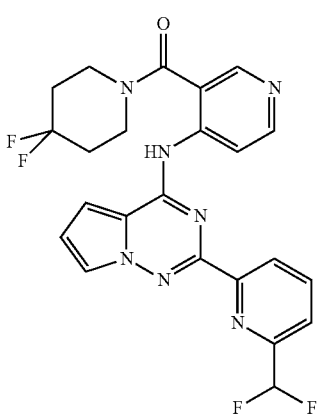 [SMILES: O=C(c1cnccc1Nc1nc(-c2cccc(C(F)F)n2)nn2cccc12)N1CCC(F)(F)CC1]

Example 203 (1.5 mg, 8%) was synthesized employing the procedure described for Example 37 (Scheme 37): LCMS m/z 486 (M+H); rt 1.36 min; Conditions G. $^1$H NMR (500 MHz, DMSO-d6) δ 8.78-8.66 (m, 2H), 8.41-8.28 (m, 2H), 8.18 (t, J=7.7 Hz, 1H), 8.10 (br. s, 1H), 7.83 (d, J=7.6 Hz, 1H), 7.24-7.12 (m, 2H), 7.12-7.02 (m, 1H), 6.96 (d, J=10.3 Hz, 1H), 3.22 (br. s, 1H), 1.93 (br. s, 5H), 1.78-1.69 (m, 1H).

Example 204

Ethyl 3-{[4-({2-[6-(difluoromethyl)pyridin-2-yl]pyrrolo[2,1-f][1,2,4]triazin-4-yl}amino)pyridin-3-yl]formamido}propanoate

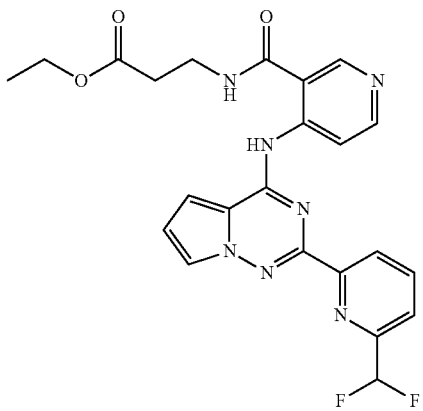 [SMILES: CCOC(=O)CCNC(=O)c1cnccc1Nc1nc(-c2cccc(C(F)F)n2)nn2cccc12]

Example 204 (1.9 mg, 10%) was synthesized employing the procedure described for Example 37 (Scheme 37): LCMS m/z 482.1 (M+H); rt 1.45 min; Conditions G. $^1$H NMR (500 MHz, DMSO-d6) δ 9.31 (br. s, 1H), 9.21 (br. s, 1H), 9.02 (br. s, 1H), 8.76 (br. s, 1H), 8.49 (d, J=7.8 Hz, 1H), 8.24 (t, J=7.8 Hz, 1H), 8.14 (br. s, 1H), 7.88 (d, J=7.7 Hz, 1H), 7.18-7.11 (m, 1H), 7.08-6.99 (m, 1H), 6.97 (br. s, 1H), 4.09 (q, J=7.0 Hz, 2H), 3.59 (d, J=5.6 Hz, 2H), 2.66 (t, J=6.8 Hz, 2H), 1.19 (t, J=7.1 Hz, 3H).

Example 205

4-({2-[6-(difluoromethyl)pyridin-2-yl]pyrrolo[2,1-f][1,2,4]triazin-4-yl}amino)-N-{[3-(methoxymethyl)-1,2,4-oxadiazol-5-yl]methyl}pyridine-3-carboxamide

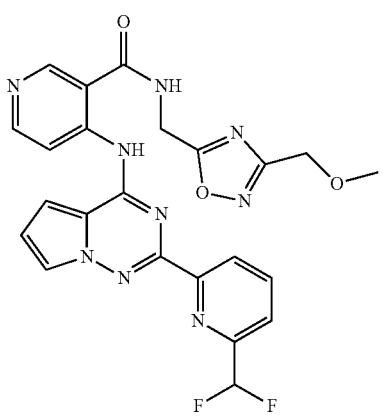 [SMILES: COCc1noc(CNC(=O)c2cnccc2Nc2nc(-c3cccc(C(F)F)n3)nn3cccc23)n1]

Example 205 (1.9 mg, 9%) was synthesized employing the procedure described for Example 37 (Scheme 37): LCMS m/z 508 (M+H); rt 1.32 min; Conditions G. $^1$H NMR (500 MHz, DMSO-d6) δ 9.16-9.00 (m, 2H), 8.79-8.65 (m, 1H), 8.47 (d, J=7.8 Hz, 1H), 8.22 (t, J=7.6 Hz, 1H), 8.09 (br. s, 1H), 7.86 (d, J=7.2 Hz, 1H), 7.02 (br. s, 1H), 6.95 (br. s, 1H), 6.85 (br. s, 1H), 4.88 (br. s, 2H), 4.54 (s, 2H).

Example 206

(4-{[2-(6-methoxypyridin-2-yl)pyrrolo[2,1-f][1,2,4]triazin-4-yl]amino}pyridin-3-yl)methanol

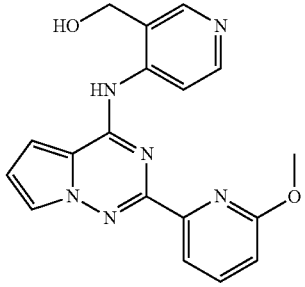 [SMILES: COc1cccc(-c2nc(Nc3ccncc3CO)c3cccn3n2)n1]

Example 206 (285 mg, 81%) was synthesized employing the procedure described for Example 38 (Scheme 38): LCMS m/z 349.2 (M+H); rt 1.135 min; Conditions C. $^1$H NMR (400 MHz, DMSO-d6) δ 10.10 ((s, 1H), 8.50-8.62 (m, 3H), 8.00 (s, 1H), 7.84-7.89 (m, 2H), 6.91-6.99 (m, 3H), 6.07 (bs, 1H), 4.82 (d, J=4.4 Hz, 2H), 4.01 (s, 3H).

Example 207

1-[({4-[(3-fluoropyridin-4-yl)amino]-2-(6-methoxypyridin-2-yl)pyrrolo[2,1-f][1,2,4]triazin-6-yl}methyl)amino]-2-methylpropan-2-ol

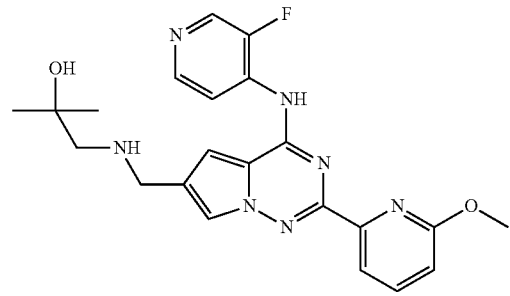 [SMILES: COc1cccc(-c2nc(Nc3ccncc3F)c3cc(CNCC(C)(C)O)cn3n2)n1]

Example 207 (8 mg, 27%) was synthesized employing the procedure described for Example 40 (Scheme 40): LCMS m/z 438.3 (M+H); rt 0.84 min; Conditions C $^1$H NMR (400 MHz, DMSO-d6) δ 1.00-1.27 (m, 5H) 1.13 (s, 5H) 1.90 (s, 2H) 2.43-2.47 (m, 1H) 4.01 (s, 2H) 6.93 (dd, J=7.78, 1.25 Hz, 1H) 7.27-7.27 (m, 1H) 7.33 (s, 1H) 7.78-7.87 (m, 2H) 7.92 (d, J=1.51 Hz, 1H) 8.40 (d, J=5.02 Hz, 1H) 8.62 (d, J=3.01 Hz, 2H).

Example 208

(3R)-3-fluoro-4-[({4-[(3-fluoropyridin-4-yl)amino]-2-(6-methoxypyridin-2-yl)pyrrolo[2,1-f][1,2,4]triazin-6-yl}methyl)amino]-2-methylbutan-2-ol

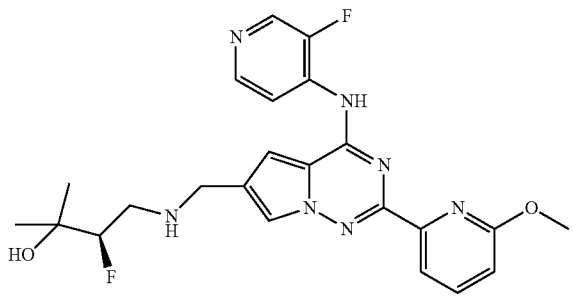 [SMILES: COc1cccc(-c2nc(Nc3ccncc3F)c3cc(CNC[C@@H](F)C(C)(C)O)cn3n2)n1]

Example 208 (5 mg, 15.7%) was synthesized employing the procedure described for Example 40 (Scheme 40): LCMS m/z 470.3 (M+H); rt 0.982 min; Conditions C $^1$H NMR (400 MHz, DMSO-d6) δ 1.08 (d, J=1.00 Hz, 7H) 1.90 (s, 4H) 2.73-2.88 (m, 1H) 2.90-2.96 (m, 1H) 3.82-3.87 (m, 2H) 4.01 (s, 3H) 4.21-4.39 (m, 1H) 6.90-6.95 (m, 1H) 7.31-7.37 (m, 1H) 7.78-7.88 (m, 2H) 7.89-7.94 (m, 1H) 8.36-8.44 (m, 1H) 8.60-8.69 (m, 2H).

Example 209

4-{3-[({4-[(3-fluoropyridin-4-yl)amino]-2-(6-methoxypyridin-2-yl)pyrrolo[2,1-f][1,2,4]triazin-6-yl}methyl)amino]propyl}-1,4-thiomorpholine-1,1-dione

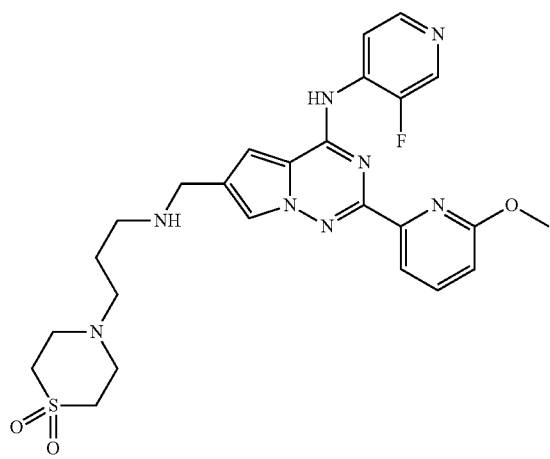 [SMILES: COc1cccc(-c2nc(Nc3ccncc3F)c3cc(CNCCCN4CCS(=O)(=O)CC4)cn3n2)n1]

Example 209 (3 mg, 7.7%) was synthesized employing the procedure described for Example 40 (Scheme 40): LCMS m/z 541.3 (M+H); rt 1.12 min; Conditions C $^1$H NMR (400 MHz, DMSO-d6) δ 8.64 (dd, J=7.03, 5.52 Hz, 1H) 8.59 (d, J=3.01 Hz, 1H) 8.38 (d, J=5.02 Hz, 1H) 7.88 (d, J=1.51 Hz, 1H) 7.84 (d, J=7.53 Hz, 1H) 7.80-7.82 (m, 1H) 7.74-7.79 (m, 1H) 7.28 (d, J=1.51 Hz, 1H) 6.86 (dd, J=7.53, 1.51 Hz, 1H) 4.00 (s, 3H)) 3.8 (s, 2H) 3.03-3.09 (m, 4H) 2.83-2.89 (m, 4H) 2.59 (t, J=6.78 Hz, 2H) 1.56-1.69 (m, 2H) 1.34 (t, J=7.03 Hz, 2H).

Example 210

N-[6-ethenyl-2-(6-methoxypyridin-2-yl)pyrrolo[2,1-f][1,2,4]triazin-4-yl]-3-fluoropyridin-4-amine

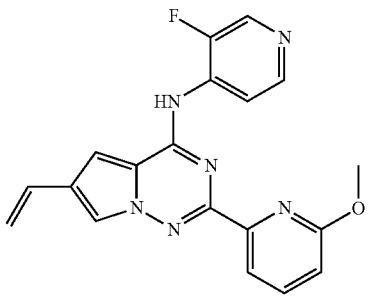 [SMILES: C=Cc1cc2c(Nc3ccncc3F)nc(-c3cccc(OC)n3)nn2c1]

Example 210 (4 mg, 13%) was synthesized employing the procedure described for Example 42 (Scheme 42): LCMS m/z 363.2 (M+H); rt 1.338 min; Conditions C. $^1$H NMR (400 MHz, DMSO-d6) δ 10.18-10.06 (m, 1H), 8.76-8.61 (m, 2H), 8.41 (d, J=5.5 Hz, 1H), 8.16 (s, 1H), 7.90-7.76 (m, 2H), 7.54 (s, 1H), 6.95 (s, 1H), 6.86-6.74 (m, 1H), 5.83-5.72 (m, 1H), 5.77 (d, J=17.6 Hz, 1H), 5.29 (s, 1H), 4.01 (s, 3H).

Example 211

(3E)-4-{4-[(3-fluoropyridin-4-yl)amino]-2-(6-methoxypyridin-2-yl)pyrrolo[2,1-f][1,2,4]triazin-6-yl}but-3-en-1-ol

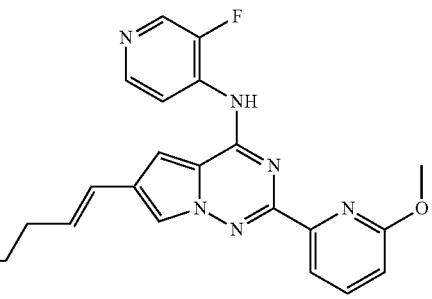

Example 211 (3 mg, 11.5%) was synthesized employing the procedure described for Example 43 (Scheme 43): LCMS m/z 407.2 (M+H); rt 1.59 min; Conditions C; $^1$H NMR (400 MHz, DMSO-d6) δ 10.08 (br. s, 1H) 8.70 (br. s, 1H) 8.61 (br. s, 1H) 8.39 (d, J=5.02 Hz, 1H) 8.02 (s, 1H) 7.77-7.89 (m, 2H) 7.43 (br. s, 1H) 6.93 (dd, J=8.0 Hz, 1H) 6.50 (d, J=14 Hz, 1H) 6.19-6.30 (m, 1H) 4.61 (t, J=5.27 Hz, 1H) 4.01 (s, 3H) 3.50-3.59 (m, 2H) 2.31-2.42 (m, 2H).

Example 212

N-(4-{[2-(6-methoxypyridin-2-yl)pyrrolo[2,1-f][1,2,4]triazin-4-yl]amino}pyridin-3-yl)-2-(morpholin-4-yl)acetamide

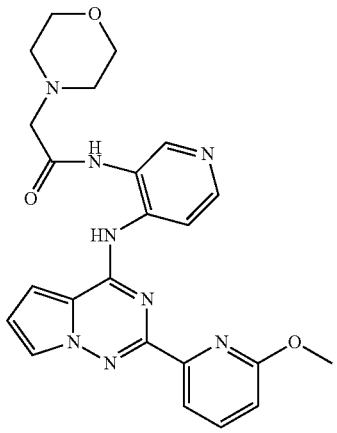 [SMILES: COc1cccc(-c2nc(Nc3ccncc3NC(=O)CN3CCOCC3)c3cccn3n2)n1]

Example 212 (11 mg, 24%) was synthesized employing the procedure described for Example 47 (Scheme 47): LCMS m/z 461.3 (M+H); rt 1.051 min; Conditions C. $^1$H NMR (400 MHz, DMSO-d6) δ 10.46-10.36 (m, 1H), 10.10-10.01 (m, 1H), 8.94-8.86 (m, 1H), 8.46-8.35 (m, 1H), 8.06-8.00 (m, 1H), 7.88-7.74 (m, 2H), 7.64-7.60 (m, 1H), 7.25-7.16 (m, 1H), 6.95-6.80 (m, 2H), 3.93 (s, 3H), 3.20-3.12 (m, 1H), 2.98 (s, 3H), 2.93-2.83 (m, 4H), 2.08 (br. s, 4H).

Example 213

N-[2-(6-fluoropyridin-2-yl)pyrrolo[2,1-f][1,2,4]triazin-4-yl]pyridin-4-amine

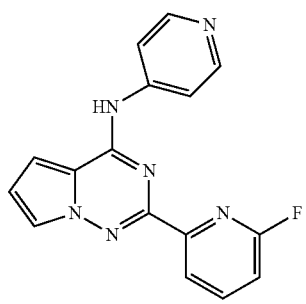 [SMILES: Fc1cccc(-c2nc(Nc3ccncc3)c3cccn3n2)n1]

Example 213 (19.8 mg, 79%) was synthesized employing the procedure described for Example 49 (Scheme 49): LCMS m/z 307.2 (M+H); rt 1.32 min; Conditions F. $^1$H NMR (500 MHz, DMSO-d6) δ 8.78 (d, J=6.4 Hz, 2H), 8.60 (d, J=6.4 Hz, 2H), 8.28 (d, J=7.1 Hz, 1H), 8.25-8.14 (m, 2H), 7.43 (d, J=4.0 Hz, 1H), 7.38 (d, J=5.7 Hz, 1H), 7.08-6.98 (m, 1H).

Example 214

N-[2-(6-methoxypyridin-2-yl)pyrrolo[2,1-f][1,2,4]triazin-4-yl]pyridin-4-amine

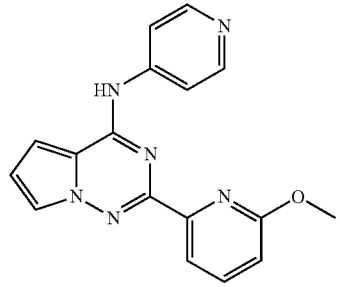 [SMILES: COc1cccc(-c2nc(Nc3ccncc3)c3cccn3n2)n1]

Example 214 (2.2 mg, 8%) was synthesized employing the procedure described for Example 49 (Scheme 49): LCMS m/z 319.2 (M+H); rt 1.16 min; Conditions G. $^1$H NMR (500 MHz, DMSO-d6) δ 8.74 (d, J=5.4 Hz, 4H), 8.13 (s, 1H), 7.98-7.86 (m, 2H), 7.40 (d, J=3.7 Hz, 1H), 7.06-6.97 (m, 2H), 4.08 (s, 3H).

Example 215

N-{2-[2-(methylsulfanyl)pyrimidin-4-yl]pyrrolo[2,1-f][1,2,4]triazin-4-yl}pyridin-4-amine

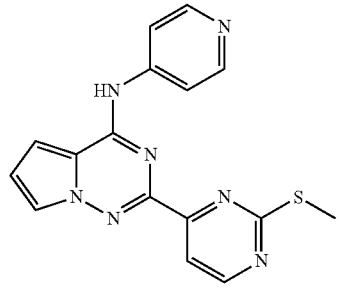 [SMILES: CSc1nccc(-c2nc(Nc3ccncc3)c3cccn3n2)n1]

Example 215 (6.0 mg, 22%) was synthesized employing the procedure described for Example 49 (Scheme 49): LCMS m/z 336.2 (M+H); rt 1.07 min; Conditions G. $^1$H NMR (500 MHz, DMSO-d6) δ 8.83 (d, J=5.0 Hz, 1H), 8.73 (d, J=6.1 Hz, 2H), 8.64 (d, J=6.1 Hz, 2H), 8.18 (s, 1H), 7.97 (d, J=5.4 Hz, 1H), 7.44 (d, J=4.4 Hz, 1H), 7.06 (br. s, 1H), 2.69 (s, 3H)

Example 216

Ethyl 2-(6-methylpyridin-2-yl)-4-[(pyridin-4-yl)amino]pyrrolo[2,1-f][1,2,4]triazine-6-carboxylate

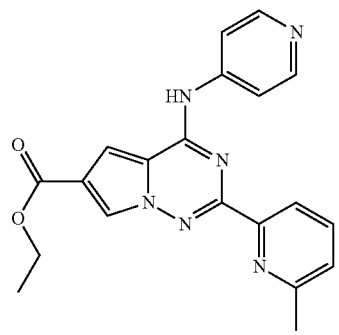 [SMILES: CCOC(=O)c1cc2c(Nc3ccncc3)nc(-c3cccc(C)n3)nn2c1]

Example 216 (9.4 mg) was synthesized employing the procedure described for Example 50 (Scheme 50): LCMS m/z 375 (M+H); rt 1.52 min; Conditions F. ¹H NMR (DMSO-d6) δ 8.80 (d, J=6.7 Hz, 2H), 8.65 (d, J=6.7 Hz, 2H), 8.48 (s, 1H), 8.08 (d, J=7.7 Hz, 1H), 7.95 (s, 1H), 7.89 (t, J=7.7 Hz, 1H), 7.77 (s, 1H), 7.44 (d, J=7.7 Hz, 1H), 4.33 (q, J=7.1 Hz, 2H), 2.62 (s, 3H), 1.35 (t, J=7.1 Hz, 3H).

Example 217

2-(6-methylpyridin-2-yl)-N-phenyl-4-[(pyridin-4-yl)amino]pyrrolo[2,1-f][1,2,4]triazine-6-carboxamide

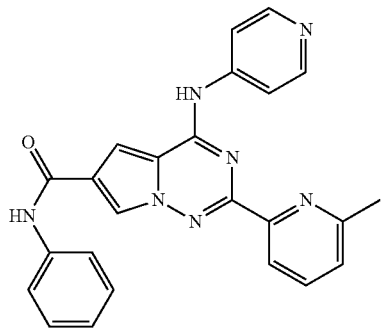 [SMILES: Cc1cccc(-c2nc(Nc3ccncc3)c3cc(C(=O)Nc4ccccc4)cn3n2)n1]

Example 217 (4.2 mg, 32%) was synthesized employing the procedure described for Example 50 (Scheme 50): LCMS m/z 422.1 (M+H); rt 1.56 min; Conditions F. ¹H NMR (500 MHz, DMSO-d6) δ 10.17 (s, 1H), 8.68 (s, 1H), 8.59 (d, J=5.7 Hz, 2H), 8.23 (d, J=6.1 Hz, 2H), 8.11 (d, J=7.7 Hz, 1H), 7.91 (t, J=7.6 Hz, 1H), 7.84 (s, 1H), 7.79 (d, J=7.7 Hz, 2H), 7.46-7.34 (m, 3H), 7.13 (t, J=7.2 Hz, 1H), 2.63 (s, 3H).

Example 218

N,N-dimethyl-2-(6-methylpyridin-2-yl)-4-[(pyridin-4-yl)amino]pyrrolo[2,1-f][1,2,4]triazine-6-carboxamide

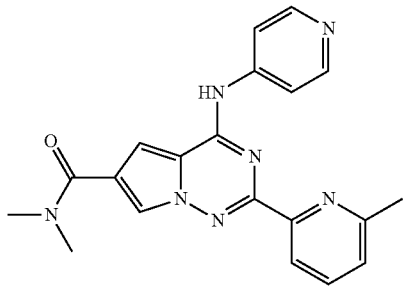

Example 218 (7.2 mg, 60%) was synthesized employing the procedure described for Example 50 (Scheme 50): LCMS m/z 374.1 (M+H); rt 1.3 min; ¹H NMR (500 MHz, DMSO-d6) δ 8.56 (d, J=5.4 Hz, 2H), 8.32 (s, 1H), 8.07-8.17 (m, 3H), 7.90 (t, J=7.7 Hz, 1H), 7.60 (s, 1H), 7.41 (d, J=7.4 Hz, 1H), 2.60 (s, 3H); The amide methyl proton signals were obscured due to presaturation pulse.

Example 219

2-(6-methylpyridin-2-yl)-4-[(pyridin-4-yl)amino]pyrrolo[2,1-f][1,2,4]triazine-6-carboxamide

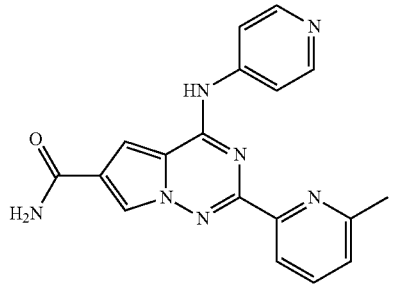 [SMILES: Cc1cccc(-c2nc(Nc3ccncc3)c3cc(C(N)=O)cn3n2)n1]

Example 219 (5 mg, 45%) was synthesized employing the procedure described for Example 50 (Scheme 50): LCMS m/z 346.2 (M+H); rt 0.84 min; Conditions G. ¹H NMR (500 MHz, DMSO-d6) δ 8.55 (d, J=5.7 Hz, 2H), 8.43 (s, 1H), 8.14 (d, J=5.7 Hz, 2H), 8.10 (d, J=7.7 Hz, 1H), 7.93-7.85 (m, 2H), 7.68 (s, 1H), 7.42 (d, J=7.7 Hz, 1H), 7.33 (br. s, 1H), 2.61 (s, 3H).

Example 220

N-methyl-2-(6-methylpyridin-2-yl)-4-[(pyridin-4-yl)amino]pyrrolo[2,1-f][1,2,4]triazine-6-carboxamide

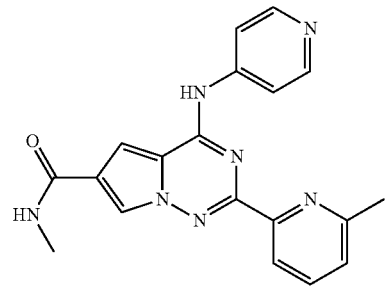 [SMILES: CNC(=O)c1cc2c(Nc3ccncc3)nc(-c3cccc(C)n3)nn2c1]

Example 220 (10 mg, 83%) was synthesized employing the procedure described for Example 50 (Scheme 50): LCMS m/z 360.3 (M+H); rt 1.03 min; Conditions F. ¹H NMR (DMSO-d$_6$) δ: 8.56 (br. s., 1H), 8.36 (br. s., 2H), 8.02-8.22 (m, 3H), 7.83-7.93 (m, 1H), 7.69 (s, 1H), 7.41 (d, J=7.4 Hz, 1H), 2.82 (d, J=3.7 Hz, 3H), 2.60 (br. s, 3H).

Example 221

4-{[2-(6-methylpyridin-2-yl)pyrrolo[2,1-f][1,2,4]triazin-4-yl]amino}-N-[3-(pyrrolidin-1-yl)propyl]pyridine-3-carboxamide

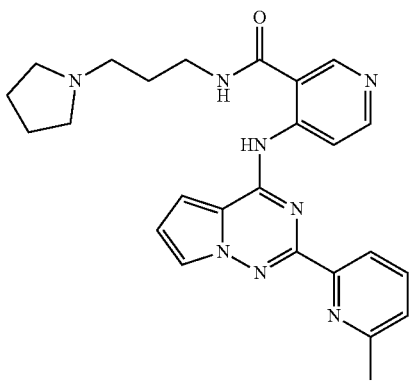 [SMILES: Cc1cccc(-c2nc(Nc3ccncc3C(=O)NCCCN3CCCC3)c3cccn3n2)n1]

Example 221 (1.9 mg, 44%) was synthesized employing the procedure described for Example 50 (Scheme 50): LCMS m/z 457 (M+H); rt 1.12 min; Conditions F. ¹H NMR (DMSO-d6) δ 9.08 (d, J=5.4 Hz, 1H), 8.97 (s, 1H), 8.68 (d, J=5.7 Hz, 1H), 8.13 (d, J=7.7 Hz, 1H), 8.06 (s, 1H), 7.90 (t, J=7.7 Hz, 1H), 7.41 (d, J=7.4 Hz, 1H), 6.94 (d, J=2.4 Hz, 1H), 6.89 (d, J=3.7 Hz, 1H), 3.48 (br. s, 1H), 3.34-3.45 (m, J=6.7, 6.7 Hz, 1H), 2.46-2.70 (m, 11H), 1.64-1.85 (m, 6H).

Example 222

N-[2-(6-methylpyridin-2-yl)pyrrolo[2,1-f][1,2,4]triazin-4-yl]-3-[3-(morpholin-4-yl)propoxy]pyridin-4-amine

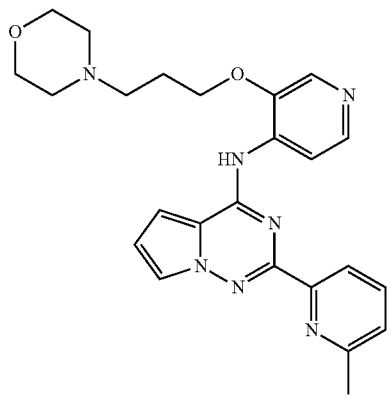 [SMILES: Cc1cccc(-c2nc(Nc3ccncc3OCCCN3CCOCC3)c3cccn3n2)n1]

Example 222 (4.6 mg, 15%) was synthesized employing the procedure described for Example 51 (Scheme 51): LCMS m/z 446 (M+H); rt 1.41 min; Conditions F. ¹H NMR (DMSO-d6) δ 8.44 (s, 1H), 8.28 (d, J=5.0 Hz, 1H), 8.18 (br. s, 1H), 7.89-8.07 (m, 2H), 7.83 (t, J=7.7 Hz, 1H), 7.36 (d, J=7.7 Hz, 1H), 7.18 (br. s, 1H), 6.87 (br. s, 1H), 4.22 (t, J=5.7 Hz, 2H), 3.33-3.58 (m, 4H), 2.57 (s, 3H), 2.07-2.40 (m, 6H), 1.88 (d, J=6.1 Hz, 2H).

Example 224

4-({2-[6-(difluoromethyl)-5-fluoropyridin-2-yl]pyrrolo[2,1-f][1,2,4]triazin-4-yl}amino)pyridine-3-carboxamide

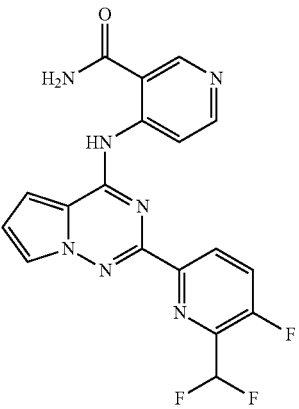 [SMILES: NC(=O)c1cnccc1Nc1nc(-c2ccc(F)c(C(F)F)n2)nn2cccc12]

To a stirred solution of 2-(6-(difluoromethyl)-5-fluoropyridin-2-yl)-4-phenoxypyrrolo[2,1-f][1,2,4]triazine (75 mg, 0.21 mmol) and 4-aminonicotinamide (57.7 mg, 0.421 mmol) in dry DMF (10 mL) was added NaH (15.15 mg, 0.631 mmol) at 0° C. and stirred at rt for 2 h. Then the reaction mixture was poured into ice-cold water and extracted with ethyl acetate (100 mL×2), washed with brine, dried over Na₂SO₄, filtered and evaporated under reduced pressure to get crude compound. The crude residue was purified by preparative HPLC to get 4-({2-[6-(difluoromethyl)-5-fluoropyridin-2-yl]pyrrolo[2,1-f][1,2,4]triazin-4-yl}amino)pyridine-3-carboxamide 224 (6.7 mg, 7.7%). LCMS: m/z, 400.3 (M+H); rt 2.15 min; Conditions E. ¹H NMR (400 MHz, DMSO-d6) δ 13.22-13.10 (m, 1H), 9.24-9.12 (m, 1H), 9.09-9.01 (m, 1H), 8.76-8.64 (m, 2H), 8.59-8.50 (m, 1H), 8.24-8.05 (m, 2H), 7.46-7.10 (m, 2H), 7.02-6.83 (m, 2H).

Scheme 55

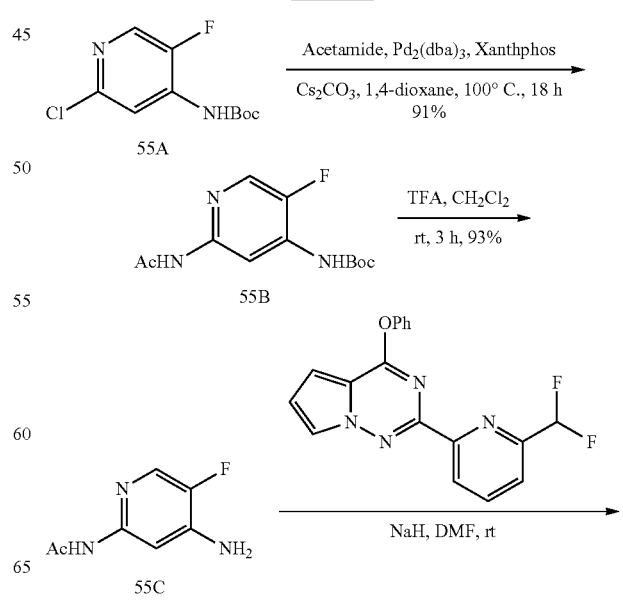

-continued

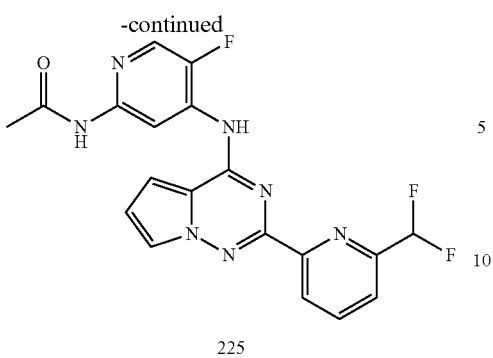

225

Example 225

N-[4-({2-[6-(difluoromethyl)pyridin-2-yl]pyrrolo[2,1-f][1,2,4]triazin-4-yl}amino)-5-fluoropyridin-2-yl]acetamide

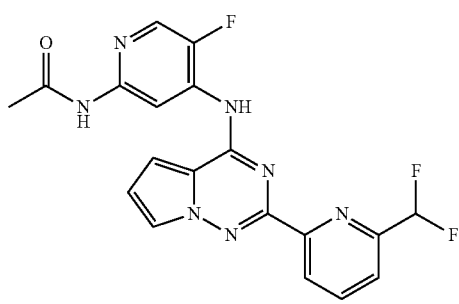 [SMILES: CC(=O)Nc1cc(Nc2nc(-c3cccc(C(F)F)n3)nn3cccc23)c(F)cn1]

Intermediate 55B: tert-butyl (2-acetamido-5-fluoropyridin-4-yl)carbamate

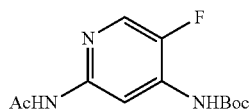 [SMILES: CC(=O)Nc1cc(NC(=O)OC(C)(C)C)c(F)cn1]

To a stirred solution of tert-butyl (2-chloro-5-fluoropyridin-4-yl)carbamate (1.0 g, 4.05 mmol) in 1,4-dioxane (50 mL) in a seal tube was added acetamide (0.718 g, 12.16 mmol), Cs$_2$CO$_3$ (2.64 g, 8.11 mmol), and 4,5-bisdiphenylphosphino)-9,9-dimethylxanthene (0.469 g, 0.811 mmol) and purged with nitrogen for 5 minutes. Then Pd$_2$(dba)$_3$ (0.371 g, 0.405 mmol) was added and again purged with nitrogen for 10 minutes and reaction mixture was heated at 100° C. for 18 h. The volatile was evaporated under reduced pressure and re-dissolved in ethyl acetate. The solid was filtered off and the filtrate was washed with water. The aqueous layer was back extracted with ethyl acetate. The combined organic layer was concentrated to give a brown solid. The crude residue was purified by silica gel chromatography (eluent=3% methanol in chloroform) to yield the desired product tert-butyl (2-acetamido-5-fluoropyridin-4-yl)carbamate (998 mg, 3.71 mmol, 91% yield) as light yellow solid. LCMS: m/z, 270.2 (M+H); rt 2.42 min; Conditions E.

Intermediate 55C: N-(4-amino-5-fluoropyridin-2-yl)acetamide

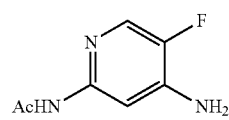

To a stirred solution of tert-butyl (2-acetamido-5-fluoropyridin-4-yl)carbamate (1.95 g, 7.24 mmol) in CH$_2$Cl$_2$ (50 mL) was added TFA (12.27 mL, 159 mmol) dropwise at 0° C. Then the reaction mixture was warmed to rt and stirred for additional 3 h. The reaction was monitored by LCMS until complete conversion. The reaction mixture was concentrated under reduced pressure to remove TFA. The residue was washed with diethyl ether three times and dried to get the desired product N-(4-amino-5-fluoropyridin-2-yl)acetamide (1.14 g, 6.74 mmol, 93% yield) (1.908 g, TFA salt) as a pale yellow solid. LCMS: m/z, 170.2 (M+H); rt 0.59 min; Conditions E.

Example 225 (2.0 mg, 3.15%) was synthesized employing the procedure described for Example 1 (Scheme 1). LCMS: m/z, 414.2 (M+H); rt 2.85 min; Conditions J. $^1$H NMR (400 MHz, DMSO-d6) δ 10.60 (s, 1H), 10.26 (s, 1H), 8.94 (d, J=6.0 Hz, 1H), 8.54 (d, J=8.0 Hz, 1H), 8.40 (d, J=2.4 Hz, 1H), 8.07-8.14 (m, 2H), 7.79 (d, J=7.6 Hz, 1H), 7.37 (d, J=3.6 Hz, 1H), 7.06 (t, J=55.2 Hz, 1H), 6.91-6.92 (m, 1H), 2.14 (s, 3H).

Scheme 56

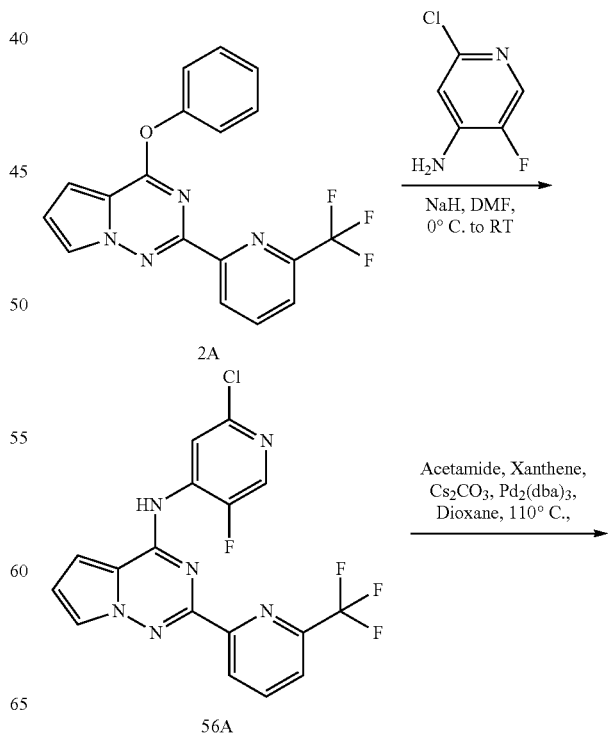

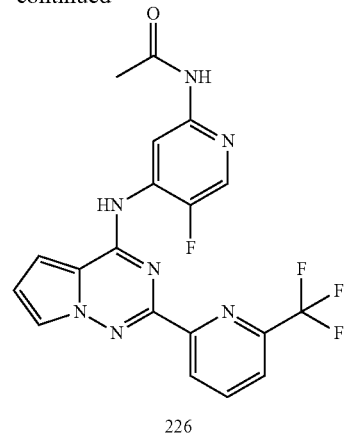

Example 226

N-[5-fluoro-4-({2-[6-(trifluoromethyl)pyridin-2-yl]pyrrolo[2,1-f][1,2,4]triazin-4-yl}amino)pyridin-2-yl]acetamide

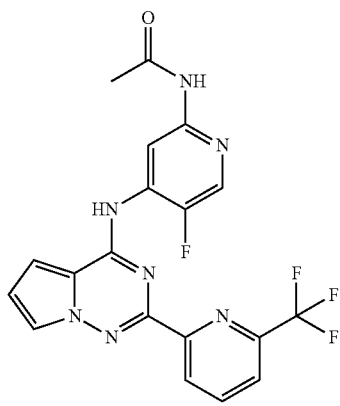 [SMILES: CC(=O)Nc1cc(Nc2nc(-c3cccc(C(F)(F)F)n3)nn3cccc23)c(F)cn1]

Intermediate 56A: N-(2-chloro-5-fluoropyridin-4-yl)-2-(6-(trifluoromethyl)pyridin-2-yl)pyrrolo[2,1-f][1,2,4]triazin-4-amine

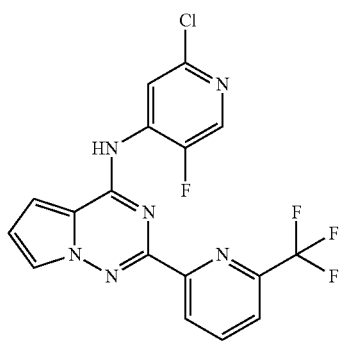 [SMILES: Fc1cnc(Cl)cc1Nc1nc(-c2cccc(C(F)(F)F)n2)nn2cccc12]

To a 50 mL RB flask, was added 2-chloro-5-fluoropyridin-4-amine.TFA (234 mg, 0.898 mmol) in DMF (10 mL) and cooled to 0° C. Then NaH (33.7 mg, 0.842 mmol) was added to the cooled solution and stirred for 5 min. A solution of 4-phenoxy-2-(6-(trifluoromethyl)pyridin-2-yl)pyrrolo[2,1-f][1,2,4]triazine (200 mg, 0.561 mmol) in DMF was added dropwise and stirred at room temperature for 2 h. An aliquot of the reaction mixture was diluted with methanol and analyzed by LCMS to ensure complete conversion. The reaction mixture was poured into ice and the solid obtained was filtered, washed with water, dried under suction to get N-(2-chloro-5-fluoropyridin-4-yl)-2-(6-(trifluoromethyl)pyridin-2-yl)pyrrolo[2,1-f][1,2,4]triazin-4-amine 56A (150 mg, 0.367 mmol, 65.4% yield) as pale brown solid. LCMS: m/z=409.2 9 (M+H); rt 3.15 min; Conditions E.

Example 226 (47 mg, 27.0% yield) was synthesized employing the procedure described for example 19 (Scheme 19). LCMS: m/z, 432.0 (M+H); rt 2.56 min; Conditions E. $^1$H NMR (400 MHz, DMSO-$d_6$) δ 10.61 (s, 1H), 10.30 (br. s., 1H), 8.93 (d, J=6.0 Hz, 1H), 8.68 (d, J=8.0 Hz, 1H), 8.40 (d, J=2.5 Hz, 1H), 8.21 (t, J=8.0 Hz, 1H), 8.13 (d, J=1.5 Hz, 1H), 8.05-7.96 (m, 1H), 7.38 (d, J=3.0 Hz, 1H), 6.93 (dd, J=4.3, 2.8 Hz, 1H), 2.17-2.12 (m, 3H).

Example 227

N-(4-{[2-(5-fluoropyridin-2-yl)pyrrolo[2,1-f][1,2,4]triazin-4-yl]amino}pyridin-2-yl)acetamide

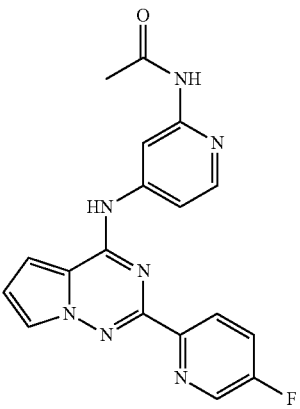 [SMILES: CC(=O)Nc1cc(Nc2nc(-c3ccc(F)cn3)nn3cccc23)ccn1]

Example 227 (2.5 mg, 4.2%) was synthesized employing the procedure described for Example 1 (Scheme 1). LCMS m/z 364.1 (M+H); rt 1.55 min; Conditions C. $^1$H NMR (400 MHz, DMSO-d6) δ 10.47 (s, 1H), 10.32 (s, 1H), 8.77 (s, 1H), 8.73 (d, J=2.8 Hz, 1H), 8.57-8.60 (m, 1H), 8.27 (d, J=5.6 Hz, 1H), 7.98-8.01 (m, 2H), 7.84-7.89 (m, 1H), 7.39-7.40 (m, 1H), 6.88-6.90 (m, 1H), 2.15 (s, 3H).

Example 228

4-({2-[6-(difluoromethyl)pyridin-2-yl]pyrrolo[2,1-f][1,2,4]triazin-4-yl}amino)pyridine-3-carboxamide

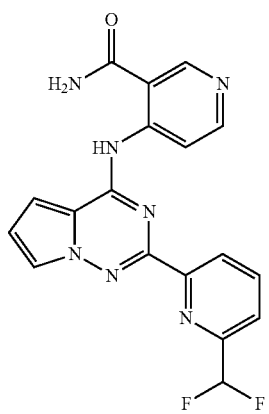 [SMILES: NC(=O)c1cnccc1Nc1nc(-c2cccc(C(F)F)n2)nn2cccc12]

To a solution of 2-(6-(difluoromethyl)pyridin-2-yl)-4-phenoxypyrrolo[2,1-f][1,2,4]triazine (0.05 g, 0.148 mmol) and 4-aminonicotinamide (0.030 g, 0.222 mmol) in DMF (1 mL) was added NaH (7.09 mg, 0.296 mmol) at 0° C. and the reaction mixture was warmed to room temperature and stirred for 2 h. After quenching with methanol (1 mL), the solvent was removed under reduced pressure to get crude compound. The crude compound was purified by preparative HPLC to get 4-({2-[6-(difluoromethyl)pyridin-2-yl]pyrrolo[2,1-f][1,2,4]triazin-4-yl}amino)pyridine-3-carboxamide 228 (2.1 mg, 3.73%). LCMS m/z 382.1 (M+H); rt 1.71 min; Conditions C. $^1$H NMR (400 MHz, DMSO-d6) δ 13.19 (s, 1H), 9.22 (d, J=6.0 Hz, 1H), 9.09 (s, 1H), 8.69-8.73 (m, 2H), 8.51 (d, J=8.4 Hz, 1H), 8.25 (t, J=7.6 Hz, 1H), 8.17 (s, 1H), 8.13-8.14 (m, 1H), 7.88 (d, J=7.6 Hz, 1H), 6.97-7.27 (m, 2H), 6.92 (d, J=1.2 Hz, 1H).

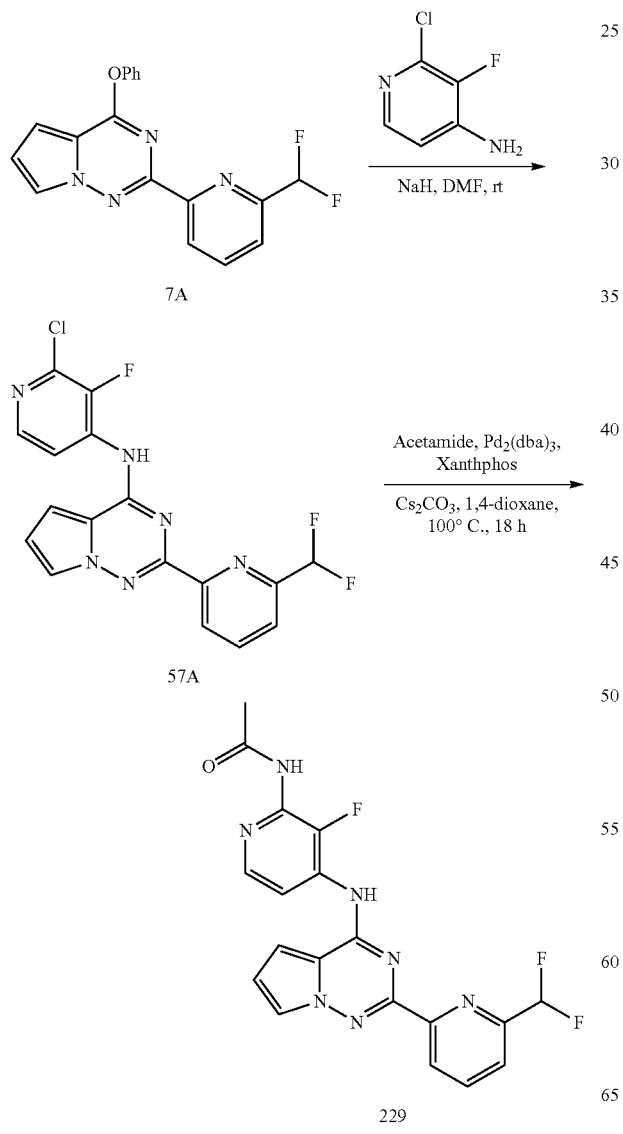

Scheme 57

Example 229

N-[4-({2-[6-(difluoromethyl)pyridin-2-yl]pyrrolo[2,1-f][1,2,4]triazin-4-yl}amino)-3-fluoropyridin-2-yl]acetamide

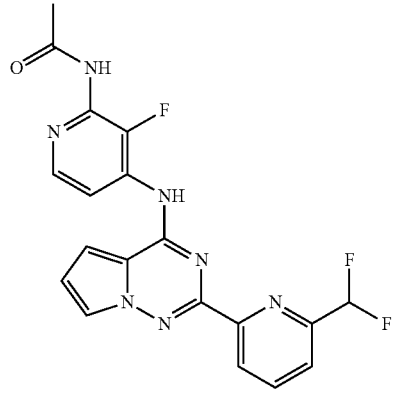 [SMILES: CC(=O)Nc1nccc(Nc2nc(-c3cccc(C(F)F)n3)nn3cccc23)c1F]

Intermediate-57A: N-(2-chloro-3-fluoropyridin-4-yl)-2-(6-(difluoromethyl)pyridin-2-yl)pyrrolo[2,1-f][1,2,4]triazin-4-amine

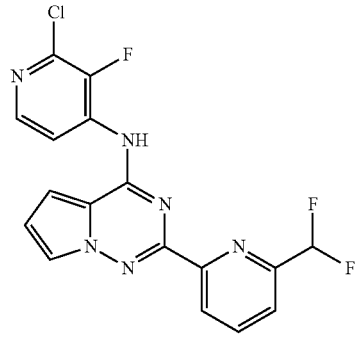 [SMILES: Fc1c(Nc2nc(-c3cccc(C(F)F)n3)nn3cccc23)ccnc1Cl]

To a solution of 2-(6-(difluoromethyl)pyridin-2-yl)-4-phenoxypyrrolo[2,1-f][1,2,4]triazine (100 mg, 0.296 mmol) and 2-chloro-3-fluoropyridin-4-amine (65.0 mg, 0.443 mmol) in DMF (2 mL) was added NaH (25.8 mg, 0.591 mmol) at 0° C. and the reaction mixture was warmed to room temperature and stirred for 2 h. The reaction mixture was poured in to 10 mL ice/H$_2$O. The resulting suspension was filtered. The isolated solid was used in the next reaction without further purification. LCMS m/z 391.1 (M+H); rt 1.29 min; Conditions I.

Example 229 (1.3 mg, 2.0%) was synthesized employing the procedure described for Example 19 (Scheme 19). LCMS m/z 414.1 (M+H); rt 1.59 min; Conditions C. $^1$H NMR (400 MHz, DMSO-d6) δ 10.37 (s, 1H), 10.31 (s, 1H), 8.46 (d, J=7.6 Hz, 1H), 8.26 (d, J=5.2 Hz, 1H), 8.13-8.18 (m, 2H), 8.07-8.08 (m, 1H), 7.81 (d, J=7.6 Hz, 1H), 7.42-7.43 (m, 1H), 7.09 (t, J=54.4 Hz, 1H), 6.91-6.93 (m, 1H), 2.13 (s, 3H).

Scheme 58

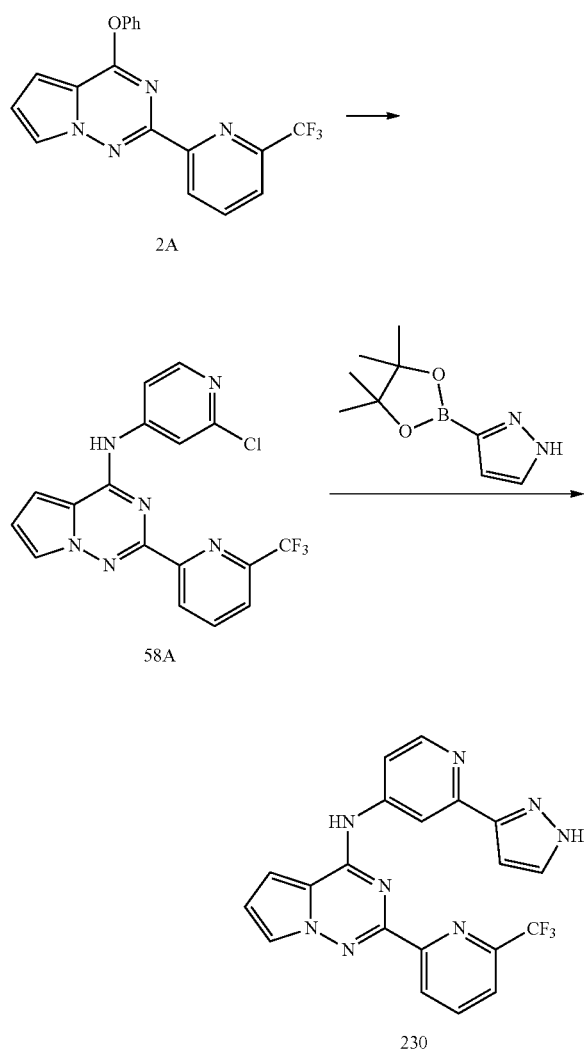

2A

58A

230

Example 230

2-(1H-pyrazol-3-yl)-N-{2-[6-(trifluoromethyl)pyridin-2-yl]pyrrolo[2,1-f][1,2,4]triazin-4-yl}pyridin-4-amine

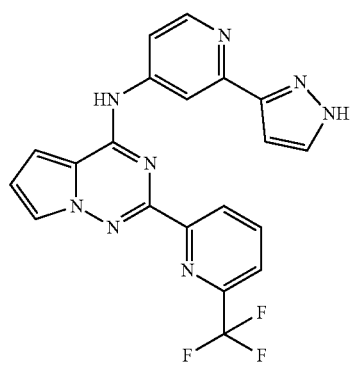 [SMILES: FC(F)(F)c1cccc(-c2nc(Nc3ccnc(-c4cc[nH]n4)c3)c3cccn3n2)n1]

Intermediate 58A: N-(2-chloropyridin-4-yl)-2-(6-(trifluoromethyl)pyridin-2-yl)pyrrolo[2,1-f][1,2,4]triazin-4-amine

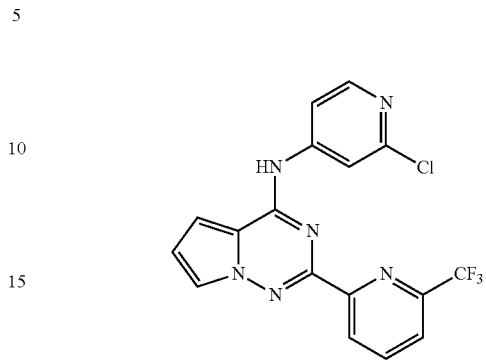

Intermediate 58A (0.42 g, 77%) was synthesized employing the procedure described for intermediate 57A (Scheme 57). LCMS m/z 390.9 (M+H); rt 3.54 min; Conditions J.

To a solution of N-(2-chloropyridin-4-yl)-2-(6-(trifluoromethyl)pyridin-2-yl)pyrrolo[2,1-f][1,2,4]triazin-4-amine (0.05 g, 0.128 mmol) and 3-(4,4,5,5-tetramethyl-1,3,2-dioxaborolan-2-yl)-1H-pyrazole (0.037 g, 0.192 mmol) in DME (2 mL)/ethanol (0.5 mL) was added PdCl$_2$(dppf) (9.36 mg, 0.013 mmol) and saturated aqueous solution of Na$_2$CO$_3$ (0.034 g, 0.320 mmol). The reaction mixture was degassed with argon and stirred under microwave irradiation for 60 min at 150° C. The reaction mixture was cooled to room temperature. The reaction mixture was diluted with water (5 mL), and extracted with EtOAc (3×25 mL). The combined organic layers were washed with water (5 mL), brine (5 mL) and dried over Na$_2$SO$_4$. The mixture was filtered, and the solvent was removed under vacuum to give the crude product which was purified by HPLC to get 2-(1H-pyrazol-3-yl)-N-{2-[6-(trifluoromethyl)pyridin-2-yl]pyrrolo[2,1-f][1,2,4]triazin-4-yl}pyridin-4-amine 230 (10.5 mg, 19.4%). LCMS: m/z, 423.0 (M+H); rt 2.50 min; Conditions J. $^1$H NMR: (400 MHz, DMSO-d6) δ 12.30-12.18 (m, 1H), 8.87-8.71 (m, 2H), 8.65 (d, J=3.0 Hz, 1H), 8.46 (d, J=5.5 Hz, 1H), 8.23 (d, J=7.8 Hz, 1H), 8.05-7.90 (m, 2H), 7.56-7.46 (m, 1H), 6.84 (d, J=2.5 Hz, 1H), 4.47-4.30 (m, 1H), 3.87 (s, 2H), 3.47 (t, J=6.3 Hz, 3H), 3.18 (s, 2H), 2.68-2.66 (m, 3H), 2.34 (t, J=6.3 Hz, 3H).

Scheme 59

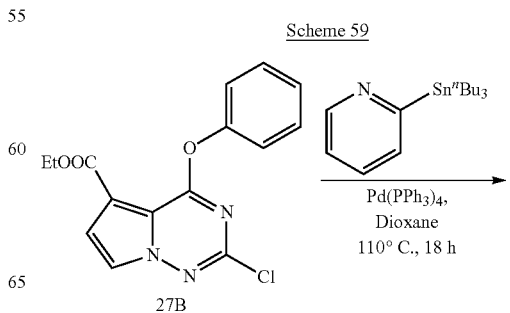

27B

257
-continued

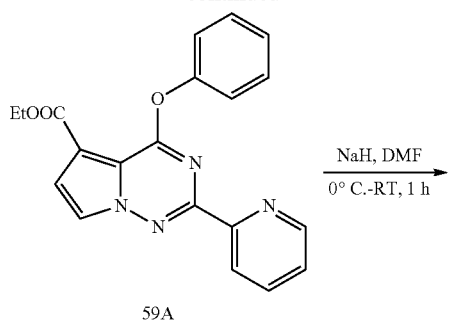

59A

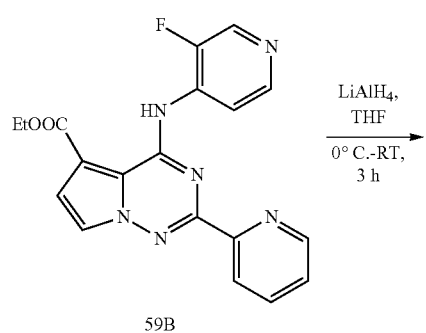

59B

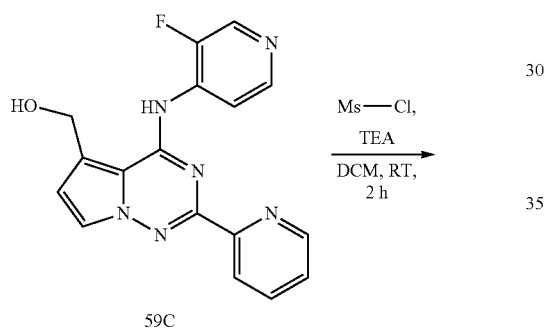

59C

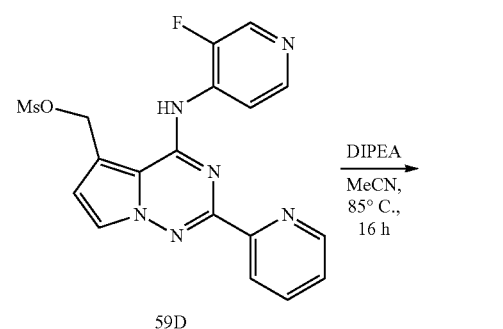

59D

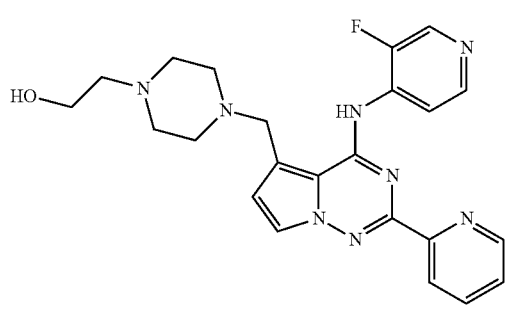 [SMILES: OCCN1CCN(Cc2ccn3nc(-c4ccccn4)nc(Nc4ccncc4F)c23)CC1]

231

258

Example 231

2-[4-({4-[(3-fluoropyridin-4-yl)amino]-2-(pyridin-2-yl)pyrrolo[2,1-f][1,2,4]triazin-5-yl}methyl)piperazin-1-yl]ethan-1-ol Intermediate-59A: ethyl 4-phenoxy-2-(pyridin-2-yl)pyrrolo[2,1-f][1,2,4]triazine-5-carboxylate To a stirred solution of ethyl 2-chloro-4-phenoxypyrrolo[2,1-f][1,2,4]triazine-5-carboxylate (0.4 g, 1.259 mmol) in dioxane (10 mL) was added 2-(tributylstannyl)pyridine (0.556 g, 1.511 mmol). The reaction mixture was purged with nitrogen for 10 min, followed by the addition of Pd(Ph$_3$P)$_4$ (0.145 g, 0.126 mmol). The purging was continued for another 10 min. The reaction was heated to 110° C. over 10 min. The reaction was continued to stir at 110° C. for 18 h and was monitored via LC-MS. Reaction mixture was quenched with ice cold water (50 mL) and was extracted with ethyl acetate (3×100 mL). The combined organic layer was dried over anhydrous sodium sulfate, filtered and evaporated under reduced pressure to get crude solid (0.54 g). The crude product was purified by silica gel chromatography (eluted with a gradient of 37-40% ethyl acetate in petroleum ether ether) to yield ethyl 4-phenoxy-2-(pyridin-2-yl)pyrrolo[2,1-f][1,2,4]triazine-5-carboxylate 59A (0.32 g, 0.861 mmol, 68.4% yield) as pale yellow solid. LCMS: m/z, 361.0 (M+H); rt 2.84 min; Conditions E. $^1$H NMR: (300 MHz, DMSO-d$_6$) δ 8.69 (s, 1H), 8.25 (d, J=3.0 Hz, 1H), 7.88 (dt, J=2.6, 1.3 Hz, 2H), 7.66-7.30 (m, 8H), 4.30 (d, J=7.2 Hz, 2H), 1.28 (t, J=7.0 Hz, 3H).

Intermediate 59B: ethyl 4-((3-fluoropyridin-4-yl) amino)-2-(pyridin-2-yl)pyrrolo[2,1-f][1,2,4]triazine-5-carboxylate

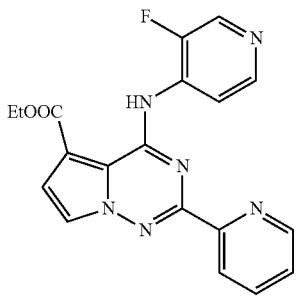 [SMILES: CCOC(=O)c1ccn2nc(-c3ccccn3)nc(Nc3ccncc3F)c12]

Intermediate 59B was synthesized employing the procedure described for intermediate 57A (Scheme 57) to obtain ethyl 4-((3-fluoropyridin-4-yl)amino)-2-(pyridin-2-yl)pyrrolo[2,1-f][1,2,4]triazine-5-carboxylate (0.075 g, 0.176 mmol, 42.4% yield) as brown solid. LCMS: m/z, 379.2 (M+H); rt 3.18 min; Conditions E. $^1$H NMR: (400 MHz, DMSO-$d_6$) δ 12.40 (s, 1H), 9.10 (s, 1H), 8.80 (br. s., 1H), 8.62 (d, J=2.5 Hz, 1H), 8.50-8.26 (m, 2H), 8.11-8.01 (m, 2H), 7.64-7.31 (m, 6H), 4.43 (d, J=7.0 Hz, 2H), 1.38 (t, J=7.0 Hz, 3H).

Intermediate 59C: (4-((3-fluoropyridin-4-yl)amino)-2-(pyridin-2-yl)pyrrolo[2,1-f][1,2,4]triazin-5-yl) methanol

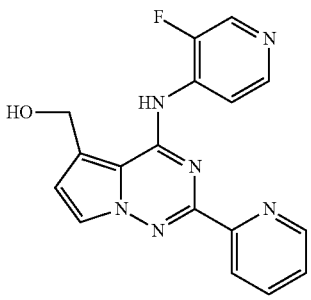 [SMILES: OCc1ccn2nc(-c3ccccn3)nc(Nc3ccncc3F)c12]

To a solution of ethyl 4-((3-fluoropyridin-4-yl)amino)-2-(pyridin-2-yl)pyrrolo[2,1-f][1,2,4]triazine-5-carboxylate (0.3 g, 0.793 mmol) in tetrahydrofuran (5 mL) was added LiAlH$_4$ (1.189 mL, 2.379 mmol) at 0° C. The reaction mixture was slowly warmed to room temperature over 10 min and stirring was continued for another 3 h. The reaction was monitored by LC-MS. Then reaction mixture was quenched with ice cold water (50 mL) and 1.5 N aq. NaOH solution (20 mL). The reaction mixture was concentrated under reduced pressure to remove the volatiles and extracted with ethyl acetate (3×100 mL). The combined organic layer was dried over anhydrous sodium sulfate, filtered and evaporated under reduced pressure to get (4-((3-fluoropyridin-4-yl)amino)-2-(pyridin-2-yl)pyrrolo[2,1-f][1,2,4]triazin-5-yl)methanol 59C (0.24 g, 0.592 mmol, 74.7% yield) as a yellow solid. The crude compound was taken for the next step without purification. LCMS: m/z, 337.2 (M+H); rt 2.49 min; Conditions E.

Intermediate 59D: (4-((3-fluoropyridin-4-yl)amino)-2-(pyridin-2-yl)pyrrolo[2,1-f][1,2,4]triazin-5-yl) methyl methanesulfonate

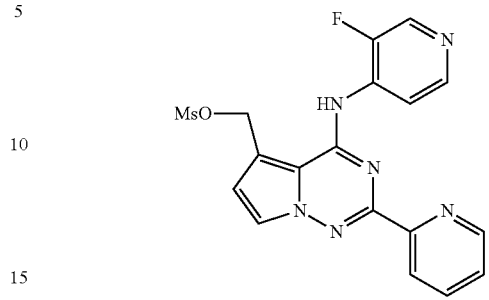

To a solution of (4-((3-fluoropyridin-4-yl)amino)-2-(pyridin-2-yl)pyrrolo[2,1-f][1,2,4]triazin-5-yl)methanol (0.24 g, 0.714 mmol) in DCM (6 mL) was added TEA (0.298 mL, 2.141 mmol) and MsCl (0.067 mL, 0.856 mmol). The reaction mixture was stirred at room temperature for 2 h. The reaction was monitored by LC-MS. The reaction mixture was quenched with ice cold water (20 mL) and extracted with ethyl acetate (3×50 mL). The combined organic layer was dried over anhydrous sodium sulfate, filtered and evaporated under reduced pressure to get crude mesylate 59D (250 mg) as brown gum. The crude compound was taken to the next step without purification. LCMS: m/z, 420.2 (M+Li); rt 2.46 min; Conditions E.

To a solution of 2-(piperazin-1-yl)ethanol (0.022 g, 0.169 mmol) in acetonitrile (6 mL) was added DIPEA (0.089 mL, 0.507 mmol). The reaction mixture was heated up to 55° C. over 5 min and was stirred for 10 min at 55° C. To the reaction mixture was added (4-((3-fluoropyridin-4-yl)amino)-2-(pyridin-2-yl)pyrrolo[2,1-f][1,2,4]triazin-5-yl) methyl methanesulfonate (0.07 g, 0.169 mmol). The reaction mixture was heated up to 85° C. over 5 min. The reaction mixture was continued to stir at the same temperature for 18 h. The reaction mixture was concentrated under reduced pressure to get crude residue which was dissolved in DMF and purified by prep HPLC to obtain 2-(4-((4-((3-fluoropyridin-4-yl)amino)-2-(pyridin-2-yl)pyrrolo[2,1-f][1,2,4]triazin-5-yl)methyl)piperazin-1-yl)ethanol 231 (22 mg, 28.7% yield). LCMS: m/z, 449.2 (M+H); rt 1.40 min; Conditions C, $^1$H NMR: (400 MHz, DMSO-$d_6$) δ 12.30-12.18 (m, 1H), 8.87-8.71 (m, 2H), 8.65 (d, J=3.0 Hz, 1H), 8.46 (d, J=5.5 Hz, 1H), 8.23 (d, J=7.8 Hz, 1H), 8.05-7.90 (m, 2H), 7.56-7.46 (m, 1H), 6.84 (d, J=2.5 Hz, 1H), 4.47-4.30 (m, 1H), 3.87 (s, 2H), 3.47 (t, J=6.3 Hz, 3H), 3.18 (s, 2H), 2.50-2.66 (m, 4H), 2.34 (t, J=6.3 Hz, 3H).

Example 232

(3S)-1-({4-[(3-fluoropyridin-4-yl)amino]-2-(pyridin-2-yl)pyrrolo[2,1-f][1,2,4]triazin-5-yl}methyl)pyrrolidin-3-ol

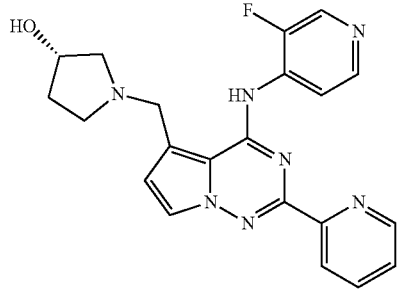 [SMILES: O[C@H]1CCN(Cc2ccn3nc(-c4ccccn4)nc(Nc4ccncc4F)c23)C1]

Example 232 (13 mg, 22.2%) was synthesized employing the procedure described for Example 231 (Scheme 59). LCMS: m/z, 406.1 (M+H); rt 1.56 min; Conditions C. ¹H NMR (400 MHz, DMSO-d₆) δ 13.52-13.21 (m, 1H), 9.02-8.91 (m, 1H), 8.82-8.72 (m, 1H), 8.57 (d, J=3.3 Hz, 1H), 8.41 (d, J=5.5 Hz, 1H), 8.24 (d, J=8.0 Hz, 1H), 8.06-7.96 (m, 1H), 7.91 (s, 1H), 7.57-7.47 (m, 1H), 6.83 (d, J=2.5 Hz, 1H), 4.88-4.69 (m, 1H), 4.39-4.24 (m, 1H), 4.11 (s, 1H), 3.89-3.79 (m, 1H), 3.18 (s, 1H), 2.99-2.72 (m, 2H), 2.47-2.41 (m, 1H), 2.15-1.97 (m, 1H), 1.79-1.63 (m, 1H).

Example 233

(3R)-1-({4-[(3-fluoropyridin-4-yl)amino]-2-(pyridin-2-yl)pyrrolo[2,1-f][1,2,4]triazin-5-yl}methyl)pyrrolidin-3-ol Example 233 (26.1 mg, 37.3%) was synthesized employing the procedure described for Example 231 (Scheme 59). LCMS: m/z, 406.1 (M+H); rt 1.56 min; Condition C, ¹H NMR: (400 MHz, DMSO-d₆) δ 13.43-13.33 (m, 1H), 8.99-8.90 (m, 1H), 8.80-8.70 (m, 1H), 8.57 (d, J=3.3 Hz, 1H), 8.41 (d, J=5.5 Hz, 1H), 8.26-8.19 (m, 1H), 8.04-7.96 (m, 1H), 7.91 (d, J=2.8 Hz, 1H), 7.61-7.48 (m, 1H), 6.82 (d, J=2.5 Hz, 1H), 4.84-4.73 (m, 1H), 4.34-4.24 (m, 1H), 4.15-4.07 (m, 1H), 3.88-3.79 (m, 1H), 2.98-2.73 (m, 3H), 2.45-2.38 (m, 1H), 2.15-1.99 (m, 1H), 1.80-1.66 (m, 1H).

Scheme 60

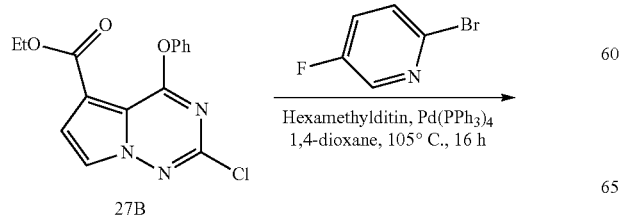

27B

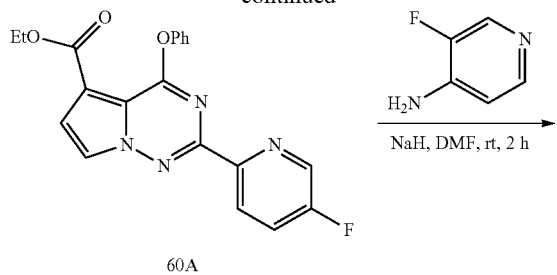

-continued

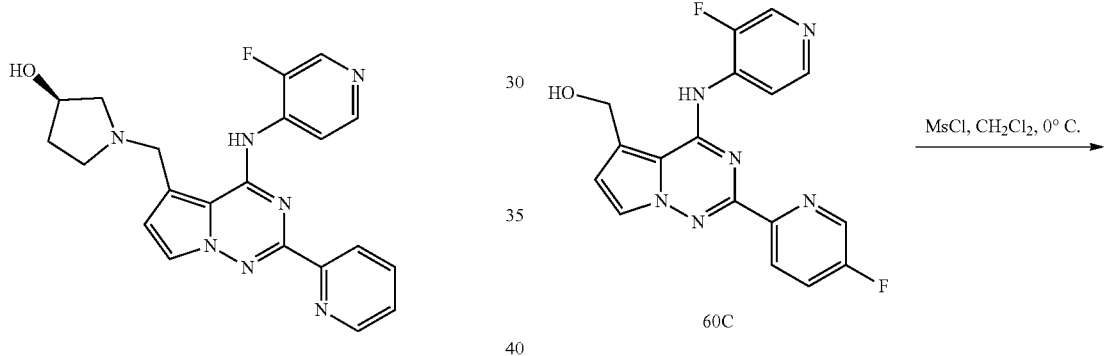

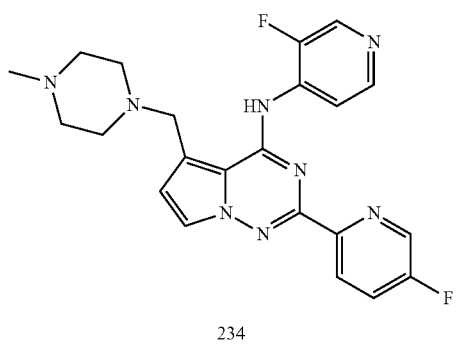 [SMILES: CN1CCN(Cc2ccn3nc(-c4ccc(F)cn4)nc(Nc4ccncc4F)c23)CC1]

234

Example 234

3-fluoro-N-[2-(5-fluoropyridin-2-yl)-5-[(4-methyl-piperazin-1-yl)methyl]pyrrolo[2,1-f][1,2,4]triazin-4-yl]pyridin-4-amine

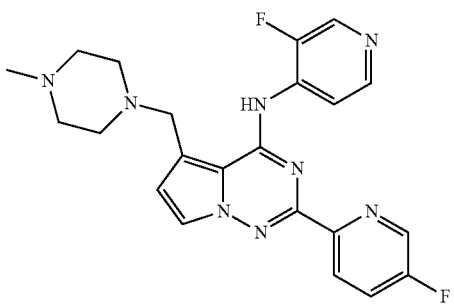 [SMILES: CN1CCN(Cc2ccn3nc(-c4ccc(F)cn4)nc(Nc4ccncc4F)c23)CC1]

Intermediate 60A: ethyl 2-(5-fluoropyridin-2-yl)-4-phenoxypyrrolo[2,1-f][1,2,4]triazine-5-carboxylate

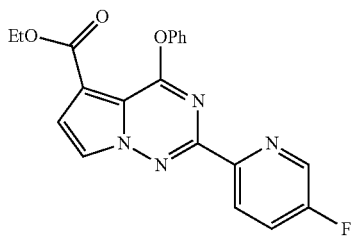 [SMILES: CCOC(=O)c1ccn2nc(-c3ccc(F)cn3)nc(Oc3ccccc3)c12]

To a solution of ethyl 2-chloro-4-phenoxypyrrolo[2,1-f][1,2,4]triazine-5-carboxylate (700 mg, 2.203 mmol) and 2-bromo-5-fluoropyridine (388 mg, 2.203 mmol) in 1,4-dioxane (50 mL) was added hexamethylditin (0.457 mL, 2.203 mmol) and Pd(Ph₃P)₄ (255 mg, 0.220 mmol). The reaction mixture was degassed with argon and was stirred at 100° C. for 18 h. The reaction was monitored by LCMS. The volatiles were removed under reduced pressure to get a brown solid. The crude product was purified by silica gel chromatography (eluted with 10-20% ethyl acetate in petroleum ether) to yield ethyl 2-(5-fluoropyridin-2-yl)-4-phenoxypyrrolo[2,1-f][1,2,4]triazine-5-carboxylate 60A (596 mg, 1.575 mmol, 71.5% yield) as a light yellow solid. LCMS m/z 378.8 (M+H); rt 1.09 min; Conditions I.

Intermediate 60B: Ethyl 2-(5-fluoropyridin-2-yl)-4-((3-fluoropyridin-4-yl)amino)pyrrolo[2,1-f][1,2,4]triazine-5-carboxylate

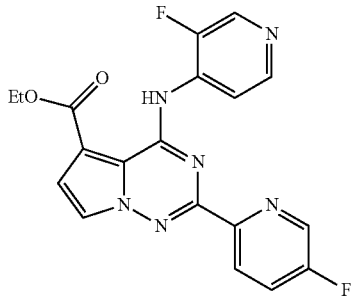

Intermediate 60B (411 mg, 1.037 mmol, 87% yield) was synthesized employing the procedure described for intermediate 57A (Scheme 57). LCMS m/z 397.1 (M+H); rt 1.12 min; Conditions I.

Intermediate 60C: (2-(5-fluoropyridin-2-yl)-4-((3-fluoropyridin-4-yl)amino)pyrrolo[2,1-f][1,2,4]triazin-5-yl)methanol

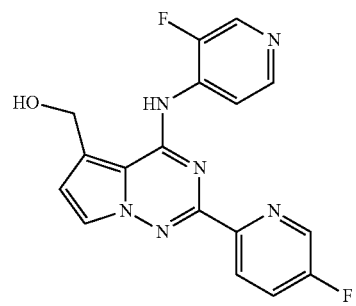 [SMILES: OCc1ccn2nc(-c3ccc(F)cn3)nc(Nc3ccncc3F)c12]

To a solution of ethyl 2-(5-fluoropyridin-2-yl)-4-((3-fluoropyridin-4-yl)amino)pyrrolo[2,1-f][1,2,4]triazine-5-carboxylate (411 mg, 1.037 mmol) in THF (5 mL) was added LAH (1.037 mL, 2.074 mmol) at 0° C. The reaction mixture was then warmed to room temperature and stirred for 5 h. The reaction was monitored by LCMS until compete conversion. The reaction mixture was diluted with 10 mL THF and the resulting mixture was cooled to 0° C. To the cooled mixture was added ethyl acetate (a few drops), followed by H₂O (a few drops) to help with the precipitation of inorganic salts. To the resulting mixture was added Na₂SO₄ and stirred for 2 h. The resulting suspension was filtered through a bed of celite bed and the filtrate was concentrated under reduced pressure to provide 2-chloro-4-phenoxypyrrolo[2,1-f][1,2,4]triazine (0.225 g, 0.635 mmol, 61% yield) as an off white solid. The crude product was used in the next reaction. LCMS m/z 355.1 (M+H); rt 0.82 min; Conditions B.

Intermediate 60D: (2-(5-fluoropyridin-2-yl)-4-((3-fluoropyridin-4-yl)amino)pyrrolo[2,1-f][1,2,4]triazin-5-yl)methyl methanesulfonate

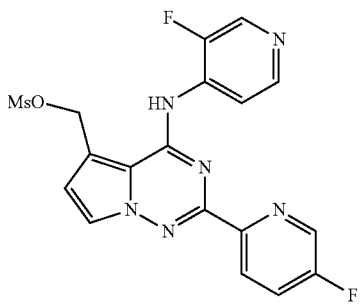 [SMILES: CS(=O)(=O)OCc1ccn2nc(-c3ccc(F)cn3)nc(Nc3ccncc3F)c12]

To stirred solution of (2-(5-fluoropyridin-2-yl)-4-((3-fluoropyridin-4-yl)amino)pyrrolo[2,1-f][1,2,4]triazin-5-yl)methanol (220 mg, 0.621 mmol) in CH₂Cl₂ (5 mL) was added TEA (0.26 mL, 1.863 mmol) at 0° C. and followed by methanesulfonyl chloride (0.072 mL, 0.931 mmol). The reaction mixture was allowed to stir at room temperature for 2 h. The reaction was monitored by TLC. The reaction mixture was diluted with CH₂Cl₂ (10 mL) and added H₂O (10 mL). The organic layer was separated and the aq. layer was extracted with CH₂Cl₂ (10 mL×2). The combined organic layer dried over anhydrous sodium sulfate and evaporated to get crude (2-(5-fluoropyridin-2-yl)-4-((3-fluoropyridin-4-yl)amino)pyrrolo[2,1-f][1,2,4]triazin-5-yl) methyl methanesulfonate 60D (0.255 g, 0.59 mmol, 95% yield). LCMS m/z 438.5 (M+Li); rt 0.74 min; Conditions H.

Example 234 (9.8 mg, 9.6%) was synthesized employing the procedure described for Example 231 (Scheme 59). LCMS: m/z, 437.1 (M+H); rt 1.60 min; Conditions C. ¹H NMR: (400 MHz, DMSO-d6) δ 12.23 (bs, 1H), 8.77-8.78 (m, 2H), 8.74 (d, J=2.8 Hz, 1H), 8.66 (d, J=2.8 Hz, 1H), 8.46 (d, J=5.6 Hz, 1H), 8.28-8.31 (m, 1H), 7.88-7.94 (m, 2H), 6.85 (d, J=2.4 Hz, 1H), 3.87 (s, 2H), 2.33-2.68 (m, 8H), 2.13 (s, 3H) ppm.

Example 235

1-({[2-(5-fluoropyridin-2-yl)-4-[(3-fluoropyridin-4-yl)amino]pyrrolo[2,1-f][1,2,4]triazin-5-yl]methyl}amino)-2-methylpropan-2-ol

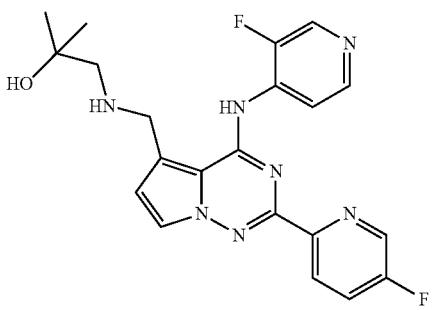 [SMILES: CC(C)(O)CNCc1ccn2nc(-c3ccc(F)cn3)nc(Nc3ccncc3F)c12]

Example 235 (2.0 mg, 2.0%) was synthesized employing the procedure described for Example 231 (Scheme 59): LCMS m/z 426.1 (M+H); rt 1.71 min; Conditions C. ¹H NMR (400 MHz, DMSO-d6) δ 8.92-8.95 (m, 1H), 8.82 (bs, 1H), 8.74 (d, J=2.8 Hz, 1H), 8.55 (d, J=3.6 Hz, 1H), 8.38 (d, J=5.2 Hz, 1H), 8.30-8.33 (m, 1H), 7.86-7.93 (m, 2H), 8.82 (d, J=2.8 Hz, 1H), 4.44 (s, 1H), 4.13 (s, 2H), 1.06 (s, 6H).

Example 236

4-[({4-[(3-fluoropyridin-4-yl)amino]-2-(pyridin-2-yl)pyrrolo[2,1-f][1,2,4]triazin-5-yl}methyl)amino]cyclohexan-1-ol

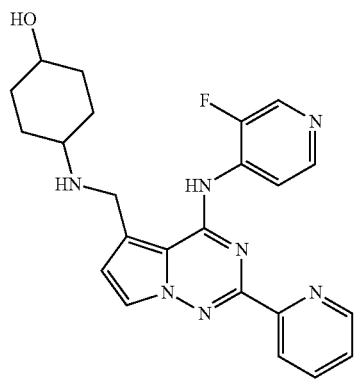 [SMILES: OC1CCC(NCc2ccn3nc(-c4ccccn4)nc(Nc4ccncc4F)c23)CC1]

Example 236 (3.8 mg, 18.16%) was synthesized employing the procedure described for Example 231 (Scheme 59). LCMS m/z 434.3 (M+H); rt 1.31 min; Conditions C. ¹H NMR (400 MHz, DMSO-d₆) δ 9.32-9.15 (m, 2H), 8.96-8.85 (m, 1H), 8.78-8.70 (m, 1H), 8.59-8.51 (m, 1H), 8.44-8.35 (m, 1H), 8.27-8.18 (m, 1H), 8.03-7.93 (m, 1H), 7.88-7.82 (m, 1H), 7.57-7.47 (m, 1H), 6.87-6.77 (m, 1H), 4.53-4.44 (m, 1H), 4.15-4.05 (m, 2H), 1.94-1.85 (m, 2H), 1.81-1.71 (m, 2H), 1.28-1.14 (m, 3H), 1.10-0.99 (m, 2H).

Example 237

(5R,7S)-3-[({4-[(3-fluoropyridin-4-yl)amino]-2-(pyridin-2-yl)pyrrolo[2,1-f][1,2,4]triazin-5-yl}methyl)amino]adamantan-1-ol

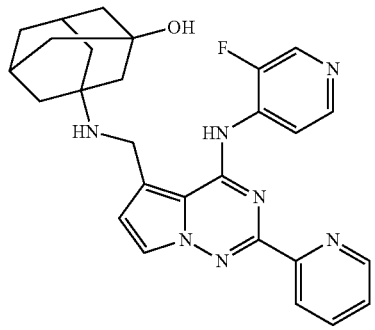 [SMILES: OC12CC3CC(C1)CC(NCc1ccn4nc(-c5ccccn5)nc(Nc5ccncc5F)c14)(C3)C2]

Example 237 (7.7 mg, 32.9%) was synthesized employing the procedure described for Example 231 (Scheme 59). LCMS m/z 486.4 (M+H); rt 1.55 min; Conditions C. ¹H NMR (400 MHz, DMSO-d₆) δ 9.10-8.93 (m, 1H), 8.78-8.65 (m, 1H), 8.61-8.55 (m, 1H), 8.44-8.36 (m, 1H), 8.25-8.16 (m, 1H), 8.02-7.93 (m, 1H), 7.87-7.80 (m, 1H), 7.55-7.44 (m, 1H), 6.85-6.76 (m, 1H), 4.51-4.44 (m, 1H), 4.14-4.05 (m, 2H), 2.15-2.06 (m, 2H), 1.56 (br. s., 6H), 1.48-1.35 (m, 6H).

Example 238

3-fluoro-N-(5-{[(piperidin-4-ylmethyl)amino]methyl}-2-(pyridin-2-yl)pyrrolo[2,1-f][1,2,4]triazin-4-yl)pyridin-4-amine

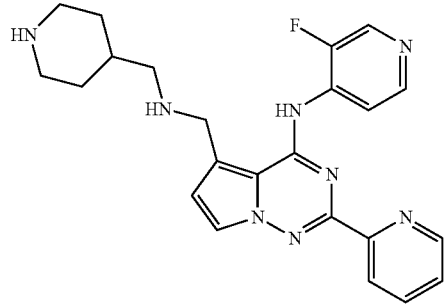 [SMILES: Fc1cnccc1Nc1nc(-c2ccccn2)nn2ccc(CNCC3CCNCC3)c12]

Example 238 (3.4 mg, 13.2%) was synthesized employing the procedure described for Example 231 (Scheme 59). LCMS m/z 433.2 (M+H); rt 1.35 min; Conditions C, ¹H NMR (400 MHz, DMSO-d₆) δ 9.30-9.08 (m, 2H), 9.02-8.89

(m, 1H), 8.80-8.70 (m, 1H), 8.61-8.52 (m, 1H), 8.46-8.37 (m, 1H), 8.30-8.19 (m, 1H), 8.09-7.95 (m, 1H), 7.91-7.85 (m, 1H), 7.61-7.46 (m, 1H), 6.88-6.77 (m, 1H), 4.14-4.00 (m, 2H), 3.04-2.92 (m, 2H), 1.89 (s, 2H), 1.75-1.60 (m, 3H), 1.28-1.20 (m, 1H), 1.11-0.94 (m, 2H).

Example 239

1-[({4-[(3-fluoropyridin-4-yl)amino]-2-(pyridin-2-yl)pyrrolo[2,1-f][1,2,4]triazin-5-yl}methyl)amino]propan-2-ol

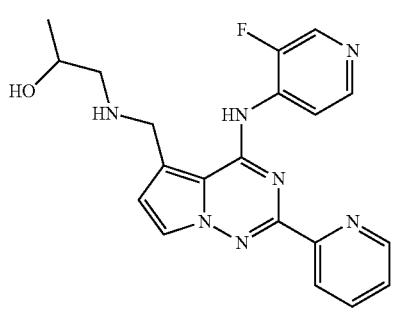 [SMILES: CC(O)CNCc1ccn2nc(-c3ccccn3)nc(Nc3ccncc3F)c12]

Example 239 (6.8 mg, 35.8%) was synthesized employing the procedure described for Example 231 (Scheme 59). LCMS m/z 394.3 (M+H); rt 1.30 min; Conditions C. $^1$H NMR (400 MHz, DMSO-d$_6$) δ 9.14-9.00 (m, 1H), 8.98-8.91 (m, 1H), 8.81-8.70 (m, 1H), 8.59-8.52 (m, 1H), 8.43-8.37 (m, 1H), 8.28-8.20 (m, 1H), 8.05-7.95 (m, 1H), 7.91-7.84 (m, 1H), 7.57-7.47 (m, 1H), 6.85-6.78 (m, 1H), 4.73-4.65 (m, 1H), 4.14-4.04 (m, 2H), 3.87-3.76 (m, 1H), 2.64-2.56 (m, 2H), 1.28-1.18 (m, 1H), 1.03 (d, J=6.5 Hz, 3H).

Example 240

1-{2-[({4-[(3-fluoropyridin-4-yl)amino]-2-(pyridin-2-yl)pyrrolo[2,1-f][1,2,4]triazin-5-yl}methyl)amino]ethyl}cyclopentan-1-ol

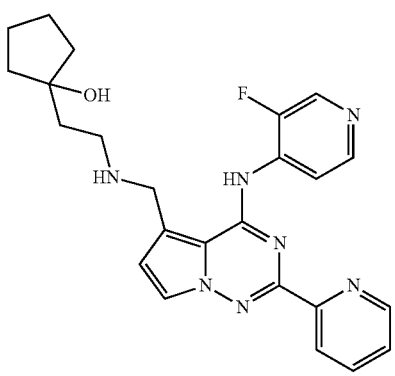 [SMILES: OC1(CCNCc2ccn3nc(-c4ccccn4)nc(Nc4ccncc4F)c23)CCCC1]

Example 240 (6.5 mg, 30.1%) was synthesized employing the procedure described for Example 231 (Scheme 59). LCMS m/z 448.3 (M+H); rt 1.59 min; Conditions C. $^1$H NMR (400 MHz, DMSO-d$_6$) δ 9.72-9.49 (m, 2H), 8.98-8.88 (m, 1H), 8.80-8.69 (m, 1H), 8.58-8.48 (m, 1H), 8.40-8.33 (m, 1H), 8.29-8.21 (m, 1H), 8.05-7.93 (m, 1H), 7.89-7.80 (m, 1H), 7.58-7.46 (m, 1H), 6.86-6.75 (m, 1H), 4.13-4.04 (m, 2H), 2.83-2.73 (m, 2H), 1.79-1.71 (m, 2H), 1.69-1.60 (m, 5H), 1.55-1.44 (m, 3H), 1.41-1.32 (m, 3H).

Example 241

3-fluoro-N-(5-{[(1-methylcyclobutyl)amino]methyl}-2-(pyridin-2-yl)pyrrolo[2,1-f][1,2,4]triazin-4-yl)pyridin-4-amine

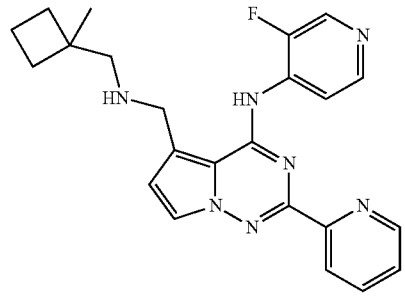 [SMILES: CC1(CNCc2ccn3nc(-c4ccccn4)nc(Nc4ccncc4F)c23)CCC1]

Example 241 (6.0 mg, 30.8%) was synthesized employing the procedure described for Example 231 (Scheme 59). LCMS m/z 404.3 (M+H); rt 1.95 min; Conditions C. $^1$H NMR (400 MHz, DMSO-d$_6$) δ 9.16-9.00 (m, 2H), 8.77-8.66 (m, 2H), 8.60-8.53 (m, 1H), 8.43-8.36 (m, 1H), 8.27-8.18 (m, 1H), 8.05-7.92 (m, 1H), 7.90-7.84 (m, 1H), 7.57-7.43 (m, 1H), 6.89-6.79 (m, 1H), 3.99-3.90 (m, 2H), 2.22-2.08 (m, 2H), 1.91-1.80 (m, 2H), 1.77-1.60 (m, 2H), 1.26 (s, 3H).

Example 242

3-fluoro-N-(5-{[(4-methyloxan-4-yl)amino]methyl}-2-(pyridin-2-yl)pyrrolo[2,1-f][1,2,4]triazin-4-yl)pyridin-4-amine

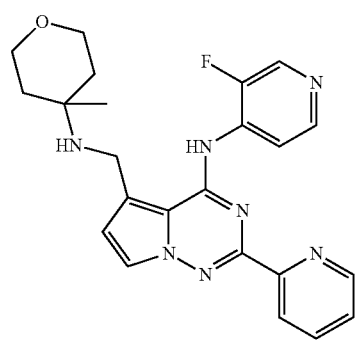 [SMILES: CC1(NCc2ccn3nc(-c4ccccn4)nc(Nc4ccncc4F)c23)CCOCC1]

Example 242 (5.3 mg, 25.3%) was synthesized employing the procedure described for Example 231 (Scheme 59). LCMS m/z 434.3 (M+H); rt 1.53 min; Conditions C. $^1$H NMR (400 MHz, DMSO-d$_6$) δ 8.79-8.70 (m, 5H), 8.68-8.57 (m, 1H), 8.47-8.38 (m, 1H), 8.26-8.17 (m, 1H), 8.04-7.94 (m, 1H), 7.90-7.84 (m, 1H), 7.56-7.45 (m, 1H), 6.89-6.77 (m, 1H), 4.14-4.04 (m, 2H), 3.74-3.64 (m, 2H), 3.53-3.39 (m, 2H), 1.76-1.60 (m, 2H), 1.57-1.45 (m, 2H), 1.18 (s, 3H).

Example 243

1-({4-[(3-fluoropyridin-4-yl)amino]-2-(pyridin-2-yl)pyrrolo[2,1-f][1,2,4]triazin-5-yl}methyl)piperidin-4-ol

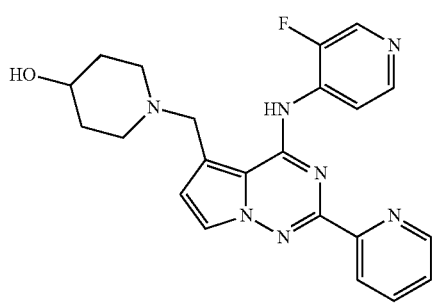 [SMILES: OC1CCN(Cc2ccn3nc(-c4ccccn4)nc(Nc4ccncc4F)c23)CC1]

Example 243 (7.1 mg, 35.1%) was synthesized employing the procedure described for Example 231 (Scheme 59). LCMS: m/z, 420.3 (M+H); rt 1.36 min; Conditions C. $^1$H NMR (400 MHz, DMSO-d$_6$) δ 12.64-12.44 (m, 1H), 8.89-8.71 (m, 2H), 8.67-8.60 (m, 1H), 8.50-8.40 (m, 1H), 8.28-8.19 (m, 1H), 8.03-7.89 (m, 2H), 7.60-7.48 (m, 1H), 6.89-6.78 (m, 1H), 4.69-4.61 (m, 1H), 3.91-3.80 (m, 2H), 3.62-3.50 (m, 1H), 2.96-2.80 (m, 3H), 2.29-2.15 (m, 2H), 1.83-1.68 (m, 1H), 1.55-1.39 (m, 12H).

Example 244

{1-[({4-[(3-fluoropyridin-4-yl)amino]-2-(pyridin-2-yl)pyrrolo[2,1-f][1,2,4]triazin-5-yl}methyl)amino]cyclopentyl}methanol

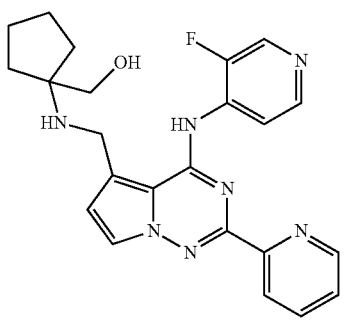 [SMILES: OCC1(NCc2ccn3nc(-c4ccccn4)nc(Nc4ccncc4F)c23)CCCC1]

Example 244 (4.9 mg, 23.4%) was synthesized employing the procedure described for Example 231 (Scheme 59). LCMS m/z 434.3 (M+H); rt 1.50 min; Conditions C, $^1$H NMR (400 MHz, DMSO-d$_6$) δ 8.83-8.66 (m, 3H), 8.61-8.53 (m, 1H), 8.46-8.35 (m, 2H), 8.20-8.10 (m, 1H), 8.01-7.90 (m, 1H), 7.86-7.79 (m, 1H), 7.52-7.41 (m, 1H), 6.88-6.73 (m, 1H), 4.95-4.80 (m, 1H), 4.12-3.98 (m, 2H), 3.46-3.35 (m, 2H), 1.67-1.41 (m, 8H).

Example 245

4-N-({4-[(3-fluoropyridin-4-yl)amino]-2-(pyridin-2-yl)pyrrolo[2,1-f][1,2,4]triazin-5-yl}methyl)-1-N,1-N-dimethylcyclohexane-1,4-diamine

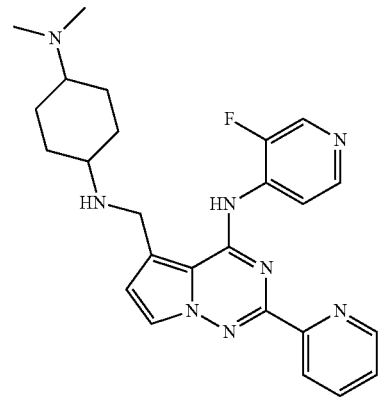 [SMILES: CN(C)C1CCC(NCc2ccn3nc(-c4ccccn4)nc(Nc4ccncc4F)c23)CC1]

Example 245 (6.0 mg, 27%) was synthesized employing the procedure described for Example 231 (Scheme 59). LCMS m/z 461.2 (M+H); rt 1.38 min; Condition C. $^1$H NMR (400 MHz, DMSO-d$_6$) δ 9.40-9.22 (m, 2H), 8.96-8.85 (m, 1H), 8.78-8.70 (m, 1H), 8.59-8.50 (m, 1H), 8.39-8.32 (m, 1H), 8.28-8.17 (m, 1H), 8.03-7.93 (m, 1H), 7.88-7.77 (m, 1H), 7.58-7.43 (m, 1H), 6.88-6.73 (m, 1H), 4.16-4.03 (m, 2H), 2.10 (s, 6H), 1.90 (s, 4H), 1.78-1.69 (m, 2H), 1.26-1.02 (m, 4H).

Example 246

3-fluoro-N-[5-({[3-(morpholin-4-yl)propyl]amino}methyl)-2-(pyridin-2-yl)pyrrolo[2,1-f][1,2,4]triazin-4-yl]pyridin-4-amine

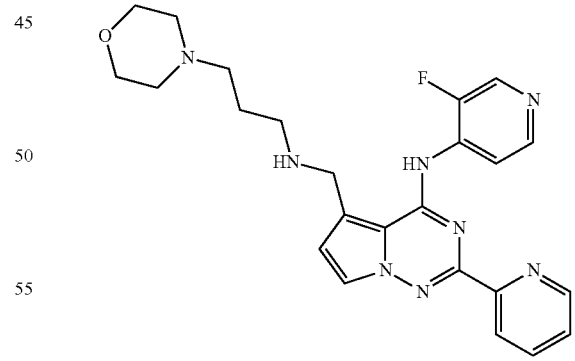

Example 246 (7.4 mg, 33.2%) was synthesized employing the procedure described for Example 231 (Scheme 59). LCMS m/z 463.3 (M+H); rt 1.38 min; Condition C. $^1$H NMR (400 MHz, DMSO-d$_6$) δ 9.62-9.17 (m, 2H), 9.04-8.89 (m, 1H), 8.81-8.70 (m, 2H), 8.57-8.46 (m, 2H), 8.38-8.13 (m, 1H), 7.86 (s, 1H), 7.58-7.37 (m, 1H), 6.94-6.63 (m, 1H), 4.08 (s, 2H), 3.60-3.38 (m, 2H), 2.75-2.58 (m, 2H), 2.40-2.10 (m, 4H), 1.89 (s, 4H), 1.78-1.54 (m, 2H).

Example 247

3-fluoro-N-(5-{[(oxolan-2-ylmethyl)amino]methyl}-2-(pyridin-2-yl)pyrrolo[2,1-f][1,2,4]triazin-4-yl)pyridin-4-amine

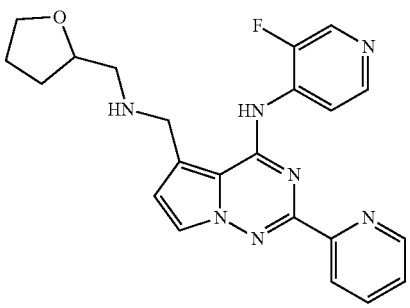 [SMILES: Fc1cnccc1Nc1nc(-c2ccccn2)nn2ccc(CNCC3CCCO3)c12]

Example 247 (6.2 mg, 30.6%) was synthesized employing the procedure described for Example 231 (Scheme 59). LCMS m/z 420.3 (M+H); rt 1.61 min; Conditions C. $^1$H NMR (400 MHz, DMSO-d$_6$) δ 9.15-8.99 (m, 2H), 8.96-8.88 (m, 1H), 8.80-8.71 (m, 1H), 8.56 (d, J=3.0 Hz, 1H), 8.40 (s, 1H), 8.28-8.20 (m, 1H), 8.06-7.95 (m, 1H), 7.88 (d, J=2.5 Hz, 1H), 7.56-7.46 (m, 1H), 6.81 (s, 1H), 4.19-4.03 (m, 2H), 4.01-3.89 (m, 1H), 3.72-3.62 (m, 1H), 3.58-3.50 (m, 1H), 2.71-2.60 (m, 2H), 1.95-1.83 (m, 1H), 1.81-1.67 (m, 2H), 1.49-1.36 (m, 1H).

Example 248

3-fluoro-N-{2-[5-(trifluoromethyl)pyridin-2-yl]pyrrolo[2,1-f][1,2,4]triazin-4-yl}pyridin-4-amine

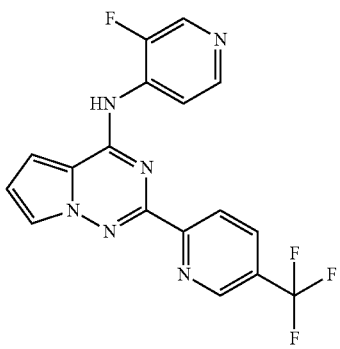 [SMILES: Fc1cnccc1Nc1nc(-c2ccc(C(F)(F)F)cn2)nn2cccc12]

Example 248 (22.2 mg, 0.059 mmol, 70.4% yield) was synthesized employing the procedure described for Example 1 (Scheme 1). LCMS m/z 375 (M+H); rt 1.61 min; Conditions F. $^1$H NMR (400 MHz, DMSO-d6) δ 13.71-13.37 (m, 1H), 9.25 (dd, J=5.5, 7.2 Hz, 1H), 8.82 (d, J=3.4 Hz, 1H), 8.66 (d, J=5.6 Hz, 1H), 8.35-8.27 (m, 1H), 8.19 (d, J=2.4 Hz, 1H), 8.13 (t, J=7.7 Hz, 1H), 7.64 (d, J=7.6 Hz, 1H), 7.07 (d, J=2.7 Hz, 1H), 4.55 (dt, J=3.2, 6.2 Hz, 1H), 4.38 (d, J=13.7 Hz, 1H), 4.10 (d, J=13.7 Hz, 1H), 3.23-2.97 (m, 3H), 2.71 (dd, J=2.8, 10.4 Hz, 1H), 2.38-2.25 (m, 1H), 2.14 (s, 2H), 2.04-1.92 (m, 1H).

Example 249

3-fluoro-N-[2-(2-methoxy-1,3-thiazol-4-yl)pyrrolo[2,1-f][1,2,4]triazin-4-yl]pyridin-4-amine

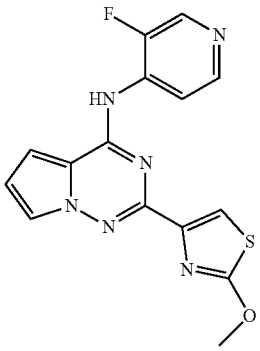 [SMILES: COc1nc(-c2nc(Nc3ccncc3F)c3cccn3n2)cs1]

Example 249 (20.2 mg, 0.057 mmol, 61.2% yield) was synthesized employing the procedure described for Example 1 (Scheme 1). LCMS m/z 343 (M+H); rt 0.97 min; Conditions G. $^1$H NMR (400 MHz, DMSO-d6) δ 13.71-13.37 (m, 1H), 9.25 (dd, J=5.5, 7.2 Hz, 1H), 8.82 (d, J=3.4 Hz, 1H), 8.66 (d, J=5.6 Hz, 1H), 8.35-8.27 (m, 1H), 8.19 (d, J=2.4 Hz, 1H), 8.13 (t, J=7.7 Hz, 1H), 7.64 (d, J=7.6 Hz, 1H), 7.07 (d, J=2.7 Hz, 1H), 4.55 (dt, J=3.2, 6.2 Hz, 1H), 4.38 (d, J=13.7 Hz, 1H), 4.10 (d, J=13.7 Hz, 1H), 3.23-2.97 (m, 3H), 2.71 (dd, J=2.8, 10.4 Hz, 1H), 2.38-2.25 (m, 1H), 2.14 (s, 2H), 2.04-1.92 (m, 1H).

Scheme 61

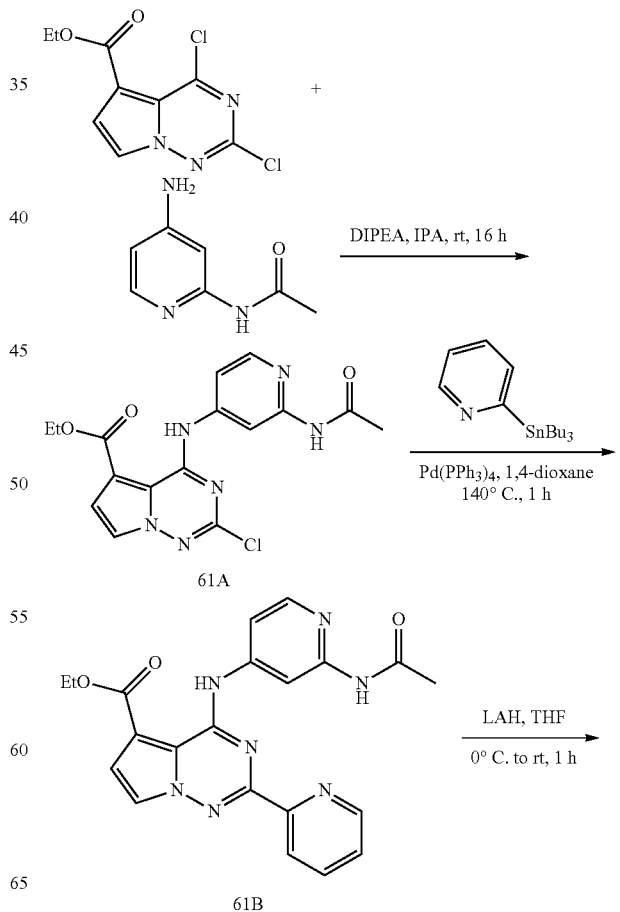

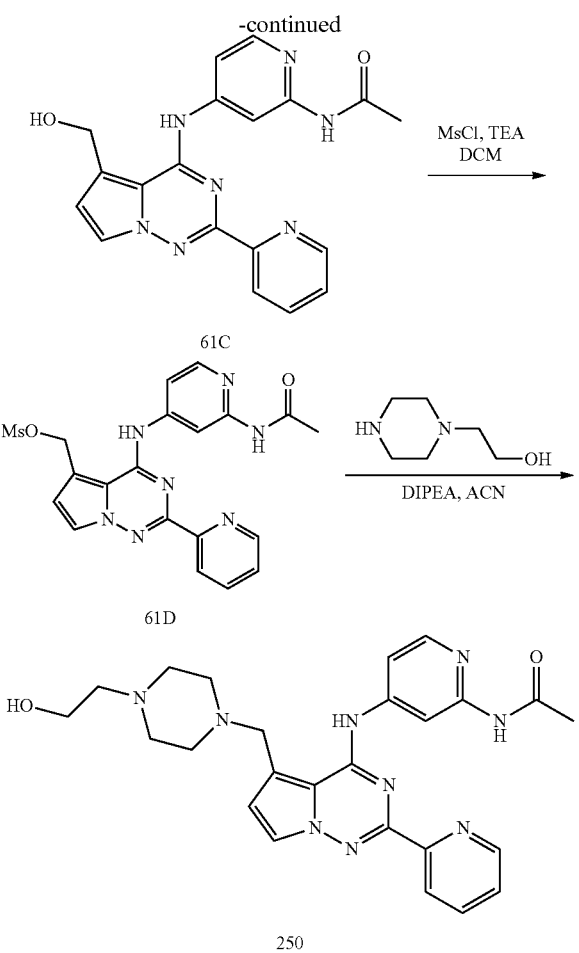

61C

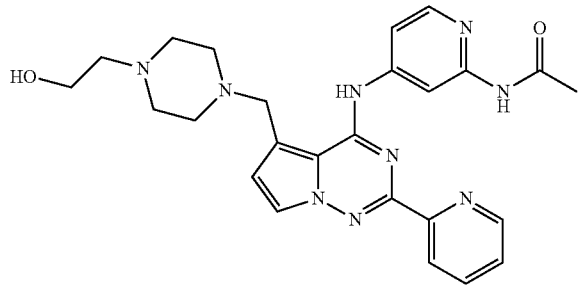 [SMILES: CC(=O)Nc1cc(Nc2nc(-c3ccccn3)nn3ccc(CN4CCN(CCO)CC4)c23)ccn1]

61D

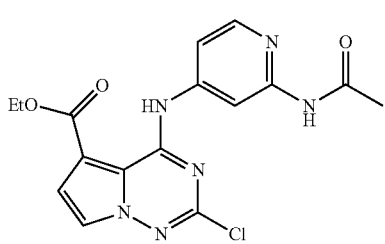 [SMILES: CCOC(=O)c1ccn2nc(Cl)nc(Nc3ccnc(NC(C)=O)c3)c12]

250

Example 250

N-{4-[(5-{[4-(2-hydroxyethyl)piperazin-1-yl]methyl}-2-(pyridin-2-yl)pyrrolo[2,1-f][1,2,4]triazin-4-yl)amino]pyridin-2-yl}acetamide Intermediate 61A: Ethyl 4-((2-acetamidopyridin-4-yl)amino)-2-chloropyrrolo[2,1-f][1,2,4]triazine-5-carboxylate To a stirred solution of ethyl 2,4-dichloropyrrolo[2,1-f][1,2,4]triazine-5-carboxylate (1 g, 3.85 mmol) and N-(4-aminopyridin-2-yl)acetamide (0.872 g, 5.77 mmol) in 2-propanol (10 mL) was added DIPEA (2.015 mL, 11.54 mmol) and stirred at 50° C. for 3 h. The resulting suspension was filtered. The residue was taken in 5% methanol in DCM, washed with aqueous sodium bicarbonate to get ethyl 4-((2-acetamidopyridin-4-yl)amino)-2-chloropyrrolo[2,1-f][1,2,4]triazine-5-carboxylate (0.7 g, 1.868 mmol, 48.6% yield) as a white solid. LCMS m/z 375.2 (M+H); rt 2.69 min; Conditions J.

Intermediate 61B: Ethyl 4-((2-acetamidopyridin-4-yl)amino)-2-(pyridin-2-yl)pyrrolo[2,1-f][1,2,4]triazine-5-carboxylate

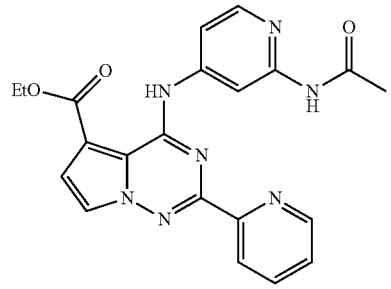 [SMILES: CCOC(=O)c1ccn2nc(-c3ccccn3)nc(Nc3ccnc(NC(C)=O)c3)c12]

To a stirred solution of ethyl 4-((2-acetamidopyridin-4-yl)amino)-2-chloropyrrolo[2,1-f][1,2,4]triazine-5-carboxylate (0.35 g, 0.934 mmol) in dioxane (8 mL) was added 2-(tributylstannyl)pyridine (0.365 mL, 1.121 mmol) and the reaction mixture was purged with nitrogen for 5 mins. Then Pd(PPh$_3$)$_4$ (0.108 g, 0.093 mmol) was added and again purged with nitrogen for 10 minutes. The resulting mixture was heated at 140° C. for 1 h under microwave irradiations. The reaction mixture was filtered on celite bed and washed with ethyl acetate (250 mL). The filtrate was concentrated. The residue was purified by silica gel chromatography (eluted with 1-3% methanol in chloroform) to yield ethyl 4-((2-acetamidopyridin-4-yl)amino)-2-(pyridin-2-yl)pyrrolo[2,1-f][1,2,4]triazine-5-carboxylate 61B (0.31 g, 1.485 mmol, 79% yield) as an white solid. LCMS m/z 418.0 (M+H); rt 2.43 min; Conditions J.

Intermediate 61C: N-(4-((5-(hydroxymethyl)-2-(pyridin-2-yl)pyrrolo[2,1-f][1,2,4]triazin-4-yl)amino)pyridin-2-yl)acetamide

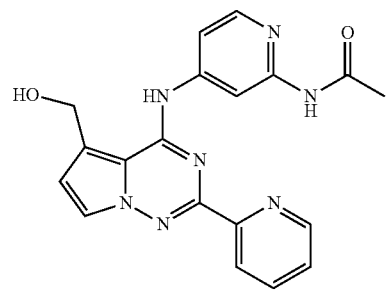 [SMILES: CC(=O)Nc1cc(Nc2nc(-c3ccccn3)nn3ccc(CO)c23)ccn1]

To a stirred solution of ethyl 4-((2-acetamidopyridin-4-yl)amino)-2-(pyridin-2-yl)pyrrolo[2,1-f][1,2,4]triazine-5- carboxylate (0.4 g, 0.958 mmol) in THF (20 mL) was dropwise added LAH (0.599 ml, 1.437 mmol) (2.4 molar in THF) at −78° C. The reaction mixture was then stirred at 0° C. for 1 h. The reaction mixture was quenched with saturated aqueous sodium sulphate and extracted with ethyl acetate (100 mL). the organic layer was dried over sodium sulphate and concentrated to get N-(4-((5-(hydroxymethyl)-2-(pyridin-2-yl)pyrrolo[2,1-f][1,2,4]triazin-4-yl)amino)pyridin-2-yl)acetamide 61C (0.25 g, 0.533 mmol, 55.6% yield) as a white solid. LCMS m/z 376.2 (M+H); rt 2.48 min; Conditions J.

Intermediate 61D: (4-((2-acetamidopyridin-4-yl)amino)-2-(pyridin-2-yl)pyrrolo[2,1-f][1,2,4]triazin-5-yl)methyl methanesulfonate

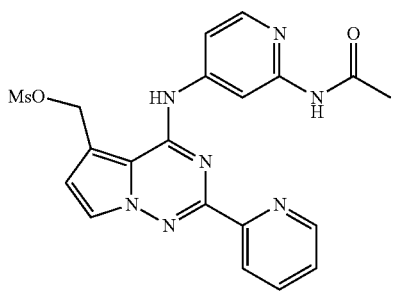 [SMILES: CC(=O)Nc1cc(Nc2nc(-c3ccccn3)nn3ccc(COS(C)(=O)=O)c23)ccn1]

To a stirred solution of N-(4-((5-(hydroxymethyl)-2-(pyridin-2-yl)pyrrolo[2,1-f][1,2,4]triazin-4-yl)amino)pyridin-2-yl)acetamide (0.1 g, 0.266 mmol) in DCM (5 mL) was added TEA (0.111 mL, 0.799 mmol) at 0° C. and stirred for 5 minutes. To the reaction mixture was added mesylchloride (0.025 mL, 0.320 mmol) and stirred at room temperature for 1 h. The reaction mixture was diluted with DCM (100 mL) and washed with aqueous sodium bicarbonate. The organic layer was dried over sodium sulphate and concentrated to get crude (4-((2-acetamidopyridin-4-yl)amino)-2-(pyridin-2-yl)pyrrolo[2,1-f][1,2,4]triazin-5-yl)methyl methanesulfonate 61D (100 mg) as a yellow oil. (parent ion was not observed in LCMS).

To a stirred solution of 2-(piperazin-1-yl)ethanol (0.014 g, 0.110 mmol) in acetonitrile (2 mL) was added DIPEA (0.039 mL, 0.221 mmol) and heated at 55° C. for 10 min. To the mixture was added dropwise, a solution of (4-((2-acetamidopyridin-4-yl)amino)-2-(pyridin-2-yl)pyrrolo[2,1-f][1,2,4]triazin-5-yl)methyl methane sulfonate (0.05 g, 0.110 mmol) in MeCN (1 mL). The resulting reaction mixture was heated at 80° C. for 16 h. The crude product was purified by preparative HPLC to provide N-(4-((5-((4-(2-hydroxy ethyl)piperazin-1-yl)methyl)-2-(pyridin-2-yl)pyrrolo[2,1-f][1,2,4]triazin-4-yl)amino)pyridin-2-yl)acetamide 250 (5 mg, 9.21%). LCMS m/z 488.2 (M+H); rt 1.95 min; Conditions C. $^1$H NMR (400 MHz, DMSO-d$_6$) δ 10.41-10.47 (m, 1H), 8.67 (d, J=1.44 Hz, 2H) 8.46-8.53 (m, 1H) 8.28 (d, J=5.65 Hz, 1H) 7.92-8.00 (m, 1H) 7.88 (d, J=2.57 Hz, 1H) 7.76-7.84 (m, 1H) 7.46-7.56 (m, 1H) 6.80 (d, J=2.57 Hz, 1H) 3.87 (s, 2H) 2.6-2.7 (m, 2H) 2.3-2.2 (m, 3) 2.13 (s, 3H) 1.84 (s, 9H).

Scheme 62

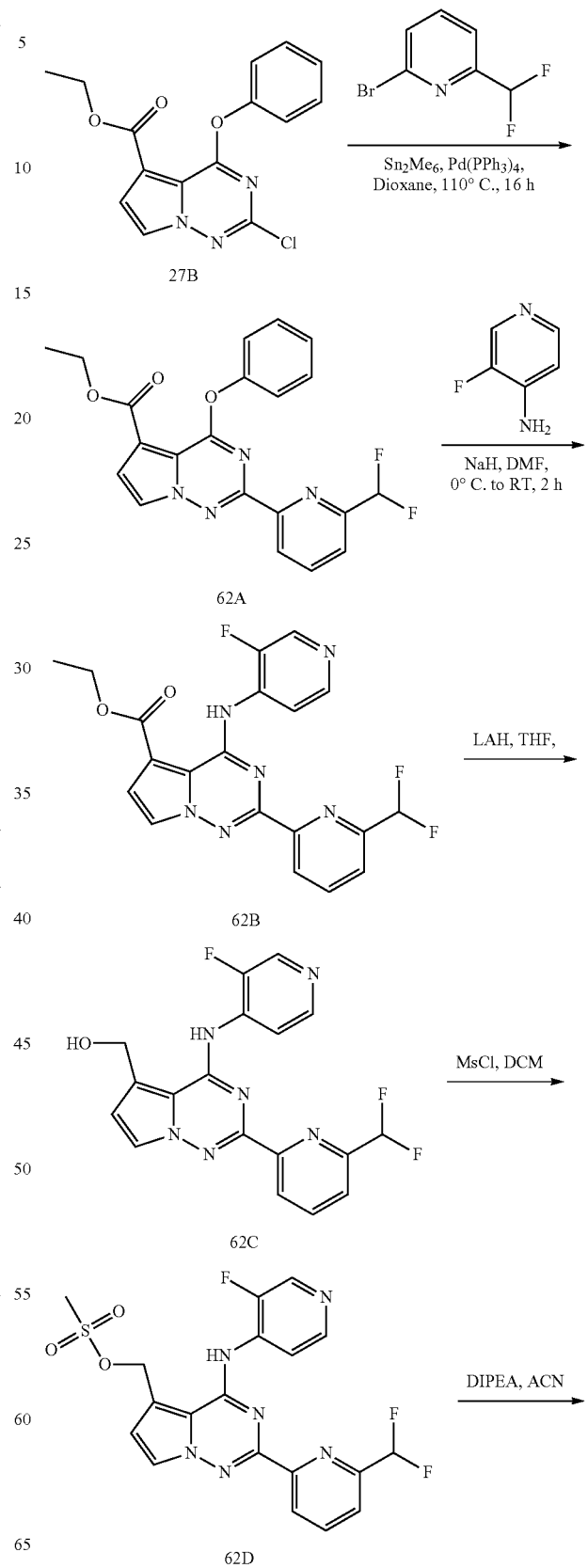

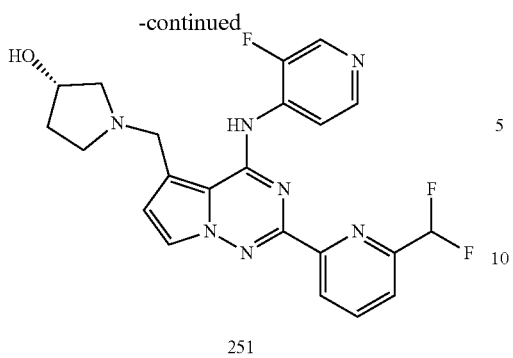

251

Example 251

(3S)-1-({2-[6-(difluoromethyl)pyridin-2-yl]-4-[(3-fluoropyridin-4-yl)amino]pyrrolo[2,1-f][1,2,4]triazin-5-yl}methyl)pyrrolidin-3-ol

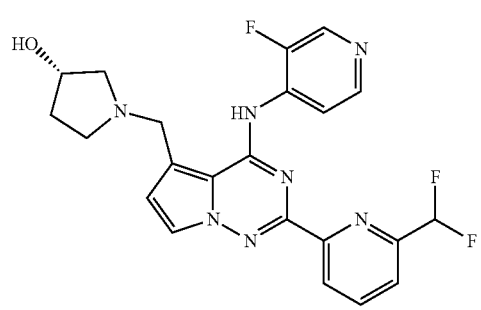 [SMILES: O[C@H]1CCN(Cc2ccn3nc(-c4cccc(C(F)F)n4)nc(Nc4ccncc4F)c23)C1]

Intermediate 62A: ethyl 2-(6-(difluoromethyl)pyridin-2-yl)-4-phenoxypyrrolo[2,1-f][1,2,4]triazine-5-carboxylate

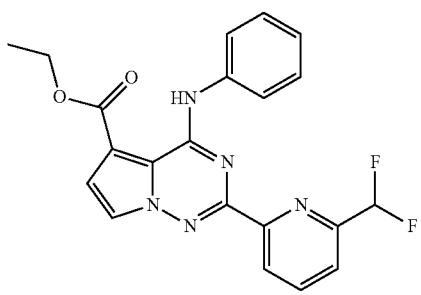 [SMILES: CCOC(=O)c1ccn2nc(-c3cccc(C(F)F)n3)nc(Nc3ccccc3)c12]

To a solution of ethyl 2-chloro-4-phenoxypyrrolo[2,1-f][1,2,4]triazine-5-carboxylate (400 mg, 1.259 mmol), 2-bromo-6-(difluoromethyl)pyridine (262 mg, 1.259 mmol), and hexamethylditin (0.261 mL, 1.259 mmol) in dioxane (10 mL) was added Pd(PPh$_3$)$_4$ (145 mg, 0.126 mmol) in a sealed tube. The reaction mixture was degassed with argon and stirred at 110° C. for 16 h. TLC indicated complete consumption of starting material. The reaction mixture was filtered through celite pad and the filtrate was concentrated. The residue was purified by silica gel chromatography (eluted with 80% ethyl acetate in petroleum ether) to yield ethyl 2-(6-(difluoromethyl)pyridin-2-yl)-4-phenoxypyrrolo[2,1-f][1,2,4]triazine-5-carboxylate 62A (520 mg, 1.267 mmol, 20.8% yield). LCMS m/z 411.0 (M+H); rt 3.31 min; Conditions E.

Intermediate 62B: ethyl 2-(6-(difluoromethyl)pyridin-2-yl)-4-((3-fluoropyridin-4-yl)amino)pyrrolo[2,1-f][1,2,4]triazine-5-carboxylate

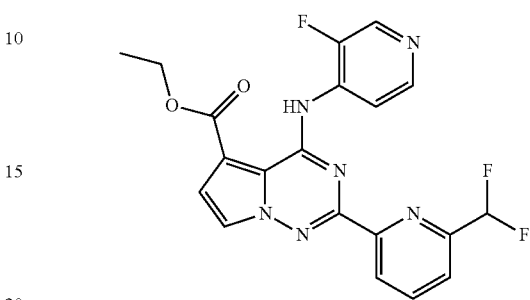

Intermediate 62B (460 mg, 0.945 mmol, 74.6% yield) was synthesized employing the procedure described for intermediate 57A (Scheme 57). LCMS m/z 429.2 (M+H); rt 1.00 min; Conditions A.

Intermediate 62C: (2-(6-(difluoromethyl)pyridin-2-yl)-4-((3-fluoropyridin-4-yl)amino)pyrrolo[2,1-f][1,2,4]triazin-5-yl)methanol

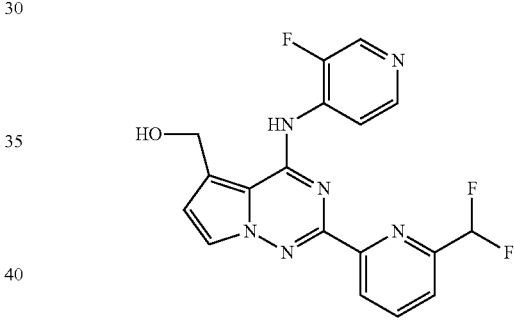

Intermediate 62C was synthesized employing the procedure described for intermediate 60C (Scheme 60). The crude residue was purified by silicagel column chromatography (eluted with 50% ethyl acetate in petroleum ether) to give (2-(6-(difluoromethyl)pyridin-2-yl)-4-((3-fluoropyridin-4-yl)amino)pyrrolo[2,1-f][1,2,4]triazin-5-yl)methanol 62C (160 mg, 0.414 mmol, 89% yield). LCMS m/z 387.1 (M+H); rt 0.68 min; Conditions A.

Intermediate 62D: (2-(6-(difluoromethyl)pyridin-2-yl)-4-((3-fluoropyridin-4-yl)amino)pyrrolo[2,1-f][1,2,4]triazin-5-yl)methyl methanesulfonate

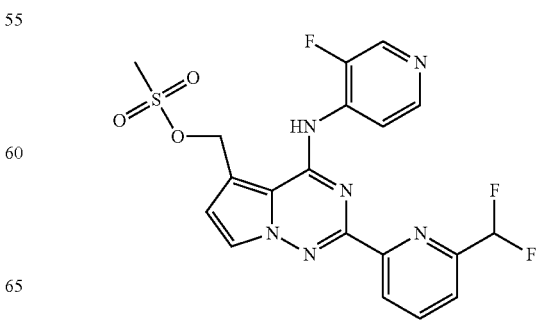

Intermediate 62D (100 mg crude) was synthesized employing the procedure described for intermediate 59D (Scheme 59). LCMS m/z 470.1 (M+H); rt 0.64 min; Conditions A.

Example 251 (5 mg, 7.1%) was synthesized employing the procedure described for Example 231 (Scheme 59). LCMS m/z 456.2 (M+H); rt 1.91 min; Conditions C. $^1$H NMR (400 MHz, DMSO-$d_6$) δ 13.70 (br. s., 1H), 9.27 (dd, J=5.5, 7.2 Hz, 1H), 8.83 (d, J=3.2 Hz, 1H), 8.70-8.63 (m, 2H), 8.50-8.41 (m, 1H), 8.22 (d, J=2.7 Hz, 1H), 8.09 (d, J=7.8 Hz, 1H), 7.53-7.20 (m, 1H), 7.10 (d, J=2.7 Hz, 1H), 4.55 (tt, J=3.2, 6.2 Hz, 1H), 4.39 (d, J=13.7 Hz, 1H), 4.11 (d, J=13.9 Hz, 1H), 3.23-2.98 (m, 3H), 2.72 (dd, J=2.9, 10.8 Hz, 1H), 2.37-2.25 (m, 1H), 1.99 (dd, J=5.4, 8.1 Hz, 1H).

Scheme 63

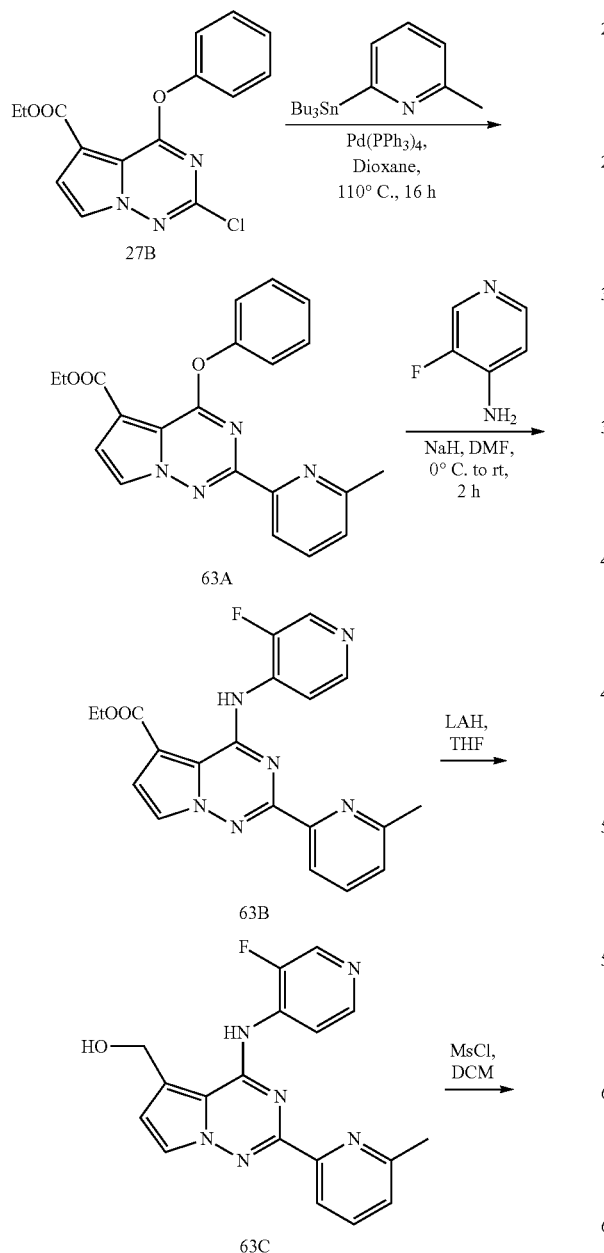

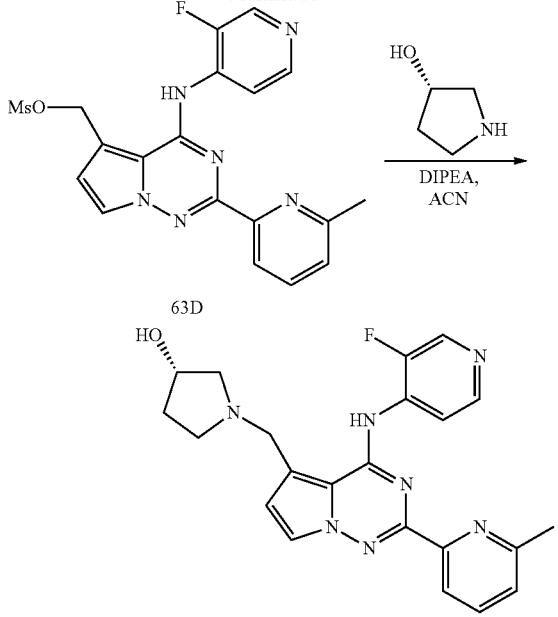

Example 252

(3S)-1-({4-[(3-fluoropyridin-4-yl)amino]-2-(6-methylpyridin-2-yl)pyrrolo[2,1-f][1,2,4]triazin-5-yl}methyl)pyrrolidin-3-ol

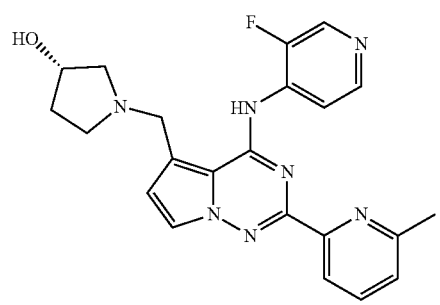 [SMILES: Cc1cccc(-c2nc(Nc3ccncc3F)c3c(CN4CC[C@H](O)C4)ccn3n2)n1]

Intermediate 63A: ethyl 2-(6-methylpyridin-2-yl)-4-phenoxypyrrolo[2,1-f][1,2,4]triazine-5-carboxylate

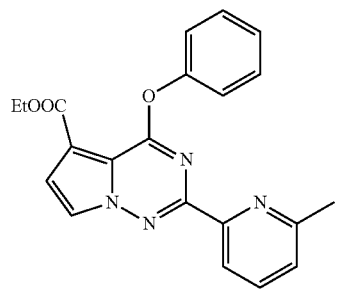 [SMILES: CCOC(=O)c1ccn2nc(-c3cccc(C)n3)nc(Oc3ccccc3)c12]

Intermediate 63A (700 mg, 1.870 mmol, 43.8% yield) was synthesized employing the procedure described for intermediate 61B (Scheme 61). LCMS m/z 375.1 (M+H); rt 1.13 min; Conditions B.

Intermediate 63B: ethyl 4-((3-fluoropyridin-4-yl)amino)-2-(6-methylpyridin-2-yl)pyrrolo[2,1-f][1,2,4]triazine-5-carboxylate

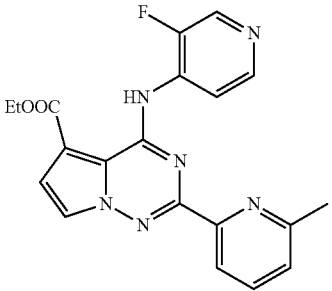 [SMILES: CCOC(=O)c1ccn2nc(-c3cccc(C)n3)nc(Nc3ccncc3F)c12]

Intermediate 63B was synthesized (600 mg, 1.529 mmol, 95% yield) employing the procedure described for intermediate 57A (Scheme 57). LCMS m/z 393.1 (M+H); rt 1.13 min; Conditions B.

Intermediate 63C: (4-((3-fluoropyridin-4-yl)amino)-2-(6-methylpyridin-2-yl)pyrrolo[2,1-f][1,2,4]triazin-5-yl)methanol

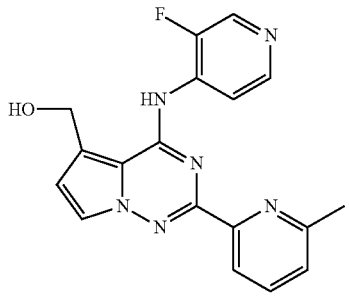 [SMILES: Cc1cccc(-c2nc(Nc3ccncc3F)c3c(CO)ccn3n2)n1]

Intermediate 63C was synthesized employing the procedure described for intermediate 60C (Scheme 60). The crude residue was purified by silicagel column chromatography (50% ethyl acetate in petroleum ether) to give (4-((3-fluoropyridin-4-yl)amino)-2-(6-methylpyridin-2-yl)pyrrolo[2,1-f][1,2,4]triazin-5-yl)methanol 63C (250 mg, 0.714 mmol, 46.7% yield) as pale yellow solid. LCMS m/z 351.2 (M+H); rt 0.83 min; Conditions B.

Intermediate 63D: (4-((3-fluoropyridin-4-yl)amino)-2-(6-methylpyridin-2-yl)pyrrolo[2,1-f][1,2,4]triazin-5-yl)methyl methanesulfonate

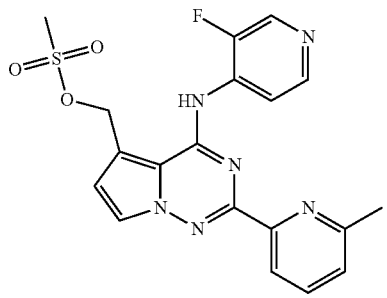 [SMILES: Cc1cccc(-c2nc(Nc3ccncc3F)c3c(COS(C)(=O)=O)ccn3n2)n1]

Intermediate 63D (250 mg crude) was synthesized employing the procedure described for intermediate 59D (Scheme 59). LCMS m/z 434.3 (M+H); rt 0.88 min; Conditions B.

Example 252 (4 mg, 6.33% yield) was synthesized employing the procedure described for Example 231 (Scheme 59). LCMS m/z 420.2 (M+H); rt 1.75 min; Conditions C. $^1$H NMR (400 MHz, DMSO-$d_6$) δ 13.71-13.37 (m, 1H), 9.25 (dd, J=5.5, 7.2 Hz, 1H), 8.82 (d, J=3.4 Hz, 1H), 8.66 (d, J=5.6 Hz, 1H), 8.35-8.27 (m, 1H), 8.19 (d, J=2.4 Hz, 1H), 8.13 (t, J=7.7 Hz, 1H), 7.64 (d, J=7.6 Hz, 1H), 7.07 (d, J=2.7 Hz, 1H), 4.55 (dt, J=3.2, 6.2 Hz, 1H), 4.38 (d, J=13.7 Hz, 1H), 4.10 (d, J=13.7 Hz, 1H), 3.23-2.97 (m, 3H), 2.71 (dd, J=2.8, 10.4 Hz, 1H), 2.38-2.25 (m, 1H), 2.14 (s, 2H), 2.04-1.92 (m, 1H).

Example 253

2-[4-({2-[6-(difluoromethyl)pyridin-2-yl]-4-[(3-fluoropyridin-4-yl)amino]pyrrolo[2,1-f][1,2,4]triazin-5-yl}methyl)piperazin-1-yl]ethan-1-ol

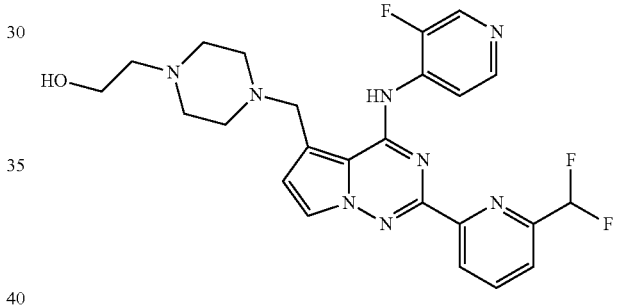

Example 253 (17 mg, 11.2% yield) was synthesized employing the procedure described for Example 231 (Scheme 59). LCMS m/z 499.2 (M+H); rt 1.73 min; Conditions C. $^1$H NMR (400 MHz, DMSO-$d_6$) δ 12.57 (br. s., 1H), 9.13 (dd, J=5.6, 7.1 Hz, 1H), 8.91 (d, J=2.9 Hz, 1H), 8.72 (d, J=5.4 Hz, 1H), 8.65 (dd, J=0.9, 7.9 Hz, 1H), 8.46 (t, J=7.8 Hz, 1H), 8.28-8.23 (m, 1H), 8.09 (d, J=7.8 Hz, 1H), 7.53-7.20 (m, 1H), 7.12 (d, J=2.7 Hz, 1H), 4.62 (br. s., 1H), 4.13 (s, 3H), 3.76-3.68 (m, 4H), 2.91-2.77 (m, 3H), 2.73-2.65 (m, 3H), 2.63-2.54 (m, 2H), 2.13 (s, 1H).

Scheme 64

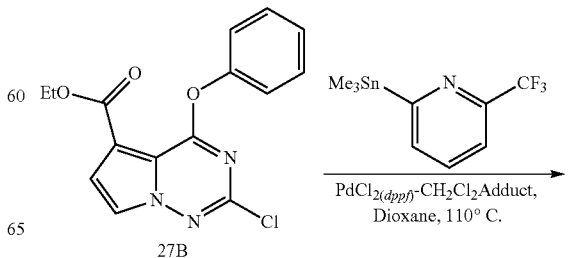

283

-continued

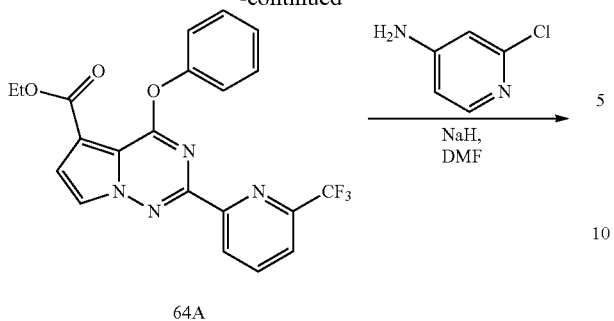

64A

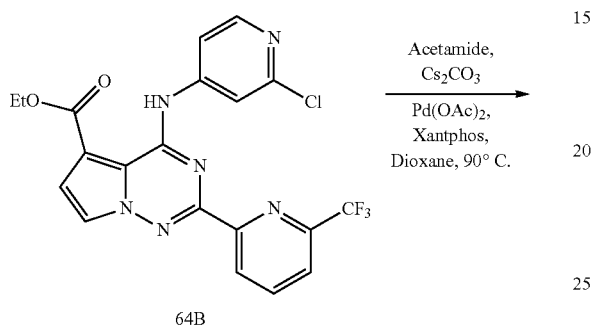

64B

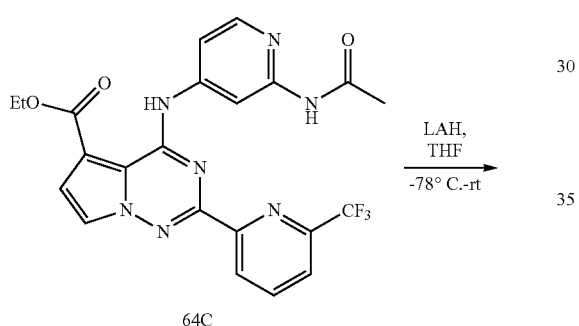

64C

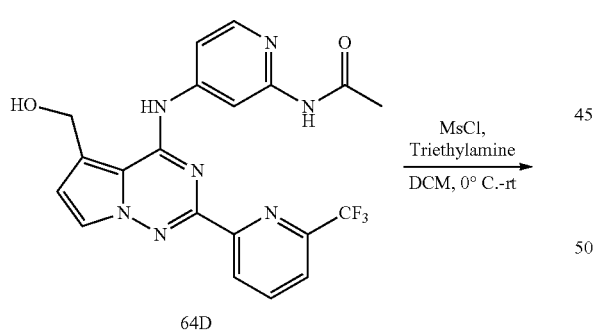

64D

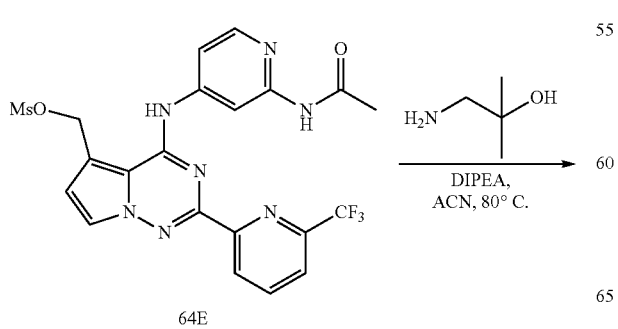

64E

284

-continued

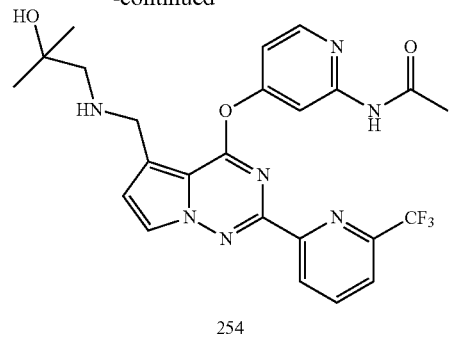

254

Example 254

N-{4-[(5-{[(2-hydroxy-2-methylpropyl)amino]methyl}-2-[6-(trifluoromethyl)pyridin-2-yl]pyrrolo[2,1-f][1,2,4]triazin-4-yl)amino]pyridin-2-yl}acetamide

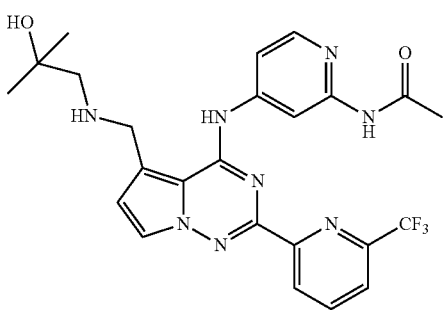 [SMILES: CC(=O)Nc1cc(Nc2nc(-c3cccc(C(F)(F)F)n3)nn3ccc(CNCC(C)(C)O)c23)ccn1]

Intermediate 64A: Ethyl 4-phenoxy-2-(6-(trifluoromethyl)pyridin-2-yl)pyrrolo[2,1-f][1,2,4]triazine-5-carboxylate

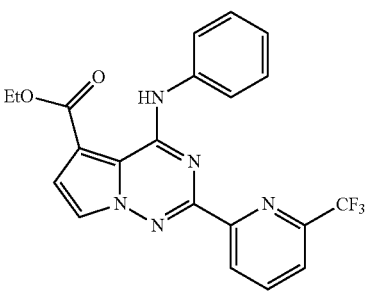 [SMILES: CCOC(=O)c1ccn2nc(-c3cccc(C(F)(F)F)n3)nc(Nc3ccccc3)c12]

In a 100 mL sealed tube was taken a solution of 2-bromo-6-(trifluoromethyl)pyridine (0.53 g, 2.36 mmol) in dioxane (20 mL), added hexamethylditin (1.15 g, 3.53 mmol), PdCl$_2$(dppf)-CH$_2$Cl$_2$ Adduct (0.096 g, 0.117 mmol), and heated to 110° C. for 1 h. To the reaction mixture was added ethyl 2-chloro-4-phenoxypyrrolo[2,1-f][1,2,4]triazine-5-carboxylate (0.5 g, 1.574 mmol) and PdCl$_2$(dppf)-CH$_2$Cl$_2$ Adduct (0.064 g, 0.079 mmol) and heated to 110° C. overnight. The reaction mixture was concentrated under reduced pressure.

To the residue was added ethyl acetate, filtered through Celite pad. The filtrate was concentrated under reduced pressure. The residue was purified by silica gel chromatography (eluted with 0-20% ethyl acetate in petroleum ether) to yield the intermediate 64A (0.35 g, 0.817 mmol, 51.9%). LCMS m/z 429.2 (M+H); rt 3.49 min; Conditions E.

Intermediate 64B: Ethyl 4-((2-chloropyridin-4-yl)amino)-2-(6-(trifluoromethyl)pyridin-2-yl)pyrrolo[2,1-f][1,2,4]triazine-5-carboxylate

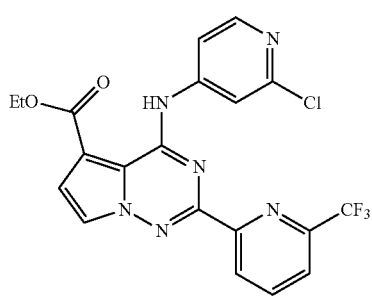 [SMILES: CCOC(=O)c1ccn2nc(-c3cccc(C(F)(F)F)n3)nc(Nc3ccnc(Cl)c3)c12]

To a solution of 2-chloropyridin-4-amine (0.273 g, 2.124 mmol) in DMF (2 mL) was added NaH (0.062 g, 1.552 mmol), followed by ethyl 4-phenoxy-2-(6-(trifluoromethyl)pyridin-2-yl)pyrrolo[2,1-f][1,2,4]triazine-5-carboxylate (0.35 g, 0.817 mmol) at 0° C. and stirred at room temperature for 3 h. The volatiles were evaporated under reduced pressure. To the residue, water was added and extracted with ethyl acetate. The organic layer was washed with water, brine and dried over sodium sulfate. The organic layer was concentrated and purified by by silica gel chromatography (eluted with 25% ethyl acetate in petroleum ether) to yield the intermediate 64B (0.40 g, 99%). LCMS m/z 463.2 (M+H); rt 3.98 min, Conditions E.

Intermediate 64C: ethyl 4-((2-acetamidopyridin-4-yl)amino)-2-(6-(trifluoromethyl)pyridin-2-yl)pyrrolo[2,1-f][1,2,4]triazine-5-carboxylate

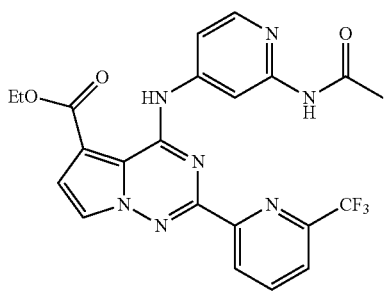 [SMILES: CCOC(=O)c1ccn2nc(-c3cccc(C(F)(F)F)n3)nc(Nc3ccnc(NC(C)=O)c3)c12]

Intermediate 64C was synthesized employing the procedure described for intermediate 55B (example-225) (Scheme 55). The crude product was purified by silica gel chromatography (24 g CombiFlash column, eluted with a gradient of 0-40% ethyl acetate in petroleum ether) to yield intermediate 64C (0.1 g, 0.206 mmol, 47.7%), LCMS m/z 486.2 (M+H); rt: 3.83, conditions E.

Intermediate 64D: N-(4-((5-(hydroxymethyl)-2-(6-(trifluoromethyl)pyridin-2-yl)pyrrolo[2,1-f][1,2,4]triazin-4-yl)amino)pyridin-2-yl)acetamide

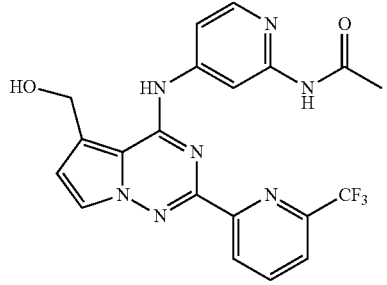 [SMILES: CC(=O)Nc1cc(Nc2nc(-c3cccc(C(F)(F)F)n3)nn3ccc(CO)c23)ccn1]

Intermediate 64D (0.13 g, 0.293 mmol, 71.2%) was synthesized employing the procedure described for intermediate 60C (Scheme 60). The crude product was purified by silica gel chromatography (eluted with 40% ethyl acetate in petroleum ether) to yield intermediate 64D. LCMS m/z 444.0 (M+H); rt 2.38 min; Conditions E.

Intermediate 64E: (4-((2-acetamidopyridin-4-yl)amino)-2-(6-(trifluoromethyl)pyridin-2-yl)pyrrolo[2,1-f][1,2,4]triazin-5-yl)methyl methanesulfonate

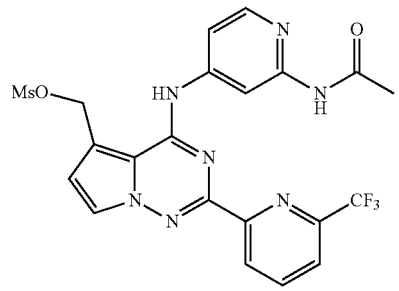 [SMILES: CC(=O)Nc1cc(Nc2nc(-c3cccc(C(F)(F)F)n3)nn3ccc(COS(C)(=O)=O)c23)ccn1]

Intermediate 64E (0.1 g, 0.192 mmol, 85%) was synthesized employing the procedure described for intermediate 59D (Scheme 59). LCMS m/z 526.0 (M+H); rt 2.41 min; Conditions E.

Example 254 (3.91 mg, 7.42 μmol, 3.87%) was synthesized employing the procedure described for Example 231 (Scheme 59). LCMS m/z 515.2 (M+H); rt 2.56 min; Conditions E. $^1$H NMR (400 MHz, DMSO-d$_6$) δ 10.42 (s, 1H), 8.95-9.06 (m, 2H), 8.20-8.28 (m, 2H), 8.01-8.03 (m, 1H), 7.96-7.98 (d, J=2.4 Hz, 1H), 7.59-7.61 (m, 1H), 6.82-6.84 (d, J=2.8 Hz, 1H), 4.41 (s, 1H), 4.11 (s, 1H), 2.51-2.53 (m, 3H), 2.15 (s, 3H), 2.08-2.09 (m, 2H), 1.15 (s, 6H).

Example 255

N-{2-[6-(trifluoromethyl)pyridin-2-yl]pyrrolo[2,1-f][1,2,4]triazin-4-yl}pyrimidin-4-amine

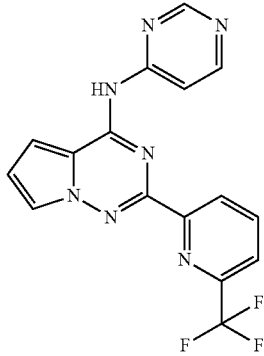 [SMILES: FC(F)(F)c1cccc(-c2nc(Nc3ccncn3)c3cccn3n2)n1]

Example 255 (18.7 mg, 73%) was synthesized employing the procedure described for Example 1 (Scheme 1). LCMS: m/z, 358.1 (M+H); rt 1.77 min; Conditions F. $^1$H NMR (400 MHz, DMSO-d6) δ 12.23 (br. s., 1H), 8.96-8.81 (m, 1H), 8.65 (d, J=2.5 Hz, 1H), 8.47 (d, J=5.5 Hz, 1H), 8.05 (d, J=8.0 Hz, 1H), 7.98 (d, J=2.5 Hz, 1H), 7.87 (t, J=7.8 Hz, 1H), 7.39 (d, J=7.5 Hz, 1H), 6.84 (d, J=2.5 Hz, 1H), 4.36 (t, J=5.3 Hz, 1H), 3.87 (s, 2H), 3.58-3.40 (m, 2H), 2.60 (s, 3H), 2.42-2.25 (m, 3H).

Example 256

2-fluoro-N-{2-[6-(trifluoromethyl)pyridin-2-yl]pyrrolo[2,1-f][1,2,4]triazin-4-yl}pyridin-4-amine

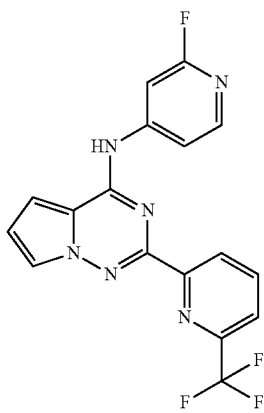 [SMILES: Fc1cc(Nc2nc(-c3cccc(C(F)(F)F)n3)nn3cccc23)ccn1]

Example 256 (18.4 mg, 69%) was synthesized employing the procedure described for Example 1 (Scheme 1). LCMS: m/z, 375.1 (M+H); rt 1.95 min; Conditions F. $^1$H NMR (400 MHz, DMSO-d6) δ $^1$H NMR (DMSO-d$_6$) δ: 8.53 (d, J=7.9 Hz, 1H), 8.43 (s, 1H), 8.30 (t, J=7.9 Hz, 1H), 8.16 (d, J=5.7 Hz, 1H), 8.09 (s, 1H), 8.05 (d, J=7.7 Hz, 1H), 7.79 (d, J=5.6 Hz, 1H), 7.35 (d, J=4.1 Hz, 1H), 6.88-7.05 (m, 1H).

Example 257

2-methyl-N-{2-[6-(trifluoromethyl)pyridin-2-yl]pyrrolo[2,1-f][1,2,4]triazin-4-yl}pyridin-4-amine

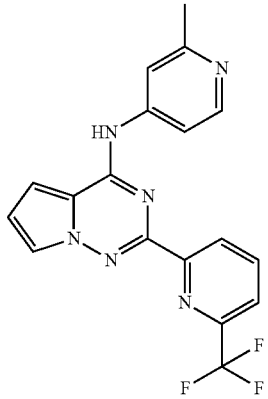 [SMILES: Cc1cc(Nc2nc(-c3cccc(C(F)(F)F)n3)nn3cccc23)ccn1]

Example 257 (20.3 mg, 77%) was synthesized employing the procedure described for Example 1 (Scheme 1). (20.3 mg). LCMS: m/z, 371.2 (M+H); rt 1.85 min; Conditions F. $^1$H NMR (400 MHz, DMSO-d6) δ $^1$H NMR (DMSO-d$_6$) δ: 10.30 (br. s., 1H), 8.55 (d, J=8.0 Hz, 1H), 8.33-8.41 (m, 2H), 8.29 (t, J=7.9 Hz, 1H), 8.04 (d, J=6.5 Hz, 2H), 7.83 (d, J=4.9 Hz, 1H), 7.34 (d, J=3.6 Hz, 1H), 6.92 (br. s., 1H), 1.90 (s, integration was obscures due to presaturation pulse).

Scheme 65

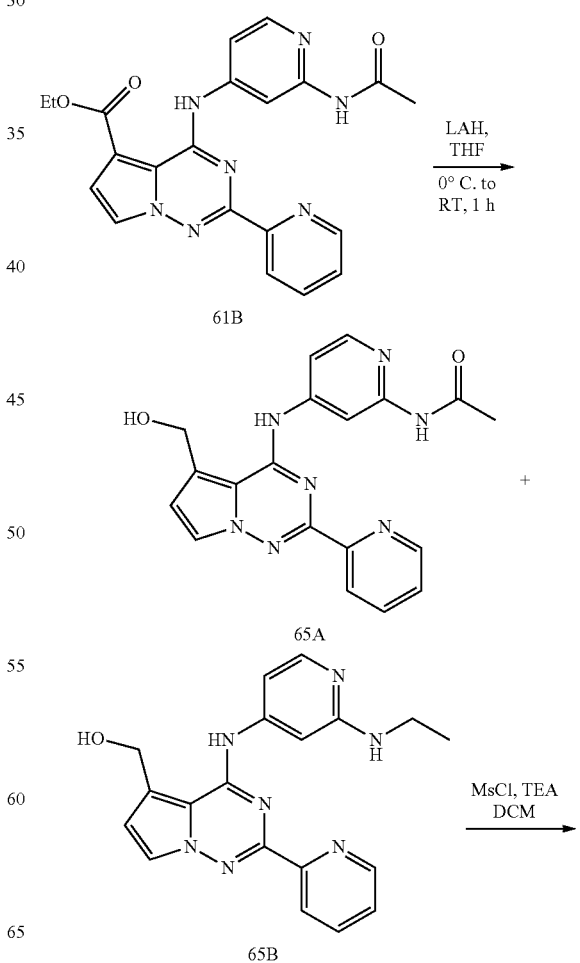

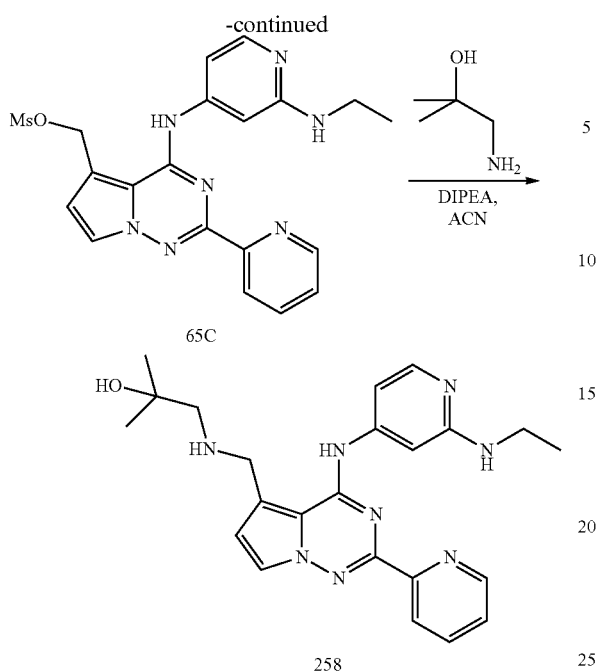

258

Example 258

1-{[(4-{[2-(ethylamino)pyridin-4-yl]amino}-2-(pyridin-2-yl)pyrrolo[2,1-f][1,2,4]triazin-5-yl)methyl]amino}-2-methylpropan-2-ol

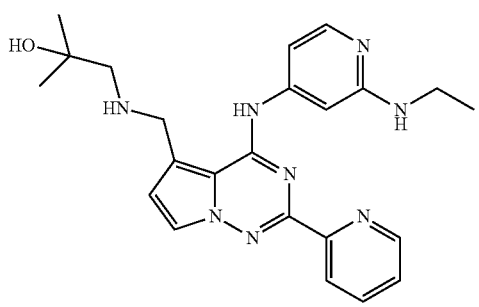 [SMILES: CCNc1cc(Nc2nc(-c3ccccn3)nn3ccc(CNCC(C)(C)O)c23)ccn1]

Intermediates 65A & 65B: To a stirred solution of ethyl 4-((2-acetamidopyridin-4-yl)amino)-2-(pyridin-2-yl)pyrrolo[2,1-f][1,2,4]triazine-5-carboxylate (0.175 g, 0.419 mmol) in THF (4 mL) LAH (0.192 mL, 0.461 mmol) (2.4 molar) was added dropwise at −78° C. to the reaction mixture and allowed to stir at room temperature for 2 h. The reaction mixture was cooled to 0° C., quenched with water (2 mL) and 10% sodium hydroxide. The resulting mixture was filtered on Celite bed and washed with ethyl acetate (200 mL). The filtrate was dried over sodium sulfate and concentrated. The residue was purified by silica gel chromatography (eluted with 5% methanol in DCM) to get (4-((2-(ethylamino)pyridin-4-yl)amino)-2-(pyridin-2-yl)pyrrolo[2,1-f][1,2,4]triazin-5-yl) methanol 65A (0.1 g, 0.277 mmol, 32.9% yield) (LCMS m/z 362.2 (M+H); rt 2.89 min; Conditions J) and N-(4-((5-(hydroxymethyl)-2-(pyridin-2-yl)pyrrolo[2,1-f][1,2,4]triazin-4-yl)amino)pyridin-2-yl)acetamide 65B (0.1 g, 0.266 mmol, 31.8% yield) (LCMS m/z 376.2 (M+H); rt 2.41 min; Conditions J).

Intermediate 65C: (4-((2-(ethylamino)pyridin-4-yl)amino)-2-(pyridin-2-yl)pyrrolo[2,1-f][1,2,4]triazin-5-yl)methyl methanesulfonate

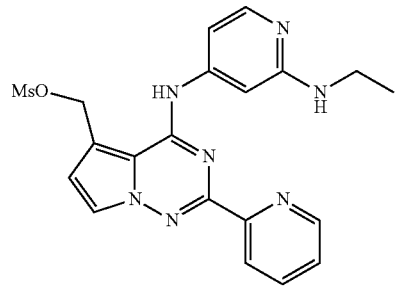 [SMILES: CCNc1cc(Nc2nc(-c3ccccn3)nn3ccc(COS(C)(=O)=O)c23)ccn1]

Intermediate 65C (100 mg, crude) was synthesized employing the procedure described for intermediate 59D (Scheme 59). The crude product was used in the next reaction.

Example 258 (9 mg, 8.83% yield) was synthesized employing the procedure described for Example 231 (Scheme 59). LCMS m/z 433.2 (M+H); rt 2.75 min; Conditions J. ¹H NMR (400 MHz, DMSO-d₆) δ 8.67-8.73 (m, 1H) 8.22-8.30 (m, 1H) 7.92-7.99 (m, 1H) 7.85-7.90 (m, 1H) 7.75-7.81 (m, 1H) 7.43-7.52 (m, 2H) 6.89-6.96 (m, 1H) 6.70-6.78 (m, 1H) 6.24-6.32 (m, 1H) 4.4 (bs, 1H) 4.02-4.08 (m, 2H) 1.88 (s, 4H) 1.12-1.18 (m, 3H) 1.09 (s, 6H).

Example 259

2-[4-({4-[(3-fluoropyridin-4-yl)amino]-2-(6-methylpyridin-2-yl)pyrrolo[2,1-f][1,2,4]triazin-5-yl}methyl)piperazin-1-yl]ethan-1-ol

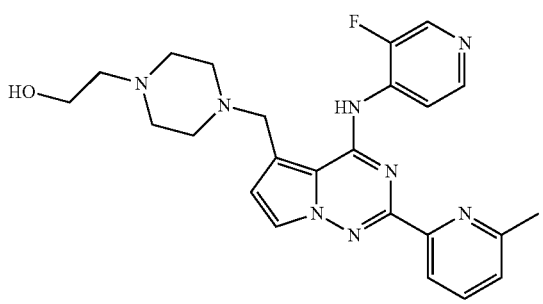 [SMILES: Cc1cccc(-c2nc(Nc3ccncc3F)c3c(CN4CCN(CCO)CC4)ccn3n2)n1]

Example 259 (1.5 mg, 2.11% yield) was synthesized employing the procedure described for Example 231 (Scheme 59). LCMS: m z, 463.2 (M+H); rt 1.57 min; Conditions C. ¹H NMR (400 MHz, DMSO-d₆) δ 12.23 (br. s., 1H), 8.96-8.81 (m, 1H), 8.65 (d, J=2.5 Hz, 1H), 8.47 (d, J=5.5 Hz, 1H), 8.05 (d, J=8.0 Hz, 1H), 7.98 (d, J=2.5 Hz, 1H), 7.87 (t, J=7.8 Hz, 1H), 7.39 (d, J=7.5 Hz, 1H), 6.84 (d, J=2.5 Hz, 1H), 4.36 (t, J=5.3 Hz, 1H), 3.87 (s, 2H), 3.58-3.40 (m, 2H), 2.60 (s, 3H), 2.42-2.25 (m, 3H).

Example 260

3-fluoro-N-[2-(3-fluoropyridin-2-yl)pyrrolo[2,1-f][1,2,4]triazin-4-yl]pyridin-4-amine

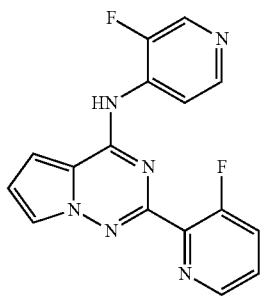 [SMILES: Fc1cnccc1Nc1nc(-c2ncccc2F)nn2cccc12]

Example 260 (18.8 mg, 65%) was synthesized employing the procedure described for Example 1 (Scheme 1). LCMS: m/z, 324.9 (M+H); rt 0.86 min; Conditions G. $^1$H NMR (400 MHz, DMSO-d$_6$) δ: 8.61 (br. s., 1H), 8.54 (d, J=4.0 Hz, 1H), 8.38 (d, J=5.3 Hz, 1H), 8.20 (br. s., 1H), 7.99 (br. s., 1H), 7.89 (t, J=9.4 Hz, 1H), 7.62 (dt, J=8.3, 4.1 Hz, 1H), 7.40 (br. s., 1H), 6.93 (br. s., 1H).

Example 261

3-fluoro-N-[2-(3-fluoro-6-methylpyridin-2-yl)pyrrolo[2,1-f][1,2,4]triazin-4-yl]pyridin-4-amine

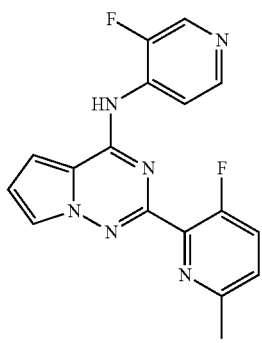 [SMILES: Cc1ccc(F)c(-c2nc(Nc3ccncc3F)c3cccn3n2)n1]

Example 261 (12.3 mg, 46%) was synthesized employing the procedure described for Example 1 (Scheme 1). LCMS: m/z, 339.1 (M+H); rt 1.45 min; conditions F. $^1$H NMR (400 MHz, DMSO-d$_6$) δ: 8.60 (d, J=2.1 Hz, 1H), 8.37 (d, J=5.3 Hz, 1H), 8.26 (br. s., 1H), 8.00 (br. s., 1H), 7.75 (t, J=9.4 Hz, 1H), 7.45 (dd, J=8.5, 3.2 Hz, 1H), 7.39 (br. s., 1H), 6.92 (br. s., 1H), 2.51 (br. s., 3H).

Example 262

3-fluoro-N-[2-(1,3-thiazol-4-yl)pyrrolo[2,1-f][1,2,4]triazin-4-yl]pyridin-4-amine

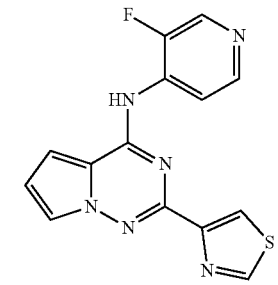 [SMILES: Fc1cnccc1Nc1nc(-c2cscn2)nn2cccc12]

Example 262 (14 mg, 52%) was synthesized employing the procedure described for Example 1 (Scheme 1). LCMS: m/z, 312.8 (M+H); rt 1.15 min; Conditions F. $^1$H NMR (400 MHz, DMSO-d$_6$) δ: 9.20 (s, 1H), 8.61-8.70 (m, J=2.4 Hz, 1H), 8.47 (d, J=5.3 Hz, 1H), 8.20-8.33 (m, 2H), 7.95 (s, 1H), 7.29-7.43 (m, J=3.4 Hz, 1H), 6.86 (br. s., 1H).

Example 263

(1R,4R)-1-N-({4-[(3-fluoropyridin-4-yl)amino]-2-(pyridin-2-yl)pyrrolo[2,1-f][1,2,4]triazin-5-yl}methyl)cyclohexane-1,4-diamine

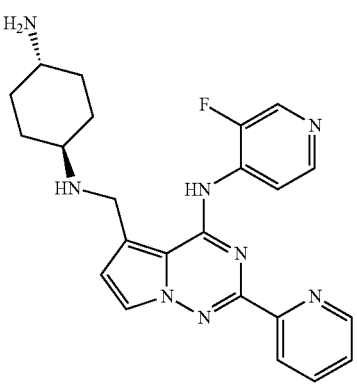 [SMILES: N[C@H]1CC[C@H](NCc2ccn3nc(-c4ccccn4)nc(Nc4ccncc4F)c23)CC1]

Example 263 (2.98 mg 14.37%) was synthesized employing the procedure described for Example 231 (Scheme 59). LCMS m/z 433.2 (M+H); rt 1.32 min; Conditions C. $^1$H NMR (400 MHz, DMSO-d$_6$) δ 9.17-9.09 (m, 1H), 9.02-8.97 (m, 1H), 8.84-8.76 (m, 1H), 8.66-8.59 (m, 1H), 8.52-8.45 (m, 1H), 8.31-8.19 (m, 1H), 8.13-8.06 (m, 1H), 7.84-7.72 (m, 1H), 7.10-7.00 (m, 1H), 4.42-4.32 (m, 2H), 2.22-2.13 (m, 2H), 2.09 (s, 4H), 2.05-1.93 (m, 2H), 1.56-1.40 (m, 3H), 1.32-1.16 (m, 2H).

Example 264

2-[({4-[(3-fluoropyridin-4-yl)amino]-2-(pyridin-2-yl)pyrrolo[2,1-f][1,2,4]triazin-5-yl}methyl)amino]propane-1,3-diol

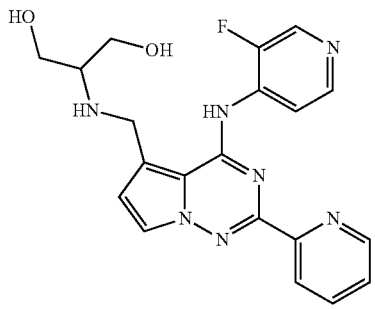 [SMILES: OCC(CO)NCc1ccn2nc(-c3ccccn3)nc(Nc3ccncc3F)c12]

Example 264 (4.0 mg, 20.2%) was synthesized employing the procedure described for Example 231 (Scheme 59). LCMS m/z 410.1 (M+H); rt 1.31 min; Conditions C. $^1$H NMR (400 MHz, DMSO-$d_6$) δ 8.86-8.72 (m, 3H), 8.62-8.53 (m, 1H), 8.44-8.37 (m, 1H), 8.27-8.19 (m, 1H), 8.04-7.95 (m, 1H), 7.91-7.84 (m, 1H), 7.56-7.50 (m, 1H), 6.88-6.80 (m, 1H), 4.62-4.51 (m, 2H), 4.21-4.12 (m, 2H), 3.58-3.42 (m, 4H), 3.20-3.14 (m, 1H), 2.66-2.58 (m, 1H).

Example 265

3-fluoro-N-(5-{[(piperidin-2-ylmethyl)amino]methyl}-2-(pyridin-2-yl)pyrrolo[2,1-f][1,2,4]triazin-4-yl)pyridin-4-amine

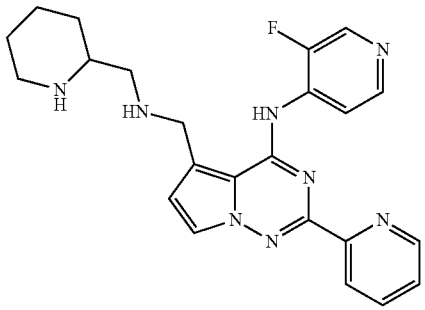 [SMILES: Fc1cnccc1Nc1nc(-c2ccccn2)nn2ccc(CNCC3CCCCN3)c12]

Example 265 (3.0 mg, 11.6%) was synthesized employing the procedure described for Example 231 (Scheme 59). LCMS m/z 433.2 (M+H); rt 1.48 min; Conditions C. $^1$H NMR (400 MHz, DMSO-$d_6$) δ 9.07-8.94 (m, 1H), 8.92-8.86 (m, 1H), 8.76-8.68 (m, 1H), 8.52-8.42 (m, 1H), 8.31-8.17 (m, 2H), 7.83-7.74 (m, 1H), 7.23-7.07 (m, 1H), 4.74-4.63 (m, 1H), 4.10-3.99 (m, 1H), 3.29-3.17 (m, 2H), 3.06-2.97 (m, 1H), 2.17 (s, 1H), 2.07-1.92 (m, 2H), 1.90-1.78 (m, 2H), 1.76-1.62 (m, 2H).

Example 266

N-(5-{[(azetidin-3-ylmethyl)amino]methyl}-2-(pyridin-2-yl)pyrrolo[2,1-f][1,2,4]triazin-4-yl)-3-fluoropyridin-4-amine

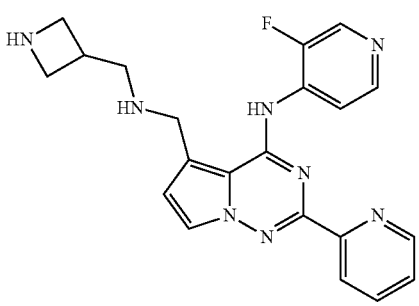 [SMILES: Fc1cnccc1Nc1nc(-c2ccccn2)nn2ccc(CNCC3CNC3)c12]

Example 266 (4.0 mg, 16.4%) was synthesized employing the procedure described for Example 231 (Scheme 59). LCMS: m/z, 405.1 (M+H); rt 1.26 min; Conditions C. $^1$H NMR (400 MHz, DMSO-$d_6$) δ 9.31-9.21 (m, 1H), 9.05-8.98 (m, 1H), 8.85-8.78 (m, 1H), 8.71-8.62 (m, 1H), 8.55-8.49 (m, 1H), 8.30-8.22 (m, 1H), 8.18-8.11 (m, 1H), 7.83-7.75 (m, 1H), 7.11-7.01 (m, 1H), 4.34-4.26 (m, 2H), 3.80-3.71 (m, 3H), 3.48-3.39 (m, 2H), 3.12-3.03 (m, 3H).

Example 267

3-fluoro-N-(5-{[(piperidin-3-yl)amino]methyl}-2-(pyridin-2-yl)pyrrolo[2,1-f][1,2,4]triazin-4-yl)pyridin-4-amine

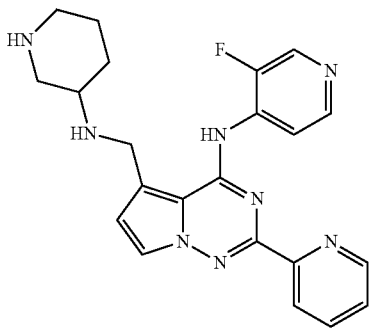 [SMILES: Fc1cnccc1Nc1nc(-c2ccccn2)nn2ccc(CNC3CCCNC3)c12]

Example 267 (4.0 mg, 15.9%) was synthesized employing the procedure described for Example 231 (Scheme 59). LCMS m/z 419.2 (M+H); rt 1.29 min; Conditions C. $^1$H NMR (400 MHz, DMSO-$d_6$) δ 9.24-9.13 (m, 1H), 9.05-8.97 (m, 1H), 8.86-8.78 (m, 1H), 8.71-8.61 (m, 1H), 8.53-8.47 (m, 1H), 8.31-8.21 (m, 1H), 8.16-8.10 (m, 1H), 7.83-7.72 (m, 1H), 7.15-7.04 (m, 1H), 4.42-4.32 (m, 2H), 3.26-3.16 (m, 2H), 3.03-2.94 (m, 1H), 2.67-2.60 (m, 2H), 1.90-1.78 (m, 1H), 1.61-1.46 (m, 4H).

Example 268

3-fluoro-N-[2-(pyridin-2-yl)-5-{[(2,2,2-trifluoro-ethyl)amino]methyl}pyrrolo[2,1-f][1,2,4]triazin-4-yl]pyridin-4-amine

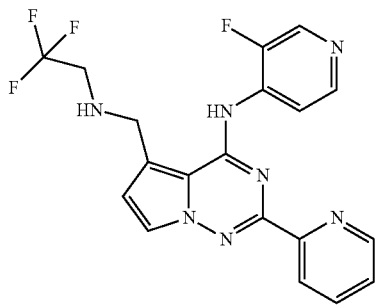 [SMILES: Fc1cnccc1Nc1nc(-c2ccccn2)nn2ccc(CNCC(F)(F)F)c12]

Example 268 (4.0 mg, 19.8%) was synthesized employing the procedure described for Example 231 (Scheme 59). LCMS: m/z, 418.1 (M+H); rt 1.90 min; Conditions C. $^1$H NMR (400 MHz, DMSO-$d_6$) δ 12.87-12.67 (m, 1H), 9.02-8.92 (m, 1H), 8.85-8.72 (m, 1H), 8.66-8.57 (m, 1H), 8.49-8.39 (m, 1H), 8.31-8.20 (m, 1H), 8.06-7.89 (m, 2H), 7.63-7.48 (m, 1H), 6.96-6.82 (m, 1H), 4.25-4.12 (m, 2H), 3.51-3.34 (m, 2H).

Example 269

3-fluoro-N-[5-({[2-(piperazin-1-yl)ethyl]amino}methyl)-2-(pyridin-2-yl)pyrrolo[2,1-f][1,2,4]triazin-4-yl]pyridin-4-amine

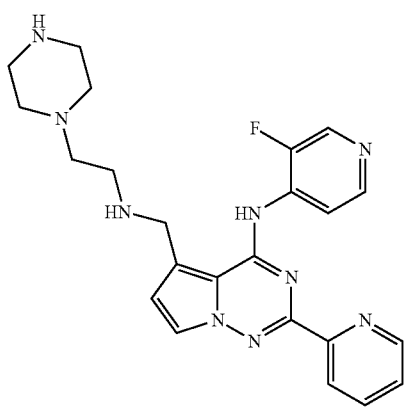 [SMILES: Fc1cnccc1Nc1nc(-c2ccccn2)nn2ccc(CNCCN3CCNCC3)c12]

Example 269 (3.0 mg, 11.3%) was synthesized employing the procedure described for Example 231 (Scheme 59). LCMS m/z 448.2 (M+H); rt 1.35 min; Conditions C. $^1$H NMR (400 MHz, DMSO-$d_6$) δ 9.29-9.20 (m, 1H), 9.05-8.96 (m, 1H), 8.83-8.73 (m, 1H), 8.68-8.59 (m, 1H), 8.54-8.45 (m, 1H), 8.31-8.20 (m, 1H), 8.16-8.07 (m, 1H), 7.86-7.72 (m, 1H), 7.14-7.01 (m, 1H), 4.41-4.30 (m, 2H), 3.06-2.90 (m, 2H), 2.68-2.55 (m, 2H), 2.49-2.37 (m, 2H), 2.09 (m, 6H).

Example 270

3-fluoro-N-[2-(pyridin-2-yl)-5-({[2-(pyrrolidin-2-yl)ethyl]amino}methyl)pyrrolo[2,1-f][1,2,4]triazin-4-yl]pyridin-4-amine

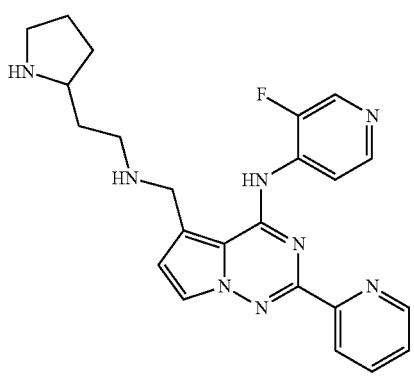 [SMILES: Fc1cnccc1Nc1nc(-c2ccccn2)nn2ccc(CNCCC3CCCN3)c12]

Example 270 (4.0 mg, 15.5%) was synthesized employing the procedure described for Example 231 (Scheme 59). LCMS m/z 433.2 (M+H); rt 1.33 min; Conditions C. $^1$H NMR (400 MHz, DMSO-$d_6$) δ 9.23-9.14 (m, 1H), 9.05-8.97 (m, 1H), 8.82-8.75 (m, 1H), 8.66-8.59 (m, 1H), 8.53-8.45 (m, 1H), 8.30-8.22 (m, 1H), 8.14-8.07 (m, 1H), 7.82-7.73 (m, 1H), 7.11-6.97 (m, 1H), 4.40-4.29 (m, 2H), 3.27-3.16 (m, 2H), 3.09-2.94 (m, 3H), 2.06-1.97 (m, 1H), 1.93-1.75 (m, 3H), 1.48-1.35 (m, 1H), 1.234 (m, 1H).

Example 271

N-(5-{[(cyclobutylmethyl)amino]methyl}-2-(pyridin-2-yl)pyrrolo[2,1-f][1,2,4]triazin-4-yl)-3-fluoro-pyridin-4-amine

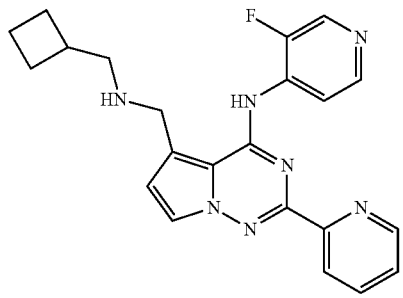 [SMILES: Fc1cnccc1Nc1nc(-c2ccccn2)nn2ccc(CNCC3CCC3)c12]

Example 271 (4.0 mg, 20.5%) was synthesized employing the procedure described for Example 231 (Scheme 59). LCMS m/z 404.1 (M+H); rt 2.25 min; Conditions C. $^1$H NMR (400 MHz, DMSO-$d_6$) δ 9.46-9.31 (m, 2H), 9.00-8.86 (m, 1H), 8.81-8.72 (m, 1H), 8.61-8.53 (m, 1H), 8.44-8.35 (m, 1H), 8.31-8.21 (m, 1H), 8.06-7.96 (m, 1H), 7.91-7.80 (m, 1H), 7.61-7.49 (m, 1H), 6.88-6.75 (m, 1H), 4.15-4.00 (m, 2H), 2.78-2.64 (m, 2H), 2.04-1.93 (m, 2H), 1.86-1.68 (m, 3H), 1.64-1.54 (m, 2H).

Example 272

2-[({4-[(3-fluoropyridin-4-yl)amino]-2-(pyridin-2-yl)pyrrolo[2,1-f][1,2,4]triazin-5-yl}methyl)amino]cyclohexan-1-ol

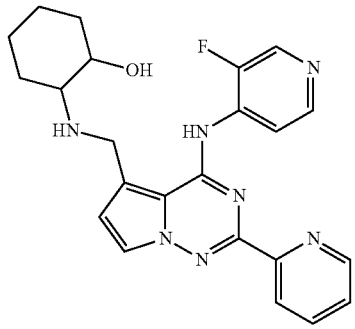 [SMILES: OC1CCCCC1NCc1ccn2nc(-c3ccccn3)nc(Nc3ccncc3F)c12]

Example 272 (2.0 mg, 9.5%) was synthesized employing the procedure described for Example 231 (Scheme 59). LCMS m/z 434.1 (M+H); rt 1.84 min; Conditions C. $^1$H NMR (400 MHz, DMSO-$d_6$) δ 9.16-8.97 (m, 2H), 8.93-8.86 (m, 1H), 8.80-8.69 (m, 1H), 8.60-8.49 (m, 1H), 8.43-8.34 (m, 1H), 8.28-8.19 (m, 1H), 8.05-7.94 (m, 1H), 7.90-7.79 (m, 1H), 7.60-7.45 (m, 1H), 6.90-6.76 (m, 1H), 4.21-4.10 (m, 2H), 4.06-3.95 (m, 1H), 1.79-1.66 (m, 2H), 1.60-1.44 (m, 2H), 1.42-1.34 (m, 2H), 1.31-1.14 (m, 3H), 1.13-1.01 (m, 1H).

Example 273

(2S)-2-[({4-[(3-fluoropyridin-4-yl)amino]-2-(pyridin-2-yl)pyrrolo[2,1-f][1,2,4]triazin-5-yl}methyl)amino]pentan-1-ol

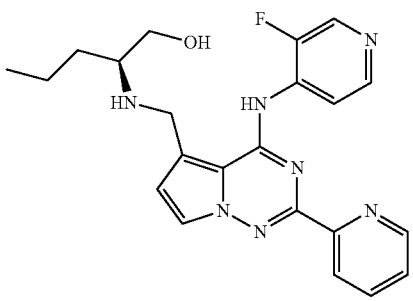 [SMILES: CCC[C@@H](CO)NCc1ccn2nc(-c3ccccn3)nc(Nc3ccncc3F)c12]

Example 273 (2.0 mg, 9.8%) was synthesized employing the procedure described for Example 231 (Scheme 59). LCMS m/z 422.1 (M+H); rt 1.79 min; Conditions C. $^1$H NMR (400 MHz, DMSO-$d_6$) δ 9.00-8.83 (m, 2H), 8.78-8.69 (m, 1H), 8.61-8.54 (m, 1H), 8.44-8.35 (m, 1H), 8.29-8.18 (m, 1H), 8.04-7.94 (m, 1H), 7.88-7.81 (m, 1H), 7.62-7.48 (m, 1H), 6.88-6.77 (m, 1H), 4.82-4.69 (m, 1H), 4.30-4.13 (m, 2H), 3.63-3.52 (m, 1H), 3.47-3.37 (m, 1H), 1.56-1.43 (m, 2H), 1.33-1.18 (m, 3H), 0.83-0.68 (m, 3H).

Example 274

4-[({4-[(3-fluoropyridin-4-yl)amino]-2-(pyridin-2-yl)pyrrolo[2,1-f][1,2,4]triazin-5-yl}methyl)amino]butan-2-ol

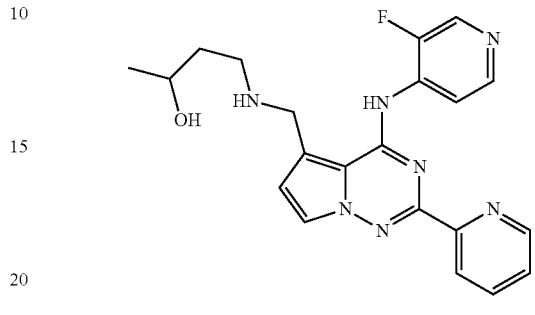

Example 274 (2.0 mg, 10.1%) was synthesized employing the procedure described for Example 231 (Scheme 59). LCMS m/z 408.2 (M+H); rt 1.58 min; Conditions C. $^1$H NMR (400 MHz, DMSO-$d_6$) δ 9.54-9.39 (m, 1H), 8.90-8.79 (m, 2H), 8.76-8.68 (m, 1H), 8.58-8.51 (m, 1H), 8.43-8.34 (m, 1H), 8.30-8.20 (m, 1H), 8.07-7.95 (m, 1H), 7.89-7.80 (m, 1H), 7.59-7.49 (m, 1H), 6.85-6.78 (m, 1H), 4.57-4.39 (m, 1H), 4.20-4.08 (m, 2H), 3.71-3.60 (m, 1H), 2.88-2.70 (m, 2H), 1.67-1.52 (m, 2H), 1.02 (d, J=6.0 Hz, 3H).

Example 275

3-[4-({4-[(3-fluoropyridin-4-yl)amino]-2-(pyridin-2-yl)pyrrolo[2,1-f][1,2,4]triazin-5-yl}methyl)piperazin-1-yl]phenol

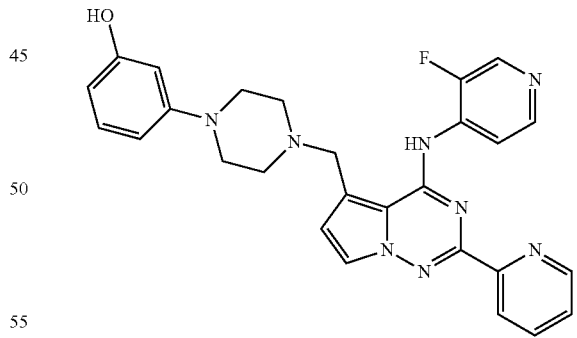

Example 275 (2.0 mg, 8.35%) was synthesized employing the procedure described for Example 231 (Scheme 59). LCMS m/z 497.3 (M+H); rt 1.78 min; Conditions C. $^1$H NMR (400 MHz, DMSO-$d_6$) δ 12.10-12.04 (m, 1H), 9.17-9.09 (m, 1H), 8.89-8.82 (m, 1H), 8.78-8.73 (m, 1H), 8.65-8.57 (m, 1H), 8.48-8.41 (m, 1H), 8.30-8.21 (m, 1H), 8.05-7.94 (m, 2H), 7.57-7.48 (m, 1H), 7.04-6.93 (m, 1H), 6.91-6.83 (m, 1H), 6.42-6.34 (m, 1H), 6.31-6.26 (m, 1H), 6.24-6.16 (m, 1H), 3.99-3.91 (m, 2H), 3.21-2.92 (m, 5H), 2.87-2.70 (m, 3H).

Example 276

3-fluoro-N-[2-(pyridin-2-yl)-5-{[4-(pyrimidin-2-yl)piperazin-1-yl]methyl}pyrrolo[2,1-f][1,2,4]triazin-4-yl]pyridin-4-amine

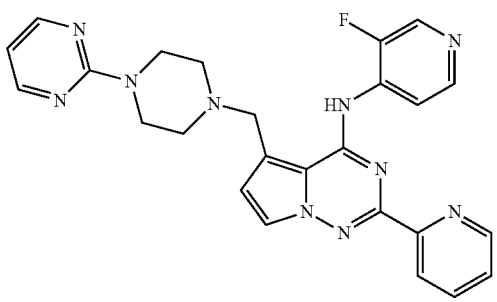 [SMILES: Fc1cnccc1Nc1nc(-c2ccccn2)nn2ccc(CN3CCN(c4ncccn4)CC3)c12]

Example 276 (1.0 mg, 4.3%) was synthesized employing the procedure described for Example 231 (Scheme 59). LCMS m/z 483.2 (M+H); rt 2.01 min; Conditions C. $^1$H NMR (400 MHz, DMSO-d$_6$) δ 12.35-12.26 (m, 1H), 9.17-9.07 (m, 1H), 9.04-8.98 (m, 1H), 8.94-8.84 (m, 1H), 8.77-8.69 (m, 1H), 8.63 (d, J=4.6 Hz, 2H), 8.52-8.44 (m, 1H), 8.30-8.18 (m, 2H), 7.85-7.73 (m, 1H), 7.19-7.06 (m, 1H), 6.98-6.85 (m, 1H), 4.24-4.17 (m, 2H), 4.10-3.74 (m, 4H), 2.90-2.81 (m, 4H).

Example 277

1-({4-[(3-fluoropyridin-4-yl)amino]-2-(pyridin-2-yl)pyrrolo[2,1-f][1,2,4]triazin-5-yl}methyl)-4-phenylpiperidin-4-ol

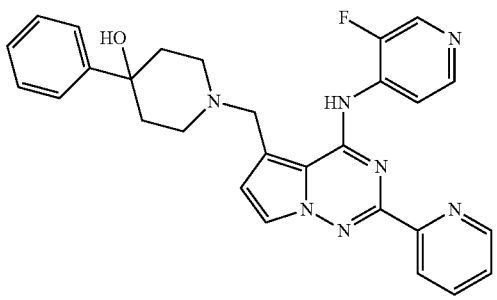 [SMILES: OC1(c2ccccc2)CCN(Cc2ccn3nc(-c4ccccn4)nc(Nc4ccncc4F)c23)CC1]

Example 277 (2.0 mg, 8.4%) was synthesized employing the procedure described for Example 231 (Scheme 59). LCMS m/z 496.2 (M+H); rt 2.06 min; Conditions C. $^1$H NMR (400 MHz, DMSO-d$_6$) δ 9.07-8.99 (m, 2H), 8.96-8.91 (m, 1H), 8.77-8.71 (m, 1H), 8.51-8.47 (m, 1H), 8.28-8.19 (m, 2H), 7.81-7.75 (m, 1H), 7.64-7.59 (m, 2H), 7.57-7.52 (m, 2H), 7.49-7.43 (m, 1H), 7.17-7.11 (m, 1H), 5.26-5.21 (m, 1H), 4.26-4.21 (m, 2H), 3.19-3.12 (m, 2H), 2.89-2.83 (m, 2H), 2.31-2.19 (m, 2H), 1.94-1.85 (m, 2H).

Example 278

1-[1-(({4-[(3-fluoropyridin-4-yl)amino]-2-(pyridin-2-yl)pyrrolo[2,1-f][1,2,4]triazin-5-yl}methyl)piperidin-4-yl]-2,3-dihydro-1H-1,3-benzodiazol-2-one

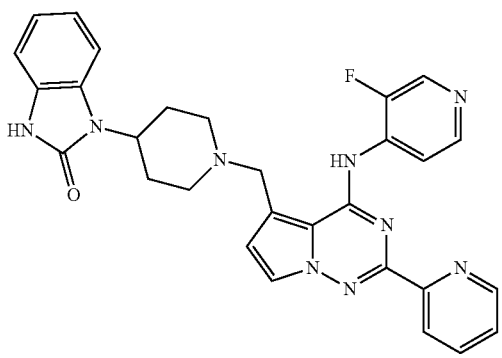 [SMILES: O=c1[nH]c2ccccc2n1C1CCN(Cc2ccn3nc(-c4ccccn4)nc(Nc4ccncc4F)c23)CC1]

Example 278 (3.0 mg, 11.6%) was synthesized employing the procedure described for Example 231 (Scheme 59). LCMS m/z 536.4 (M+H); rt 1.77 min; Conditions C. $^1$H NMR (400 MHz, DMSO-d$_6$) δ 12.60-12.55 (m, 1H), 10.86-10.82 (m, 1H), 8.94-8.89 (m, 1H), 8.78-8.74 (m, 1H), 8.72-8.69 (m, 1H), 8.57-8.52 (m, 1H), 8.28-8.23 (m, 1H), 8.03-7.94 (m, 2H), 7.56-7.50 (m, 1H), 6.98-6.87 (m, 2H), 6.73-6.67 (m, 2H), 4.34-4.26 (m, 2H), 4.01-3.96 (m, 2H), 3.25-3.18 (m, 2H), 2.62-2.58 (m, 1H), 2.41-2.35 (m, 2H), 1.76-1.69 (m, 2H).

Example 279

3-fluoro-N-(5-{[methyl(1-methylpiperidin-4-yl)amino]methyl}-2-(pyridin-2-yl)pyrrolo[2,1-f][1,2,4]triazin-4-yl)pyridin-4-amine

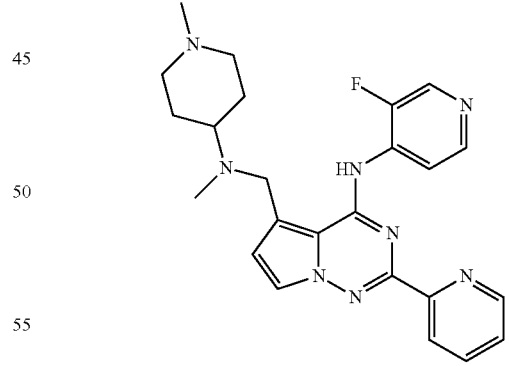

Example 279 (3.0 mg, 13.9%) was synthesized employing the procedure described for Example 231 (Scheme 59). LCMS m/z 447.2 (M+H); rt 1.44 min; Conditions C. $^1$H NMR (400 MHz, DMSO-d$_6$) δ 13.25-13.17 (m, 1H), 8.93-8.86 (m, 1H), 8.78-8.73 (m, 1H), 8.64-8.57 (m, 1H), 8.46-8.41 (m, 1H), 8.28-8.20 (m, 1H), 8.03-7.92 (m, 2H), 7.56-7.49 (m, 1H), 6.89-6.85 (m, 1H), 3.99-3.94 (m, 2H), 2.98-2.87 (m, 3H), 2.65-2.57 (m, 1H), 2.41 (d, J=1.5 Hz, 3H), 2.35-2.30 (m, 1H), 2.27-2.16 (m, 3H), 1.74-1.64 (m, 4H).

Example 280

N-[5-({[2-(dimethylamino)ethyl]amino}methyl)-2-(pyridin-2-yl)pyrrolo[2,1-f][1,2,4]triazin-4-yl]-3-fluoropyridin-4-amine

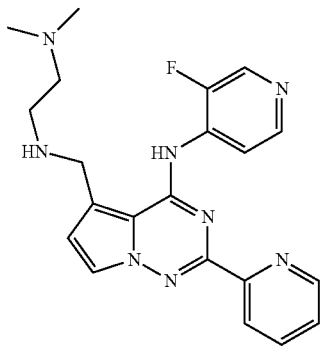 [SMILES: CN(C)CCNCc1ccn2nc(-c3ccccn3)nc(Nc3ccncc3F)c12]

Example 280 (2.0 mg, 10.2%) was synthesized employing the procedure described for Example 231 (Scheme 59). LCMS m/z 407.3 (M+H); rt 1.37 min; Conditions C. ¹H NMR (400 MHz, DMSO-d₆) δ 9.24-9.08 (m, 2H), 8.99-8.89 (m, 1H), 8.82-8.72 (m, 1H), 8.60-8.51 (m, 1H), 8.43-8.34 (m, 1H), 8.28-8.20 (m, 1H), 7.96 (s, 1H), 7.90-7.81 (m, 1H), 7.57-7.47 (m, 1H), 6.84-6.78 (m, 1H), 4.13-4.05 (m, 2H), 2.76-2.65 (m, 2H), 2.44-2.34 (m, 2H), 2.08 (s, 6H).

Example 281

3-fluoro-N-[5-({[3-(1H-imidazol-1-yl)propyl]amino}methyl)-2-(pyridin-2-yl)pyrrolo[2,1-f][1,2,4]triazin-4-yl]pyridin-4-amine

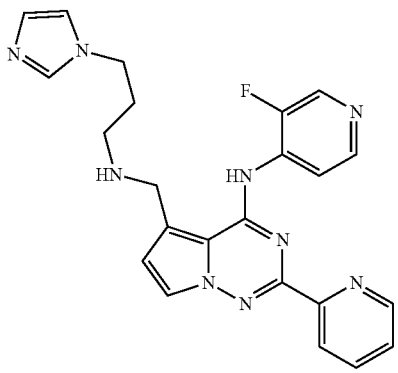 [SMILES: Fc1cnccc1Nc1nc(-c2ccccn2)nn2ccc(CNCCCn3ccnc3)c12]

Example 281 (2.0 mg, 9.3%) was synthesized employing the procedure described for Example 231 (Scheme 59). LCMS m/z 444.2 (M+H); rt 1.57 min; Conditions C. ¹H NMR (400 MHz, DMSO-d₆) δ 9.18-9.08 (m, 2H), 8.99-8.90 (m, 1H), 8.78-8.73 (m, 1H), 8.59-8.54 (m, 1H), 8.44-8.38 (m, 1H), 8.28-8.22 (m, 1H), 8.03-7.96 (m, 1H), 7.92-7.86 (m, 2H), 7.56-7.49 (m, 1H), 7.28-7.22 (m, 1H), 7.07-7.02 (m, 1H), 6.86-6.80 (m, 1H), 4.10-4.01 (m, 4H), 2.64-2.56 (m, 2H), 2.03-1.94 (m, 2H).

Example 282

N-(5-{[(adamantan-1-yl)amino]methyl}-2-(pyridin-2-yl)pyrrolo[2,1-f][1,2,4]triazin-4-yl)-3-fluoropyridin-4-amine

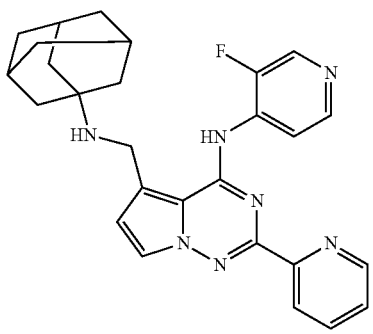 [SMILES: Fc1cnccc1Nc1nc(-c2ccccn2)nn2ccc(CNC34CC5CC(CC(C5)C3)C4)c12]

Example 282 (2.0 mg, 8.8%) was synthesized employing the procedure described for Example 231 (Scheme 59). LCMS m/z 470.2 (M+H); rt 2.63 min; Conditions C. ¹H NMR (400 MHz, DMSO-d₆) δ 9.15-8.97 (m, 2H), 8.79-8.66 (m, 1H), 8.61-8.54 (m, 2H), 8.44-8.35 (m, 1H), 8.24-8.13 (m, 1H), 8.04-7.94 (m, 1H), 7.89-7.78 (m, 1H), 7.59-7.44 (m, 1H), 6.85-6.75 (m, 1H), 4.23-4.07 (m, 2H), 2.10-1.96 (m, 3H), 1.81-1.67 (m, 6H), 1.65-1.47 (m, 6H).

Example 283

3-fluoro-N-[5-({[3-(4-methylpiperazin-1-yl)propyl]amino}methyl)-2-(pyridin-2-yl)pyrrolo[2,1-f][1,2,4]triazin-4-yl]pyridin-4-amine

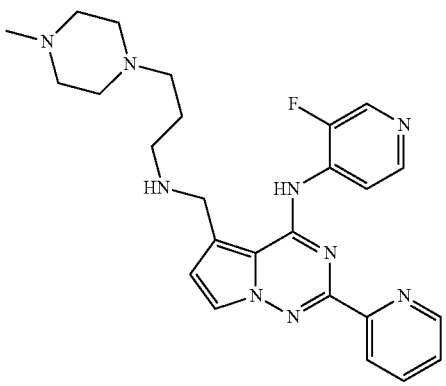 [SMILES: CN1CCN(CCCNCc2ccn3nc(-c4ccccn4)nc(Nc4ccncc4F)c23)CC1]

Example 283 (2.0 mg, 8.7%) was synthesized employing the procedure described for Example 231 (Scheme 59). LCMS m/z 476.3 (M+H); rt 1.45 min; Conditions C. ¹H NMR (400 MHz, DMSO-d₆) δ 9.51-9.36 (m, 2H), 9.00-8.90 (m, 1H), 8.77-8.73 (m, 1H), 8.57-8.49 (m, 1H), 8.41-8.34 (m, 1H), 8.28-8.21 (m, 1H), 8.03-7.94 (m, 1H), 7.88-7.83 (m, 1H), 7.56-7.46 (m, 1H), 6.86-6.78 (m, 1H), 4.12-4.03 (m, 2H), 2.71-2.64 (m, 2H), 2.31-2.10 (m, 10H), 2.18-2.06 (m, 2H), 1.73-1.60 (m, 2H), 1.28-1.20 (m, 1H).

Example 284

3-fluoro-N-[5-({[2-(piperidin-1-yl)ethyl]
amino}methyl)-2-(pyridin-2-yl)pyrrolo[2,1-f][1,2,4]
triazin-4-yl]pyridin-4-amine

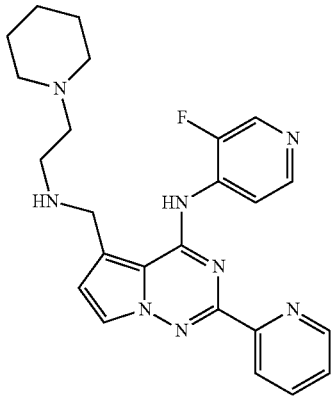 [SMILES: Fc1cnccc1Nc1nc(-c2ccccn2)nn2ccc(CNCCN3CCCCC3)c12]

Example 284 (1.0 mg, 4.6%) was synthesized employing the procedure described for Example 231 (Scheme 59). LCMS m/z 447.2 (M+H); rt 1.59 min; Conditions C. $^1$H NMR (400 MHz, DMSO-$d_6$) δ 9.31-9.15 (m, 1H), 9.04-8.93 (m, 1H), 8.79-8.72 (m, 1H), 8.56-8.50 (m, 1H), 8.41-8.33 (m, 1H), 8.28-8.19 (m, 1H), 8.03-7.94 (m, 1H), 7.89-7.82 (m, 1H), 7.57-7.48 (m, 1H), 6.84-6.75 (m, 1H), 4.13-4.06 (m, 2H), 2.77-2.69 (m, 2H), 2.43-2.35 (m, 2H), 2.26-2.15 (m, 5H), 1.36-1.22 (m, 6H).

Example 285

N-[5-({[(3S)-1-benzylpyrrolidin-3-yl]
amino}methyl)-2-(pyridin-2-yl)pyrrolo[2,1-f][1,2,4]
triazin-4-yl]-3-fluoropyridin-4-amine

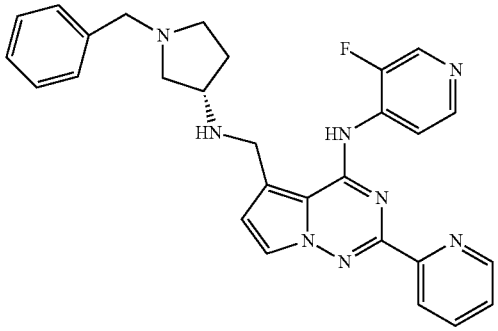 [SMILES: Fc1cnccc1Nc1nc(-c2ccccn2)nn2ccc(CN[C@H]3CCN(Cc4ccccc4)C3)c12]

Example 285 (2.0 mg, 8.3%) was synthesized employing the procedure described for Example 231 (Scheme 59). LCMS m/z 495.2 (M+H); rt 2.02 min; Conditions C. $^1$H NMR (400 MHz, DMSO-$d_6$) δ 8.90-8.82 (m, 1H), 8.78-8.72 (m, 1H), 8.57-8.52 (m, 1H), 8.44-8.37 (m, 1H), 8.28-8.19 (m, 1H), 8.03-7.95 (m, 1H), 7.91-7.85 (m, 1H), 7.56-7.48 (m, 1H), 7.35-7.17 (m, 7H), 6.84-6.78 (m, 1H), 4.06-4.00 (m, 2H), 3.62-3.53 (m, 2H), 2.65-2.54 (m, 2H), 2.46-2.36 (m, 2H), 2.08-1.97 (m, 1H), 1.77-1.65 (m, 1H).

Example 286

N-(5-{[(3-aminopropyl)amino]methyl}-2-(pyridin-2-
yl)pyrrolo[2,1-f][1,2,4]triazin-4-yl)-3-fluoropyridin-
4-amine

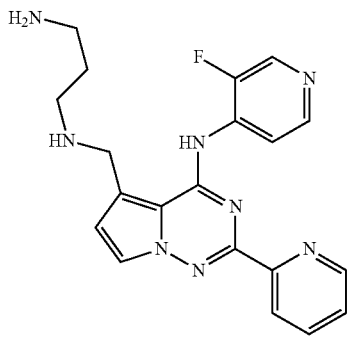 [SMILES: NCCCNCc1ccn2nc(-c3ccccn3)nc(Nc3ccncc3F)c12]

Example 286 (2.0 mg, 8.4%) was synthesized employing the procedure described for Example 231 (Scheme 59). LCMS m/z 393.3 (M+H); rt 1.26 min; Conditions C. $^1$H NMR (400 MHz, DMSO-$d_6$) δ 9.00-8.94 (m, 1H), 8.79-8.72 (m, 1H), 8.58-8.52 (m, 1H), 8.42-8.35 (m, 1H), 8.29-8.21 (m, 1H), 8.06-7.95 (m, 1H), 7.90-7.85 (m, 1H), 7.56-7.45 (m, 1H), 6.86-6.79 (m, 1H), 4.11-4.05 (m, 2H), 2.66-2.61 (m, 3H), 1.74-1.62 (m, 2H), 1.20-1.15 (m, 2H), 0.90-0.79 (m, 1H).

Example 287

(2S)-3-[({4-[(3-fluoropyridin-4-yl)amino]-2-(pyri-
din-2-yl)pyrrolo[2,1-f][1,2,4]triazin-5-yl}methyl)
amino]propane-1,2-diol

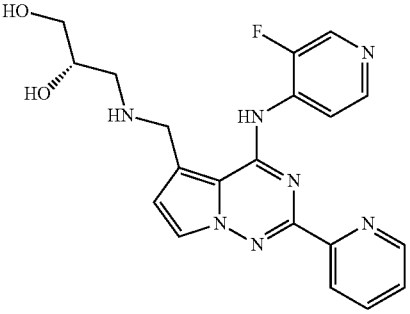 [SMILES: OC[C@@H](O)CNCc1ccn2nc(-c3ccccn3)nc(Nc3ccncc3F)c12]

Example 287 (4.0 mg, 20.2%) was synthesized employing the procedure described for Example 231 (Scheme 59). LCMS m/z 410.1 (M+H); rt 1.34 min; Conditions C. $^1$H NMR (400 MHz, DMSO-$d_6$) δ 9.18-9.03 (m, 2H), 8.99-8.90 (m, 1H), 8.79-8.72 (m, 1H), 8.59-8.51 (m, 1H), 8.45-8.35 (m, 1H), 8.29-8.22 (m, 1H), 8.05-7.94 (m, 1H), 7.91-7.84 (m, 1H), 7.60-7.46 (m, 1H), 6.86-6.77 (m, 1H), 4.80-4.71 (m, 1H), 4.60-4.44 (m, 1H), 4.19-4.04 (m, 2H), 3.75-3.63 (m, 1H), 3.30-3.19 (m, 2H), 2.87-2.74 (m, 1H) 1.905 (s, 1H).

Example 288

(1R,4R)-4-[({4-[(3-fluoropyridin-4-yl)amino]-2-(pyridin-2-yl)pyrrolo[2,1-f][1,2,4]triazin-5-yl}methyl)amino]cyclohexan-1-ol

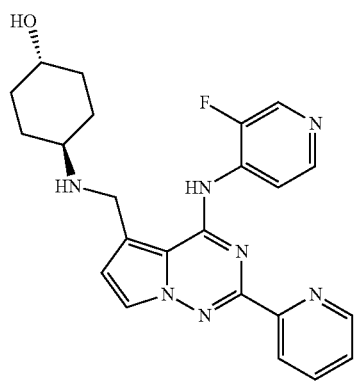 [SMILES: O[C@H]1CC[C@H](NCc2ccn3nc(-c4ccccn4)nc(Nc4ccncc4F)c23)CC1]

Example 288 (4.0 mg, 19.1%) was synthesized employing the procedure described for Example 231 (Scheme 59). LCMS m/z 434.2 (M+H); rt 1.58 min; Conditions C. ¹H NMR (400 MHz, DMSO-d₆) δ 9.32-9.15 (m, 2H), 8.95-8.85 (m, 1H), 8.78-8.70 (m, 1H), 8.60-8.50 (m, 1H), 8.44-8.34 (m, 1H), 8.30-8.19 (m, 1H), 8.05-7.93 (m, 1H), 7.90-7.82 (m, 1H), 7.56-7.46 (m, 1H), 6.87-6.77 (m, 1H), 4.52-4.43 (m, 1H), 4.14-4.04 (m, 2H), 1.92 (s, 3H), 1.82-1.72 (m, 2H), 1.29-1.15 (m, 3H), 1.12-0.99 (m, 2H).

Example 289

3-fluoro-N-{2-[6-(trifluoromethoxy)pyridin-2-yl]pyrrolo[2,1-f][1,2,4]triazin-4-yl}pyridin-4-amine

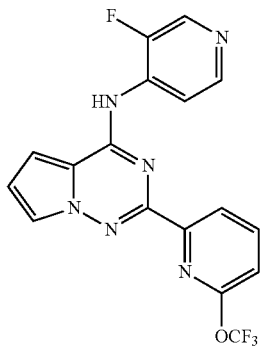 [SMILES: Fc1cnccc1Nc1nc(-c2cccc(OC(F)(F)F)n2)nn2cccc12]

Example 289 (20 mg, 69%) was synthesized employing the procedure described for Example 1 (Scheme 1). LCMS: m/z, 390.9 (M+H); rt 1.87 min; Conditions F. ¹H NMR (400 MHz, DMSO-d₆) δ: 8.54-8.68 (m, 2H), 8.38 (d, J=5.3 Hz, 1H), 8.12-8.25 (m, 2H), 8.03 (br. s., 1H), 7.35-7.47 (m, 2H), 6.92 (br. s., 1H).

Example 290

3-fluoro-N-[5-(morpholin-4-ylmethyl)-2-(pyridin-2-yl)pyrrolo[2,1-f][1,2,4]triazin-4-yl]pyridin-4-amine

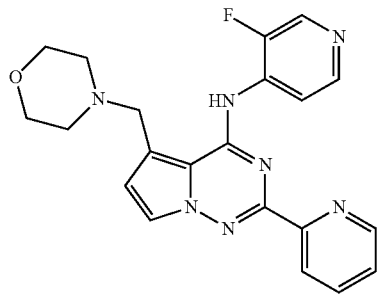 [SMILES: Fc1cnccc1Nc1nc(-c2ccccn2)nn2ccc(CN3CCOCC3)c12]

Example 290 (5.5 mg, 9.3% yield) was synthesized employing the procedure described for Example 231 (Scheme 59). LCMS m/z 406.2 (M+H); rt 2.85 min; Conditions E. ¹H NMR (400 MHz, DMSO-d₆) δ 12.04-11.93 (m, 1H), 8.94-8.87 (m, 1H), 8.80-8.74 (m, 1H), 8.67-8.60 (m, 1H), 8.51-8.43 (m, 1H), 8.33-8.21 (m, 1H), 8.04-7.92 (m, 2H), 7.62-7.46 (m, 1H), 6.91-6.83 (m, 1H), 3.91 (s, 2H), 3.70-3.62 (m, 4H), 2.53 (m, 4H).

Scheme 66

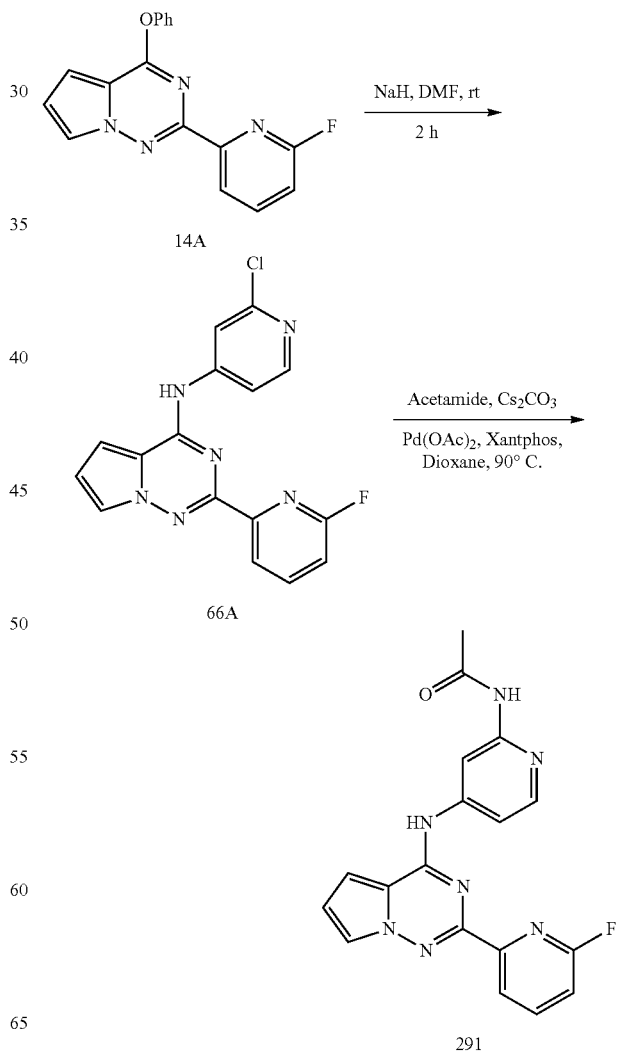

Example 291

N-(4-{[2-(6-fluoropyridin-2-yl)pyrrolo[2,1-f][1,2,4]triazin-4-yl]amino}pyridin-2-yl)acetamide

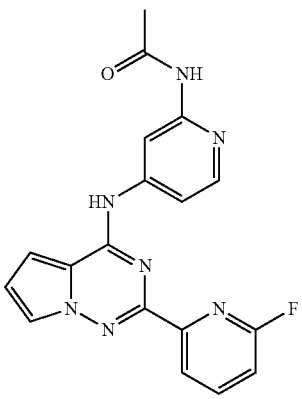 [SMILES: CC(=O)Nc1cc(Nc2nc(-c3cccc(F)n3)nn3cccc23)ccn1]

Intermediate 66A: N-(2-chloropyridin-4-yl)-2-(6-fluoropyridin-2-yl)pyrrolo[2,1-f][1,2,4]triazin-4-amine

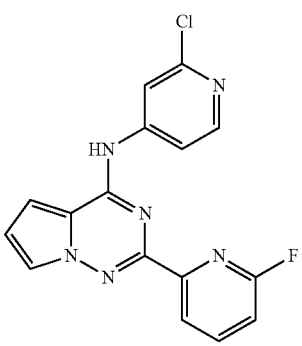 [SMILES: Fc1cccc(-c2nc(Nc3ccnc(Cl)c3)c3cccn3n2)n1]

Intermediate 66A (325 mg, 97%) was synthesized employing the procedure described for intermediate 57A (Scheme 57). LCMS m/z 341.3 (M+H); rt 1.36 min; Conditions B.

Example 291 (25.0 mg, 11.7%) was synthesized employing the procedure described for intermediate 55B in Scheme 55. LCMS m/z 364.1 (M+H); rt 1.55 min; Conditions C. $^1$H NMR (400 MHz, DMSO-d6) δ 10.47 (s, 1H), 10.33 (s, 1H), 8.79 (d, J=1.6 Hz, 1H), 8.48-8.50 (m, 1H), 8.28 (d, J=5.6 Hz, 1H), 8.13-8.12 (m, 1H), 8.02-8.03 (m, 1H), 7.98-7.99 (m, 1H), 7.40 (dd, J=1.6, 4.4 Hz, 1H), 7.32 (dd, J=2.8, 8.6 Hz, 1H), 6.90 (dd, J=2.4, 4.4 Hz, 1H), 2.14 (s, 3H). $^{19}$F NMR (400 MHz, DMSO-d6): δ −67.0.

Scheme 67

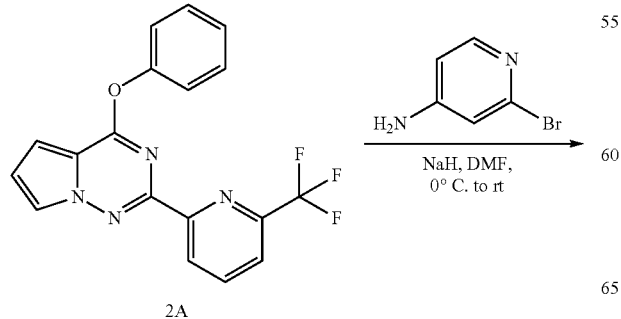

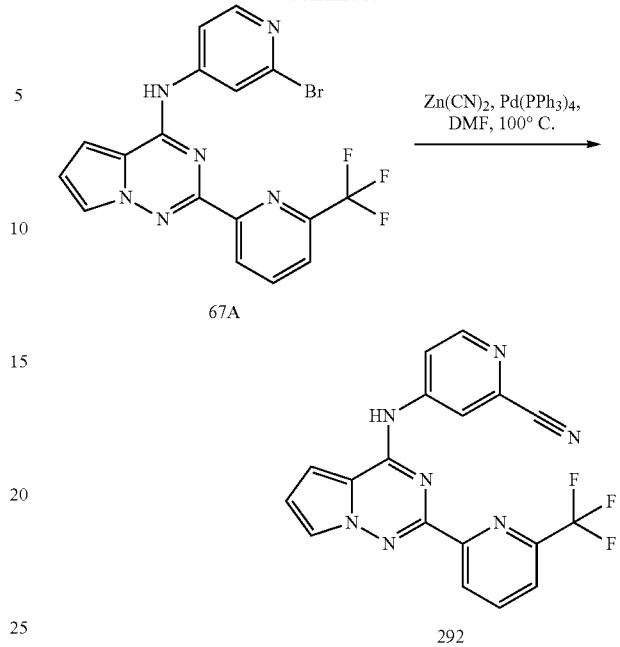

Example 292

4-({2-[6-(trifluoromethyl)pyridin-2-yl]pyrrolo[2,1-f][1,2,4]triazin-4-yl}amino)pyridine-2-carbonitrile

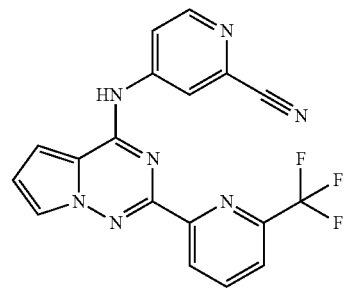 [SMILES: N#Cc1cc(Nc2nc(-c3cccc(C(F)(F)F)n3)nn3cccc23)ccn1]

Intermediate 67A: N-(2-bromopyridin-4-yl)-2-(6-(trifluoromethyl)pyridin-2-yl)pyrrolo[2,1-f][1,2,4]triazin-4-amine

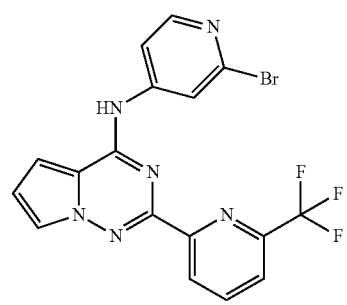 [SMILES: FC(F)(F)c1cccc(-c2nc(Nc3ccnc(Br)c3)c3cccn3n2)n1]

Intermediate 67A (200 mg, 82% yield) was synthesized employing the procedure described for intermediate 57A (Scheme 57). LCMS m/z 435.0 (M+H); rt 0.99 min; Conditions A.

To a solution of N-(2-bromopyridin-4-yl)-2-(6-(trifluoromethyl)pyridin-2-yl)pyrrolo[2,1-f][1,2,4]triazin-4-amine (100 mg, 0.230 mmol) in DMF (10 mL) was added zinc cyanide (54.0 mg, 0.460 mmol) and degassed with argon for 10 min. Pd(PPh₃)₄ (26.6 mg, 0.023 mmol) was added to the degassed solution and stirred at 100° C. for 16 h. An aliquot of the reaction mixture was diluted with methanol and analyzed by LCMS to ensure complete conversion. The reaction mixture was partitioned between water and ethyl acetate. The organic layer was washed with brine, dried over Na₂SO₄ and evaporated to get the crude residue which was purified by preparative HPLC to give 4-((2-(6-(trifluoromethyl)pyridin-2-yl)pyrrolo[2,1-f][1,2,4]triazin-4-yl)amino)picolinonitrile 292 (56 mg, 0.145 mmol, 63.3% yield) as an off white solid. LCMS m/z 382.2 (M+H); rt 1.97 min; Conditions C. ¹H NMR (400 MHz, DMSO-d₆) δ 10.94 (s, 1H), 9.29 (d, J=1.7 Hz, 1H), 8.92 (dd, J=5.6, 0.5 Hz, 1H), 8.82 (d, J=7.8 Hz, 1H), 8.62-8.48 (m, 2H), 8.38 (dd, J=2.4, 1.5 Hz, 1H), 8.32 (dd, J=7.7, 0.9 Hz, 1H), 7.62 (dd, J=4.6, 1.5 Hz, 1H), 7.25 (dd, J=4.5, 2.6 Hz, 1H).

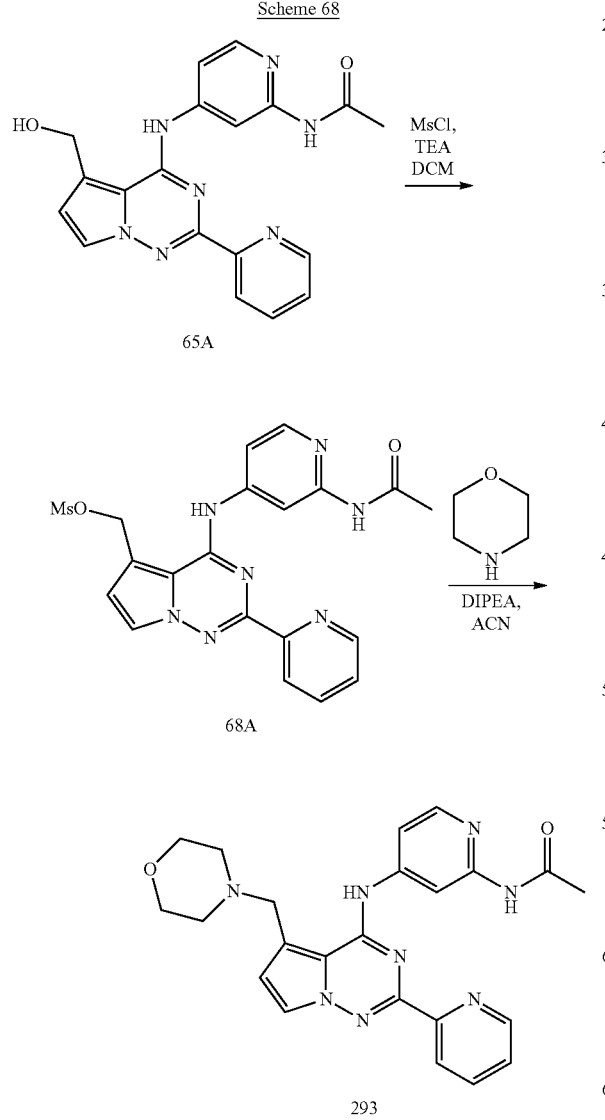

Scheme 68

65A

68A

293

Example 293

N-(4-{[5-(morpholin-4-ylmethyl)-2-(pyridin-2-yl)pyrrolo[2,1-f][1,2,4]triazin-4-yl]amino}pyridin-2-yl)acetamide

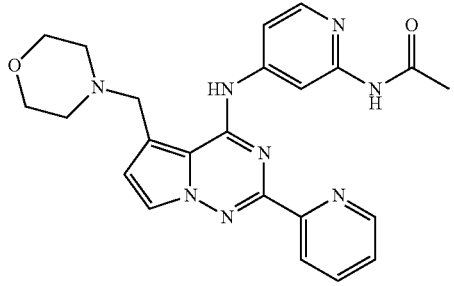 [SMILES: CC(=O)Nc1cc(Nc2nc(-c3ccccn3)nn3ccc(CN4CCOCC4)c23)ccn1]

Intermediate 68A: (4-((2-acetamidopyridin-4-yl)amino)-2-(pyridin-2-yl)pyrrolo[2,1-f][1,2,4]triazin-5-yl)methyl methanesulfonate

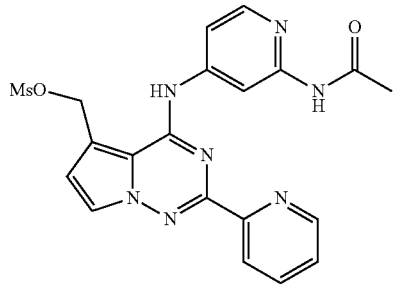 [SMILES: CC(=O)Nc1cc(Nc2nc(-c3ccccn3)nn3ccc(COS(C)(=O)=O)c23)ccn1]

Intermediate 68A (100 mg, crude) was synthesized employing the procedure described for intermediate 59D (Scheme 59). The crude compound was used in the next reaction without further purification.

Example 293 (3 mg, 3%) was synthesized employing the procedure described for Example 231 (Scheme 59). LCMS m/z 445.3 (M+H); rt 1.52 min; Conditions C. ¹H NMR (400 MHz, DMSO-d₆) δ ppm 12.37-12.45 (m, 1H), 10.70-10.78 (m, 1H), 8.94-9.04 (m, 1H), 8.66-8.81 (m, 2H), 8.51-8.59 (m, 1H), 8.12-8.36 (m, 3H), 7.72-7.83 (m, 1H), 7.01-7.10 (m, 1H), 3.89 (s, 2H), 3.73 (s, 4H), 2.6-2.67 (m, 4H), 2.13 (s, 3H).

Example 294

N-(5-{[(2H-1,3-benzodioxol-5-ylmethyl)amino]methyl}-2-(pyridin-2-yl)pyrrolo[2,1-f][1,2,4]triazin-4-yl)-3-fluoropyridin-4-amine

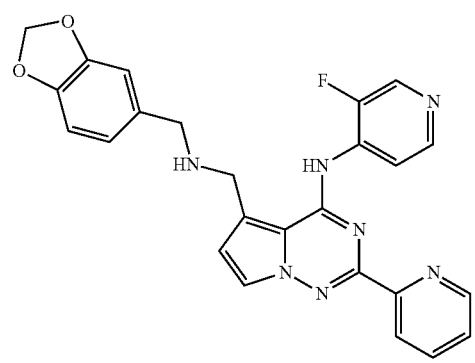 [SMILES: Fc1cnccc1Nc1nc(-c2ccccn2)nn2ccc(CNCc3ccc4c(c3)OCO4)c12]

Example 294 (4.0 mg, 17.6%) was synthesized employing the procedure described for Example 231 (Scheme 59).

LCMS m/z 470.3 (M+H); rt 1.92 min; Conditions C. $^1$H NMR (400 MHz, DMSO-d$_6$) δ 9.21-9.15 (m, 1H), 9.05-8.99 (m, 1H), 8.82-8.76 (m, 1H), 8.71-8.63 (m, 1H), 8.56-8.45 (m, 1H), 8.31-8.22 (m, 1H), 8.19-8.12 (m, 1H), 7.83-7.74 (m, 1H), 7.23-7.17 (m, 1H), 7.12-7.05 (m, 1H), 7.04-6.96 (m, 2H), 6.27-6.19 (m, 2H), 4.23-4.17 (m, 2H), 4.06-3.98 (m, 2H).

Example 295

N-({4-[(3-fluoropyridin-4-yl)amino]-2-(pyridin-2-yl)pyrrolo[2,1-f][1,2,4]triazin-5-yl}methyl)-2-methyl-1,3-benzothiazol-6-amine

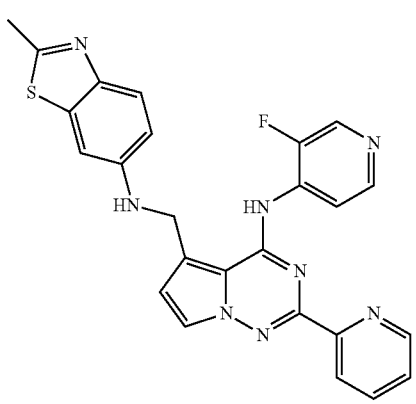 [SMILES: Cc1nc2ccc(NCc3ccn4nc(-c5ccccn5)nc(Nc5ccncc5F)c34)cc2s1]

Example 295 (2.0 mg, 12.9%) was synthesized employing the procedure described for Example 231 (Scheme 59). LCMS m/z 483.1 (M+H); rt 1.93 min; Conditions C. $^1$H NMR (400 MHz, DMSO-d$_6$) δ 8.98-8.93 (m, 1H), 8.78 (br. s., 1H), 8.52-8.48 (m, 1H), 8.44-8.41 (m, 1H), 8.29-8.25 (m, 1H), 8.08-7.98 (m, 1H), 7.77-7.71 (m, 1H), 7.59-7.52 (m, 1H), 7.51-7.47 (m, 1H), 7.27-7.24 (m, 1H), 7.17-7.12 (m, 1H), 7.10-7.05 (m, 1H), 7.01-6.98 (m, 1H), 4.64-4.59 (m, 2H), 2.75-2.71 (m, 3H).

Example 296

(3-{[({4-[(3-fluoropyridin-4-yl)amino]-2-(pyridin-2-yl)pyrrolo[2,1-f][1,2,4]triazin-5-yl}methyl)amino]methyl}oxetan-3-yl)methanol

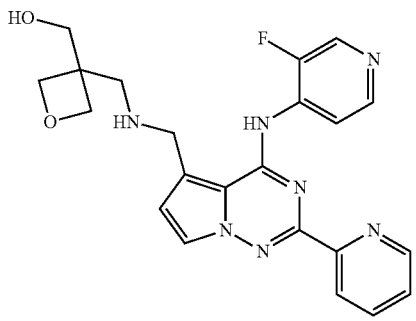 [SMILES: OCC1(CNCc2ccn3nc(-c4ccccn4)nc(Nc4ccncc4F)c23)COC1]

Example 296 (2.0 mg, 9.5%) was synthesized employing the procedure described for Example 231 (Scheme 59). LCMS: m/z, 436.3 (M+H); rt 1.33 min; Conditions C. $^1$H NMR (400 MHz, DMSO-d$_6$) δ 9.29-9.22 (m, 1H), 9.05-8.98 (m, 1H), 8.84-8.78 (m, 1H), 8.69-8.64 (m, 1H), 8.55-8.49 (m, 1H), 8.30-8.22 (m, 1H), 8.20-8.14 (m, 1H), 7.82-7.75 (m, 1H), 7.16-7.07 (m, 1H), 4.53-4.48 (m, 2H), 4.46-4.41 (m, 2H), 4.35-4.30 (m, 2H), 3.91-3.86 (m, 2H), 3.15-3.08 (m, 2H).

Example 297

3-fluoro-N-[5-({[4-(1,3-oxazol-5-yl)phenyl]amino}methyl)-2-(pyridin-2-yl)pyrrolo[2,1-f][1,2,4]triazin-4-yl]pyridin-4-amine

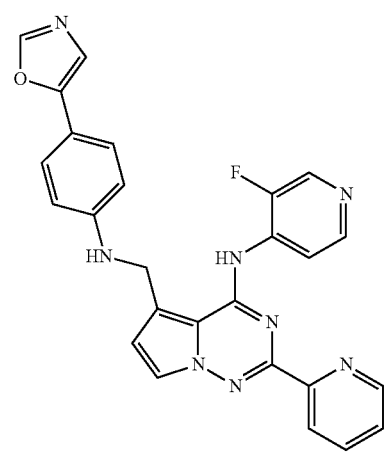 [SMILES: Fc1cnccc1Nc1nc(-c2ccccn2)nn2ccc(CNc3ccc(-c4cnco4)cc3)c12]

Example 297 (6.0 mg, 25.9%) was synthesized employing the procedure described for Example 231 (Scheme 59). LCMS m/z 479.3 (M+H); rt 1.85 min; Conditions C. $^1$H NMR (400 MHz, DMSO-d$_6$) δ 8.96-8.90 (m, 1H), 8.80-8.75 (m, 1H), 8.53-8.49 (m, 1H), 8.44-8.39 (m, 1H), 8.35-8.32 (m, 1H), 8.29-8.23 (m, 1H), 8.06-7.98 (m, 2H), 7.60-7.52 (m, 3H), 7.47-7.44 (m, 1H), 7.08-7.00 (m, 3H), 6.86-6.77 (m, 1H), 4.63-4.58 (m, 2H).

Example 298

3-fluoro-N-(5-{[(5-phenyl-1H-pyrazol-3-yl)amino]methyl}-2-(pyridin-2-yl)pyrrolo[2,1-f][1,2,4]triazin-4-yl)pyridin-4-amine

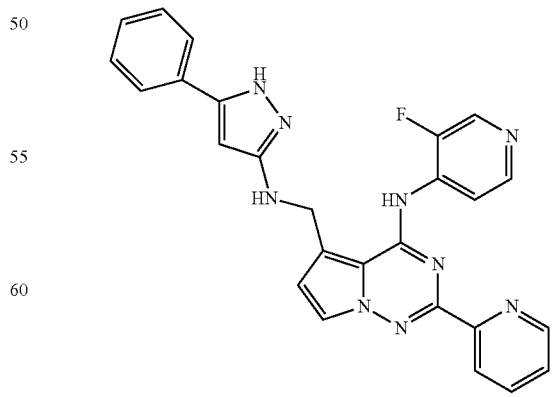

Example 298 (4.0 mg, 17.3%) was synthesized employing the procedure described for Example 231 (Scheme 59).

LCMS m/z 478.3 (M+H); rt 1.73 min; Conditions C. ¹H NMR (400 MHz, DMSO-d₆) δ 12.47-12.22 (m, 1H), 8.97-8.86 (m, 1H), 8.81-8.74 (m, 1H), 8.56-8.50 (m, 1H), 8.45-8.39 (m, 1H), 8.30-8.21 (m, 1H), 8.04-7.95 (m, 2H), 7.71-7.64 (m, 2H), 7.58-7.50 (m, 1H), 7.45-7.38 (m, 2H), 7.35-7.27 (m, 1H), 7.02-6.93 (m, 1H), 6.48-6.35 (m, 1H), 6.16-6.07 (m, 1H), 4.59-4.51 (m, 2H).

Example 299

3-fluoro-N-(5-{[(morpholin-2-ylmethyl)amino]methyl}-2-(pyridin-2-yl)pyrrolo[2,1-f][1,2,4]triazin-4-yl)pyridin-4-amine

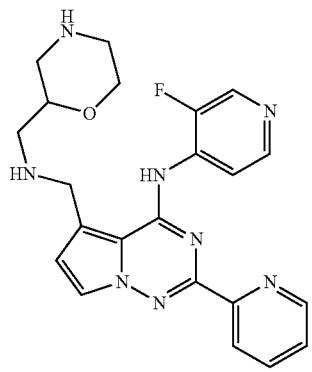 [SMILES: Fc1cnccc1Nc1nc(-c2ccccn2)nn2ccc(CNCC3CNCCO3)c12]

Example 299 (3.0 mg, 14.3%) was synthesized employing the procedure described for Example 231 (Scheme 59). LCMS m/z 435.3 (M+H); rt 1.33 min; Conditions C, ¹H NMR (400 MHz, DMSO-d₆) δ 8.98-8.92 (m, 1H), 8.79-8.73 (m, 1H), 8.59-8.49 (m, 2H), 8.43-8.37 (m, 1H), 8.30-8.23 (m, 1H), 8.03-7.96 (m, 1H), 7.90-7.84 (m, 1H), 7.57-7.48 (m, 1H), 6.86-6.77 (m, 1H), 4.10-4.04 (m, 2H), 3.56-3.45 (m, 3H), 2.73-2.65 (m, 2H), 2.62-2.54 (m, 3H), 2.31-2.23 (m, 1H).

Example 300

N-[5-({[(2R)-3,3-dimethylbutan-2-yl]amino}methyl)-2-(pyridin-2-yl)pyrrolo[2,1-f][1,2,4]triazin-4-yl]-3-fluoropyridin-4-amine

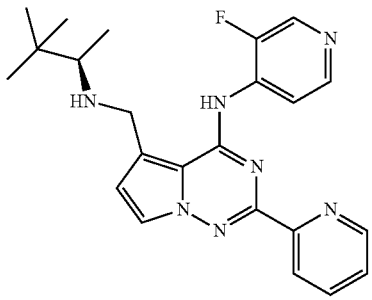 [SMILES: C[C@@H](NCc1ccn2nc(-c3ccccn3)nc(Nc3ccncc3F)c12)C(C)(C)C]

Example 300 (6.0 mg, 29.6%) was synthesized employing the procedure described for Example 231 (Scheme 59). LCMS m/z 420.3 (M+H); rt 2.21 min; Conditions C. ¹H NMR (400 MHz, DMSO-d₆) δ 9.13-9.07 (m, 1H), 9.02-8.97 (m, 1H), 8.83-8.79 (m, 1H), 8.66-8.61 (m, 1H), 8.51-8.45 (m, 1H), 8.28-8.20 (m, 1H), 8.11-8.05 (m, 1H), 7.81-7.72 (m, 1H), 7.11-7.06 (m, 1H), 4.45-4.30 (m, 2H), 2.56-2.50 (m, 1H), 1.31-1.25 (m, 3H), 1.07 (s, 9H).

Example 301

3-fluoro-N-[2-(pyridin-2-yl)-5-({[2-(pyridin-2-yl)propan-2-yl]amino}methyl)pyrrolo[2,1-f][1,2,4]triazin-4-yl]pyridin-4-amine

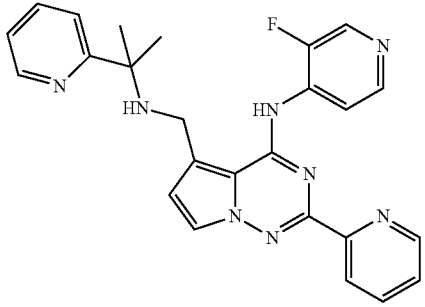 [SMILES: CC(C)(NCc1ccn2nc(-c3ccccn3)nc(Nc3ccncc3F)c12)c1ccccn1]

Example 301 (5.0 mg, 22.8%) was synthesized employing the procedure described for Example 231 (Scheme 59). LCMS m/z 455.3 (M+H); rt 1.97 min; Conditions C. ¹H NMR (400 MHz, DMSO-d₆) δ 9.01-8.96 (m, 1H), 8.89-8.79 (m, 2H), 8.73-8.66 (m, 2H), 8.49-8.42 (m, 1H), 8.29-8.19 (m, 1H), 8.12-8.01 (m, 2H), 7.86-7.73 (m, 2H), 7.56-7.48 (m, 1H), 6.92-6.87 (m, 1H), 4.07-4.01 (m, 2H), 1.76 (s, 6H).

Example 302

3-fluoro-N-[5-({[1-(propan-2-yl)-1H-pyrazol-4-yl]amino}methyl)-2-(pyridin-2-yl)pyrrolo[2,1-f][1,2,4]triazin-4-yl]pyridin-4-amine

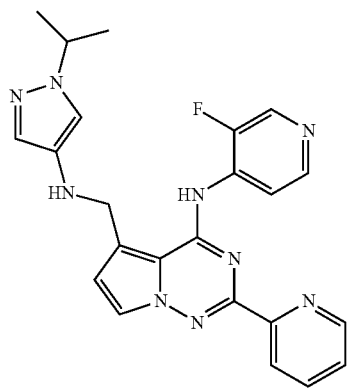 [SMILES: CC(C)n1cc(NCc2ccn3nc(-c4ccccn4)nc(Nc4ccncc4F)c23)cn1]

Example 302 (4.0 mg, 18.7%) was synthesized employing the procedure described for Example 231 (Scheme 59). LCMS m/z 444.3 (M+H); rt 1.62 min; Conditions C. ¹H NMR (400 MHz, DMSO-d₆) δ 9.19-9.12 (m, 1H), 9.03-8.99 (m, 1H), 8.82-8.75 (m, 1H), 8.68-8.60 (m, 1H), 8.53-8.47 (m, 1H), 8.28-8.20 (m, 2H), 7.81-7.75 (m, 1H), 7.59-7.53 (m, 1H), 7.40-7.34 (m, 1H), 7.24-7.13 (m, 2H), 4.64-4.56 (m, 3H), 1.58 (d, J=6.8 Hz, 6H).

Example 303

3-fluoro-N-[5-({[2-(1-methylpiperidin-4-yl)ethyl]amino}methyl)-2-(pyridin-2-yl)pyrrolo[2,1-f][1,2,4]triazin-4-yl]pyridin-4-amine

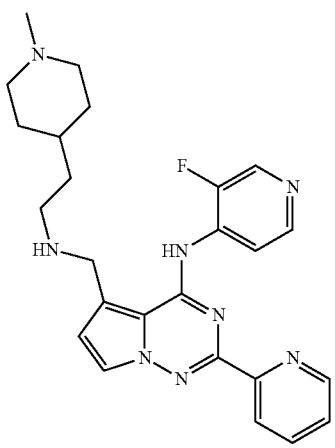 [SMILES: CN1CCC(CCNCc2ccn3nc(-c4ccccn4)nc(Nc4ccncc4F)c23)CC1]

Example 303 (9.0 mg, 40.5%) was synthesized employing the procedure described for Example 231 (Scheme 59). LCMS m/z 461.4 (M+H); rt 1.39 min; Conditions C. $^1$H NMR (400 MHz, DMSO-d$_6$) δ 8.95 (dd, J=7.0, 5.5 Hz, 1H), 8.77-8.71 (m, 1H), 8.54 (d, J=3.5 Hz, 1H), 8.38 (d, J=5.0 Hz, 1H), 8.29-8.21 (m, 1H), 7.99 (td, J=7.8, 2.0 Hz, 1H), 7.85 (d, J=2.5 Hz, 1H), 7.52 (ddd, J=7.5, 4.8, 1.3 Hz, 1H), 6.79 (d, J=2.5 Hz, 1H), 4.07 (s, 2H), 2.71-2.60 (m, 4H), 2.06 (s, 3H), 1.66 (td, J=11.5, 2.0 Hz, 2H), 1.53-1.38 (m, 4H), 1.26-1.15 (m, 1H), 1.05 (dd, J=12.0, 3.5 Hz, 2H).

Example 304

3-fluoro-N-[2-(pyridin-2-yl)-5-({[2-(pyridin-2-yl)ethyl]amino}methyl)pyrrolo[2,1-f][1,2,4]triazin-4-yl]pyridin-4-amine

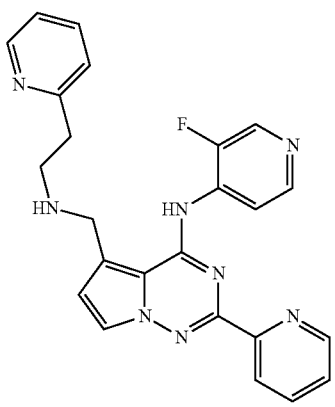 [SMILES: Fc1cnccc1Nc1nc(-c2ccccn2)nn2ccc(CNCCc3ccccn3)c12]

Example 304 (5.0 mg, 23.5%) was synthesized employing the procedure described for Example 231 (Scheme 59). LCMS m/z 441.3 (M+H); rt 1.63 min; Conditions C. $^1$H NMR (400 MHz, DMSO-d$_6$) δ 9.23-9.16 (m, 1H), 9.05-9.00 (m, 1H), 8.80-8.73 (m, 1H), 8.63 (s, 2H), 8.54-8.47 (m, 2H), 8.30-8.21 (m, 1H), 8.15 (d, J=2.4 Hz, 1H), 7.87-7.75 (m, 2H), 7.49-7.43 (m, 1H), 7.39-7.32 (m, 1H), 7.12-7.05 (m, 1H), 4.37 (s, 2H), 3.32-3.21 (m, 4H).

Example 305

3-fluoro-N-[5-({[(5-methylpyrazin-2-yl)methyl]amino}methyl)-2-(pyridin-2-yl)pyrrolo[2,1-f][1,2,4]triazin-4-yl]pyridin-4-amine

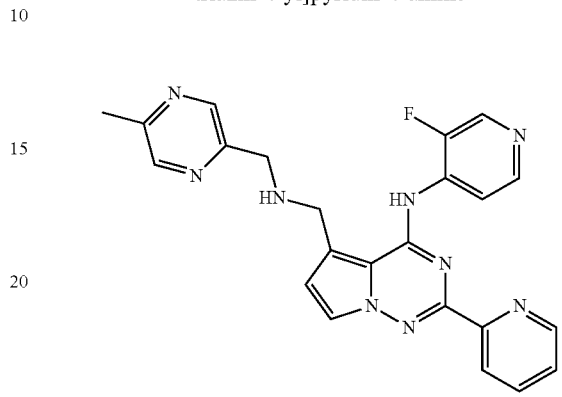

Example 305 (7.0 mg, 32.8%) was synthesized employing the procedure described for Example 231 (Scheme 59). LCMS m/z 442.3 (M+H); rt 1.54 min; Conditions C. $^1$H NMR (400 MHz, CH$_3$CN+D$_2$O) δ 11.41-11.35 (m, 1H), 11.26-11.20 (m, 1H), 10.98-10.92 (m, 2H), 10.89-10.84 (m, 2H), 10.76-10.70 (m, 1H), 10.51-10.43 (m, 1H), 10.39-10.34 (m, 1H), 10.03-9.95 (m, 1H), 9.30-9.23 (m, 1H), 6.56-6.52 (m, 2H), 6.46-6.39 (m, 2H), 4.92 (s, 3H).

Example 306

N-({4-[(3-fluoropyridin-4-yl)amino]-2-(pyridin-2-yl)pyrrolo[2,1-f][1,2,4]triazin-5-yl}methyl)-1H-1,2,3-benzotriazol-5-amine

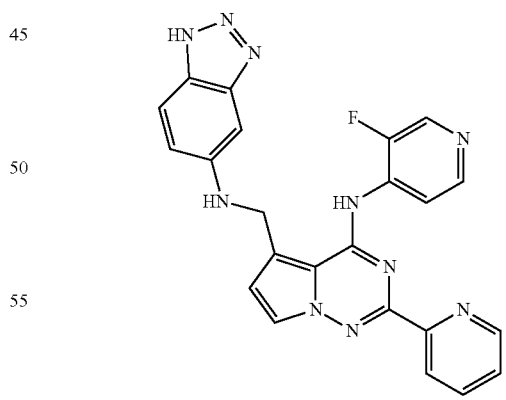

Example 306 (4.0 mg, 18.3%) was synthesized employing the procedure described for Example 231 (Scheme 59). LCMS m/z 453.3 (M+H); rt 1.39 min; Conditions C. $^1$H NMR (400 MHz, DMSO-d$_6$) δ 8.92-8.80 (m, 1H), 8.78-8.73 (m, 1H), 8.50-8.44 (m, 1H), 8.42-8.33 (m, 1H), 8.29-8.21 (m, 1H), 8.05-7.95 (m, 2H), 7.81-7.72 (m, 1H), 7.57-7.49 (m, 1H), 7.12-6.96 (m, 3H), 4.68-4.59 (m, 2H).

Example 307

3-fluoro-N-(5-{[(piperidin-4-yl)amino]methyl}-2-(pyridin-2-yl)pyrrolo[2,1-f][1,2,4]triazin-4-yl)pyridin-4-amine

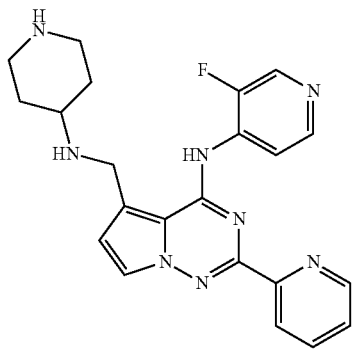 [SMILES: Fc1cnccc1Nc1nc(-c2ccccn2)nn2ccc(CNC3CCNCC3)c12]

Example 307 (6.0 mg, 29.7%) was synthesized employing the procedure described for Example 231 (Scheme 59). LCMS m/z 419.3 (M+H); rt 1.22 min; Conditions C. $^1$H NMR (400 MHz, DMSO-$d_6$) δ 8.91 (dd, J=7.0, 5.5 Hz, 1H), 8.75 (dt, J=4.0, 1.0 Hz, 1H), 8.55 (d, J=3.5 Hz, 1H), 8.38 (d, J=5.5 Hz, 1H), 8.28-8.20 (m, 1H), 8.04-7.95 (m, 1H), 7.86 (d, J=2.5 Hz, 1H), 7.56-7.48 (m, 1H), 6.82 (d, J=3.0 Hz, 1H), 4.13 (s, 2H), 2.92 (br. s., 2H), 2.63-2.55 (m, 2H), 2.39 (br. s., 2H), 1.81 (br. s., 1H), 1.36-1.23 (m, 2H).

Example 308

3-fluoro-N-(5-{[(5-methyl-1,3,4-thiadiazol-2-yl)amino]methyl}-2-(pyridin-2-yl)pyrrolo[2,1-f][1,2,4]triazin-4-yl)pyridin-4-amine

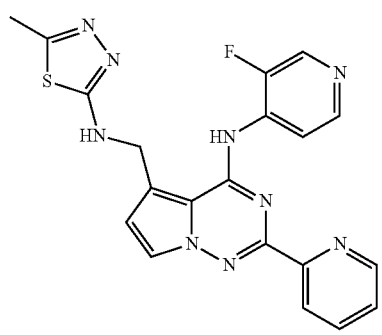 [SMILES: Cc1nnc(NCc2ccn3nc(-c4ccccn4)nc(Nc4ccncc4F)c23)s1]

Example 308 (2 mg, 9.6%) was synthesized employing the procedure described for Example 231 (Scheme 59). LCMS m/z, 434.2 (M+H); rt 1.64 min; Conditions C. $^1$H NMR (400 MHz, DMSO-$d_6$) δ 8.97-8.92 (m, 1H), 8.85-8.77 (m, 1H), 8.66-8.60 (m, 1H), 8.38-8.29 (m, 2H), 8.25-8.13 (m, 2H), 7.77-7.69 (m, 1H), 7.13-7.03 (m, 1H), 5.61-5.55 (m, 2H), 2.59 (s, 3H).

Scheme 69

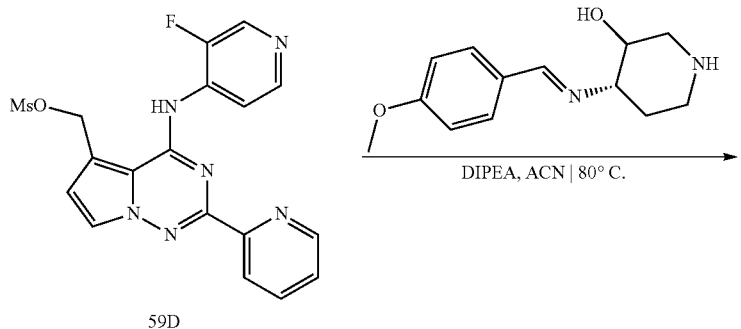

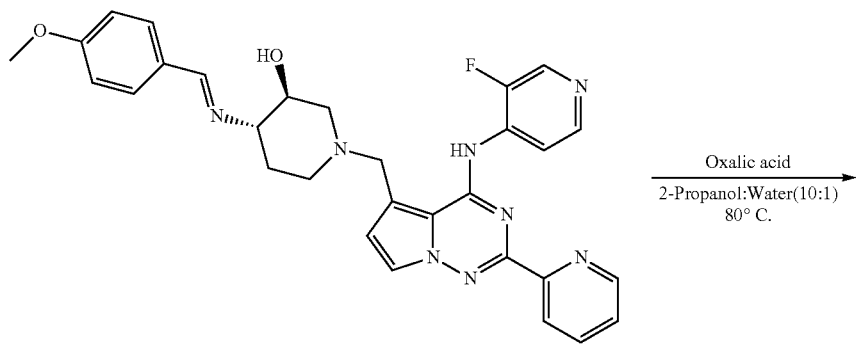

69A

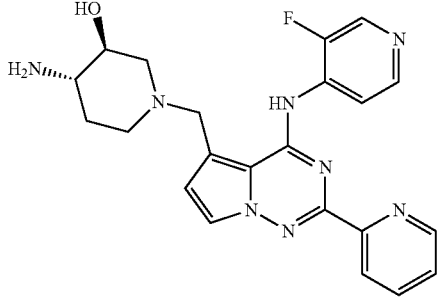 [SMILES: N[C@H]1CCN(Cc2ccn3nc(-c4ccccn4)nc(Nc4ccncc4F)c23)C[C@@H]1O]
309

Example 309

(3S,4S)-4-amino-1-({4-[(3-fluoropyridin-4-yl)amino]-2-(pyridin-2-yl)pyrrolo[2,1-f][1,2,4]triazin-5-yl}methyl)piperidin-3-ol

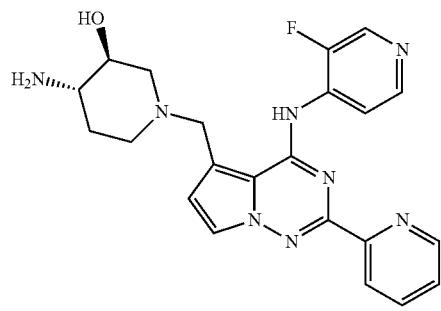

Intermediate 69A: (3S,4S)-1-((4-((3-fluoropyridin-4-yl)amino)-2-(pyridin-2-yl)pyrrolo[2,1-f][1,2,4]triazin-5-yl)methyl)-4-((E)-(4-methoxybenzylidene)amino)piperidin-3-ol

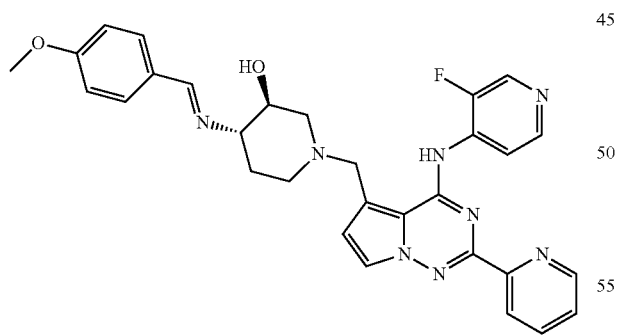

Intermediate 69A (100 mg, 0.65 mmol, 36% yield) was synthesized employing the procedure described for Example 231 (Scheme 59). LCMS m/z 553.2 (M+H); rt 2.64 min; Conditions E.

To a solution of (3S,4S)-1-((4-((3-fluoropyridin-4-yl)amino)-2-(pyridin-2-yl)pyrrolo[2,1-f][1,2,4]triazin-5-yl)methyl)-4-((E)-(4-methoxybenzylidene)amino)piperidin-3-ol (100 mg, 0.065 mmol) in 2-propanol (5 mL) and water (0.5 mL) was added oxalic acid (8.80 mg, 0.098 mmol). The resulting mixture was heated at 80° C. for 1 h. An aliquot of the reaction mixture was diluted with methanol and analyzed by LCMS to ensure complete conversion. The reaction mixture was concentrated. The residue was purified by preparative HPLC to obtain (3S,4S)-4-amino-1-({4-[(3-fluoropyridin-4-yl)amino]-2-(pyridin-2-yl)pyrrolo[2,1-f][1,2,4]triazin-5-yl}methyl)piperidin-3-ol 309 (4 mg, 14% yield). LCMS m/z 435.2 (M+H); rt 1.21 min; Conditions C. $^1$H NMR (400 MHz, DMSO-$d_6$) δ 12.22 (br. s., 1H) 8.83 (dd, J=6.97, 5.50 Hz, 1H) 8.75 (ddd, J=4.77, 1.83, 0.98 Hz, 1H) 8.63 (d, J=2.93 Hz, 1H) 8.42-8.49 (m, 1H) 8.23 (dt, J=7.89, 1.07 Hz, 1H) 7.99 (td, J=7.70, 1.71 Hz, 1H) 7.95 (d, J=2.69 Hz, 1H) 7.52 (ddd, J=7.52, 4.83, 1.10 Hz, 1H) 6.84 (d, J=2.69 Hz, 1H) 4.91 (br. s, 2H) 3.93 (d, J=13.69 Hz, 1H) 3.82 (d, J=13.69 Hz, 1H) 2.97 (d, J=11.74 Hz, 2H) 2.42 (br. s., 1H) 2.12 (br. s., 1H) 1.75 (d, J=10.27 Hz, 1H) 1.27-1.43 (m, 1H).

Example 310

(1R)-2-[({4-[(3-fluoropyridin-4-yl)amino]-2-(pyridin-2-yl)pyrrolo[2,1-f][1,2,4]triazin-5-yl}methyl)amino]-1-phenylethan-1-ol

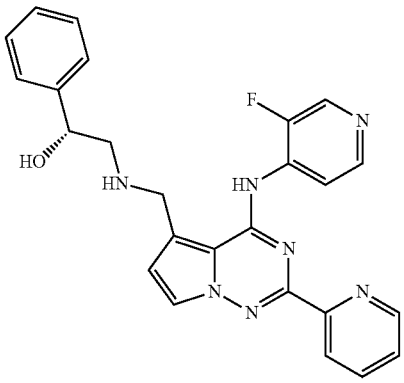 [SMILES: O[C@@H](CNCc1ccn2nc(-c3ccccn3)nc(Nc3ccncc3F)c12)c1ccccc1]

Example 310 (3.0 mg, 13.6%) was synthesized employing the procedure described for Example 231 (Scheme 59). LCMS m/z 456.1 (M+H); rt 1.88 min; Conditions C. $^1$H NMR (400 MHz, DMSO-$d_6$) δ 9.72-9.48 (m, 1H), 8.76-8.61 (m, 1H), 8.50-8.37 (m, 1H), 8.31-7.74 (m, 3H), 7.66-7.53 (m, 1H), 7.33 (br. s., 4H), 7.13-7.04 (m, 1H), 6.94-6.77 (m, 2H), 6.18-5.96 (m, 1H), 5.02-4.86 (m, 1H), 4.61-4.43 (m, 2H), 3.27-3.14 (m, 2H), 3.11-2.97 (m, 2H).

Example 311

N-(5-{[(azetidin-3-yl)amino]methyl}-2-(pyridin-2-yl)pyrrolo[2,1-f][1,2,4]triazin-4-yl)-3-fluoropyridin-4-amine

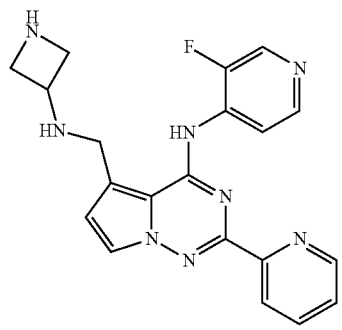 [SMILES: Fc1cnccc1Nc1nc(-c2ccccn2)nn2ccc(CNC3CNC3)c12]

Example 311 (2.0 mg, 10.6%) was synthesized employing the procedure described for Example 231 (Scheme 59). LCMS m/z 391.1 (M+H); rt 1.21 min; Conditions C. ¹H NMR (400 MHz, DMSO-d₆) δ 9.18-9.13 (m, 1H), 9.02-8.99 (m, 1H), 8.82-8.78 (m, 1H), 8.68-8.64 (m, 1H), 8.54-8.48 (m, 1H), 8.28-8.22 (m, 1H), 8.16-8.12 (m, 1H), 7.81-7.75 (m, 1H), 7.09-7.04 (m, 1H), 4.23-4.18 (m, 3H), 3.43 (m, 5H).

Scheme 70

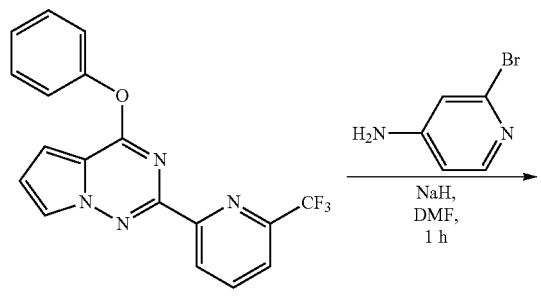

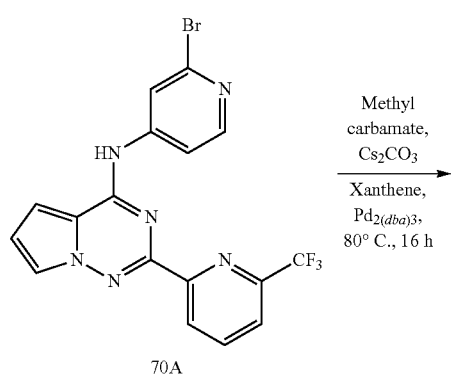

Example 312

Methyl N-[4-({2-[6-(trifluoromethyl)pyridin-2-yl]pyrrolo[2,1-f][1,2,4]triazin-4-yl}amino)pyridin-2-yl]carbamate

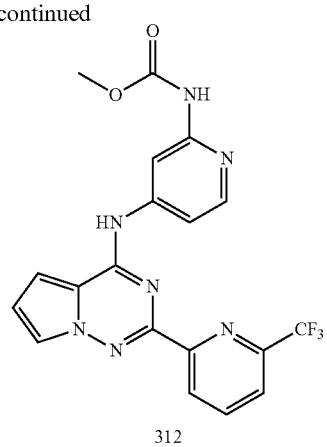

312

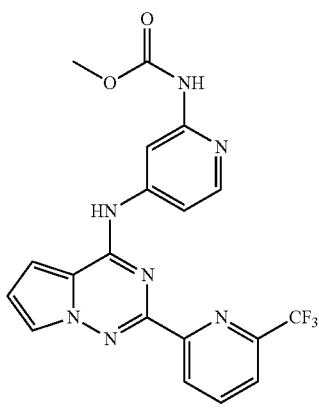 [SMILES: COC(=O)Nc1cc(Nc2nc(-c3cccc(C(F)(F)F)n3)nn3cccc23)ccn1]

Example 70A: N-(2-bromopyridin-4-yl)-2-(6-(trifluoromethyl)pyridin-2-yl)pyrrolo[2,1-f][1,2,4]triazin-4-amine

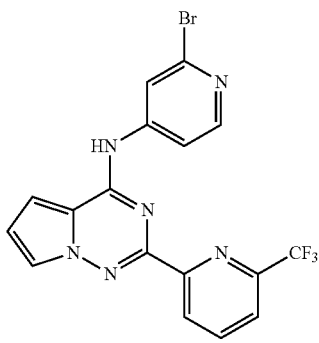 [SMILES: FC(F)(F)c1cccc(-c2nc(Nc3ccnc(Br)c3)c3cccn3n2)n1]

Intermediate 70A (0.2 g, 0.460 mmol, 82% yield) was synthesized employing the procedure described for intermediate 57A (Scheme 57). LCMS m/z 437.2 (M+H); rt 1.34 min; Conditions B.

To a stirred solution of N-(2-bromopyridin-4-yl)-2-(6-(trifluoro methyl)pyridin-2-yl)pyrrolo[2,1-f][1,2,4]triazin-4-amine (0.05 g, 0.115 mmol) in 1,4-dioxane (1 mL) was added methyl carbamate (9.49 mg, 0.126 mmol), Cs$_2$CO$_3$ (0.112 g, 0.345 mmol) and 4,5-bis(diphenylphosphino)-9,9-dimethylxanthene (5.98 mg, 10.34 μmol) in a sealed tube. The reaction mixture was purged with nitrogen for 5 min and Pd$_2$(dba)$_3$ (3.30 mg, 5.74 μmol) was added and again purged with nitrogen for 10 minutes. The reaction mixture was heated at 90° C. for 16 h. The reaction mixture was diluted with ethyl acetate (100 mL), filtered through a Celite bed and washed with ethyl acetate. The filtrate was concentrated under reduced pressure. The residue was purified by HPLC to get methyl (4-((2-(6-(trifluoromethyl)pyridin-2-yl)pyrrolo[2,1-f][1,2,4]triazin-4-yl)amino)pyridin-2-yl)carbamate 312 (10 mg, 20%). LCMS m/z 430.2 (M+H); rt 2.05 min; Conditions C. $^1$H NMR (400 MHz, DMSO-d$_6$) δ 10.58-10.63 (m, 1H), 10.44 (s, 1H), 9.06-9.12 (m, 1H), 8.94-8.98 (m, 1H), 8.52-8.59 (m, 1H), 8.47 (s, 1H), 8.34-8.39 (m, 1H), 8.27-8.32 (m, 1H), 8.13-8.20 (m, 1H), 7.65-7.70 (m, 1H), 7.15-7.21 (m, 1H), 4.00 (s, 3H).

Scheme 71

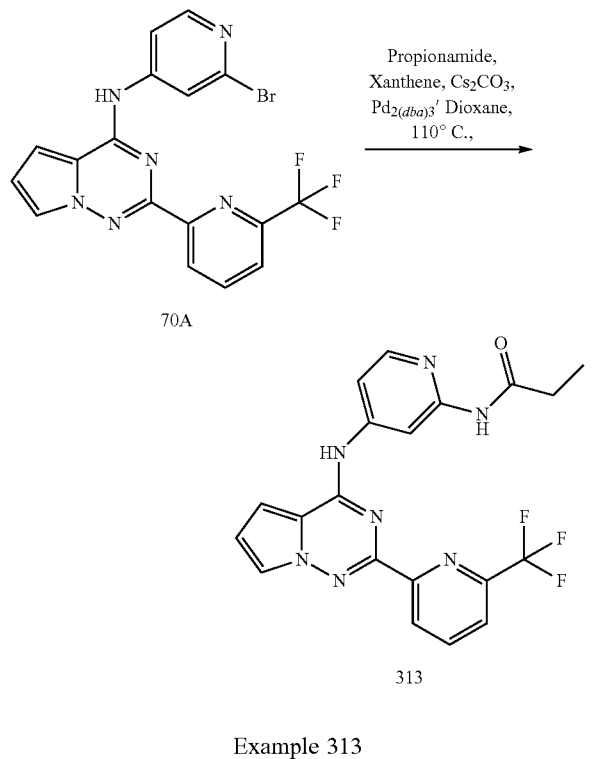

Example 313

N-[4-({2-[6-(trifluoromethyl)pyridin-2-yl]pyrrolo[2,1-f][1,2,4]triazin-4-yl}amino)pyridin-2-yl]propanamide Example 313 (45 mg, 57.3%) was synthesized employing the procedure described for Intermediate 55B (Scheme 55). LCMS m/z 428.1 (M+H); rt 2.06 min; Conditions C. $^1$H NMR (400 MHz, DMSO-d$_6$) δ 10.70 (s, 1H), 10.62 (s, 1H), 9.19-9.08 (m, 2H), 8.57-8.47 (m, 2H), 8.36 (dd, J=2.6, 1.6 Hz, 1H), 8.31 (dd, J=7.7, 0.9 Hz, 1H), 8.26 (dd, J=5.6, 2.0 Hz, 1H), 7.68 (dd, J=4.4, 1.5 Hz, 1H), 7.22-7.15 (m, 1H), 2.73-2.68 (m, 2H), 1.39 (t, J=7.5 Hz, 3H).

Example 314

3-methyl-N-[4-({2-[6-(trifluoromethyl)pyridin-2-yl]pyrrolo[2,1-f][1,2,4]triazin-4-yl}amino)pyridin-2-yl]butanamide

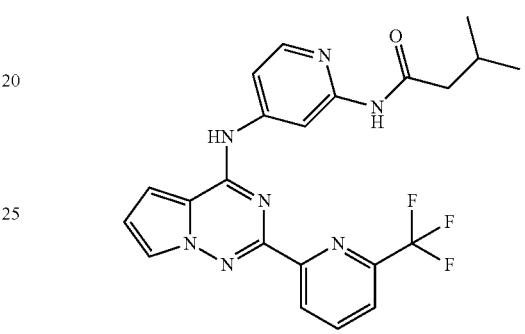

Example 314 (28 mg, 33% yield) was synthesized employing the procedure described for Intermediate 55B (Scheme 55). LCMS m/z 456.1 (M+H); rt 2.31 min; Conditions C. $^1$H NMR (400 MHz, DMSO-d$_6$) δ 10.67 (br. s., 1H), 10.50 (s, 1H), 8.86-8.72 (m, 2H), 8.31-8.21 (m, 2H), 8.15-7.98 (m, 2H), 7.41 (dd, J=4.4, 1.5 Hz, 1H), 6.94 (dd, J=4.4, 2.7 Hz, 1H), 2.37-2.28 (m, 2H), 2.23-2.06 (m, 1H), 0.98 (d, J=6.6 Hz, 6H), 1.05-0.88 (m, 6H).

Scheme 72

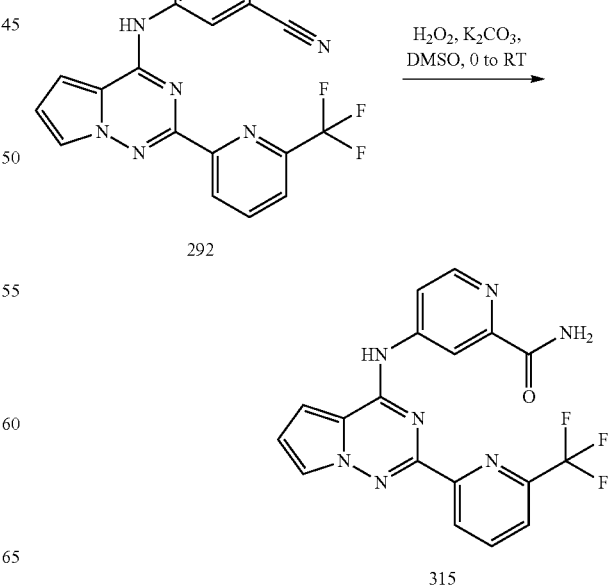

Example 315

4-({2-[6-(trifluoromethyl)pyridin-2-yl]pyrrolo[2,1-f][1,2,4]triazin-4-yl}amino)pyridine-2-carboxamide

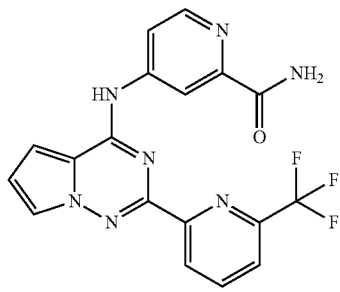 [SMILES: NC(=O)c1cc(Nc2nc(-c3cccc(C(F)(F)F)n3)nn3cccc23)ccn1]

To a solution of 4-((2-(6-(trifluoromethyl)pyridin-2-yl)pyrrolo[2,1-f][1,2,4]triazin-4-yl)amino)picolinonitrile (130 mg, 0.341 mmol) in DMSO (20 mL) was added K₂CO₃ (141 mg, 1.023 mmol). The mixture was cooled to 0° C. and H₂O₂ (0.784 mL, 10.23 mmol, 40% w/v) was added dropwise. The reaction mixture was warmed to room temperature and stirred for 3 h. An aliquot of the reaction mixture was diluted with methanol and analyzed by LCMS to ensure complete conversion. The reaction mixture was diluted with ice/water and the resulting precipitate was filtered, washed with water and dried to give 4-((2-(6-(trifluoromethyl)pyridin-2-yl)pyrrolo[2,1-f][1,2,4]triazin-4-yl)amino)picolinamide 315 (100 mg, 0.250 mmol, 73.5% yield) as an off white solid. LCMS m/z 400.0 (M+H); rt 2.42 min; Conditions E. ¹H NMR (400 MHz, DMSO-d₆) δ 10.56 (s, 1H), 8.75-8.63 (m, 3H), 8.58 (d, J=5.5 Hz, 1H), 8.30 (t, J=7.8 Hz, 1H), 8.12 (dd, J=2.5, 1.5 Hz, 2H), 8.08-8.02 (m, 1H), 7.66 (br. s., 1H), 7.39 (dd, J=4.5, 1.5 Hz, 1H), 6.95 (dd, J=4.5, 2.5 Hz, 1H).

Scheme 73

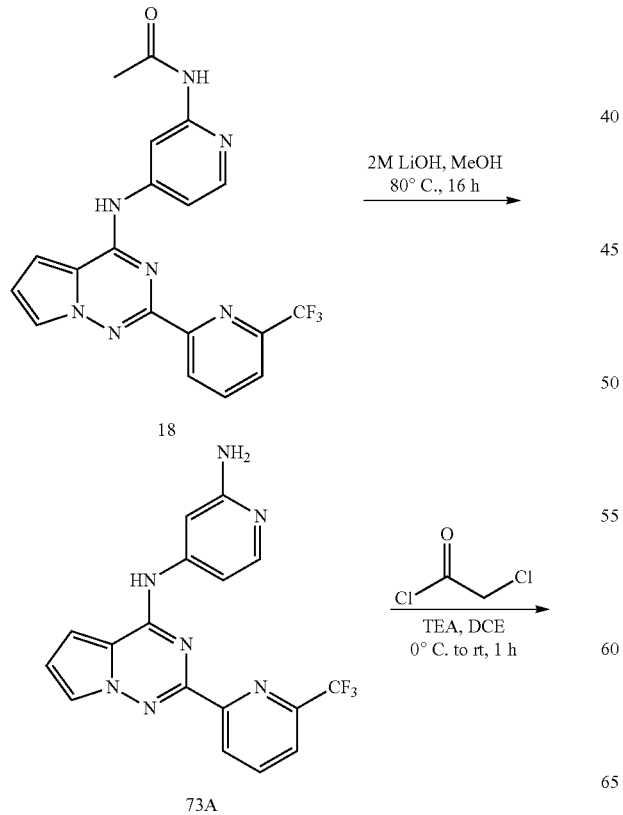

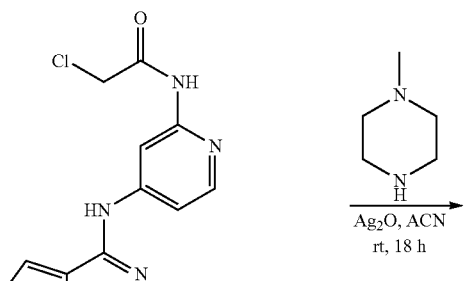

73B

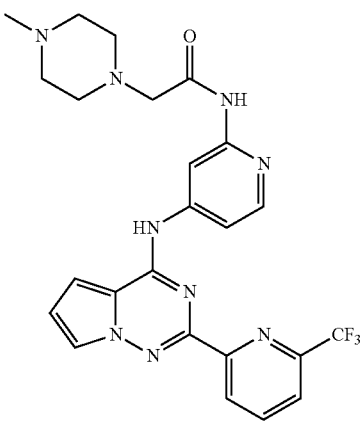

316

Example 316

2-(4-methylpiperazin-1-yl)-N-[4-({2-[6-(trifluoromethyl)pyridin-2-yl]pyrrolo[2,1-f][1,2,4]triazin-4-yl}amino)pyridin-2-yl]acetamide

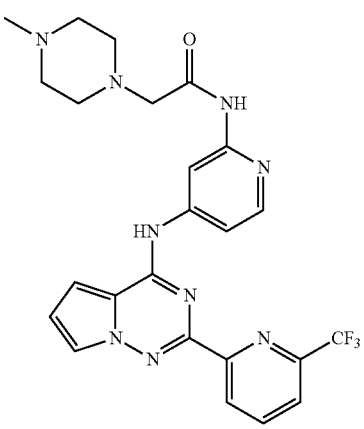 [SMILES: CN1CCN(CC(=O)Nc2cc(Nc3nc(-c4cccc(C(F)(F)F)n4)nn4cccc34)ccn2)CC1]

Intermediate 73A: N4-(2-(6-(trifluoromethyl)pyridin-2-yl)pyrrolo[2,1-f][1,2,4]triazin-4-yl)pyridine-2,4-diamine

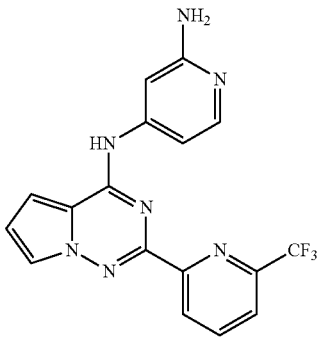 [SMILES: Nc1cc(Nc2nc(-c3cccc(C(F)(F)F)n3)nn3cccc23)ccn1]

To a stirred solution of N-(4-((2-(6-(trifluoromethyl)pyridin-2-yl)pyrrolo[2,1-f][1,2,4]triazin-4-yl)amino)pyridin-2-yl)acetamide (0.28 g, 0.677 mmol) in methanol (6 mL) was added 2 M aq. LiOH (3.39 mL, 6.77 mmol) and the reaction mixture was heated at 80° C. for 16 h. The reaction mixture was evaporated under reduced pressure and the residue was diluted with water. The resulting precipitate was filtered, washed with excess of water and dried to get N4-(2-(6-(trifluoromethyl)pyridin-2-yl)pyrrolo[2,1-f][1,2,4]triazin-4-yl)pyridine-2,4-diamine 73A (0.16 g, 0.431 mmol, 63.6% yield) as a yellow solid.

Intermediate 73B: 2-chloro-N-(4-((2-(6-(trifluoromethyl)pyridin-2-yl)pyrrolo[2,1-f][1,2,4]triazin-4-yl)amino)pyridin-2-yl)acetamide

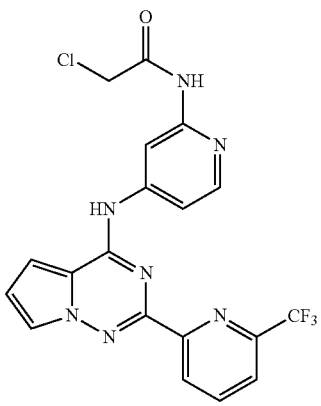 [SMILES: O=C(CCl)Nc1cc(Nc2nc(-c3cccc(C(F)(F)F)n3)nn3cccc23)ccn1]

To a solution of N4-(2-(6-(trifluoromethyl)pyridin-2-yl)pyrrolo[2,1-f][1,2,4]triazin-4-yl)pyridine-2,4-diamine (0.16 g, 0.431 mmol) in dichloroethane (5 mL) was added triethylamine (0.300 mL, 2.154 mmol), chloroacetyl chloride (0.155 mL, 1.939 mmol) at 0° C. and the reaction mixture was allowed to stir at room temperature for 1 h. The reaction mixture was concentrated and diluted with dichloromethane (100 mL), washed with water (20 mL), dried over sodium sulfate and concentrated to get 2-chloro-N-(4-((2-(6-(trifluoromethyl)pyridin-2-yl) pyrrolo[2,1-f][1,2,4]triazin-4-yl)amino)pyridin-2-yl)acetamide 73B (160 mg, crude) as an dark oil. LCMS m/z 448.2 (M+H); rt 2.72 min; Conditions C.

To a stirred solution of 2-chloro-N-(4-((2-(6-(trifluoromethyl)pyridin-2-yl)pyrrolo[2,1-f][1,2,4]triazin-4-yl)amino)pyridin-2-yl)acetamide (0.08 g, 0.179 mmol) in acetonitrile was added 1-methylpiperazine (0.098 g, 0.983 mmol) in acetonitrile (4 mL), silver oxide (0.083 g, 0.357 mmol) and the reaction mixture was stirred for 4 h at room temperature. LCMS indicated formation of the desired product. The reaction mixture was filtered through a syringe filter and the filtrate was concentrated under reduced pressure. The crude residue was purified by preparative HPLC to get 2-(4-methylpiperazin-1-yl)-N-[4-({2-[6-(trifluoromethyl)pyridin-2-yl]pyrrolo[2,1-f][1,2,4]triazin-4-yl}amino)pyridin-2-yl]acetamide 316 (13 mg, 14.2%). LCMS m/z 512.2 (M+H); rt 1.838 min; Conditions C. $^1$HNMR (400 MHz, DMSO-d6) δ 9.89 (s, 1H), 8.82-8.88 (m, 2H), 8.26-8.29 (m, 2H), 8.03-8.10 (m, 3H), 7.42-7.43 (m, 1H), 6.92-6.94 (m, 1H), 3.23 (s, 2H), 3.17 (s, 3H), 2.53-2.61 (m, 4H), 2.38-2.40 (m, 2H), 2.20 (s, 3H).

Scheme 74

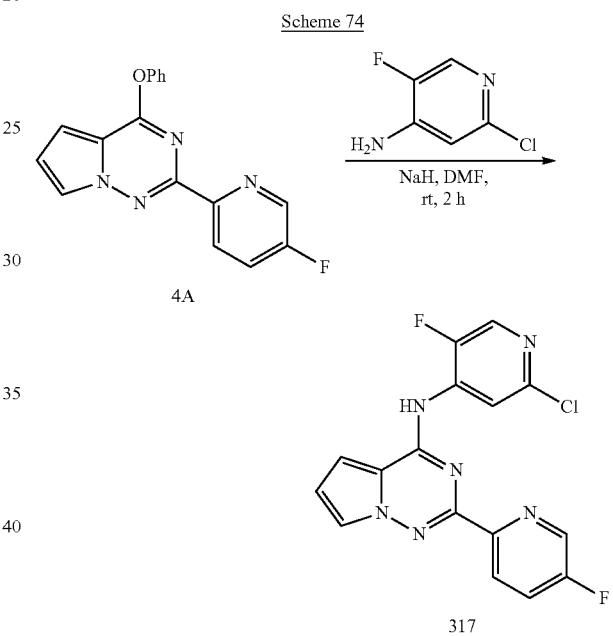

Example 317

2-chloro-5-fluoro-N-[2-(5-fluoropyridin-2-yl)pyrrolo[2,1-f][1,2,4]triazin-4-yl]pyridin-4-amine

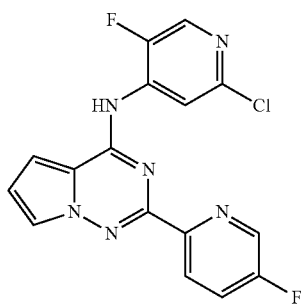 [SMILES: Fc1ccc(-c2nc(Nc3cc(Cl)ncc3F)c3cccn3n2)nc1]

Example 317 (10.0 mg, 8.5%) was synthesized employing the procedure described for Example 229 (Scheme 57):

LCMS m/z 359.0 (M+H); rt 1.93 min; Conditions D. ¹H NMR (400 MHz, DMSO-d6) δ 10.37 (s, 1H), 8.71 (d, J=2.8 Hz, 1H), 8.67-8.68 (m, 1H), 8.50 (d, J=2.8 Hz, 1H), 8.18-8.26 (m, 1H), 8.02 (s, 1H), 7.91 (dt, J=2.8, 8.8 Hz, 1H), 7.40 (s, 1H), 6.91 (s, 1H).

Scheme 75

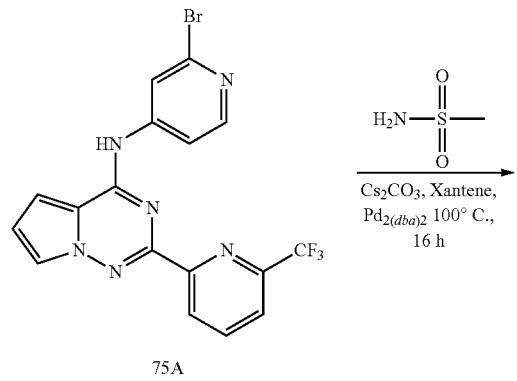

Example 318

N-[4-({2-[6-(trifluoromethyl)pyridin-2-yl]pyrrolo[2,1-f][1,2,4]triazin-4-yl}amino)pyridin-2-yl]methanesulfonamide Intermediate 75A: N-(2-bromopyridin-4-yl)-2-(6-(trifluoromethyl)pyridin-2-yl)pyrrolo[2,1-f][1,2,4]triazin-4-amine

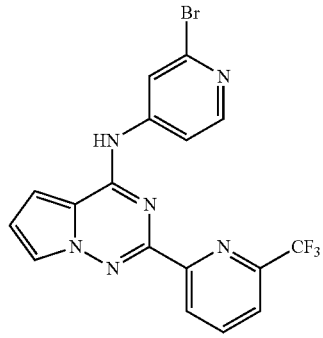

Intermediate 75A (350 mg, 43%) was synthesized employing the procedure described for intermediate 18A (Scheme 18). LCMS m/z 486.1 (M+H); rt 1.44 min; Conditions C.

Example 318 (6.0 mg, 6.0%) was synthesized employing the procedure described for Intermediate 55B (Scheme 55). LCMS m/z 450.2 (M+H); rt 1.63 min; Conditions C. ¹H NMR (400 MHz, DMSO-d6) δ 10.40 (s, 1H), 8.74 (d, J=8.00 Hz, 1H), 8.26 (t, J=2.80 Hz, 1H), 8.12 (s, 1H), 8.02-8.04 (m, 1H), 7.96 (s, 1H), 7.87 (s, 1H), 7.67 (s, 1H), 7.39 (d, J=4.40 Hz, 1H), 6.93-6.94 (m, 1H), 3.05 (s, 3H).

Scheme 76

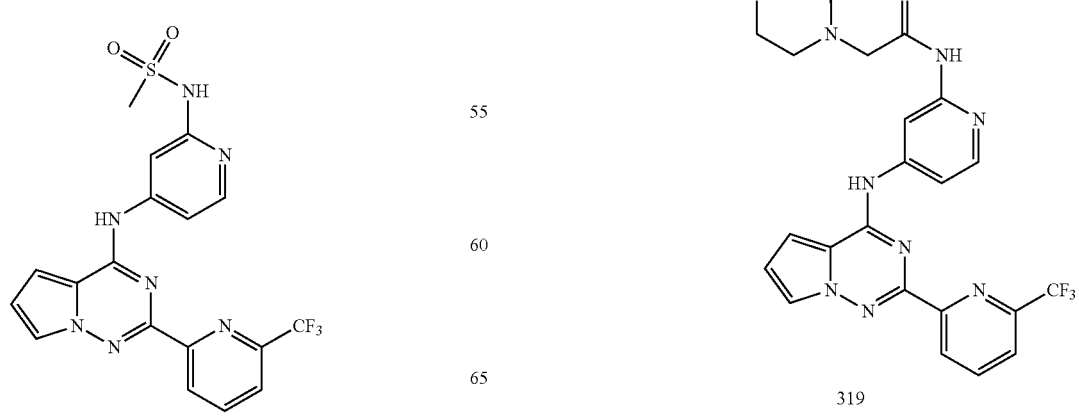

Example 319

2-[4-(2-hydroxyethyl)piperazin-1-yl]-N-[4-({2-[6-(trifluoromethyl)pyridin-2-yl]pyrrolo[2,1-f][1,2,4]triazin-4-yl}amino)pyridin-2-yl]acetamide

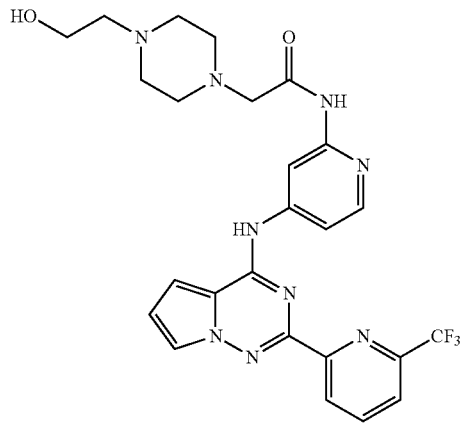 [SMILES: O=C(CN1CCN(CCO)CC1)Nc1cc(Nc2nc(-c3cccc(C(F)(F)F)n3)nn3cccc23)ccn1]

Example 319 (20 mg, 21%) was synthesized employing the procedure described for Example 316 (Scheme 73). LCMS m/z 542.2 (M+H); rt 1.80 min; Conditions C. $^1$H NMR (400 MHz, DMSO-d6) δ 9.89 (s, 1H), 8.82-8.88 (m, 2H), 8.26-8.30 (m, 2H), 8.03-8.11 (m, 3H), 7.41-7.43 (m, 1H), 6.92-6.94 (m, 1H), 3.51 (t, J=16.00 Hz, 2H), 3.23 (s, 3H), 2.58-2.61 (m, 4H), 2.41-2.49 (m, 2H), 1.90 (s, 4H).

Scheme 77

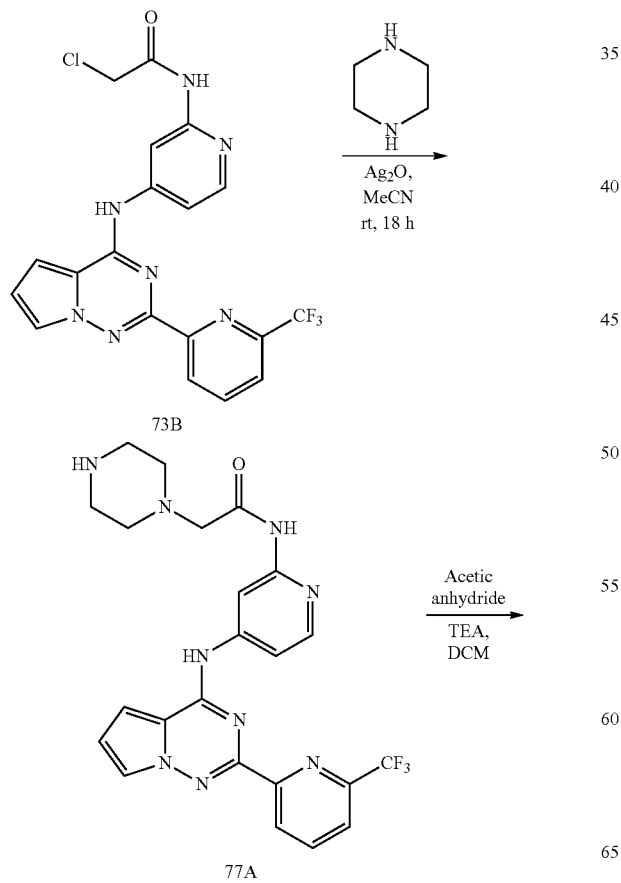

Example 320

2-(4-acetylpiperazin-1-yl)-N-[4-({2-[6-(trifluoromethyl)pyridin-2-yl]pyrrolo[2,1-f][1,2,4]triazin-4-yl}amino)pyridin-2-yl]acetamide

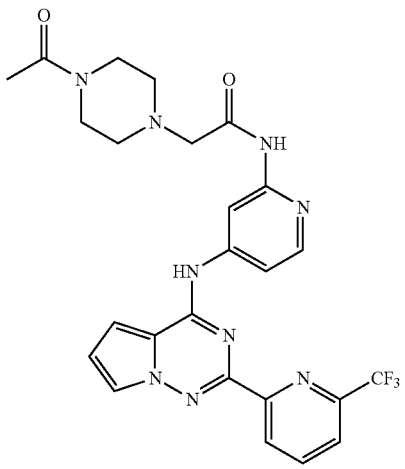 [SMILES: CC(=O)N1CCN(CC(=O)Nc2cc(Nc3nc(-c4cccc(C(F)(F)F)n4)nn4cccc34)ccn2)CC1]

Intermediate 77A: 2-(piperazin-1-yl)-N-(4-((2-(6-(trifluoromethyl)pyridin-2-yl)pyrrolo[2,1-f][1,2,4]triazin-4-yl)amino)pyridin-2-yl)acetamide

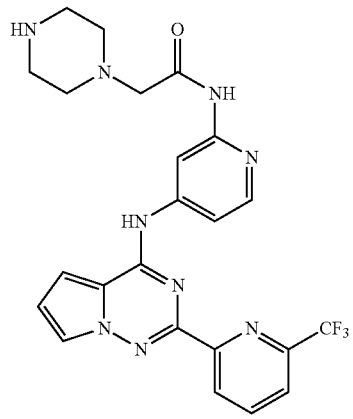 [SMILES: O=C(CN1CCNCC1)Nc1cc(Nc2nc(-c3cccc(C(F)(F)F)n3)nn3cccc23)ccn1]

Intermediate 77A (0.08 g, crude) was synthesized employing the procedure described for Example 316 (Scheme 73). LCMS m/z 498.2 (M+H); rt 1.59 min; Conditions C.

To a stirred solution of 2-(piperazin-1-yl)-N-(4-((2-(6-(trifluoromethyl)pyridin-2-yl)pyrrolo[2,1-f][1,2,4]triazin-4-yl)amino)pyridin-2-yl)acetamide (0.08 g, 0.161 mmol) in DCM (5 mL) was added TEA (0.067 mL, 0.482 mmol), acetic anhydride (0.025 g, 0.241 mmol) and the reaction mixture was stirred at room temperature for 1 h. The reaction was monitored by LCMS until completion. The reaction mixture was passed through syringe filter and concentrated under reduced pressure. The crude compound was purified by preparative HPLC to get 2-(4-acetylpiperazin-1-yl)-N-[4-({2-[6-(trifluoromethyl)pyridin-2-yl]pyrrolo[2,1-f][1,2,4]triazin-4-yl}amino)pyridin-2-yl]acetamide 320 (13 mg, 15%). LCMS m/z 540.2 (M+H); rt 1.87 min; Conditions C. $^1$H NMR (400 MHz, DMSO-d$_6$) δ 10.25-10.30 (m, 1H), 9.14-9.17 (m, 1H), 9.07-9.12 (m, 1H), 8.49-8.56 (m, 2H), 8.35-8.39 (m, 1H), 8.26-8.34 (m, 2H), 7.65-7.70 (m, 1H), 7.17-7.22 (m, 1H), 3.73-3.80 (m, 4H), 2.92-2.96 (m, 1H), 2.84-2.90 (m, 2H), 2.57-2.62 (m, 1H), 2.27 (s, 3H), 2.0 (s, 3H).

Example 321 (60 mg, 0.127 mmol, 69% yield) was synthesized employing the procedure described for Intermediate 55B (Scheme 55). LCMS m/z 470.2 (M+H); rt 2.51 min; Conditions C. $^1$H NMR (400 MHz, DMSO-d$_6$) δ 10.34 (s, 2H), 8.90-8.78 (m, 2H), 8.29-8.18 (m, 2H), 8.12-8.00 (m, 3H), 7.41 (dd, J=4.4, 1.5 Hz, 1H), 6.92 (dd, J=4.5, 2.6 Hz, 1H), 2.37-2.27 (m, 2H), 1.06 (s, 9H).

Example 322

2-(piperazin-1-yl)-N-[4-({2-[6-(trifluoromethyl)pyridin-2-yl]pyrrolo[2,1-f][1,2,4]triazin-4-yl}amino)pyridin-2-yl]acetamide

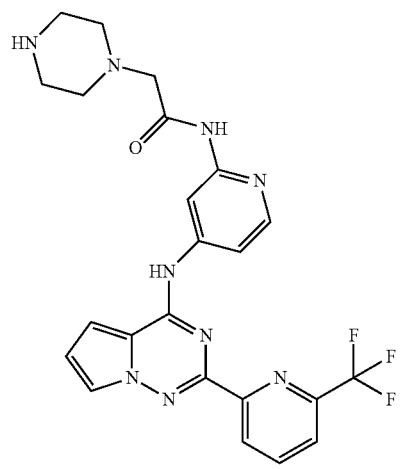

Scheme 78

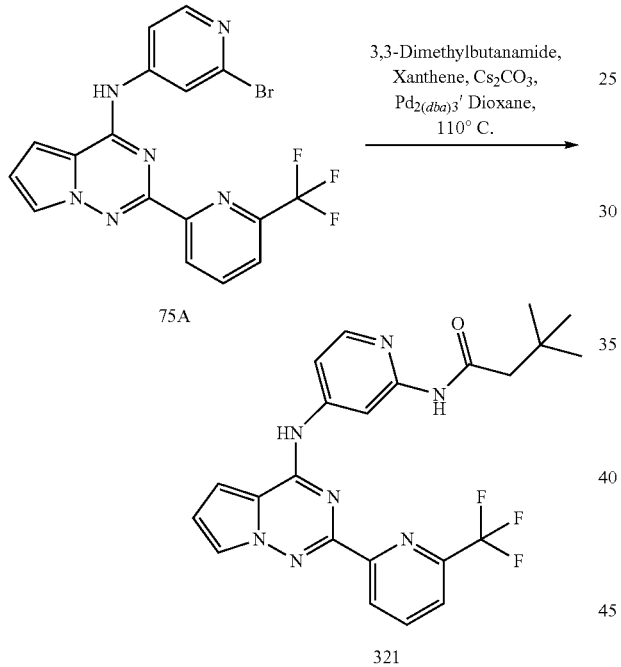

Example 322 (18 mg, 11%) was synthesized employing the procedure described for Example 316 (Scheme 73). LCMS m/z 498.2 (M+H); rt 1.59 min; Conditions C. $^1$H NMR (400 MHz, DMSO-d6) δ 10.40 (s, 1H), 9.89 (s, 1H), 8.82-8.88 (m, 2H), 8.26-8.29 (m, 2H), 8.04-8.11 (m, 3H), 7.42-7.43 (m, 1H), 6.92-6.94 (m, 1H), 3.19 (s, 4H), 2.76-2.78 (m, 4H), 1.88 (s, 3H).

Example 321

3,3-dimethyl-N-[4-({2-[6-(trifluoromethyl)pyridin-2-yl]pyrrolo[2,1-f][1,2,4]triazin-4-yl}amino)pyridin-2-yl]butanamide

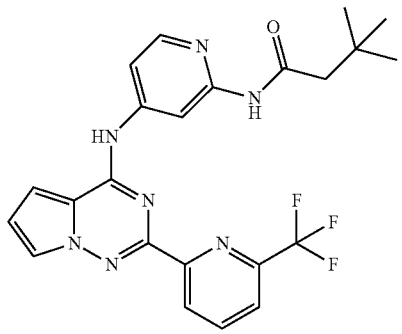 [SMILES: CC(C)(C)CC(=O)Nc1cc(Nc2nc(-c3cccc(C(F)(F)F)n3)nn3cccc23)ccn1]

Scheme 79

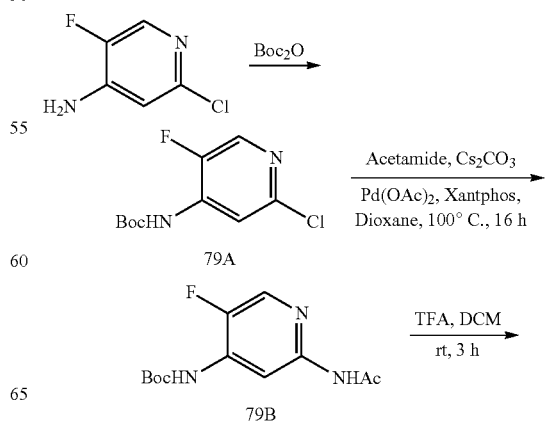

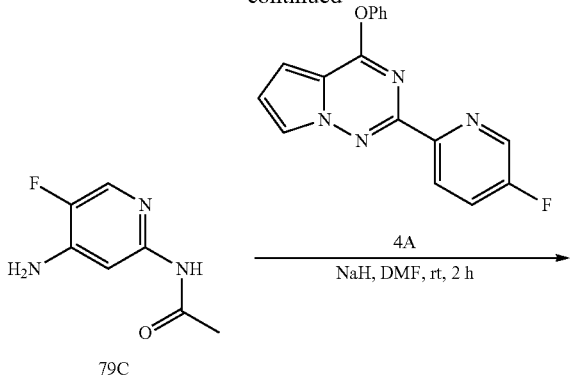

Example 323

N-(5-fluoro-4-{[2-(5-fluoropyridin-2-yl)pyrrolo[2,1-f][1,2,4]triazin-4-yl]amino}pyridin-2-yl)acetamide

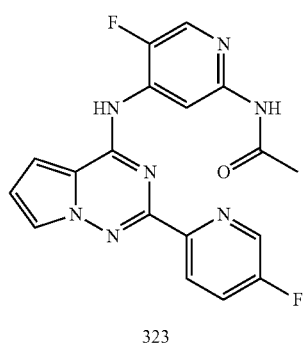

Intermediate 79A: tert-butyl (2-chloro-5-fluoropyridin-4-yl)carbamate

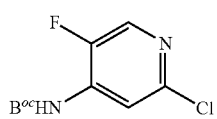

To a solution of 2-chloro-5-fluoropyridin-4-amine (1.0 g, 6.82 mmol) in DCM (50 mL) at 0° C. was added TEA (1.046 mL, 7.51 mmol), DMAP (0.083 g, 0.682 mmol) and Boc₂O (1.584 mL, 6.82 mmol). The reaction mixture was stirred at room temperature for 18 h. The reaction mixture was evaporated under reduced pressure to afford crude product as a black residue. The crude product was purified by silica gel chromatography (eluted with 10% ethyl acetate in petroleum ether) to yield tert-butyl (2-chloro-5-fluoropyridin-4-yl)carbamate 79A (1.0 g, 59.4%). LCMS m/z 247.0 (M+H); rt 0.95 min; Conditions H.

Intermediate 79B: tert-butyl (2-chloro-5-fluoropyridin-4-yl)carbamate

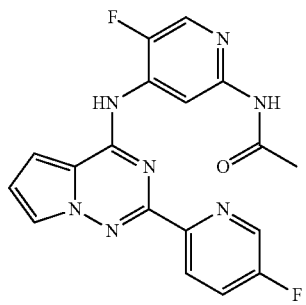 [SMILES: CC(=O)Nc1cc(Nc2nc(-c3ccc(F)cn3)nn3cccc23)c(F)cn1]

Intermediate 79B was synthesized employing the procedure described for intermediate 55B (Scheme 55). The crude product was purified by silica gel chromatography (eluted with 50% ethyl acetate in petroleum ether) to yield tert-butyl (2-acetamido-5-fluoropyridin-4-yl)carbamate (0.8 g, 73.3%). LCMS m/z 270.2 (M+H); rt 1.74 min; Conditions J.

Intermediate 79C: N-(4-amino-5-fluoropyridin-2-yl)acetamide

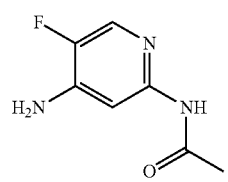

To a solution of tert-butyl (2-acetamido-5-fluoropyridin-4-yl)carbamate (0.8 g, 2.97 mmol) in DCM (15 mL) at 0° C. was added TFA (2.289 mL, 29.7 mmol) and the reaction mixture was stirred at room temperature for 3 h. The reaction mixture was evaporated under reduced pressure to get a solid residue. The crude compound was dissolved in DCM (100 mL) and washed with 10% aqueous NaHCO₃ (20 mL). The organic layer was separated and concentrated under reduced pressure to afford intermediate 79C as a pale yellow solid. LCMS m/z 170.2 (M+H); rt 0.46 min; Conditions J.

Example 323 (24.0 mg, 25.4%) was synthesized employing the procedure described for Example 229 (Scheme 57). LCMS m/z 382.1 (M+H); rt 1.56 min; Conditions C. $^1$H NMR (400 MHz, DMSO-d6) δ 10.61 (s, 1H), 10.25 (s, 1H), 8.88 (d, J=6.0 Hz, 1H), 8.68 (d, J=3.2 Hz, 1H), 8.45 (dd, J=4.8, 8.8, Hz, 1H), 8.40 (d, J=2.8 Hz, 1H), 8.00-8.01 (m, 1H), 7.80 (dt, J=2.8, 8.4 Hz, 1H), 7.34 (dd, J=1.2, 4.4, 1H), 6.90 (dd, J=2.4, 4.4, Hz, 1H), 2.15 (s, 3H).

Scheme 80

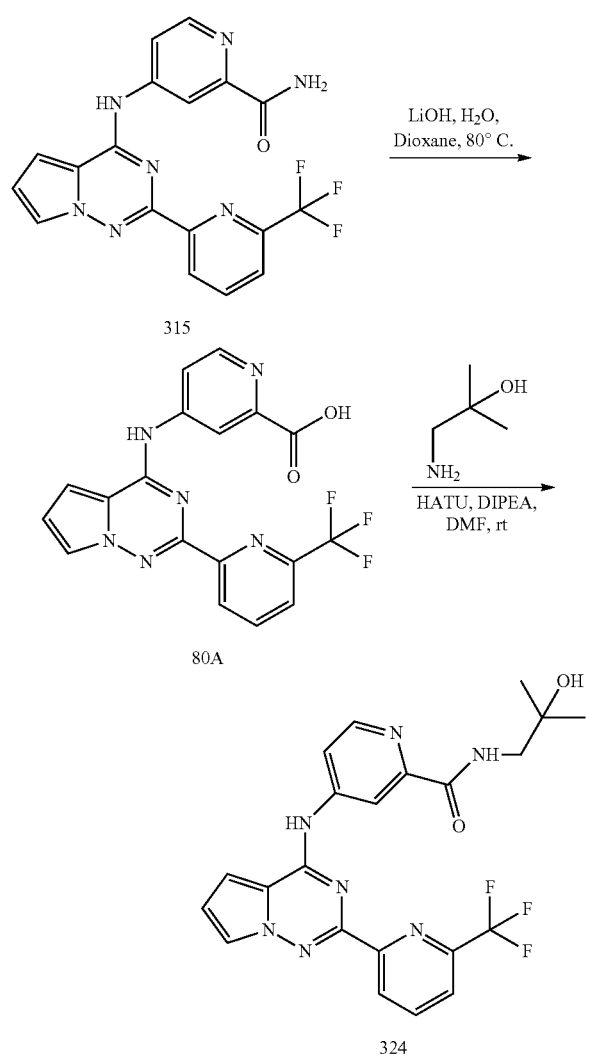

Example 324

N-(2-hydroxy-2-methylpropyl)-4-({2-[6-(trifluoromethyl)pyridin-2-yl]pyrrolo[2,1-f][1,2,4]triazin-4-yl}amino)pyridine-2-carboxamide

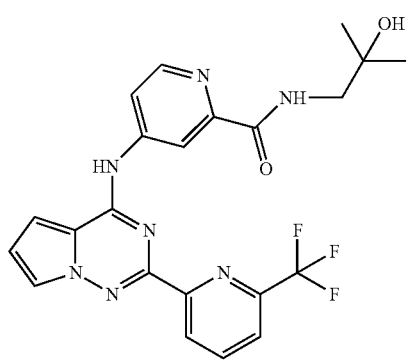 [SMILES: CC(C)(O)CNC(=O)c1cc(Nc2nc(-c3cccc(C(F)(F)F)n3)nn3cccc23)ccn1]

Intermediate 80A: 4-((2-(6-(trifluoromethyl)pyridin-2-yl)pyrrolo[2,1-f][1,2,4]triazin-4-yl)amino)picolinic acid To a solution of 4-((2-(6-(trifluoromethyl)pyridin-2-yl)pyrrolo[2,1-f][1,2,4]triazin-4-yl)amino)picolinamide (90 mg, 0.225 mmol) in dioxane (5 mL) and water (1 mL) was added LiOH (21.59 mg, 0.902 mmol) and stirred at 80° C. for 8 h. An aliquot of the reaction mixture was diluted with methanol and analyzed by LCMS to ensure complete conversion. The reaction mixture was concentrated, the residue was acidified with acetic acid, extracted with ethyl acetate, washed with brine, dried over $Na_2SO_4$ and evaporated to give 4-((2-(6-(trifluoromethyl)pyridin-2-yl)pyrrolo[2,1-f][1,2,4]triazin-4-yl)amino)picolinic acid 80A (50 mg, 0.125 mmol, 55.4% yield) as an off white solid. LCMS m/z 401.4 (M+H); rt 0.76 min; Conditions A.

To a solution of 4-((2-(6-(trifluoromethyl)pyridin-2-yl)pyrrolo[2,1-f][1,2,4]triazin-4-yl)amino)picolinic acid (40 mg, 0.100 mmol) in DMF (0.2 mL) was added 1-amino-2-methylpropan-2-ol (10.69 mg, 0.120 mmol), DIPEA (0.052 mL, 0.300 mmol) followed by HATU (45.6 mg, 0.120 mmol) and the reaction mixture was stirred at room temperature for 24 h. Crude LCMS indicated the completion of reaction. The reaction mixture was diluted with water and extracted with ethyl acetate. The organic layer was washed with brine, dried over $Na_2SO_4$ and evaporated to get the crude compound. The crude residue was purified by preparative HPLC to get N-(2-hydroxy-2-methylpropyl)-4-({2-[6-(trifluoromethyl)pyridin-2-yl]pyrrolo[2,1-f][1,2,4]triazin-4-yl}amino)pyridine-2-carboxamide 324 (25.8 mg, 54.2% yield). LCMS m/z 472.1 (M+H); rt 1.99 min; Conditions C. $^1$H NMR (400 MHz, DMSO-$d_6$) δ 10.77-10.25 (m, 1H), 9.01-8.74 (m, 5H), 8.56 (t, J=7.6 Hz, 1H), 8.42-8.26 (m, 2H), 7.65 (dd, J=4.5, 1.3 Hz, 1H), 7.21 (dd, J=4.4, 2.7 Hz, 1H), 4.99 (s, 1H), 3.43 (d, J=2.9 Hz, 2H), 1.40 (s, 4H).

Scheme 81

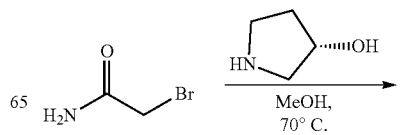

-continued

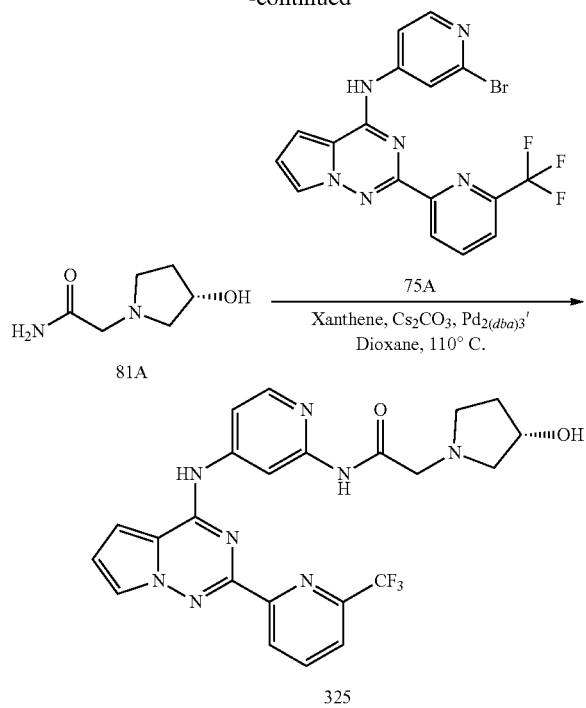

Example 325

2-[(3S)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide

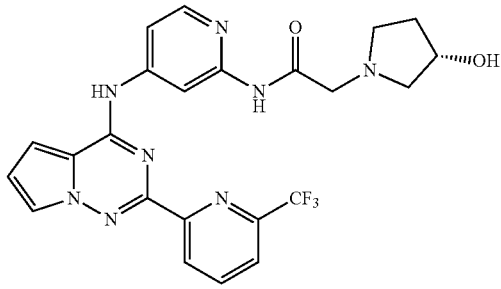 [SMILES: O=C(CN1CC[C@H](O)C1)Nc1cc(Nc2nc(-c3cccc(C(F)(F)F)n3)nn3cccc23)ccn1]

Intermediate 81A: (S)-2-(3-hydroxypyrrolidin-1-yl)acetamide

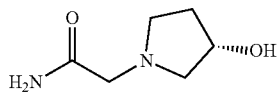

To a solution of 2-bromoacetamide (500 mg, 3.62 mmol) in MeOH (5 mL) was added (S)-pyrrolidin-3-ol (CAS: 100243-39-8) (316 mg, 3.62 mmol) and heated at 70° C. for 16 h. An aliquot of the reaction mixture was diluted with methanol and analyzed by LCMS to ensure complete conversion. The reaction mixture was evaporated to give the crude (S)-2-(3-hydroxypyrrolidin-1-yl)acetamide (Crude 500 mg) which was taken for next reaction without further purification.

Example 325 (12 mg, 13% yield) was synthesized employing the procedure described for Intermediate 55B (Scheme 55). LCMS m/z 499.2 (M+H); rt 1.85 min; Conditions C. $^1$H NMR (400 MHz, DMSO-d$_6$) δ 10.41 (s, 1H), 9.93 (br. s., 1H), 8.90-8.78 (m, 2H), 8.34-8.22 (m, 2H), 8.15-7.99 (m, 3H), 7.42 (dd, J=4.4, 1.5 Hz, 1H), 6.93 (dd, J=4.4, 2.4 Hz, 1H), 4.86 (br. s., 1H), 4.26 (br. s., 1H), 3.42-3.34 (m, 2H), 3.17 (d, J=5.4 Hz, 1H), 2.94-2.79 (m, 2H), 2.61 (d, J=1.5 Hz, 2H), 2.16-1.98 (m, 1H), 1.66 (br. s., 1H).

Scheme 82

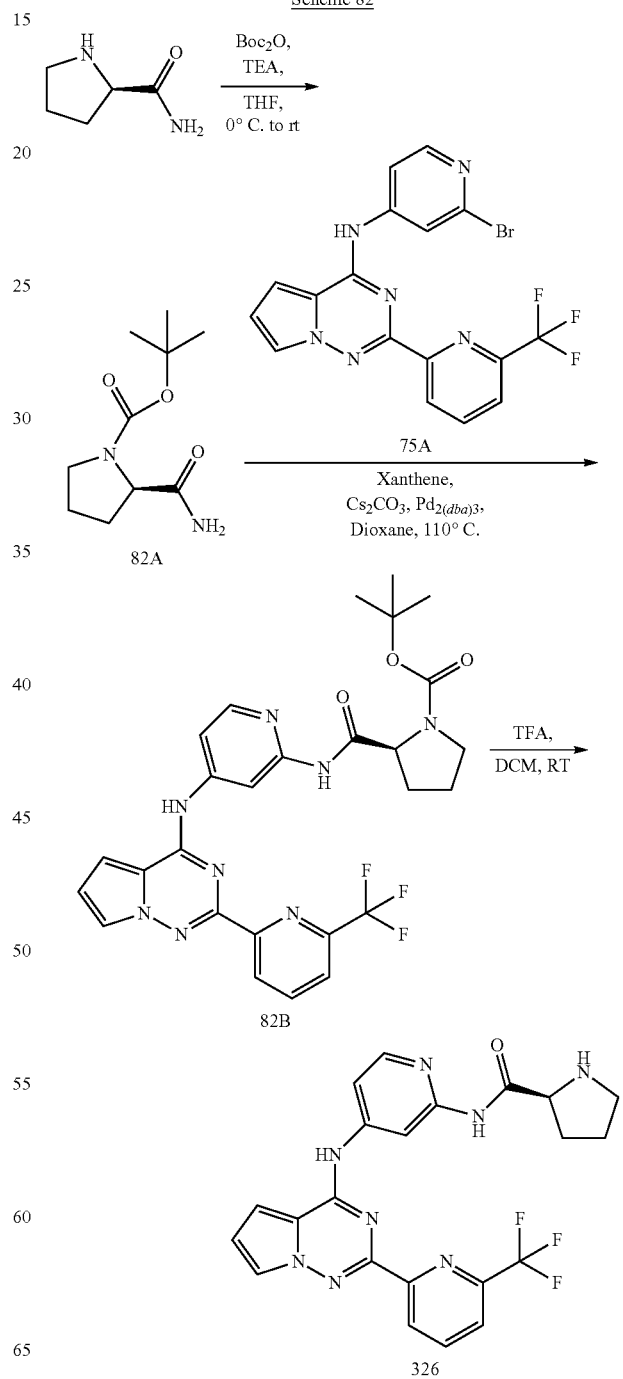

Example 326

(2S)—N-[4-({2-[6-(trifluoromethyl)pyridin-2-yl]pyrrolo[2,1-f][1,2,4]triazin-4-yl}amino)pyridin-2-yl]pyrrolidine-2-carboxamide

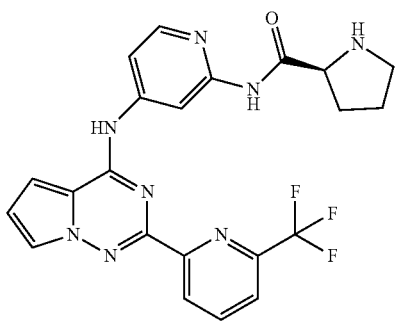 [SMILES: O=C(Nc1cc(Nc2nc(-c3cccc(C(F)(F)F)n3)nn3cccc23)ccn1)[C@@H]1CCCN1]

Intermediate 82A: (R)-tert-butyl 2-carbamoylpyrrolidine-1-carboxylate

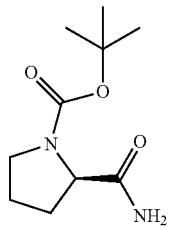

Intermediate 82A (230 mg, 1.073 mmol, 49.0% yield) was synthesized employing the procedure described for intermediate 79A (Scheme 79). Crude (R)-tert-butyl 2-carbamoylpyrrolidine-1-carboxylate was used in the next step without further purification.

Intermediate 82B: (S)-tert-butyl 2-((4-((2-(6-(trifluoromethyl)pyridin-2-yl)pyrrolo[2,1-f][1,2,4]triazin-4-yl)amino)pyridin-2-yl)carbamoyl)pyrrolidine-1-carboxylate

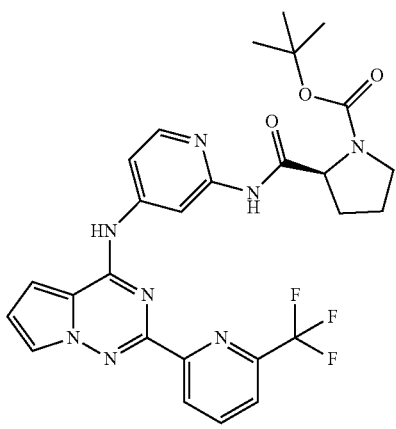 [SMILES: CC(C)(C)OC(=O)N1CCC[C@H]1C(=O)Nc1cc(Nc2nc(-c3cccc(C(F)(F)F)n3)nn3cccc23)ccn1]

Intermediate 82B was synthesized employing the procedure described for intermediate 55B (Scheme 55). The crude compound was purified by silicagel column chromatography (eluting with 70% ethyl acetate in petroleum ether) to give (S)-tert-butyl 2-((4-((2-(6-(trifluoromethyl)pyridin-2-yl)pyrrolo[2,1-f][1,2,4]triazin-4-yl)amino)pyridin-2-yl)carbamoyl)pyrrolidine-1-carboxylate 82B (130 mg, 0.053 mmol, 22.9% yield) as a brown solid. LCMS m/z 569.5 (M+H); rt 1.27 min; Conditions B.

To a solution of (S)-tert-butyl 2-((4-((2-(6-(trifluoromethyl)pyridin-2-yl)pyrrolo[2,1-f][1,2,4]triazin-4-yl)amino)pyridin-2-yl)carbamoyl)pyrrolidine-1-carboxylate (130 mg, 0.229 mmol) in DCM (1 mL) was added a solution of TFA (0.388 mL, 5.03 mmol) in DCM (1 mL) at 0° C. and then the reaction mixture was stirred at room temperature for 2 h. The reaction mixture was evaporated to get the crude compound. The crude was purified by preparative HPLC to get (S)—N-(4-((2-(6-(trifluoromethyl)pyridin-2-yl)pyrrolo[2,1-f][1,2,4]triazin-4-yl)amino)pyridin-2-yl)pyrrolidine-2-carboxamide 326 (29 mg, 0.059 mmol, 25.7% yield). LCMS m/z 469.2 (M+H); rt 1.88 min; Conditions C. $^{1}$H NMR (400 MHz, DMSO-$d_6$) δ 11.07 (s, 1H), 10.46 (s, 1H), 8.90 (s, 1H), 8.80 (d, J=8.1 Hz, 1H), 8.39-8.27 (m, 2H), 8.13-7.99 (m, 3H), 7.46-7.38 (m, 1H), 6.98-6.88 (m, 1H), 4.43 (br. s., 1H), 4.07 (q, J=5.3 Hz, 1H), 3.16 (d, J=5.4 Hz, 2H), 2.42 (dd, J=13.3, 6.2 Hz, 1H), 2.08-1.88 (m, 3H).

Example 327

2-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide

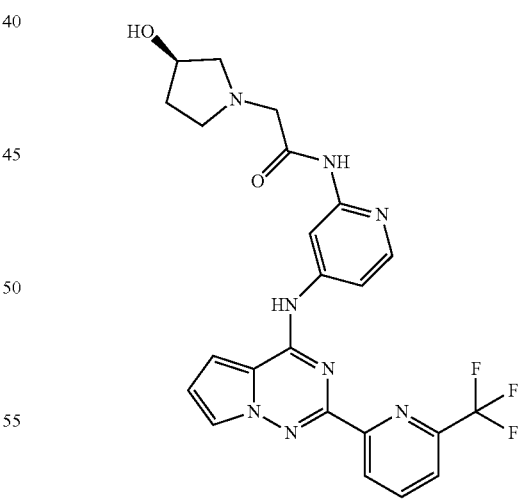

Example 327 (30 mg, 34%) was synthesized employing the procedure described for Example 316 (Scheme 73). LCMS m/z 499.2 (M+H); rt 1.79 min; Conditions C. $^{1}$H NMR (400 MHz, DMSO-$d_6$) δ 10.14-10.21 (m, 1H) 9.06-9.14 (m, 2H) 8.48-8.57 (m, 2H) 8.28-8.38 (m, 3H) 7.65-7.71 (m, 1H) 7.16-7.23 (m, 1H) 4.47-4.56 (m, 1H) 3.04-3.15 (m, 2H) 2.81-2.90 (m, 6H) 2.25-2.39 (m, 2H).

Example 328

3-fluoro-N-(5-{[(1-methylpiperidin-4-yl)oxy]methyl}-2-(pyridin-2-yl)pyrrolo[2,1-f][1,2,4]triazin-4-yl)pyridin-4-amine

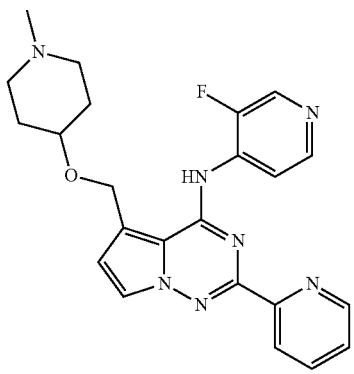 [SMILES: CN1CCC(OCc2ccn3nc(-c4ccccn4)nc(Nc4ccncc4F)c23)CC1]

To a stirred solution of (4-((3-fluoropyridin-4-yl)amino)-2-(pyridin-2-yl)pyrrolo[2,1-f][1,2,4]triazin-5-yl)methanol (0.05 g, 0.149 mmol) in tetrahydrofuran (8 mL) was added DEAD (0.039 g, 0.223 mmol) and 1-methylpiperidin-4-ol (0.021 g, 0.178 mmol) followed by triphenylphosphine (0.039 g, 0.149 mmol). The reaction mixture was stirred at room temperature for 18 h. The reaction mixture was filtered through Celite bed and the filtrate was concentrated under reduced pressure to get crude residue. The crude compound was purified by preparative HPLC to get N-(3-fluoropyridin-4-yl)-5-(((1-methylpiperidin-4-yl)oxy)methyl)-2-(pyridin-2-yl)pyrrolo[2,1-f][1,2,4]triazin-4-amine 328 (24 mg, 0.055 mmol, 36.9% yield). LCMS m/z 434.2 (M+H)+; rt 1.18 min; Conditions C. $^1$H NMR (400 MHz, DMSO-$d_6$) δ 9.02-8.90 (m, 2H), 8.76-8.65 (m, 1H), 8.58-8.09 (m, 3H), 8.01-7.77 (m, 2H), 7.33-7.11 (m, 2H), 5.33-5.20 (m, 1H), 4.23 (s, 1H), 4.17-4.08 (m, 1H), 4.05-3.99 (m, 1H), 3.93-3.84 (m, 2H), 3.59-3.49 (m, 1H), 3.43 (s, 1H), 2.96-2.89 (m, 1H), 2.62-2.56 (m, 1H), 2.41-2.23 (m, 2H), 2.10-1.94 (m, 2H).

Scheme 83

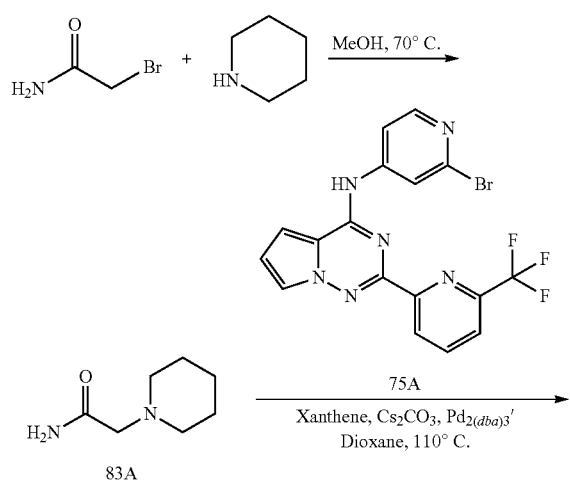

Example 329

2-(piperidin-1-yl)-N-[4-({2-[6-(trifluoromethyl)pyridin-2-yl]pyrrolo[2,1-f][1,2,4]triazin-4-yl}amino)pyridin-2-yl]acetamide

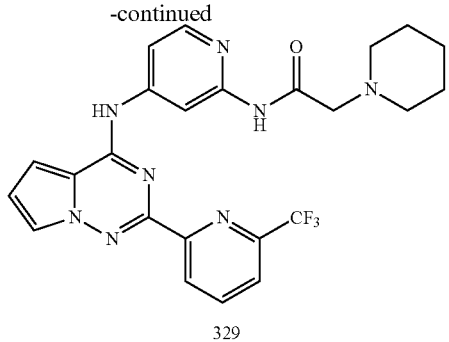

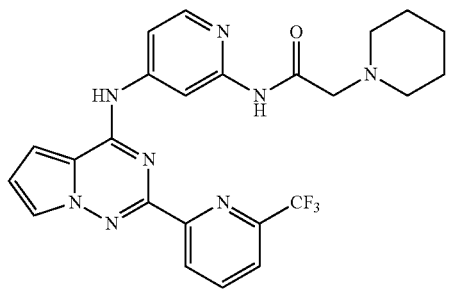 [SMILES: O=C(CN1CCCCC1)Nc1cc(Nc2nc(-c3cccc(C(F)(F)F)n3)nn3cccc23)ccn1]

Intermediate 83A: 2-(piperidin-1-yl)acetamide
A0480-534-01

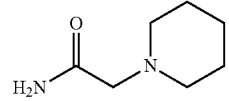

Intermediate 83A was synthesized employing the procedure described for intermediate 20A (Scheme 81) to obtain to give 2-(piperidin-1-yl)acetamide (400 mg, 2.81 mmol, 78% yield).

Example 329 (1.6 mg, 1.74% yield) was synthesized employing the procedure described for Intermediate 55B (Scheme 55). LCMS m/z 497.2 (M+H); rt 2.47 min; Conditions C. $^1$H NMR (400 MHz, DMSO-$d_6$) δ 11.13 (s, 1H), 10.43 (s, 1H), 9.58 (d, J=12.7 Hz, 1H), 8.96 (br. s., 1H), 8.80 (d, J=7.6 Hz, 1H), 8.35-8.24 (m, 2H), 8.14-8.04 (m, 2H), 7.99 (dd, J=5.4, 2.0 Hz, 1H), 7.40 (dd, J=4.5, 1.6 Hz, 1H), 6.95-6.91 (m, 1H), 4.20 (br. s., 2H), 3.51 (br. s., 4H), 3.09 (d, J=10.8 Hz, 3H), 1.90-1.65 (m, 5H).

Scheme 84

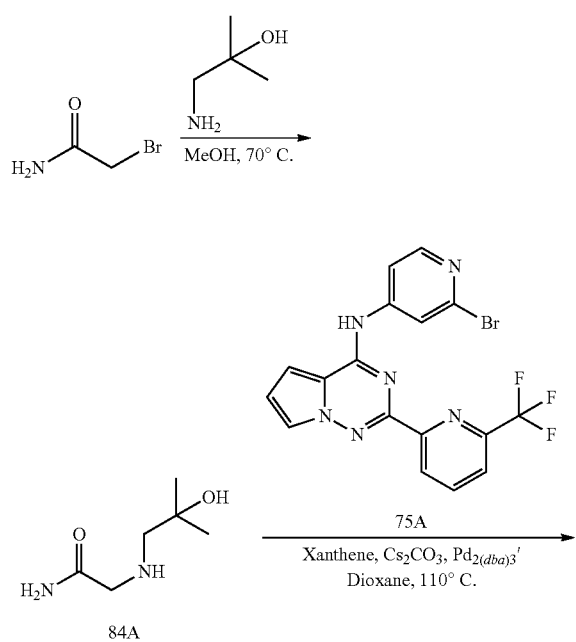

Example 330

2-[(2-hydroxy-2-methylpropyl)amino]-N-[4-({2-[6-(trifluoromethyl)pyridin-2-yl]pyrrolo[2,1-f][1,2,4]triazin-4-yl}amino)pyridin-2-yl]acetamide

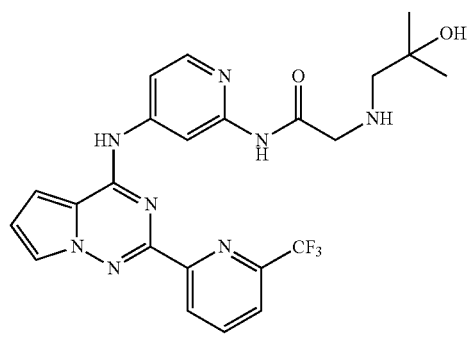 [SMILES: CC(C)(O)CNCC(=O)Nc1cc(Nc2nc(-c3cccc(C(F)(F)F)n3)nn3cccc23)ccn1]

Intermediate 84A:
2-((2-hydroxy-2-methylpropyl)amino)acetamide
A0480-535-01

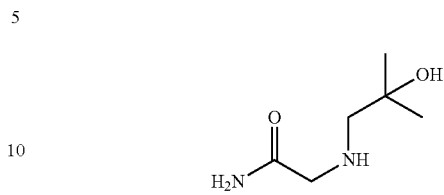

Intermediate 84A (300 mg, 2.05 mmol, 56.6% yield) was synthesized employing the procedure described for intermediate 81A (Scheme 81).

Example 330 (4.8 mg, 5.06% yield) was synthesized employing the procedure described for Intermediate 55B (Scheme 55). LCMS m/z 501.2 (M+H); rt 1.91 min; Conditions C. $^1$H NMR (400 MHz, DMSO-$d_6$) δ 11.00 (s, 1H), 10.43 (s, 1H), 8.89 (br. s., 1H), 8.82 (d, J=8.1 Hz, 1H), 8.62 (br. s., 2H), 8.38 (t, J=7.9 Hz, 1H), 8.30 (d, J=5.6 Hz, 1H), 8.11 (dd, J=2.7, 1.5 Hz, 1H), 8.08-8.00 (m, 2H), 7.41 (dd, J=4.4, 1.5 Hz, 1H), 6.93 (dd, J=4.5, 2.6 Hz, 1H), 5.27 (br. s., 1H), 4.04 (br. s., 2H), 3.05 (br. s., 2H), 1.29-1.20 (m, 6H).

Scheme 85

[Scheme 85 showing reaction of bromoacetamide with morpholine in MeOH, 70° C. to give 85A, then coupled with 75A using Xanthene, Cs$_2$CO$_3$, Pd$_{2(dba)3}$, Dioxane, 110° C. to give compound 331]

Example 331

2-(morpholin-4-yl)-N-[4-({2-[6-(trifluoromethyl)pyridin-2-yl]pyrrolo[2,1-f][1,2,4]triazin-4-yl}amino)pyridin-2-yl]acetamide

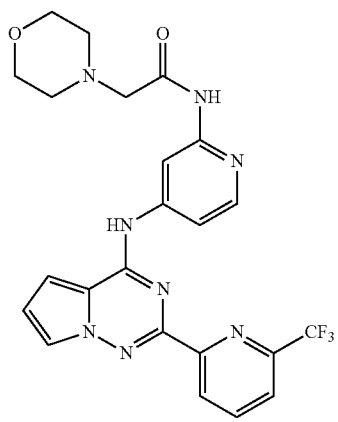 [SMILES: O=C(CN1CCOCC1)Nc1cc(Nc2nc(-c3cccc(C(F)(F)F)n3)nn3cccc23)ccn1]

Intermediate 85A: 2-morpholinoacetamide

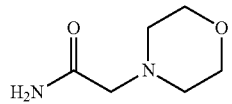

Intermediate 85A (450 mg, 3.12 mmol, 86% yield) was synthesized employing the procedure described for intermediate 81A (Scheme 81).

Example 331 (4.8 mg, 5.06% yield) was synthesized employing the procedure described for Intermediate 55B (Scheme 55). LCMS m/z 499.2 (M+H); rt 2.20 min; Conditions C. $^1$H NMR (400 MHz, DMSO-d$_6$) δ 11.00 (s, 1H), 10.43 (s, 1H), 8.89 (br. s., 1H), 8.82 (d, J=8.1 Hz, 1H), 8.62 (br. s., 2H), 8.38 (t, J=7.9 Hz, 1H), 8.30 (d, J=5.6 Hz, 1H), 8.11 (dd, J=2.7, 1.5 Hz, 1H), 8.08-8.00 (m, 2H), 7.41 (dd, J=4.4, 1.5 Hz, 1H), 6.93 (dd, J=4.5, 2.6 Hz, 1H), 5.27 (br. s., 1H), 4.04 (br. s., 2H), 3.05 (br. s., 2H), 1.29-1.20 (m, 6H).

Example 332

N-[4-({2-[5-(trifluoromethyl)pyridin-2-yl]pyrrolo[2,1-f][1,2,4]triazin-4-yl}amino)pyridin-2-yl]acetamide

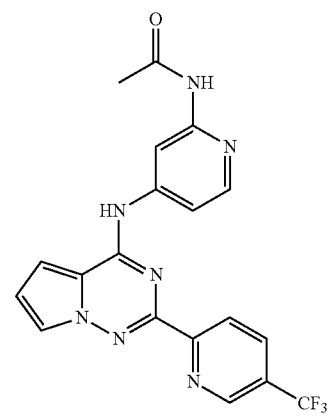 [SMILES: CC(=O)Nc1cc(Nc2nc(-c3ccc(C(F)(F)F)cn3)nn3cccc23)ccn1]

Example 332 (4.5 mg, 7.5%) was synthesized employing the procedure described for Intermediate 57A (Scheme 57): LCMS m/z 414.1 (M+H); rt 1.82 min; Conditions C. $^1$H NMR (400 MHz, DMSO-d6) δ 10.46 (s, 1H), 10.38 (s, 1H), 9.13 (s, 1H), 8.80 (s, 1H), 8.73 (d, J=8.0 Hz, 1H), 8.34-8.37 (m, 1H), 8.27 (d, J=5.6 Hz, 1H), 8.05 (s, 1H), 8.00 (d, J=4.0 Hz, 1H), 7.42 (d, J=3.2 Hz, 1H), 6.93 (dd, J=2.4, 4.0 Hz, 1H), 2.16 (s, 3H).

Example 333

N-(5-fluoro-4-{[2-(5-fluoro-6-methylpyridin-2-yl)pyrrolo[2,1-f][1,2,4]triazin-4-yl]amino}pyridin-2-yl)acetamide

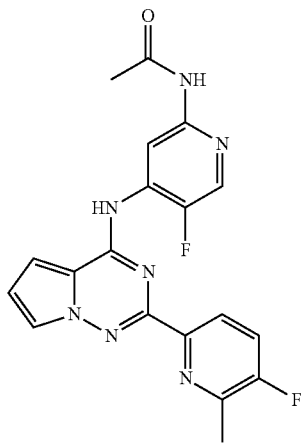 [SMILES: CC(=O)Nc1cc(Nc2nc(-c3ccc(F)c(C)n3)nn3cccc23)c(F)cn1]

Example 333 (32.0 mg, 25.3%) was synthesized employing the procedure described for Intermediate 57A (Scheme 57): LCMS m/z 396.2 (M+H); rt 2.21 min; Conditions E. $^1$H NMR (400 MHz, DMSO-d6) δ 10.57 (s, 1H), 10.17 (s, 1H), 8.87 (s, 1H), 8.36 (d, J=2.0 Hz, 1H), 8.26 (dd, J=3.6, 8.4 Hz, 1H), 8.00 (s, 1H), 7.68 (t, J=9.2 Hz, 1H), 7.28 (s, 1H), 6.86 (s, 1H), 2.53 (s, 3H, merged with residual DMSO peak), 2.11 (s, 3H). $^{19}$F NMR (400 MHz, DMSO-d6) δ −124.0, −141.3 ppm.

Scheme 86

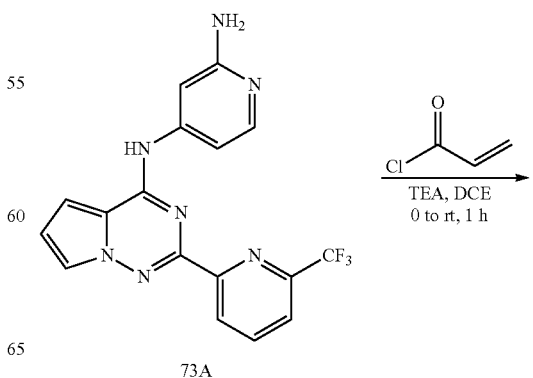

73A

-continued

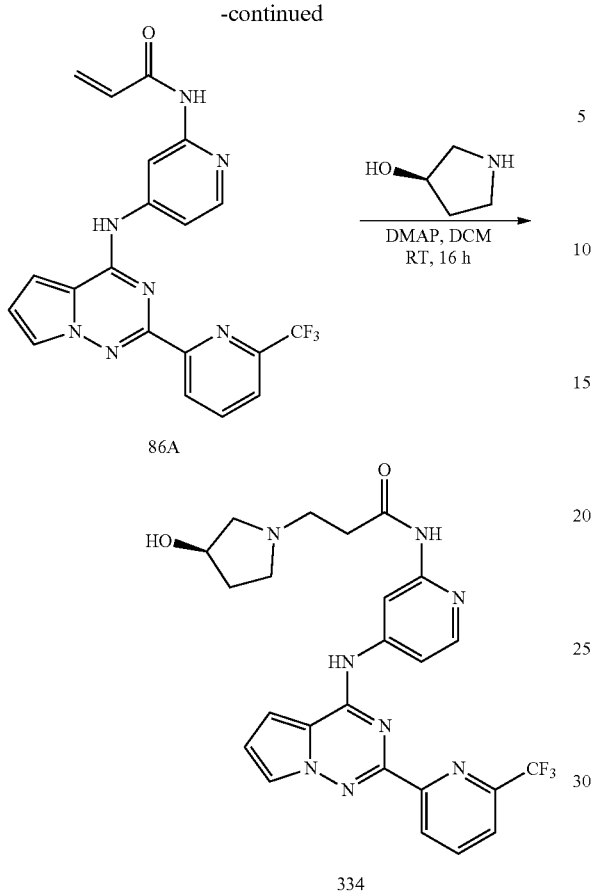

86A

Intermediate 86A: N-(4-((2-(6-(trifluoromethyl)pyridin-2-yl)pyrrolo[2,1-f][1,2,4]triazin-4-yl)amino)pyridin-2-yl)acrylamide

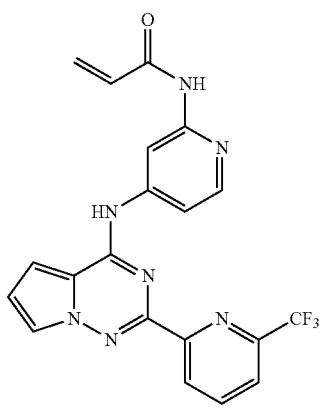 [SMILES: C=CC(=O)Nc1cc(Nc2nc(-c3cccc(C(F)(F)F)n3)nn3cccc23)ccn1]

To a stirred solution of N4-(2-(6-(trifluoromethyl)pyridin-2-yl)pyrrolo[2,1-f][1,2,4]triazin-4-yl)pyridine-2,4-diamine (0.25 g, 0.673 mmol) in DCE (5 mL) TEA (0.469 mL, 3.37 mmol) and acryloyl chloride (0.163 mL, 2.020 mmol) were added at 0° C. and the reaction mixture was stirred at room temperature for 1 h. The reaction mixture was concentrated. The residue was diluted with DCM (100 mL), washed with water (20 mL) dried over sodium sulfate and concentrated to get N-(4-((2-(6-(trifluoromethyl)pyridin-2-yl)pyrrolo[2,1-f][1,2,4]triazin-4-yl)amino)pyridin-2-yl) acrylamide 86A (240 mg, crude) as an dark black oil. LCMS m/z 426.2 (M+H); rt 0.90 min; Conditions I.

Example 334

3-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]propanamide

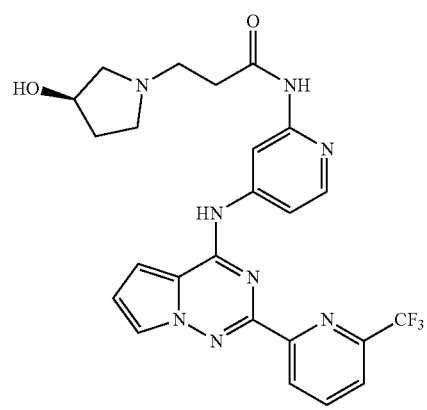 [SMILES: O=C(CCN1CC[C@@H](O)C1)Nc1cc(Nc2nc(-c3cccc(C(F)(F)F)n3)nn3cccc23)ccn1]

To a stirred solution of N-(4-((2-(6-(trifluoromethyl)pyridin-2-yl)pyrrolo[2,1-f][1,2,4]triazin-4-yl)amino)pyridin-2-yl)acrylamide (0.04 g, 0.094 mmol) in DCM (5 mL) was added (R)-pyrrolidin-3-ol (0.041 g, 0.470 mmol), DMAP (5.74 mg, 0.047 mmol) at room temperature and allowed to stir for 16 h. The reaction mixture was passed through a syringe filter and the filtrate was concentrated under reduced pressure to get crude compound. The crude residue was purified by preparative HPLC to get example 334 (4 mg, 5%). LCMS m/z 527.2 (M+H); rt 1.67 min; Conditions C. $^1$H NMR (400 MHz, DMSO-$d_6$) δ 10.73-10.79 (m, 1H) 10.37-10.44 (m, 1H) 8.77-8.93 (m, 2H) 8.24-8.40 (m, 2H) 8.01-8.14 (m, 3H) 7.38-7.44 (m, 1H) 7.21 (s, 1H) 7.09 (s, 1H) 6.96 (s, 2H) 3.18 (s, 2H) 2.91-3.06 (m, 5H) 1.94-2.05 (m, 1H) 1.73-1.91 (m, 2H) 1.49-1.63 (m, 1H)

Scheme 87

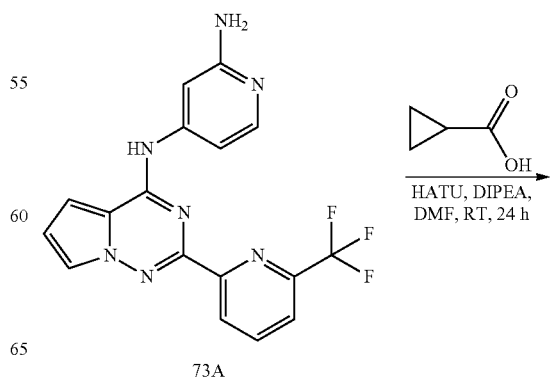

73A

-continued

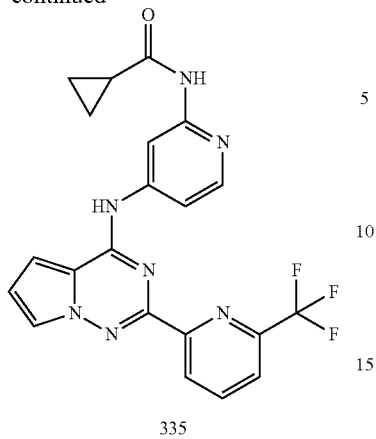

335

Example 335
N-[4-({2-[6-(trifluoromethyl)pyridin-2-yl]pyrrolo[2,1-f][1,2,4]triazin-4-yl}amino)pyridin-2-yl]cyclopropanecarboxamide

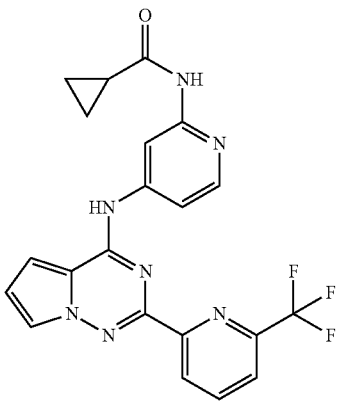 [SMILES: O=C(Nc1cc(Nc2nc(-c3cccc(C(F)(F)F)n3)nn3cccc23)ccn1)C1CC1]

Example 335 (45 mg, 63% yield) was synthesized employing the procedure described for Example 324 (Scheme 80). LCMS m/z 440.1 (M+H); rt 2.14 min; Conditions C. $^1$H NMR (400 MHz, DMSO-$d_6$) δ 10.79 (s, 1H), 10.33 (s, 1H), 8.91 (d, J=2.0 Hz, 1H), 8.84 (d, J=8.0 Hz, 1H), 8.29-8.18 (m, 2H), 8.09 (dd, J=2.5, 1.5 Hz, 1H), 8.07-7.92 (m, 2H), 7.43-7.38 (m, 1H), 6.96-6.89 (m, 1H), 2.12-2.02 (m, 1H), 0.93-0.80 (m, 4H).

Example 336
2-methoxy-N-[4-({2-[6-(trifluoromethyl)pyridin-2-yl]pyrrolo[2,1-f][1,2,4]triazin-4-yl}amino)pyridin-2-yl]acetamide

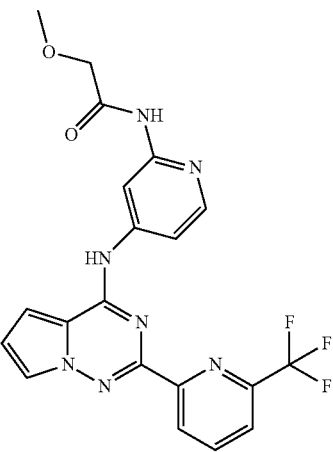 [SMILES: COCC(=O)Nc1cc(Nc2nc(-c3cccc(C(F)(F)F)n3)nn3cccc23)ccn1]

Example 336 (62 mg, 83% yield) was synthesized employing the procedure described for Example 324 (Scheme 80). LCMS m/z 444.1 (M+H); rt 2.05 min; Conditions C. $^1$H NMR (400 MHz, DMSO-$d_6$) δ 10.45 (s, 1H), 9.98 (s, 1H), 8.85-8.77 (m, 2H), 8.31-8.23 (m, 2H), 8.15-8.09 (m, 2H), 8.07-8.02 (m, 1H), 7.42 (dd, J=4.5, 1.5 Hz, 1H), 6.96-6.90 (m, 1H), 4.13 (s, 2H), 3.45-3.41 (m, 3H).

Example 337
4,4,4-trifluoro-N-[4-({2-[6-(trifluoromethyl)pyridin-2-yl]pyrrolo[2,1-f][1,2,4]triazin-4-yl}amino)pyridin-2-yl]butanamide

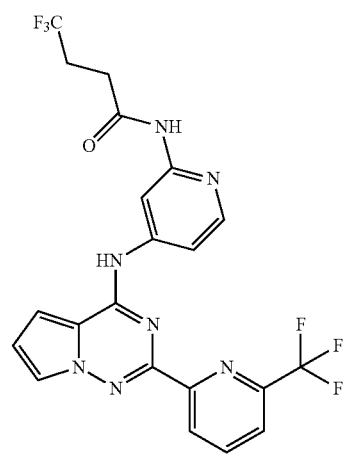

Example 337 (60 mg, 72% yield) was synthesized employing the procedure described for Example 324 (Scheme 80). LCMS m/z 496.1 (M+H); rt 2.30 min; Conditions C. $^1$H NMR (400 MHz, DMSO-$d_6$) δ 10.65 (s, 1H), 10.37 (s, 1H), 8.92-8.80 (m, 2H), 8.33-8.24 (m, 2H), 8.10 (dd, J=2.5, 1.5 Hz, 1H), 8.08-7.97 (m, 2H), 7.44-7.39 (m, 1H), 6.93 (dd, J=4.5, 2.5 Hz, 1H), 2.80-2.72 (m, 2H), 2.71-2.63 (m, 2H).

Example 338
3-cyano-N-[4-({2-[6-(trifluoromethyl)pyridin-2-yl]pyrrolo[2,1-f][1,2,4]triazin-4-yl}amino)pyridin-2-yl]propanamide

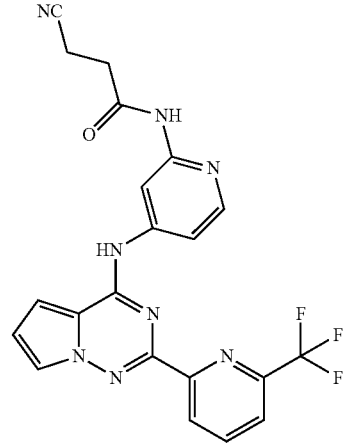 [SMILES: N#CCCC(=O)Nc1cc(Nc2nc(-c3cccc(C(F)(F)F)n3)nn3cccc23)ccn1]

Example 338 (14.7 mg, 19.9% yield) was synthesized employing the procedure described for Example 324 (Scheme 80). LCMS m/z 453.1 (M+H); rt 1.94 min; Conditions C. $^1$H NMR (400 MHz, DMSO-$d_6$) δ 10.66 (s, 1H), 10.35 (s, 1H), 8.95 (s, 1H), 8.87 (d, J=7.8 Hz, 1H), 8.34 (t, J=7.8 Hz, 1H), 8.27 (d, J=5.6 Hz, 1H), 8.10 (dd, J=2.7, 1.5 Hz, 1H), 8.03 (d, J=7.8 Hz, 1H), 7.96 (dd, J=5.9, 2.0 Hz, 1H), 7.41 (dd, J=4.6, 1.5 Hz, 1H), 6.97-6.88 (m, 1H), 2.86-2.74 (m, 4H).

Example 339

N-(5-fluoro-4-{[2-(6-fluoropyridin-2-yl)pyrrolo[2,1-f][1,2,4]triazin-4-yl]amino}pyridin-2-yl)acetamide

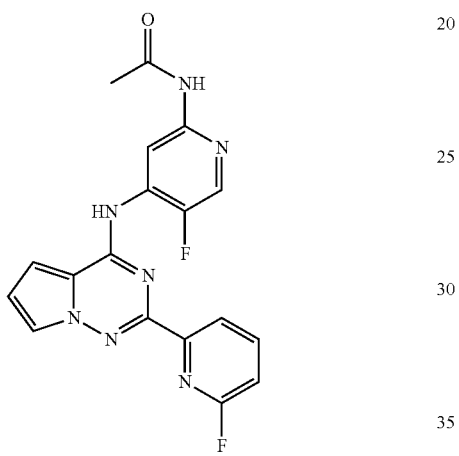

Example 339 (10.3 mg, 6.8%) was synthesized employing the procedure described for Intermediate 57A (Scheme 57). LCMS m/z 382.1 (M+H); rt 1.60 min; Conditions C. $^1$H NMR (400 MHz, DMSO-d6) δ 10.61 (s, 1H), 10.26 (s, 1H), 8.88 (d, J=6.0 Hz, 1H), 8.40 (d, J=2.4 Hz, 1H), 8.35 (dd, J=2.0, 7.2 Hz, 1H), 8.04-8.11 (m, 2H), 7.35 (d, J=1.2, 4.4 Hz, 1H), 7.28 (dd, J=2.8, 8.0 Hz, 1H), 6.91 (dd, J=2.8, 4.4 Hz, 1H), 2.13 (s, 3H).

Scheme 88

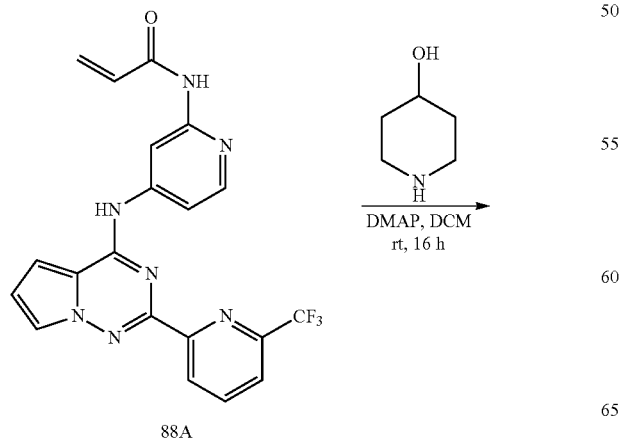

88A

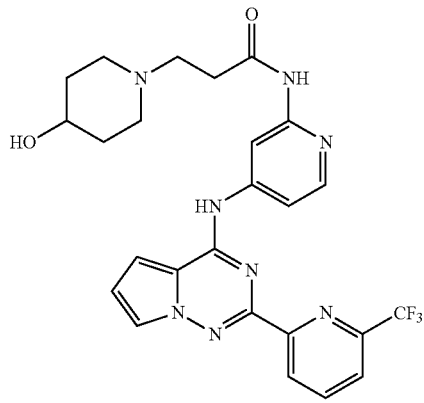 [SMILES: O=C(CCN1CCC(O)CC1)Nc1cc(Nc2nc(-c3cccc(C(F)(F)F)n3)nn3cccc23)ccn1]

340

Example 340

3-(4-hydroxypiperidin-1-yl)-N-[4-({2-[6-(trifluoromethyl)pyridin-2-yl]pyrrolo[2,1-f][1,2,4]triazin-4-yl}amino)pyridin-2-yl]propanamide

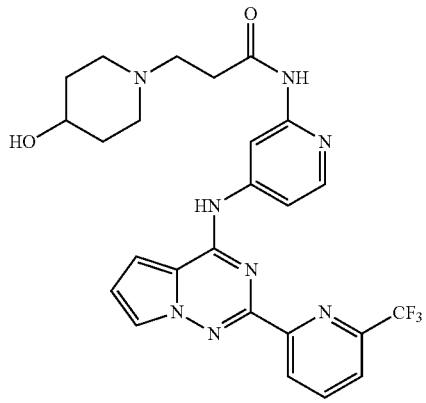

Example 340 (3.3 mg, 4.4%) was synthesized employing the procedure described for Example 334 (Scheme 86). LCMS m/z 527.2 (M+H); rt 1.674 min; Condition C. $^1$H NMR (400 MHz, DMSO-$d_6$) δ 10.73-10.79 (m, 1H) 10.37-10.44 (m, 1H) 8.77-8.93 (m, 2H) 8.24-8.40 (m, 2H) 8.01-8.14 (m, 3H) 7.38-7.44 (m, 1H) 7.21 (s, 1H) 7.09 (s, 1H) 6.96 (s, 2H) 3.18 (s, 2H) 2.91-3.06 (m, 5H) 1.94-2.05 (m, 1H) 1.73-1.91 (m, 2H) 1.49-1.63 (m, 1H).

Example 341

3-(3,3-difluoroazetidin-1-yl)-N-[4-({2-[6-(trifluoromethyl)pyridin-2-yl]pyrrolo[2,1-f][1,2,4]triazin-4-yl}amino)pyridin-2-yl]propanamide

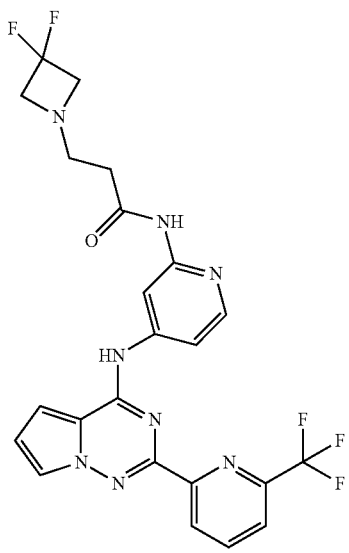 [SMILES: O=C(CCN1CC(F)(F)C1)Nc1cc(Nc2nc(-c3cccc(C(F)(F)F)n3)nn3cccc23)ccn1]

Example 341 (4.5 mg, 6%) was synthesized employing the procedure described for Example 334 (Scheme 86). LCMS m/z 519.1 (M+H); rt 2.13 min; Conditions C. $^1$H NMR (400 MHz, DMSO-d$_6$) δ 10.68-10.77 (m, 1H) 10.38-10.44 (m, 1H) 8.78-8.87 (m, 2H) 8.26-8.34 (m, 3H) 8.01-8.14 (m, 5H) 7.38-7.44 (m, 2H) 7.19-7.24 (m, 1H) 7.05-7.12 (m, 1H) 6.89-6.98 (m, 2H) 3.18-3.25 (m, 1H).

Example 342

2,2-dimethyl-N-[4-({2-[6-(trifluoromethyl)pyridin-2-yl]pyrrolo[2,1-f][1,2,4]triazin-4-yl}amino)pyridin-2-yl]propanamide

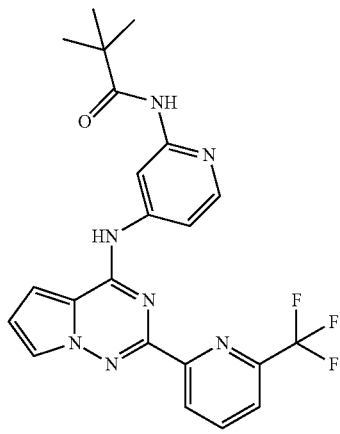 [SMILES: CC(C)(C)C(=O)Nc1cc(Nc2nc(-c3cccc(C(F)(F)F)n3)nn3cccc23)ccn1]

Example 342 (46.2 mg, 61.5% yield) was synthesized employing the procedure described for Example 324 (Scheme 80). LCMS m/z 456.1 (M+H); rt 2.41 min; Conditions C. $^1$H NMR (400 MHz, DMSO-d$_6$) δ 9.73 (s, 1H), 8.97-8.86 (m, 2H), 8.31-8.21 (m, 2H), 8.10 (dd, J=2.5, 1.5 Hz, 1H), 8.07-8.03 (m, 1H), 8.01-7.96 (m, 1H), 7.42 (dd, J=4.5, 1.5 Hz, 1H), 6.93 (dd, J=4.3, 2.8 Hz, 1H), 1.35-1.26 (m, 9H).

Example 343

3-methoxy-N-[4-({2-[6-(trifluoromethyl)pyridin-2-yl]pyrrolo[2,1-f][1,2,4]triazin-4-yl}amino)pyridin-2-yl]propanamide

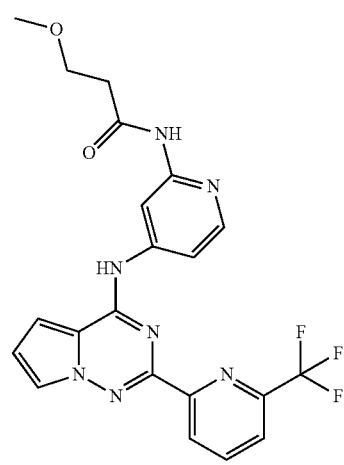 [SMILES: COCCC(=O)Nc1cc(Nc2nc(-c3cccc(C(F)(F)F)n3)nn3cccc23)ccn1]

Example 343 (35 mg, 47.4% yield) was synthesized employing the procedure described for Example 324 (Scheme 80). LCMS m/z 458.2 (M+H); rt 1.99 min; Conditions C. $^1$H NMR (400 MHz, DMSO-d$_6$) δ 10.46 (s, 1H), 10.37 (br. s., 1H), 8.90 (s, 1H), 8.84 (d, J=7.8 Hz, 1H), 8.30-8.21 (m, 2H), 8.16-7.94 (m, 3H), 7.40 (d, J=3.7 Hz, 1H), 6.92 (dd, J=4.4, 2.7 Hz, 1H), 3.68 (t, J=6.2 Hz, 2H), 3.27 (s, 3H), 2.69 (t, J=6.1 Hz, 2H).

Example 344

3,3,3-trifluoro-N-[4-({2-[6-(trifluoromethyl)pyridin-2-yl]pyrrolo[2,1-f][1,2,4]triazin-4-yl}amino)pyridin-2-yl]propanamide

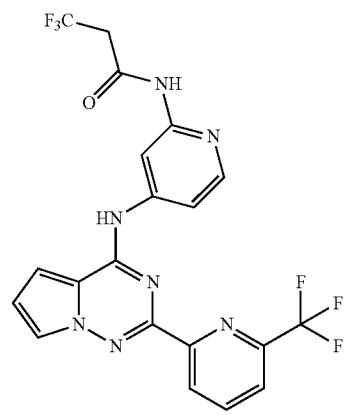 [SMILES: O=C(CC(F)(F)F)Nc1cc(Nc2nc(-c3cccc(C(F)(F)F)n3)nn3cccc23)ccn1]

Example 344 (7.1 mg, 9.1% yield) was synthesized employing the procedure described for Example 324 (Scheme 80). LCMS m/z 482.1 (M+H); rt 2.23 min; Conditions C. $^1$H NMR (400 MHz, DMSO-$d_6$) δ 10.88 (s, 1H), 10.39 (s, 1H), 8.94 (s, 1H), 8.85 (d, J=8.0 Hz, 1H), 8.29 (d, J=5.5 Hz, 1H), 8.22 (t, J=7.8 Hz, 1H), 8.13-7.98 (m, 3H), 7.41 (dd, J=4.0, 1.5 Hz, 1H), 6.93 (dd, J=4.3, 2.8 Hz, 1H), 3.69 (q, J=11.0 Hz, 2H).

Scheme 89

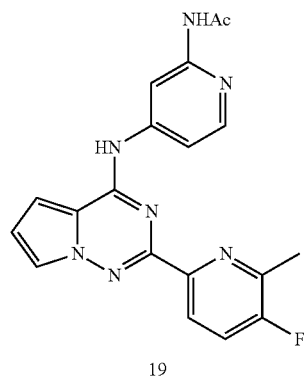

19

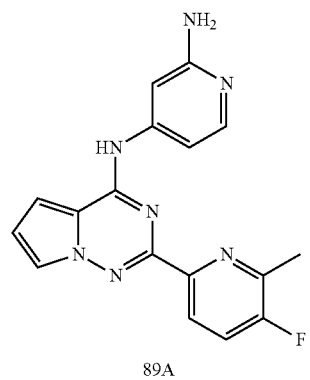

89A

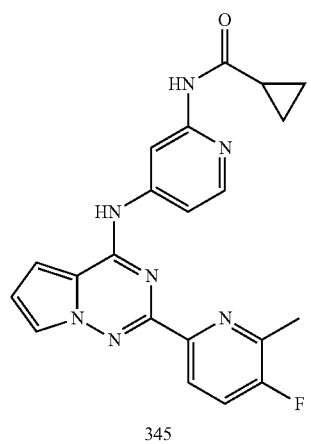

345

Example 345

N-(4-{[2-(5-fluoro-6-methylpyridin-2-yl)pyrrolo[2,1-f][1,2,4]triazin-4-yl]amino}pyridin-2-yl)cyclopropanecarboxamide

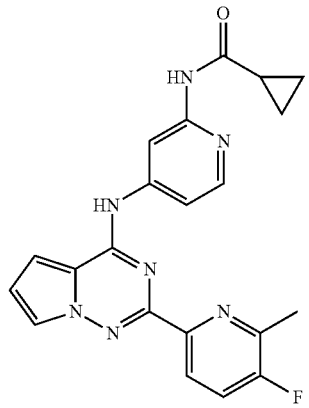 [SMILES: Cc1nc(-c2nc(Nc3ccnc(NC(=O)C4CC4)c3)c3cccn3n2)ccc1F]

Intermediate 89A: N4-(2-(5-fluoro-6-methylpyridin-2-yl)pyrrolo[2,1-f][1,2,4]triazin-4-yl)pyridine-2,4-diamine

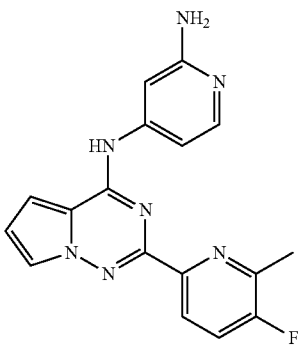 [SMILES: Cc1nc(-c2nc(Nc3ccnc(N)c3)c3cccn3n2)ccc1F]

Intermediate 89A (0.15 g, 0.477 mmol, 67.5%) was synthesized employing the procedure described for intermediate 73A (Scheme 73) and was used in the next step without any purification. LCMS m/z 336.2 (M+H); rt 1.90 min; Conditions J.

Example 345 (3.0 mg, 7.44 μmol, 3.1%) was synthesized employing the procedure described for Example 324 (Scheme 80). LCMS m/z 404.1 (M+H); rt 1.95 min; Condition C. $^1$H NMR (400 MHz, DMSO-$d_6$) δ 10.76 (s, 1H) 10.24 (s, 1H) 8.84 (s, 1H) 8.42 (dd, J=8.80, 3.91 Hz, 1H) 8.26 (d, J=5.62 Hz, 1H) 8.00 (s, 1H) 7.93 (d, J=5.62 Hz, 1H) 7.68 (t, J=8.93 Hz, 1H) 7.35 (d, J=3.91 Hz, 1H) 6.84-6.90 (m, 1H) 2.01-2.08 (m, 1H) 0.79-0.90 (m, 4H).

Biological Assays

Assays are conducted in 1536-well plates and 2 mL reactions are prepared from addition of HIS-TGFβR1

T204D or HIS-TGFβR2 WT, anti-HIS detection antibody, a labeled small molecule probe ($K_d$=<100 nM; $k_{off}$=<0.001 s$^{-1}$.) and test compounds in assay buffer (20 mM HEPES pH 7.4, 10 mM MgCl$_2$, 0.015% Brij35, 4 mM DTT, and 0.05 mg/ml BSA). The reaction is incubated for 1 hour at room temperature and the HTRF signal was measured on an Envision plate reader (Ex: 340 nm; Em: 520 nm/495 nm). Inhibition data were calculated by comparison to no enzyme control reactions for 100% inhibition and vehicle-only reactions for 0% inhibition. The final concentration of reagents in the assay are 1 nM HIS-TGFβR1 T204D or HIS-TGFβR2 WT, 0.2 nM anti-HIS detection antibody, labeled small molecule probe (at $K_d$) and 0.5% DMSO. Dose response curves were generated to determine the concentration required inhibiting 50% of kinase activity (IC$_{50}$). Compounds were dissolved at 10 mM in dimethylsulfoxide (DMSO) and evaluated at eleven concentrations. IC$_{50}$ values were derived by non-linear regression analysis.

Table 1 shows the TGFβR1 and TGFβR2 IC$_{50}$ values for Examples 1-222 of this invention.

| Example# | TGFβR1 IC$_{50}$ (uM) | TGFβR2 IC$_{50}$ (uM) |
|---|---|---|
| 1 | 0.0025 | 0.08 |
| 2 | 0.011 | >15 |
| 3 | 0.00082 | 2.50 |
| 4 | 0.00059 | 0.22 |
| 5 | 0.065 | >15 |
| 6 | 0.068 | >15 |
| 7 | 0.088 | >15 |
| 8 | 0.012 | >15 |
| 9 | 0.042 | >15 |
| 10 | 0.61 | 5.13 |
| 11 | 0.0061 | >15 |
| 12 | 0.00080 | 0.33 |
| 13 | 0.00019 | 0.31 |
| 14 | 0.00079 | 0.61 |
| 15 | 0.010 | >15 |
| 16 | 0.0094 | >15 |
| 17 | 0.00072 | >15 |
| 18 | 0.0015 | |
| 19 | 0.00084 | 0.96 |
| 20 | 0.080 | >15 |
| 21 | 0.00019 | 0.31 |
| 22 | 0.056 | >15 |
| 23 | 0.0011 | >15 |
| 24 | 0.00040 | 0.16 |
| 25 | 0.0090 | >15 |
| 26 | 0.032 | >15 |
| 27 | 0.0013 | 1.79 |
| 28 | 0.016 | 7.84 |
| 29 | 0.016 | >15 |
| 30 | 0.26 | >15 |
| 31 | 0.81 | >15 |
| 32 | 0.070 | 6.73 |
| 33 | 0.00090 | >15 |
| 34 | 0.48 | >15 |
| 35 | 0.022 | 9.32 |
| 36 | 0.0030 | 9.96 |
| 37 | 0.047 | >15 |
| 38 | 0.68 | >15 |
| 39 | 1.6 | >15 |
| 40 | 0.23 | >15 |
| 41 | 0.087 | >15 |
| 42 | 0.16 | >15 |
| 43 | 2.2 | >15 |
| 44 | 1.7 | >15 |
| 45 | 4.9 | >15 |
| 46 | 0.0030 | >15 |
| 47 | 0.18 | >15 |
| 48 | 0.032 | 3.17 |
| 49 | 0.0015 | 0.76 |
| 50 | 0.076 | >15 |
| 51 | 0.030 | >15 |
| 52 | 0.035 | >15 |
| 53 | 0.0016 | 2.32 |
| 54 | 0.0016 | 0.14 |
| 55 | 0.069 | 1.38 |
| 56 | 0.0015 | 0.13 |
| 57 | 0.00093 | 0.77 |
| 58 | 0.0040 | >15 |
| 59 | 0.0016 | 0.91 |
| 60 | 0.0054 | >15 |
| 61 | 0.0024 | >15 |
| 62 | 1.7* | 0.080* |
| 63 | 0.15 | 0.69 |
| 64 | 0.0022 | 5.30 |
| 65 | 0.00079 | 0.38 |
| 66 | 0.00046 | >15 |
| 67 | 0.055 | >15 |
| 68 | 0.0050 | >15 |
| 69 | 0.0019 | 2.37 |
| 70 | 0.00039 | 0.20 |
| 71 | 0.096 | >15 |
| 72 | 0.37 | >15 |
| 73 | 0.074 | >15 |
| 74 | 0.0061* | 1.5* |
| 75 | 0.21 | >15 |
| 76 | 0.00025 | 3.61 |
| 77 | 0.012 | >15 |
| 78 | 0.00092 | 9.62 |
| 79 | 0.013 | 0.43 |
| 80 | 0.0011 | 9.69 |
| 81 | 0.36 | 4.01 |
| 82 | 2.7 | >15 |
| 83 | 0.00076 | 0.00 |
| 84 | 0.0037 | >15 |
| 85 | 0.0047 | 8.48 |
| 86 | 0.0019 | >15 |
| 87 | 0.00092 | 0.35 |
| 88 | 0.0015 | 0.40 |
| 89 | 0.19 | >15 |
| 90 | 0.0088 | >15 |
| 91 | 0.049 | >15 |
| 92 | 1.5 | >15 |
| 93 | 6.6 | >15 |
| 94 | 0.63 | >15 |
| 95 | 0.020 | >15 |
| 96 | 0.65 | >15 |
| 97 | 0.0029 | 2.29 |
| 98 | 0.0091 | >15 |
| 99 | 2.9 | >15 |
| 100 | 0.015 | >15 |
| 101 | 0.53 | 0.10 |
| 102 | 0.015 | >15 |
| 103 | 0.14 | >15 |
| 104 | 0.086 | >15 |
| 105 | 0.69 | >15 |
| 106 | 1.4 | >15 |
| 107 | 0.081 | >15 |
| 108 | 0.33 | >15 |
| 109 | 1.6 | >15 |
| 110 | 0.13 | >15 |
| 111 | 0.052 | >15 |
| 112 | 0.36 | >15 |
| 113 | 0.12 | >15 |
| 114 | 0.26 | >15 |
| 115 | 0.0057 | >15 |
| 116 | 0.0023 | >15 |
| 117 | 0.00085 | 0.34 |
| 118 | 0.0097 | >15 |
| 119 | 0.063 | >15 |
| 120 | 0.098 | >15 |
| 121 | 0.022 | >15 |
| 122 | 0.006* | 1.5* |
| 123 | 0.013 | >15 |
| 124 | 0.0060 | >15 |
| 125 | 0.0016 | 2.83 |

| Example# | TGFβR1 IC$_{50}$ (uM) | TGFβR2 IC$_{50}$ (uM) |
|---|---|---|
| 126 | 0.0016 | 6.41 |
| 127 | 0.0091 | |
| 128 | 0.95 | >15 |
| 129 | 0.038 | >15 |
| 130 | 0.54 | >15 |
| 131 | 0.056 | 7.29 |
| 132 | 0.70 | >15 |
| 133 | 3.3 | >15 |
| 134 | 0.36 | >15 |
| 135 | 0.088 | >15 |
| 136 | 0.72 | >15 |
| 137 | 0.12 | >15 |
| 138 | 6.6 | >15 |
| 139 | 0.19 | >15 |
| 140 | 0.0031 | >15 |
| 141 | 0.0050 | 10.67 |
| 142 | 0.019 | 0.20 |
| 143 | 0.019 | 0.27 |
| 144 | 0.025 | 0.78 |
| 145 | 0.21 | 1.03 |
| 146 | 0.17 | 1.09 |
| 147 | 2.6* | 3.3* |
| 148 | 0.083 | 1.11 |
| 149 | 0.049 | 1.13 |
| 150 | 0.016 | 0.42 |
| 151 | 0.049 | 1.76 |
| 152 | 0.0053 | 1.27 |
| 153 | 0.022 | |
| 154 | 0.033 | 0.54 |
| 155 | 0.0068 | 8.51 |
| 156 | 0.050 | 7.25 |
| 157 | 0.034 | 1.31 |
| 158 | 0.0079 | 6.06 |
| 159 | 0.0048 | 3.24 |
| 160 | 0.0035 | >15 |
| 161 | 0.028 | |
| 162 | 0.11 | |
| 163 | 0.030 | 3.46 |
| 164 | 0.075 | >15 |
| 165 | 0.014 | >15 |
| 166 | 0.045 | >15 |
| 167 | 0.062 | >15 |
| 168 | 0.0086 | >15 |
| 169 | 0.045 | >15 |
| 170 | 0.017 | >15 |
| 171 | 0.12 | >15 |
| 172 | 0.024 | >15 |
| 173 | 0.048 | >15 |
| 174 | 0.023 | >15 |
| 175 | 0.48 | >15 |
| 176 | 0.0085 | >15 |
| 177 | 0.021 | >15 |
| 178 | 0.22 | >15 |
| 179 | 0.26 | >15 |
| 180 | 0.38 | >15 |
| 181 | 0.032 | >15 |
| 182 | 0.016 | 12.01 |
| 183 | 0.044 | 8.79 |
| 184 | 0.014 | >15 |
| 185 | 1.2 | >15 |
| 186 | 0.032 | 9.00 |
| 187 | 0.021 | >15 |
| 188 | 0.049 | >15 |
| 189 | 0.0043 | 0.73 |
| 190 | 0.022 | >15 |
| 191 | 0.064 | >15 |
| 192 | 0.0039 | 2.66 |
| 193 | 0.023 | >15 |
| 194 | 0.11 | >15 |
| 195 | 0.026 | >15 |
| 196 | 0.23 | >15 |
| 197 | 0.042 | >15 |
| 198 | 0.14 | >15 |
| 199 | 0.061 | >15 |
| 200 | 3.5 | >15 |
| 201 | 0.41 | >15 |
| 202 | 0.14 | >15 |
| 203 | 0.75 | >15 |
| 204 | 0.053 | >15 |
| 205 | 0.022 | >15 |
| 206 | 0.0092 | 8.18 |
| 207 | 1.7 | >15 |
| 208 | 0.88 | >15 |
| 209 | 7.7 | >15 |
| 210 | 0.030 | >15 |
| 211 | 0.030 | >15 |
| 212 | 3.0 | >15 |
| 213 | 0.014 | 1.03 |
| 214 | 0.013 | >15 |
| 215 | 0.0069 | 6.18 |
| 216 | 0.033 | >15 |
| 217 | 0.0077 | >15 |
| 218 | 0.13 | >15 |
| 219 | 0.010 | >15 |
| 220 | 0.011 | >15 |
| 221 | 0.0040 | 3.60 |
| 222 | 0.067 | >15 |
| 224 | 0.0014 | >15 |
| 225 | 0.0051 | >15 |
| 226 | 0.022 | >15 |
| 227 | 0.0036 | 0.19 |
| 228 | 0.0016 | 0.20 |
| 229 | 0.0051 | 8.3 |
| 230 | 0.10 | >15 |
| 231 | 0.0023 | 7.4 |
| 232 | 0.00093 | 0.11 |
| 233 | 0.00085 | 0.30 |
| 234 | 0.0030 | 10 |
| 235 | <0.00025 | 0.65 |
| 236 | 0.0022 | 6.4 |
| 237 | 0.0012 | 9.7 |
| 238 | 0.0029 | 2.9 |
| 239 | 0.0012 | 0.47 |
| 240 | 0.00070 | 0.42 |
| 241 | 0.00027 | 1.1 |
| 242 | <0.00076 | 3.4 |
| 243 | 0.00058 | >15 |
| 244 | 0.0063 | 1.1 |
| 245 | 0.0010 | 7.6 |
| 246 | 0.0039 | 3.7 |
| 247 | 0.0010 | 0.89 |
| 248 | 0.070 | 5.0 |
| 249 | 0.0058 | >15 |
| 250 | 0.0012 | 1.3 |
| 251 | 0.00059 | 0.68 |
| 252 | 0.00049 | 0.20 |
| 253 | 0.0012 | >15 |
| 254 | 0.0020 | >15 |
| 255 | 0.028 | >15 |
| 256 | 0.25 | >15 |
| 257 | 0.66 | >15 |
| 258 | 0.0045 | >15 |
| 259 | 0.00093 | >15 |
| 260 | 0.0032 | 0.37 |
| 261 | <0.00076 | 7.5 |
| 262 | 0.0082 | 0.070 |
| 263 | 0.0029 | 4.1 |
| 264 | 0.0017 | 0.96 |
| 265 | 0.0067 | 6.6 |
| 266 | 0.010 | 6.4 |
| 267 | 0.0024 | 5.8 |
| 268 | 0.0011 | 0.51 |
| 269 | 0.0042 | 3.0 |
| 270 | 0.0036 | 4.2 |
| 271 | 0.0012 | 0.99 |
| 272 | 0.0011 | 2.3 |
| 273 | 0.0016 | 0.24 |
| 274 | 0.00052 | 0.066 |
| 275 | 0.00047 | 3.6 |
| 276 | 0.0016 | 1.1 |
| 277 | 0.0015 | 2.2 |
| 278 | 0.0018 | 1.6 |

-continued

| Example# | TGFβR1 IC$_{50}$ (uM) | TGFβR2 IC$_{50}$ (uM) |
|---|---|---|
| 279 | 0.012 | 3.9 |
| 280 | 0.0014 | 1.1 |
| 281 | 0.0016 | 0.55 |
| 282 | 0.015 | 7.8 |
| 283 | 0.012 | 2.2 |
| 284 | 0.0044 | 3.2 |
| 285 | 0.0012 | 0.99 |
| 286 | 0.0029 | 1.9 |
| 287 | 0.00084 | 0.47 |
| 288 | 0.0032 | 4.7 |
| 289 | 0.0030 | >15 |
| 290 | 0.0012 | 0.94 |
| 291 | 0.00086 | 0.015 |
| 292 | 0.36 | >15 |
| 293 | 0.00025 | 0.016 |
| 294 | 0.00040 | 0.051 |
| 295 | 0.030 | 6.1 |
| 296 | <0.00025 | 1.9 |
| 297 | 0.071 | 8.5 |
| 298 | 0.027 | 6.5 |
| 299 | 0.023 | 13 |
| 300 | 0.0033 | 13 |
| 301 | 0.00058 | 0.24 |
| 302 | 0.0017 | 0.81 |
| 303 | 0.0054 | 8.1 |
| 304 | 0.0025 | 2.5 |
| 305 | 0.0026 | 0.97 |
| 306 | 0.0053 | 3.0 |
| 307 | 0.0091 | 12 |
| 308 | 0.0047 | 3.4 |
| 309 | 0.0029 | 5.8 |
| 310 | 0.0040 | 0.80 |
| 311 | 0.013 | 14 |
| 312 | 0.00087 | >15 |
| 313 | 0.00089 | >15 |
| 314 | 0.0056 | >15 |
| 315 | 0.89 | >15 |
| 316 | 0.0010 | >15 |
| 317 | 3.0 | >15 |
| 318 | 4.0 | >15 |
| 319 | 0.0018 | >15 |
| 320 | 0.00085 | >15 |
| 321 | 0.091 | >15 |
| 322 | 0.0013 | >15 |
| 323 | 0.016 | >15 |
| 324 | 4.4 | >15 |
| 325 | 0.010 | >15 |
| 326 | 0.088 | >15 |
| 327 | 0.00030 | >15 |
| 328 | 0.013 | >15 |
| 329 | 0.0017 | >15 |
| 330 | 0.0006 | >15 |
| 331 | 0.0026 | >15 |
| 332 | 0.047 | >15 |
| 333 | 0.0036 | >15 |
| 334 | 0.0018 | >15 |
| 335 | 0.00037 | 0.40 |
| 336 | 0.0016 | >15 |
| 337 | 0.0033 | >15 |
| 338 | 0.00079 | 14 |
| 339 | 0.0033 | >15 |
| 340 | 0.0012 | |
| 341 | 0.0027 | >15 |
| 342 | 0.16 | >15 |
| 343 | 0.0018 | >15 |
| 344 | 0.0051 | >15 |
| 345 | 0.0014 | 0.084 |

*GST tagged wild type proteins were used instead of HIS-tagged proteins

What is claimed is:
1. A compound selected from
N-[2-(pyridin-2-yl)pyrrolo[2,1-f][1,2,4]triazin-4-yl]pyridin-4-amine,
3-(difluoromethyl)-N-{2-[6-(trifluoromethyl)pyridin-2-yl]pyrrolo[2,1-f][1,2,4]triazin-4-yl}pyridin-4-amine,
3-chloro-N-[2-(5-fluoro-6-methylpyridin-2-yl)pyrrolo[2,1-f][1,2,4]triazin-4-yl]pyridin-4-amine,
3-chloro-N-[2-(5-fluoropyridin-2-yl)pyrrolo[2,1-f][1,2,4]triazin-4-yl]pyridin-4-amine
6-{4-[(3-fluoropyridin-4-yl)amino]pyrrolo[2,1-f][1,2,4]triazin-2-yl}pyridine-2-carboxamide,
3-chloro-N-[2-(6-methylpyrazin-2-yl)pyrrolo[2,1-f][1,2,4]triazin-4-yl]pyridin-4-amine,
2-chloro-N-{2-[6-(difluoromethyl)pyridin-2-yl]pyrrolo[2,1-f][1,2,4]triazin-4-yl}-3-fluoropyridin-4-amine,
N-(6-{4-[(pyridin-4-yl)amino]pyrrolo[2,1-f][1,2,4]triazin-2-yl}pyridin-2-yl)methanesulfonamide,
N-(6-(4-((3-fluoropyridin-4-yl)amino)pyrrolo[2,1-f][1,2,4]triazin-2-yl)pyridin-2-yl)acetamide,
3-fluoro-N-[2-(1-methyl-1H-pyrazol-5-yl)pyrrolo[2,1-f][1,2,4]triazin-4-yl]pyridin-4-amine,
N-[4-({2-[6-(difluoromethyl)-5-fluoropyridin-2-yl]pyrrolo[2,1-f][1,2,4]triazin-4-yl}amino)pyridin-2-yl]acetamide,
3-fluoro-N-[2-(4-methyl-1,3-thiazol-2-yl)pyrrolo[2,1-f][1,2,4]triazin-4-yl]pyridin-4-amine,
N-[4-({2-[6-(difluoromethyl)pyridin-2-yl]pyrrolo[2,1-f][1,2,4]triazin-4-yl}amino)pyridin-2-yl]acetamide,
3-fluoro-N-[2-(6-fluoropyridin-2-yl)pyrrolo[2,1-f][1,2,4]triazin-4-yl]pyridin-4-amine,
3-(difluoromethyl)-N-[2-(6-methoxypyridin-2-yl)pyrrolo[2,1-f][1,2,4]triazin-4-yl]pyridin-4-amine,
N-[2-(6-methoxypyridin-2-yl)-5-methylpyrrolo[2,1-f][1,2,4]triazin-4-yl]pyridin-4-amine,
N-(3-fluoropyridin-4-yl)-2-(4-(trifluoromethyl)thiazol-2-yl)pyrrolo[2,1-f][1,2,4]triazin-4-amine,
N-(4-((2-(6-(trifluoromethyl)pyridin-2-yl)pyrrolo[2,1-f][1,2,4]triazin-4-yl)amino)pyridin-2-yl)acetamide,
N-(4-{[2-(5-fluoro-6-methylpyridin-2-yl)pyrrolo[2,1-f][1,2,4]triazin-4-yl]amino}pyridin-2-yl)acetamide,
N-[3-fluoro-4-({2-[6-(trifluoromethyl)pyridin-2-yl]pyrrolo[2,1-f][1,2,4]triazin-4-yl}amino)pyridin-2-yl]acetamide,
N-[4-({2-[6-(difluoromethyl)pyridin-2-yl]pyrrolo[2,1-f][1,2,4]triazin-4-yl}amino)pyridin-2-yl]acetamide,
N-{4-[(3-fluoropyridin-4-yl)amino]-2-(6-methoxypyridin-2-yl)pyrrolo[2,1-f][1,2,4]triazin-6-yl}methanesulfonamide,
N-{2-[6-(difluoromethyl)pyridin-2-yl]-5-[(4,4-difluoropiperidin-1-yl)methyl]pyrrolo[2,1-f][1,2,4]triazin-4-yl}-3-fluoropyridin-4-amine,
N-[4-({5-[(4,4-difluoropiperidin-1-yl)methyl]-2-(pyridin-2-yl)pyrrolo[2,1-f][1,2,4]triazin-4-yl}amino)pyridin-2-yl]acetamide,
N-{5-[(4,4-difluoropiperidin-1-yl)methyl]-2-(6-methoxypyridin-2-yl)pyrrolo[2,1-f][1,2,4]triazin-4-yl}-3-fluoropyridin-4-amine,
3-fluoro-N-{5-[(4-methylpiperazin-1-yl)methyl]-2-[6-(trifluoromethyl)pyridin-2-yl]pyrrolo[2,1-f][1,2,4]triazin-4-yl}pyridin-4-amine,
N-{5-[(4,4-difluoropiperidin-1-yl)methyl]-2-(pyridin-2-yl)pyrrolo[2,1-f][1,2,4]triazin-4-yl}-3-fluoropyridin-4-amine,
1-{4-[(3-fluoropyridin-4-yl)amino]-2-(6-methoxypyridin-2-yl)pyrrolo[2,1-f][1,2,4]triazin-5-yl}ethane-1,2-diol,
6-ethyl-N-(3-fluoropyridin-4-yl)-2-(6-methoxypyridin-2-yl)pyrrolo[2,1-f][1,2,4]triazin-4-amine,
2-[4-(dimethylamino)piperidin-1-yl]-1-{4-[(3-fluoropyridin-4-yl)amino]-2-(6-methoxypyridin-2-yl)pyrrolo[2,1-f][1,2,4]triazin-5-yl}ethan-1-ol,

2-(6-methoxypyridin-2-yl)-N-(pyridin-4-ylmethyl)pyr-rolo[2,1-f][1,2,4]triazin-4-amine,
1-(6-{4-[(3-fluoropyridin-4-yl)amino]pyrrolo[2,1-f][1,2,4]triazin-2-yl}pyridin-2-yl)ethan-1-ol,
N-[4-({2-[6-(difluoromethyl)pyridin-2-yl]pyrrolo[2,1-f][1,2,4]triazin-4-yl}amino)pyridin-2-yl]-2-(pyrrolidin-1-yl)acetamide,
2-N-[2-(4,4-difluoropiperidin-1-yl)ethyl]-4-N-[2-(6-methoxypyridin-2-yl)pyrrolo[2,1-f][1,2,4]triazin-4-yl]pyridine-2,4-diamine,
N-[2-(1,1-dioxo-1,4-thiomorpholin-4-yl)ethyl]-4-{[2-(5-fluoro-6-methylpyridin-2-yl)pyrrolo[2,1-f][1,2,4]triazin-4-yl]amino}pyridine-3-carboxamide,
N-(3-(1,1-dioxidothiomorpholino)propyl)-4-((2-(6-methylpyridin-2-yl)pyrrolo[2,1-f][1,2,4]triazin-4-yl)amino)nicotinamide,
N-[3-(pyrrolidin-1-yl)propyl]-4-({2-[6-(trifluoromethyl)pyridin-2-yl]pyrrolo[2,1-f][1,2,4]triazin-4-yl}amino)pyridine-3-carboxamide,
N-[2-(6-methoxypyridin-2-yl)pyrrolo[2,1-f][1,2,4]triazin-4-yl]-3-{[3-(morpholin-4-yl)propoxy]methyl}pyridin-4-amine,
2-{4-[(3-fluoropyridin-4-yl)amino]-2-(6-methoxypyridin-2-yl)pyrrolo[2,1-f][1,2,4]triazin-6-yl}propan-2-ol,
N-{6-[(4,4-difluoropiperidin-1-yl)methyl]-2-(6-methoxypyridin-2-yl)pyrrolo[2,1-f][1,2,4]triazin-4-yl}-3-fluoropyridin-4-amine,
3-fluoro-N-[7-fluoro-2-(6-methoxypyridin-2-yl)pyrrolo[2,1-f][1,2,4]triazin-4-yl]pyridin-4-amine,
N-[6-ethyl-2-(6-methoxypyridin-2-yl)pyrrolo[2,1-f][1,2,4]triazin-4-yl]-3-fluoropyridin-4-amine,
3-fluoro-N-[2-(6-methoxypyridin-2-yl)-6-[4-(4-methylpiperazin-1-yl)butyl]pyrrolo[2,1-f][1,2,4]triazin-4-yl]pyridin-4-amine,
3-fluoro-N-[2-(6-methoxypyridin-2-yl)-6-[2-(4-methylpiperazin-1-yl)ethyl]pyrrolo[2,1-f][1,2,4]triazin-4-yl]pyridin-4-amine,
3-fluoro-N-[2-(6-methoxypyridin-2-yl)-5-[2-(pyrrolidin-1-yl)ethoxy]pyrrolo[2,1-f][1,2,4]triazin-4-yl]pyridin-4-amine,
2-{4-[(3-fluoropyridin-4-yl)amino]-2-(6-methoxypyridin-2-yl)pyrrolo[2,1-f][1,2,4]triazin-5-yl}ethan-1-ol,
N-(4-{[2-(6-methoxypyridin-2-yl)pyrrolo[2,1-f][1,2,4]triazin-4-yl]amino}pyridin-3-yl)acetamide,
2-{4-[(3-fluoropyridin-4-yl)amino]-2-(6-methoxypyridin-2-yl)pyrrolo[2,1-f][1,2,4]triazin-5-yl}propan-2-ol,
N-[2-(6-methylpyridin-2-yl)pyrrolo[2,1-f][1,2,4]triazin-4-yl]pyridin-4-amine,
2-(6-methylpyridin-2-yl)-4-[(pyridin-4-yl)amino]-N-[3-(pyrrolidin-1-yl)propyl]pyrrolo[2,1-f][1,2,4]triazine-6-carboxamide,
3-[4-(dimethylamino)butoxy]-N-[2-(6-methylpyridin-2-yl)pyrrolo[2,1-f][1,2,4]triazin-4-yl]pyridin-4-amine,
4-[(3-fluoropyridin-4-yl)amino]-2-(6-methylpyridin-2-yl)pyrrolo[2,1-f][1,2,4]triazine-7-carboxylic acid,
2-(6-aminopyridin-2-yl)-N-(3-fluoropyridin-4-yl)pyrrolo[2,1-f][1,2,4]triazin-4-amine,
3-chloro-N-[2-(pyridin-2-yl)pyrrolo[2,1-f][1,2,4]triazin-4-yl]pyridin-4-amine,
3-fluoro-N-[2-(pyridin-2-yl)pyrrolo[2,1-f][1,2,4]triazin-4-yl]pyridin-4-amine,
3-fluoro-N-[2-(6-methylpyridin-2-yl)pyrrolo[2,1-f][1,2,4]triazin-4-yl]pyridin-4-amine,
3-fluoro-N-[2-(6-methoxypyridin-2-yl)pyrrolo[2,1-f][1,2,4]triazin-4-yl]pyridin-4-amine,
3-chloro-N-[2-(6-methylpyridin-2-yl)pyrrolo[2,1-f][1,2,4]triazin-4-yl]pyridin-4-amine,
3-chloro-N-[2-(6-methoxypyridin-2-yl)pyrrolo[2,1-f][1,2,4]triazin-4-yl]pyridin-4-amine,
3,5-difluoro-N-[2-(6-methylpyridin-2-yl)pyrrolo[2,1-f][1,2,4]triazin-4-yl]pyridin-4-amine,
3-fluoro-N-[2-(4-methylpyridin-2-yl)pyrrolo[2,1-f][1,2,4]triazin-4-yl]pyridin-4-amine,
N-[2-(4-chloropyridin-2-yl)pyrrolo[2,1-f][1,2,4]triazin-4-yl]-3-fluoropyridin-4-amine,
N-[2-(6-methylpyridin-2-yl)pyrrolo[2,1-f][1,2,4]triazin-4-yl]pyrimidin-4-amine,
3-fluoro-N-[2-(5-fluoropyridin-2-yl)pyrrolo[2,1-f][1,2,4]triazin-4-yl]pyridin-4-amine,
N-{2-[6-(difluoromethyl)-5-fluoropyridin-2-yl]pyrrolo[2,1-f][1,2,4]triazin-4-yl}-3-fluoropyridin-4-amine,
N-[2-(6-methoxypyridin-2-yl)pyrrolo[2,1-f][1,2,4]triazin-4-yl]pyrimidin-4-amine,
Methyl N-(4-{[2-(6-methoxypyridin-2-yl)pyrrolo[2,1-f][1,2,4]triazin-4-yl]amino}pyridin-2-yl)carbamate,
N-[2-(5-fluoro-6-methylpyridin-2-yl)pyrrolo[2,1-f][1,2,4]triazin-4-yl]pyridin-4-amine,
3-chloro-N-[2-(6-fluoropyridin-2-yl)pyrrolo[2,1-f][1,2,4]triazin-4-yl]pyridin-4-amine,
3-fluoro-N-[2-(6-methylpyrazin-2-yl)pyrrolo[2,1-f][1,2,4]triazin-4-yl]pyridin-4-amine,
3-ethyl-1-{4-[(3-fluoropyridin-4-yl)amino]-2-(6-methoxypyridin-2-yl)pyrrolo[2,1-f][1,2,4]triazin-6-yl}urea,
Methyl N-{4-[(3-fluoropyridin-4-yl)amino]-2-(6-methoxypyridin-2-yl)pyrrolo[2,1-f][1,2,4]triazin-6-yl}carbamate,
3-fluoro-N-[2-(5-fluoro-6-methylpyridin-2-yl)pyrrolo[2,1-f][1,2,4]triazin-4-yl]pyridin-4-amine,
3-[3-(morpholin-4-yl)propoxy]-N-{2-[6-(trifluoromethyl)pyridin-2-yl]pyrrolo[2,1-f][1,2,4]triazin-4-yl}pyridin-4-amine, 75
N-{5-[(4,4-difluoropiperidin-1-yl)methyl]-2-(6-methylpyridin-2-yl)pyrrolo[2,1-f][1,2,4]triazin-4-yl}-3-fluoropyridin-4-amine,
N-(6-{4-[(3-fluoropyridin-4-yl)amino]pyrrolo[2,1-f][1,2,4]triazin-2-yl}pyridin-2-yl)methanesulfonamide,
N-{2-[6-(difluoromethyl)pyridin-2-yl]pyrrolo[2,1-f][1,2,4]triazin-4-yl}-3-fluoropyridin-4-amine,
3-(prop-2-en-1-yloxy)-N-[2-(pyridin-2-yl)pyrrolo[2,1-f][1,2,4]triazin-4-yl]pyridin-4-amine,
3-chloro-N-{2-[6-(difluoromethyl)pyridin-2-yl]pyrrolo[2,1-f][1,2,4]triazin-4-yl}pyridin-4-amine,
3-chloro-N-[2-(1-methyl-1H-pyrazol-5-yl)pyrrolo[2,1-f][1,2,4]triazin-4-yl]pyridin-4-amine,
2-chloro-N-{2-[6-(trifluoromethyl)pyridin-2-yl]pyrrolo[2,1-f][1,2,4]triazin-4-yl}pyridin-4-amine,
4-{[2-(pyridin-2-yl)pyrrolo[2,1-f][1,2,4]triazin-4-yl]amino}pyridine-3-carboxamide,
3-fluoro-N-{2-[6-(trifluoromethyl)pyridin-2-yl]pyrrolo[2,1-f][1,2,4]triazin-4-yl}pyridin-4-amine,
N-{2-[6-(trifluoromethyl)pyridin-2-yl]pyrrolo[2,1-f][1,2,4]triazin-4-yl}pyridin-4-amine,
3-chloro-N-{2-[6-(trifluoromethyl)pyridin-2-yl]pyrrolo[2,1-f][1,2,4]triazin-4-yl}pyridin-4-amine,
3-chloro-N-[2-(4-methyl-1,3-thiazol-2-yl)pyrrolo[2,1-f][1,2,4]triazin-4-yl]pyridin-4-amine,
N-[2-(4-methyl-1,3-thiazol-2-yl)pyrrolo[2,1-f][1,2,4]triazin-4-yl]pyridin-4-amine,
3-fluoro-N-[2-(1H-pyrrol-2-yl)pyrrolo[2,1-f][1,2,4]triazin-4-yl]pyridin-4-amine,
N-(6-{4-[(3-chloropyridin-4-yl)amino]pyrrolo[2,1-f][1,2,4]triazin-2-yl}pyridin-2-yl)methanesulfonamide, N-[5-chloro-2-(6-methoxypyridin-2-yl)pyrrolo[2,1-f][1,2,4]triazin-4-yl]pyridin-4-amine,
N-[2-(6-methoxypyridin-2-yl)pyrrolo[2,1-f][1,2,4]triazin-4-yl]-2-methylpyridin-4-amine,
2-chloro-N-[2-(6-methoxypyridin-2-yl)pyrrolo[2,1-f][1,2,4]triazin-4-yl]pyridin-4-amine,
2-fluoro-N-[2-(6-methoxypyridin-2-yl)pyrrolo[2,1-f][1,2,4]triazin-4-yl]pyridin-4-amine,
4-N-[2-(6-methoxypyridin-2-yl)pyrrolo[2,1-f][1,2,4]triazin-4-yl]pyridine-3,4-diamine,
2-fluoro-N-[2-(6-methoxypyridin-2-yl)-5-methylpyrrolo[2,1-f][1,2,4]triazin-4-yl]pyridin-4-amine,
N-(4-{[2-(6-methoxypyridin-2-yl)pyrrolo[2,1-f][1,2,4]triazin-4-yl]amino}pyridin-2-yl)acetamide,
4-{[2-(6-methoxypyridin-2-yl)pyrrolo[2,1-f][1,2,4]triazin-4-yl]amino}pyridine-3-carboxamide,
N-[2-(6-methoxypyridin-2-yl)pyrrolo[2,1-f][1,2,4]triazin-4-yl]-2-(morpholin-4-yl)pyridin-4-amine,
3-fluoro-N-{2-[2-(trifluoromethyl)pyrimidin-4-yl]pyrrolo[2,1-f][1,2,4]triazin-4-yl}pyridin-4-amine,
3-fluoro-N-[2-(2-methoxypyrimidin-4-yl)pyrrolo[2,1-f][1,2,4]triazin-4-yl]pyridin-4-amine,
N-[2-(6-ethoxypyridin-2-yl)pyrrolo[2,1-f][1,2,4]triazin-4-yl]-3-fluoropyridin-4-amine,
4-N-(3-fluoropyridin-4-yl)-2-(6-methoxypyridin-2-yl)pyrrolo[2,1-f][1,2,4]triazine-4,6-diamine,
N-{4-[(3-fluoropyridin-4-yl)amino]-2-(6-methoxypyridin-2-yl)pyrrolo[2,1-f][1,2,4]triazin-6-yl}acetamide,
N-{4-[(3-fluoropyridin-4-yl)amino]-2-(6-methoxypyridin-2-yl)pyrrolo[2,1-f][1,2,4]triazin-6-yl}morpholine-4-carboxamide,
N-{4-[(3-fluoropyridin-4-yl)amino]-2-(6-methoxypyridin-2-yl)pyrrolo[2,1-f][1,2,4]triazin-6-yl}-2-(morpholin-4-yl)acetamide,
N-{4-[(3-fluoropyridin-4-yl)amino]-2-(6-methoxypyridin-2-yl)pyrrolo[2,1-f][1,2,4]triazin-6-yl}cyclopropanesulfonamide,
tert-butyl N-[({4-[(3-fluoropyridin-4-yl)amino]-2-(6-methoxypyridin-2-yl)pyrrolo[2,1-f][1,2,4]triazin-6-yl}carbamoyl)methyl]carbamate,
2-amino-N-{4-[(3-fluoropyridin-4-yl)amino]-2-(6-methoxypyridin-2-yl)pyrrolo[2,1-f][1,2,4]triazin-6-yl}acetamide,
N-{4-[(3-fluoropyridin-4-yl)amino]-2-(6-methoxypyridin-2-yl)pyrrolo[2,1-f][1,2,4]triazin-6-yl}-2-methanesulfonamidoacetamide,
N-{4-[(3-fluoropyridin-4-yl)amino]-2-[6-(trifluoromethyl)pyridin-2-yl]pyrrolo[2,1-f][1,2,4]triazin-6-yl}-N-methanesulfonylmethanesulfonamide,
3-fluoro-N-[2-(6-methoxypyridin-2-yl)-5-[2-(4-methylpiperazin-1-yl)ethyl]pyrrolo[2,1-f][1,2,4]triazin-4-yl]pyridin-4-amine,
3-fluoro-N-[2-(6-methoxypyridin-2-yl)-5-[2-(morpholin-4-yl)ethyl]pyrrolo[2,1-f][1,2,4]triazin-4-yl]pyridin-4-amine,
N-{5-[2-(4-aminopiperidin-1-yl)ethyl]-2-(6-methoxypyridin-2-yl)pyrrolo[2,1-f][1,2,4]triazin-4-yl}-3-fluoropyridin-4-amine,
N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine,
1-[({2-[6-(difluoromethyl)pyridin-2-yl]-4-[(3-fluoropyridin-4-yl)amino]pyrrolo[2,1-f][1,2,4]triazin-5-yl}methyl)amino]-2-methylpropan-2-ol,
N-{4-[(5-{[(2-hydroxy-2-methylpropyl)amino]methyl}-2-(pyridin-2-yl)pyrrolo[2,1-f][1,2,4]triazin-4-yl)amino]pyridin-2-yl}acetamide,
1-[({4-[(3-fluoropyridin-4-yl)amino]-2-(6-methoxypyridin-2-yl)pyrrolo[2,1-f][1,2,4]triazin-5-yl}methyl)amino]-2-methylpropan-2-ol,
3-fluoro-N-[2-(6-methoxypyridin-2-yl)-5-({[2-(pyrrolidin-1-yl)ethyl]amino}methyl)pyrrolo[2,1-f][1,2,4]triazin-4-yl]pyridin-4-amine,
(3R)-3-fluoro-4-[({4-[(3-fluoropyridin-4-yl)amino]-2-(6-methoxypyridin-2-yl)pyrrolo[2,1-f][1,2,4]triazin-5-yl}methyl)amino]-2-methylbutan-2-ol,
3-fluoro-N-[2-(6-methoxypyridin-2-yl)-5-[(4-methylpiperazin-1-yl)methyl]pyrrolo[2,1-f][1,2,4]triazin-4-yl]pyridin-4-amine,
N-{2-[6-(difluoromethyl)pyridin-2-yl]-5-[(4-methylpiperazin-1-yl)methyl]pyrrolo[2,1-f][1,2,4]triazin-4-yl}-3-fluoropyridin-4-amine,
N-{5-[(4,4-difluoropiperidin-1-yl)methyl]-2-[6-(trifluoromethyl)pyridin-2-yl]pyrrolo[2,1-f][1,2,4]triazin-4-yl}-3-fluoropyridin-4-amine,
1-[({4-[(3-fluoropyridin-4-yl)amino]-2-[6-(trifluoromethyl)pyridin-2-yl]pyrrolo[2,1-f][1,2,4]triazin-5-yl}methyl)amino]-2-methylpropan-2-ol,
1-[({4-[(3-fluoropyridin-4-yl)amino]-2-(pyridin-2-yl)pyrrolo[2,1-f][1,2,4]triazin-5-yl}methyl)amino]-2-methylpropan-2-ol,
(3R,4R)-4-amino-1-({4-[(3-fluoropyridin-4-yl)amino]-2-(pyridin-2-yl)pyrrolo[2,1-f][1,2,4]triazin-5-yl}methyl)piperidin-3-ol,
3-fluoro-N-{5-[(4-methylpiperazin-1-yl)methyl]-2-(pyridin-2-yl)pyrrolo[2,1-f][1,2,4]triazin-4-yl}pyridin-4-amine,
1-{4-[(3-fluoropyridin-4-yl)amino]-2-(6-methoxypyridin-2-yl)pyrrolo[2,1-f][1,2,4]triazin-5-yl}-2-(4-methylpiperazin-1-yl)ethan-1-ol,
2-(4,4-difluoropiperidin-1-yl)-1-{4-[(3-fluoropyridin-4-yl)amino]-2-(6-methoxypyridin-2-yl)pyrrolo[2,1-f][1,2,4]triazin-5-yl}ethan-1-ol,
1-{4-[(3-fluoropyridin-4-yl)amino]-2-(6-methoxypyridin-2-yl)pyrrolo[2,1-f][1,2,4]triazin-5-yl}-2-{[2-(piperidin-1-yl)ethyl]amino}ethan-1-ol,
4-{2-[(2-{4-[(3-fluoropyridin-4-yl)amino]-2-(6-methoxypyridin-2-yl)pyrrolo[2,1-f][1,2,4]triazin-5-yl}-2-hydroxyethyl)amino]ethyl}-1,4-thiomorpholine-1,1-dione,
1-{2-[(4-{[2-(6-methoxypyridin-2-yl)pyrrolo[2,1-f][1,2,4]triazin-4-yl]amino}pyridin-2-yl)amino]ethyl}piperidin-4-ol,
1-[(4-{[2-(6-methoxypyridin-2-yl)pyrrolo[2,1-f][1,2,4]triazin-4-yl]amino}pyridin-2-yl)amino]-2-methylpropan-2-ol,
4-[(4-{[2-(6-methoxypyridin-2-yl)pyrrolo[2,1-f][1,2,4]triazin-4-yl]amino}pyridin-2-yl)amino]-2-methylbutan-2-ol,
2-N-[3-(dimethylamino)propyl]-4-N-[2-(6-methoxypyridin-2-yl)pyrrolo[2,1-f][1,2,4]triazin-4-yl]pyridine-2,4-diamine,
1-{2-[(4-{[2-(6-methoxypyridin-2-yl)-5-methylpyrrolo[2,1-f][1,2,4]triazin-4-yl]amino}pyridin-2-yl)amino]ethyl}piperidin-4-ol,
4-N-[2-(6-methoxypyridin-2-yl)-5-methylpyrrolo[2,1-f][1,2,4]triazin-4-yl]-2-N-[2-(morpholin-4-yl)ethyl]pyridine-2,4-diamine,
1-[(4-{[2-(6-methoxypyridin-2-yl)-5-methylpyrrolo[2,1-f][1,2,4]triazin-4-yl]amino}pyridin-2-yl)amino]-2-methylpropan-2-ol,
4-N-[2-(6-methoxypyridin-2-yl)pyrrolo[2,1-f][1,2,4]triazin-4-yl]-2-N-[2-(morpholin-4-yl)ethyl]pyridine-2,4-diamine, N-[3-(1,1-dioxo-1,4-thiomorpholin-4-yl)propyl]-4-{[2-(5-fluoro-6-methylpyridin-2-yl)pyrrolo[2,1-f][1,2,4]triazin-4-yl]amino}pyridine-3-carboxamide,
4-{[2-(5-fluoro-6-methylpyridin-2-yl)pyrrolo[2,1-f][1,2,4]triazin-4-yl]amino}-N-[2-(piperidin-1-yl)ethyl]pyridine-3-carboxamide,
4-{[2-(pyridin-2-yl)pyrrolo[2,1-f][1,2,4]triazin-4-yl]amino}-N-[2-(pyrrolidin-1-yl)ethyl]pyridine-3-carboxamide,
N-[2-(diethylamino)ethyl]-4-{[2-(pyridin-2-yl)pyrrolo[2,1-f][1,2,4]triazin-4-yl]amino}pyridine-3-carboxamide,
N-[2-(piperidin-1-yl)ethyl]-4-{[2-(pyridin-2-yl)pyrrolo[2,1-f][1,2,4]triazin-4-yl]amino}pyridine-3-carboxamide,
tert-butyl 4-{2-[(4-{[2-(pyridin-2-yl)pyrrolo[2,1-f][1,2,4]triazin-4-yl]amino}pyridin-3-yl)formamido]ethyl}piperazine-1-carboxylate,
N-{2-[cis-2,6-dimethylmorpholin-4-yl]ethyl}-4-{[2-(pyridin-2-yl)pyrrolo[2,1-f][1,2,4]triazin-4-yl]amino}pyridine-3-carboxamide,
N-[2-(1,1-dioxo-1,4-thiomorpholin-4-yl)ethyl]-4-{[2-(pyridin-2-yl)pyrrolo[2,1-f][1,2,4]triazin-4-yl]amino}pyridine-3-carboxamide,
N-[3-(1,1-dioxo-1,4-thiomorpholin-4-yl)propyl]-4-{[2-(pyridin-2-yl)pyrrolo[2,1-f][1,2,4]triazin-4-yl]amino}pyridine-3-carboxamide,
N-[3-(2-oxopyrrolidin-1-yl)propyl]-4-{[2-(pyridin-2-yl)pyrrolo[2,1-f][1,2,4]triazin-4-yl]amino}pyridine-3-carboxamide,
4-{[2-(pyridin-2-yl)pyrrolo[2,1-f][1,2,4]triazin-4-yl]amino}-N-[3-(pyrrolidin-1-yl)propyl]pyridine-3-carboxamide,
N-[2-(piperazin-1-yl)ethyl]-4-{[2-(pyridin-2-yl)pyrrolo[2,1-f][1,2,4]triazin-4-yl]amino}pyridine-3-carboxamide,
4-{[2-(6-methylpyridin-2-yl)pyrrolo[2,1-f][1,2,4]triazin-4-yl]amino}-N-[2-(pyrrolidin-1-yl)ethyl]pyridine-3-carboxamide,
N-[2-(1,1-dioxo-1,4-thiomorpholin-4-yl)ethyl]-4-{[2-(6-methylpyridin-2-yl)pyrrolo[2,1-f][1,2,4]triazin-4-yl]amino}pyridine-3-carboxamide,
N-[(4-hydroxy-1-methylpiperidin-4-yl)methyl]-4-{[2-(6-methylpyridin-2-yl)pyrrolo[2,1-f][1,2,4]triazin-4-yl]amino}pyridine-3-carboxamide,
4-{[2-(6-methylpyridin-2-yl)pyrrolo[2,1-f][1,2,4]triazin-4-yl]amino}-N-[2-(piperidin-1-yl)ethyl]pyridine-3-carboxamide,
N-(2-hydroxy-2-methylpropyl)-4-{[2-(6-methylpyridin-2-yl)pyrrolo[2,1-f][1,2,4]triazin-4-yl]amino}pyridine-3-carboxamide,
N-(1-hydroxy-2-methylpropan-2-yl)-4-{[2-(6-methylpyridin-2-yl)pyrrolo[2,1-f][1,2,4]triazin-4-yl]amino}pyridine-3-carboxamide,
N-[(2S)-2,3-dihydroxypropyl]-4-{[2-(6-methylpyridin-2-yl)pyrrolo[2,1-f][1,2,4]triazin-4-yl]amino}pyridine-3-carboxamide,
N-(3-hydroxypropyl)-4-{[2-(6-methylpyridin-2-yl)pyrrolo[2,1-f][1,2,4]triazin-4-yl]amino}pyridine-3-carboxamide,
N-[3-(4-methylpiperazin-1-yl)propyl]-4-{[2-(6-methylpyridin-2-yl)pyrrolo[2,1-f][1,2,4]triazin-4-yl]amino}pyridine-3-carboxamide,
4-{[2-(6-methylpyridin-2-yl)pyrrolo[2,1-f][1,2,4]triazin-4-yl]amino}-N-(oxolan-3-yl)pyridine-3-carboxamide,
N-[2-(dimethylamino)ethyl]-N-methyl-4-{[2-(6-methylpyridin-2-yl)pyrrolo[2,1-f][1,2,4]triazin-4-yl]amino}pyridine-3-carboxamide,
N-[2-(6-methylpyridin-2-yl)pyrrolo[2,1-f][1,2,4]triazin-4-yl]-3-(morpholine-4-carbonyl)pyridin-4-amine,
4-{[2-(6-methylpyridin-2-yl)pyrrolo[2,1-f][1,2,4]triazin-4-yl]amino}-N-(oxan-4-yl)pyridine-3-carboxamide,
4-{[2-(6-methylpyridin-2-yl)pyrrolo[2,1-f][1,2,4]triazin-4-yl]amino}-N-(oxetan-3-yl)pyridine-3-carboxamide,
4-{[2-(6-methylpyridin-2-yl)pyrrolo[2,1-f][1,2,4]triazin-4-yl]amino}-N-(propan-2-yl)pyridine-3-carboxamide,
4-({2-[6-(difluoromethyl)pyridin-2-yl]pyrrolo[2,1-f][1,2,4]triazin-4-yl}amino)-N-[2-(1,1-dioxo-1,4-thiomorpholin-4-yl)ethyl]pyridine-3-carboxamide,
4-({2-[6-(difluoromethyl)pyridin-2-yl]pyrrolo[2,1-f][1,2,4]triazin-4-yl}amino)-N-[3-(1,1-dioxo-1,4-thiomorpholin-4-yl)propyl]pyridine-3-carboxamide,
N-[3-(morpholin-4-yl)propyl]-4-({2-[6-(trifluoromethyl)pyridin-2-yl]pyrrolo[2,1-f][1,2,4]triazin-4-yl}amino)pyridine-3-carboxamide,
N-[2-(pyrrolidin-1-yl)ethyl]-4-({2-[6-(trifluoromethyl)pyridin-2-yl]pyrrolo[2,1-f][1,2,4]triazin-4-yl}amino)pyridine-3-carboxamide,
N-[2-(piperidin-1-yl)ethyl]-4-({2-[6-(trifluoromethyl)pyridin-2-yl]pyrrolo[2,1-f][1,2,4]triazin-4-yl}amino)pyridine-3-carboxamide,
4-({2-[6-(difluoromethyl)pyridin-2-yl]pyrrolo[2,1-f][1,2,4]triazin-4-yl}amino)-N-(3-ethoxypropyl)pyridine-3-carboxamide,
N-[2-(tert-butoxy)ethyl]-4-({2-[6-(difluoromethyl)pyridin-2-yl]pyrrolo[2,1-f][1,2,4]triazin-4-yl}amino)pyridine-3-carboxamide,
4-({2-[6-(difluoromethyl)pyridin-2-yl]pyrrolo[2,1-f][1,2,4]triazin-4-yl}amino)-N-[2-(2-hydroxyethoxy)ethyl]pyridine-3-carboxamide,
4-({2-[6-(difluoromethyl)pyridin-2-yl]pyrrolo[2,1-f][1,2,4]triazin-4-yl}amino)-N-[(1S,2S)-2-hydroxycyclohexyl]pyridine-3-carboxamide,
4-({2-[6-(difluoromethyl)pyridin-2-yl]pyrrolo[2,1-f][1,2,4]triazin-4-yl}amino)-N-[3-(4-methylpiperazin-1-yl)propyl]pyridine-3-carboxamide,
4-({2-[6-(difluoromethyl)pyridin-2-yl]pyrrolo[2,1-f][1,2,4]triazin-4-yl}amino)-N-(oxolan-3-yl)pyridine-3-carboxamide,
4-({2-[6-(difluoromethyl)pyridin-2-yl]pyrrolo[2,1-f][1,2,4]triazin-4-yl}amino)-N-(oxan-4-yl)pyridine-3-carboxamide,
N-[2-(1,1-dioxo-1,4-thiomorpholin-4-yl)ethyl]-4-({2-[6-(trifluoromethyl)pyridin-2-yl]pyrrolo[2,1-f][1,2,4]triazin-4-yl}amino)pyridine-3-carboxamide,
4-({2-[6-(difluoromethyl)pyridin-2-yl]pyrrolo[2,1-f][1,2,4]triazin-4-yl}amino)-N-[(1R,2R)-2-hydroxycyclohexyl]pyridine-3-carboxamide,
4-({2-[6-(difluoromethyl)pyridin-2-yl]pyrrolo[2,1-f][1,2,4]triazin-4-yl}amino)-N-(pyridin-2-ylmethyl)pyridine-3-carboxamide,
4-({2-[6-(difluoromethyl)pyridin-2-yl]pyrrolo[2,1-f][1,2,4]triazin-4-yl}amino)-N-[(5-ethyl-1,3,4-oxadiazol-2-yl)methyl]pyridine-3-carboxamide,
4-({2-[6-(difluoromethyl)pyridin-2-yl]pyrrolo[2,1-f][1,2,4]triazin-4-yl}amino)-N-(1,3-thiazol-2-ylmethyl)pyridine-3-carboxamide,
4-({2-[6-(difluoromethyl)pyridin-2-yl]pyrrolo[2,1-f][1,2,4]triazin-4-yl}amino)-N-propylpyridine-3-carboxamide,
1-[4-({2-[6-(difluoromethyl)pyridin-2-yl]pyrrolo[2,1-f][1,2,4]triazin-4-yl}amino)pyridine-3-carbonyl]-4-phenylpiperidin-4-ol, N-{2-[6-(difluoromethyl)pyridin-2-yl]pyrrolo[2,1-f][1,2,4]triazin-4-yl}-3-(pyrrolidine-1-carbonyl)pyridin-4-amine, 4-({2-[6-(difluoromethyl)pyridin-2-yl]pyrrolo[2,1-f][1,2,4]triazin-4-yl}amino)-N-(3-hydroxy-3-methylbutyl)pyridine-3-carboxamide, 4-({2-[6-(difluoromethyl)pyridin-2-yl]pyrrolo[2,1-f][1,2,4]triazin-4-yl}amino)-N-(2-hydroxy-2-methylpropyl)pyridine-3-carboxamide, 3-(azetidine-1-carbonyl)-N-{2-[6-(difluoromethyl)pyridin-2-yl]pyrrolo[2,1-f][1,2,4]triazin-4-yl}pyridin-4-amine, Ethyl 2-{[4-({2-[6-(difluoromethyl)pyridin-2-yl]pyrrolo[2,1-f][1,2,4]triazin-4-yl}amino)pyridin-3-yl]formamido}acetate, 4-({2-[6-(difluoromethyl)pyridin-2-yl]pyrrolo[2,1-f][1,2,4]triazin-4-yl}amino)-N-(1H-1,2,4-triazol-3-ylmethyl)pyridine-3-carboxamide, 4-({2-[6-(difluoromethyl)pyridin-2-yl]pyrrolo[2,1-f][1,2,4]triazin-4-yl}amino)-N-(2-hydroxyethyl)pyridine-3-carboxamide, N-cyclobutyl-4-({2-[6-(difluoromethyl)pyridin-2-yl]pyrrolo[2,1-f][1,2,4]triazin-4-yl}amino)pyridine-3-carboxamide, 4-({2-[6-(difluoromethyl)pyridin-2-yl]pyrrolo[2,1-f][1,2,4]triazin-4-yl}amino)-N-(propan-2-yl)pyridine-3-carboxamide, 4-({2-[6-(difluoromethyl)pyridin-2-yl]pyrrolo[2,1-f][1,2,4]triazin-4-yl}amino)-N-(1,3-oxazol-4-ylmethyl)pyridine-3-carboxamide, tert-butyl 2-{[4-({2-[6-(difluoromethyl)pyridin-2-yl]pyrrolo[2,1-f][1,2,4]triazin-4-yl}amino)pyridin-3-yl]formamido}acetate, 4-({2-[6-(difluoromethyl)pyridin-2-yl]pyrrolo[2,1-f][1,2,4]triazin-4-yl}amino)-N-(1H-pyrazol-5-ylmethyl)pyridine-3-carboxamide, 4-({2-[6-(difluoromethyl)pyridin-2-yl]pyrrolo[2,1-f][1,2,4]triazin-4-yl}amino)-N-[(1R,2S)-2-hydroxycyclopentyl]pyridine-3-carboxamide, 4-({2-[6-(difluoromethyl)pyridin-2-yl]pyrrolo[2,1-f][1,2,4]triazin-4-yl}amino)-N-[(1S,2S)-2-hydroxycyclopentyl]pyridine-3-carboxamide, 1-[4-({2-[6-(difluoromethyl)pyridin-2-yl]pyrrolo[2,1-f][1,2,4]triazin-4-yl}amino)pyridine-3-carbonyl]piperidin-4-ol, N-(4,4-difluorocyclohexyl)-4-({2-[6-(difluoromethyl)pyridin-2-yl]pyrrolo[2,1-f][1,2,4]triazin-4-yl}amino)pyridine-3-carboxamide, 4-({2-[6-(difluoromethyl)pyridin-2-yl]pyrrolo[2,1-f][1,2,4]triazin-4-yl}amino)-N-(3,3,3-trifluoropropyl)pyridine-3-carboxamide, N-{2-[6-(difluoromethyl)pyridin-2-yl]pyrrolo[2,1-f][1,2,4]triazin-4-yl}-3-(4,4-difluoropiperidine-1-carbonyl)pyridin-4-amine, Ethyl 3-{[4-({2-[6-(difluoromethyl)pyridin-2-yl]pyrrolo[2,1-f][1,2,4]triazin-4-yl}amino)pyridin-3-yl]formamido}propanoate, 4-({2-[6-(difluoromethyl)pyridin-2-yl]pyrrolo[2,1-f][1,2,4]triazin-4-yl}amino)-N-{[3-(methoxymethyl)-1,2,4-oxadiazol-5-yl]methyl}pyridine-3-carboxamide, (4-{[2-(6-methoxypyridin-2-yl)pyrrolo[2,1-f][1,2,4]triazin-4-yl]amino}pyridin-3-yl)methanol, 1-[({4-[(3-fluoropyridin-4-yl)amino]-2-(6-methoxypyridin-2-yl)pyrrolo[2,1-f][1,2,4]triazin-6-yl}methyl)amino]-2-methylpropan-2-ol, (3R)-3-fluoro-4-[({4-[(3-fluoropyridin-4-yl)amino]-2-(6-methoxypyridin-2-yl)pyrrolo[2,1-f][1,2,4]triazin-6-yl}methyl)amino]-2-methylbutan-2-ol, 4-{3-[({4-[(3-fluoropyridin-4-yl)amino]-2-(6-methoxypyridin-2-yl)pyrrolo[2,1-f][1,2,4]triazin-6-yl}methyl)amino]propyl}-1,4-thiomorpholine-1, 1-dione, N-[6-ethenyl-2-(6-methoxypyridin-2-yl)pyrrolo[2,1-f][1,2,4]triazin-4-yl]-3-fluoropyridin-4-amine, (3E)-4-{4-[(3-fluoropyridin-4-yl)amino]-2-(6-methoxypyridin-2-yl)pyrrolo[2,1-f][1,2,4]triazin-6-yl}but-3-en-1-ol, N-(4-{[2-(6-methoxypyridin-2-yl)pyrrolo[2,1-f][1,2,4]triazin-4-yl]amino}pyridin-3-yl)-2-(morpholin-4-yl)acetamide, N-[2-(6-fluoropyridin-2-yl)pyrrolo[2,1-f][1,2,4]triazin-4-yl]pyridin-4-amine, N-[2-(6-methoxypyridin-2-yl)pyrrolo[2,1-f][1,2,4]triazin-4-yl]pyridin-4-amine, N-{2-[2-(methylsulfanyl)pyrimidin-4-yl]pyrrolo[2,1-f][1,2,4]triazin-4-yl}pyridin-4-amine, Ethyl 2-(6-methylpyridin-2-yl)-4-[(pyridin-4-yl)amino]pyrrolo[2,1-f][1,2,4]triazine-6-carboxylate, 2-(6-methylpyridin-2-yl)-N-phenyl-4-[(pyridin-4-yl)amino]pyrrolo[2,1-f][1,2,4]triazine-6-carboxamide, N,N-dimethyl-2-(6-methylpyridin-2-yl)-4-[(pyridin-4-yl)amino]pyrrolo[2,1-f][1,2,4]triazine-6-carboxamide, 2-(6-methylpyridin-2-yl)-4-[(pyridin-4-yl)amino]pyrrolo[2,1-f][1,2,4]triazine-6-carboxamide, N-methyl-2-(6-methylpyridin-2-yl)-4-[(pyridin-4-yl)amino]pyrrolo[2,1-f][1,2,4]triazine-6-carboxamide, 4-{[2-(6-methylpyridin-2-yl)pyrrolo[2,1-f][1,2,4]triazin-4-yl]amino}-N-[3-(pyrrolidin-1-yl)propyl]pyridine-3-carboxamide, N-[2-(6-methylpyridin-2-yl)pyrrolo[2,1-f][1,2,4]triazin-4-yl]-3-[3-(morpholin-4-yl)propoxy]pyridin-4-amine, 4-({2-[6-(difluoromethyl)-5-fluoropyridin-2-yl]pyrrolo[2,1-f][1,2,4]triazin-4-yl}amino)pyridine-3-carboxamide, N-[4-({2-[6-(difluoromethyl)pyridin-2-yl]pyrrolo[2,1-f][1,2,4]triazin-4-yl}amino)-5-fluoropyridin-2-yl]acetamide, N-[5-fluoro-4-({2-[6-(trifluoromethyl)pyridin-2-yl]pyrrolo[2,1-f][1,2,4]triazin-4-yl}amino)pyridin-2-yl]acetamide, N-(4-{[2-(5-fluoropyridin-2-yl)pyrrolo[2,1-f][1,2,4]triazin-4-yl]amino}pyridin-2-yl)acetamide, 4-({2-[6-(difluoromethyl)pyridin-2-yl]pyrrolo[2,1-f][1,2,4]triazin-4-yl}amino)pyridine-3-carboxamide, N-[4-({2-[6-(difluoromethyl)pyridin-2-yl]pyrrolo[2,1-f][1,2,4]triazin-4-yl}amino)-3-fluoropyridin-2-yl]acetamide, 2-(1H-pyrazol-3-yl)-N-{2-[6-(trifluoromethyl)pyridin-2-yl]pyrrolo[2,1-f][1,2,4]triazin-4-yl}pyridin-4-amine, 2-[4-({4-[(3-fluoropyridin-4-yl)amino]-2-(pyridin-2-yl)pyrrolo[2,1-f][1,2,4]triazin-5-yl}methyl)piperazin-1-yl]ethan-1-ol, (3S)-1-({4-[(3-fluoropyridin-4-yl)amino]-2-(pyridin-2-yl)pyrrolo[2,1-f][1,2,4]triazin-5-yl}methyl)pyrrolidin-3-ol, (3R)-1-({4-[(3-fluoropyridin-4-yl)amino]-2-(pyridin-2-yl)pyrrolo[2,1-f][1,2,4]triazin-5-yl}methyl)pyrrolidin-3-ol, 3-fluoro-N-[2-(5-fluoropyridin-2-yl)-5-[(4-methylpiperazin-1-yl)methyl]pyrrolo[2,1-f][1,2,4]triazin-4-yl]pyridin-4-amine, 1-({[2-(5-fluoropyridin-2-yl)-4-[(3-fluoropyridin-4-yl)amino]pyrrolo[2,1-f][1,2,4]triazin-5-yl]methyl}amino)-2-methylpropan-2-ol, 4-[({4-[(3-fluoropyridin-4-yl)amino]-2-(pyridin-2-yl)pyrrolo[2,1-f][1,2,4]triazin-5-yl}methyl)amino]cyclohexan-1-ol, (5R,7S)-3-[({4-[(3-fluoropyridin-4-yl)amino]-2-(pyridin-2-yl)pyrrolo[2,1-f][1,2,4]triazin-5-yl}methyl)amino]adamantan-1-ol, 3-fluoro-N-(5-{[(piperidin-4-ylmethyl)amino]methyl}-2-(pyridin-2-yl)pyrrolo[2,1-f][1,2,4]triazin-4-yl)pyridin-4-amine, 1-[({4-[(3-fluoropyridin-4-yl)amino]-2-(pyridin-2-yl)pyrrolo[2,1-f][1,2,4]triazin-5-yl}methyl)amino]propan-2-ol, 1-{2-[({4-[(3-fluoropyridin-4-yl)amino]-2-(pyridin-2-yl)pyrrolo[2,1-f][1,2,4]triazin-5-yl}methyl)amino]ethyl}cyclopentan-1-ol, 3-fluoro-N-(5-{[(1-methylcyclobutyl)amino]methyl}-2-(pyridin-2-yl)pyrrolo[2,1-f][1,2,4]triazin-4-yl)pyridin-4-amine, 3-fluoro-N-(5-{[(4-methyloxan-4-yl)amino]methyl}-2-(pyridin-2-yl)pyrrolo[2,1-f][1,2,4]triazin-4-yl)pyridin-4-amine, 1-({4-[(3-fluoropyridin-4-yl)amino]-2-(pyridin-2-yl)pyrrolo[2,1-f][1,2,4]triazin-5-yl}methyl)piperidin-4-ol, {1-[({4-[(3-fluoropyridin-4-yl)amino]-2-(pyridin-2-yl)pyrrolo[2,1-f][1,2,4]triazin-5-yl}methyl)amino]cyclopentyl}methanol, 4-N-({4-[(3-fluoropyridin-4-yl)amino]-2-(pyridin-2-yl)pyrrolo[2,1-f][1,2,4]triazin-5-yl}methyl)-1-N, 1-N-dimethylcyclohexane-1,4-diamine, 3-fluoro-N-[5-({[3-(morpholin-4-yl)propyl]amino}methyl)-2-(pyridin-2-yl)pyrrolo[2,1-f][1,2,4]triazin-4-yl]pyridin-4-amine, 3-fluoro-N-(5-{[(oxolan-2-ylmethyl)amino]methyl}-2-(pyridin-2-yl)pyrrolo[2,1-f][1,2,4]triazin-4-yl)pyridin-4-amine, 3-fluoro-N-{2-[5-(trifluoromethyl)pyridin-2-yl]pyrrolo[2,1-f][1,2,4]triazin-4-yl}pyridin-4-amine, 3-fluoro-N-[2-(2-methoxy-1,3-thiazol-4-yl)pyrrolo[2,1-f][1,2,4]triazin-4-yl]pyridin-4-amine, N-{4-[(5-{[4-(2-hydroxyethyl)piperazin-1-yl]methyl}-2-(pyridin-2-yl)pyrrolo[2,1-f][1,2,4]triazin-4-yl)amino]pyridin-2-yl}acetamide, (3S)-1-({2-[6-(difluoromethyl)pyridin-2-yl]-4-[(3-fluoropyridin-4-yl)amino]pyrrolo[2,1-f][1,2,4]triazin-5-yl}methyl)pyrrolidin-3-ol, (3S)-1-({4-[(3-fluoropyridin-4-yl)amino]-2-(6-methylpyridin-2-yl)pyrrolo[2,1-f][1,2,4]triazin-5-yl}methyl)pyrrolidin-3-ol, 2-[4-({2-[6-(difluoromethyl)pyridin-2-yl]-4-[(3-fluoropyridin-4-yl)amino]pyrrolo[2,1-f][1,2,4]triazin-5-yl}methyl)piperazin-1-yl]ethan-1-ol, N-{4-[(5-{[(2-hydroxy-2-methylpropyl)amino]methyl}-2-[6-(trifluoromethyl)pyridin-2-yl]pyrrolo[2,1-f][1,2,4]triazin-4-yl)amino]pyridin-2-yl}acetamide, N-{2-[6-(trifluoromethyl)pyridin-2-yl]pyrrolo[2,1-f][1,2,4]triazin-4-yl}pyrimidin-4-amine, 2-fluoro-N-{2-[6-(trifluoromethyl)pyridin-2-yl]pyrrolo[2,1-f][1,2,4]triazin-4-yl}pyridin-4-amine, 2-methyl-N-{2-[6-(trifluoromethyl)pyridin-2-yl]pyrrolo[2,1-f][1,2,4]triazin-4-yl}pyridin-4-amine, 1-{[(4-{[2-(ethylamino)pyridin-4-yl]amino}-2-(pyridin-2-yl)pyrrolo[2,1-f][1,2,4]triazin-5-yl)methyl]amino}-2-methylpropan-2-ol, 2-[4-({4-[(3-fluoropyridin-4-yl)amino]-2-(6-methylpyridin-2-yl)pyrrolo[2,1-f][1,2,4]triazin-5-yl}methyl)piperazin-1-yl]ethan-1-ol, 3-fluoro-N-[2-(3-fluoropyridin-2-yl)pyrrolo[2,1-f][1,2,4]triazin-4-yl]pyridin-4-amine, 3-fluoro-N-[2-(3-fluoro-6-methylpyridin-2-yl)pyrrolo[2,1-f][1,2,4]triazin-4-yl]pyridin-4-amine, 3-fluoro-N-[2-(1,3-thiazol-4-yl)pyrrolo[2,1-f][1,2,4]triazin-4-yl]pyridin-4-amine, (1R,4R)-1-N-({4-[(3-fluoropyridin-4-yl)amino]-2-(pyridin-2-yl)pyrrolo[2,1-f][1,2,4]triazin-5-yl}methyl)cyclohexane-1,4-diamine, 2-[({4-[(3-fluoropyridin-4-yl)amino]-2-(pyridin-2-yl)pyrrolo[2,1-f][1,2,4]triazin-5-yl}methyl)amino]propane-1,3-diol, 3-fluoro-N-(5-{[(piperidin-2-ylmethyl)amino]methyl}-2-(pyridin-2-yl)pyrrolo[2,1-f][1,2,4]triazin-4-yl)pyridin-4-amine, N-(5-{[(azetidin-3-ylmethyl)amino]methyl}-2-(pyridin-2-yl)pyrrolo[2,1-f][1,2,4]triazin-4-yl)-3-fluoropyridin-4-amine, 3-fluoro-N-(5-{[(piperidin-3-yl)amino]methyl}-2-(pyridin-2-yl)pyrrolo[2,1-f][1,2,4]triazin-4-yl)pyridin-4-amine, 3-fluoro-N-[2-(pyridin-2-yl)-5-{[(2,2,2-trifluoroethyl)amino]methyl}pyrrolo[2,1-f][1,2,4]triazin-4-yl]pyridin-4-amine, 3-fluoro-N-[5-({[2-(piperazin-1-yl)ethyl]amino}methyl)-2-(pyridin-2-yl)pyrrolo[2,1-f][1,2,4]triazin-4-yl]pyridin-4-amine, 3-fluoro-N-[2-(pyridin-2-yl)-5-({[2-(pyrrolidin-2-yl)ethyl]amino}methyl)pyrrolo[2,1-f][1,2,4]triazin-4-yl]pyridin-4-amine, N-(5-{[(cyclobutylmethyl)amino]methyl}-2-(pyridin-2-yl)pyrrolo[2,1-f][1,2,4]triazin-4-yl)-3-fluoropyridin-4-amine, 2-[({4-[(3-fluoropyridin-4-yl)amino]-2-(pyridin-2-yl)pyrrolo[2,1-f][1,2,4]triazin-5-yl}methyl)amino]cyclohexan-1-ol, (2S)-2-[({4-[(3-fluoropyridin-4-yl)amino]-2-(pyridin-2-yl)pyrrolo[2,1-f][1,2,4]triazin-5-yl}methyl)amino]pentan-1-ol, 4-[({4-[(3-fluoropyridin-4-yl)amino]-2-(pyridin-2-yl)pyrrolo[2,1-f][1,2,4]triazin-5-yl}methyl)amino]butan-2-ol, 3-[4-({4-[(3-fluoropyridin-4-yl)amino]-2-(pyridin-2-yl)pyrrolo[2,1-f][1,2,4]triazin-5-yl}methyl)piperazin-1-yl]phenol, 3-fluoro-N-[2-(pyridin-2-yl)-5-{[4-(pyrimidin-2-yl)piperazin-1-yl]methyl}pyrrolo[2,1-f][1,2,4]triazin-4-yl]pyridin-4-amine, 1-({4-[(3-fluoropyridin-4-yl)amino]-2-(pyridin-2-yl)pyrrolo[2,1-f][1,2,4]triazin-5-yl}methyl)-4-phenylpiperidin-4-ol, 1-[1-({4-[(3-fluoropyridin-4-yl)amino]-2-(pyridin-2-yl)pyrrolo[2,1-f][1,2,4]triazin-5-yl}methyl)piperidin-4-yl]-2,3-dihydro-1H-1,3-benzodiazol-2-one, 3-fluoro-N-(5-{[methyl(1-methylpiperidin-4-yl)amino]methyl}-2-(pyridin-2-yl)pyrrolo[2,1-f][1,2,4]triazin-4-yl)pyridin-4-amine, N-[5-({[2-(dimethylamino)ethyl]amino}methyl)-2-(pyridin-2-yl)pyrrolo[2,1-f][1,2,4]triazin-4-yl]-3-fluoropyridin-4-amine, 3-fluoro-N-[5-({[3-(1H-imidazol-1-yl)propyl]amino}methyl)-2-(pyridin-2-yl)pyrrolo[2,1-f][1,2,4]triazin-4-yl]pyridin-4-amine, N-(5-{[(adamantan-1-yl)amino]methyl}-2-(pyridin-2-yl)pyrrolo[2,1-f][1,2,4]triazin-4-yl)-3-fluoropyridin-4-amine, 3-fluoro-N-[5-({[3-(4-methylpiperazin-1-yl)propyl]amino}methyl)-2-(pyridin-2-yl)pyrrolo[2,1-f][1,2,4]triazin-4-yl]pyridin-4-amine, 3-fluoro-N-[5-({[2-(piperidin-1-yl)ethyl]amino}methyl)-2-(pyridin-2-yl)pyrrolo[2,1-f][1,2,4]triazin-4-yl]pyridin-4-amine, N-[5-({[(3S)-1-benzylpyrrolidin-3-yl]amino}methyl)-2-(pyridin-2-yl)pyrrolo[2,1-f][1,2,4]triazin-4-yl]-3-fluoropyridin-4-amine, N-(5-{[(3-aminopropyl)amino]methyl}-2-(pyridin-2-yl)pyrrolo[2,1-f][1,2,4]triazin-4-yl)-3-fluoropyridin-4-amine, (2S)-3-[({4-[(3-fluoropyridin-4-yl)amino]-2-(pyridin-2-yl)pyrrolo[2,1-f][1,2,4]triazin-5-yl}methyl)amino]propane-1,2-diol, (1R,4R)-4-[({4-[(3-fluoropyridin-4-yl)amino]-2-(pyridin-2-yl)pyrrolo[2,1-f][1,2,4]triazin-5-yl}methyl)amino]cyclohexan-1-ol, 3-fluoro-N-{2-[6-(trifluoromethoxy)pyridin-2-yl]pyrrolo[2,1-f][1,2,4]triazin-4-yl}pyridin-4-amine, 3-fluoro-N-[5-(morpholin-4-ylmethyl)-2-(pyridin-2-yl)pyrrolo[2,1-f][1,2,4]triazin-4-yl]pyridin-4-amine, N-(4-{[2-(6-fluoropyridin-2-yl)pyrrolo[2,1-f][1,2,4]triazin-4-yl]amino}pyridin-2-yl)acetamide, 4-({2-[6-(trifluoromethyl)pyridin-2-yl]pyrrolo[2,1-f][1,2,4]triazin-4-yl}amino)pyridine-2-carbonitrile, N-(4-{[5-(morpholin-4-ylmethyl)-2-(pyridin-2-yl)pyrrolo[2,1-f][1,2,4]triazin-4-yl]amino}pyridin-2-yl)acetamide, N-(5-{[(2H-1,3-benzodioxol-5-ylmethyl)amino]methyl}-2-(pyridin-2-yl)pyrrolo[2,1-f][1,2,4]triazin-4-yl)-3-fluoropyridin-4-amine, N-({4-[(3-fluoropyridin-4-yl)amino]-2-(pyridin-2-yl)pyrrolo[2,1-f][1,2,4]triazin-5-yl}methyl)-2-methyl-1,3-benzothiazol-6-amine, (3-{[(({4-[(3-fluoropyridin-4-yl)amino]-2-(pyridin-2-yl)pyrrolo[2,1-f][1,2,4]triazin-5-yl}methyl)amino]methyl}oxetan-3-yl)methanol, 3-fluoro-N-[5-({[4-(1,3-oxazol-5-yl)phenyl]amino}methyl)-2-(pyridin-2-yl)pyrrolo[2,1-f][1,2,4]triazin-4-yl]pyridin-4-amine, 3-fluoro-N-(5-{[(5-phenyl-1H-pyrazol-3-yl)amino]methyl}-2-(pyridin-2-yl)pyrrolo[2,1-f][1,2,4]triazin-4-yl)pyridin-4-amine, 3-fluoro-N-(5-{[(morpholin-2-ylmethyl)amino]methyl}-2-(pyridin-2-yl)pyrrolo[2,1-f][1,2,4]triazin-4-yl)pyridin-4-amine, N-[5-({[(2R)-3,3-dimethylbutan-2-yl]amino}methyl)-2-(pyridin-2-yl)pyrrolo[2,1-f][1,2,4]triazin-4-yl]-3-fluoropyridin-4-amine, 3-fluoro-N-[2-(pyridin-2-yl)-5-({[2-(pyridin-2-yl)propan-2-yl]amino}methyl)pyrrolo[2,1-f][1,2,4]triazin-4-yl]pyridin-4-amine, 3-fluoro-N-[5-({[1-(propan-2-yl)-1H-pyrazol-4-yl]amino}methyl)-2-(pyridin-2-yl)pyrrolo[2,1-f][1,2,4]triazin-4-yl]pyridin-4-amine, 3-fluoro-N-[5-({[2-(1-methylpiperidin-4-yl)ethyl]amino}methyl)-2-(pyridin-2-yl)pyrrolo[2,1-f][1,2,4]triazin-4-yl]pyridin-4-amine, 3-fluoro-N-[2-(pyridin-2-yl)-5-({[2-(pyridin-2-yl)ethyl]amino}methyl)pyrrolo[2,1-f][1,2,4]triazin-4-yl]pyridin-4-amine, 3-fluoro-N-[5-({[(5-methylpyrazin-2-yl)methyl]amino}methyl)-2-(pyridin-2-yl)pyrrolo[2,1-f][1,2,4]triazin-4-yl]pyridin-4-amine, N-({4-[(3-fluoropyridin-4-yl)amino]-2-(pyridin-2-yl)pyrrolo[2,1-f][1,2,4]triazin-5-yl}methyl)-1H-1,2,3-benzotriazol-5-amine, 3-fluoro-N-(5-{[(piperidin-4-yl)amino]methyl}-2-(pyridin-2-yl)pyrrolo[2,1-f][1,2,4]triazin-4-yl)pyridin-4-amine, 3-fluoro-N-(5-{[(5-methyl-1,3,4-thiadiazol-2-yl)amino]methyl}-2-(pyridin-2-yl)pyrrolo[2,1-f][1,2,4]triazin-4-yl)pyridin-4-amine, (3S,4S)-4-amino-1-({4-[(3-fluoropyridin-4-yl)amino]-2-(pyridin-2-yl)pyrrolo[2,1-f][1,2,4]triazin-5-yl}methyl)piperidin-3-ol, (1R)-2-[({4-[(3-fluoropyridin-4-yl)amino]-2-(pyridin-2-yl)pyrrolo[2,1-f][1,2,4]triazin-5-yl}methyl)amino]-1-phenylethan-1-ol, N-(5-{[(azetidin-3-yl)amino]methyl}-2-(pyridin-2-yl)pyrrolo[2,1-f][1,2,4]triazin-4-yl)-3-fluoropyridin-4-amine, Methyl N-[4-({2-[6-(trifluoromethyl)pyridin-2-yl]pyrrolo[2,1-f][1,2,4]triazin-4-yl}amino)pyridin-2-yl]carbamate, N-[4-({2-[6-(trifluoromethyl)pyridin-2-yl]pyrrolo[2,1-f][1,2,4]triazin-4-yl}amino)pyridin-2-yl]propanamide, 3-methyl-N-[4-({2-[6-(trifluoromethyl)pyridin-2-yl]pyrrolo[2,1-f][1,2,4]triazin-4-yl}amino)pyridin-2-yl]butanamide, 4-({2-[6-(trifluoromethyl)pyridin-2-yl]pyrrolo[2,1-f][1,2,4]triazin-4-yl}amino)pyridine-2-carboxamide, 2-(4-methylpiperazin-1-yl)-N-[4-({2-[6-(trifluoromethyl)pyridin-2-yl]pyrrolo[2,1-f][1,2,4]triazin-4-yl}amino)pyridin-2-yl]acetamide, 2-chloro-5-fluoro-N-[2-(5-fluoropyridin-2-yl)pyrrolo[2,1-f][1,2,4]triazin-4-yl]pyridin-4-amine, N-[4-({2-[6-(trifluoromethyl)pyridin-2-yl]pyrrolo[2,1-f][1,2,4]triazin-4-yl}amino)pyridin-2-yl]methanesulfonamide, 2-[4-(2-hydroxyethyl)piperazin-1-yl]-N-[4-({2-[6-(trifluoromethyl)pyridin-2-yl]pyrrolo[2,1-f][1,2,4]triazin-4-yl}amino)pyridin-2-yl]acetamide, 2-(4-acetylpiperazin-1-yl)-N-[4-({2-[6-(trifluoromethyl)pyridin-2-yl]pyrrolo[2,1-f][1,2,4]triazin-4-yl}amino)pyridin-2-yl]acetamide, 3,3-dimethyl-N-[4-({2-[6-(trifluoromethyl)pyridin-2-yl]pyrrolo[2,1-f][1,2,4]triazin-4-yl}amino)pyridin-2-yl]butanamide, 2-(piperazin-1-yl)-N-[4-({2-[6-(trifluoromethyl)pyridin-2-yl]pyrrolo[2,1-f][1,2,4]triazin-4-yl}amino)pyridin-2-yl]acetamide, N-(5-fluoro-4-{[2-(5-fluoropyridin-2-yl)pyrrolo[2,1-f][1,2,4]triazin-4-yl]amino}pyridin-2-yl)acetamide, N-(2-hydroxy-2-methylpropyl)-4-({2-[6-(trifluoromethyl)pyridin-2-yl]pyrrolo[2,1-f][1,2,4]triazin-4-yl}amino)pyridine-2-carboxamide, 2-[(3S)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide, (2S)—N-[4-({2-[6-(trifluoromethyl)pyridin-2-yl]pyrrolo[2,1-f][1,2,4]triazin-4-yl}amino)pyridin-2-yl]pyrrolidine-2-carboxamide, 2-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]acetamide, 3-fluoro-N-(5-{[(1-methylpiperidin-4-yl)oxy]methyl}-2-(pyridin-2-yl)pyrrolo[2,1-f][1,2,4]triazin-4-yl)pyridin-4-amine,
2-(piperidin-1-yl)-N-[4-({2-[6-(trifluoromethyl)pyridin-2-yl]pyrrolo[2,1-f][1,2,4]triazin-4-yl}amino)pyridin-2-yl]acetamide,
2-[(2-hydroxy-2-methylpropyl)amino]-N-[4-({2-[6-(trifluoromethyl)pyridin-2-yl]pyrrolo[2,1-f][1,2,4]triazin-4-yl}amino)pyridin-2-yl]acetamide,
2-(morpholin-4-yl)-N-[4-({2-[6-(trifluoromethyl)pyridin-2-yl]pyrrolo[2,1-f][1,2,4]triazin-4-yl}amino)pyridin-2-yl]acetamide,
N-[4-({2-[5-(trifluoromethyl)pyridin-2-yl]pyrrolo[2,1-f][1,2,4]triazin-4-yl}amino)pyridin-2-yl]acetamide,
N-(5-fluoro-4-{[2-(5-fluoro-6-methylpyridin-2-yl)pyrrolo[2,1-f][1,2,4]triazin-4-yl]amino}pyridin-2-yl)acetamide,
3-[(3R)-3-hydroxypyrrolidin-1-yl]-N-[4-({2-[6-(trifluoromethyl)pyridin-2-yl]pyrrolo[2,1-f][1,2,4]triazin-4-yl}amino)pyridin-2-yl]propanamide,
N-[4-({2-[6-(trifluoromethyl)pyridin-2-yl]pyrrolo[2,1-f][1,2,4]triazin-4-yl}amino)pyridin-2-yl]cyclopropanecarboxamide,
2-methoxy-N-[4-({2-[6-(trifluoromethyl)pyridin-2-yl]pyrrolo[2,1-f][1,2,4]triazin-4-yl}amino)pyridin-2-yl]acetamide,
4,4,4-trifluoro-N-[4-({2-[6-(trifluoromethyl)pyridin-2-yl]pyrrolo[2,1-f][1,2,4]triazin-4-yl}amino)pyridin-2-yl]butanamide,
3-cyano-N-[4-({2-[6-(trifluoromethyl)pyridin-2-yl]pyrrolo[2,1-f][1,2,4]triazin-4-yl}amino)pyridin-2-yl]propanamide,
N-(5-fluoro-4-{[2-(6-fluoropyridin-2-yl)pyrrolo[2,1-f][1,2,4]triazin-4-yl]amino}pyridin-2-yl)acetamide,
3-(4-hydroxypiperidin-1-yl)-N-[4-({2-[6-(trifluoromethyl)pyridin-2-yl]pyrrolo[2,1-f][1,2,4]triazin-4-yl}amino)pyridin-2-yl]propanamide,
3-(3,3-difluoroazetidin-1-yl)-N-[4-({2-[6-(trifluoromethyl)pyridin-2-yl]pyrrolo[2,1-f][1,2,4]triazin-4-yl}amino)pyridin-2-yl]propanamide,
2,2-dimethyl-N-[4-({2-[6-(trifluoromethyl)pyridin-2-yl]pyrrolo[2,1-f][1,2,4]triazin-4-yl}amino)pyridin-2-yl]propanamide,
3-methoxy-N-[4-({2-[6-(trifluoromethyl)pyridin-2-yl]pyrrolo[2,1-f][1,2,4]triazin-4-yl}amino)pyridin-2-yl]propanamide,
3,3,3-trifluoro-N-[4-({2-[6-(trifluoromethyl)pyridin-2-yl]pyrrolo[2,1-f][1,2,4]triazin-4-yl}amino)pyridin-2-yl]propanamide,
N-(4-{[2-(5-fluoro-6-methylpyridin-2-yl)pyrrolo[2,1-f][1,2,4]triazin-4-yl]amino}pyridin-2-yl)cyclopropanecarboxamide, or a pharmaceutically acceptable salt, tautomer or stereoisomer thereof.

2. A pharmaceutical composition which comprises a compound according to claim 1 or a pharmaceutically acceptable salt thereof and one or more pharmaceutically acceptable carriers, diluents or excipients.

3. A combination pharmaceutical product comprising a compound according to claim 1 or a pharmaceutically acceptable salt thereof together with one or more other therapeutically active agents.

4. A method of treating diseases or conditions for which a TGFβR antagonist is indicated in a subject in need thereof which comprises administering a therapeutically effective amount of compound according to claim 1 or a pharmaceutically acceptable salt thereof.

5. The method of claim 4 wherein the disease or condition is cancer.

6. The method of claim 5 wherein the cancer is small cell lung cancer, non-small cell lung cancer, triple-negative breast cancer, ovarian cancer, colorectal cancer, prostate cancer, melanoma, pancreatic cancer, multiple myeloma, T-acute lymphoblastic leukemia or AML.

* * * * *